US012617829B2

(12) United States Patent
Winston et al.

(10) Patent No.: US 12,617,829 B2
(45) Date of Patent: *May 5, 2026

(54) ACTIVATABLE CYTOKINE POLYPEPTIDES AND METHODS OF USE THEREOF

(71) Applicant: Werewolf Therapeutics, Inc., Watertown, MA (US)

(72) Inventors: William Winston, West Newton, MA (US); Heather Brodkin, West Newton, MA (US); Cynthia Seidel-Dugan, Belmont, MA (US); Daniel Hicklin, Boston, MA (US); Jose Andres Salmeron-Garcia, Acton, MA (US)

(73) Assignee: Werewolf Therapeutics, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/601,474

(22) Filed: Mar. 11, 2024

(65) Prior Publication Data

US 2024/0262880 A1     Aug. 8, 2024

Related U.S. Application Data

(63) Continuation of application No. 18/312,245, filed on May 4, 2023, which is a continuation of application No. 17/028,643, filed on Sep. 22, 2020, which is a continuation-in-part of application No. PCT/US2019/032320, filed on May 14, 2019.

(60) Provisional application No. 62/935,605, filed on Nov. 14, 2019, provisional application No. 62/756,515, filed on Nov. 6, 2018, provisional application No. 62/756,504, filed on Nov. 6, 2018, provisional application No. 62/756,507, filed on Nov. 6, 2018, provisional application No. 62/671,225, filed on May 14, 2018.

(51) Int. Cl.
| | |
|---|---|
| *C07K 14/715* | (2006.01) |
| *C07K 14/54* | (2006.01) |
| *C07K 14/555* | (2006.01) |
| *C07K 16/28* | (2006.01) |
| *C07K 14/55* | (2006.01) |

(52) U.S. Cl.
CPC ........ *C07K 14/555* (2013.01); *C07K 14/7156* (2013.01); *C07K 14/5434* (2013.01); *C07K 14/55* (2013.01); *C07K 16/2818* (2013.01); *C07K 16/2827* (2013.01); *C07K 2319/31* (2013.01)

(58) Field of Classification Search
CPC .. C07K 2319/31; C07K 14/54; C07K 14/555; C07K 14/7156; C07K 2319/30; C07K 2319/00; C07K 2319/50
See application file for complete search history.

(56) References Cited

U.S. PATENT DOCUMENTS

| | | | |
|---|---|---|---|
| 2,008,167 | A | 7/1935 | Bergstein |
| 4,419,446 | A | 12/1983 | Howley et al. |
| 4,560,655 | A | 12/1985 | Baker |
| 4,601,978 | A | 7/1986 | Karin |
| 4,657,866 | A | 4/1987 | Kumar |
| 4,676,980 | A | 6/1987 | Segal et al. |
| 4,767,704 | A | 8/1988 | Cleveland |
| 4,816,567 | A | 3/1989 | Cabilly et al. |
| 4,927,762 | A | 5/1990 | Darfler |
| 4,965,199 | A | 10/1990 | Capon et al. |
| 5,089,261 | A | 2/1992 | Nitecki et al. |
| 5,122,464 | A | 6/1992 | Wilson et al. |
| 5,122,469 | A | 6/1992 | Mather et al. |
| 5,208,020 | A | 5/1993 | Chari et al. |
| 5,264,365 | A | 11/1993 | Georgiou |
| 5,416,064 | A | 5/1995 | Chari et al. |
| 5,508,192 | A | 4/1996 | Georgiou et al. |
| 5,571,894 | A | 11/1996 | Weis et al. |
| 5,587,458 | A | 12/1996 | King et al. |
| 5,624,821 | A | 4/1997 | Winter et al. |
| 5,635,483 | A | 6/1997 | Pettit et al. |
| 5,639,635 | A | 6/1997 | Joly et al. |

(Continued)

FOREIGN PATENT DOCUMENTS

| | | |
|---|---|---|
| CN | 10775997 A | 3/2018 |
| DE | 19701141 C1 | 4/1998 |

(Continued)

OTHER PUBLICATIONS

Krieg et al., "Improved IL-2 immunotherapy by selective stimulation of IL-2 receptors on lymphocytes and endothelial cells," PNAS, 107(26):11906-11911 (2010).

(Continued)

*Primary Examiner* — Vanessa L. Ford
*Assistant Examiner* — Sandra Carter
(74) *Attorney, Agent, or Firm* — Hogan Lovells US LLP

(57) ABSTRACT

The disclosure features fusion proteins that are conditionally active variants of a cytokine of interest. In one aspect, the full-length polypeptides of the invention have reduced or minimal cytokine-receptor activating activity even though they contain a functional cytokine polypeptide. Upon activation, e.g., by cleavage of a linker that joins a blocking moiety, e.g. a steric blocking polypeptide, in sequence to the active cytokine, the cytokine can bind its receptor and effect signaling. Typically, the fusion proteins further comprise an in vivo half-life extension element, which may be cleaved from the cytokine in the tumor microenvironment.

13 Claims, 199 Drawing Sheets

Specification includes a Sequence Listing.

(56)                    References Cited

U.S. PATENT DOCUMENTS

| | | |
|---|---|---|
| 5,641,870 A | 6/1997 | Rinderknecht et al. |
| 5,648,237 A | 7/1997 | Carter et al. |
| 5,648,260 A | 7/1997 | Winter et al. |
| 5,712,374 A | 1/1998 | Kunstmann et al. |
| 5,714,586 A | 2/1998 | Kunstmann et al. |
| 5,739,277 A | 4/1998 | Presta et al. |
| 5,767,285 A | 6/1998 | Hamann et al. |
| 5,770,701 A | 6/1998 | McGahren et al. |
| 5,770,710 A | 6/1998 | McGahren et al. |
| 5,773,001 A | 6/1998 | Hamann et al. |
| 5,780,588 A | 7/1998 | Pettit et al. |
| 5,834,597 A | 11/1998 | Tso et al. |
| 5,869,046 A | 2/1999 | Presta et al. |
| 5,877,296 A | 3/1999 | Hamann et al. |
| 5,891,693 A | 4/1999 | Bebbington et al. |
| 5,939,598 A | 8/1999 | Kucherlapati et al. |
| 6,027,888 A | 2/2000 | Georgiou et al. |
| 6,075,181 A | 6/2000 | Kucherlapati et al. |
| 6,083,715 A | 7/2000 | Georgiou et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,165,745 A | 12/2000 | Ward et al. |
| 6,248,516 B1 | 6/2001 | Winter et al. |
| 6,602,684 B1 | 8/2003 | Umana et al. |
| 6,630,579 B2 | 10/2003 | Chari et al. |
| 6,670,147 B1 | 12/2003 | Heidtman et al. |
| 6,821,505 B2 | 11/2004 | Ward et al. |
| 6,942,853 B2 | 9/2005 | Chernajovsky et al. |
| 7,498,298 B2 | 3/2009 | Doronina et al. |
| 7,514,073 B2 | 4/2009 | Epstein et al. |
| 8,399,219 B2 | 3/2013 | Stagliano et al. |
| 8,563,269 B2 | 10/2013 | Stagliano et al. |
| 8,734,774 B2 | 5/2014 | Frelinger et al. |
| 8,809,504 B2 | 8/2014 | Lauermann et al. |
| 8,969,538 B2 | 3/2015 | Rosen et al. |
| 8,993,266 B2 | 3/2015 | Stagliano et al. |
| 9,206,243 B2 | 12/2015 | Leon Monzon et al. |
| 9,309,510 B2 | 4/2016 | La Porte et al. |
| 9,453,078 B2 | 9/2016 | Stagliano et al. |
| 9,487,590 B2 | 11/2016 | West et al. |
| 9,517,276 B2 | 12/2016 | Lowman et al. |
| 9,540,440 B2 | 1/2017 | Lowman et al. |
| 9,644,016 B2 | 5/2017 | Stagliano et al. |
| 9,708,412 B2 | 7/2017 | Baeuerle et al. |
| 9,737,623 B2 | 8/2017 | Desnoyers et al. |
| 9,775,913 B2 | 10/2017 | Lauermann |
| 9,856,314 B2 | 1/2018 | Lowman et al. |
| 9,861,705 B2 | 1/2018 | Bossard et al. |
| 9,889,211 B2 | 2/2018 | Lowman et al. |
| 10,059,762 B2 | 8/2018 | Stagliano et al. |
| 10,077,300 B2 | 9/2018 | Daugherty et al. |
| 10,100,106 B2 | 10/2018 | Dubridge et al. |
| 10,138,272 B2 | 11/2018 | Moore et al. |
| 10,179,817 B2 | 1/2019 | Sagert et al. |
| 10,233,244 B2 | 3/2019 | Sagert et al. |
| 10,261,083 B2 | 4/2019 | Vasiljeva et al. |
| 10,301,380 B2 | 5/2019 | West et al. |
| 10,513,549 B2 | 12/2019 | Stagliano et al. |
| 2002/0164328 A1 | 11/2002 | Shinkawa et al. |
| 2003/0106381 A1 | 6/2003 | Krouth et al. |
| 2003/0157108 A1 | 8/2003 | Presta et al. |
| 2003/0190311 A1 | 10/2003 | Dall'Acqua et al. |
| 2004/0014652 A1 | 1/2004 | Trouet et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110682 A1 | 6/2004 | Heidtmann et al. |
| 2004/0132140 A1 | 7/2004 | Satoh et al. |
| 2004/0136952 A1 | 7/2004 | Bhaskaran et al. |
| 2005/0014934 A1 | 1/2005 | Hinton et al. |
| 2006/0205926 A1 | 9/2006 | Ross et al. |
| 2006/0236411 A1 | 10/2006 | Dreher et al. |
| 2007/0048282 A1 | 3/2007 | Rosen et al. |
| 2007/0269422 A1 | 11/2007 | Beirnaert et al. |

| | | |
|---|---|---|
| 2010/0254944 A1 | 10/2010 | Subramanian et al. |
| 2011/0190209 A1 | 8/2011 | Culbertson et al. |
| 2013/0064788 A1 | 3/2013 | Barnes et al. |
| 2013/0089516 A1 | 4/2013 | Frelinger et al. |
| 2015/0079088 A1 | 3/2015 | Lowman et al. |
| 2015/0087810 A1 | 3/2015 | Moore et al. |
| 2015/0113676 A1 | 4/2015 | Abad et al. |
| 2016/0152686 A1 | 6/2016 | Camphausen et al. |
| 2016/0194399 A1 | 7/2016 | Irving et al. |
| 2016/0289324 A1 | 10/2016 | Moore et al. |
| 2016/0311903 A1 | 10/2016 | West et al. |
| 2016/0354472 A1 | 12/2016 | Merchant et al. |
| 2016/0355587 A1 | 12/2016 | West et al. |
| 2017/0044259 A1 | 2/2017 | Tipton et al. |
| 2017/0096472 A1 | 4/2017 | Rosen et al. |
| 2017/0240608 A1 | 8/2017 | Stagliano et al. |
| 2018/0016316 A1 | 1/2018 | Garcia et al. |
| 2018/0119128 A1 | 5/2018 | Metzner et al. |
| 2018/0134789 A1 | 5/2018 | Baeuerle et al. |
| 2018/0200346 A1 | 7/2018 | Ballance et al. |
| 2018/0303952 A1 | 10/2018 | Sagert et al. |
| 2018/0344810 A1 | 12/2018 | Addepali et al. |
| 2019/0008978 A1 | 1/2019 | Huang et al. |
| 2019/0016814 A1 | 1/2019 | Humphrey et al. |
| 2019/0117789 A1 | 4/2019 | Carman et al. |
| 2019/0135943 A1 | 5/2019 | Boustany et al. |
| 2019/0222296 A1 | 7/2019 | Khandani |
| 2019/0225702 A1 | 7/2019 | Baeuerle et al. |
| 2020/0040052 A1* | 2/2020 | Winston ................. C07K 14/55 |
| 2020/0123227 A1 | 4/2020 | Yang-Xin et al. |
| 2020/0207846 A1 | 7/2020 | Igawa et al. |
| 2021/0130430 A1 | 5/2021 | Winston et al. |

FOREIGN PATENT DOCUMENTS

| | | |
|---|---|---|
| EP | 547163 B1 | 2/2002 |
| EP | 1867660 A1 | 12/2007 |
| EP | 2639241 A2 | 9/2013 |
| EP | 3134102 A4 | 11/2017 |
| EP | 3792277 A1 | 3/2021 |
| WO | 198700195 | 1/1987 |
| WO | 199003430 | 4/1990 |
| WO | 199101743 | 2/1991 |
| WO | 199308829 | 5/1993 |
| WO | 199316185 | 8/1993 |
| WO | 199411026 | 5/1994 |
| WO | 199429351 | 12/1994 |
| WO | 1996027011 | 9/1996 |
| WO | 199730087 | 8/1997 |
| WO | 199858964 | 12/1998 |
| WO | 199922764 | 5/1999 |
| WO | 199951642 | 10/1999 |
| WO | 200061739 | 10/2000 |
| WO | 200130460 A1 | 5/2001 |
| WO | 2001079271 A1 | 10/2001 |
| WO | 2002022833 A1 | 3/2002 |
| WO | 200243478 | 6/2002 |
| WO | 2002055098 A2 | 7/2002 |
| WO | 2002076489 | 10/2002 |
| WO | 2003011878 | 2/2003 |
| WO | 200359934 A2 | 7/2003 |
| WO | 20030139575 A1 | 7/2003 |
| WO | 2003084570 | 10/2003 |
| WO | 2003085119 | 10/2003 |
| WO | 2003106381 A2 | 12/2003 |
| WO | 2004041865 | 5/2004 |
| WO | 2004056312 | 7/2004 |
| WO | 2005035586 | 4/2005 |
| WO | 2005035778 | 4/2005 |
| WO | 2005053742 | 6/2005 |
| WO | 20060166329 A1 | 7/2006 |
| WO | 2006110728 A1 | 10/2006 |
| WO | 2008147530 A1 | 12/2008 |
| WO | 2009025846 A2 | 2/2009 |
| WO | 2009103965 A1 | 8/2009 |
| WO | 2010020766 A2 | 2/2010 |
| WO | 2011011797 A2 | 1/2011 |
| WO | 2011123683 A2 | 10/2011 |
| WO | 2011124718 | 10/2011 |

(56)　　　　References Cited

FOREIGN PATENT DOCUMENTS

| WO | 2012059486 |  | 5/2012 |
| WO | 2013163631 | A2 | 10/2013 |
| WO | 2013177187 | A2 | 11/2013 |
| WO | 2014100014 | A1 | 6/2014 |
| WO | 2014120555 | A1 | 8/2014 |
| WO | 2015066279 | A2 | 5/2015 |
| WO | 2016200645 | A1 | 12/2016 |
| WO | 2017156178 | A1 | 9/2017 |
| WO | 2018071777 | A1 | 4/2018 |
| WO | 2018071918 |  | 4/2018 |
| WO | 2018136725 | A1 | 4/2018 |
| WO | 2018160754 | A2 | 9/2018 |
| WO | 2018160877 | A1 | 9/2018 |
| WO | 2018085555 | A1 | 11/2018 |
| WO | 2018204528 | A1 | 11/2018 |
| WO | 2018236701 | A1 | 12/2018 |
| WO | 2019014586 | A1 | 1/2019 |
| WO | 2019018828 | A1 | 1/2019 |
| WO | 2019036031 | A2 | 2/2019 |
| WO | 2019051122 | A2 | 3/2019 |
| WO | 2019094396 | A1 | 5/2019 |
| WO | 2019173832 | A2 | 9/2019 |
| WO | 2019214757 | A1 | 11/2019 |
| WO | 2019222294 | A1 | 11/2019 |
| WO | 2019222295 | A1 | 11/2019 |
| WO | 2020069398 | A1 | 4/2020 |
| WO | 2020232305 | A1 | 11/2020 |
| WO | 2020252264 | A1 | 12/2020 |
| WO | 2021016599 | A1 | 1/2021 |
| WO | 2021030483 | A1 | 2/2021 |
| WO | 2021062406 | A1 | 4/2021 |
| WO | 2021202673 | A1 | 7/2021 |
| WO | 2021202675 | A1 | 7/2021 |
| WO | 2021202678 | A1 | 10/2021 |

OTHER PUBLICATIONS

International Search Report and Written Opinion for International Application No. PCT/US2020/032988 mailed Sep. 24, 2020.
Xue et al, "A tumor-specific pro-IL-12 activates preexisting cytotoxic T cells to control established tumors" Science Immunology, vol. 7, Jan. 7, 2022, pp. 1-14.
Xue et al, "Supplementary Materials for A tumor-specific pro-IL-12 activates preexisting cytotoxic T cells to control established tumors" Science Immunology, vol. 7, (2022), pp. 1-26.
Arie et al. "Chaperone function of FkpA, a heat shock prolyl isomerase, in the periplasm of Escherichia coli,", Mol. Micro biol. 39:199-210 (2001).
Atwell et al., "Stable heterodimers from remodeling the domain interface of a homodimer using a phage display library," J. Mol. Biol., 270(1):26-35 (1997).
Bachmann, Cellular and Molecular Biology, vol. 2 (Washington, D.C.: American Society for Microbiology), pp. 1190-1219 (1987).
Barnes et al., "Methods for growth of cultured cells in serum-free medium," Anal. Biochem. 102:255 (1980).
Bass et al., "Hormone phage: an enrichment method for variant proteins with altered binding properties," Proteins, 8:309-314 (1990).
Bernett et al., "Potency-reduced IL 15/IL 15Ra heterodimeric Fe-fusions display enhanced in vivo activity through increased exposure," Xencor, AACR (2018) Abstract #5565.
Boerner et al., "Production of antigen-specific human monoclonal antibodies from in vitro-primed human splenocytes," J. Immunol., 147: 86 (1991).
Bothmann and Pluckthun. "Improving Expression of scFv Fragments by Coexpression of Periplasmic Chaperones," J. Biol. Chem. 275:17100-17105 (2000).
Brennan et al., "Preparation of bispecific antibodies by chemical recombination of monoclonal immunoglobulin G1 fragments," Science, 229:81 (1985).
Brodeur et al., Monoclonal Antibody Production Techniques and Applications, pp. 51-63 Marcel Dekker, Inc., New York, (1987).

Caescu et al., "Active site determinants of substrate recognition by the metalloproteinases TACE and ADAM10," Biochem. J., 424(1):79-88 (2010).
Carter et al., "High level Escherichia coli expression and production of a bivalent humanized antibody fragment," BiofTechnology 10: 163-167 (1992).
Carter et al., "Bispecific human IgG by design," J. Immunol. Methods, 248: 7-15 (2001).
Kratz et al., "Prodrugs of anthracyclines in cancer chemotherapy," Current Med. Chem. 13:477-523 (2006).
Chapman et al. "Therapeutic antibody fragments with prolonged in vivo half-lives," Nature Biotechnol., 17:780-783 (1999).
Chari et al., "Immunoconjugates containing novel maytansinoids: promising anticancer drugs," Cancer Res. 52:127-131 (1992).
Chen et al., "Chaperone activity of DsbC," J. Biol. Chem. 274:19601-19605 (1999).
Choe et al. , "Fe-Binding Ligands of Immunoglobulin G: An Overview of High Affinity Proteins and Peptides," Materials 9(12): 994 (2016).
Cunningham and Wells ,"High-resolution epitope mapping of hGH-receptor interactions by alanine-scanning mutagenesis," Science, 244:1081-1085 (1989).
Davies et al., "Antibody-antigen complexes," Annual Rev Biochem. 59:439-473, (1990).
Dennis et al., "Albumin binding as a general strategy for improving the pharmacokinetics of proteins," JBC 277(38): 35035-35043 (2002).
Dubowchik et al., "Doxorubicin Immunoconjugates Containing Bivalent, Lysosomally-Cleavable Dipeptide Linkages," Bioorg. & Med. Chem. Letters 12:1529-1532 (2002).
Duncan and Winter, "The binding site for C1q on IgG," Nature 322:738-40 (1988).
Damodaran, "Protein PEGylation: An overview of chemistry and process considerations," European Pharmaceutical Review, 15(1): 18-26 (2010).
Firan, M., et al., "The MHC class I-related receptor, FcRn, plays an essential role in the maternofetal transfer of y-globulin in humans," Int. Immunol. 13: 993-1002 (2001).
Fishwild, D. et al., "High-avidity human IgG kappa monoclonal antibodies from a novel strain of minilocus transgenic mice," Nature Biotechnology 14: 845-851 (1996).
Graham et al., "Characteristics of a human cell line transformed by DNA from human adenovirus type 5," J. Gen Virol. 36:59 (1977).
Gunasekaran et al., "Enhancing antibody Fe heterodimer formation through electrostatic steering effects: applications to bispecific molecules and monovalent IgG," J Biol Chem., 285(25): 19637-19646 (2010).
Guss et al., "Structure of the IgG-binding regions of streptococcal protein G.," EMBO J. 5:15671575 (1986).
Guyer et al., "Immunoglobulin Binding by Mouse Intestinal Epithelial Cell Receptors," J. Immunol. 117:587 (1976).
Ham et al., "Media and Growth Requirements," Meth. Enz. 58:44 (1979).
Hara et al., "Overproduction of Penicillin-Binding Protein 7 Suppresses Thermosensitive Growth Defect at Low Osmolarity due to an spr Mutation of Escherichia coli," Microbial Drug Resistance, 2:63-72 (1996).
Hinman et al., "Preparation and characterization of monoclonal antibody conjugates of the calicheamicins: a novel and potent family of antitumor antibiotics," Cancer Res. 53:3336-3342 (1993).
Hudson et al., "Engineered antibodies," Nat. Med., 9:129-134 (2003).
Idusogie et al., "Mapping of the C1q Binding Site on Rituxan, a Chimeric Antibody with a Human IgG1 Fe," J. Immunol., 164:4178-4184, (2000).
Imai-Nishiya et al., "Double knockdown of a1 ,6-fucosyltransferase (FUT8) and GDP-mannose 4,6-dehydratase (GMD) in antibody-producing cells: a new strategy for generating fully non-fucosylated therapeutic antibodies with enhanced ADCC," BMC Biotechnol., 7:84, 13 pages (2007).
Jefferis et al., "Human immunoglobulin allotypes: Possible implications for immunogenicity," mAbs, 1 (4):332-8 (2009).

(56) References Cited

OTHER PUBLICATIONS

Jeffrey et al., "Dipeptide-based highly potent doxorubicin antibody conjugates," Bioorganic & Med. Chem. Letters, 16:358-362 (2006).
Jones et al., "Replacing the complementarity-determining regions in a human antibody with those from a mouse," Nature, 321 :522-525 (1986).
Kim et al., "Localization of the site of the murine lgG1 molecule that is involved in binding to the murine intestinal Fe receptor," European Journal of Immunology, 24:2429-2434 (1994).
King et al., "Monoclonal Antibody Conjugates of Doxorubicin Prepared with Branched Peptide Linkers: Inhibition of Aggregation by Methoxytriethyleneglycol Chains," J. Med. Chem., 45:4336-4343 (2002).
Klein et al., "Progress in overcoming the chain association issue in bispecific heterodimeric lgG antibodies," MAbs, 4(6):653-663 (2012).
Kontermann et al., "Bispecific antibodies," Drug Discovery Today, 20(7) :838-84 7 (2015).
Kozbor et al., "A human hybrid myeloma for production of human monoclonal antibodies," J. Immunol., 133:3001-5 (1984).
Shields et al., "Lack of fucose on human lgG1 N-linked oligosaccharide improves binding to human Fcgamma Rlii and antibody-dependent cellular toxicity," J. Biol. Chem., 277(30):26733-40 (2002).
Lehninger, in Biochemistry, second ed., pp. 73-75, Worth Publishers, New York (1975).
Lindmark et al., "Binding of immunoglobulins to protein A and immunoglobulin levels in mammalian sera," J. Immunol. Meth., 62:1-13 (1983).
Lode et al., "Targeted Therapy with a Novel Enediyene Antibiotic Calicheamicin-al 1 Effectively Suppresses Growth and Dissemination of Liver Metastases in a Syngeneic Model of Murine Neuroblastoma," Cancer Res., 58:2925-2928 (1998).
Lonberg, et al., "Antigen-specific human antibodies from mice comprising four distinct genetic modifications," Nature 368:856-859 (1994).
Mather et al., "Culture of testicular cells in hormone-supplemented serum-free medium," Annals N.Y. Acad. Sci., 383:44-68 (1982).
Mather, "Establishment and characterization of two distinct mouse testicular epithelial cell lines," Biol. Reprod. 23:243-251 (1980).
Merchant et al., "An efficient route to human bispecific lgG," Nat. Biotechnol., 16(7):677-681 (1998).
Milstein et al.,. "Hybrid hybridomas and their use in immunohistochemistry," Nature, 305:537 (1983).
Moore et al., "A novel bispecific antibody format enables simultaneous bivalent and monovalent co-engagement of distinct target antigens," MAbs., 3(6): 546-557 (2011).
Mori et al., "Engineering Chinese hamster ovary cells to maximize effector function of produced antibodies using FUT8 siRNA," Biotechnol. Bioeng. 88(7):901-908 (2004).
Morimoto et al., "Single-step purification of F(ab12 fragments of mouse monoclonal antibodies (immunoglobulins G1) by hydrophobic interaction high performance liquid chromatography using TSKgel Phenyl-5PW," Journal of Biochemical and Biophysical Methods, 24:107-117 (1992).
Nagy et al., "Stability of cytotoxic luteinizing hormone-releasing hormone conjugate (AN-152) containing doxorubicin 14-O-hemiglutarate in mouse and human serum in vitro: Implications for the design of preclinical studies," Proc. Natl. Acad. Sci. USA, 97:829-834 (2000).
Nilvebrant et al., "The albumin-binding domain as a scaffold for protein engineering," Comput. Struct. Biotechol. J., 6:e201303009, 8 pages (2013).
Keunok Jung et al., "Heterodimeric Fc-fused IL12 shows potent antitumor activity by generating memory CD8+ T cells", Oncoimmunology, vol. 7, No. 7, Mar. 6, 2018, pp. e1438800, XP055653232.
Nygren et al., "Analysis and use of the serum albumin binding domains of streptococcal protein G," J. Mal. Recogn., 1 (2):69-74 (1988).

Okazaki et al., "Fucose depletion from human lgG1 oligosaccharide enhances binding enthalpy and association rate between lgG1 and FcgammaRllla," J. Mal. Biol., 336:1239-1249 (2004).
Omasa et al., "Decrease in antithrombin III fucosylation by expressing GDP-fucose transporter siRNA in Chinese hamster ovary cells," J. Biosci. Bioeng., 106(2):168-173 (2008).
Podust et al., "Extension of in vivo half-life of biologically active molecules by XTEN protein polymers," J. Controlled Release, 240:52-66 (2016).
Proba et al., "Functional antibody single-chain fragments from the cytoplasm of Escherichia coli: influence of thioredoxin reductase (TrxB)," Gene, 159:203-7 (1995).
Puskas et al., "Development of an attenuated interleukin-2 fusion protein that can be activated by tumour-expressed proteases," Immunology, Mar. 23, 2011 (Mar. 23, 2011), vol. 133, pp. 206-220.
Ramm et al., "The periplasmic Escherichia coli peptidylprolyl cis, trans-isomerase FkpA II. Isomerase-independent chaperone activity in vitro," J. Biol. Chem., 275:17106-17113 (2000).
Reyes et al., "Expression of human 13-interferon cDNA under the control of a thymidine kinase promoter from herpes simplex virus," Nature, 297:598-601 (1982).
Riechmann et al., "Reshaping human antibodies for therapy," Nature, 332:323-327 (1988).
Ridgway et al., "Knobs-into-holes' engineering of antibody CH3 domains for heavy chain heterodimerization," Protein Eng., 9(7):617-621 (1996).
Ripka et al., "Two chinese hamster ovary glycosylation mutants affected in the conversion of GDP-man nose to GDP-fucose," Arch. Biochem. Biophys., 249:533-545 (1986).
Roux et al., "Comparisons of the ability of human lgG3 hinge mutants, IgM, IgE, and IgA2, to form small immune complexes: a role for flexibility and geometry," J Immunol, 161 :4083-90 (1998).
Sali et al. "Characterization of a Novel Human-Specific STING Agonist that Elicits Antiviral Activity Against Emerging Alphaviruses," PloS Pathog., 11(12):e1005324, 30 pages (2015).
Schlapschy et al., "PASylation: a biological alternative to PEGylation for extending the plasma half-life of pharmaceutically active proteins," Protein Eng. Des. Sel., 26(8):489-501 (2013).
Shields et al., "High resolution mapping of the binding site on human lgG1 for Fe gamma RI, Fe gamma RII, Fe gamma Rlii, and FcRn and design of lgG1 variants with improved binding to the Fe gamma R," J. Biol. Chem., 276:6591-6604 (2001).
Shinkawa et al., The absence of fucose but not the presence of galactose or bisecting N-acetylglucosamine of human lgG1 complex-type oligosaccharides shows the critical role of enhancing antibody-dependent cellular cytotoxicity, J. Biol. Chem., 278(5):3466-73 (2003).
Simmons et al., "Expression of full-length immunoglobulins in Escherichia coli: rapid and efficient production of aglycosylated antibodies," J. Immunol. Methods, 263:133-147 (2002).
Sola et al., "Modulation of protein biophysical properties by chemical glycosylation: biochemical insights and biomedical implications," Cell. Mol. Life Sci., 64(16):2133-2152 (2007).
Sola et al., "Effects of Glycosylation on the Stability of Protein Pharmaceuticals," J. Pharm. Sci., 98(4):1223-1245 (2009).
Sties et al. (eds), Basic and Clinical Immunology, 8th Edition, Appleton & Lange, Nmwalk, CT, p. 71 and Chapter 6 (1994).
Suresh et al., "Bispecific monoclonal antibodies from hybrid hybridomas," Methods in Enzymology, 121:210-228 (1986).
Tomizuka et al., "Double trans-chromosomic mice: Maintenance of two individual human chromosome fragments containing lg heavy and K loci and expression of fully human antibodies," Proc. Natl. Acad. Sci. USA, 97:722-727 (2000).
Torgov et al., "Generation of an Intensely Potent Anthracycline by a Monoclonal Antibody-[3-Galactosidase Conjugate," Bioconj. Chem., 16:717-721 (2005).
Traunecker et al., "Bispecific single chain molecules (Janusins) target cytotoxic lymphocytes on HIV infected cells," EMBO J., 10:3655-365 (1991).
Urlaub et al., "Isolation of Chinese hamster cell mutants deficient in dihydrofolate reductase activity," Proc. Natl. Acad. Sci. USA, 77:4216-4220 (1980).

(56)                    References Cited

OTHER PUBLICATIONS

Verhoeven et al., "Reshaping human antibodies: grafting an antilysozyme activity," Science, 239:1534-1536. (1988).

Vitetta et al., "Redesigning nature's poisons to create anti-tumor reagents," Science, 238:1098-1104 (1987).

Yamane-Ohnuki et al., "Establishment of FUT8 knockout Chinese hamster ovary cells: an ideal host cell line for producing completely defucosylated antibodies with enhanced antibody-dependent cellular cytotoxicity," Biotech. Bioeng., 87:614-22 (2004).

Yamane-Ohnuki et al., "Production of therapeutic antibodies with controlled fucosylation," MAbs, 1 (3):230-236 (2009).

Yaniv, "Enhancing elements for activation of eukaryotic promoters," Nature 297:17-18 (1982).

Yeung et al., "Engineering Human lgG1 Affinity to Human Neonatal Fe Receptor: Impact of Affinity Improvement on Pharmacokinetics in Primates," J. Immunol., 182:7667-7671 (2009).

Zapata et al., "Engineering linear F(ab')2 fragments for efficient production in *Escherichia coli* and enhanced antiproliferative activity," Protein Eng., 8(10):1057-1062 (1995).

Skrombolas, et al. "Development of Protease Activated Interleukin-12 Cytokine Fusion Proteins for Tumor Immunotherapy (TUM7P.946)," The Journal of Immunology; 203:28, 192 (1 Supplement) (2014).

Skrombolas, etl al. "Development of an Interleukin-12 Fusion Protein That Is Activated by Cleavage with Matrix Metalloproteinase 9," Journal of Interferon & Cytokine Research, 39(4):233-245 (2019).

Polu et al., Probody therapeutics for targeting antibodies to diseased tissue, May 20, 2014, Expert Opinion on Biological Therapy, 1049-1053, vol. 14, Issue 8, Taylor & Francis Online.

Kato et al., (2003), The Structure and Binding Mode of Interleukin-18, Nature Structural Biology, vol. 10, No. 11, pp. 966-971.

Adusumilli et al., New Cancer Immunotherapy Agents in Development: a report from an associated program of the 31stAnnual Meeting of the Society for Immunotherapy of Cancer, 2016, J Immunother Cancer, Jun. 20, 2017, 1-9, vol. 5, Issue 50, BioMed Central, USA.

Afonina et al., Proteolytic Processing of Interleukin-1 Family Cytokines: Variations on a Common Theme, Immunity Review16 Jun. 2015, 991-1004, vol. 42, Issue 6, Elsevier, USA.

Agard et al. et al., Methods for the proteomic identification of protease substrates, Curr Opin Chem Biol., Dec. 2009, 503-509, vol. 12, Issue 5-6, Elsevier, USA.

Berger et al "An Operational definition of epigenetics." Genes Dev 2009; 23: 781-783.

Berger et al "Safety and immunologic effects of IL-15 administration in nonhuman primates." Blood 2009; 114(12): 2417-2426.

Bessard et al High antitumor activity of RLI, an interleukin-15 (IL-15)-IL-15 receptor alpha fusion protein, in metastatic melanoma and colorectal cancer. Mol Cancer Ther 2009; 8(9): 2736-2745.

Boulware et al., Protease specificity determination by using cellular libraries of peptide substrates (CLiPS), PNAS, May 16, 2006, 7583-7588, vol. 103, Issue 20, National Academy of Sciences, USA.

Boulware et al., Evolutionary optimization of peptide substrates for proteases that exhibit rapid hydrolysis kinetics, Biotechnol Bioeng., Jun. 15, 2010, 339-46, vol. 106, Issue 3, Wiley, USA.

Cao,et al., "Next generation of tumor-activating type I Ifn enhances anti-tumor immune responses to overcome therapy resistance", Nature Communications, 12:5866, pp. 1-11 (2021).

Conlon et al "Redistribution, hyperproliferation, activation of natural killer cells and CD8 T cells, and cytokine production during first-in-human clinical trial of recombinant human interleukin-15 in patients with cancer." J Clin Oncol 2015; 33(1): 74-82.

Darragh et al., Specific targeting of proteolytic activity for tumor detection in vivo, Cancer Res., Feb. 15, 2010, 1505-1512, vol. 70, Issue 5, AACR, USA.

De Luca et al., Potency-matched Dual Cytokine-Antibody Fusion Proteins for Cancer Therapy. Mol Cancer Ther, Nov. 2017, 2442-2451, vol. 16, Issue 11, AACR, USA.

Declerck et al., Proteases, extracellular matrix, and cancer: a workshop of the path B study section, Am J Pathol., Apr. 2004, 1131-1139, vol. 164, Issue 4, Elsevier, USA.

Deluca et al., Potentiation of PD-L1 blockade with a potency-matched dual cytokine-antibody fusion protein leads to cancer eradication in BALB/c-derived tumors but not in other mouse strains, Cancer Immunol Immunother, Sep. 6, 2018, 1381-1391, vol. 67, Issue 9, Springer.

Denise Skrombolas et al., Challenges and developing solutions for increasing the benefits of IL-2 treatment in tumor therapy, Expert Review of Clinical Immunology, vol. 10, No. 2, Feb. 1, 2014, pp. 207-217.

Desbois et al IL-15 Trans-signaling with the superagonist RLI Promotes Effector/Memory CD8+ T cell responses and enhances antitumor activity of PD-1 antagonists. 2016 J Immunol 1-11.

Desnoyers et al., Tumor-Specific Activation of an EGFR-Targeting Probody Enhances Therapeutic Index, Science Translational Medicine, Oct. 16, 2013, , vol. 5, Issue 207, American Association for the Advancement of Science, USA.

Drag et al., Emerging principles in protease-based drug discovery, Nat Rev Drug Discov., Nov. 5, 2010, 690-701, vol. 9, Issue 9, Springer Nature, USA.

Erster et al., Site-specific targeting of antibody activity in vivo mediated by disease-associated proteases, Journal of Controlled Release, Aug. 10, 2012, 804-812, vol. 161, Issue 3, Elsevier, USA.

Fercher et al., Evolution of the magic bullet: Single chain antibody fragments for the targeted delivery of immunomodulatory proteins, Exp Biol Med, Jan. 2018, 166-183, vol. 243, Issue 2, Sage Journals.

Gao et al "High-throughput screening using patient-derived tumor xenografts to predict clinical trial drug response." Nature Medicine 2015; 21(11): 1318-1325.

Geletu et al., Effect of Caveolin-1 upon Stat3-ptyr705 levels in breast and lung carcinoma cells., Biochem Cell Biol., Apr. 15, 2019, 1-19, Canadian Science Publishing.

Gerber et al Preferential attachment of peritoneal tumor metastases to omental immune aggregates and possible role of a unique vascular microenvironment in metastatic survival and growth. Am J Pathol 169(5): 1739-1752.

Gillies, et al "Improved circulating half-life and efficacy of an antibody-interleukin 2 immunocytokine based on reduced intracellular proteolysis" Clinical Cancer Research, the American Association for Cancer Research, US, 8(1) Jan. 2002, 210-216.

Giesen et al., 8O89Zr-labeled anti-PD-L1 CX-072 PET imaging in human xenograft and syngeneic tumors, Annals of Oncology, Feb. 27, 2019, vol. 30, Issue Supplement 1, Oxford Academic.

Halin et al., Synergistic Therapeutic Effects of a Tumor Targeting Antibody Fragment, Fused to Interleukin 12 and to Tumor Necrosis Factor α, Cancer Research, Jun. 2003, 3202-3210, vol. 63, Issue 12, AACR, USA.

Helguera, et al "Antibody-Cytokine fusion proteins: Harnessing the combined power of cytokines and antibodies for cancer therapy" Clinical immunology 105 (3) Dec. 2002, 233-246.

Hemar et al "Endocytosis of Interleukin 2 receptors in human T lymphocytes: distinct intracellular localization and fate of the receptor alpha, beta, and gamma chains." J. Cell Biol. 1995; 129(1): 55-64.

Hoos et al., CCR 20th Anniversary Commentary: Immune-Related Response Criteria—Capturing Clinical Activity in Immuno-Oncology, Clin Cancer Res. Nov. 15, 2015, 4989-4991, vol. 21, Issue 22, American Association of Cancer Research, USA.

Irving et al., A Clue to Antigen Receptor Tails, J Immunol, May 1, 2014, 4013-4014, vol. 192, Issue 9, The American Association of Immunologists, Inc., USA.

Jabaiah et al., Identification of protease exosite-interacting peptides that enhance substrate cleavage kinetics, Biol Chem., Sep. 2012, 933-941, vol. 393, Issue 9, ASBMB Publications, USA.

Jana et al."Interleukin-12 (IL-12), but not IL-23, induces the expression of IL-7 in microglia and macrophages: implications for multiple sclerosis." Immunology 2013; 141: 549-563.

Puskas et al., Development of an attenuated interleukin-2 fusion protein that can be activated by tumour-expressed proteases, Jun. 23, 2011, Immunology, vol. 133, No. 2, pp. 206-220.

(56) References Cited

OTHER PUBLICATIONS

Kaspar et al., The antibody-mediated targeted delivery of interleukin-15 and GM-CSF to the tumor neovasculature inhibits tumor growth and metastasis, Cancer Res, May 15, 2007, 4940-4098, vol. 67 Issue 10, AACR. USA.

Kim et al., Novel immunocytokine IL12-SS1 (Fv) inhibits mesothelioma tumor growth in nude mice, PLoS One, Nov. 15, 2013, 1-11, vol. 8, Issue 11, PLOS.

Klatzmann, D and Abbas, A.K. "The promise of low-dose interleukin-2 therapy for autoimmune and inflammatory diseases." Nat. Rev. Immunol. 2015; 15: 283-294.

Koreth et al "Interleukin-2 and Regulatory T Cells in Graft-versus-host disease." N. Engl. J. Med. 2011; 365(22): 2055-2066.

Lasek et al "Interleukin 12: still a promising candidate for tumor immunotherapy?" Cancer Immunol Immunother (2014) 63:419-435.

Lebeau et al., Imaging a functional tumorigenic biomarker in the transformed epithelium, PNAS, Jan. 2, 2013, 93-98, vol. 110, Issue 1, National Academy of Sciences, USA.

Lebeau et al., Imaging Active Urokinase Plasminogen Activator in Prostate Cancer, Cancer Res, 1225-1235, vol. 75, Issue 7, AACR, USA (2015).

Lin et al., Targeting Drug Conjugates to the Tumor Microenvironment: Probody Drug Conjugates, Innovations for Next-Generation Antibody-Drug Conjugates, 2018, 281-298, Humana Press, USA.

Malek, T.R. and Castro, I. Interleukin-2 receptor signaling: at the interface between tolerance and immunity. Immunity 2010 33(2): 153-165.

Manuale L. Penichet, "Antibody-cytokine fusion proteins for the therapy of cancer", Immunology, 2001, pp. 91-101.

Marks-Konczalik et al "IL-2-induced cell death is inhibited in IL-15 transgenic mice." PNAS 2000; 97(21): 11445-11450.

Mitsiades et al., Matrix Metalloproteinase-7-mediated Cleavage of Fas Ligand Protects Tumor Cells from Chemotherapeutic Drug Cytotoxicity, Cancer Research, Jan. 15, 2001, 577-581, vol. 61, AACR, USA.

Montepaone et al "Profile of ustekinumab and its potential in the treatment of active psoriatic arthritis" Open Access Rheumatol. 2014; 6: 7-13.

Oh et al "IL-15 as a mediator of CD4+ help for CD8+ T cell longevity and avoidance of TRAIL-mediated apoptosis." PNAS 2008; 105(13): 5201-5206.

Osorio et al., Understanding and quantifying the immune microenvironment in hepatocellular carcinoma, Transl Gastroenterol Hepatol. Dec. 24, 2018, 3:107, AME Publishing Company.

Pandya et al., PKCα Attenuates Jagged-1-Mediated Notch Signaling in ErbB-2-Positive Breast Cancer to Reverse Trastuzumab Resistance, Clin Cancer Res, 175-186, Jan. 1, 2016, vol. 22 Issue 1, AACR, USA.

Pedretti et al, Combination of temozolomide with immunocytokine F16-IL2 for the treatment of glioblastoma, Br J Cancer, Sep. 7, 2010, 827-836, vol. 103, Issue 6, SpringerNature, UK.

Rice et al., Bacterial display using circularly permuted outer membrane protein OmpX yields high affinity peptide ligands, Protein Sci., 825-836, Apr. 2006, vol. 15, Issue 4, Wiley.

Rochman et al. "New insights into the regulation of T cells by gamma-c family cytokines." Nat Rev Immunol 2009; 9 (7): 480.

Rodrigo Vazquez-Lombardi et al., Molecular Engineering of Therapeutic Cytokines, Antibodies, vol. 2 No. 3, Jul. 3, 2013, pp. 426-451.

Saadoun, et al. "Regulatory T-Cell Responses to Low-Dose Interleukin-2 in HCV-Induced Vasculitis." N. Engl. J. Med. 2011; 365(22): 2067-2077.

Zavrsnik et al., Cystatin C deficiency suppresses tumor growth in a breast cancer model through decreased proliferation of tumor cells, Oncotarget, Apr. 24, 2017, 73793-73809, vol. 8, Issue 43, Impact Journals, LLC.

Sadlack et al "Ulcerative colitis-like disease in mice with a disrupted interleukin 2 gene." Cell 1993; 75: 253-261.

Germa N L. Rosano et al., "Recombinant protein expression in *Escherichia coli*: advances and challenges", Frontiers in Microbiology, vol. 5, Apr. 17, 2014 (Apr. 17, 2014), XP055474138.

Xiaoying Chen, et al., "Fusion protein linkers: Property, design and functionality", Advanced Drug Delivery Reviews, (2012), XP055062583, ISSN: 0169-409X, DOI: 10.1016/j.addr.2012.09.039.

Smith, T.F. and Waterman, M.S. "Comparison of biosequences." Advances in applied mathermatics 1981; 2: 482-489.

Suzuki et al. "Deregulated T cell activation and autoimmunity in Mice lacking interleukin-2 Receptor Beta." Science 1995; 268: 1472-1476.

Trinchieri et al "The IL-2 family of heterodimeric cytokines: new players in the regulation of T cell responses." Immunity 2003; 19: 641-644.

Uhland, Matriptase and its putative role in cancer, Cell Mol Life Sci., Dec. 2006, 2968-2978, vol. 63, Issue 24.

Ulisse et al., The urokinase plasminogen activator system: a target for anti-cancer therapy, Curr Cancer Drug Targets, Feb. 2009, 32-71, vol. 9, Issue 1, Bentham Science.

Vartak et al. Matrix metalloproteases: underutilized targets for drug delivery, J Drug Target, Jan. 2007, 1-20, vol. 15, Issue 1.

Vasiljeva et al., The multifaceted roles of tumor-associated proteases and harnessing their activity for prodrug activation, Biological Chemistry, Apr. 22, 2019, Walter de Gruyter GmbH, (abstract only).

Wang et al Structure of the Quaternary Complex of Interleukin-2 with its alpha, beta, and gamma-c receptors. Science Nov. 18, 2005 vol. 310, 1159-1163.

Willerford, et al "Interleukin-2 receptor alpha chain regulates the size and content of the peripheral lymphoid compartment." Immunity 1995; 3: 521-530.

William R. Strohl, Fusion Proteins for Half-Life Extension of Biologics as a Strategy to Make Biobetters, Biodrugs, vol. 29, No. 4, Jul. 16, 2015, pp. 215-239.

Wong et al., In vivo imaging of protease activity by Probody therapeutic activation, Biochimie, Nov. 4, 2015, 62-67, vol. 122, Elsevier, USA.

Yu, A and Malek, T.R. "The Proteosome regulates receptor-mediated endocytosis of interleukin-2" The Journal of Biological Chemistry 2001; 276(1): 381-385.

Zhao et al., FGFR1β is a driver isoform of FGFR1 alternative splicing in breast cancer cells, Oncotarget, Jan. 1, 2019, 30-44, vol. 10, Issue 1, Impact Journals, LLC.

* cited by examiner

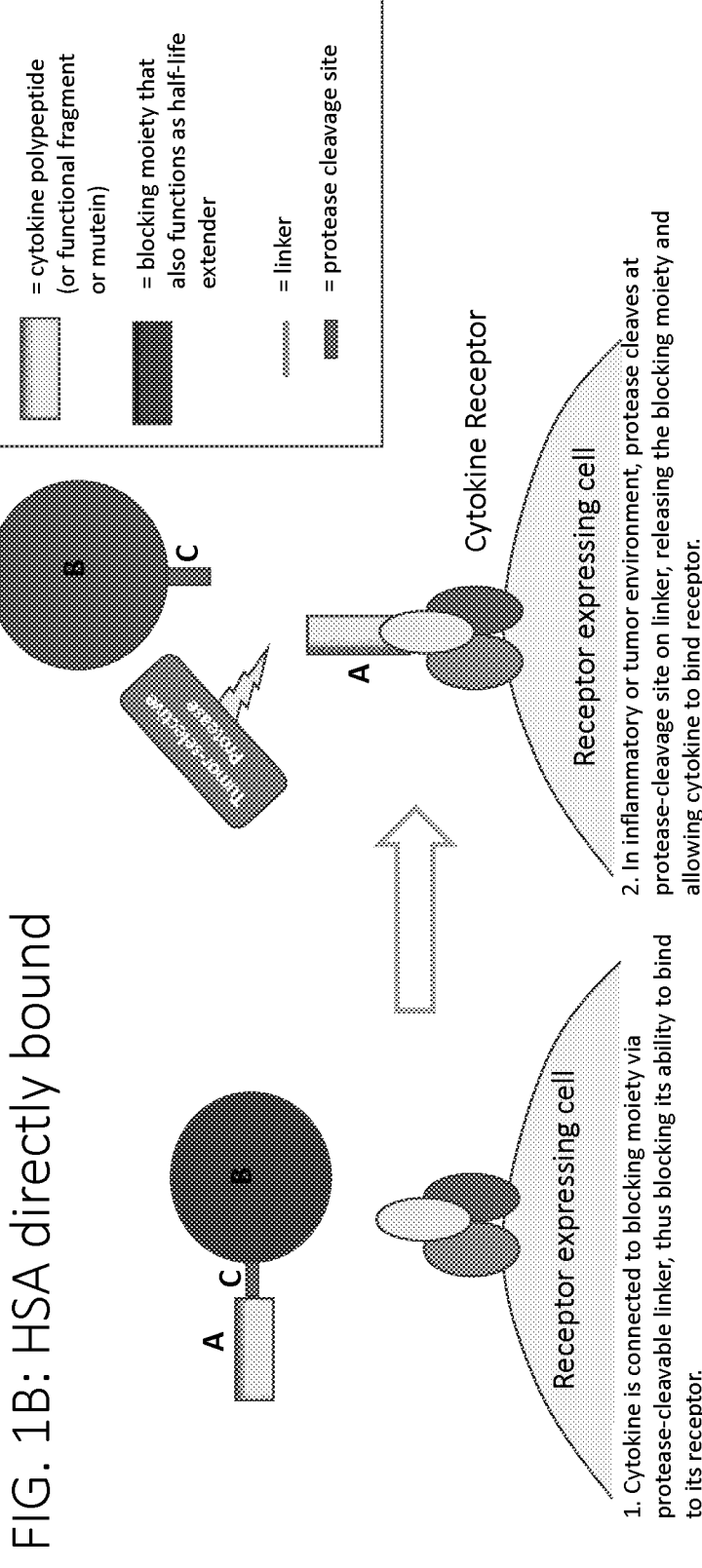

FIG. 1B: HSA directly bound

= cytokine polypeptide (or functional fragment or mutein)

= blocking moiety that also functions as half-life extender

= linker

= protease cleavage site

Cytokine Receptor

Receptor expressing cell

1. Cytokine is connected to blocking moiety via protease-cleavable linker, thus blocking its ability to bind to its receptor.

Receptor expressing cell

2. In inflammatory or tumor environment, protease cleaves at protease-cleavage site on linker, releasing the blocking moiety and allowing cytokine to bind receptor.

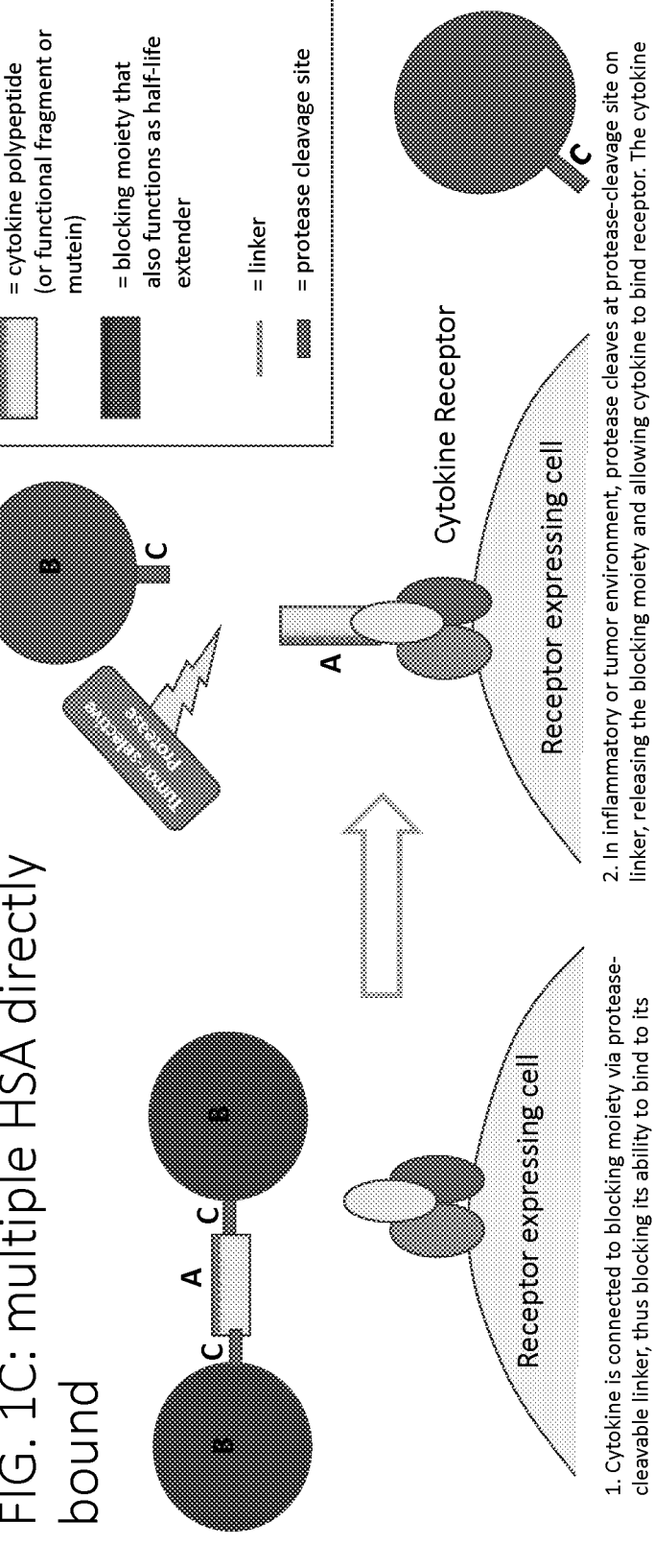
FIG. 1C: multiple HSA directly bound

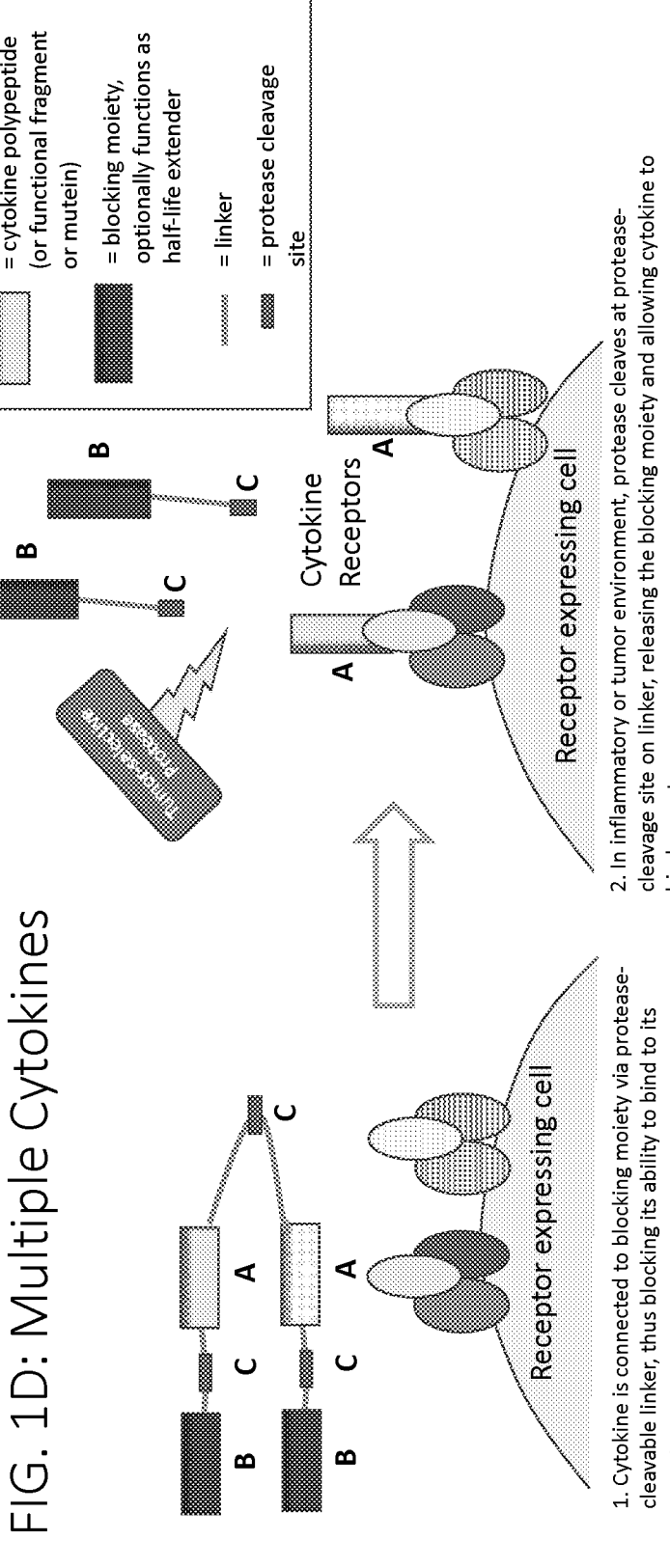
FIG. 1D: Multiple Cytokines

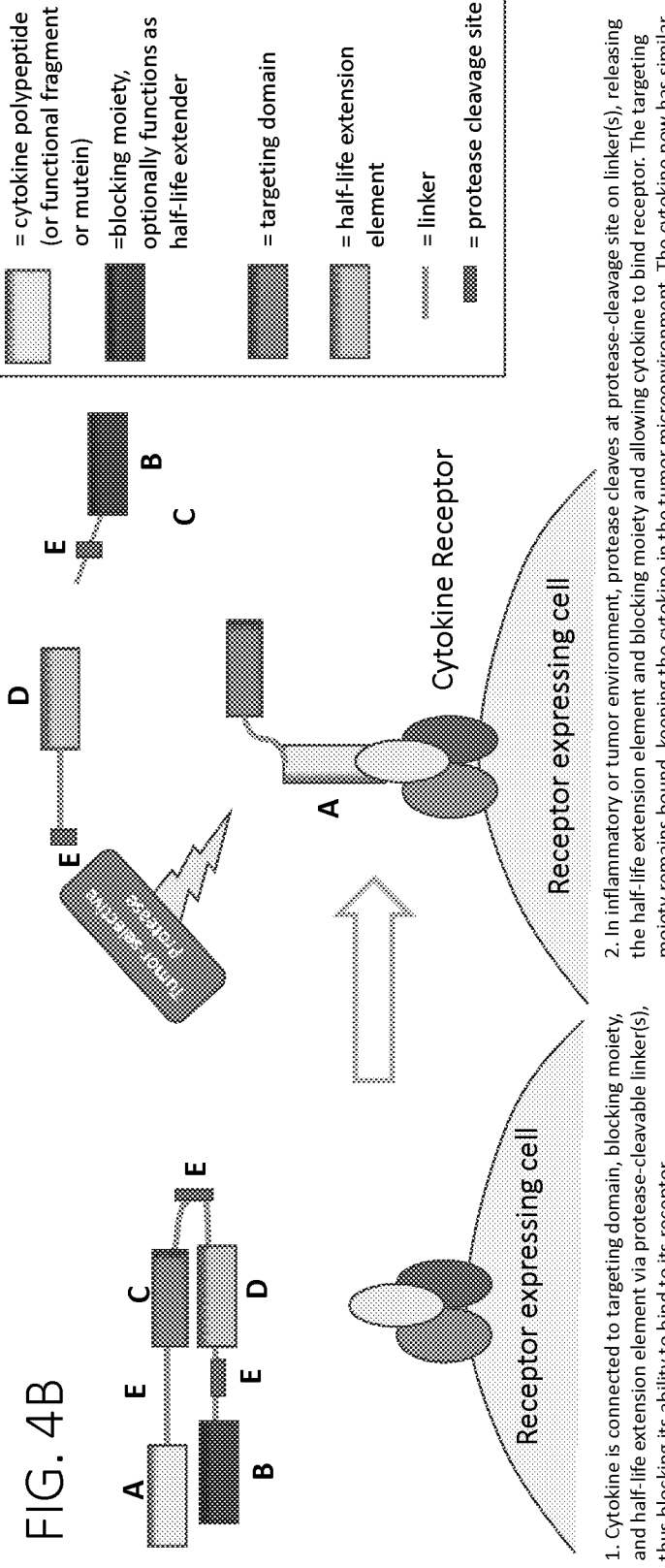

FIG. 4B

Legend:
= cytokine polypeptide (or functional fragment or mutein)

=blocking moiety, optionally functions as half-life extender

= targeting domain

= half-life extension element

= linker

= protease cleavage site

Receptor expressing cell

Cytokine Receptor

Receptor expressing cell

1. Cytokine is connected to targeting domain, blocking moiety, and half-life extension element via protease-cleavable linker(s), thus blocking its ability to bind to its receptor.

2. In inflammatory or tumor environment, protease cleaves at protease-cleavage site on linker(s), releasing the half-life extension element and blocking moiety and allowing cytokine to bind receptor. The targeting moiety remains bound, keeping the cytokine in the tumor microenvironment. The cytokine now has similar pK properties as compared to the native cytokine (e.g. short half-life).

Place hold

FIG. 6

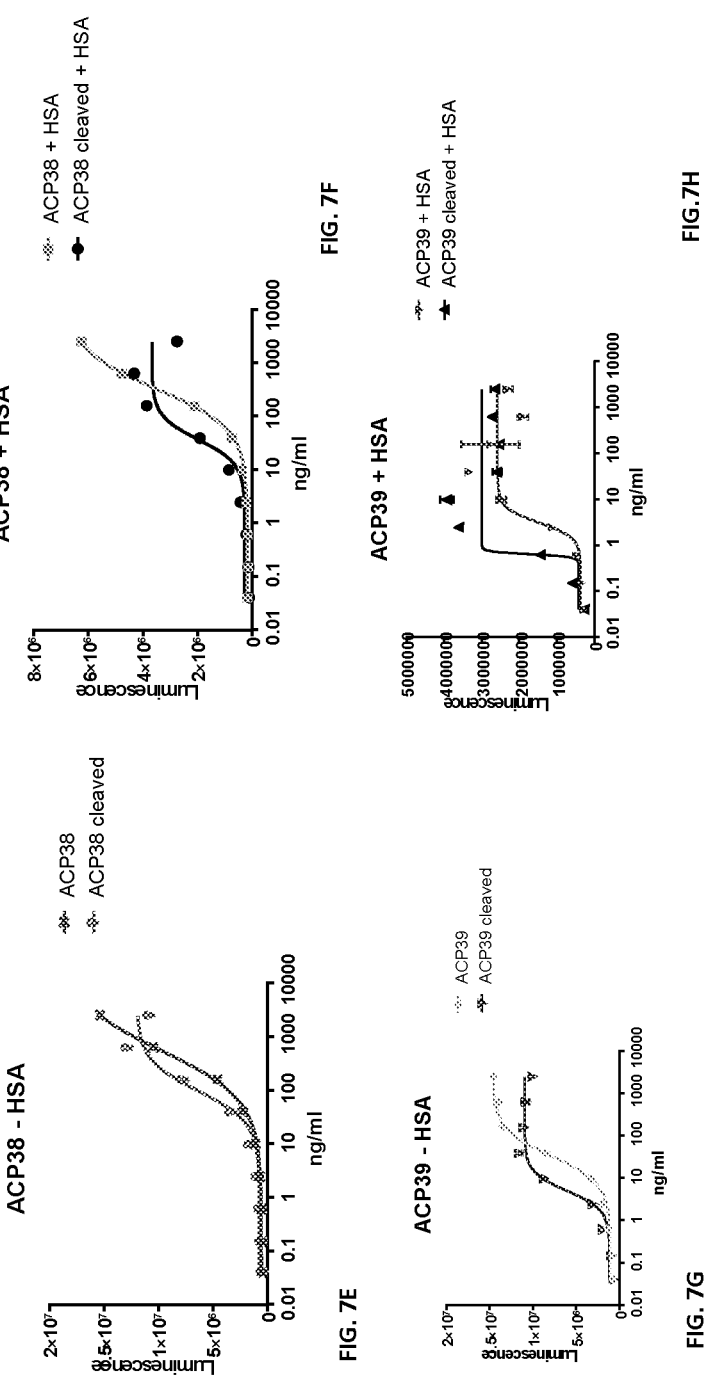

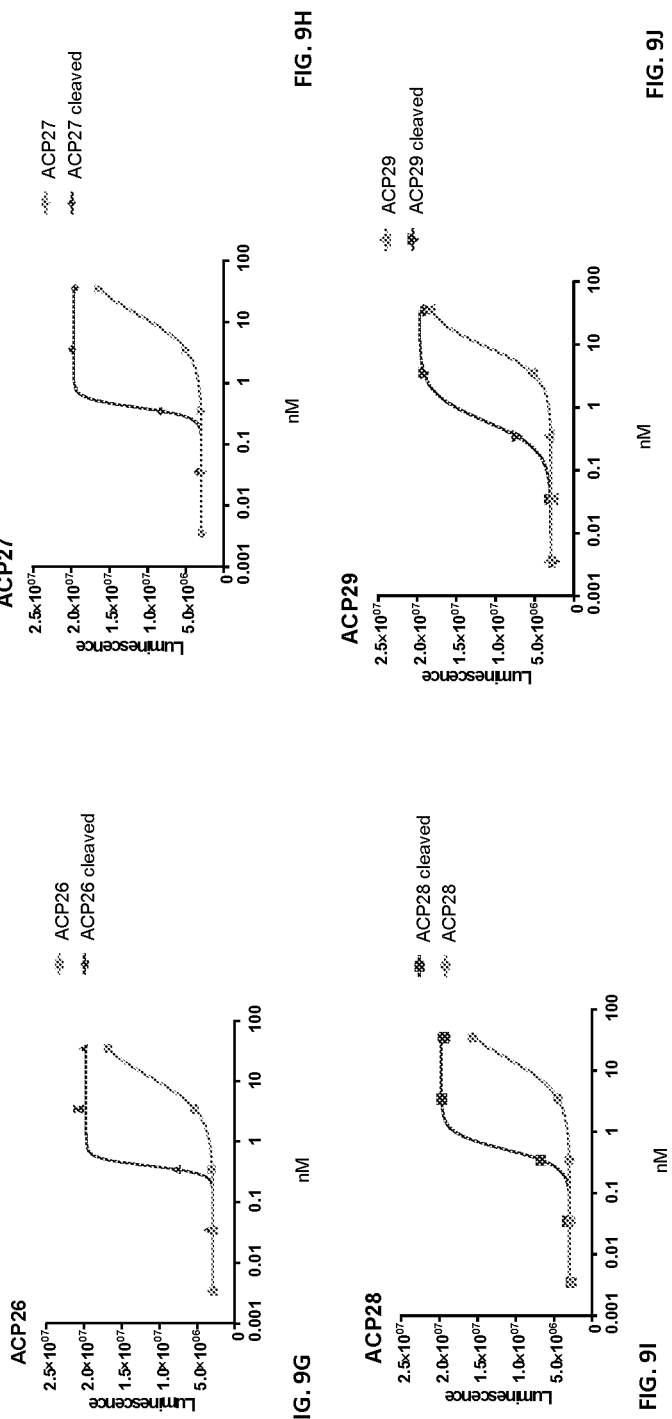

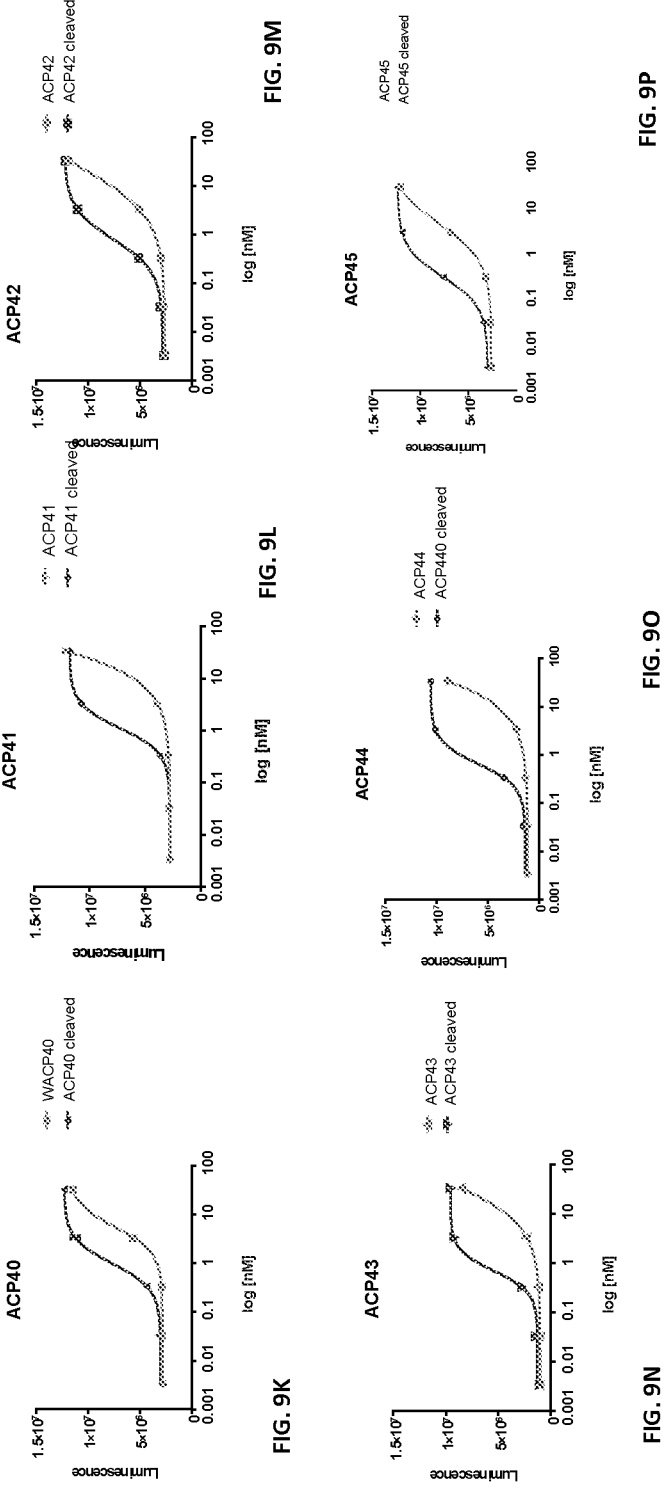

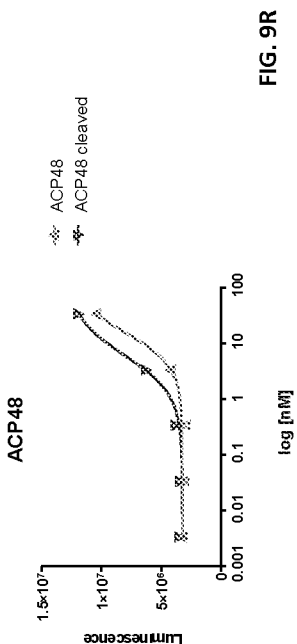
FIG. 9R
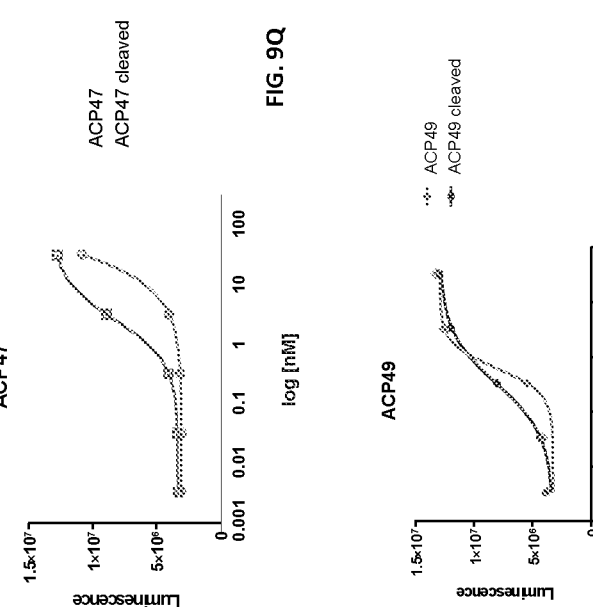
FIG. 9Q
FIG. 9S

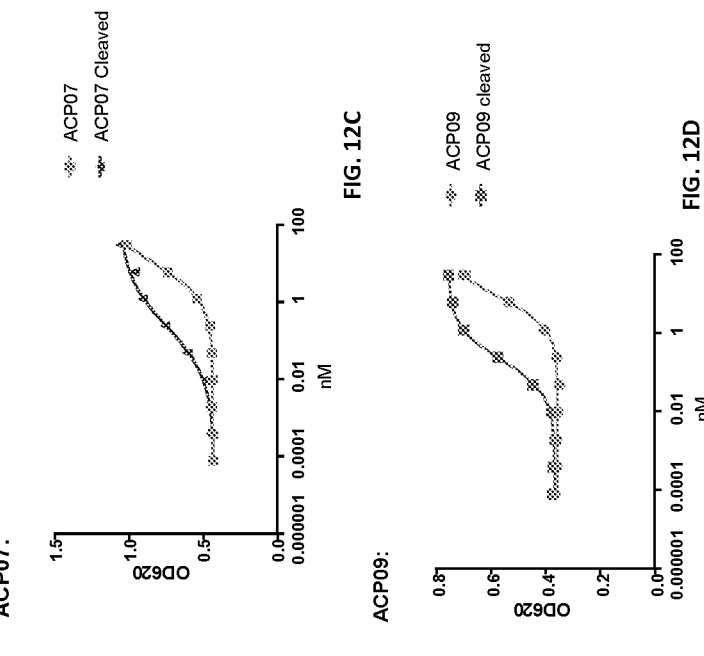
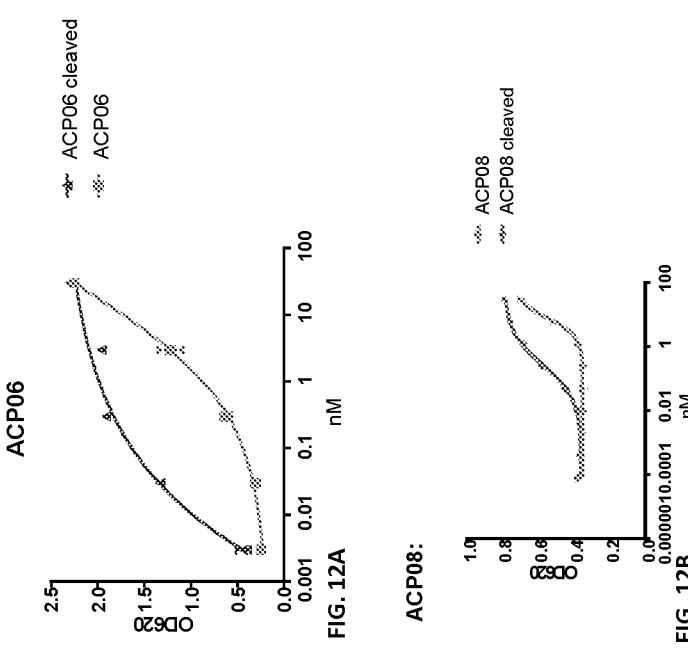

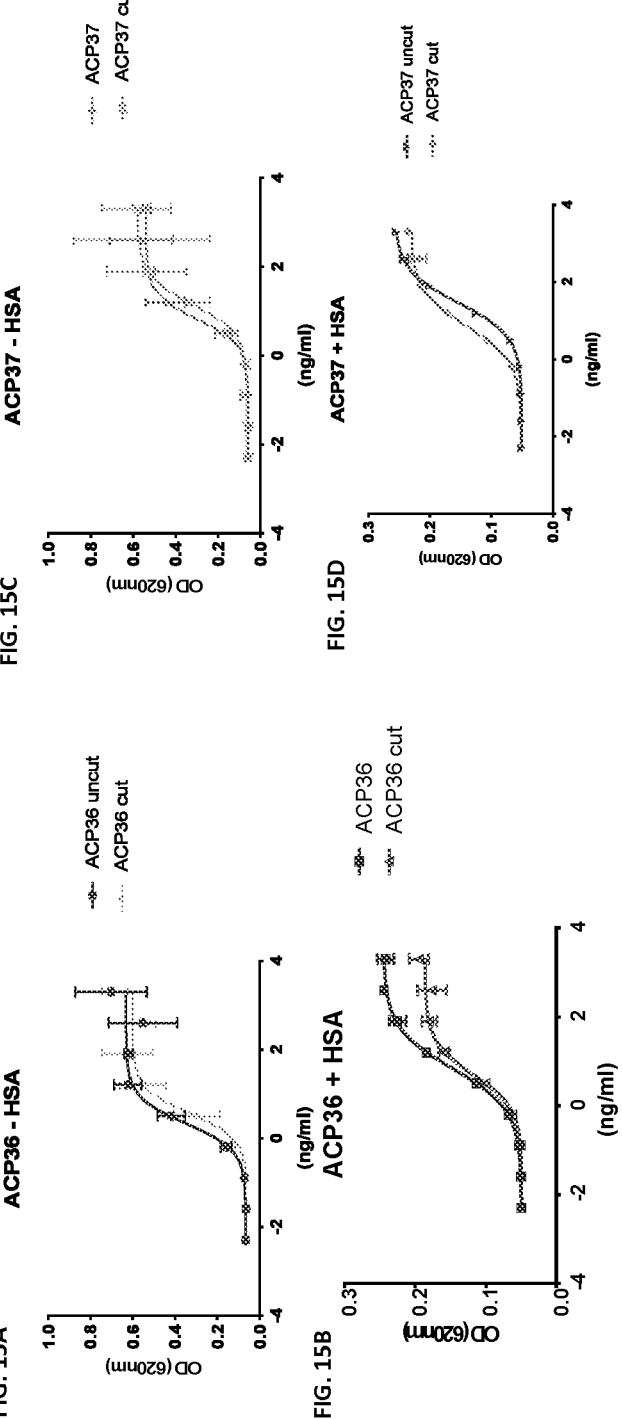

| | ACP01 uncut + HSA | ACP01 cut + HSA |
|---|---|---|
| EC50 | 163.4 | 0.2990 |

| | ACP01 uncut - HSA | ACP01 cut - HSA |
|---|---|---|
| EC50 | 0.3787 | 0.1521 |

| | ACP02 uncut +HSA | ACP02 cut +HSA |
|---|---|---|
| EC50 | 2.797 | 0.02478 |

| | ACP02 uncut -HSA | ACP02 cut -HSA |
|---|---|---|
| EC50 | 0.08499 | 0.02230 |

| | ACP03 uncut +HSA | ACP03 cut +HSA |
|---|---|---|
| EC50 | 3.196 | 0.02615 |

| | ACP03 uncut -HSA | ACP03 cut -HSA |
|---|---|---|
| EC50 | 0.0261 | 0.01697 |

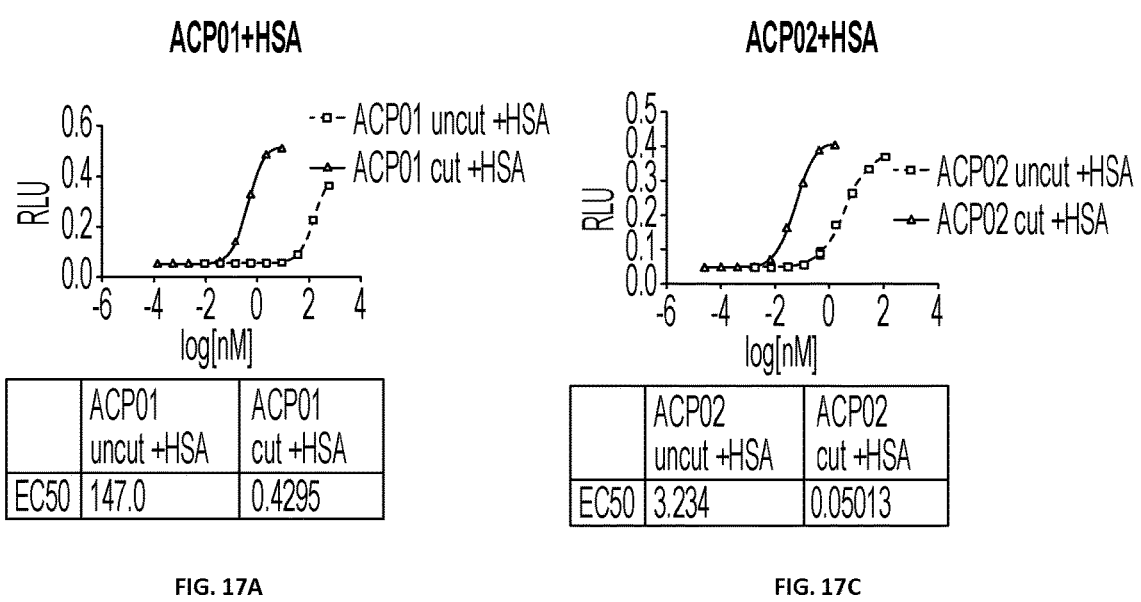
FIG. 17A
FIG. 17C
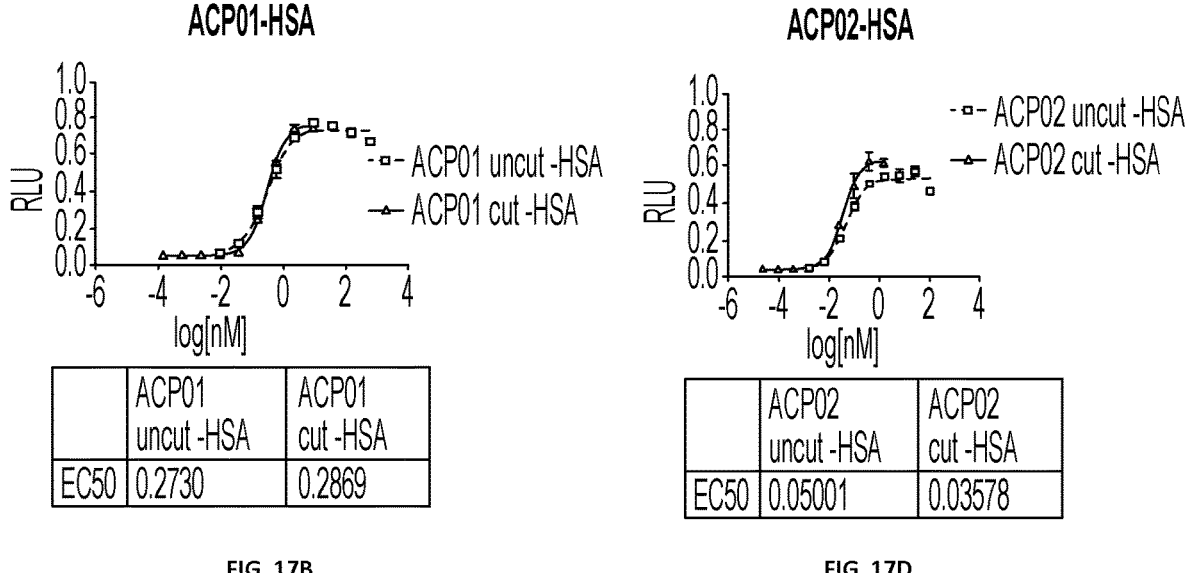
FIG. 17B
FIG. 17D

ACP03+HSA

| | ACP03 uncut +HSA | ACP03 cut +HSA |
|---|---|---|
| EC50 | 2.587 | 0.04462 |

ACP03-HSA

| | ACP03 uncut -HSA | ACP03 cut -HSA |
|---|---|---|
| EC50 | 0.04556 | 0.04677 |

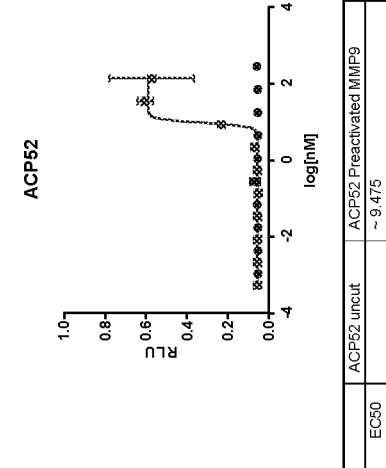
FIG. 22B
ACP52
| | ACP52 uncut | ACP52 Preactivated MMP9 |
|---|---|---|
| EC50 | | ~ 9.475 |
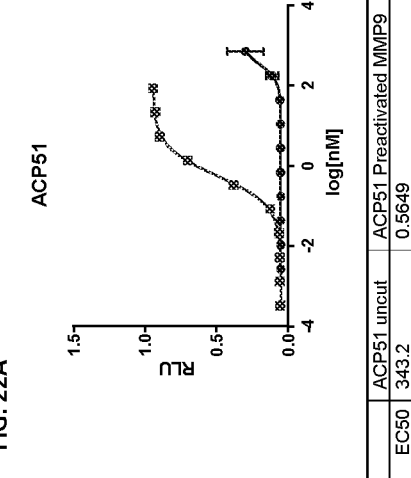
FIG. 22A
ACP51
| | ACP51 uncut | ACP51 Preactivated MMP9 |
|---|---|---|
| EC50 | 343.2 | 0.5649 |

ACP54

| | ACP54 uncut | ACP54 Preactivated MMP9 | ACP54 Catalytic domain MMP9 |
|---|---|---|---|
| EC50 | 3.03 | 0.05893 | 0.1647 |

ACP53

| | ACP53 uncut | ACP53 Preactivated MMP9 |
|---|---|---|
| EC50 | 283.5 | 0.164 |

FIG. 24B
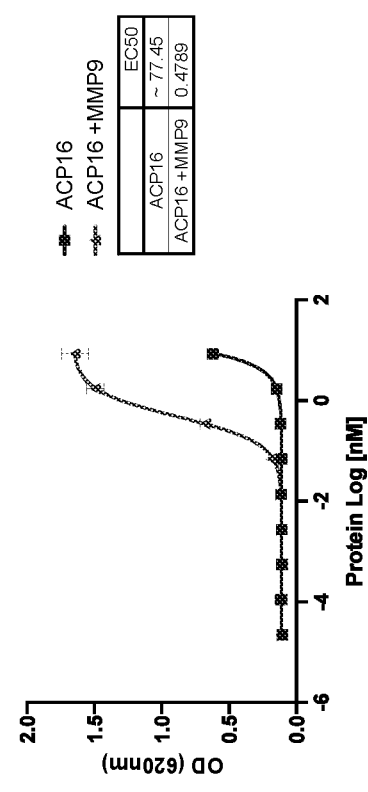
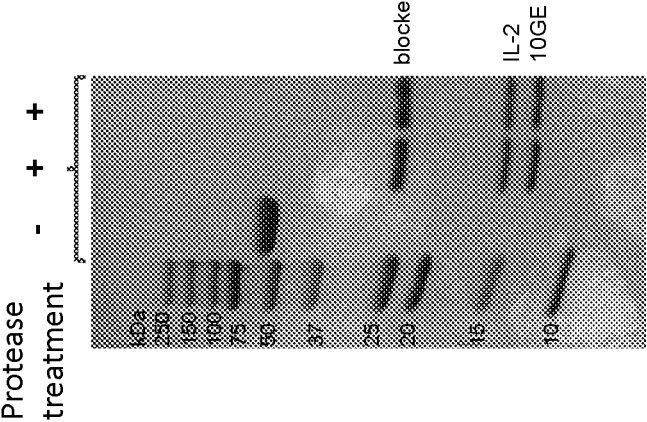

FIG. 25C
ACP16
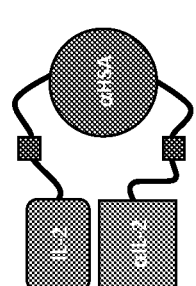
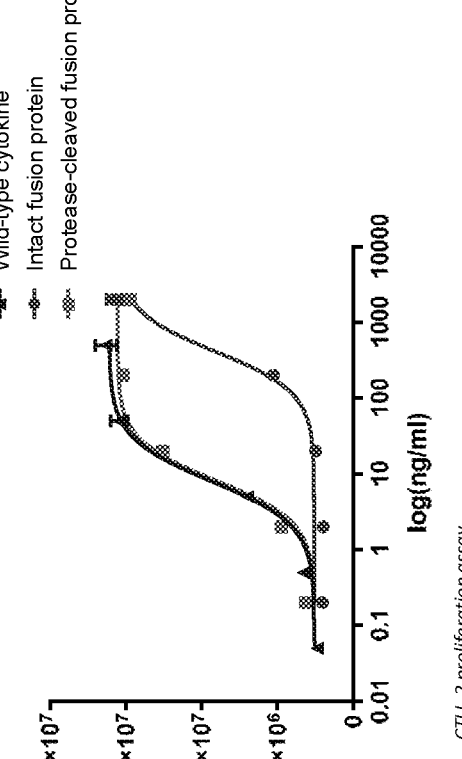
CTLL-2 proliferation assay

FIG. 27A
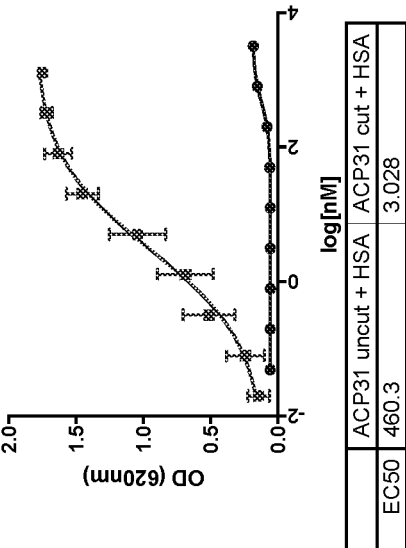
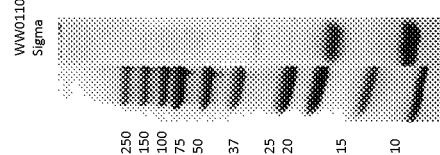
| | ACP31 uncut + HSA | ACP31 cut + HSA |
|---|---|---|
| EC50 | 460.3 | 3.028 |
ACP31 uncut + HSA
ACP31 cut + HSA

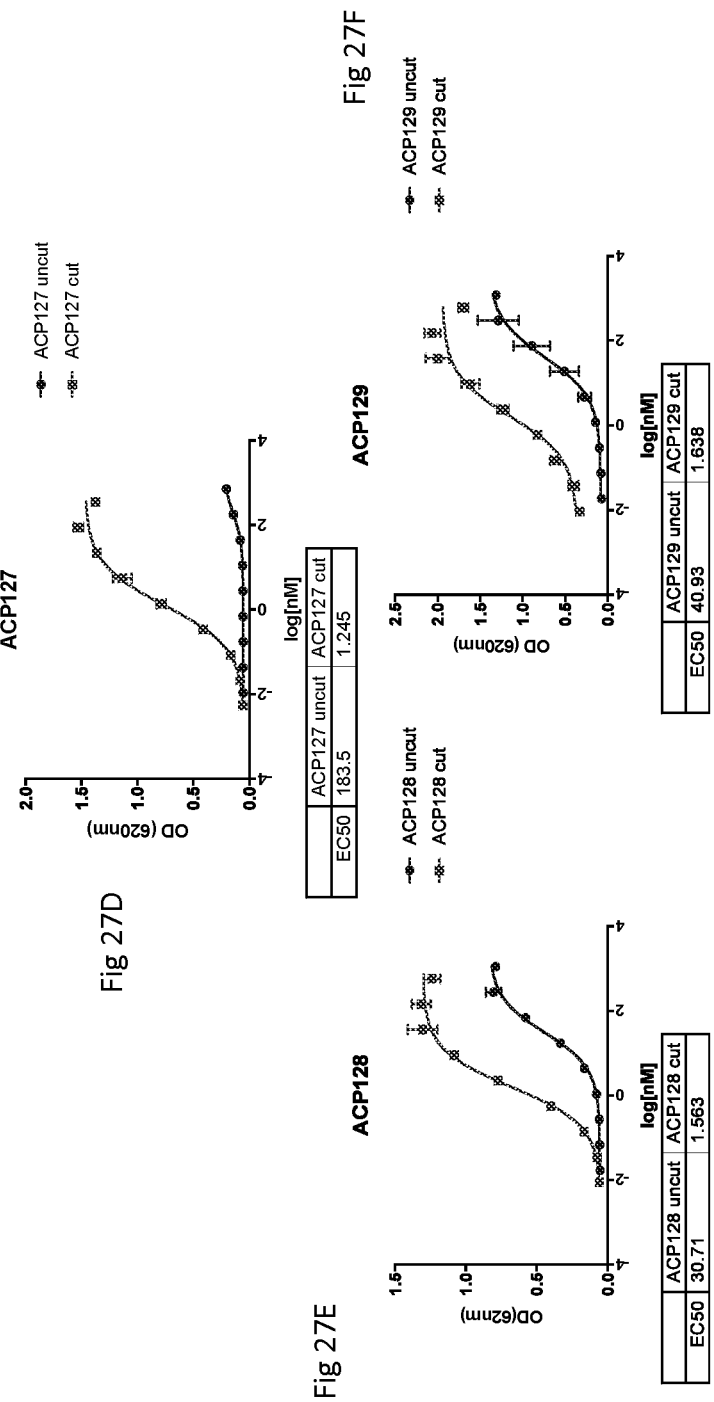

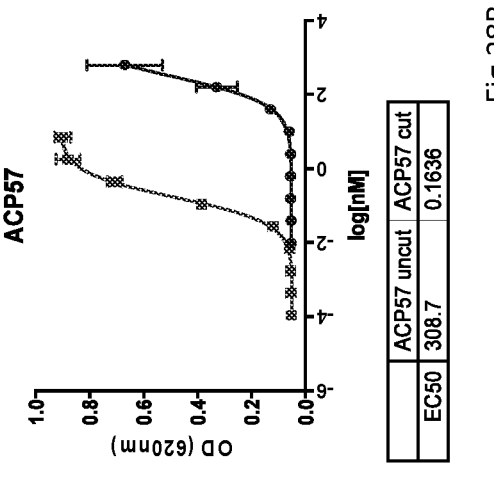
Fig 28B
Fig 28A

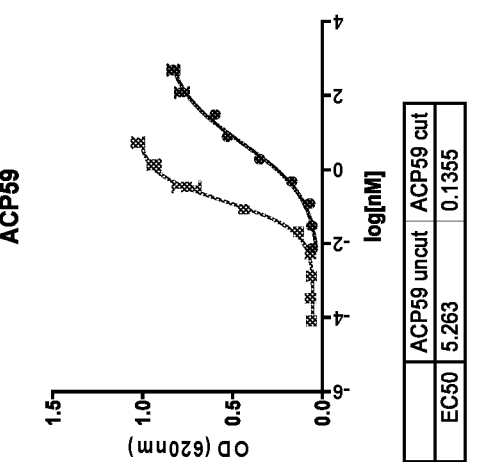
Fig 28D
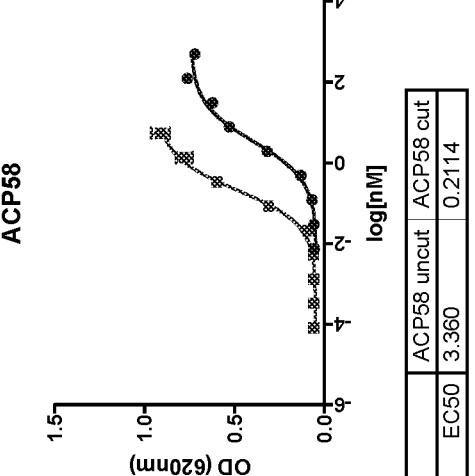
Fig 28C

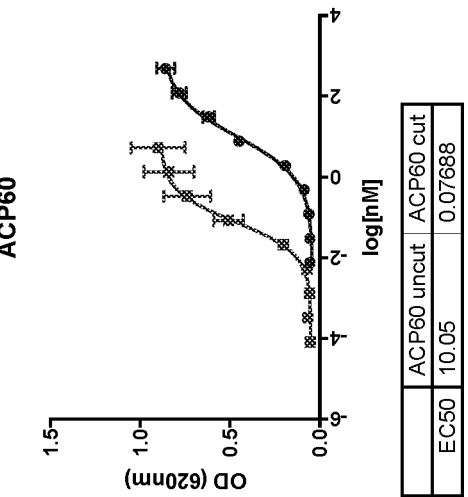
FIG. 28E

FIG. 28M
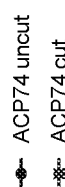
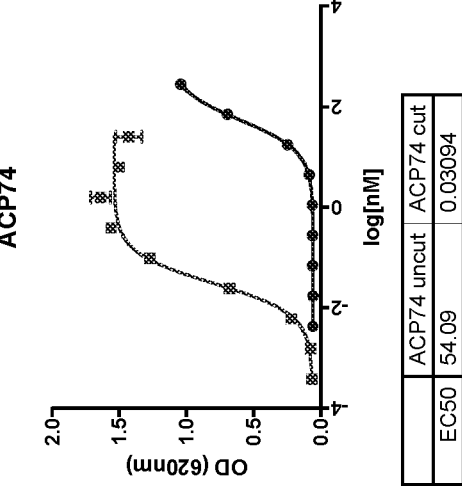

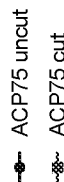
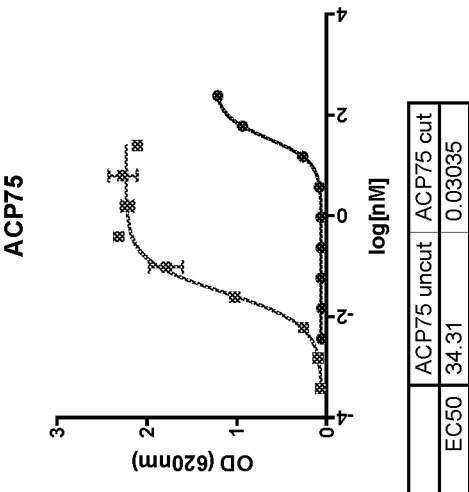
FIG. 28N

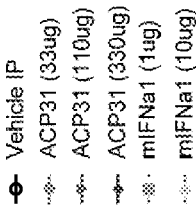
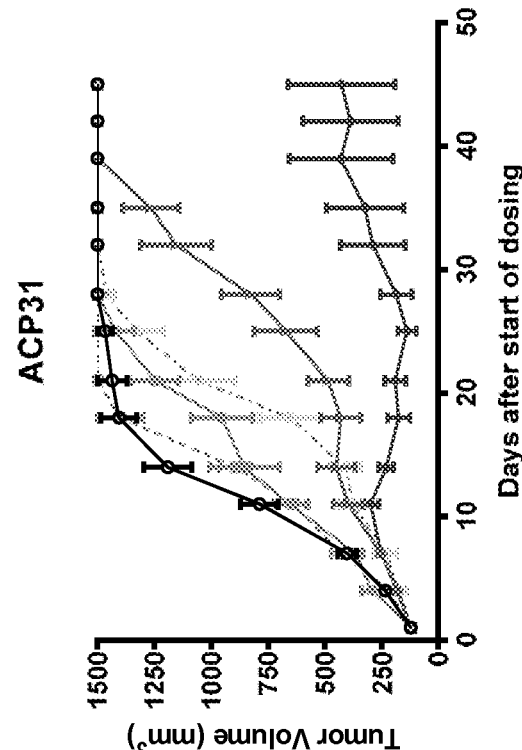
FIG. 29A

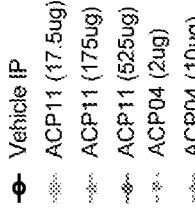
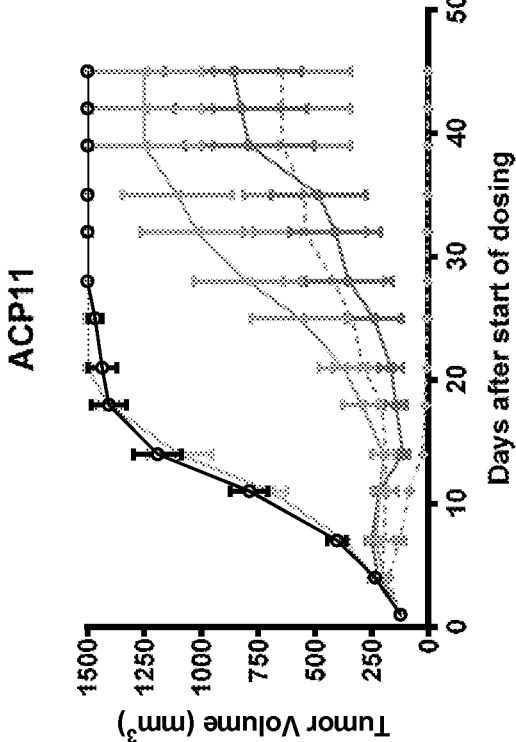
FIG. 29B

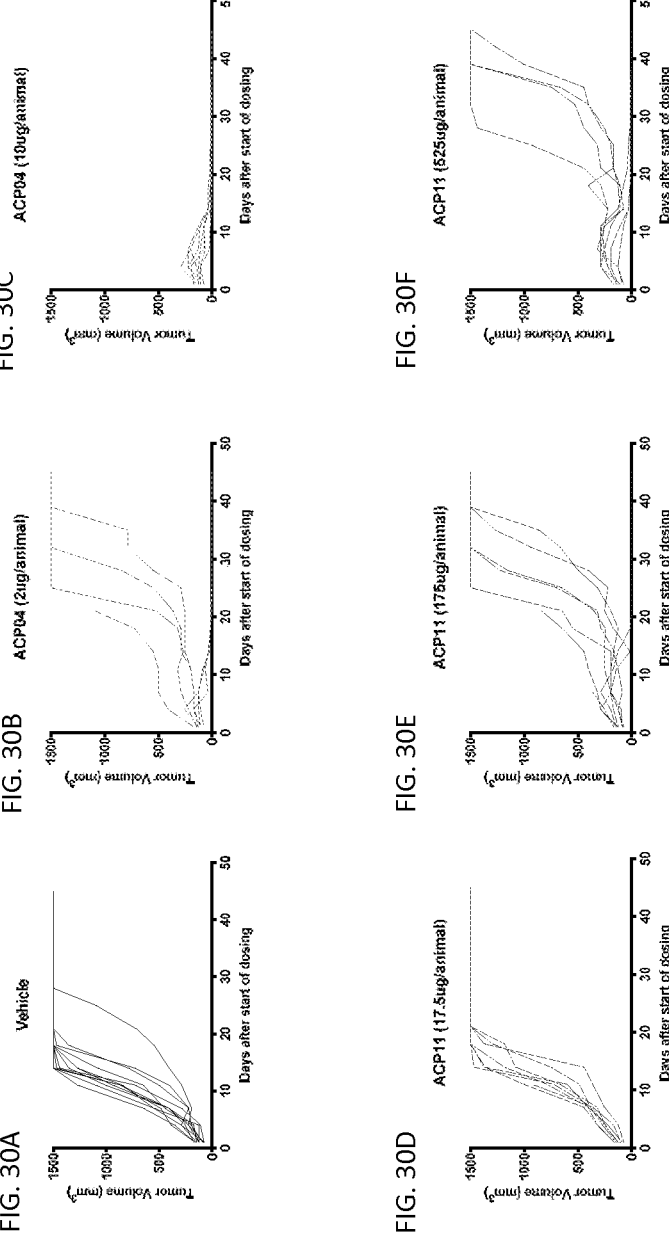

Place hold

FIG. 32A

FIG. 32B
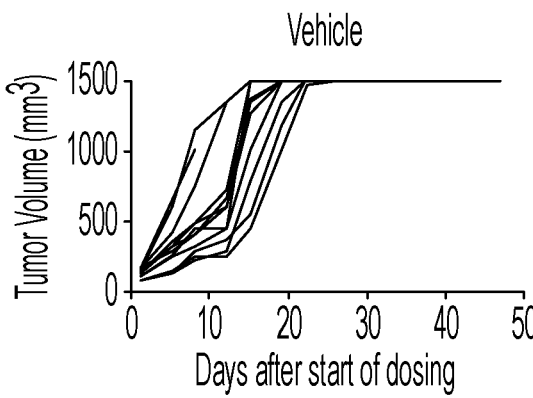
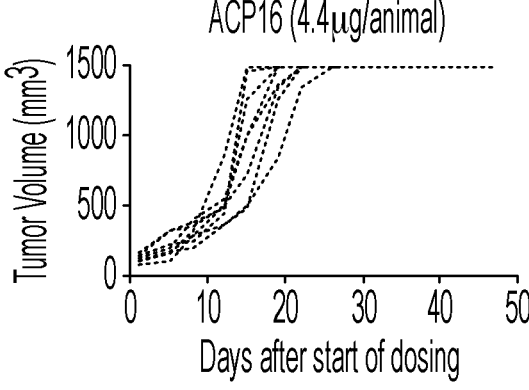
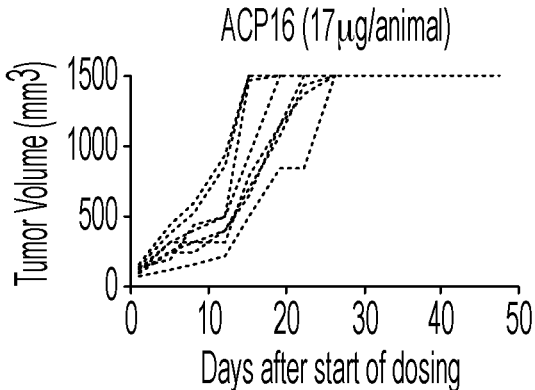
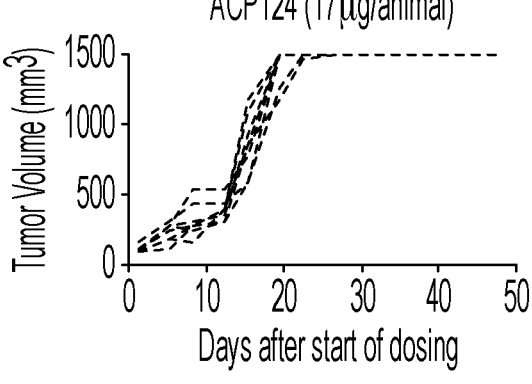
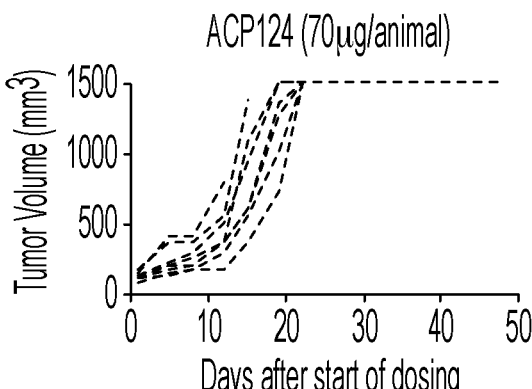

FIG. 35A

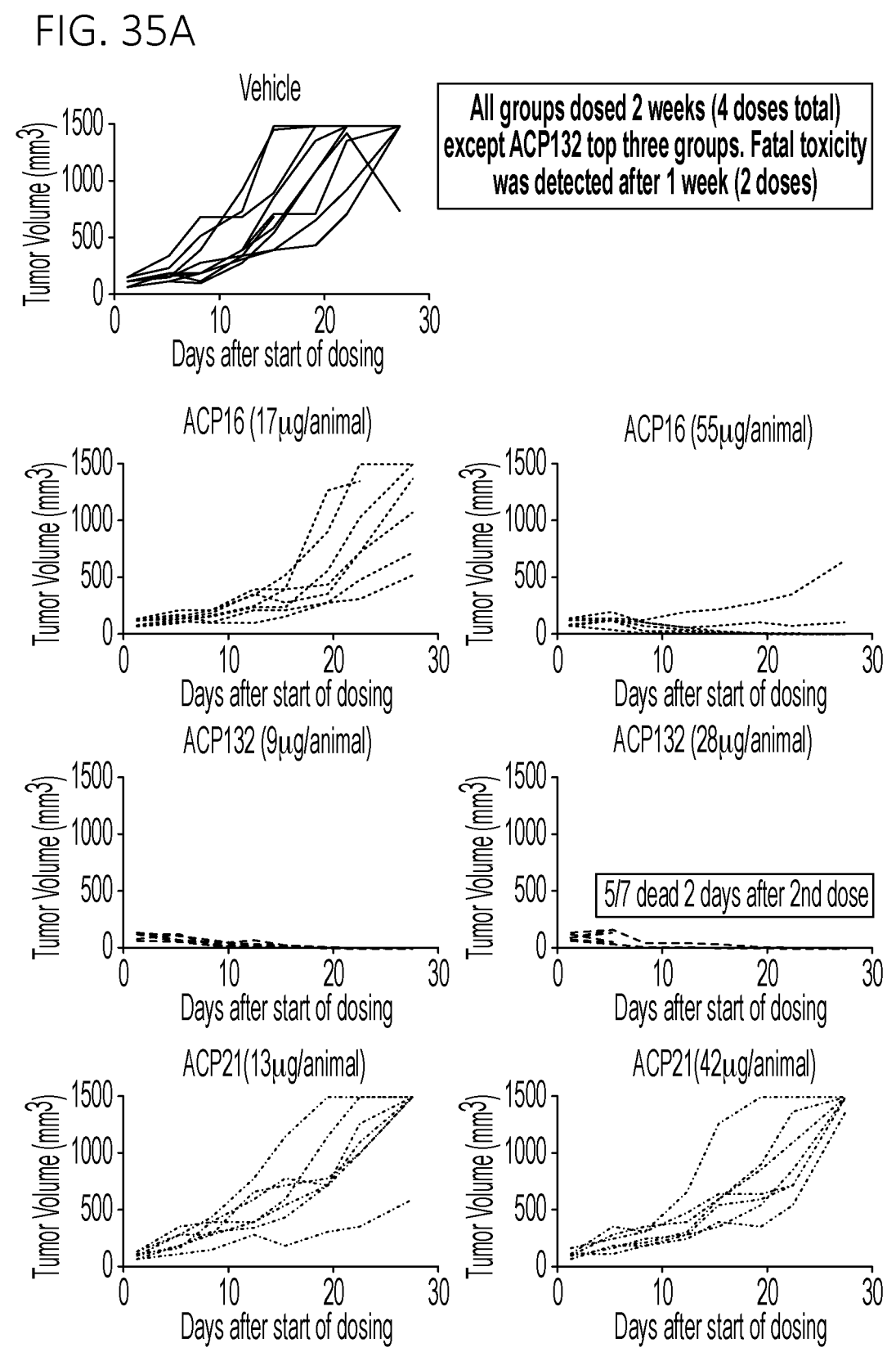

Vehicle

All groups dosed 2 weeks (4 doses total) except ACP132 top three groups. Fatal toxicity was detected after 1 week (2 doses)

ACP16 (17μg/animal)

ACP16 (55μg/animal)

ACP132 (9μg/animal)

ACP132 (28μg/animal)

5/7 dead 2 days after 2nd dose

ACP21(13μg/animal)

ACP21(42μg/animal)

Place hold

FIG. 36

Place hold

FIG. 37

Place hold

FIG. 38

Place hold

FIG. 39

Place hold

FIG. 40

Place hold

FIG. 41

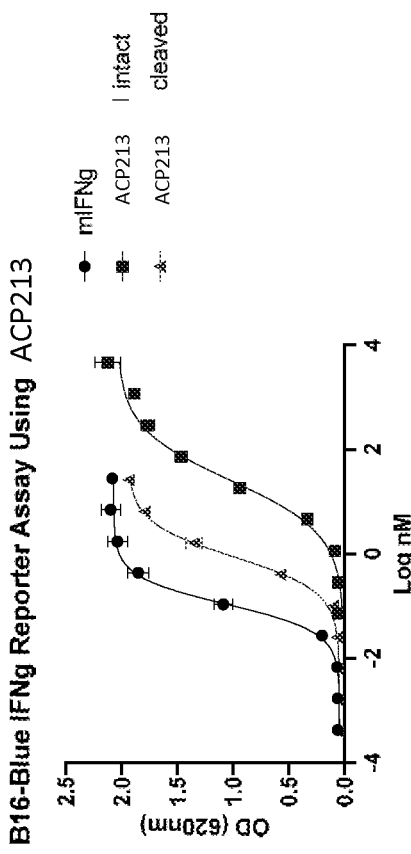
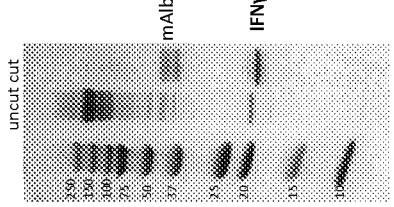
FIG. 42B

| Mouse Serum Albumin | KB (nM) | Kon (1/Ms) | Kdis (1/s) |
|---|---|---|---|
| ACP16 | 2.6 | 4.3E+4 | 1.1E-4 |
| ACP10 | 0.38 | 2.5E+5 | 9.7E-5 |
| ACP11 | No binding | No binding | No binding |

| Human Serum Albumin | KD (nM) | Kon (1/Ms) | Kdis (1/s) |
|---|---|---|---|
| ACP16 | 4.3 | 3.4E+5 | 1.5E-3 |
| ACP10 | 4.4 | 2.8E+5 | 1.2E-3 |
| ACP11 | 79 | 3.1E+4 | 2.5E-3 |

FIG. 43

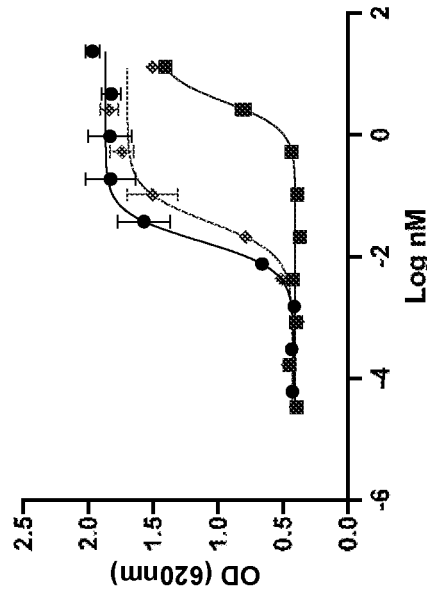
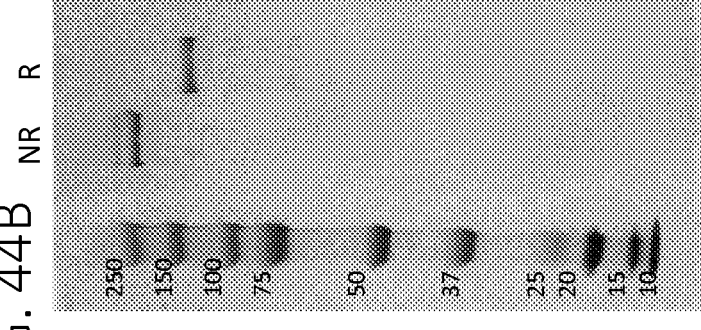
FIG. 44B

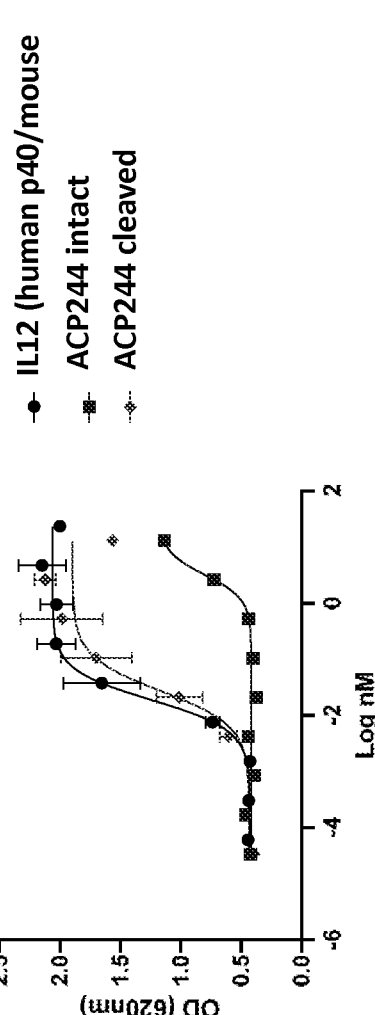
- IL12 (human p40/mouse
- ACP244 intact
- ACP244 cleaved
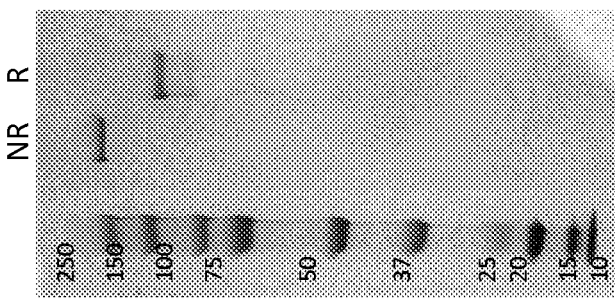
FIG. 44C

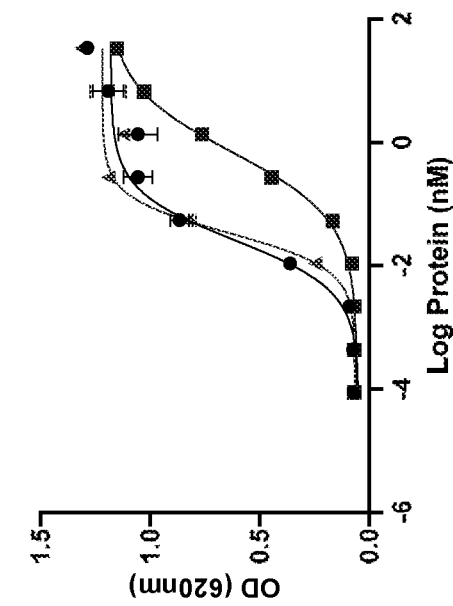
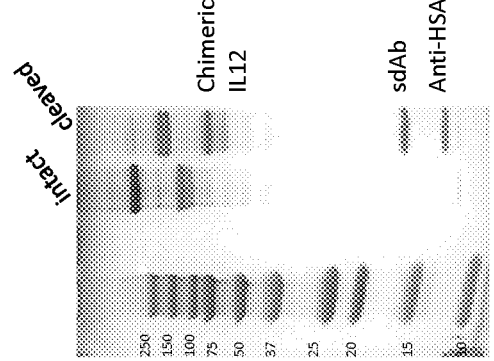
FIG. 44D

FIG. 45A
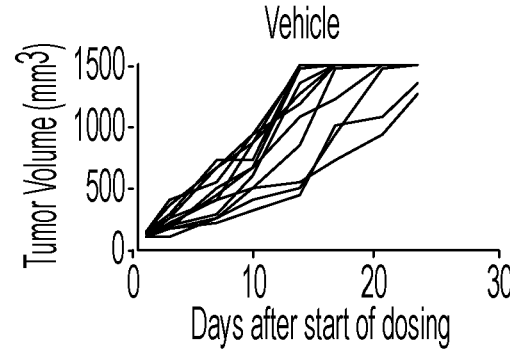
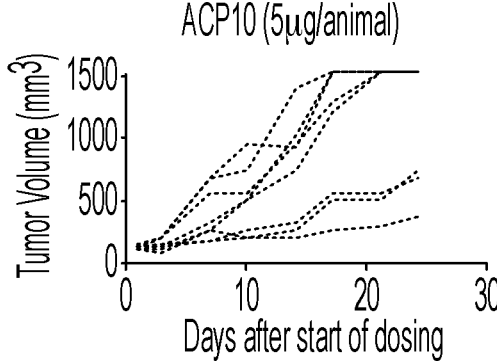
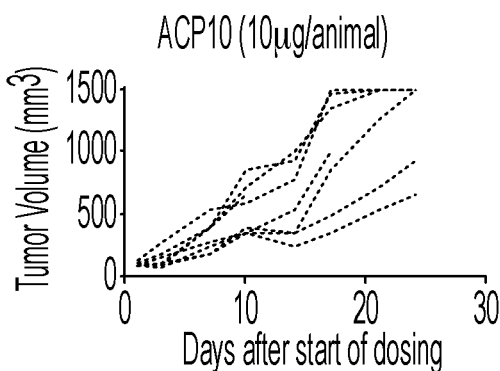

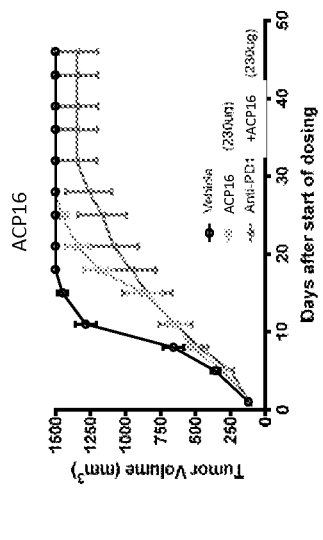
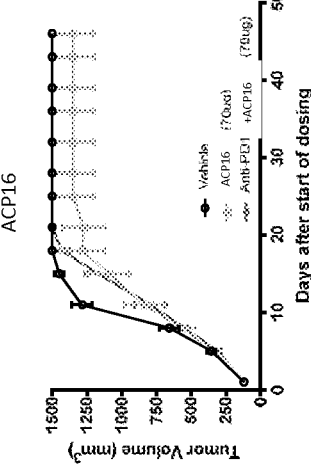
FIG. 47A

FIG. 49H

Body Weight

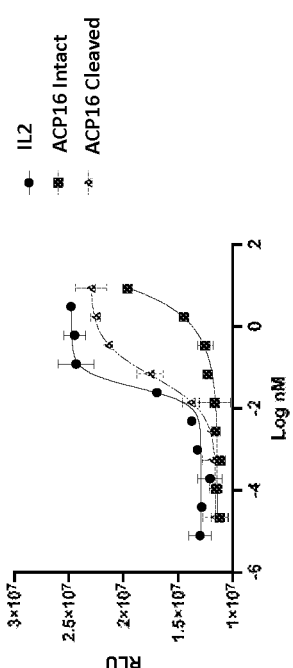
FIG. 52A
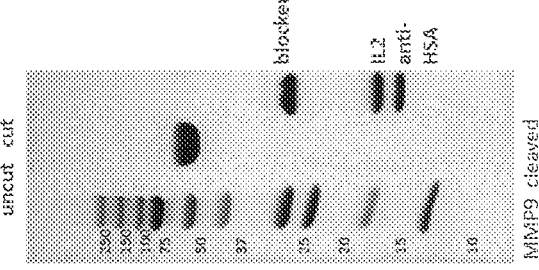

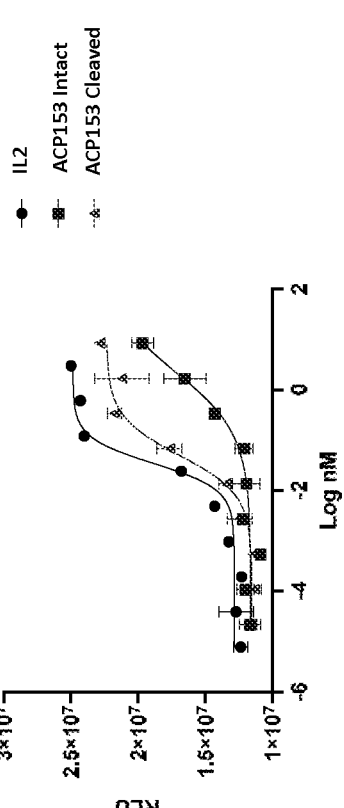
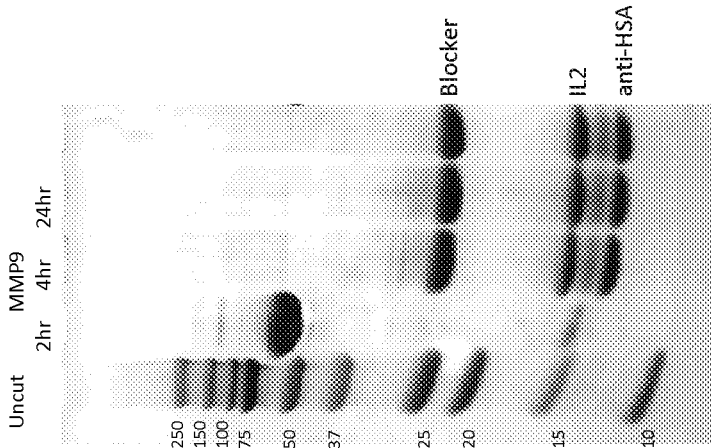
FIG. 52B

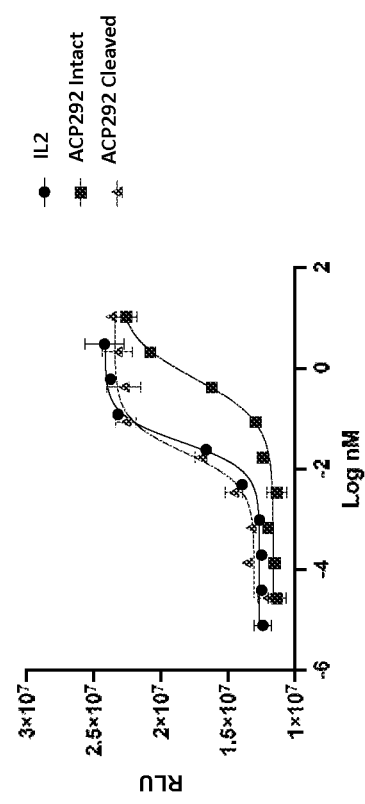
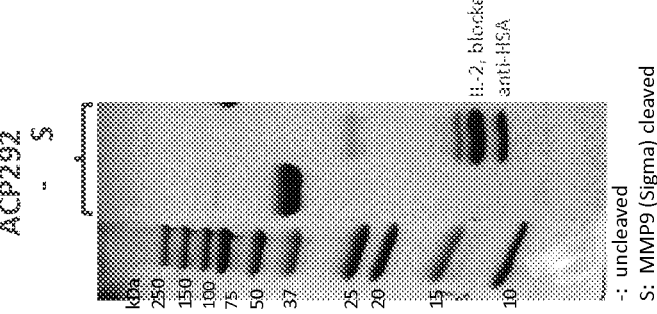
FIG. 52C

FIG. 52E
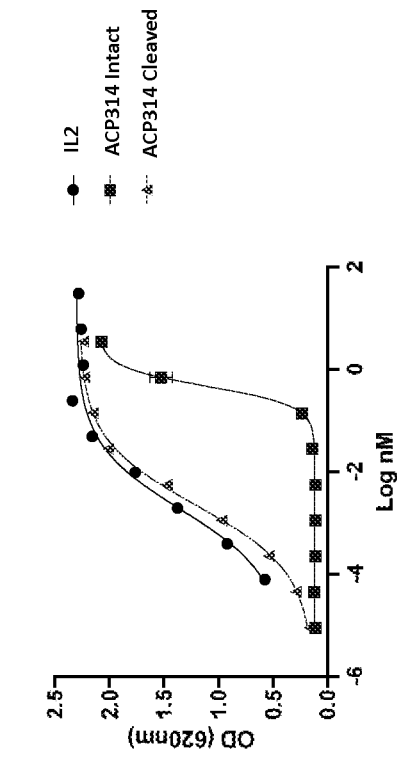
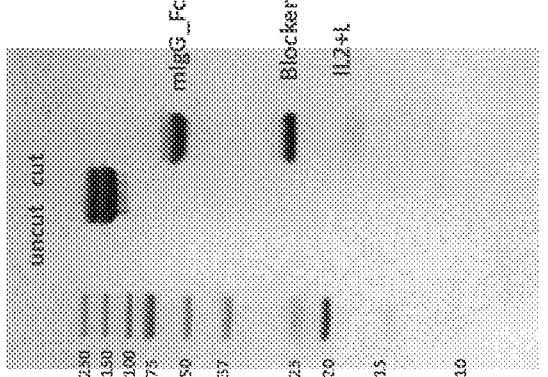

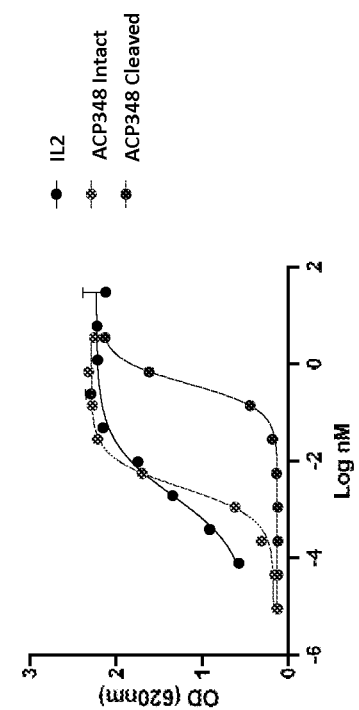
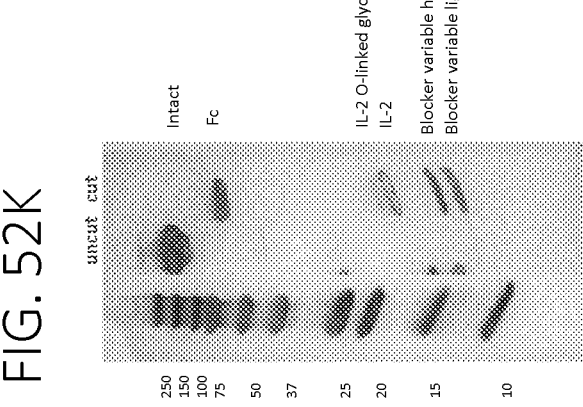
FIG. 52K

FIG. 52L
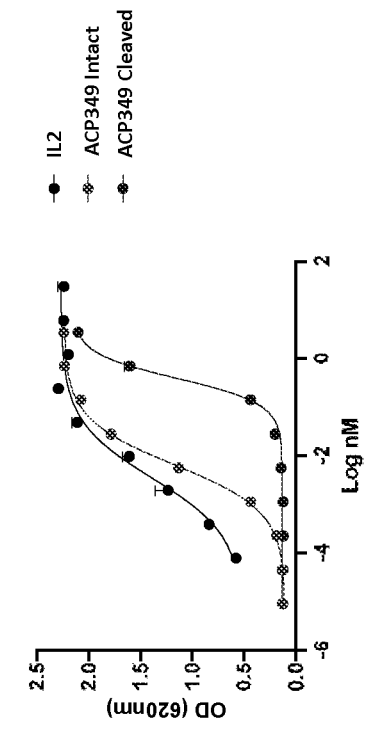
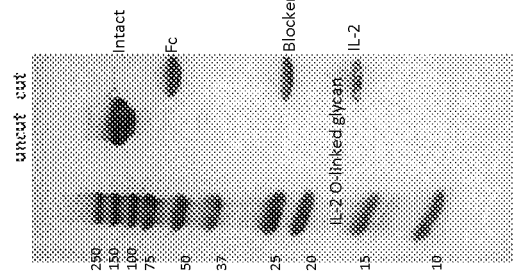

FIG. 52N
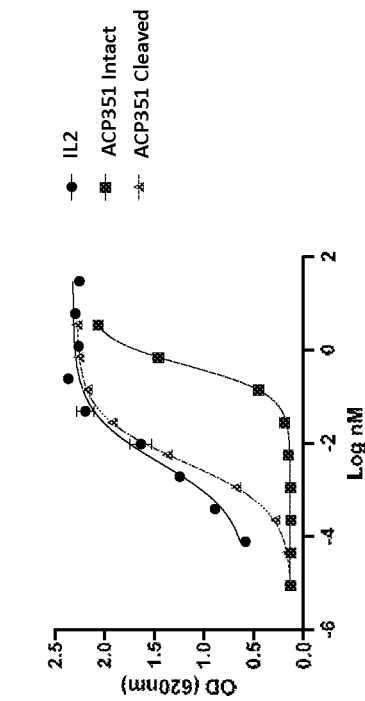
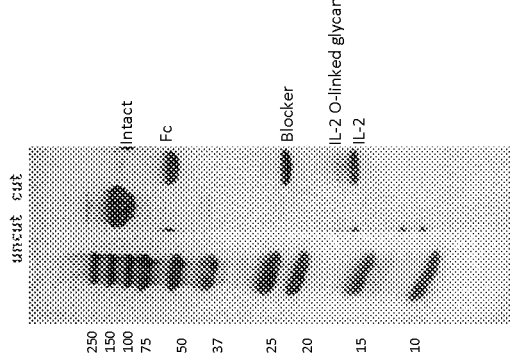

FIG. 54A
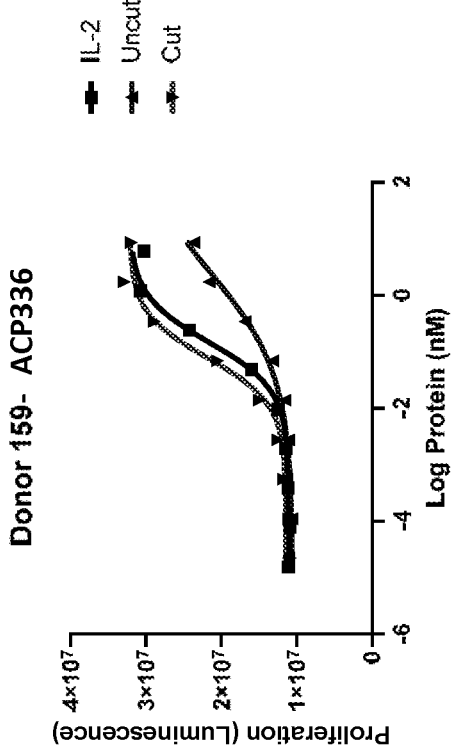
Donor 159- ACP336
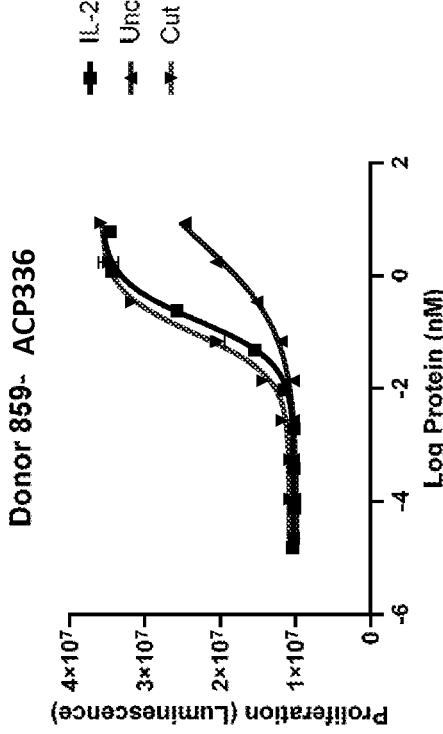
Donor 859- ACP336

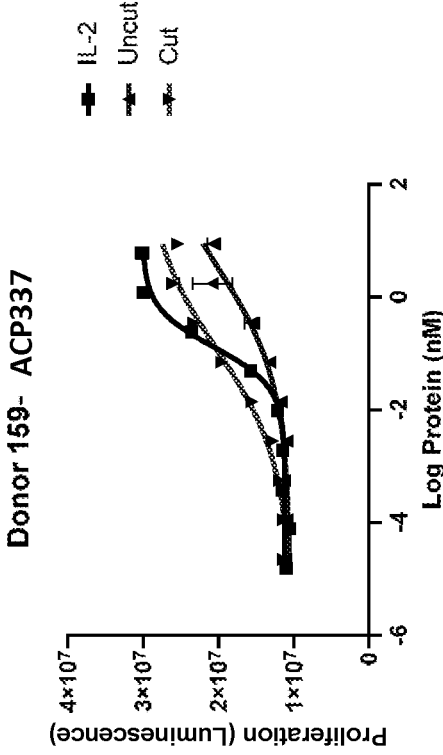
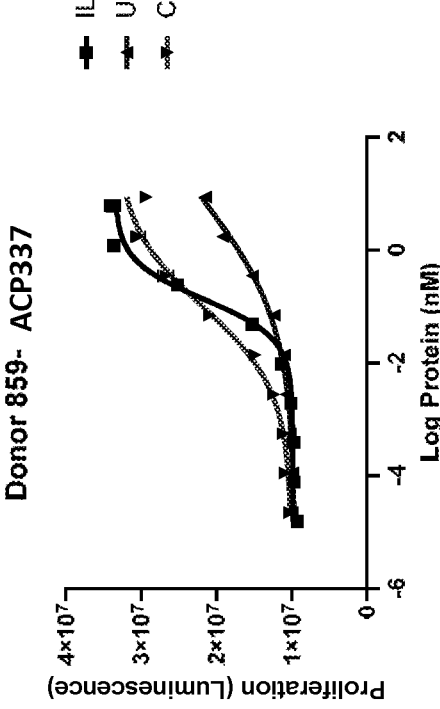
FIG. 54B

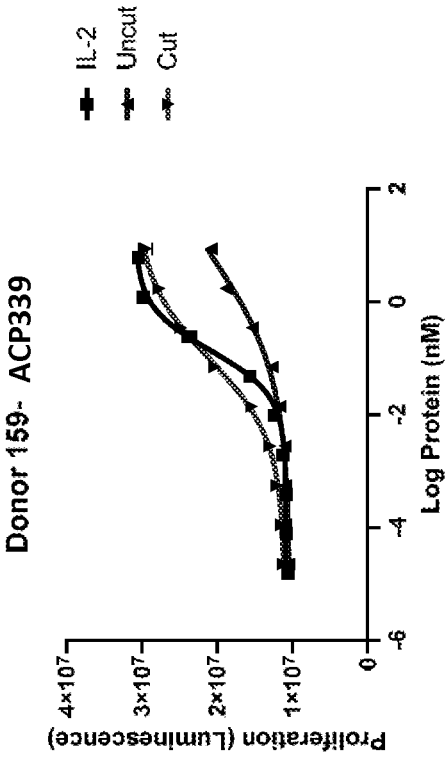
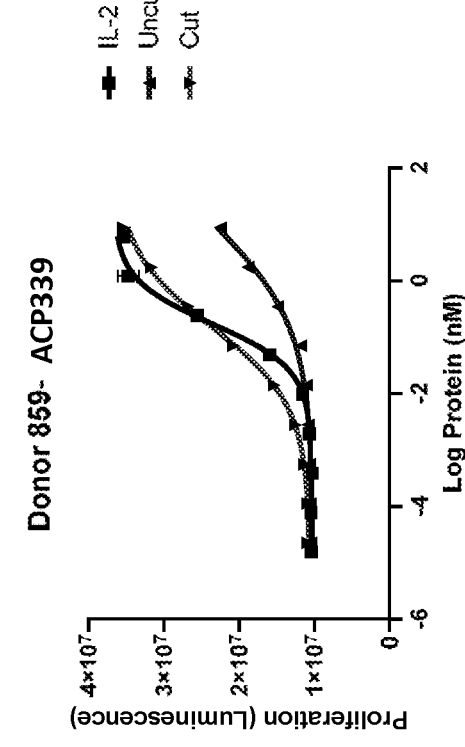
FIG. 54D

FIG. 54F
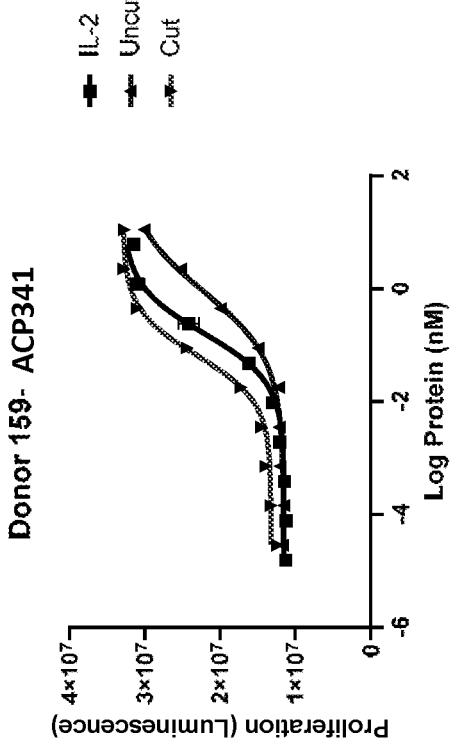
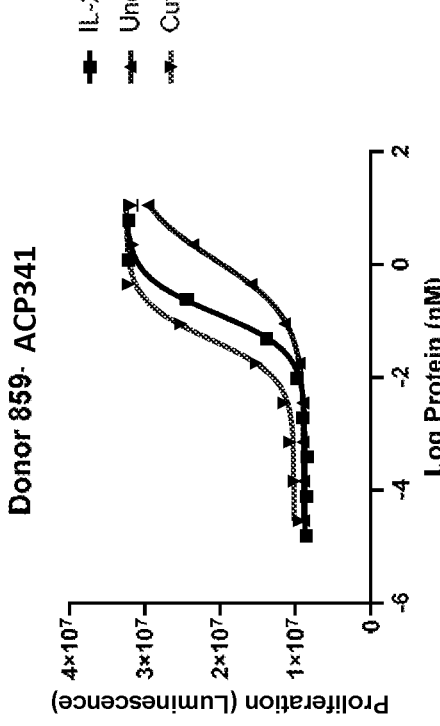

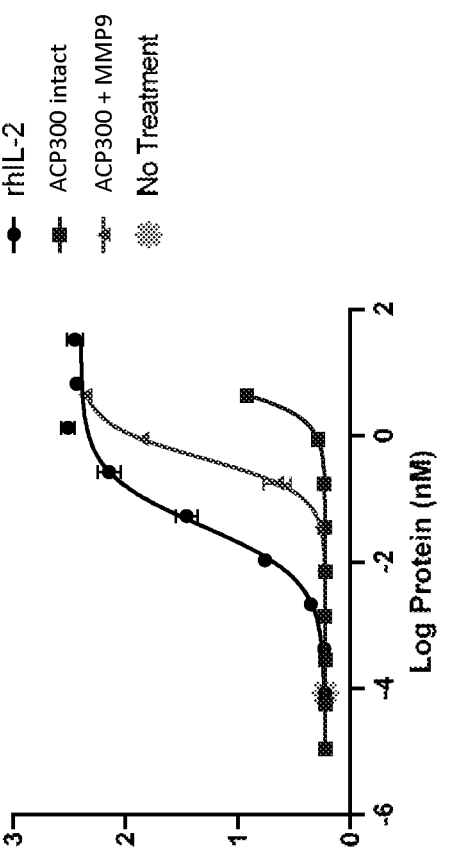
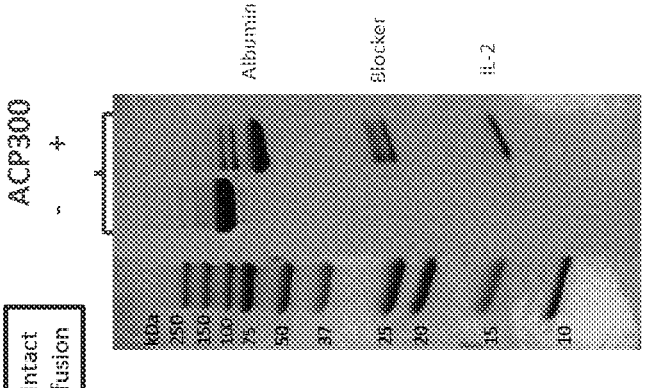
FIG. 55G

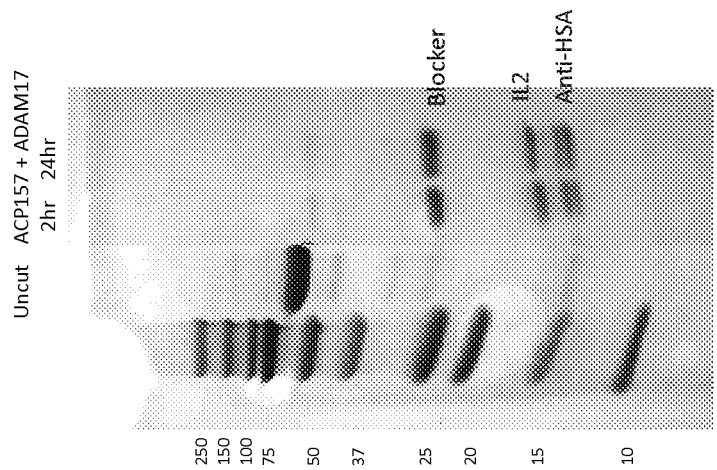
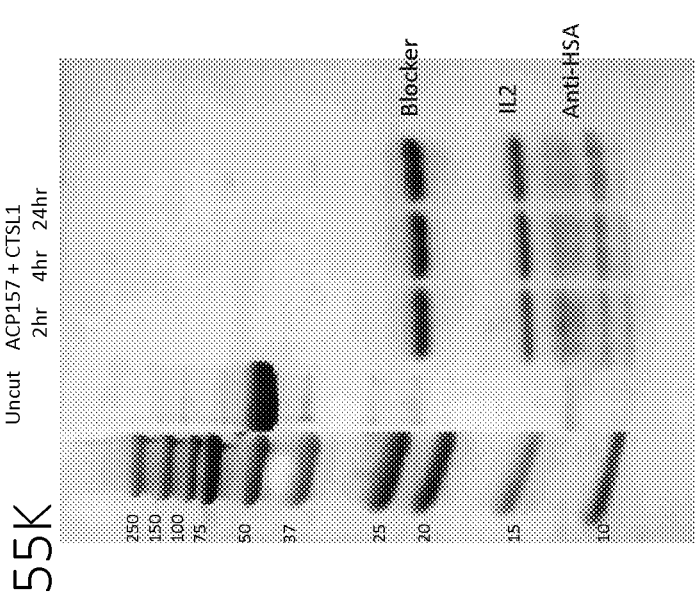
FIG. 55K

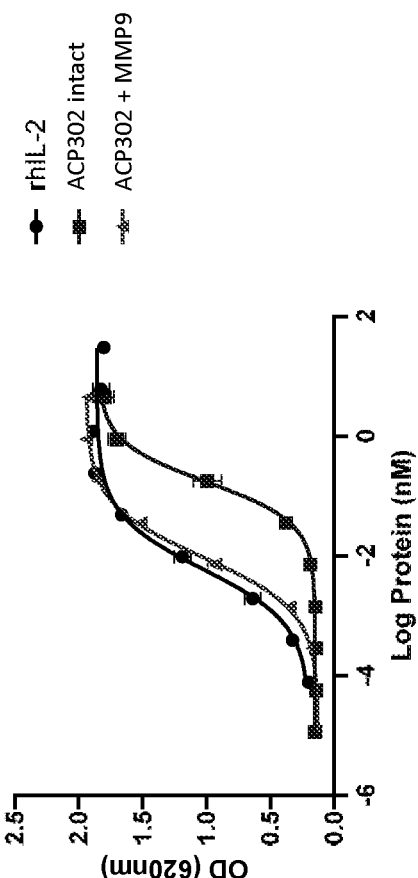
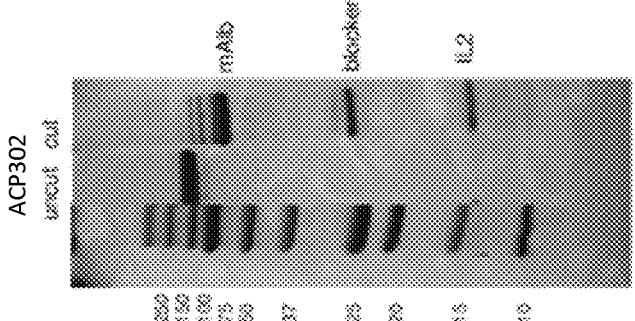
FIG. 55M

FIG. 56

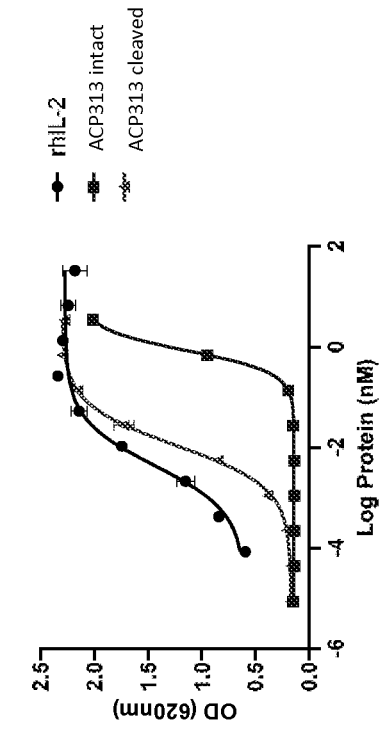
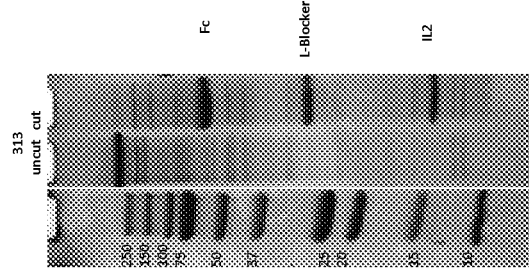
FIG. 57D

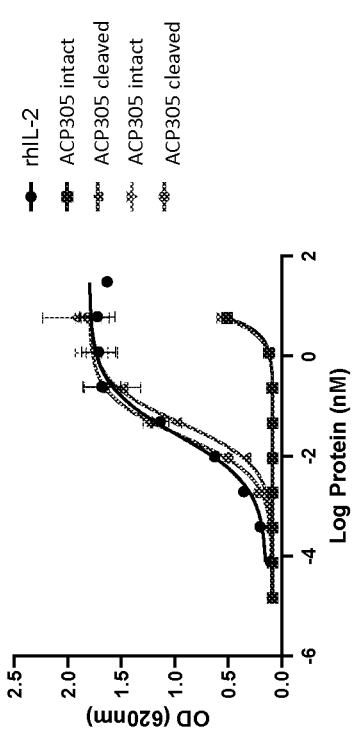
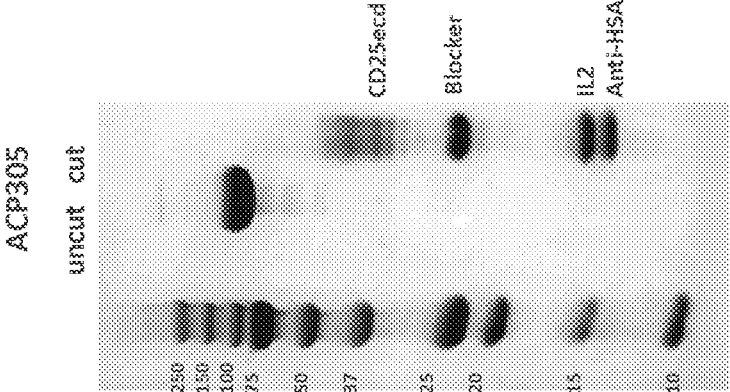
FIG. 59A

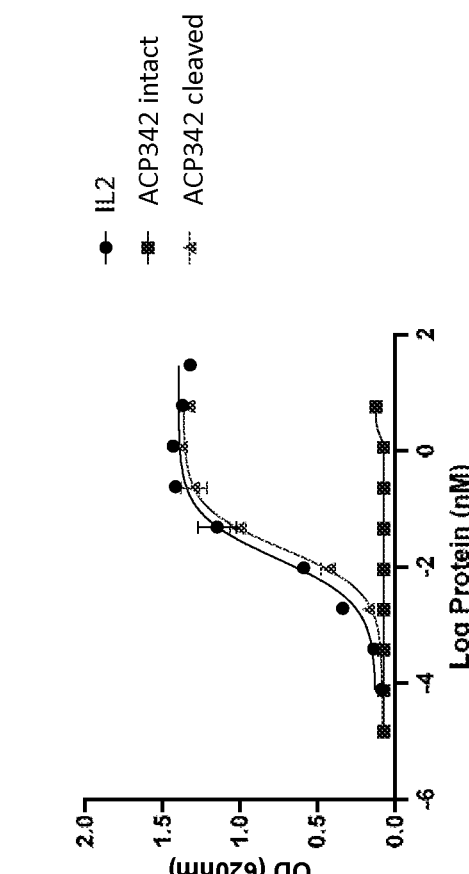
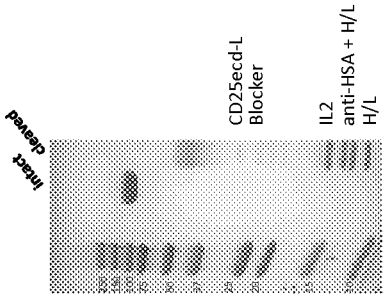
FIG. 59B

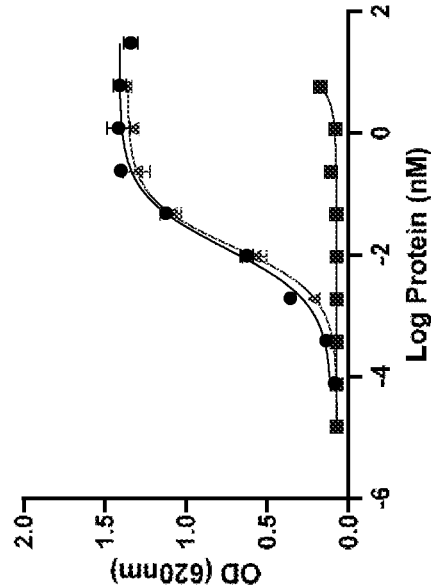
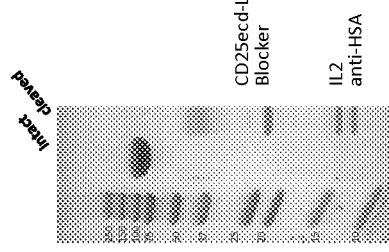
FIG. 59C

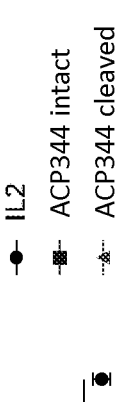
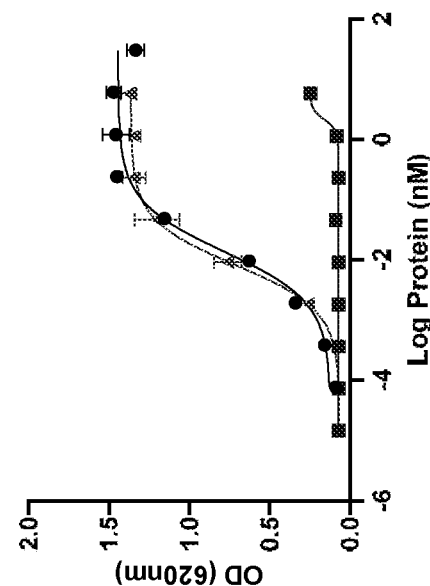
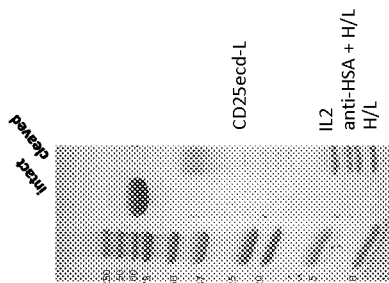
FIG. 59E

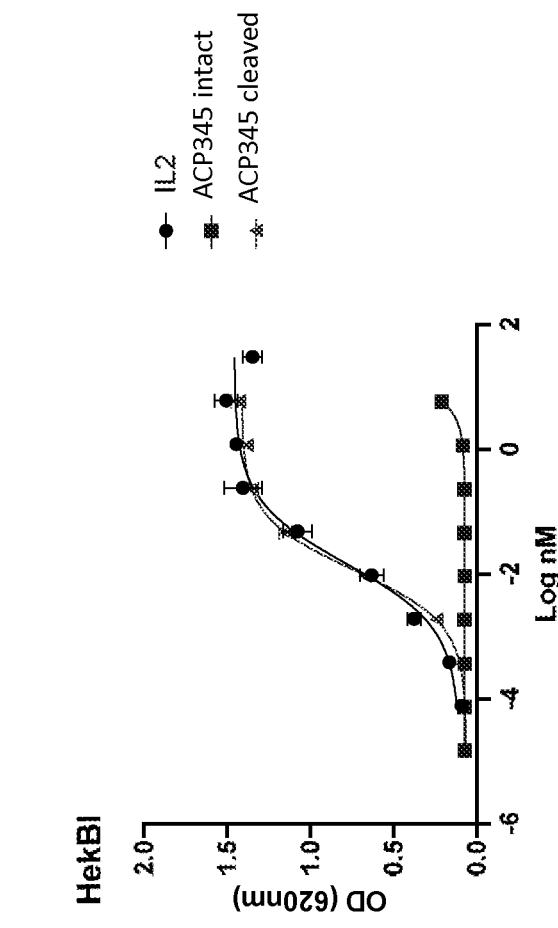
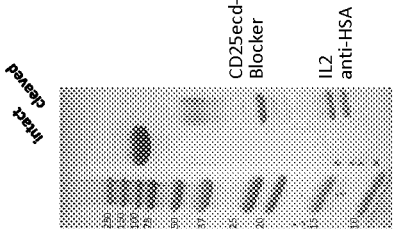
FIG. 59F

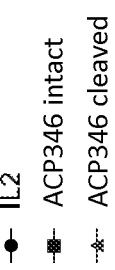
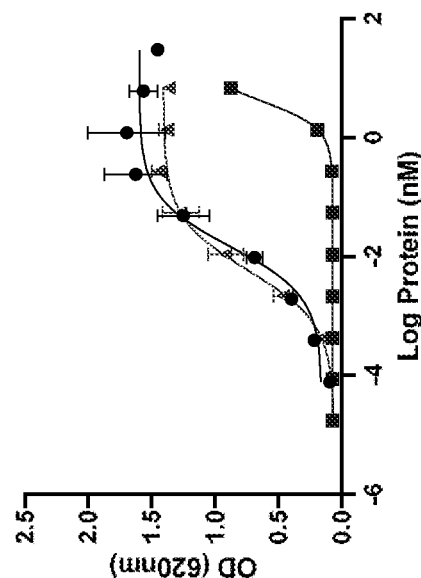
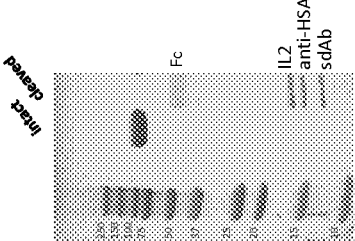
FIG. 59G

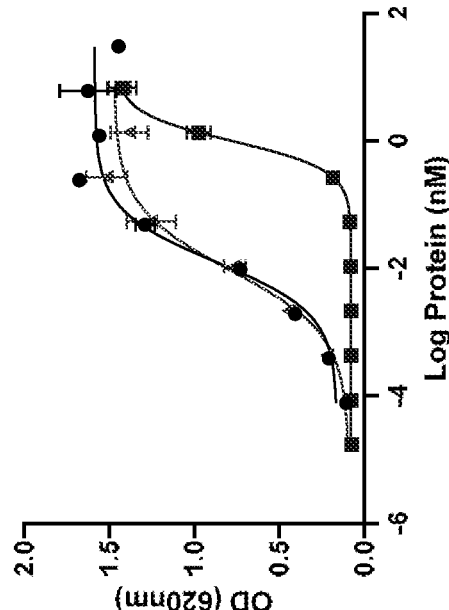
FIG. 59H

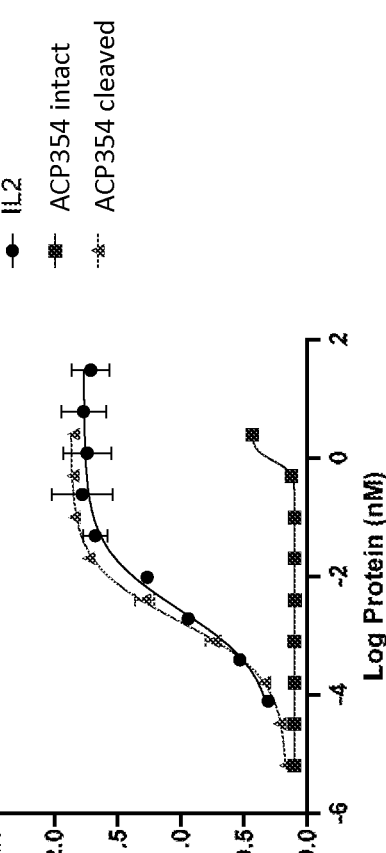
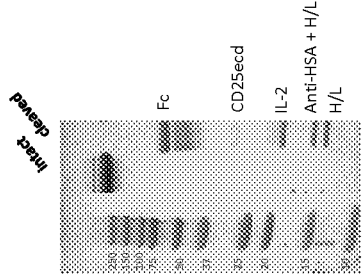
FIG. 59I

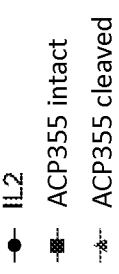
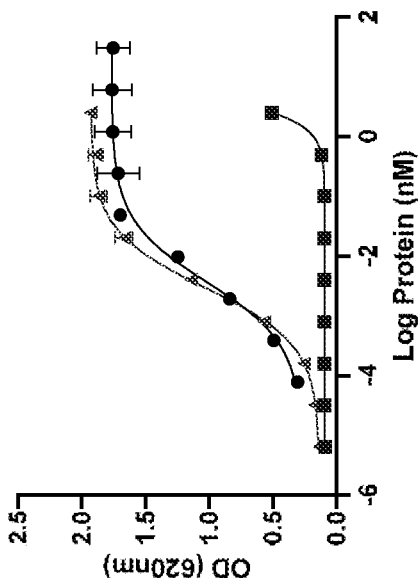
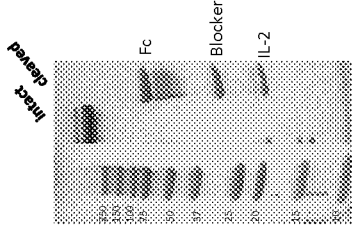
FIG. 59J

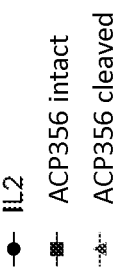
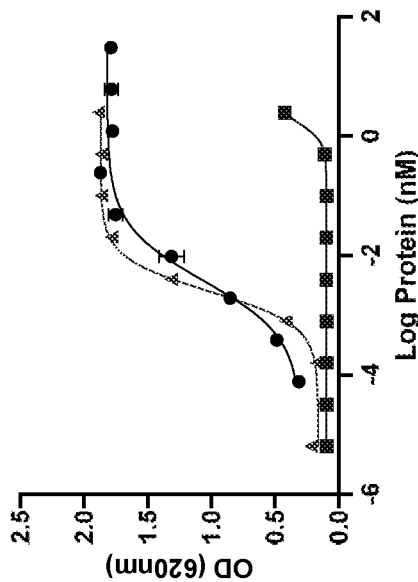
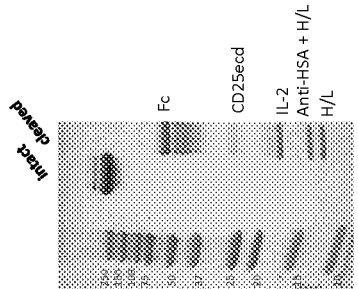
FIG. 59K

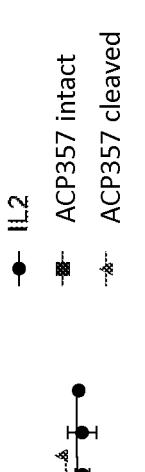
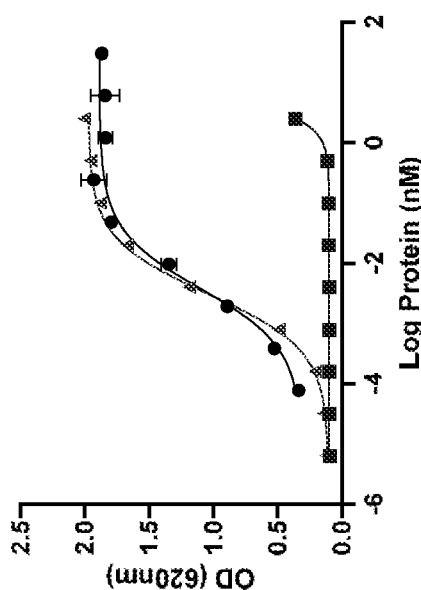
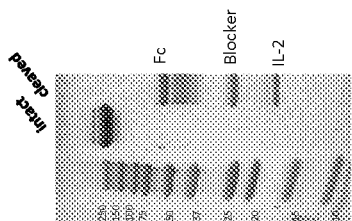
FIG. 59L

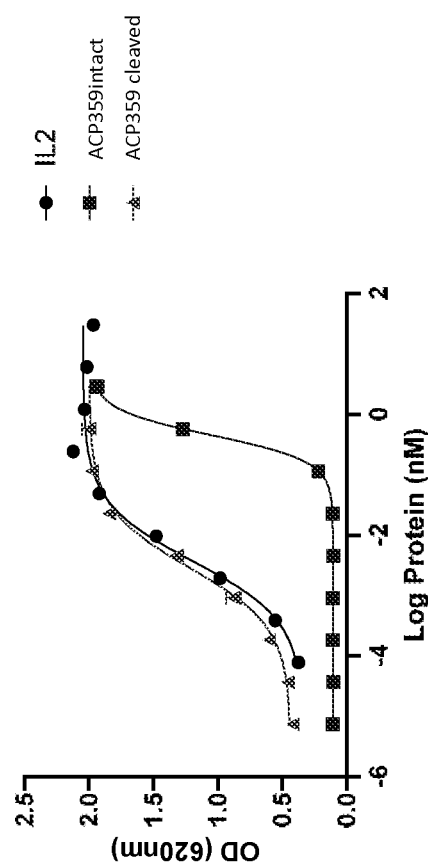
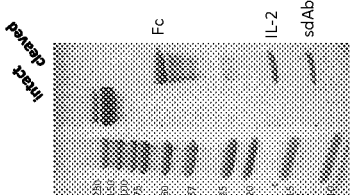
FIG. 59N

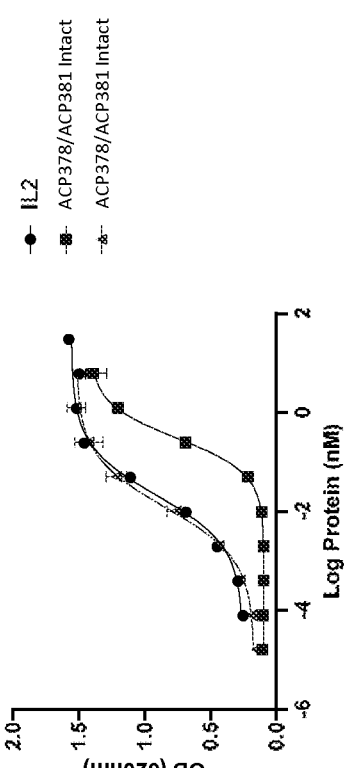
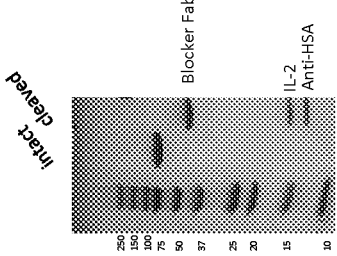
FIG. 590

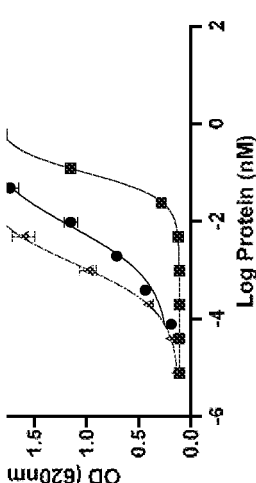
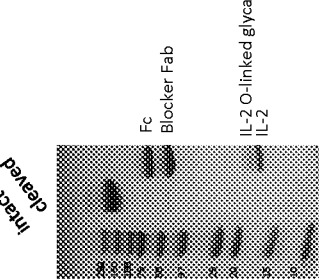
FIG. 59P

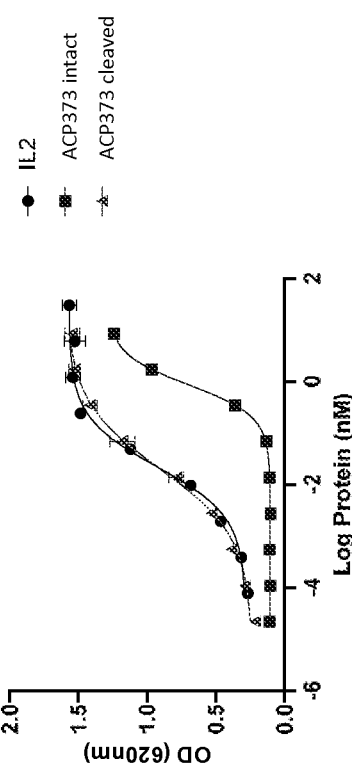
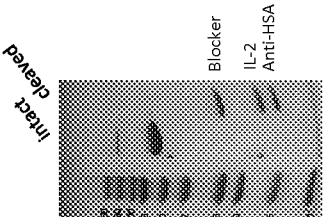
FIG. 59Q

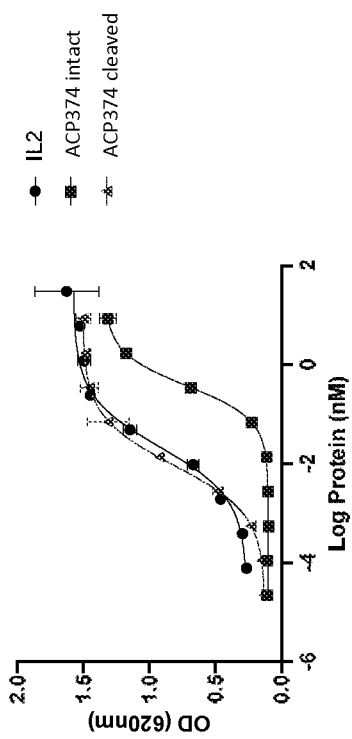
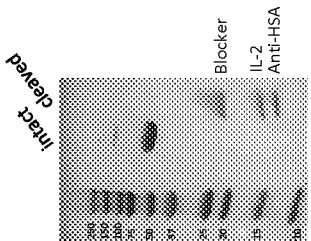
FIG. 59R

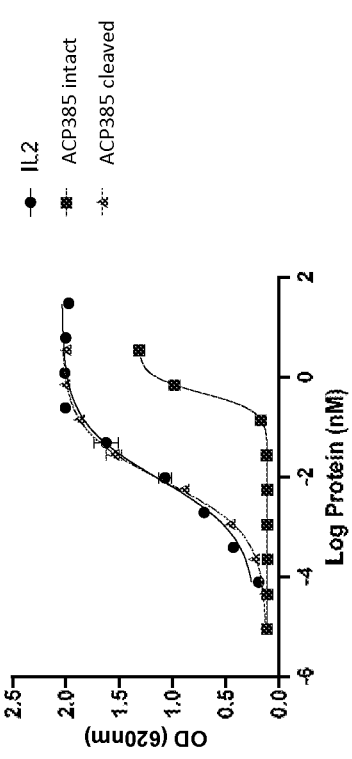
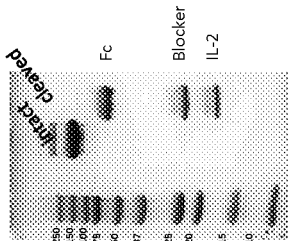
FIG. 59S

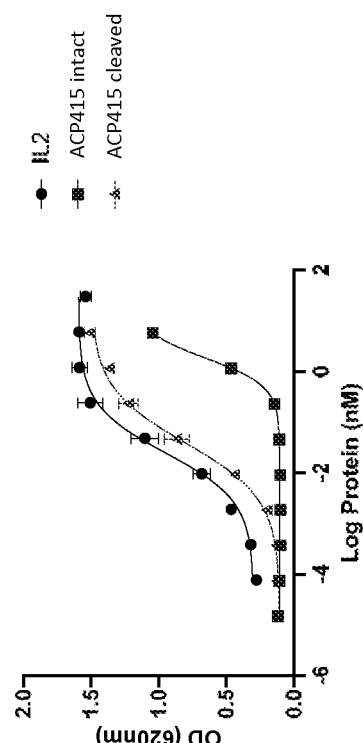
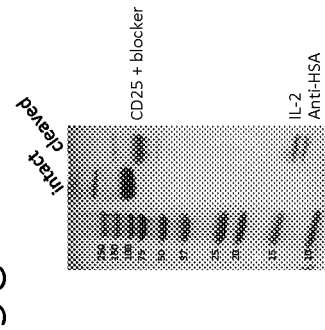
FIG. 59U

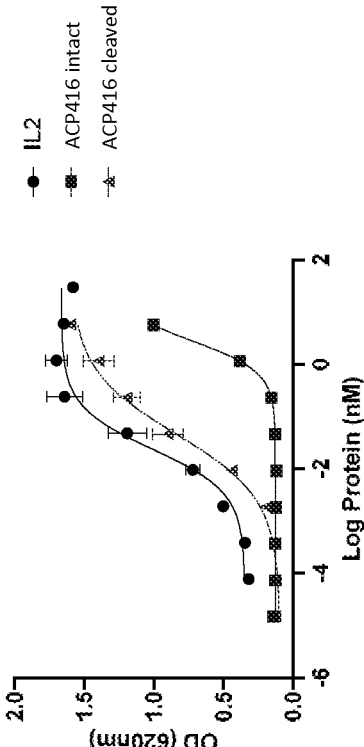
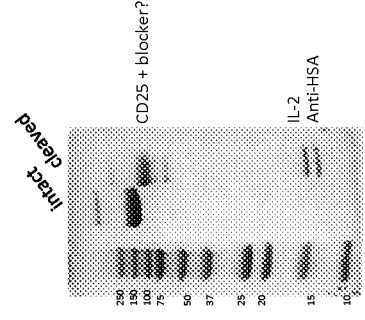
FIG. 59V

FIG. 59W

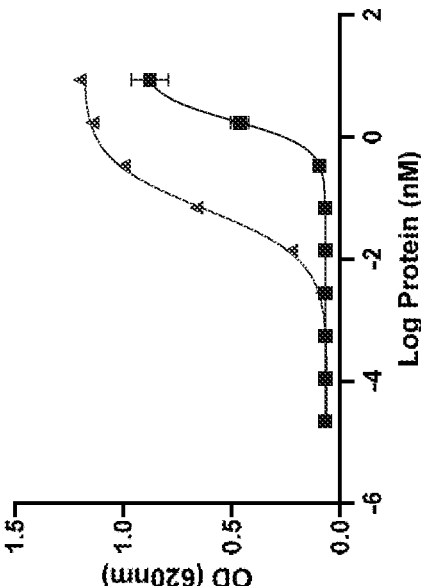
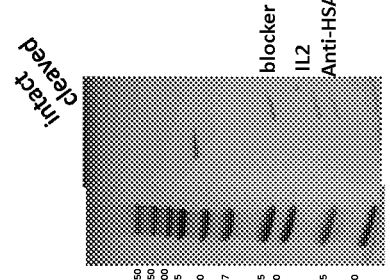
FIG. 59X

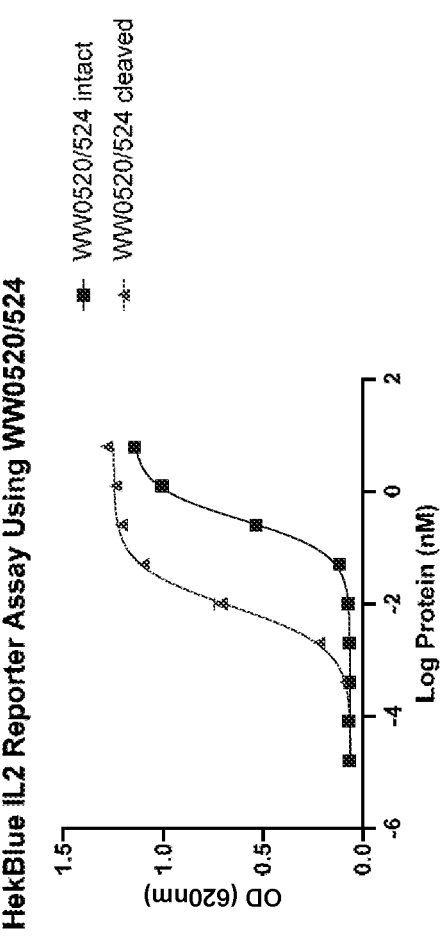
FIG. 59Y
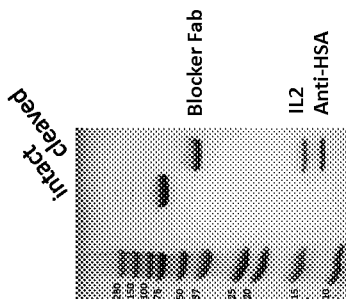

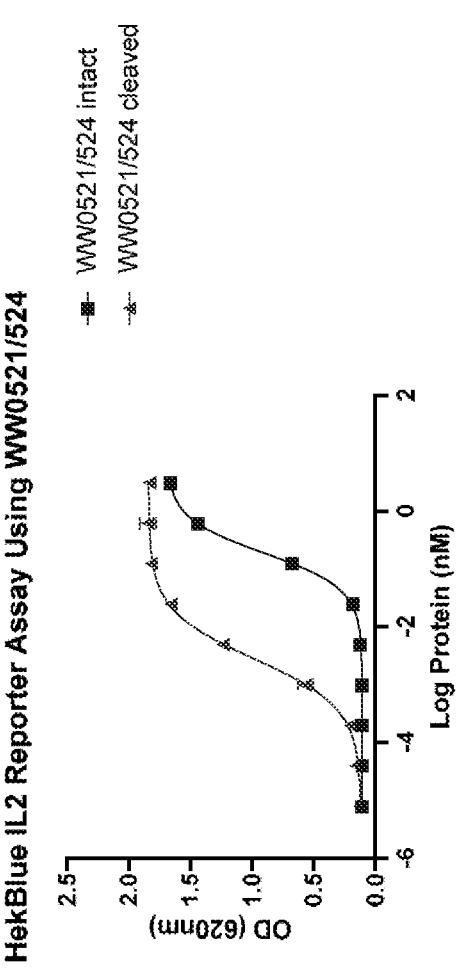
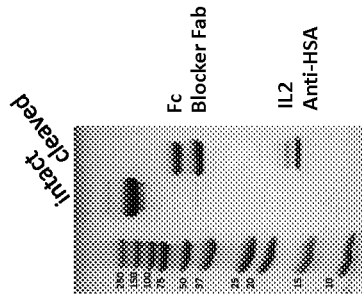
FIG. 59Z

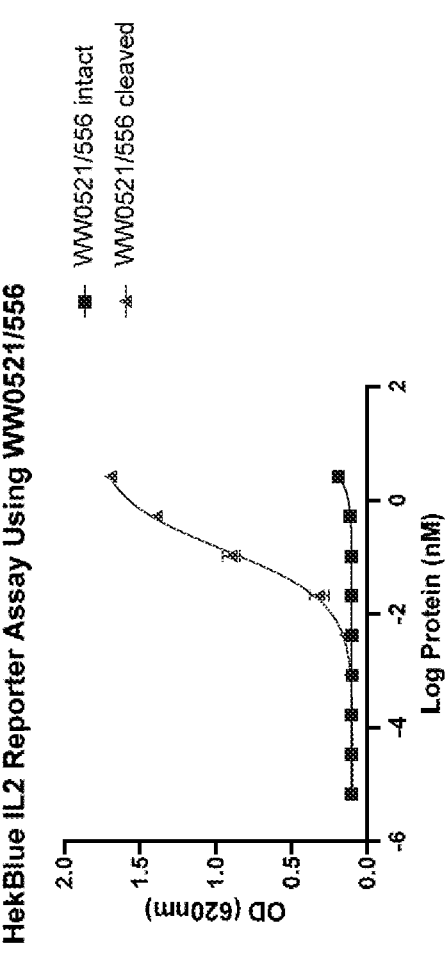
FIG. 59AA
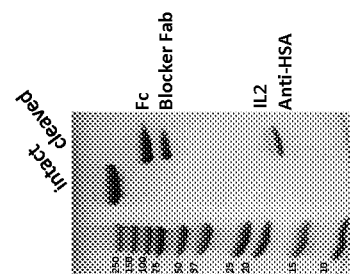

1

ACTIVATABLE CYTOKINE POLYPEPTIDES AND METHODS OF USE THEREOF

RELATED APPLICATIONS

This application is a continuation of Ser. No. 18/312,245, filed May 4, 2023, which is a continuation of Ser. No. 17/208,643, filed Sep. 22, 2020, which is a continuation-in-part of PCT/US2019/032320, filed on May 14, 2019, which claims the benefit of U.S. Provisional Application 62/671,225, filed on May 14, 2018, U.S. Provisional Application No. 62/756,504, filed on Nov. 6, 2018, U.S. Provisional Application No. 62/756,507, filed on Nov. 6, 2018, and U.S. Provisional Application No. 62/756,515, filed on Nov. 6, 2018; and claims the benefit of U.S. Provisional Application No. 62/935,605, filed on Nov. 14, 2019, each of which are incorporated herein by reference in their entireties.

SEQUENCE LISTING

The instant application contains a Sequence Listing which has been submitted electronically in XML format and is hereby incorporated by reference in its entirety. Said XML file, created on May 4, 2023, is named 761146.200011_SL.xml and is 618,247 bytes in size.

BACKGROUND

The development of mature immunocompetent lymphoid cells from less-committed precursors, their subsequent antigen-driven immune responses, and the suppression of these and unwanted autoreactive responses are highly dependent and regulated by cytokines (including interleukin-2 [IL-2], IL-4, IL-7, IL-9, IL-15, and IL-21) that utilize receptors in the common γ-chain (γc) family (Rochman et al., 2009) and family members including IL-12, 18 and 23. IL-2 is essential for thymic development of Treg cells and critically regulates several key aspects of mature peripheral Treg and antigen-activated conventional T cells. Because of its potent T cell growth factor activity in vitro, IL-2 has been extensively studied in part because this activity offered a potential means to directly boost immunity, e.g., in cancer and AIDS-HIV patients, or a target to antagonize unwanted responses, e.g., transplantation rejection and autoimmune diseases. Although in vitro studies with IL-2 provided a strong rationale for these studies, the function of IL-2 in vivo is clearly much more complex as first illustrated in IL-2-deficient mice, where a rapid lethal autoimmune syndrome, not lack of immunity, was observed (Sadlack et al., 1993, 1995). Similar observations were later made when the gene encoding IL-2Rα (Il2ra) and IL-2Rβ (Il2rb) were individually ablated (Suzuki et al., 1995; Willerford et al., 1995).

The present invention refers to conditionally active and/or targeted cytokines for use in the treatment of cancer and other diseases dependent on immune up or down regulation. For example, the antitumoral activity of some cytokines is well known and described and some cytokines have already been used therapeutically in humans. Cytokines such as interleukin-2 (IL-2) and interferon α (IFNα) have shown positive antitumoral activity in patients with different types of tumors, such as kidney metastatic carcinoma, hairy cell leukemia, Kaposi sarcoma, melanoma, multiple myeloma, and the like. Other cytokines like IFNβ, the Tumor Necrosis Factor (TNF) α, TNFβ, IL-1, 4, 6, 12, 15 and the CSFs have shown a certain antitumoral activity on some types of tumors and therefore are the object of further studies.

2

SUMMARY

Provided herein are therapeutic proteins, nucleic acids that encode the proteins, and compositions and methods of using the proteins and nucleic acids for the treatment of a disease or disorder, such as proliferative disease, a tumorous disease, an inflammatory disease, an immunological disorder, an autoimmune disease, an infectious disease, a viral disease, an allergic reaction, a parasitic reaction, graft-versus-host disease and the like. In certain embodiments, the protein is one or more of, including any combinations, SEQ ID NOs.: 193-271 and the protein referred to herein as:

ACP200
ACP201
ACP202
ACP203
ACP204
ACP205
ACP206
ACP207
ACP208
ACP211
ACP213
ACP214
ACP215
ACP240
ACP241
ACP242
ACP243
ACP244
ACP245
ACP247
ACP284
ACP285
ACP286
ACP287
ACP288
ACP289
ACP290
ACP291
ACP292
ACP296
ACP297
ACP298
ACP299
ACP300
ACP302
ACP303
ACP304
ACP305
ACP306
ACP309
ACP310
ACP311
ACP312
ACP313
ACP314
ACP336
ACP337
ACP338
ACP339
ACP340
ACP341
ACP342
ACP343
ACP344
ACP345
ACP346
ACP347
ACP348
ACP349
ACP350
ACP351
ACP352
ACP353
ACP354
ACP355

-continued

ACP356
ACP357
ACP358
ACP359
ACP371
ACP372
ACP373
ACP374
ACP375
ACP376
ACP377
ACP378
ACP379
ACP383
ACP384
ACP385
ACP386
ACP387
ACP388
ACP389
ACP390
ACP391
ACP392
ACP393
ACP394
ACP395
ACP396
ACP397
ACP398
ACP399
ACP400
ACP401
ACP402
ACP403
ACP404
ACP405
ACP406
ACP407
ACP408
ACP409
ACP410
ACP411
ACP412
ACP413
ACP414
ACP415
ACP416
ACP417
ACP418
ACP419
ACP420
ACP421
ACP422
ACP423
ACP424
ACP425
ACP426
ACP427
ACP428
ACP429
ACP430
ACP431
ACP432
ACP433
ACP434
ACP439
ACP440
ACP441
ACP442
ACP443
ACP444
ACP445
ACP446
ACP447
ACP451
ACP452
ACP453
ACP454
ACP455

-continued

ACP456
ACP457
ACP458
ACP459
ACP460
ACP461
ACP462
ACP463
ACP464
ACP465
ACP466
ACP467
ACP468
ACP469
ACP470
ACP471

The invention features fusion proteins that are conditionally active variants of a cytokine of interest. In one aspect, the full-length polypeptides of the invention have reduced or minimal cytokine-receptor activating activity even though they contain a functional cytokine polypeptide. Upon activation, e.g., by cleavage of a linker that joins a blocking moiety, e.g. a steric blocking polypeptide, in sequence to the active cytokine, the cytokine, e.g., IL-2, IL-7, IL-12, IL-15, IL-18, IL-21, IL-23, IFNalpha, IFNbeta, IFNgamma, TNFalpha, lymphotoxin, TGF-beta1, TGFbeta2, TGFbeta3, GM-CSF, CXCL10, CCL19, CCL20, CCL21 or functional fragment or mutein of any of the foregoing, can bind its receptor and effect signaling. If desired, the full-length polypeptides can include a blocking polypeptide moiety that also provides additional advantageous properties. For example, the full-length polypeptide can contain a blocking polypeptide moiety that also extends the serum half-life and/or targets the full-length polypeptide to a desired site of cytokine activity. Alternatively, the full-length fusion polypeptides can contain a serum half-life extension element and/or targeting domain that are distinct from the blocking polypeptide moiety. Preferably, the fusion protein contains at least one element or domain capable of extending in vivo circulating half-life. Preferably, this element is removed enzymatically in the desired body location (e.g. protease cleavage in the tumor microenvironment), restoring pharmacokinetic properties to the payload molecule (e.g. IL2 or IFNa) substantially similar to the naturally occurring payload molecule. The fusion proteins may be targeted to a desired cell or tissue. As described herein targeting is accomplished through the action of a blocking polypeptide moiety that also binds to a desired target, or through a targeting domain. The domain that recognizes a target antigen on a preferred target (for example a tumor-specific antigen), may be attached to the cytokine via a cleavable or non-cleavable linker. If attached by a non-cleavable linker, the targeting domain may further aid in retaining the cytokine in the tumor, and it may be considered a retention domain. The targeting domain does not necessarily need to be directly linked to the payload molecule, and it may be linked directly to another element of the fusion protein. This is especially true if the targeting domain is attached via a cleavable linker.

In one aspect is provided a fusion polypeptide comprising a cytokine polypeptide, or functional fragment or mutein thereof, and a blocking moiety, e.g. a steric blocking domain. The blocking moiety is fused to the cytokine polypeptide, directly or through a linker, and can be separated from the cytokine polypeptide by cleavage (e.g, protease mediated cleavage) of the fusion polypeptide at or near the fusion site or linker or in the blocking moiety. For example, when the cytokine polypeptide is fused to a blocking moiety through a linker that contains a protease cleavage site, the cytokine polypeptide is released from the blocking moiety and can bind its receptor, upon protease mediated cleavage of the linker. The linker is designed to be cleaved at the site of desired cytokine activity, for example in the tumor microenvironment, avoiding off-target cytokine activity and reducing overall toxicity of cytokine therapy.

The blocking moiety can also function as a serum half-life extension element. In some embodiments, the fusion polypeptide further comprises a separate serum half-life extension element. In some embodiments, the fusion polypeptide further comprises a targeting domain. In various embodiments, the serum half-life extension element is a water-soluble polypeptide such as optionally branched or multi-armed polyethylene glycol (PEG), full length human serum albumin (HSA) or a fragment that preserves binding to FcRn, an Fc fragment, or a nanobody that binds to FcRn directly or to human serum albumin.

In addition to serum half-life extension elements, the pharmaceutical compositions described herein preferably comprise at least one, or more targeting domains that bind to one or more target antigens or one or more regions on a single target antigen. It is contemplated herein that a polypeptide construct of the invention is cleaved, for example, in a disease-specific microenvironment or in the blood of a subject at the protease cleavage site and that the targeting domain(s) will bind to a target antigen on a target cell. At least one target antigen is involved in and/or associated with a disease, disorder or condition. Exemplary target antigens include those associated with a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

In some embodiments, a target antigen is a cell surface molecule such as a protein, lipid or polysaccharide. In some embodiments, a target antigen is a on a tumor cell, virally infected cell, bacterially infected cell, damaged red blood cell, arterial plaque cell, or fibrotic tissue cell.

Target antigens, in some cases, are expressed on the surface of a diseased cell or tissue, for example a tumor or a cancer cell. Target antigens for tumors include but are not limited to Fibroblast activation protein alpha (FAPa), Trophoblast glycoprotein (5T4), Tumor-associated calcium signal transducer 2 (Trop2), Fibronectin EDB (EDB-FN), fibronectin EIIIB domain, CGS-2, EpCAM, EGFR, HER-2, HER-3, c-Met, FOLR1, FAP, and CEA. Pharmaceutical compositions disclosed herein, also include proteins comprising two antigen binding domains that bind to two different target antigens known to be expressed on a diseased cell or tissue. Exemplary pairs of antigen binding domains include but are not limited to EGFR/CEA, EpCAM/CEA, and HER-2/HER-3.

In some embodiments, the targeting polypeptides independently comprise a scFv, a VH domain, a VL domain, a non-Ig domain, or a ligand that specifically binds to the target antigen. In some embodiments, the targeting polypeptides specifically bind to a cell surface molecule. In some embodiments, the targeting polypeptides specifically bind to a tumor antigen. In some embodiments, the targeting polypeptides specifically and independently bind to a tumor antigen selected from at least one of EpCAM, EGFR, HER-2, HER-3, cMet, CEA, and FOLR1. In some embodiments, the targeting polypeptides specifically and independently bind to two different antigens, wherein at least one of the antigens is a tumor antigen selected from EpCAM, EGFR, HER-2, HER-3, cMet, CEA, and FOLR1. In some embodiments, the targeting polypeptide serves as a retention domain and is attached to the cytokine via a non-cleavable linker.

As described herein, the cytokine blocking moiety can bind to the cytokine and thereby block activation of the cognate receptor of the cytokine.

This disclosure also related to nucleic acids, e.g., DNA, RNA, mRNA, that encode the conditionally active proteins described herein, as well as vectors and host cells that contain such nucleic acids.

This disclosure also relates to pharmaceutical compositions that contain a conditionally active protein, nucleic acid that encodes the conditionally active protein, and vectors and host cells that contain such nucleic acids. Typically, the pharmaceutical composition contains one or more physiologically acceptable carriers and/or excipients.

The disclosure also relates to therapeutic methods that include administering to a subject in need thereof an effective amount of a conditionally active protein, nucleic acid that encodes the conditionally active protein, vector or host cells that contain such a nucleic acid, and pharmaceutical compositions of any of the foregoing. Typically, the subject has, or is at risk of developing, a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

The disclosure also relates to the use of a conditionally active protein, nucleic acid that encodes the conditionally active protein, vector or host cells that contain such a nucleic acid, and pharmaceutical compositions of any of the foregoing, for treating a subject in need thereof. Typically the subject has, or is at risk of developing, a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

The disclosure also relates to the use of a conditionally active protein, nucleic acid that encodes the conditionally active protein, vector or host cells that contain such a nucleic acid for the manufacture of a medicament for treating a disease, such as a proliferative disease, a tumorous disease, an inflammatory disease, an immunological disorder, an autoimmune disease, an infectious disease, a viral disease, an allergic reaction, a parasitic reaction, a graft-versus-host disease or a host-versus-graft disease.

BRIEF DESCRIPTION OF THE DRAWINGS

FIG. 1B is a schematic illustrating a protease-activated cytokine or chemokine wherein HSA (blocking moiety) is directly bound to the cytokine or chemokine of interest, with a protease cleavage site between the HSA and a cytokine or chemokine of interest. To the left of the arrow the drawing shows that a cytokine is connected to a blocking moiety via a protease-cleavable linker, thus blocking its ability to bind to its receptor. To the right of the arrow the drawing shows that in an inflammatory or tumor environment, the protease cleaves at a protease-cleavage site on linker, releasing the blocking moiety and allowing the cytokine to bind to its receptor.

FIG. 1C is a schematic illustrating a protease-activated cytokine or chemokine wherein more than one HSA (blocking moiety) is bound directly to the molecule of interest. If desired, one or more of the HSA can be bonded to the cytokine or chemokine through a linker, such as a linker that contains a protease cleavage site. To the left of the arrow the drawing shows that a cytokine is connected to a blocking moiety via a protease-cleavable linker, thus blocking its ability to bind to its receptor. To the right of the arrow the drawing shows that in an inflammatory or tumor environment, protease cleaves at protease-cleavage site on linker, releasing the blocking moiety and allowing cytokine to bind receptor. The cytokine now has similar pK properties as compared to the native cytokine (e.g., has a short half-life).

FIG. 1D is a schematic illustrating a protease-activated cytokine or chemokine comprising more than one cytokine, of the same type or different type, each of which is bonded to a binding domain through a protease-cleavable linker. To the left of the arrow the drawing shows that a cytokine is connected to a blocking moiety via a protease-cleavable linker, thus blocking its ability to bind to its receptor. To the right of the arrow the drawing shows that in an inflammatory or tumor environment a protease cleaves at a protease cleavage site on linker, releasing the blocking moiety and allowing the cytokine to bind to its receptor.

FIG. 4B is a schematic illustrating a protease-activated cytokine or chemokine comprising a cytokine or chemokine polypeptide, a blocking moiety, a targeting domain, and a serum half-life extending domain connected by at least one protease-cleavable linker. To the left of the arrow, the drawing shows that a cytokine is connected to targeting domain, a blocking moiety, and a half-life extension element via protease-cleavable linker(s), thus blocking its ability to bind to its receptor. To the right of the arrow the drawing shows that in an inflammatory or tumor environment, the protease cleaves at a protease-cleavage site on linker(s), releasing the half-life extension element and the blocking moiety and allowing the cytokine to bind to the receptor. The targeting moiety remains bound, keeping the cytokine in the tumor microenvironment. The cytokine now has similar pK properties as compared to the native cytokine (e.g., a short half-life).

FIG. 6. Place holder

FIGS. 7A-7H are a series of graphs showing activity of exemplary IL-2 fusion proteins in IL-2 dependent cytotoxic T lymphocyte cell line CTLL-2. Each graph shows results of the IL-2 proliferation assay as quantified by CellTiter-Glo® (Promega) luminescence-based cell viability assay. Each proliferation assay was performed with HSA (FIGS. 7B, 7D, 7F, 7H) or without (FIGS. 7A, 7C, 7E, 7G). Each fusion protein comprises an anti-HSA binder, and both uncleaved and MMP9 protease cleaved versions of the fusion protein were used in each assay.

FIGS. 12A-12F show a series of graphs depicting the results of HEK-blue assay of four IL-12 fusion proteins, before and after cleavage by MMP9. Analysis was performed based on quantification of Secreted Alkaline Phosphatase (SEAP) activity using the reagent QUANTI-Blue (InvivoGen). The data show greater activity in the cleaved IL12 than in the full fusion protein. Constructs tested were ACP06 (FIG. 12A), ACP07 (FIG. 12C), ACP08 (FIG. 12B), ACP09 (FIG. 12D), ACP10 (FIG. 12E), ACP11 (FIG. 12F).

FIGS. 15A-15D are graphs depicting results from a HEK-Blue assay performed on human p40/murine p35 IL12 fusion proteins before and after protease cleavage. Results confirm that IL12 protein fusion proteins are active. Each proliferation assay was performed with HSA or without HSA.

FIGS. 17A-17F are a series of graphs showing activity of exemplary IFNγ fusion proteins compared to activity of mouse IFNγ control using B16 reporter assay. Each assay was performed with medium containing HSA (+HSA) or not containing HSA (−HSA). Each fusion protein comprises an anti-HSA binder, and both uncleaved and MMP9 protease cleaved versions of the fusion protein were used in each assay.

FIG. 18A) and ACP55 (IFN-γ fusion protein; 18B), were run on an SDS-PAGE gel in both cleaved and uncleaved form. As can be seen in the gel, cleavage was complete.

FIGS. 21A-C show the effect of IFNγ and IFNγ fusion proteins on tumor growth when injected intraperitoneally (IP) using different dosing levels and schedules (ug=micrograms, BID=twice daily, BIW=twice weekly, QW=weekly). FIG. 21D shows the effect of intratumoral (IT) injection of IFNγ and IL-2 on tumor growth.

FIGS. 22A-22B are a series of graphs showing activity of exemplary IFNγ fusion proteins (ACP51 (FIG. 22A), and ACP52 (FIG. 22B)) cleaved by MMP9 protease compared to activity of uncleaved fusion proteins using B16 reporter assay. Each fusion protein comprises an anti-HSA binder and a tumor targeting domain.

FIGS. 24A-24D are graphs depicting results from a HEK-Blue IL-2 reporter assay performed on IL-2 fusion proteins and recombinant human IL2 (Rec hIL-2). Analysis was performed based on quantification of Secreted Alkaline Phosphatase (SEAP) activity using the reagent QUANTI-Blue (InvivoGen). FIG. 24A shows results of IL-2 constructs ACP132 and ACP 133 with and without albumin. FIG. 24B shows results of IL-2 construct ACP16 cleaved and uncleaved. Results of a protein cleavage assay of ACP16 in cleaved and uncleaved forms is also depicted. FIG. 24C shows results of IL-2 construct ACP153 in cleaved and uncleaved forms. Results of a protein cleavage assay are also depicted. FIG. 24D illustrates the results from a HEK-Blue IL-2 assay using wild-type cytokine, intact fusion protein, and protease-cleaved fusion protein.

FIG. 25C is a graph showing results of a CTLL-2 proliferation assay. CTLL2 cells (ATCC) were plated in suspension at a concentration of 500,000 cells/well in culture media with or without 40 mg/ml human serum albumin (HSA) and stimulated with a dilution series of activatable hIL2 for 72 hours at 37° C. and 5% $CO_2$. Activity of uncleaved and cleaved activatable ACP16 was tested. Cleaved activatable hIL2 was generated by incubation with active MMP9. Cell activity was assessed using a CellTiter-Glo (Promega) luminescence-based cell viability assay. Circles depict intact fusion protein, and squares depict protease-cleaved fusion protein.

FIG. 26A depicts IL-12/STAT4 activation in a comparison of ACP11 (a human p40/murine p35 IL12 fusion protein) to ACP04 (negative control). FIG. 26B is a graph showing analysis of ACP91 (a chimeric IL-12 fusion protein). Squares depict activity of the uncut ACP91 polypeptide, and triangles depict the activity of the cut polypeptide (ACP91+ MMP9). EC50 values for each are shown in the table. FIG. 26C is a graph showing analysis of ACP136 (a chimeric IL-12 fusion protein). Squares depict activity of the uncut ACP136 polypeptide, and triangles depict the activity of the cut polypeptide (ACP136+MMP9). EC50 values for each are shown in the table insert.

FIGS. 27A-27F are a series of graphs showing that cleaved mouse IFNα1 polypeptides ACP31 (FIG. 27A), ACP125 (FIG. 27B), ACP126 (FIG. 27C) are active in an B16-Blue IFN-α/β reporter assay.

FIGS. 29A-29B are two graphs showing results of analyzing ACP31 (mouse IFNα1 fusion protein) and ACP11 (a human p40/murine p35 IL12 fusion protein) in a tumor xenograft model. FIG. 29A shows tumor volume over time in mice treated with 33 µg ACP31 (circles), 110 µg ACP31 (triangles), 330 µg ACP31 (diamonds), and as controls 1 µg murine wild type IFNα1 (dashed line, squares) and 10 µg mIFNα1 (dashed line, small circles). Vehicle alone is indicated by large open circles. The data show tumor volume decreasing over time in a dose-dependent manner in mice treated with ACP31. FIG. 29B shows tumor volume over time in mice treated with 17.5 µg ACP11 (squares), 175 µg ACP31 (triangles), 525 µg ACP31 (circles), and as controls 2 µg ACP04 (dashed line, triangles) and 10 µg ACP04 (dashed line, diamonds). Vehicle alone is indicated by large open circles. The data show tumor volume decreasing over time in a dose-dependent manner in mice treated with both ACP11 and ACP04 (a human p40/murine p35 IL12 fusion protein).

FIGS. 30A-30F are a series of spaghetti plots showing tumor volume over time in a mouse xenograft tumor model in mice each treated with vehicle alone (FIG. 30A), 2 µg ACP04 (FIG. 30B), 10 µg ACP04 (FIG. 30C, 17.5 µg ACP11 (FIG. 30D), 175 µg ACP11 (FIG. 30E), and 525 µg ACP11 (FIG. 30F). Each line represents a single mouse.

FIG. 31A shows tumor volume over time in mice treated with 4.4 µg ACP16 (squares), 17 µg ACP16 (triangles), 70 µg ACP16 (downward triangles), 232 µg ACP16 (dark circles), and as a comparator 12 µg wild type IL-2 (dashed line, triangles) and 36 µg wild type IL-2 (dashed line, diamonds). Vehicle alone is indicated by large open circles. The data show tumor volume decreasing over time in a dose-dependent manner in mice treated with ACP16 at higher concentrations. FIG. 31B shows tumor volume over time in mice treated with 17 µg ACP124 (squares), 70 µg ACP124 (triangles), 230 µg ACP124 (downward triangles), and 700 µg ACP124. Vehicle alone is indicated by large open circles. FIG. 31C shows tumor volume over time in mice treated with 17 µg ACP16 (triangles), 70 µg ACP16 (circles), 232 µg ACP16 (dark circles), and as a comparator 17 µg ACP124 (dashed line, triangles) 70 µg ACP124 (dashed line, diamonds), 230 µg ACP124 (dashed line, diamonds). Vehicle alone is indicated by dark downward triangles. The data show tumor volume decreasing over time in a dose-dependent manner in mice treated with ACP16, but not ACP124.

FIG. 32A Place holder

FIG. 34A shows data for mice treated with vehicle alone (gray line), 17 µg ACP16 (dark line), and 17 µg ACP124 (dashed line). FIG. 34B shows data for mice treated with vehicle alone (gray line), 70 µg ACP16 (dark line), and 70 µg ACP124 (dashed line). FIG. 34C shows data for mice treated with vehicle alone (gray line), 232 µg ACP16 (dark line), and 230 µg ACP124 (dashed line). FIG. 34D shows data for mice treated with vehicle alone (gray line), 232 µg ACP16 (dark line), and 700 µg ACP124 (dashed line).

FIGS. 35A-35B a series of spaghetti plots showing activity of fusion proteins in an MC38 mouse xenograft model. All mouse groups were given four doses total except for the highest three doses of APC132, wherein fatal toxicity was detected after 1 week/2 doses. Shown are vehicle alone, 17, 55, 70, and 230 µg ACP16, 9, 28, 36, and 119 µg ACP132, and 13, 42, 54, and 177 µg ACP21. Each line in the plots represents an individual animal.

FIGS. 36-41 Place holder

FIGS. 42A-42E shows the results of B16 IFN reporter assays. Inducible interferon constructs of interest were tested before and after cleavage. The relevant wildtype IFN was tested as a control.

FIG. 43 shows binding data of ACP16, ACP10, ACP11

FIGS. 44A-44D depict the activity of cytokine fusion proteins constructs ACP243, ACP244, ACP243, ACP244, and ACP247.

FIGS. 45A-45B shows a series of spider plots showing tumor volume over time during treatment with vehicle, IL-12, ACP11 or ACP10.

FIGS. 46A-46D, 47A-47D, 48A-48B, 49A-49I, 50A-50B and 51A-51C shows data (tumor volume and/or body weight) for mice treated with cytokine fusion proteins constructs.

Figure 56:
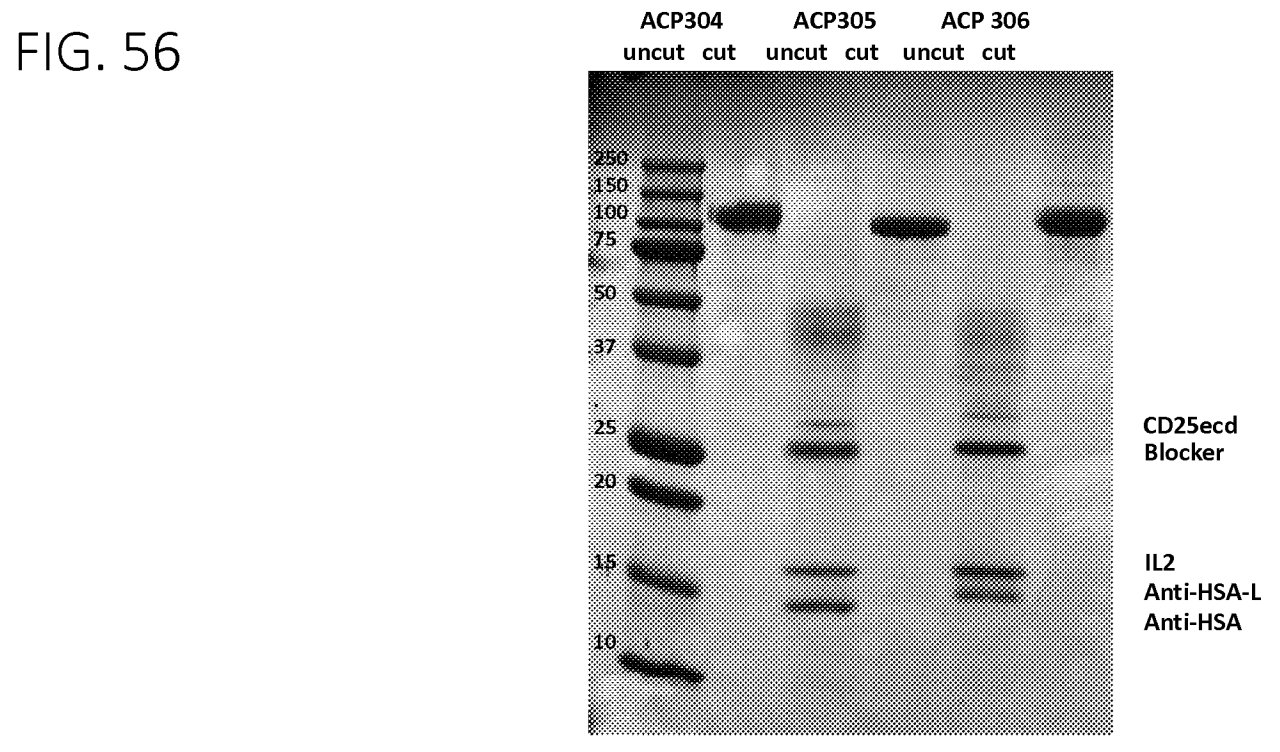
Figure 59W:
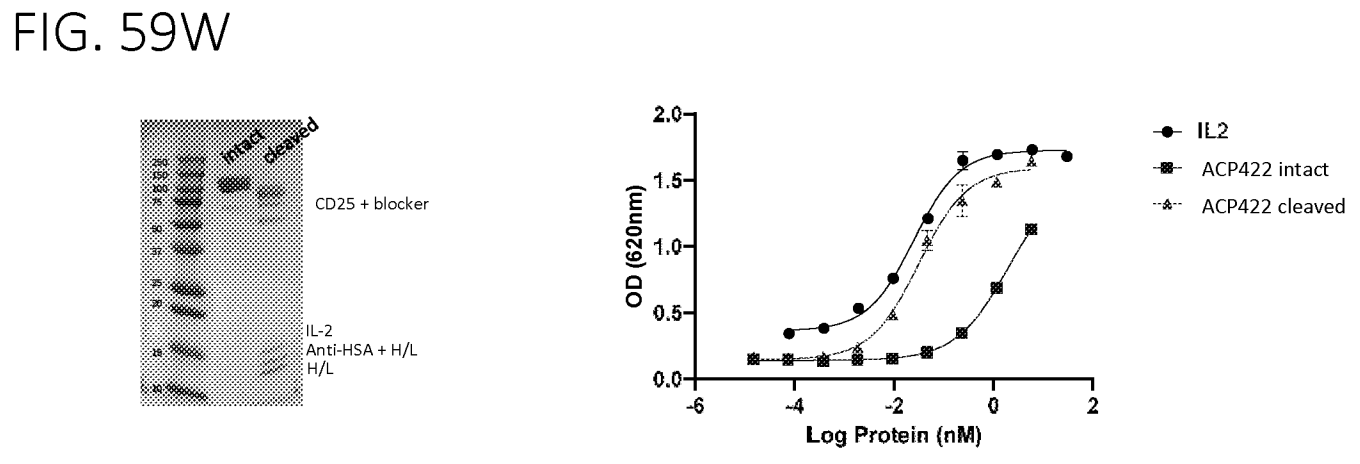

FIGS. 56, 57A-57D, 58, 59A-59C, 59E-59Z and 59AA depict the activity of cytokine fusion proteins constructs.

DETAILED DESCRIPTION

Figure 1A:
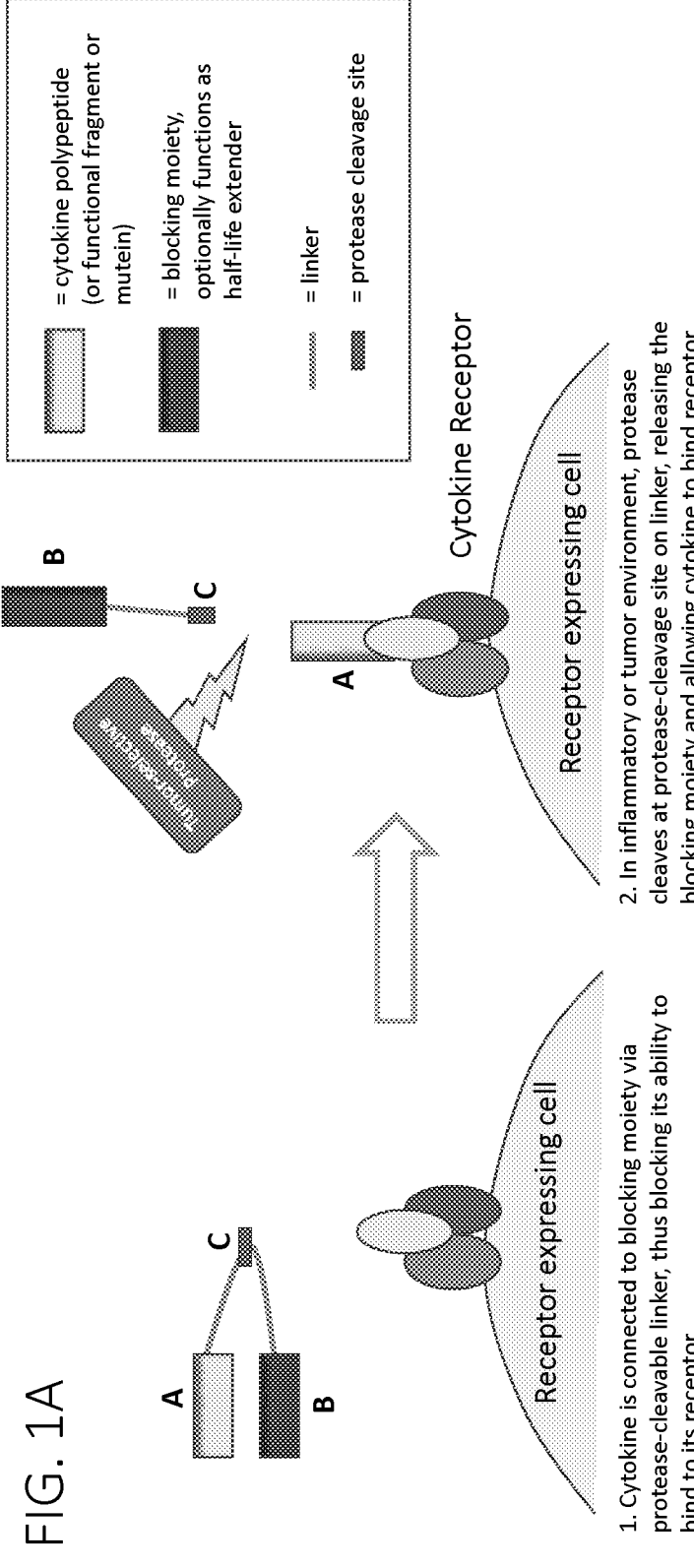
FIG. 1A is a schematic illustrating a protease-activated cytokine or chemokine that includes a blocking moiety. The blocking moiety may optionally function as a serum half-life extending domain. To the left of the arrow the drawing shows that a cytokine is connected to a blocking moiety via a protease-cleavable linker, thus blocking its ability to bind to its receptor. To the right of the arrow the drawing shows that in an inflammatory or tumor environment a protease cleaves at a protease-cleavage site on the linker, releasing the blocking moiety and allowing the cytokine to bind to its receptor.
Figure 2:
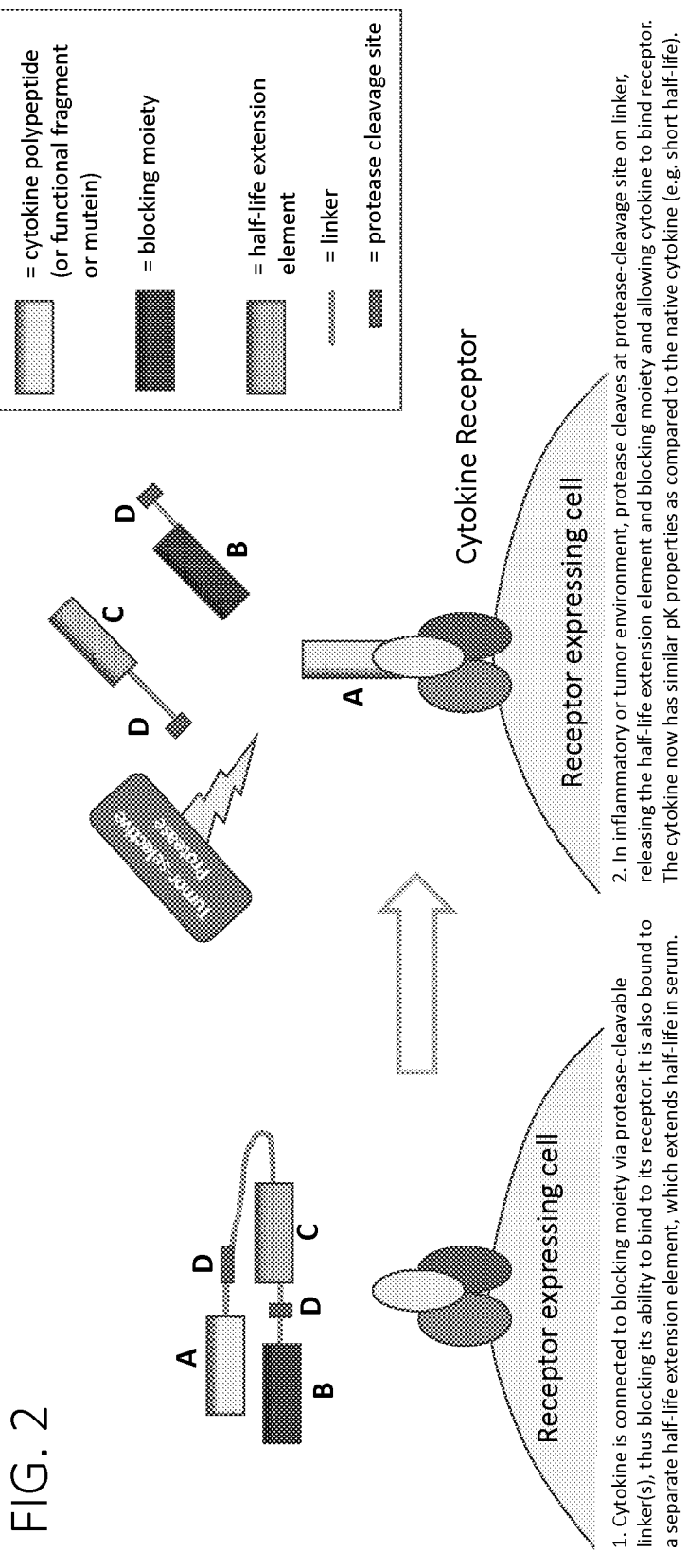
FIG. 2 is a schematic illustrating a protease-activated cytokine or chemokine comprising a cytokine or chemokine polypeptide, a blocking moiety, and a serum half-life extending domain connected by at least one protease-cleavable linker. To the left of the arrow the drawing shows that a cytokine is connected to a blocking moiety via protease-cleavable linkers, thus blocking its ability to bind to its receptor. It is also bound to a separate half-life extension element, which extends half-life in serum. To the right of the arrow the drawing shows that in an inflammatory or tumor environment a protease cleaves at a protease-cleavage site on linker, thus releasing the serum half-life extension element and the blocking moiety and allowing the cytokine to bind to its receptor. The cytokine now has similar pK properties as compared to the native cytokine (e.g., a short half-life).
Figure 3:
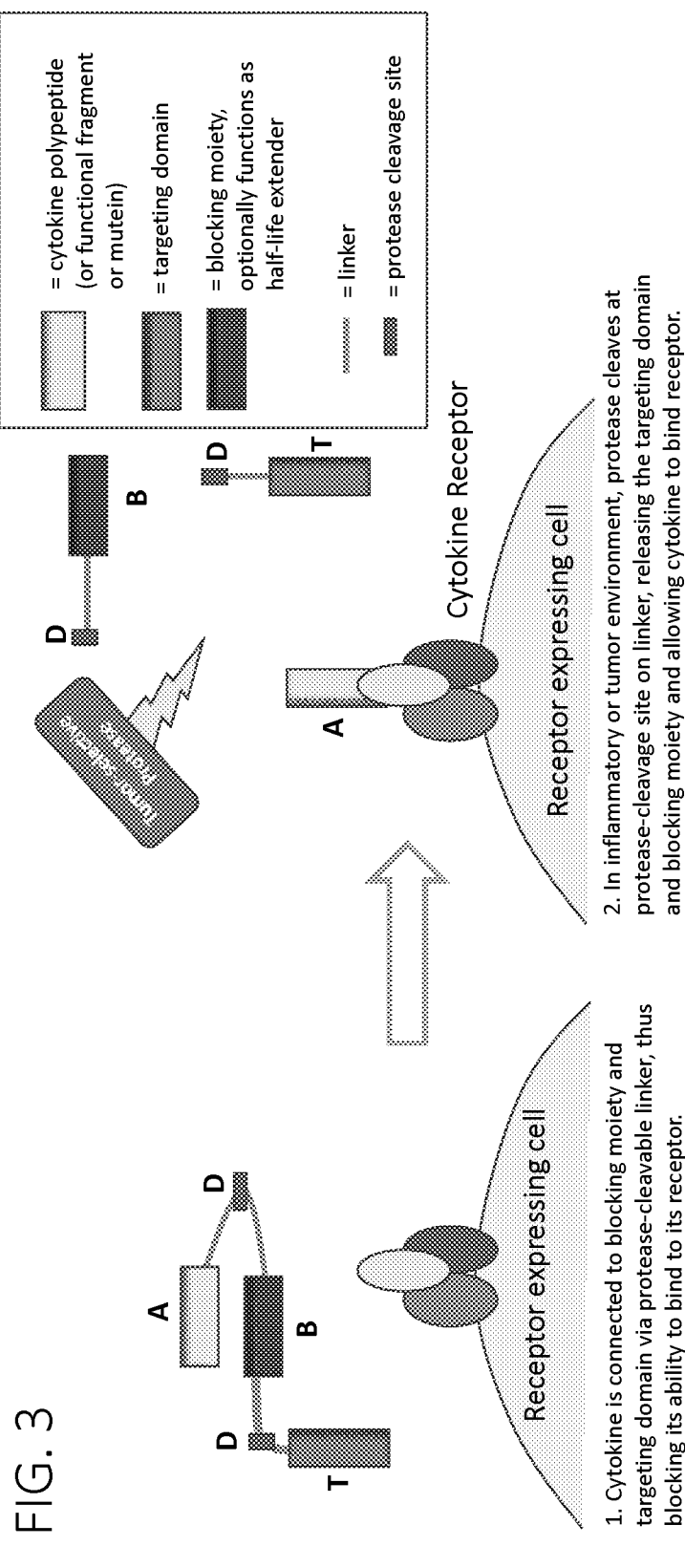
FIG. 3 is a schematic illustrating a protease-activated cytokine or chemokine comprising a cytokine or chemokine polypeptide, a blocking moiety, and a targeting domain connected by at least one protease-cleavable linker. To the left of the arrow the drawing shows that a cytokine is connected to a blocking moiety and a targeting domain via a protease-cleavable linker, thus blocking its ability to bind to its receptor. To the right of the arrow the drawing shows that in an inflammatory or tumor microenvironment a protease cleaves at the protease cleavage site in the linker, releasing the targeting domain and the blocking moiety and allowing the cytokine to bind to its receptor.
Figure 4A:
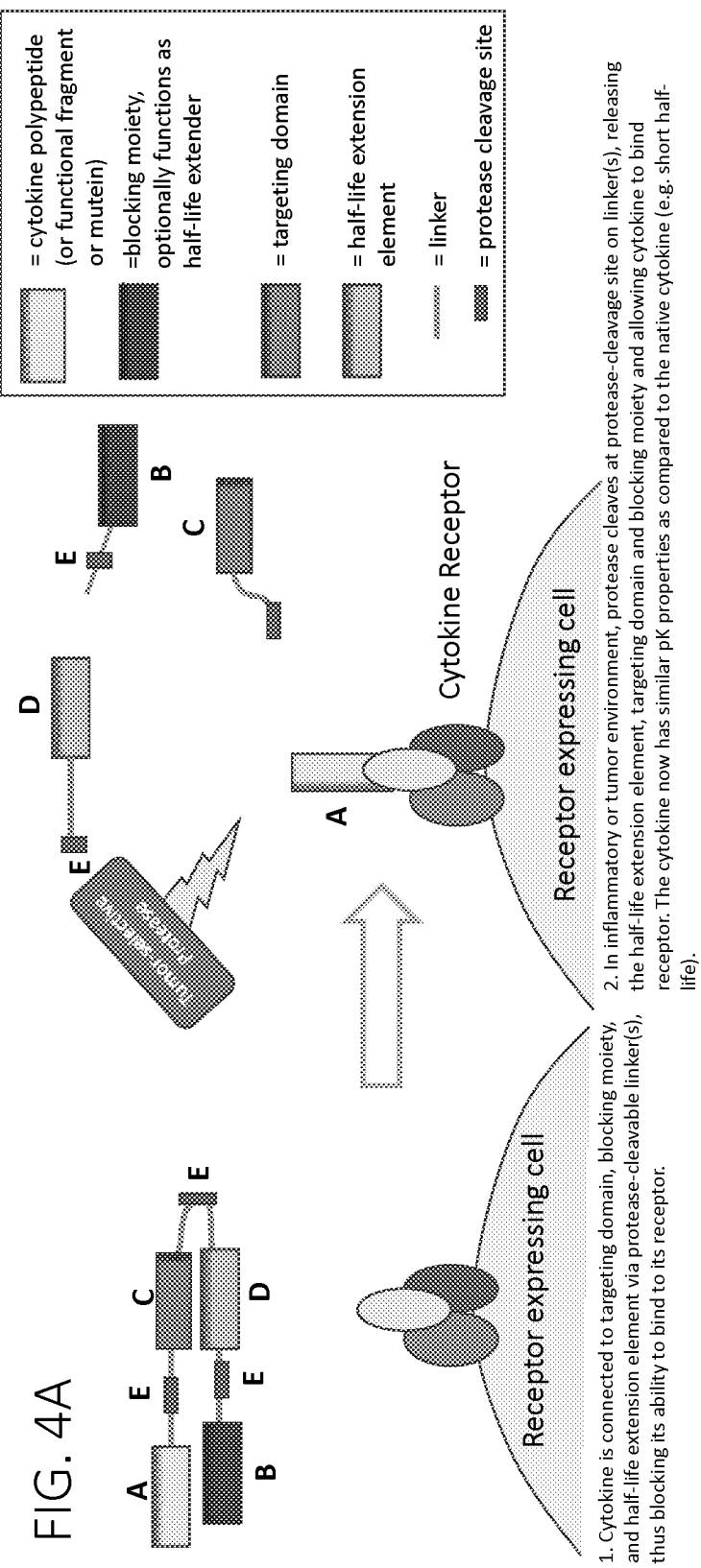
FIG. 4A is a schematic illustrating a protease-activated cytokine or chemokine comprising a cytokine or chemokine polypeptide, a blocking moiety, a targeting domain, and a serum half-life extending domain connected by at least one protease-cleavable linker, wherein the cytokine polypeptide and the targeting domain are connected by a protease-cleavable linker. To the left of the arrow, the drawing shows that a cytokine polypeptide is connected to targeting domain, blocking moiety, and half-life extension element via protease-cleavable linker(s), thus blocking its ability to bind to its receptor. To the right of the arrow the drawing shows that in an inflammatory or tumor environment, the protease cleaves at a protease-cleavage site on linker(s), releasing the half-life extension element, the targeting domain, and the blocking moiety, and allowing the cytokine to bind to its receptor. The cytokine now has similar pK properties as compared to the native cytokine (e.g., short half-life).

Disclosed herein are methods and compositions to engineer and use constructs comprising inducible cytokines. Cytokines are potent immune agonists, which lead to them being considered promising therapeutic agents for oncology. However, cytokines proved to have a very narrow therapeutic window. Cytokines have short serum half-lives and are also considered to be highly potent. Consequently, therapeutic administration of cytokines produced undesirable systemic effects and toxicities. These were exacerbated by the need to administer large quantities of cytokine in order to achieve the desired levels of cytokine at the intended site of cytokine action (e.g., a tumor). Unfortunately, due to the biology of cytokines and inability to effectively target and control their activity, cytokines did not achieve the hoped-for clinical advantages in the treatment of tumors.

Disclosed herein are fusion proteins that overcome the toxicity and short half-life problems that have severely limited the clinical use of cytokines in oncology. The fusion proteins contain cytokine polypeptides that have receptor agonist activity. But in the context of the fusion protein, the cytokine receptor agonist activity is attenuated and the circulating half-life is extended. The fusion proteins include protease cleave sites, which are cleaved by proteases that are associated with a desired site of cytokine activity (e.g., a tumor), and are typically enriched or selectively present at the site of desired activity. Thus, the fusion proteins are preferentially (or selectively) and efficiently cleaved at the desired site of activity to limit cytokine activity substantially to the desired site of activity, such as the tumor microenvironment. Protease cleavage at the desired site of activity, such as in a tumor microenvironment, releases a form of the cytokine from the fusion protein that is much more active as a cytokine receptor agonist than the fusion protein (typically at least about 100× more active than the fusion protein). The form of the cytokine that is released upon cleavage of the fusion protein typically has a short half-life, which is often substantially similar to the half-life of the naturally occurring cytokine, further restricting cytokine activity to the tumor microenvironment. Even though the half-life of the fusion protein is extended, toxicity is dramatically reduced or eliminated because the circulating fusion protein is attenuated and active cytokine is targeted to the tumor microenvironment. The fusion proteins described herein, for the first time, enable the administration of an effective therapeutic dose of a cytokine to treat tumors with the activity of the cytokine substantially limited to the tumor microenvironment, and dramatically reduces or eliminates unwanted systemic effects and toxicity of the cytokine.

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 4th ed. (2012) Cold Spring Harbor Laboratory Press, Cold Spring Harbor, NY. As appropriate, procedures involving the use of commercially available kits and reagents are generally carried out in accordance with manufacturer-defined protocols and conditions unless otherwise noted.

"Cytokine" is a well-known term of art that refers to any of a class of immunoregulatory proteins (such as interleukin or interferon) that are secreted by cells especially of the immune system and that are modulators of the immune system. Cytokine polypeptides that can be used in the fusion proteins disclosed herein include, but are not limited to transforming growth factors, such as TGF-α and TGF-β (e.g., TGFbeta1, TGFbeta2, TGFbeta3); interferons, such as interferon-α, interferon-β, interferon-γ, interferon-kappa and interferon-omega; interleukins, such as IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21 and IL-25; tumor necrosis factors, such as tumor necrosis factor alpha and lymphotoxin; chemokines (e.g., C-X-C motif chemokine 10 (CXCL10), CCL19, CCL20, CCL21), and granulocyte macrophage-colony stimulating factor (GM-CS), as well as fragments of such polypeptides that active the cognate receptors for the cytokine (i.e., functional fragments of the foregoing). "Chemokine" is a term of art that refers to any of a family of small cytokines with the ability to induce directed chemotaxis in nearby responsive cells.

Cytokines are well-known to have short serum half-lives that frequently are only a few minutes or hours. Even forms of cytokines that have altered amino acid sequences intended to extend the serum half-life yet retain receptor agonist activity typically also have short serum half-lives. As used herein, a "short-half-life cytokine" refers to a cytokine that has a substantially brief half-life circulating in the serum of a subject, such as a serum half-life that is less than 10, less than 15, less than 30, less than 60, less than 90, less than 120, less than 240, or less than 480 minutes. As used herein, a short half-life cytokine includes cytokines which have not been modified in their sequence to achieve a longer than usual half-life in the body of a subject and polypeptides that have altered amino acid sequences intended to extend the serum half-life yet retain receptor agonist activity. This latter case is not meant to include the addition of heterologous protein domains, such as a bona fide half-life extension element, such as serum albumin.

"Sortases" are transpeptidases that modify proteins by recognizing and cleaving a carboxyl-terminal sorting signal embedded in or terminally attached to a target protein or peptide. Sortase A catalyzes the cleavage of the LPXTG motif (SEQ ID NO.: 442) (where X is any standard amino acid) between the Thr and Gly residue on the target protein, with transient attachment of the Thr residue to the active site Cys residue on the enzyme, forming an enzyme-thioacyl intermediate. To complete transpeptidation and create the peptide-monomer conjugate, a biomolecule with an N-terminal nucleophilic group, typically an oligoglycine motif, attacks the intermediate, displacing Sortase A and joining the two molecules.

As used herein, the term "steric blocker" refers to a polypeptide or polypeptide moiety that can be covalently bonded to a cytokine polypeptide directly or indirectly through other moieties such as linkers, for example in the form of a chimeric polypeptide (fusion protein), but otherwise does not covalently bond to the cytokine polypeptide. A steric blocker can non-covalently bond to the cytokine polypeptide, for example though electrostatic, hydrophobic, ionic or hydrogen bonding. A steric blocker typically inhibits or blocks the activity of the cytokine moiety due to its proximity to the cytokine moiety and comparative size. A steric blocker may also block by virtue of recruitment of a large protein binding partner. An example of this is an antibody which binds to serum albumin; while the antibody itself may or may not be large enough to block activation or binding on its own, recruitment of albumin allows for sufficient steric blocking.

As used and described herein, a "half-life extension element" is a part of the chimeric polypeptide that increases the serum half-life and improve pK, for example, by altering its size (e.g., to be above the kidney filtration cutoff), shape, hydrodynamic radius, charge, or parameters of absorption, biodistribution, metabolism, and elimination.

As used herein, the terms "activatable," "activate," "induce," and "inducible" refer to the ability of a protein, i.e. a cytokine, that is part of a fusion protein, to bind its receptor and effectuate activity upon cleavage of additional elements from the fusion protein.

As used herein, "plasmids" or "viral vectors" are agents that transport the disclosed nucleic acids into the cell without degradation and include a promoter yielding expression of the nucleic acid molecule and/or polypeptide in the cells into which it is delivered.

As used herein, the terms "peptide", "polypeptide", or "protein" are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more.

As used throughout, "subject" can be a vertebrate, more specifically a mammal (e.g. a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered.

As used herein, "patient" or "subject" may be used interchangeably and can refer to a subject with a disease or disorder (e.g. cancer). The term patient or subject includes human and veterinary subjects.

As used herein the terms "treatment", "treat", or "treating" refers to a method of reducing the effects of a disease or condition or symptom of the disease or condition. Thus, in the disclosed method, treatment can refer to at least about 10%, at least about 20%, at least about 30%, at least about 40%, at least about 50%, at least about 60%, at least about 70%, at least about 80%, at least about 90%, or substantially complete reduction in the severity of an established disease or condition or symptom of the disease or condition. For example, a method for treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms "prevent", "preventing", and "prevention" of a disease or disorder refers to an action, for example, administration of the chimeric polypeptide or nucleic acid sequence encoding the chimeric polypeptide, that occurs before or at about the same time a subject begins to show one or more symptoms of the disease or disorder, which inhibits or delays onset or exacerbation of one or more symptoms of the disease or disorder.

As used herein, references to "decreasing", "reducing", or "inhibiting" include a change of at least about 10%, of at least about 20%, of at least about 30%, of at least about 40%, of at least about 50%, of at least about 60%, of at least about 70%, of at least about 80%, of at least about 90% or greater as compared to a suitable control level. Such terms can include but do not necessarily include complete elimination of a function or property, such as agonist activity.

An "attenuated cytokine receptor agonist" is a cytokine receptor agonist that has decreased receptor agonist activity as compared to the cytokine receptor's naturally occurring agonist. An attenuated cytokine agonist may have at least about 10×, at least about 50×, at least about 100×, at least about 250×, at least about 500×, at least about 1000× or less agonist activity as compared to the receptor's naturally occurring agonist. When a fusion protein that contains a cytokine polypeptide as described herein is described as "attenuated" or having "attenuated activity", it is meant that the fusion protein is an attenuated cytokine receptor agonist.

An "intact fusion protein" is a fusion protein in which no domain has been removed, for example by protease cleavage. A domain may be removable by protease cleavage or other enzymatic activity, but when the fusion protein is "intact", this has not occurred.

As used herein "moiety" refers to a portion of a molecule that has a distinct function within that molecule, and that function may be performed by that moiety in the context of another molecule. A moiety may be a chemical entity with a particular function, or a portion of a biological molecule with a particular function. For example, a "blocking moiety" within a fusion protein is a portion of the fusion protein which is capable of blocking the activity of some or all of the fusion polypeptide. This may be a protein domain, such as serum albumin. Blocking may be accomplished by a steric blocker or a specific blocker. A steric blocker blocks by virtue of size and position and not based upon specific binding; an examples is serum albumin. A specific blocker blocks by virtue of specific interactions with the moiety to be blocked. A specific blocker must be tailored to the particular cytokine or active domain; a steric blocker can be used regardless of the payload, as long as it is large enough.

In general, the therapeutic use of cytokines is strongly limited by their systemic toxicity. TNF, for example, was originally discovered for its capacity of inducing the hemorrhagic necrosis of some tumors, and for its in vitro cytotoxic effect on different tumoral lines, but it subsequently proved to have strong pro-inflammatory activity, which can, in case of overproduction conditions, dangerously affect the human body. As the systemic toxicity is a fundamental problem with the use of pharmacologically active amounts of cytokines in humans, novel derivatives and therapeutic strategies are now under evaluation, aimed at reducing the toxic effects of this class of biological effectors while keeping their therapeutic efficacy.

IL-2 exerts both stimulatory and regulatory functions in the immune system and is, along with other members of the common γ chain (γc) cytokine family, central to immune homeostasis. IL-2 mediates its action by binding to IL-2 receptors (IL-2R), consisting of either trimeric receptors made of IL-2Rα (CD25), IL-2Rβ (CD122), and IL-2Rγ (γc, CD132) chains or dimeric βγ IL-2Rs (1, 3). Both IL-2R variants are able to transmit signal upon IL-2 binding. However, trimeric αβγ IL-2Rs have a roughly 10-100 times higher affinity for IL-2 than dimeric βγ IL-2Rs (3), implicating that CD25 confers high-affinity binding of IL-2 to its receptor but is not crucial for signal transduction. Trimeric IL-2Rs are found on activated T cells and CD4+ forkhead box P3 (FoxP3)+ T regulatory cells (Treg), which are sensitive to IL-2 in vitro and in vivo. Conversely, antigen-experienced (memory) CD8+, CD44 high memory-phenotype (MP) CD8+, and natural killer (NK) cells are endowed with high levels of dimeric βγ IL-2Rs, and these cells also respond vigorously to IL-2 in vitro and in vivo.

Expression of the high-affinity IL-2R is critical for endowing T cells to respond to low concentrations of IL-2 that is transiently available in vivo. IL-2Rα expression is absent on naive and memory T cells but is induced after antigen activation. IL-2Rβ is constitutively expressed by NK, NKT, and memory CD8+ T cells but is also induced on naive T cells after antigen activation. γc is much less stringently regulated and is constitutively expressed by all lymphoid cells. Once the high-affinity IL-2R is induced by antigen, IL-2R signaling upregulates the expression of IL-2Rα in part through Stat5-dependent regulation of Il2ra transcription (Kim et al., 2001). This process represents a mechanism to maintain expression of the high-affinity IL-2R and sustain IL-2 signaling while there remains a source of IL-2.

IL-2 is captured by IL-2Rα through a large hydrophobic binding surface surrounded by a polar periphery that results in a relatively weak interaction (Kd 10-8 M) with rapid on-off binding kinetics. However, the IL-2Rα-IL-2 binary complex leads to a very small conformational change in IL-2 that promotes association with IL-2Rβ through a distinct polar interaction between IL-2 and IL-2Rβ. The pseudo-high affinity of the IL2/α/β trimeric complex (i.e. Kd~300 pM) clearly indicates that the trimeric complex is more stable than either IL2 bound to the α chain alone (Kd=10 nM) or to the β chain alone (Kd=450 nM) as shown by Ciardelli's data. In any event, the IL2/α/β trimer then recruits the γ chain into the quaternary complex capable of signaling, which is facilitated by the large composite binding site on the IL2-bound β chain for the γ chain.

In other words, the ternary IL-2Rα-IL-2Rβ-IL-2 complex then recruits γc through a weak interaction with IL-2 and a stronger interaction with IL-2Rβ to produce a stable quaternary high-affinity IL-2R (Kd 10-11 M which is 10 pM). The formation of the high-affinity quaternary IL-2-IL-2R complex leads to signal transduction through the tyrosine kinases Jak1 and Jak3, which are associated with IL-2Rβ and γc, respectively (Nelson and Willerford, 1998). The quaternary IL-2-IL-2R complex is rapidly internalized, where IL-2, IL-2Rβ, and γc are rapidly degraded, but IL-2Rα is recycled to the cell surface (Hémar et al., 1995; Yu and Malek, 2001). Thus, those functional activities that require sustained IL-2R signaling require a continued source of IL-2 to engage IL-2Rα and form additional IL-2-IL-2R signaling complexes.

Interleukin-15 (IL-15), another member of the 4-alpha-helix bundle family of cytokines, has also emerged as an immunomodulator for the treatment of cancer. IL-15 is initially captured via IL-15Rα, which is expressed on antigen-presenting dendritic cells, monocytes and macrophages. IL-15 exhibits broad activity and induces the differentiation and proliferation of T, B and natural killer (NK) cells via signaling through the IL-15/IL-2-R-β (CD122) and the common γ chain (CD132). It also enhances cytolytic activity of CD8+ T cells and induces long-lasting antigen-experienced CD8+CD44 memory T cells. IL-15 stimulates differentiation and immunoglobulin synthesis by B cells and induces maturation of dendritic cells. It does not stimulate immunosuppressive T regulatory cells (Tregs). Thus, boosting IL-15 activity selectively in the tumor micro-environment could enhance innate and specific immunity and fight tumors (Waldmann et al., 2012). IL-15 was initially identified for its ability to stimulate T cell proliferation in an IL-2-like manner through common receptor components (IL-2R/15Rβ-γc) and signaling through JAK1/JAK3 and STAT3/STAT5. Like IL-2, IL-15 has been shown to stimulate proliferation of activated CD4−CD8−, CD4+CD8+, CD4+ and CD8+ T cells as well as facilitate the induction of cytotoxic T-lymphocytes, and the generation, proliferation and activation of NK cells (Waldmann et al., 1999). However, unlike IL-2 which is required to maintain forkhead box P3 (FOXP3)-expressing CD4+CD25+ Treg cells and for the retention of these cells in the periphery, IL-15 has little effect on Tregs (Berger et al., 2009). This is important as FOXP3-expressing CD4+CD25+ Tregs inhibit effector T cells, thereby inhibiting immune responses including those directed against the tumor. IL-2 also has a crucial role in initiating activation induced cell death (AICD), a process that leads to the elimination of self-reactive T cells, whereas IL-15 is an anti-apoptotic factor for T cells (Marks-Konczalik et al., 2000). IL-15 co-delivered with HIV peptide vaccines has been shown to overcome CD4+ T cell deficiency by promoting longevity of antigen-specific CD8+ T cells and blocking TRAIL-mediated apoptosis (Oh et al., 2008). Furthermore, IL-15 promotes the long-term maintenance of CD8+CD44hi memory T cells (Kanegane et al., 1996).

The importance of IL-15 and IL-15Rα to T and NK cell development is further highlighted by the phenotype of IL-15Rα$^{-/-}$ and IL-15$^{-/-}$ mice. Knockout mice demonstrate decreased numbers of total CD8+ T cells, and are deficient in memory-phenotype CD8+ T cells, NK cells, NK/T cells and some subsets of intestinal intraepithelial lymphocytes, indicating that IL-15 provides essential positive homeostatic functions for these subsets of cells (Lodolce et al., 1996; Kennedy et al., 1998). The similarities in the phenotypes of these two strains of knockout mice suggest the importance of IL-15Rα in maintaining physiologically relevant IL-15 signals.

IL-15 is presented in trans by the IL-15 receptor alpha-chain to the IL-15Rβγc complex displayed on the surface of T cells and natural killer (NK) cells (Han et al., 2011). The IL-15Rα-chain plays a role of chaperone protein, stabilizes, and increases IL-15 activity (Desbois et al., 2016). It has been shown that exogenous IL-15 may have a limited impact on patients with cancer due to its dependency on IL-15Rα frequently downregulated in cancer patients. Therefore, the fusion protein RLI, composed of the sushi+ domain of IL15Rα coupled via a linker to IL-15, has been suggested as an alternative approach to IL15 therapy (Bessard et al., 2009). It was found that administration of soluble IL-15/IL-15Rα complexes greatly enhanced IL-15 serum half-life and bioavailability in vivo (Stoklasek et al., 2010).

In addition to the effects on T and NK cells, IL-15 also has several effects on other components of the immune system. IL-15 protects neutrophils from apoptosis, modulates phagocytosis and stimulates the secretion of IL-8 and IL-1R antagonist. It functions through the activation of JAK2, p38 and ERK1/2 MAPK, Syk kinase and the NF-kB transcriptional factor (Pelletier et al., 2002). In mast cells, IL-15 can act as a growth factor and an inhibitor of apoptosis. In these cells IL-15 activates the JAK2/STAT5 pathway without the requirement of γc binding (Tagaya et al., 1996). IL-15 also induces B lymphocyte proliferation and differentiation, and increases immunoglobulin secretion (Armitage et al., 1995). It also prevents Fas-mediated apoptosis and allows induction of antibody responses partially independent of CD4-help (Demerci et al., 2004; Steel et al., 2010). Monocytes, macrophages and dendritic cells effectively transcribe and translate IL-15. They also respond to IL-15 stimulation. Macrophages respond by increasing phagocytosis, inducing IL-8, IL-12 and MCP-1 expression, and secreting IL-6, IL-8 and TNF α (Budagian et al., 2006). Dendritic cells incubated with IL-15 demonstrate maturation with increased CD83, CD86, CD40, and MHC class II expression, are also resistant to apoptosis, and show enhanced interferon-γ secretion (Anguille et al., 2009).

IL-15 has also been shown to have effects on non-hematological cells including myocytes, adipocytes, endothelial and neural cells. IL-15 has an anabolic effect on muscle and may support muscle cell differentiation (Quinn et al., 1995). It stimulates myocytes and muscle fibers to accumulate contractile protein and is able to slow muscle wasting in rats with cancer-related cachexia (Figueras et al., 2004). IL-15 has also been shown to stimulate angiogenesis (Angiolillo et al., 1997) and induce microglial growth and survival (Hanisch et al., 1997).

Interleukin-7 (IL-7), also of the IL-2/IL-15 family, is a well-characterized pleiotropic cytokine, and is expressed by stromal cells, epithelial cells, endothelial cells, fibroblasts, smooth muscle cells and keratinocytes, and following activation, by dendritic cells (Alpdogan et al., 2005). Although it was originally described as a growth and differentiation factor for precursor B lymphocytes, subsequent studies have shown that IL-7 is critically involved in T-lymphocyte development and differentiation. Interleukin-7 signaling is essential for optimal CD8 T-cell function, homeostasis and establishment of memory (Schluns et al., 2000); it is required for the survival of most T-cell subsets, and its expression has been proposed to be important for regulating T-cell numbers.

IL-7 binds to a dimeric receptor, including IL-7Rα and γc to form a ternary complex that plays fundamental roles in extracellular matrix remodeling, development, and homeostasis of T and B cells (Mazzucchelli and Durum, 2007). IL-7Rα also cross-reacts to form a ternary complex with thymic stromal lymphopoietin (TSLP) and its receptor (TSLPR), and activates the TSLP pathway, resulting in T and dendritic cell proliferation in humans and further B cell development in mice (Leonard, 2002). Tight regulation of the signaling cascades activated by the complexes are therefore crucial to normal cellular function. Under-stimulation of the IL-7 pathway caused by mutations in the IL-7Rα ectodomain inhibits T and B cell development, resulting in patients with a form of severe combined immunodeficiency (SCID) (Giliani et al., 2005; Puel et al., 1998).

IL-7 has a potential role in enhancing immune reconstitution in cancer patients following cytotoxic chemotherapy. IL-7 therapy enhances immune reconstitution and can augment even limited thymic function by facilitating peripheral expansion of even small numbers of recent thymic emigrants. Therefore, IL-7 therapy could potentially repair the immune system of patients who have been depleted by cytotoxic chemotherapy (Capitini et al., 2010).

Interleukin-12 (IL-12) is a disulfide-linked heterodimer of two separately encoded subunits (p35 and p40), which are linked covalently to give rise to the so-called bioactive heterodimeric (p70) molecule (Lieschke et al., 1997; Jana et al., 2014). Apart from forming heterodimers (IL-12 and IL-23), the p40 subunit is also secreted as a monomer (p40) and a homodimer (p40$_2$). It is known in the art that synthesis of the heterodimer as a single chain with a linker connecting the p35 to the p40 subunit preserves the full biological activity of the heterodimer. IL-12 plays a critical role in the early inflammatory response to infection and in the generation of Th1 cells, which favor cell-mediated immunity. It has been found that overproduction of IL-12 can be dangerous to the host because it is involved in the pathogenesis of a number of autoimmune inflammatory diseases (e.g. MS, arthritis, type 1 diabetes).

The IL-12 receptor (IL-12R) is a heterodimeric complex consisting of IL-12Rβ1 and IL-12Rβ2 chains expressed on the surface of activated T-cells and natural killer cells (Trinchieri et al., 2003). The IL-12Rβ1 chain binds to the IL-12p40 subunit, whereas IL-12p35 in association with IL-12Rβ2 confers an intracellular signaling ability (Benson et al., 2011). Signal transduction through IL-12R induces phosphorylation of Janus kinase (Jak2) and tyrosine kinase (Tyk2), that phosphorylate and activate signal transducer and activator of transcription (STAT)1, STAT3, STAT4, and STAT5. The specific cellular effects of IL-12 are due mainly to activation of STAT4. IL-12 induces natural killer and T-cells to produce cytokines, in particular interferon (IFN)γ, that mediate many of the proinflammatory activities of IL-12, including CD4+ T-cell differentiation toward the Th1 phenotype (Montepaone et al., 2014).

Regulatory T cells actively suppress activation of the immune system and prevent pathological self-reactivity and consequent autoimmune disease. Developing drugs and methods to selectively activate regulatory T cells for the treatment of autoimmune disease is the subject of intense research and, until the development of the present invention, which can selectively deliver active interleukins at the site of inflammation, has been largely unsuccessful. Regulatory T cells (Treg) are a class of CD4+CD25+ T cells that suppress the activity of other immune cells. Treg are central to immune system homeostasis, and play a major role in maintaining tolerance to self-antigens and in modulating the immune response to foreign antigens. Multiple autoimmune and inflammatory diseases, including Type 1 Diabetes (T1D), Systemic Lupus Erythematosus (SLE), and Graft-versus-Host Disease (GVHD) have been shown to have a deficiency of Treg cell numbers or Treg function.

Consequently, there is great interest in the development of therapies that boost the numbers and/or function of Treg cells. One treatment approach for autoimmune diseases being investigated is the transplantation of autologous, ex vivo-expanded Treg cells (Tang, Q., et al, 2013, Cold Spring Harb. Perspect. Med., 3:1-15). While this approach has shown promise in treating animal models of disease and in several early stage human clinical trials, it requires personalized treatment with the patient's own T cells, is invasive, and is technically complex. Another approach is treatment with low dose Interleukin-2 (IL-2). Treg cells characteristically express high constitutive levels of the high affinity IL-2 receptor, IL2Rαβγ, which is composed of the subunits IL2Rα (CD25), IL2Rβ (CD122), and IL2Rγ (CD132), and Treg cell growth has been shown to be dependent on IL-2 (Malek, T. R., et al., 2010, Immunity, 33:153-65).

Conversely, immune activation has also been achieved using IL-2, and recombinant IL-2 (Proleukin®) has been approved to treat certain cancers. High-dose IL-2 is used for the treatment of patients with metastatic melanoma and metastatic renal cell carcinoma with a long-term impact on overall survival.

Clinical trials of low-dose IL-2 treatment of chronic GVHD (Koreth, J., et al., 2011, N Engl J Med., 365:2055-66) and HCV-associated autoimmune vasculitis patients (Saadoun, D., et al., 2011, N Engl J Med., 365:2067-77) have demonstrated increased Treg levels and signs of clinical efficacy. New clinical trials investigating the efficacy of IL-2 in multiple other autoimmune and inflammatory diseases have been initiated. The rationale for using so-called low dose IL-2 was to exploit the high IL-2 affinity of the trimeric IL-2 receptor which is constitutively expressed on Tregs while leaving other T cells which do not express the high affinity receptor in the inactivated state. Aldesleukin (marketed as Proleukin® by Prometheus Laboratories, San Diego, CA), the recombinant form of IL-2 used in these trials, is associated with high toxicity. Aldesleukin, at high doses, is approved for the treatment of metastatic melanoma and metastatic renal cancer, but its side effects are so severe that its use is only recommended in a hospital setting with access to intensive care (Web address: www.proleukin.com/assets/pdf/proleukin.pdf).

The clinical trials of IL-2 in autoimmune diseases have employed lower doses of IL-2 in order to target Treg cells, because Treg cells respond to lower concentrations of IL-2 than many other immune cell types due to their expression of IL2R alpha (Klatzmann D, 2015 Nat Rev Immunol. 15:283-94). However, even these lower doses resulted in safety and tolerability issues, and the treatments used have employed daily subcutaneous injections, either chronically or in intermittent 5-day treatment courses. Therefore, there is a need for an autoimmune disease therapy that potentiates Treg cell numbers and function, that targets Treg cells more specifically than IL-2, that is safer and more tolerable, and that is administered less frequently.

One approach that has been suggested for improving the therapeutic index of IL-2-based therapy for autoimmune diseases is to use variants of IL-2 that are selective for Treg cells relative to other immune cells. IL-2 receptors are expressed on a variety of different immune cell types, including T cells, NK cells, eosinophils, and monocytes, and this broad expression pattern likely contributes to its pleiotropic effect on the immune system and high systemic toxicity. In particular, activated T effector cells express IL2Rαβγ, as do pulmonary epithelial cells. But, activating T effector cells runs directly counter to the goal of down-modulating and controlling an immune response, and activating pulmonary epithelial cells leads to known dose-limiting side effects of IL-2 including pulmonary edema. In fact, the major side effect of high-dose IL-2 immunotherapy is vascular leak syndrome (VLS), which leads to accumulation of intravascular fluid in organs such as lungs and liver with subsequent pulmonary edema and liver cell damage. There is no treatment of VLS other than withdrawal of IL-2. Low-dose IL-2 regimens have been tested in patients to avoid VLS, however, at the expense of suboptimal therapeutic results.

According to the literature, VLS is believed to be caused by the release of proinflammatory cytokines from IL-2-activated NK cells. However, there is some evidence that pulmonary edema results from direct binding of IL-2 to lung endothelial cells, which expressed low to intermediate levels of functional αβγ IL-2Rs. And, the pulmonary edema associated with interaction of IL-2 with lung endothelial cells was abrogated by blocking binding to CD25 with an anti-CD25 monoclonal antibody (mAb), in CD25-deficient host mice, or by the use of CD122-specific IL-2/anti-IL-2 mAb (IL-2/mAb) complexes, thus preventing VLS.

Treatment with interleukin cytokines other than IL-2 has been more limited. IL-15 displays immune cell stimulatory activity similar to that of IL-2 but without the same inhibitory effects, thus making it a promising immunotherapeutic candidate. Clinical trials of recombinant human IL-15 for the treatment of metastatic malignant melanoma or renal cell cancer demonstrated appreciable changes in immune cell distribution, proliferation, and activation and suggested potential antitumor activity (Conlon et. al., 2014). IL-15 is currently in clinical trials to treat various forms of cancer. However, IL-15 therapy is known to be associated with undesired and toxic effects, such as exacerbating certain leukemias, graft-versus-host disease, hypotension, thrombocytopenia, and liver injury. (Mishra A., et al., Cancer Cell, 2012, 22(5):645-55; Alpdogan O. et al., Blood, 2005, 105 (2):866-73; Conlon K C et al., J Clin Oncol, 2015, 33(1): 74-82.)

IL-7 promotes lymphocyte development in the thymus and maintains survival of naive and memory T cell homeostasis in the periphery. Moreover, it is important for the organogenesis of lymph nodes (LN) and for the maintenance of activated T cells recruited into the secondary lymphoid organs (SLOs) (Gao et. al., 2015). In clinical trials of IL-7, patients receiving IL-7 showed increases in both CD4+ and CD8+ T cells, with no significant increase in regulatory T cell numbers as monitored by FoxP3 expression (Sportes et al., 2008). In clinical trials reported in 2006, 2008 and 2010, patients with different kinds of cancers such as metastatic melanoma or sarcoma were injected subcutaneously with different doses of IL-7. Little toxicity was seen except for transient fevers and mild erythema. Circulating levels of both CD4+ and CD8+ T cells increased significantly and the number of Treg reduced. TCR repertoire diversity increased after IL-7 therapy. However, the anti-tumor activity of IL-7 was not well evaluated (Gao et. al., 2015). Results suggest that IL-7 therapy could enhance and broaden immune responses.

IL-12 is a pleiotropic cytokine, the actions of which create an interconnection between the innate and adaptive immunity. IL-12 was first described as a factor secreted from PMA-induced EBV-transformed B-cell lines. Based on its actions, IL-12 has been designated as cytotoxic lymphocyte maturation factor and natural killer cell stimulatory factor. Due to bridging the innate and adaptive immunity and potently stimulating the production of IFNγ, a cytokine coordinating natural mechanisms of anticancer defense, IL-12 seemed ideal candidate for tumor immunotherapy in humans. However, severe side effects associated with systemic administration of IL-12 in clinical investigations and the very narrow therapeutic index of this cytokine markedly tempered enthusiasm for the use of this cytokine in cancer patients (Lasek et. al., 2014). Approaches to IL-12 therapy in which delivery of the cytokine is tumor-targeted, which may diminish some of the previous issues with IL-12 therapy, are currently in clinical trials for cancers.

The direct use of IL-2 as an agonist to bind the IL-2R and modulate immune responses therapeutically has been problematic due its well-documented therapeutic risks, e.g., its short serum half-life and high toxicity. These risks have also limited the therapeutic development and use of other cytokines. New forms of cytokines that reduce these risks are needed. Disclosed herein are compositions and methods comprising IL-2 and IL-15 and other cytokines, functional fragments and muteins of cytokines as well as conditionally active cytokines designed to address these risks and provide needed immunomodulatory therapeutics.

The present invention is designed to address the shortcomings of direct IL-2 therapy and therapy using other cytokines, for example using cytokine blocking moieties, e.g. steric blocking polypeptides, serum half-life extending polypeptides, targeting polypeptides, linking polypeptides, including protease cleavable linkers, and combinations thereof. Cytokines, including interleukins (e.g., IL-2, IL-7, IL-12, IL-15, IL-18, IL-21 IL-23), interferons (IFNs, including IFNalpha, IFNbeta and IFNgamma), tumor necrosis factors (e.g., TNFalpha, lymphotoxin), transforming growth factors (e.g., TGFbeta1, TGFbeta2, TGFbeta3), chemokines (C-X-C motif chemokine 10 (CXCL10), CCL19, CCL20, CCL21), and granulocyte macrophage-colony stimulating factor (GM-CS) are highly potent when administered to patients. As used herein, "chemokine" means a family of small cytokines with the ability to induce directed chemotaxis in nearby responsive cells Cytokines can provide powerful therapy, but are accompanied by undesired effects that are difficult to control clinically and which have limited the clinical use of cytokines. This disclosure relates to new forms of cytokines that can be used in patients with reduced or eliminated undesired effects. In particular, this disclosure relates to pharmaceutical compositions including chimeric polypeptides (fusion proteins), nucleic acids encoding fusion proteins and pharmaceutical formulations of the foregoing that contain cytokines or active fragments or muteins of cytokines that have decreased cytokine receptor activating activity in comparison to the corresponding cytokine. However, under selected conditions or in a selected biological environment the chimeric polypeptides activate their cognate receptors, often with the same or higher potency as the corresponding naturally occurring cytokine. As described herein, this is typically achieved using a cytokine blocking moiety that blocks or inhibits the receptor activating function of the cytokine, active fragment or mutein thereof under general conditions but not under selected conditions, such as those present at the desired site of cytokine activity (e.g., an inflammatory site or a tumor).

The chimeric polypeptides and nucleic acids encoding the chimeric polypeptides can be made using any suitable method. For example, nucleic acids encoding a chimeric polypeptide can be made using recombinant DNA techniques, synthetic chemistry or combinations of these techniques, and expressed in a suitable expression system, such as in CHO cells. Chimeric polypeptides can similarly be made, for example by expression of a suitable nucleic acid, using synthetic or semi-synthetic chemical techniques, and the like. In some embodiments, the blocking moiety can be attached to the cytokine polypeptide via sortase-mediated conjugation. "Sortases" are transpeptidases that modify proteins by recognizing and cleaving a carboxyl-terminal sorting signal embedded in or terminally attached to a target protein or peptide. Sortase A catalyzes the cleavage of the LPXTG motif (SEQ ID No.: 442) (where X is any standard amino acid) between the Thr and Gly residue on the target protein, with transient attachment of the Thr residue to the active site Cys residue on the enzyme, forming an enzyme-thioacyl intermediate. To complete transpeptidation and create the peptide-monomer conjugate, a biomolecule with an N-terminal nucleophilic group, typically an oligoglycine motif, attacks the intermediate, displacing Sortase A and joining the two molecules.

To form the cytokine-blocking moiety fusion protein, the cytokine polypeptide is first tagged at the N-terminus with a polyglycine sequence, or alternatively, with at the C-terminus with a LPXTG motif (SEQ ID NO.: 442). The blocking moiety or other element has respective peptides attached that serve as acceptor sites for the tagged polypeptides. For conjugation to domains carrying a LPXTG (SEQ ID NO.: 442) acceptor peptide attached via its N-terminus, the polypeptide will be tagged with an N-terminal poly-glycine stretch. For conjugation to domain carrying a poly-glycine peptide attached via its C-terminus, the polypeptide will be tagged at its C-terminus with a LPXTG (SEQ ID NO.: 442) sortase recognition sequence. Recognizing poly-glycine and LPXTG (SEQ ID NO.: 442) sequences, sortase will form a peptide bond between polymer-peptide and tagged polypeptides. The sortase reaction cleaves off glycine residues as intermediates and occurs at room temperature.

A variety of mechanisms can be exploited to remove or reduce the inhibition caused by the blocking moiety. For example, the pharmaceutical compositions can include a cytokine moiety and a blocking moiety, e.g. a steric blocking moiety, with a protease cleavable linker comprising a protease cleavage site located between the cytokine and cytokine blocking moiety or within the cytokine blocking moiety. When the protease cleavage site is cleaved, the blocking moiety can dissociate from cytokine, and the cytokine can then activate cytokine receptor. A cytokine moiety can also be blocked by a specific blocking moiety, such as an antibody, which binds an epitope found on the relevant cytokine.

Any suitable linker can be used. For example, the linker can comprise glycine-glycine, a sortase-recognition motif, or a sortase-recognition motif and a peptide sequence $(Gly_4Ser)_n$ (SEQ ID NO.: 443) or $(Gly_3Ser)_n$, (SEQ ID NO.: 444) wherein n is 1, 2, 3, 4 or 5. Typically, the sortase-recognition motif comprises a peptide sequence LPXTG (SEQ ID NO.: 442), where X is any amino acid. In some embodiments, the covalent linkage is between a reactive lysine residue attached to the C-terminal of the cytokine polypeptide and a reactive aspartic acid attached to the N-terminal of the blocker or other domain. In other embodiments, the covalent linkage is between a reactive aspartic acid residue attached to the N-terminal of the cytokine polypeptide and a reactive lysine residue attached to the C-terminal of said blocker or other domain.

Accordingly, as described in detail herein, the cytokine blocking moieties used can be steric blockers. As used herein, a "steric blocker" refers to a polypeptide or polypeptide moiety that can be covalently bonded to a cytokine polypeptide directly or indirectly through other moieties such as linkers, for example in the form of a chimeric polypeptide (fusion protein), but otherwise does not covalently bond to the cytokine polypeptide. A steric blocker can non-covalently bond to the cytokine polypeptide, for example though electrostatic, hydrophobic, ionic or hydrogen bonding. A steric blocker typically inhibits or blocks the activity of the cytokine moiety due to its proximity to the cytokine moiety and comparative size. The steric inhibition of the cytokine moiety can be removed by spatially separating the cytokine moiety from the steric blocker, such as by enzymatically cleaving a fusion protein that contains a steric blocker and a cytokine polypeptide at a site between the steric blocker and the cytokine polypeptide.

As described in greater detail herein, the blocking function can be combined with or due to the presence of additional functional components in the pharmaceutical composition, such as a targeting domain, a serum half-life extension element, and protease-cleavable linking polypeptides. For example, a serum half-life extending polypeptide can also be a steric blocker.

In the interest of presenting a concise disclosure of the full scope of the invention, aspects of the invention are described in detail using the cytokine IL-2 as an exemplary cytokine. However, the invention and this disclosure are not limited to IL-2. It will be clear to a person of skill in the art that this disclosure, including the disclosed methods, polypeptides and nucleic acids, adequately describes and enables the use of other cytokines, fragments and muteins, such as IL-2, IL-7, IL-12, IL-15, IL-18, IL-21 IL-23, IFNalpha, IFNbeta, IFNgamma, TNFalpha, lymphotoxin, TGF-beta1, TGF-beta2, TGFbeta3, GM-CSF, CXCL10, CCL19, CCL20, CCL21 and functional fragments or muteins of any of the foregoing.

Various elements ensure the delivery and activity of IL-2 preferentially at the site of desired IL-2 activity and to severely limit systemic exposure to the interleukin via a blocking and/or a targeting strategy preferentially linked to a serum half-life extension strategy. In this serum half-life extension strategy, the blocked version of interleukin circulates for extended times (preferentially 1-2 or more weeks) but the activated version has the typical serum half-life of the interleukin.

By comparison to a serum half-life extended version, the serum half-life of IL-2 administered intravenously is only ~10 minutes due to distribution into the total body extracellular space, which is large, ~15 L in an average sized adult. Subsequently, IL-2 is metabolized by the kidneys with a half-life of ~2.5 hours. (Smith, K. "Interleukin 2 immunotherapy." *Therapeutic Immunology* 240 (2001)). By other measurements, IL-2 has a very short plasma half-life of 85 minutes for intravenous administration and 3.3 hours subcutaneous administration (Kirchner, G. I., et al., 1998, Br J Clin Pharmacol. 46:5-10). In some embodiments of this invention, the half-life extension element is linked to the interleukin via a linker which is cleaved at the site of action (e.g. by inflammation-specific or tumor-specific proteases) releasing the interleukin's full activity at the desired site and also separating it from the half-life extension of the uncleaved version. In such embodiments, the fully active and free interleukin would have very different pharmacokinetic (pK) properties—a half-life of hours instead of weeks. In addition, exposure to active cytokine is limited to the site of desired cytokine activity (e.g., an inflammatory site or tumor) and systemic exposure to active cytokine, and associated toxicity and side effects, are reduced.

Other cytokines envisioned in this invention have similar pharmacology (e.g. IL-15 as reported by Blood 2011 117: 4787-4795; doi: doi.org/10.1182/blood-2010-10-311456) as IL-2 and accordingly, the designs of this invention address the shortcomings of using these agents directly, and provide chimeric polypeptides that can have extended half-life and/or be targeted to a site of desired activity (e.g., a site of inflammation or a tumor).

If desired, IL-2 can be engineered to bind the IL-2R complex generally or one of the three IL-2R subunits specifically with an affinity that differs from that of the corresponding wild-type IL-2, for example toto selectively activate Tregs or Teff. For example, IL-2 polypeptides that are said to have higher affinity for the trimeric form of the IL-2 receptor relative to the dimeric beta/gamma form of the 11-2 receptor in comparison to wild type IL-2 can have an amino acid sequence that includes one of the following sets of mutations with respect to SEQ ID NO:1 (a mature IL-2 protein comprising amino acids 21-153 of human IL-2 having the Uniprot Accession No. P60568-1): (a) K64R, V69A, and Q74P; (b) V69A, Q74P, and T101A; (c) V69A, Q74P, and I128T; (d) N30D, V69A, Q74P, and F103S; (e) K49E, V69A, A73V, and K76E; (f) V69A, Q74P, T101A, and T133N; (g) N30S, V69A, Q74P, and I128A; (h) V69A, Q74P, N88D, and S99P; (i) N30S, V69A, Q74P, and I128T; ( ) K9T, Q11R, K35R, V69A, and Q74P; (k) A1T, M46L, K49R, E61D, V69A, and H79R; (1) K48E, E68D, N71T, N90H, F103S, and I114V; (m) S4P, T10A, Q11R, V69A, Q74P, N88D, and T133A; (n) E15K, N30S Y31H, K35R, K48E, V69A, Q74P, and I92T; (o) N30S, E68D, V69A, N71A, Q74P, S75P, K76R, and N90H; (p) N30S, Y31C, T37A, V69A, A73V, Q74P, H79R, and I128T; (q) N26D, N29S, N30S, K54R, E67G, V69A, Q74P, and I92T; (r) K8R, Q13R, N26D, N30T, K35R, T37R, V69A, Q74P, and I92T; and (s) N29S, Y31H, K35R, T37A, K48E, V69A, N71R, Q74P, N88D, and 189V. This approach can also be applied to prepare muteins of other cytokines including interleukins (e.g., IL-2, IL-7, IL-12, IL-15, IL-18, IL-23), interferons (IFNs, including IFNalpha, IFNbeta and IFNgamma), tumor necrosis factors (e.g., TNFalpha, lymphotoxin), transforming growth factors (e.g., TGFbeta1, TGFbeta2, TGFbeta3) and granulocyte macrophage-colony stimulating factor (GM-CS). For example, muteins can be prepared that have desired binding affinity for a cognate receptor.

As noted above, any of the mutant IL-2 polypeptides disclosed herein can include the sequences described; they can also be limited to the sequences described and otherwise identical to SEQ ID NO:1. Moreover, any of the mutant IL-2 polypeptides disclosed herein can optionally include a substitution of the cysteine residue at position 125 with another residue (e.g., serine) and/or can optionally include a deletion of the alanine residue at position 1 of SEQ ID NO:1.

Another approach to improving the therapeutic index of an IL-2 based therapy is to optimize the pharmacokinetics of the molecule to maximally activate Treg cells. Early studies of IL-2 action demonstrated that IL-2 stimulation of human T cell proliferation in vitro required a minimum of 5-6 hours exposure to effective concentrations of IL-2 (Cantrell, D. A., et. al., 1984, Science, 224: 1312-1316). When administered to human patients, IL-2 has a very short plasma half-life of 85 minutes for intravenous administration and 3.3 hours subcutaneous administration (Kirchner, G. I., et al., 1998, Br J Clin Pharmacol. 46:5-10). Because of its short half-life, maintaining circulating IL-2 at or above the level necessary to stimulate T cell proliferation for the necessary duration necessitates high doses that result in peak IL-2 levels significantly above the EC50 for Treg cells or will require frequent administration. These high IL-2 peak levels can activate IL2Rβγ receptors and have other unintended or adverse effects, for example VLS as noted above. An IL-2 analog, or a multifunctional protein with IL-2 attached to a domain that enables binding to the FcRn receptor, with a longer circulating half-life than IL-2 can achieve a target drug concentration for a specified period of time at a lower dose than IL-2, and with lower peak levels. Such an IL-2 analog will therefore require either lower doses or less frequent administration than IL-2 to effectively stimulate Treg cells. Less frequent subcutaneous administration of an IL-2 drug will also be more tolerable for patients. A therapeutic with these characteristics will translate clinically into improved pharmacological efficacy, reduced toxicity, and improved patient compliance with therapy. Alternatively, IL-2 or muteins of IL-2 (herein, "IL-2*") can be selectively targeted to the intended site of action (e.g. sites of inflammation or a tumor). This targeting can be achieved by one of several strategies, including the addition of domains to the administered agent that comprise blockers of the IL-2 (or muteins) that are cleaved away or by targeting domains or a combination of the two.

In some embodiments, IL-2* partial agonists can be tailored to bind with higher or lower affinity depending on the desired target; for example, an IL-2* can be engineered to bind with enhanced affinity to one of the receptor subunits and not the others. These types of partial agonists, unlike full agonists or complete antagonists, offer the ability to tune the signaling properties to an amplitude that elicits desired functional properties while not meeting thresholds for undesired properties. Given the differential activities of the partial agonists, a repertoire of IL-2 variants could be engineered to exhibit an even finer degree of distinctive signaling activities, ranging from almost full to partial agonism to complete antagonism.

In some embodiments, the IL-2* has altered affinity for IL-2Rα. In some embodiments, the IL-2* has a higher affinity for IL-2Rα than wild-type IL-2. In other embodiments, the IL-2* has altered affinity for IL-2Rβ. In one embodiment, IL-2* has enhanced binding affinity for IL-2Rβ, e.g., the N-terminus of IL-2Rβ, that eliminates the functional requirement for IL-2Rα. In another embodiment, an IL-2* is generated that has increased binding affinity for IL-2Rβ but that exhibited decreased binding to IL-2Rγ, and thereby is defective IL-2Rβγ heterodimerization and signaling.

Blocking moieties, described in further detail below, can also be used to favor binding to or activation of one or more receptors. In one embodiment, blocking moieties are added such that IL-2Rβγ binding or activation is blocked but IL-2Rα binding or activation is not changed. In another embodiment, blocking moieties are added such that IL-2Rα binding or activation is diminished. In another embodiment, blocking moieties are added such that binding to and or activation of all three receptors is inhibited. This blocking may be relievable by removal of the blocking moieties in a particular environment, for example by proteolytic cleavage of a linker linking one or more blocking moieties to the cytokine.

A similar approach can be applied to improve other cytokines, particularly for use as immunostimulatory agents, for example for treating cancer. For example, in this aspect, the pharmacokinetics and/or pharmacodynamics of the cytokine (e.g., IL-2, IL-7, IL-12, IL-15, IL-18, IL-21 IL-23, IFNalpha, IFNbeta and IFNgamma, TNFalpha, lymphotoxin, TGFbeta1, TGFbeta2, TGFbeta3 GM-CSF, CXCL10, CCL19, CCL20, and CCL21 can be tailored to maximally activate effector cells (e.g., effect T cells, NK cells) and/or cytotoxic immune response promoting cells (e.g., induce dendritic cell maturation) at a site of desired activity, such as in a tumor, but preferably not systemically.

Thus, provided herein are pharmaceutical compositions comprising at least one cytokine polypeptide, such as interleukins (e.g., IL-2, IL-7, IL-12, IL-15, IL-18, IL-21, IL-23), interferons (IFNs, including IFNalpha, IFNbeta and IFNgamma), tumor necrosis factors (e.g., TNFalpha, lymphotoxin), transforming growth factors (e.g., TGFbeta1, TGFbeta2, TGFbeta3), chemokines (e.g. CXCL10, CCL19, CCL20, CCL21) and granulocyte macrophage-colony stimulating factor (GM-CS) or a functional fragment or mutein of any of the foregoing. The polypeptide typically also includes at least one linker amino acid sequence, wherein the amino acid sequence is in certain embodiments capable of being cleaved by an endogenous protease. In one embodiment, the linker comprises an amino acid sequence comprising HSSKLQ (SEQ ID NO.: 25), GPLGVRG (SEQ ID NO.: 445), IPVSLRSG (SEQ ID NO.: 446), VPLSLYSG (SEQ ID NO. 447), or SGESPAYYTA (SEQ ID NO. 448). In other embodiments, the chimeric polypeptide further contains a blocking moiety, e.g. a steric blocking polypeptide moiety, capable of blocking the activity of the interleukin polypeptide. The blocking moiety, for example, can comprise a human serum albumin (HSA) binding domain or an optionally branched or multi-armed polyethylene glycol (PEG). Alternatively, the pharmaceutical composition comprises a first cytokine polypeptide or a fragment thereof, and blocking moiety, e.g. a steric blocking polypeptide moiety, wherein the blocking moiety blocks the activity of the cytokine polypeptide on the cytokine receptor, and wherein the blocking moiety in certain embodiments comprises a protease cleavable domain. In some embodiments, blockade and reduction of cytokine activity is achieved simply by attaching additional domains with very short linkers to the N or C terminus of the interleukin domain. In such embodiments, it is anticipated the blockade is relieved by protease digestion of the blocking moiety or of the short linker that tethers the blocker to the interleukin. Once the domain is clipped or is released, it will no longer be able to achieve blockade of cytokine activity.

The pharmaceutical composition e.g., chimeric polypeptide can comprise two or more cytokines, which can be the same cytokine polypeptide or different cytokine polypeptides. For example, the two or more different types of cytokines have complementary functions. In some examples, a first cytokine is IL-2 and a second cytokine is IL-12. In some embodiments, each of the two or more different types of cytokine polypeptides have activities that modulate the activity of the other cytokine polypeptides. In some examples of chimeric polypeptides that contain two cytokine polypeptides, a first cytokine polypeptide is T-cell activating, and a second cytokine polypeptide is non-T-cell-activating. In some examples of chimeric polypeptides that contain two cytokine polypeptides, a first cytokine is a chemoattractant, e.g. CXCL10, and a second cytokine is an immune cell activator.

Preferably, the cytokine polypeptides (including functional fragments) that are included in the fusion proteins disclosed herein are not mutated or engineered to alter the properties of the naturally occurring cytokine, including receptor binding affinity and specificity or serum half-life. However, changes in amino acid sequence from naturally occurring (including wild type) cytokine are acceptable to facilitate cloning and to achieve desired expression levels, for example.

Blocking Moiety

The blocking moiety can be any moiety that inhibits the ability of the cytokine to bind and/or activate its receptor. The blocking moiety can inhibit the ability of the cytokine to bind and/or activate its receptor sterically blocking and/or by noncovalently binding to the cytokine. Examples of suitable blocking moieties include the full length or a cytokine-binding fragment or mutein of the cognate receptor of the cytokine. Antibodies and fragments thereof including, a polyclonal antibody, a recombinant antibody, a human antibody, a humanized antibody a single chain variable fragment (scFv), single-domain antibody such as a heavy chain variable domain (VH), a light chain variable domain (VL) and a variable domain of camelid-type nanobody (VHH), a dAb and the like that bind the cytokine can also be used. Other suitable antigen-binding domain that bind the cytokine can also be used, include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocalin and CTLA4 scaffolds. Further examples of suitable blocking polypeptides include polypeptides that sterically inhibit or block binding of the cytokine to its cognate receptor. Advantageously, such moieties can also function as half-life extending elements. For example, a peptide that is modified by conjugation to a water-soluble polymer, such as PEG, can sterically inhibit or prevent binding of the cytokine to its receptor. Polypeptides, or fragments thereof, that have long serum half-lives can also be used, such as serum albumin (human serum albumin), immunoglobulin Fc, transferrin and the like, as well as fragments and muteins of such polypeptides. Antibodies and antigen-binding domains that bind to, for example, a protein with a long serum half-life such as HSA, immunoglobulin or transferrin, or to a receptor that is recycled to the plasma membrane, such as FcRn or transferrin receptor, can also inhibit the cytokine, particularly when bound to their antigen. Examples of such antigen-binding polypeptides include a single chain variable fragment (scFv), single-domain antibody such as a heavy chain variable domain (VH), a light chain variable domain (VL) and a variable domain of camelid-type nanobody (VHH), a dAb and the like. Other suitable antigen-binding domain that bind the cytokine can also be used, include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocalin and CTLA4 scaffolds.

In illustrative examples, when IL-2 is the cytokine in the chimeric polypeptide, the blocking moiety can be the full length or fragment or mutein of the alpha chain of IL-2 receptor (IL-2Rα) or beta (IL-2Rβ) or gamma chain of IL-2 receptor (IL-2Rγ), an anti-IL-2 single-domain antibody (dAb) or scFv, a Fab, an anti-CD25 antibody or fragment thereof, and anti-HAS dAb or scFv, and the like.

In Vivo Half-Life Extension Elements

Preferably, the chimeric polypeptides comprise an in vivo half-life extension element. Increasing the in vivo half-life of therapeutic molecules with naturally short half-lives allows for a more acceptable and manageable dosing regimen without sacrificing effectiveness. As used herein, a "half-life extension element" is a part of the chimeric polypeptide that increases the in vivo half-life and improve pK, for example, by altering its size (e.g., to be above the kidney filtration cutoff), shape, hydrodynamic radius, charge, or parameters of absorption, biodistribution, metabolism, and elimination. An exemplary way to improve the pK of a polypeptide is by expression of an element in the polypeptide chain that binds to receptors that are recycled to the plasma membrane of cells rather than degraded in the lysosomes, such as the FcRn receptor on endothelial cells and transferrin receptor. Three types of proteins, e.g., human IgGs, HSA (or fragments), and transferrin, persist for much longer in human serum than would be predicted just by their size, which is a function of their ability to bind to receptors that are recycled rather than degraded in the lysosome. These proteins, or fragments of them that retain the FcRn binding are routinely linked to other polypeptides to extend their serum half-life. In one embodiment, the half-life extension element is a human serum albumin (HSA) binding domain. HSA (SEQ ID NO: 2) may also be directly bound to the pharmaceutical compositions or bound via a short linker. Fragments of HSA may also be used. HSA and fragments thereof can function as both a blocking moiety and a half-life extension element. Human IgGs and Fc fragments can also carry out a similar function.

The serum half-life extension element can also be antigen-binding polypeptide that binds to a protein with a long serum half-life such as serum albumin, transferrin and the like. Examples of such polypeptides include antibodies and fragments thereof including, a polyclonal antibody, a recombinant antibody, a human antibody, a humanized antibody a single chain variable fragment (scFv), single-domain antibody such as a heavy chain variable domain (VH), a light chain variable domain (VL) and a variable domain of camelid-type nanobody (VHH), a dAb and the like. Other suitable antigen-binding domain include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocalin and CTLA4 scaffolds. Further examples of antigen-binding polypeptides include a ligand for a desired receptor, a ligand-binding portion of a receptor, a lectin, and peptides that binds to or associates with one or more target antigens.

Figure 5:
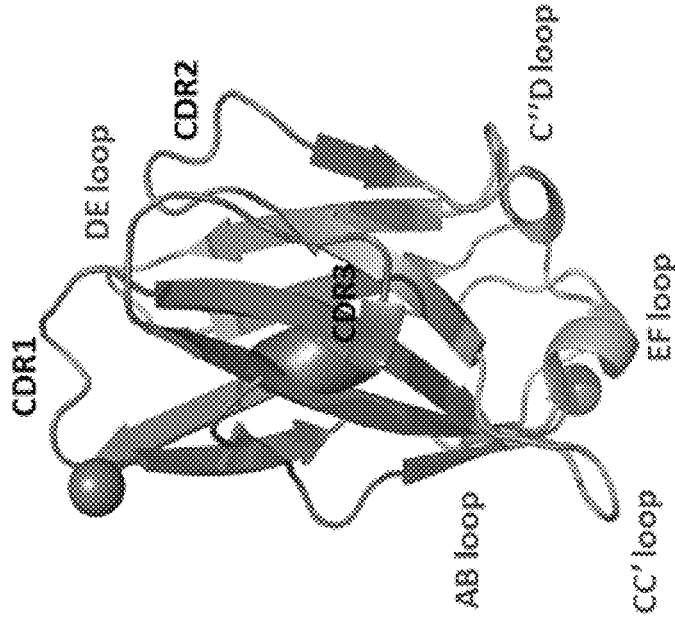
FIG. 5 is a schematic illustrating the structure of a variable domain of an immunoglobulin molecule. The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are the loops that connect beta strands B-C, C'-C", and F-G of the immunoglobulin fold, whereas the bottom loops that connect beta strands AB, CC', C"-D and E-F of the immunoglobulin fold, and the top loop that connects the D-E strands of the immunoglobulin fold are the non-CDR loops.
Figures 7A, 7B, 7C, 7D:
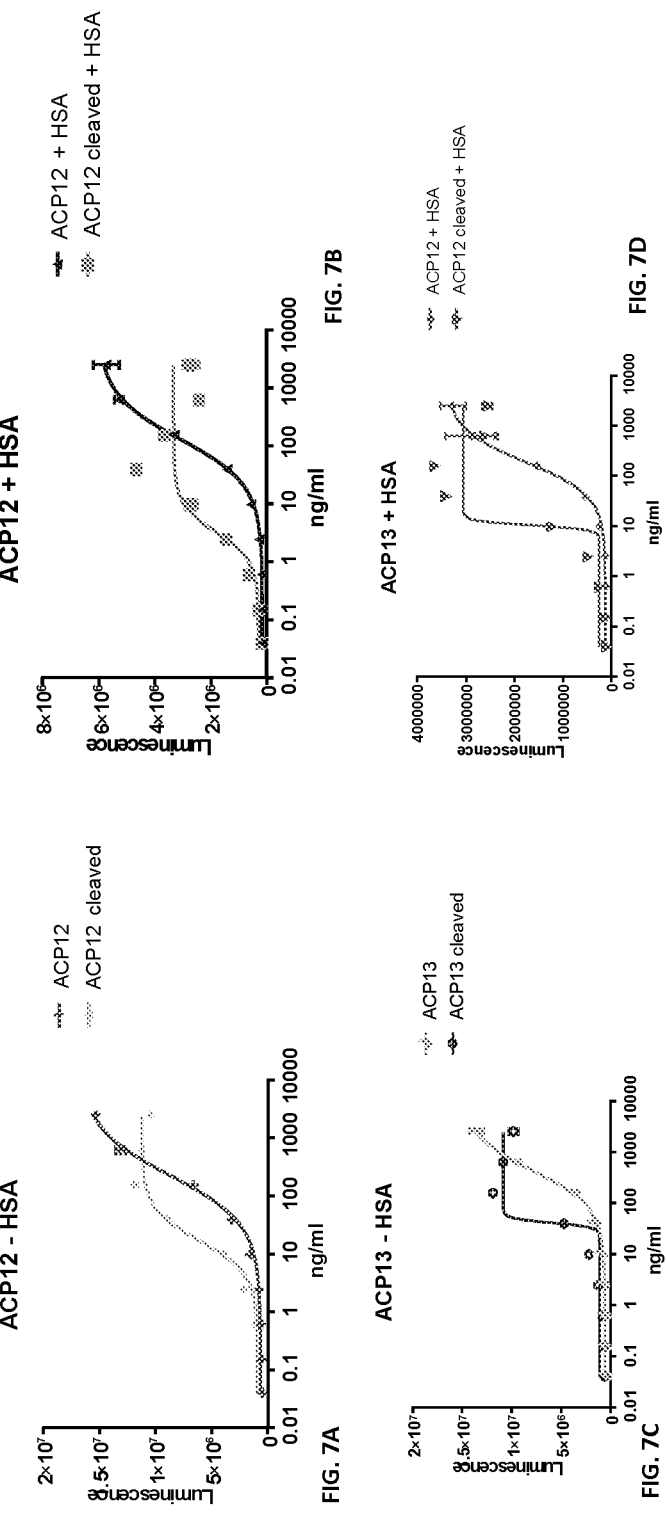

Some preferred serum half-life extension elements are polypeptides that comprise complementarity determining regions (CDRs), and optionally non-CDR loops. Advantageously, such serum half-life extension elements can extend the serum half-life of the cytokine, and also function as inhibitors of the cytokine (e.g., via steric blocking, non-covalent interaction or combination thereof) and/or as targeting domains. In some instances, the serum half-life extension elements are domains derived from an immunoglobulin molecule (Ig molecule) or engineered protein scaffolds that mimic antibody structure and/or binding activity. The Ig may be of any class or subclass (IgG1, IgG2, IgG3, IgG4, IgA, IgE, IgM etc). A polypeptide chain of an Ig molecule folds into a series of parallel beta strands linked by loops. In the variable region, three of the loops constitute the "complementarity determining regions" (CDRs) which determine the antigen binding specificity of the molecule. An IgG molecule comprises at least two heavy (H) chains and two light (L) chains inter-connected by disulfide bonds, or an antigen binding fragment thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs) with are hypervariable in sequence and/or involved in antigen recognition and/or usually form structurally defined loops, interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In some embodiments of this disclosure, at least some or all of the amino acid sequences of FR1, FR2, FR3, and FR4 are part of the "non-CDR loop" of the binding moieties described herein. As shown in FIG. 5, a variable domain of an immunoglobulin molecule has several beta strands that are arranged in two sheets. The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are the loops that connect beta strands B-C, C'-C", and F-G of the immunoglobulin fold, whereas the bottom loops that connect beta strands AB, CC', C"-D and E-F of the immunoglobulin fold, and the top loop that connects the D-E strands of the immunoglobulin fold are the non-CDR loops. In some embodiments of this disclosure, at least some amino acid residues of a constant domain, CH1, CH2, or CH3, are part of the "non-CDR loop" of the binding moieties described herein. Non-CDR loops comprise, in some embodiments, one or more of AB, CD, EF, and DE loops of a C1-set domain of an Ig or an Ig-like molecule; AB, CC', EF, FG, BC, and EC' loops of a C2-set domain of an Ig or an Ig-like molecule; DE, BD, GF, A(A1A2)B, and EF loops of I(Intermediate)-set domain of an Ig or Ig-like molecule.

Within the variable domain, the CDRs are believed to be responsible for antigen recognition and binding, while the FR residues are considered a scaffold for the CDRs. However, in certain cases, some of the FR residues play an important role in antigen recognition and binding. Framework region residues that affect Ag binding are divided into two categories. The first are FR residues that contact the antigen, thus are part of the binding-site, and some of these residues are close in sequence to the CDRs. Other residues are those that are far from the CDRs in sequence, but are in close proximity to it in the 3-D structure of the molecule, e.g., a loop in heavy chain.

The binding moieties are any kinds of polypeptides. For example, in certain instances the binding moieties are natural peptides, synthetic peptides, or fibronectin scaffolds, or engineered bulk serum proteins. The bulk serum protein comprises, for example, albumin, fibrinogen, or a globulin. In some embodiments, the binding moieties are engineered scaffolds. Engineered scaffolds comprise, for example, sdAb, a scFv, a Fab, a VHH, a fibronectin type III domain, immunoglobulin-like scaffold (as suggested in Halaby et al., 1999. Prot Eng 12(7):563-571), DARPin, cystine knot peptide, lipocalin, three-helix bundle scaffold, protein G-related albumin-binding module, or a DNA or RNA aptamer scaffold.

In some cases, the serum half-life extending element comprises a binding site for a bulk serum protein. In some embodiments, the CDRs provide the binding site for the bulk serum protein. The bulk serum protein is, in some examples, a globulin, albumin, transferrin, IgG1, IgG2, IgG4, IgG3, IgA monomer, Factor XIII, Fibrinogen, IgE, or pentameric IgM. In some embodiments, the CDR form a binding site for an immunoglobulin light chain, such as an Igκ free light chain or an Ig, free light chain.

The serum half-life extension element can be any type of binding domain, including but not limited to, domains from a monoclonal antibody, a polyclonal antibody, a recombinant antibody, a human antibody, a humanized antibody. In some embodiments, the binding moiety is a single chain variable fragment (scFv), single-domain antibody such as a heavy chain variable domain (VH), a light chain variable domain (VL) and a variable domain (VHH) of camelid derived nanobody. In other embodiments, the binding moieties are non-Ig binding domains, i.e., antibody mimetic, such as anticalins, affilins, affibody molecules, affimers, affitins, alphabodies, avimers, DARPins, fynomers, kunitz domain peptides, and monobodies.

In other embodiments, the serum half-life extension element can be a water-soluble polymer or a peptide that is conjugated to a water-soluble polymer, such as PEG. "PEG," "polyethylene glycol" and "poly(ethylene glycol)" as used herein, are interchangeable and encompass any nonpeptidic water-soluble poly(ethylene oxide). The term "PEG" also means a polymer that contains a majority, that is to say, greater than 50%, of —$OCH_2CH_2$— repeating subunits. With respect to specific forms, the PEG can take any number of a variety of molecular weights, as well as structures or geometries such as "branched," "linear," "forked," "multifunctional," and the like, to be described in greater detail below. The PEG is not limited to a particular structure and can be linear (e.g., an end capped, e.g., alkoxy PEG or a bifunctional PEG), branched or multi-armed (e.g., forked PEG or PEG attached to a polyol core), a dendritic (or star) architecture, each with or without one or more degradable linkages. Moreover, the internal structure of the PEG can be organized in any number of different repeat patterns and can be selected from the group consisting of homopolymer, alternating copolymer, random copolymer, block copolymer, alternating tripolymer, random tripolymer, and block tripolymer. PEGs can be conjugated to polypeptide and peptides through any suitable method. Typically a reactive PEG derivative, such as N-hydroxysuccinamidyl ester PEG, is reacted with a peptide or polypeptide that includes amino acids with a side chain that contains an amine, sulfhydryl, carboxylic acid or hydroxyl functional group, such as cysteine, lysine, asparagine, glutamine, theonine, tyrosine, serine, aspartic acid, and glutamic acid.

Targeting and Retention Domains

For certain applications, it may be desirable to maximize the amount of time the construct is present in its desired location in the body. This can be achieved by including one further domain in the chimeric polypeptide (fusion protein) to influence its movements within the body. For example, the chimeric nucleic acids can encode a domain that directs the polypeptide to a location in the body, e.g., tumor cells or a site of inflammation; this domain is termed a "targeting domain" and/or encode a domain that retains the polypeptide in a location in the body, e.g., tumor cells or a site of inflammation; this domain is termed a "retention domain". In some embodiments a domain can function as both a targeting and a retention domain. In some embodiments, the targeting domain and/or retention domain are specific to a protease-rich environment. In some embodiments, the encoded targeting domain and/or retention domain are specific for regulatory T cells (Tregs), for example targeting the CCR4 or CD39 receptors. Other suitable targeting and/or retention domains comprise those that have a cognate ligand that is overexpressed in inflamed tissues, e.g., the IL-1 receptor, or the IL-6 receptor. In other embodiments, the suitable targeting and/or retention domains comprise those who have a cognate ligand that is overexpressed in tumor tissue, e.g., Epcam, CEA or mesothelin. In some embodiments, the targeting domain is linked to the interleukin via a linker which is cleaved at the site of action (e.g. by inflammation or cancer specific proteases) releasing the interleukin full activity at the desired site. In some embodiments, the targeting and/or retention domain is linked to the interleukin via a linker which is not cleaved at the site of action (e.g. by inflammation or cancer specific proteases), causing the cytokine to remain at the desired site.

Antigens of choice, in some cases, are expressed on the surface of a diseased cell or tissue, for example a tumor or a cancer cell. Antigens useful for tumor targeting and retention include but are not limited to EpCAM, EGFR, HER-2, HER-3, c-Met, FOLR1, and CEA. Pharmaceutical compositions disclosed herein, also include proteins comprising two targeting and/or retention domains that bind to two different target antigens known to be expressed on a diseased cell or tissue. Exemplary pairs of antigen binding domains include but are not limited to EGFR/CEA, EpCAM/CEA, and HER-2/HER-3.

Suitable targeting and/or retention domains include antigen-binding domains, such as antibodies and fragments thereof including, a polyclonal antibody, a recombinant antibody, a human antibody, a humanized antibody a single chain variable fragment (scFv), single-domain antibody such as a heavy chain variable domain (VH), a light chain variable domain (VL) and a variable domain of camelid-type nanobody (VHH), a dAb and the like. Other suitable antigen-binding domain include non-immunoglobulin proteins that mimic antibody binding and/or structure such as, anticalins, affilins, affibody molecules, affimers, affitins, alphabodies, avimers, DARPins, fynomers, kunitz domain peptides, monobodies, and binding domains based on other engineered scaffolds such as SpA, GroEL, fibronectin, lipocalin and CTLA4 scaffolds. Further examples of antigen-binding polypeptides include a ligand for a desired receptor, a ligand-binding portion of a receptor, a lectin, and peptides that binds to or associates with one or more target antigens.

In some embodiments, the targeting and/or retention domains specifically bind to a cell surface molecule. In some embodiments, the targeting and/or retention domains specifically bind to a tumor antigen. In some embodiments, the targeting polypeptides specifically and independently bind to a tumor antigen selected from at least one of Fibroblast activation protein alpha (FAPa), Trophoblast glycoprotein (5T4), Tumor-associated calcium signal transducer 2

(Trop2), Fibronectin EDB (EDB-FN), fibronectin EIIIB domain, CGS-2, EpCAM, EGFR, HER-2, HER-3, cMet, CEA, and FOLR1. In some embodiments, the targeting polypeptides specifically and independently bind to two different antigens, wherein at least one of the antigens is a tumor antigen selected from EpCAM, EGFR, HER-2, HER-3, cMet, CEA, and FOLR1.

The targeting and/or retention antigen can be a tumor antigen expressed on a tumor cell. Tumor antigens are well known in the art and include, for example, EpCAM, EGFR, HER-2, HER-3, c-Met, FOLR1, PSMA, CD38, BCMA, and CEA. 5T4, AFP, B7-H3, Cadherin-6, CAIX, CD117, CD123, CD138, CD166, CD19, CD20, CD205, CD22, CD30, CD33, CD352, CD37, CD44, CD52, CD56, CD70, CD71, CD74, CD79b, DLL3, EphA2, FAP, FGFR2, FGFR3, GPC3, gpA33, FLT-3, gpNMB, HPV-16 E6, HPV-16 E7, ITGA2, ITGA3, SLC39A6, MAGE, mesothelin, Muc1, Muc16, NaPi2b, Nectin-4, β-cadherin, NY-ESO-1, PRLR, PSCA, PTK7, ROR1, SLC44A4, SLTRK5, SLTRK6, STEAP1, TIM1, Trop2, WT1.

The targeting and/or retention antigen can be an immune checkpoint protein. Examples of immune checkpoint proteins include but are not limited to CD27, CD137, 2B4, TIGIT, CD155, ICOS, HVEM, CD40L, LIGHT, TIM-1, OX40, DNAM-1, PD-L1, PD1, PD-L2, CTLA-4, CD8, CD40, CEACAM1, CD48, CD70, A2AR, CD39, CD73, B7-H3, B7-H4, BTLA, IDO1, IDO2, TDO, KIR, LAG-3, TIM-3, or VISTA.

The targeting and/or retention antigen can be a cell surface molecule such as a protein, lipid or polysaccharide. In some embodiments, a targeting and/or retention antigen is a on a tumor cell, virally infected cell, bacterially infected cell, damaged red blood cell, arterial plaque cell, inflamed or fibrotic tissue cell. The targeting and/or retention antigen can comprise an immune response modulator. Examples of immune response modulator include but are not limited to granulocyte-macrophage colony stimulating factor (GM-CSF), macrophage colony stimulating factor (M-CSF), granulocyte colony stimulating factor (G-CSF), interleukin 2 (IL-2), interleukin 3 (IL-3), interleukin 12 (IL-12), interleukin 15 (IL-15), B7-1 (CD80), B7-2 (CD86), GITRL, CD3, or GITR.

The targeting and/or retention antigen can be a cytokine receptor. Examples, of cytokine receptors include but are not limited to Type I cytokine receptors, such as GM-CSF receptor, G-CSF receptor, Type I IL receptors, Epo receptor, LIF receptor, CNTF receptor, TPO receptor; Type II Cytokine receptors, such as IFN-alpha receptor (IFNAR1, IFNAR2), IFB-beta receptor, IFN-gamma receptor (IFNGR1, IFNGR2), Type II IL receptors; chemokine receptors, such as CC chemokine receptors, CXC chemokine receptors, CX3C chemokine receptors, XC chemokine receptors; tumor necrosis receptor superfamily receptors, such as TNFRSF5/CD40, TNFRSF8/CD30, TNFRSF7/CD27, TNFRSF1A/TNFR1/CD120a, TNFRSF1B/TNFR2/CD120b; TGF-beta receptors, such as TGF-beta receptor 1, TGF-beta receptor 2; Ig super family receptors, such as IL-1 receptors, CSF-1R, PDGFR (PDGFRA, PDGFRB), SCFR.

Linkers

As stated above, the pharmaceutical compositions comprise one or more linker sequences. A linker sequence serves to provide flexibility between polypeptides, such that, for example, the blocking moiety is capable of inhibiting the activity of the cytokine polypeptide. The linker sequence can be located between any or all of the cytokine polypeptide, the serum half-life extension element, and/or the blocking moiety. As described herein at least one of the linkers is protease cleavable, and contains a (one or more) cleavage site for a (one or more) desired protease. Preferably, the desired protease is enriched or selectively expressed at the desired site of cytokine activity (e.g., the tumor microenvironment). Thus, the fusion protein is preferentially or selectively cleaved at the site of desired cytokine activity.

Suitable linkers can be of different lengths, such as from 1 amino acid (e.g., Gly) to 20 amino acids, from 2 amino acids to 15 amino acids, from 3 amino acids to 12 amino acids, including 4 amino acids to 10 amino acids, amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids.

The orientation of the components of the pharmaceutical composition, are largely a matter of design choice and it is recognized that multiple orientations are possible and all are intended to be encompassed by this disclosure. For example, a blocking moiety can be located C-terminally or N-terminally to a cytokine polypeptide.

Proteases known to be associated with diseased cells or tissues include but are not limited to serine proteases, cysteine proteases, aspartate proteases, threonine proteases, glutamic acid proteases, metalloproteases, asparagine peptide lyases, serum proteases, cathepsins, Cathepsin B, Cathepsin C, Cathepsin D, Cathepsin E, Cathepsin K, Cathepsin L, kallikreins, hK1, hK10, hK15, plasmin, collagenase, Type IV collagenase, stromelysin, Factor Xa, chymotrypsin-like protease, trypsin-like protease, elastase-like protease, subtilisin-like protease, actinidain, bromelain, calpain, caspases, caspase-3, Mirl-CP, papain, HIV-1 protease, HSV protease, CMV protease, chymosin, renin, pepsin, matriptase, legumain, plasmepsin, nepenthesin, metalloexopeptidases, metalloendopeptidases, matrix metalloproteases (MMP), MMP1, MMP2, MMP3, MMP8, MMP9, MMP13, MMP11, MMP14, urokinase plasminogen activator (uPA), enterokinase, prostate-specific antigen (PSA, hK3), interleukin-1β converting enzyme, thrombin, FAP (FAP-a), dipeptidyl peptidase, meprins, granzymes and dipeptidyl peptidase IV (DPPIV/CD26). Proteases capable of cleaving amino acid sequences encoded by the chimeric nucleic acid sequences provided herein can, for example, be selected from the group consisting of a prostate specific antigen (PSA), a matrix metalloproteinase (MMP), an A Disintigrin and a Metalloproteinase (ADAM), a plasminogen activator, a cathepsin, a caspase, a tumor cell surface protease, and an elastase. The MMP can, for example, be matrix metalloproteinase 2 (MMP2) or matrix metalloproteinase 9 (MMP9).

Proteases useful in the methods disclosed herein are presented in Table 1, and exemplary proteases and their cleavage site are presented in Table 1a:

TABLE 1

| Proteases relevant to inflammation and cancer | | |
|---|---|---|
| Protease | Specificity | Other aspects |
| Secreted by killer T cells: | | |
| Granzyme B (grB) | Cleaves after Asp residues (asp-ase) | Type of serine protease; strongly implicated in inducing perforin-dependent target cell apoptosis |
| Granzyme A (grA) | trypsin-like, cleaves after basic residues | Type of serine protease; |
| Granzyme H (grH) | Unknown substrate specificity | Type of serine protease; Other granzymes are also secreted by killer T cells, but not all are present in humans |
| Caspase-8 | Cleaves after Asp residues | Type of cysteine protease; plays essential role in TCR-induced cellular expansion-exact molecular role unclear |
| Mucosa-associated lymphoid tissue (MALT1) | Cleaves after arginine residues | Type of cysteine protease; likely acts both as a scaffold and proteolytically active enzyme in the CBM-dependent signaling pathway |
| Tryptase | Targets: angiotensin I, fibrinogen, prourokinase, TGFβ; preferentially cleaves proteins after lysine or arginine residues | Type of mast cell-specific serine protease; trypsin-like; resistant to inhibition by macromolecular protease inhibitors expressed in mammals due to their tetrameric structure, with all sites facing narrow central pore; also associated with inflammation |
| Associated with inflammation: | | |
| Thrombin | Targets: FGF-2, HB-EGF, Osteo-pontin, PDGF, VEGF | Type of serine protease; modulates activity of vascular growth factors, chemokines and extracellular proteins; strengthens VEGF-induced proliferation; induces cell migration; angiogenic factor; regulates hemostasis |
| Chymase | Exhibit chymotrypsin-like specificity, cleaving proteins after aromatic amino acid residues | Type of mast cell-specific serine protease |
| Carboxypeptidase A (MC-CPA) | Cleaves amino acid residues from C-terminal end of peptides and proteins | Type of zinc-dependent metalloproteinase |
| Kallikreins | Targets: high molecular weight kininogen, pro-urokinase | Type of serine protease; modulate relaxation response; contribute to inflammatory response; fibrin degradation |
| Elastase | Targets: E-cadherin, GM-CSF, IL-1, IL-2, IL-6, IL8, p38$^{MAPK}$, TNFα, VE-cadherin | Type of neutrophil serine protease; degrades ECM components; regulates inflammatory response; activates pro-apoptotic signaling |
| Cathepsin G | Targets: EGF, ENA-78, IL-8, MCP-1, MMP-2, MT1-MMP, PAI-1, RANTES, TGFβ, TNFα | Type of serine protease; degrades ECM components; chemo-attractant of leukocytes; regulates inflammatory response; promotes apoptosis |
| PR-3 | Targets: ENA-78, IL-8, IL-18, JNK, p38$^{MAPK}$, TNFα | Type of serine protease; promotes inflammatory response; activates pro-apoptotic signaling |
| Granzyme M (grM) | Cleaves after Met and other long, unbranched hydrophobic residues | Type of serine protease; only expressed in NK cells |
| Calpains | Cleave between Arg and Gly | Family of cysteine proteases; calcium-dependent; activation is involved in the process of numerous inflammation-associated diseases |

TABLE 1a

Exemplary Proteases and Protease Recognition Sequences

| Protease | Cleavage Domain Sequence | SEQ ID NO: |
|---|---|---|
| MMP7 | KRALGLPG | 3 |
| MMP7 | (DE)$_8$RPLALWRS(DR)$_8$ | 4 |
| MMP9 | PR(S/T)(L/I)(S/T) | 5 |
| MMP9 | LEATA | 6 |
| MMP11 | GGAANLVRGG | 7 |
| MMP14 | SGRIGFLRTA | 8 |
| MMP | PLGLAG | 9 |
| MMP | PLGLAX | 10 |
| MMP | PLGC(me)AG | 11 |
| MMP | ESPAYYTA | 12 |
| MMP | RLQLKL | 13 |
| MMP | RLQLKAC | 14 |
| MMP2, MMP9, MMP14 | EP(Cit)G(Hof)YL | 15 |
| Urokinase plasminogen activator (uPA) | SGRSA | 16 |
| Urokinase plasminogen activator (uPA) | DAFK | 17 |
| Urokinase plasminogen activator (uPA) | GGGRR | 18 |
| Lysosomal Enzyme | GFLG | 19 |
| Lysosomal Enzyme | ALAL | 20 |
| Lysosomal Enzyme | FK | 21 |
| Cathepsin B | NLL | 22 |
| Cathepsin D | PIC(Et)FF | 23 |
| Cathepsin K | GGPRGLPG | 24 |
| Prostate Specific Antigen | HSSKLQ | 25 |
| Prostate Specific Antigen | HSSKLQL | 26 |
| Prostate Specific Antigen | HSSKLQEDA | 27 |
| Herpes Simplex Virus Protease | LVLASSSFGY | 28 |
| HIV Protease | GVSQNYPIVG | 29 |
| CMV Protease | GVVQASCRLA | 30 |
| Thrombin | F(Pip)RS | 31 |
| Thrombin | DPRSFL | 32 |
| Thrombin | PPRSFL | 33 |
| Caspase-3 | DEVD | 34 |
| Caspase-3 | DEVDP | 35 |

TABLE 1a-continued

Exemplary Proteases and Protease Recognition Sequences

| Protease | Cleavage Domain Sequence | SEQ ID NO: |
|---|---|---|
| Caspase-3 | KGSGDVEG | 36 |
| Interleukin 1β converting enzyme | GWEHDG | 37 |
| Enterokinase | EDDDDKA | 38 |
| FAP | KQEQNPGST | 39 |
| Kallikrein 2 | GKAFRR | 40 |
| Plasmin | DAFK | 41 |
| Plasmin | DVLK | 42 |
| Plasmin | DAFK | 43 |
| TOP | ALLLALL | 44 |

Provided herein are pharmaceutical compositions comprising polypeptide sequences. As with all peptides, polypeptides, and proteins, including fragments thereof, it is understood that additional modifications in the amino acid sequence of the chimeric polypeptides (amino acid sequence variants) can occur that do not alter the nature or function of the peptides, polypeptides, or proteins. Such modifications include conservative amino acid substitutions and are discussed in greater detail below.

The compositions provided herein have a desired function. The compositions are comprised of at least a cytokine polypeptide, such as IL-2, IL-7, IL-12, IL-15, IL-18, IL-21, IFNa, or IFNγ, or a chemokine, such as CXCL10, CCL19, CCL20, CCL21, a blocking moiety, e. g. a steric blocking polypeptide, and an optional serum half-life extension element, and an optional targeting polypeptide, with one or more linkers connecting each polypeptide in the composition. The first polypeptide, e.g., an IL-2 mutein, is provided to be an active agent. The blocking moiety is provided to block the activity of the interleukin. The linker polypeptide, e.g., a protease cleavable polypeptide, is provided to be cleaved by a protease that is specifically expressed at the intended target of the active agent. Optionally, the blocking moiety blocks the activity of the first polypeptide by binding the interleukin polypeptide. In some embodiments, the blocking moiety, e.g. a steric blocking peptide, is linked to the interleukin via a protease-cleavable linker which is cleaved at the site of action (e.g. by inflammation-specific or tumor-specific proteases) releasing the cytokine full activity at the desired site.

The protease cleavage site may be a naturally occurring protease cleavage site or an artificially engineered protease cleavage site. The artificially engineered protease cleavage site can be cleaved by more than one protease specific to the desired environment in which cleavage will occur, e.g. a tumor. The protease cleavage site may be cleavable by at least one protease, at least two proteases, at least three proteases, or at least four proteases.

In some embodiments, the linker comprises glycine-glycine, a sortase-recognition motif, or a sortase-recognition motif and a peptide sequence (Gly$_4$Ser)$_n$ (SEQ ID NO.: 443) or (Gly$_3$Ser)$_n$, (SEQ ID NO.: 444), wherein n is 1, 2, 3, 4 or 5. In one embodiment, the sortase-recognition motif comprises a peptide sequence LPXTG (SEQ ID NO.: 442), where X is any amino acid. In one embodiment, the covalent linkage is between a reactive lysine residue attached to the C-terminal of the cytokine polypeptide and a reactive aspartic acid attached to the N-terminal of the blocking or other moiety. In one embodiment, the covalent linkage is between a reactive aspartic acid residue attached to the N-terminal of the cytokine polypeptide and a reactive lysine residue attached to the C-terminal of the blocking or other moiety.

Cleavage and Inducibility

As described herein, the activity of the cytokine polypeptide the context of the fusion protein is attenuated, and protease cleavage at the desired site of activity, such as in a tumor microenvironment, releases a form of the cytokine from the fusion protein that is much more active as a cytokine receptor agonist than the fusion protein. For example, the cytokine-receptor activating (agonist) activity of the fusion polypeptide can be at least about 10×, at least about 50×, at least about 100×, at least about 250×, at least about 500×, or at least about 1000× less than the cytokine receptor activating activity of the cytokine polypeptide as a separate molecular entity. The cytokine polypeptide that is part of the fusion protein exists as a separate molecular entity when it contains an amino acid that is substantially identical to the cytokine polypeptide and does not substantially include additional amino acids and is not associated (by covalent or non-covalent bonds) with other molecules. If necessary, a cytokine polypeptide as a separate molecular entity may include some additional amino acid sequences, such as a tag or short sequence to aid in expression and/or purification.

In other examples, the cytokine-receptor activating (agonist) activity of the fusion polypeptide is at least about 10×, at least about 50×, at least about 100×, at least about 250×, at least about 500×, or about 1000× less than the cytokine receptor activating activity of the polypeptide that contains the cytokine polypeptide that is produced by cleavage of the protease cleavable linker in the fusion protein. In other words, the cytokine receptor activating (agonist) activity of the polypeptide that contains the cytokine polypeptide that is produced by cleavage of the protease cleavable linker in the fusion protein is at least about 10×, at least about 50×, at least about 100×, at least about 250×, at least about 500×, or at least about 1000× greater than the cytokine receptor activating activity of the fusion protein.

Polypeptide Substitutions

The polypeptides described herein can include components (e.g., the cytokine, the blocking moiety) that have the same amino acid sequence of the corresponding naturally occurring protein (e.g., IL-2, IL-15, HSA) or can have an amino acid sequence that differs from the naturally occurring protein so long as the desired function is maintained. It is understood that one way to define any known modifications and derivatives or those that might arise, of the disclosed proteins and nucleic acids that encode them is through defining the sequence variants in terms of identity to specific known reference sequences. Specifically disclosed are polypeptides and nucleic acids which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the chimeric polypeptides provided herein. For example, provided are polypeptides or nucleic acids that have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the sequence of any of the nucleic acids or polypeptides described herein. Those of skill in the art readily understand how to determine the identity of two polypeptides or two nucleic acids. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman Adv. Appl. Math. 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-7710 (1989); Jaeger et al., Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

Protein modifications include amino acid sequence modifications. Modifications in amino acid sequence may arise naturally as allelic variations (e.g., due to genetic polymorphism), may arise due to environmental influence (e.g., by exposure to ultraviolet light), or may be produced by human intervention (e.g., by mutagenesis of cloned DNA sequences), such as induced point, deletion, insertion and substitution mutants. These modifications can result in changes in the amino acid sequence, provide silent mutations, modify a restriction site, or provide other specific mutations. Amino acid sequence modifications typically fall into one or more of three classes: substitutional, insertional or deletional modifications. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. Such substitutions generally are made in accordance with the following Table 2 and are referred to as conservative substitutions.

TABLE 2

| Exemplary amino acid substitutions | |
| --- | --- |
| Amino Acid | Exemplary Substitutions |
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

Modifications, including the specific amino acid substitutions, are made by known methods. For example, modifications are made by site specific mutagenesis of nucleotides in the DNA encoding the polypeptide, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

Modifications can be selected to optimize binding. For example, affinity maturation techniques can be used to alter binding of the scFv by introducing random mutations inside the complementarity determining regions (CDRs). Such random mutations can be introduced using a variety of techniques, including radiation, chemical mutagens or error-prone PCR. Multiple rounds of mutation and selection can be performed using, for example, phage display.

The disclosure also relates to nucleic acids that encode the chimeric polypeptides described herein, and to the use of such nucleic acids to produce the chimeric polypeptides and for therapeutic purposes. For example, the invention includes DNA and RNA molecules (e.g., mRNA, self-replicating RNA) that encode a chimeric polypeptide and to the therapeutic use of such DNA and RNA molecules.

Exemplary Compositions

Exemplary fusion proteins of the invention combine the above described elements in a variety of orientations. The orientations described in this section are meant as examples and are not to be considered limiting.

In some embodiments, the fusion protein comprises a cytokine, a blocking moiety and a half-life extension element. In some embodiments, the cytokine is positioned between the half-life extension element and the blocking moiety. In some embodiments, the cytokine is N-terminal to the blocking moiety and the half-life extension element. In some such embodiments, the cytokine is proximal to the blocking moiety; in some such embodiments, the cytokine is proximal to the half-life extension element. At least one protease-cleavable linker must be included in all embodiments, such that the cytokine may be active upon cleavage. In some embodiments, the cytokine is C-terminal to the blocking moiety and the half-life extension element. Additional elements may be attached to one another by a cleavable linker, a non-cleavable linker, or by direct fusion.

In some embodiments, the blocking domains used are capable of extending half-life, and the cytokine is positioned between two such blocking domains. In some embodiments, the cytokine is positioned between two blocking domains, one of which is capable of extending half-life.

In some embodiments, two cytokines are included in the same construct. In some embodiments, the cytokines are connected to two blocking domains each (three in total in one molecule), with a blocking domain between the two cytokine domains. In some embodiments, one or more additional half-life extension domains may be included to optimize pharmacokinetic properties. In some cases, it is beneficial to include two of the same cytokine to facilitate dimerization. An example of a cytokine that works as a dimer is IFN.

In some embodiments, three cytokines are included in the same construct. In some embodiments, the third cytokine may function to block the other two in place of a blocking domain between the two cytokines.

Preferred half-life extension elements for use in the fusion proteins are human serum albumin (HSA), an antibody or antibody fragment (e.g., scFV, dAb) which binds serum albumin, a human or humanized IgG, or a fragment of any of the foregoing. In some preferred embodiments, the blocking moiety is human serum albumin (HSA), or an antibody or antibody fragment which binds serum albumin, an antibody which binds the cytokine and prevents activation of binding or activation of the cytokine receptor, another cytokine, or a fragment of any of the foregoing. In preferred embodiments comprising an additional targeting domain, the targeting domain is an antibody which binds a cell surface protein which is enriched on the surface of cancer cells, such as EpCAM, FOLR1, and Fibronectin.

Methods of Treatment and Pharmaceutical Compositions

Further provided are methods of treating a subject with or at risk of developing an of a disease or disorder, such as proliferative disease, a tumorous disease, an inflammatory disease, an immunological disorder, an autoimmune disease, an infectious disease, a viral disease, an allergic reaction, a parasitic reaction, or graft-versus-host disease. The methods administering to a subject in need thereof an effective amount of a fusion protein as disclosed herein that is typically administered as a pharmaceutical composition. In some embodiments, the method further comprises selecting a subject with or at risk of developing such a disease or disorder. The pharmaceutical composition preferably comprises a blocked cytokine, fragment or mutein thereof that is activated at a site of inflammation or a tumor. In one embodiment, the chimeric polypeptide comprises a cytokine polypeptide, fragment or mutein thereof and a serum half-life extension element. In another embodiment, the chimeric polypeptide comprises a cytokine polypeptide, fragment or mutein thereof and a blocking moiety, e.g. a steric blocking polypeptide, wherein the steric blocking polypeptide is capable of sterically blocking the activity of the cytokine polypeptide, fragment or mutein thereof. In another embodiment, the chimeric polypeptide comprises a cytokine polypeptide, fragment or mutein thereof, a blocking moiety, and a serum half-life extension element.

Inflammation is part of the complex biological response of body tissues to harmful stimuli, such as pathogens, damaged cells, or irritants, and is a protective response involving immune cells, blood vessels, and molecular mediators. The function of inflammation is to eliminate the initial cause of cell injury, clear out necrotic cells and tissues damaged from the original insult and the inflammatory process, and to initiate tissue repair. Inflammation can occur from infection, as a symptom or a disease, e.g., cancer, atherosclerosis, allergies, myopathies, HIV, obesity, or an autoimmune disease. An autoimmune disease is a chronic condition arising from an abnormal immune response to a self-antigen. Autoimmune diseases that may be treated with the polypeptides disclosed herein include but are not limited to lupus, celiac disease, diabetes mellitus type 1, Graves disease, inflammatory bowel disease, multiple sclerosis, psoriasis, rheumatoid arthritis, and systemic lupus erythematosus.

The pharmaceutical composition can comprise one or more protease-cleavable linker sequences. The linker sequence serves to provide flexibility between polypeptides, such that each polypeptide is capable of inhibiting the activity of the first polypeptide. The linker sequence can be located between any or all of the cytokine polypeptide, fragment or mutein thereof, the blocking moiety, and serum half-life extension element. Optionally, the composition comprises, two, three, four, or five linker sequences. The linker sequence, two, three, or four linker sequences can be the same or different linker sequences. In one embodiment, the linker sequence comprises GGGGS (SEQ ID NO.: 449), GSGSGS (SEQ ID NO.: 450), or G(SGGG)$_2$SGGT (SEQ ID NO.: 451). In another embodiment, the linker comprises a protease-cleavable sequence selected from group consisting of HSSKLQ (SEQ ID NO.: 25), GPLGVRG (SEQ ID NO.: 445), IPVSLRSG (SEQ ID NO.: 446), VPLSLYSG (SEQ ID NO.: 447, and SGESPAYYTA (SEQ ID NO.: 448).

In some embodiments, the linker is cleaved by a protease selected from the group consisting of a kallikrein, thrombin, chymase, carboxypeptidase A, cathepsin G, an elastase, PR-3, granzyme M, a calpain, a matrix metalloproteinase (MMP), a plasminogen activator, a cathepsin, a caspase, a tryptase, or a tumor cell surface protease.

Suitable linkers can be of different lengths, such as from 1 amino acid (e.g., Gly) to 20 amino acids, from 2 amino acids to 15 amino acids, from 3 amino acids to 12 amino acids, including 4 amino acids to 10 amino acids, amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 amino acids.

Further provided are methods of treating a subject with or at risk of developing cancer. The methods comprise administering to the subject in need thereof an effective amount of a chimeric polypeptide (a fusion protein) as disclosed herein that is typically administered as a pharmaceutical composition. In some embodiments, the method further comprises selecting a subject with or at risk of developing cancer. The pharmaceutical composition preferably comprises a blocked cytokine, fragment or mutein thereof that is activated at a tumor site. Preferably, the tumor is a solid tumor. The cancer may be, but not limited to, a colon cancer, a lung cancer, a melanoma, a sarcoma, a renal cell carcinoma, and a breast cancer.

The method can further involve the administration of one or more additional agents to treat cancer, such as chemotherapeutic agents (e.g., Adriamycin, Cerubidine, Bleomycin, Alkeran, Velban, Oncovin, Fluorouracil, Thiotepa, Methotrexate, Bisantrene, Noantrone, Thiguanine, Cytaribine, Procarabizine), immuno-oncology agents (e.g., anti-PD-L1, anti-CTLA4, anti-PD-1, anti-CD47, anti-GD2), cellular therapies (e.g, CAR-T, T-cell therapy), oncolytic viruses and the like.

Provided herein are pharmaceutical formulations or compositions containing the chimeric polypeptides and a pharmaceutically acceptable carrier. The herein provided compositions are suitable for administration in vitro or in vivo. By pharmaceutically acceptable carrier is meant a material that is not biologically or otherwise undesirable, i.e., the material is administered to a subject without causing undesirable biological effects or interacting in a deleterious manner with the other components of the pharmaceutical formulation or composition in which it is contained. The carrier is selected to minimize degradation of the active ingredient and to minimize adverse side effects in the subject.

Suitable carriers and their formulations are described in *Remington: The Science and Practice of Pharmacy*, 21$^{st}$ Edition, David B. Troy, ed., Lippicott Williams & Wilkins (2005). Typically, an appropriate amount of a pharmaceutically-acceptable salt is used in the formulation to render the formulation isotonic, although the formulate can be hypertonic or hypotonic if desired. Examples of the pharmaceutically-acceptable carriers include, but are not limited to, sterile water, saline, buffered solutions like Ringer's solution, and dextrose solution. The pH of the solution is generally about 5 to about 8 or from about 7 to 7.5. Other carriers include sustained release preparations such as semipermeable matrices of solid hydrophobic polymers containing the immunogenic polypeptides. Matrices are in the form of shaped articles, e.g., films, liposomes, or microparticles. Certain carriers may be more preferable depending upon, for instance, the route of administration and concentration of composition being administered. Carriers are those suitable for administration of the chimeric polypeptides or nucleic acid sequences encoding the chimeric polypeptides to humans or other subjects.

The pharmaceutical formulations or compositions are administered in a number of ways depending on whether local or systemic treatment is desired and on the area to be treated. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy. In some embodiments, the compositions are administered locally (non-systemically), including intratumorally, intra-articularly, intrathecally, etc.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, anti-oxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally desirable.

Optionally, the chimeric polypeptides or nucleic acid sequences encoding the chimeric polypeptides are administered by a vector. There are a number of compositions and methods which can be used to deliver the nucleic acid molecules and/or polypeptides to cells, either in vitro or in vivo via, for example, expression vectors. These methods and compositions can largely be broken down into two classes: viral based delivery systems and non-viral based delivery systems. Such methods are well known in the art and readily adaptable for use with the compositions and methods described herein. Such compositions and methods can be used to transfect or transduce cells in vitro or in vivo, for example, to produce cell lines that express and preferably secrete the encoded chimeric polypeptide or to therapeutically deliver nucleic acids to a subject. The components of the chimeric nucleic acids disclosed herein typically are operably linked in frame to encode a fusion protein.

As used herein, plasmid or viral vectors are agents that transport the disclosed nucleic acids into the cell without degradation and include a promoter yielding expression of the nucleic acid molecule and/or polypeptide in the cells into which it is delivered. Viral vectors are, for example, Adenovirus, Adeno-associated virus, herpes virus, Vaccinia virus, Polio virus, Sindbis, and other RNA viruses, including these viruses with the HIV backbone. Also preferred are any viral families which share the properties of these viruses which make them suitable for use as vectors. Retroviral vectors, in general are described by Coffin et al., Retroviruses, Cold Spring Harbor Laboratory Press (1997), which is incorporated by reference herein for the vectors and methods of making them. The construction of replication-defective adenoviruses has been described (Berkner et al., J. Virol. 61:1213-20 (1987); Massie et al., Mol. Cell. Biol. 6:2872-83 (1986); Haj-Ahmad et al., J. Virol. 57:267-74 (1986); Davidson et al., J. Virol. 61:1226-39 (1987); Zhang et al., BioTechniques 15:868-72 (1993)). The benefit and the use of these viruses as vectors is that they are limited in the extent to which they can spread to other cell types, since they can replicate within an initial infected cell, but are unable to form new infectious viral particles. Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors.

The provided polypeptides and/or nucleic acid molecules can be delivered via virus like particles. Virus like particles (VLPs) consist of viral protein(s) derived from the structural proteins of a virus. Methods for making and using virus like particles are described in, for example, Garcea and Gissmann, Current Opinion in Biotechnology 15:513-7 (2004).

The provided polypeptides can be delivered by subviral dense bodies (DBs). DBs transport proteins into target cells by membrane fusion. Methods for making and using DBs are described in, for example, Pepperl-Klindworth et al., Gene Therapy 10:278-84 (2003).

The provided polypeptides can be delivered by tegument aggregates. Methods for making and using tegument aggregates are described in International Publication No. WO 2006/110728.

Non-viral based delivery methods, can include expression vectors comprising nucleic acid molecules and nucleic acid sequences encoding polypeptides, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clonetech (Pal Alto, Calif), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns. Such vectors can also be used to make the chimeric polypeptides by expression is a suitable host cell, such as CHO cells.

Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. β-actin promoter or EF1α promoter, or from hybrid or chimeric promoters (e.g., CMV promoter fused to the β-actin promoter). Of course, promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs (bp) in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g. chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type are the CMV promoter, the SV40 promoter, the β-actin promoter, the EF1α promoter, and the retroviral long terminal repeat (LTR).

The vectors also can include, for example, origins of replication and/or markers. A marker gene can confer a selectable phenotype, e.g., antibiotic resistance, on a cell.

The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the *E. coli* lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

As used herein, the terms peptide, polypeptide, or protein are used broadly to mean two or more amino acids linked by a peptide bond. Protein, peptide, and polypeptide are also used herein interchangeably to refer to amino acid sequences. It should be recognized that the term polypeptide is not used herein to suggest a particular size or number of amino acids comprising the molecule and that a peptide of the invention can contain up to several amino acid residues or more. As used throughout, subject can be a vertebrate, more specifically a mammal (e.g. a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g. cancer). The term patient or subject includes human and veterinary subjects.

A subject at risk of developing a disease or disorder can be genetically predisposed to the disease or disorder, e.g., have a family history or have a mutation in a gene that causes the disease or disorder, or show early signs or symptoms of the disease or disorder. A subject currently with a disease or disorder has one or more than one symptom of the disease or disorder and may have been diagnosed with the disease or disorder.

The methods and agents as described herein are useful for both prophylactic and therapeutic treatment. For prophylactic use, a therapeutically effective amount of the chimeric polypeptides or chimeric nucleic acid sequences encoding the chimeric polypeptides described herein are administered to a subject prior to onset (e.g., before obvious signs of cancer or inflammation) or during early onset (e.g., upon initial signs and symptoms of cancer or inflammation). Prophylactic administration can occur for several days to years prior to the manifestation of symptoms of cancer or inflammation. Prophylactic administration can be used, for example, in the preventative treatment of subjects diagnosed with a genetic predisposition to cancer. Therapeutic treatment involves administering to a subject a therapeutically effective amount of the chimeric polypeptides or nucleic acid sequences encoding the chimeric polypeptides described herein after diagnosis or development of cancer or inflammation (e.g., an autoimmune disease). Prophylactic use may also apply when a patient is undergoing a treatment, e.g., a chemotherapy, in which inflammation is expected.

According to the methods taught herein, the subject is administered an effective amount of the agent (e.g., a chimeric polypeptide). The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products.

As used herein the terms treatment, treat, or treating refers to a method of reducing the effects of a disease or condition or symptom of the disease or condition. Thus, in the disclosed method, treatment can refer to a 10%, 20%, 30%, 40%, 50%, 60%, 70%, 80%, 90%, or 100% reduction in the severity of an established disease or condition or symptom of the disease or condition. For example, a method for treating a disease is considered to be a treatment if there is a 10% reduction in one or more symptoms of the disease in a subject as compared to a control. Thus, the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refers to an action, for example, administration of the chimeric polypeptide or nucleic acid sequence encoding the chimeric polypeptide, that occurs before or at about the same time a subject begins to show one or more symptoms of the disease or disorder, which inhibits or delays onset or exacerbation of one or more symptoms of the disease or disorder. As used herein, references to decreasing, reducing, or inhibiting include a change of 10%, 20%, 30%, 40%, 50%, 60%, 70%, 80%, 90% or greater as compared to a control level. Such terms can include but do not necessarily include complete elimination.

IL-2 variants have been developed that are selective for IL2Rαβγ relative to IL2Rβγ (Shanafelt, A. B., et al., 2000, Nat Biotechnol. 18:1197-202; Cassell, D. J., et. al., 2002, Curr Pharm Des., 8:2171-83). These variants have amino acid substitutions which reduce their affinity for IL2RB. Because IL-2 has undetectable affinity for IL2RG, these variants consequently have reduced affinity for the IL2Rβγ receptor complex and reduced ability to activate IL2Rβγ-expressing cells, but retain the ability to bind IL2RA and the ability to bind and activate the IL2Rαβγ receptor complex.

One of these variants, IL2/N88R (Bay 50-4798), was clinically tested as a low-toxicity version of IL-2 as an immune system stimulator, based on the hypothesis that IL2Rβγ-expressing NK cells are a major contributor to toxicity. Bay 50-4798 was shown to selectively stimulate the proliferation of activated T cells relative to NK cells, and was evaluated in phase I/II clinical trials in cancer patients (Margolin, K., et. al., 2007, Clin Cancer Res., 13:3312-9) and HIV patients (Davey, R. T., et. al., 2008, J Interferon Cytokine Res., 28:89-100). These clinical trials showed that Bay 50-4798 was considerably safer and more tolerable than aldesleukin, and also showed that it increased the levels of CD4+CD25+ T cells, a cell population enriched in Treg cells. Subsequent to these trials, research in the field more fully established the identity of Treg cells and demonstrated that Treg cells selectively express IL2Rαβγ (reviewed in Malek, T. R., et al., 2010, Immunity, 33:153-65).

In addition, mutants can be made that selectively alter the affinity for the CD25 chain relative to native 11-2.

IL-2 can be engineered to produce mutants that bind the IL-2R complex generally or the IL-2Rα subunit specifically with an affinity that differs from that of the corresponding wild-type IL-2 or of a presently available mutant (referred to as C125S, as the cysteine residue at position 125 is replaced with a serine residue).

Accordingly, the present invention features mutant interleukin-2 (IL-2*) polypeptides that include an amino acid sequence that is at least 80% identical to wild-type IL-2 (e.g., 85, 87, 90, 95, 97, 98, or 99% identical) and that bind, as compared to WT IL-2, with higher to the IL-2 trimeric receptor relative to the dimeric IL-2 receptor. Typically, the muteins will also bind an IL-2 receptor a subunit (IL-2Rα) with an affinity that is greater than the affinity with which wild type IL-2 binds the IL-2Rα. The amino acid sequence within mutant IL-2 polypeptides can vary from SEQ ID NO:1 (UniProtKB accession number P60568) by virtue of containing (or only containing) one or more amino acid substitutions, which may be considered conservative or non-conservative substitutions. Non-naturally occurring amino acids can also be incorporated. Alternatively, or in addition, the amino acid sequence can vary from SEQ ID NO:1 (which may be considered the "reference" sequence) by virtue of containing and addition and/or deletion of one or more amino acid residues. More specifically, the amino acid sequence can differ from that of SEQ ID NO:1 by virtue of a mutation at least one of the following positions of SEQ ID NO:1: 1, 4, 8, 9, 10, 11, 13, 15, 26, 29, 30, 31, 35, 37, 46, 48, 49, 54, 61, 64, 67, 68, 69, 71, 73, 74, 75, 76, 79, 88, 89, 90, 92, 99, 101, 103, 114, 125, 128, or 133 (or combinations thereof). As noted, as few as one of these positions may be altered, as may two, three, four, five, six, seven, eight, nine, ten, or 11 or more (including up to all) of the positions. For example, the amino acid sequence can differ from SEQ ID NO:1 at positions 69 and 74 and further at one or more of positions 30, 35, and 128. The amino acid sequence can also differ from SEQ ID NO:2 (as disclosed in U.S. Pat. No. 7,569,215, incorporated herein by reference) at one of the following sets of positions: (a) positions 64, 69, and 74; (b) positions 69, 74, and 101; (c) positions 69, 74, and 128; (d) positions 30, 69, 74, and 103; (e) positions 49, 69, 73, and 76; (f) positions 69, 74, 101, and 133; (g) positions 30, 69, 74, and 128; (h) positions 69, 74, 88, and 99; (i) positions 30, 69, 74, and 128; (j) positions 9, 11, 35, 69, and 74; (k) positions 1, 46, 49, 61, 69, and 79; (l) positions 48, 68, 71, 90, 103, and 114; (m) positions 4, 10, 11, 69, 74, 88, and 133; (n) positions 15, 30 31, 35, 48, 69, 74, and 92; (O) positions 30, 68, 69, 71, 74, 75, 76, and 90; (p) positions 30, 31, 37, 69, 73, 74, 79, and 128; (q) positions 26, 29, 30, 54, 67, 69, 74, and 92; (r) positions 8, 13, 26, 30, 35, 37, 69, 74, and 92; and (s) positions 29, 31, 35, 37, 48, 69, 71, 74, 88, and 89. Aside from mutations at these positions, the amino acid sequence of the mutant IL-2 polypeptide can otherwise be identical to SEQ ID NO:1.

With respect to specific substitutions, the amino acid sequence can differ from SEQ ID NO:1 by virtue of having one or more of the following mutations: A1T, S4P, K8R, K9T, T10A, Q11R, Q13R, E15K, N26D, N29S, N30S, N30D, N30T, Y31H, Y31C, K35R, T37A, T37R, M46L, K48E, K49R, K49E, K54R, E61D, K64R, E67G, E68D, V69A, N71T, N71A, N71R, A73V, Q74P, S75P, K76E, K76R, H79R, N88D, I89V, N90H, I92T, S99P, T101A, F103S, I114V, I128T, I128A, T133A, or T133N. Our nomenclature is consistent with that of the scientific literature, where the single letter code of the amino acid in the wild-type or reference sequence is followed by its position within the sequence and then by the single letter code of the amino acid with which it is replaced. Thus, A1T designates a substitution of the alanine residue a position 1 with threonine. Other mutant polypeptides within the scope of the invention include those that include a mutant of SEQ ID NO:2 having substitutions at V69 (e.g. A) and Q74 (e.g., P). For example, the amino acid sequence can include one of the following sets of mutations with respect to SEQ ID NO:2: (a) K64R, V69A, and Q74P; (b) V69A, Q74P, and T101A; (c) V69A, Q74P, and I128T; (d) N30D, V69A, Q74P, and F103S; (e) K49E, V69A, A73V, and K76E; (f) V69A, Q74P, T101A, and T133N; (g) N30S, V69A, Q74P, and I128A; (h) V69A, Q74P, N88D, and S99P; (i) N30S, V69A, Q74P, and I128T; (j) K9T, Q11R, K35R, V69A, and Q74P; (k) A1T, M46L, K49R, E61D, V69A, and H79R; (l) K48E, E68D, N71T, N90H, F103S, and I114V; (m) S4P, T10A, Q11R, V69A, Q74P, N88D, and T133A; (n) E15K, N30S Y31H, K35R, K48E, V69A, Q74P, and I92T; (o) N30S, E68D, V69A, N71A, Q74P, S75P, K76R, and N90H; (p) N30S, Y31C, T37A, V69A, A73V, Q74P, H79R, and I128T; (q) N26D, N29S, N30S, K54R, E67G, V69A, Q74P, and I92T; (r) K8R, Q13R, N26D, N30T, K35R, T37R, V69A, Q74P, and I92T; and (s) N29S, Y31H, K35R, T37A, K48E, V69A, N71R, Q74P, N88D, and I89V. SEQ ID NO:2 is disclosed in U.S. Pat. No. 7,569,215, which is incorporated herein by reference as an exemplary IL-2 polypeptide sequence that can be used in the invention.

As noted above, any of the mutant IL-2 polypeptides disclosed herein can include the sequences described; they can also be limited to the sequences described and otherwise identical to SEQ ID NO: 1. Moreover, any of the mutant IL-2 polypeptides described herein can optionally include a substitution of the cysteine residue at position 125 with another residue (e.g., serine) and/or can optionally include a deletion of the alanine residue at position 1 of SEQ ID NO:1.

The mutant IL-2 polypeptides disclosed herein can bind to the IL-2Rα subunit with a $K_d$ of less than about 28 nM (e.g., less than about 25 nM; less than about 5 nM; about 1 nM; less than about 500 pM; or less than about 100 pM). More specifically, a mutant IL-2 polypeptide can have an affinity equilibrium constant less than 1.0 nM (e.g., about 0.8, 0.6, 0.4, or 0.2 nM). Affinity can also be expressed as a relative rate of dissociation from an IL-2Rα subunit or from an IL-2 receptor complex (e.g., a complex expressed on the surface of a cell or otherwise membrane bound). For example, the mutant IL-2 polypeptides can dissociate from, e.g., IL-2Rα, at a decreased rate relative to a wild-type polypeptide or to an IL-2 based therapeutic, e.g., IL-2*. Alternatively, affinity can be characterized as the time, or average time, an IL-2* polypeptide persists on, for example, the surface of a cell expressing an IL-2R. For example, an IL-2*polypeptide can persist on the receptor for at least about 2, 5, 10, 50, 100, or 250 times (or more).

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

The following are examples of methods and compositions of the invention. It is understood that various other embodiments may be practiced, given the general description provided herein.

Example 1: Detection of IL-2, IL-2 Mutein,
IL-2Rα and IL-2Rγ in Fusion Proteins by ELISA IL-2 mutein is detected with a commercially available antibody, e.g., the anti-IL-2 monoclonal (JES6-1A12) (BD Pharmingen; San Jose, Calif.). A positive control is used to show whether the monoclonal antibody recognizes the cytokine or mutein. Antibodies against IL-2Rα and IL-2Rγ chain are also used. Wells of a 96-well plate are coated with an antibody (2.5 µg/ml) in PBS. Wells are blocked with 5% non-fat milk in PBS with 0.2% Tween®20 (PBS-M-Tw) and fusion proteins are added for 1-2 hours at 37° C. After washing, an anti-IL-2 biotin-labeled antibody, e.g., JES5H4 (BD Pharmingen) is added and binding is detected using Strepavidin HRP (Southern Biotechnology Associates; Birmingham, Ala.). The ELISA plate is developed by adding 50 µl O-phenylenediamine (OPD) (Sigma-Aldrich) in 0.1M Citrate pH 4.5 and 0.04% $H_2O_2$, stopped by adding 50 µl/well 2N $H_2SO_4$ and the absorbance was read at 490 nm.

Example 2: Protease Cleavage of Fusion Protein by
MMP9 Protease

One of skill in the art would be familiar with methods of setting up protein cleavage assay. 100 ug of protein in 1×PBS pH 7.4 were cleaved with 1 µg active MMP9 (Sigma catalog #SAE0078-50 or Enzo catalog BML-SE360) and incubated at room temperature for up to 16 hours. Digested protein is subsequently used in functional assays or stored at −80° C. prior to testing. Extent of cleavage was monitored by SDS PAGE using methods well known in the art. As shown in FIGS. 10, 13, 18A, 18B, 24B, 24C, and 27A full cleavage of the fusion proteins by MMP9 protease is seen.

Example 3: CTLL-2 Assay

Figures 8A, 8B, 8C, 8D, 8E, 8F:
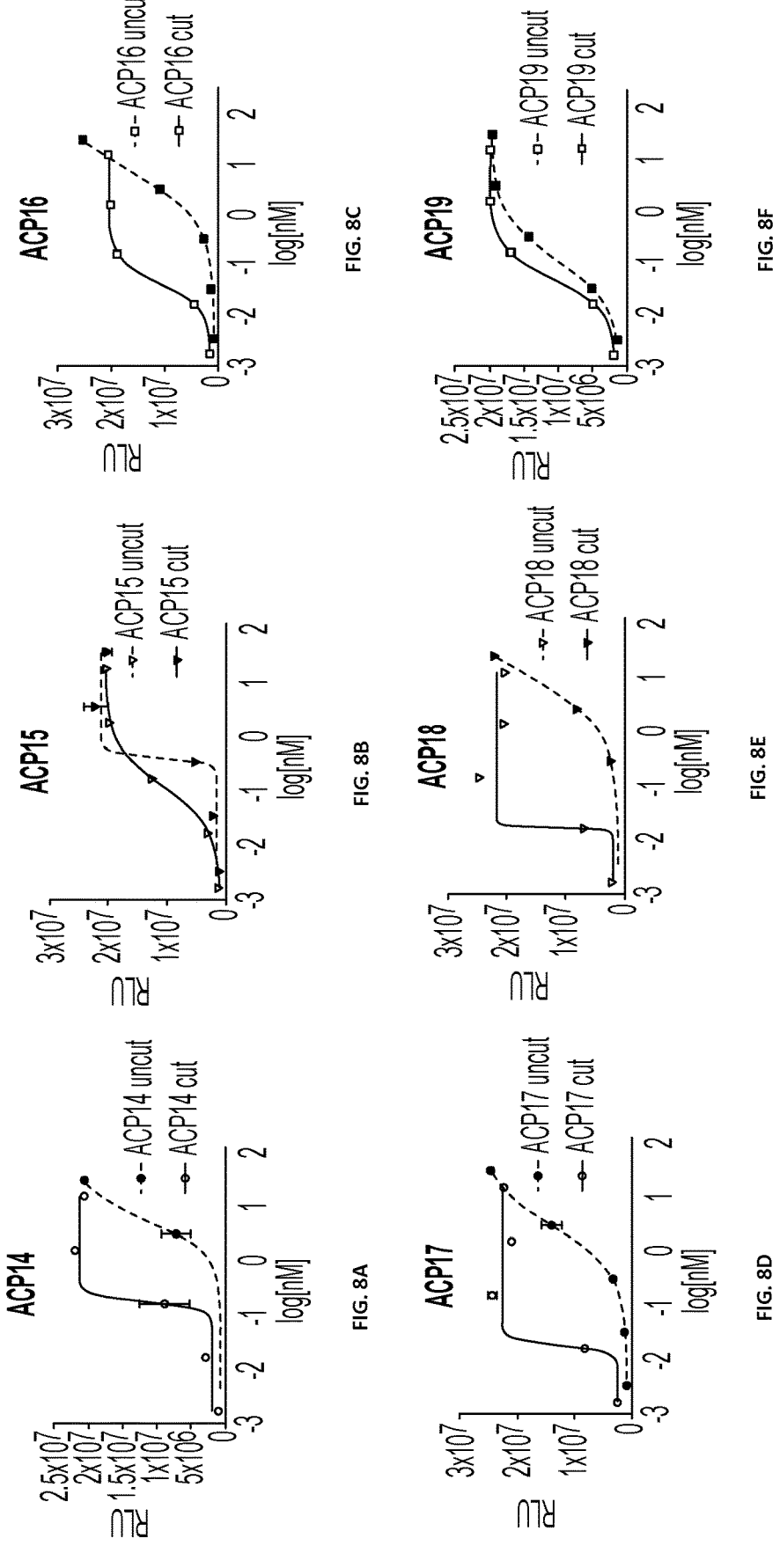
FIGS. 8A-8F are a series of graphs showing activity of exemplary IL-2 fusion proteins in IL-2 dependent cytotoxic T lymphocyte cell line CTLL-2. Each graph shows results of the IL-2 proliferation assay as quantified by CellTiter-Glo (Promega) luminescence-based cell viability assay. Both uncleaved and MMP9 protease cleaved versions of the fusion protein were used in each assay.
Figures 9A, 9B, 9C, 9D, 9E, 9F:
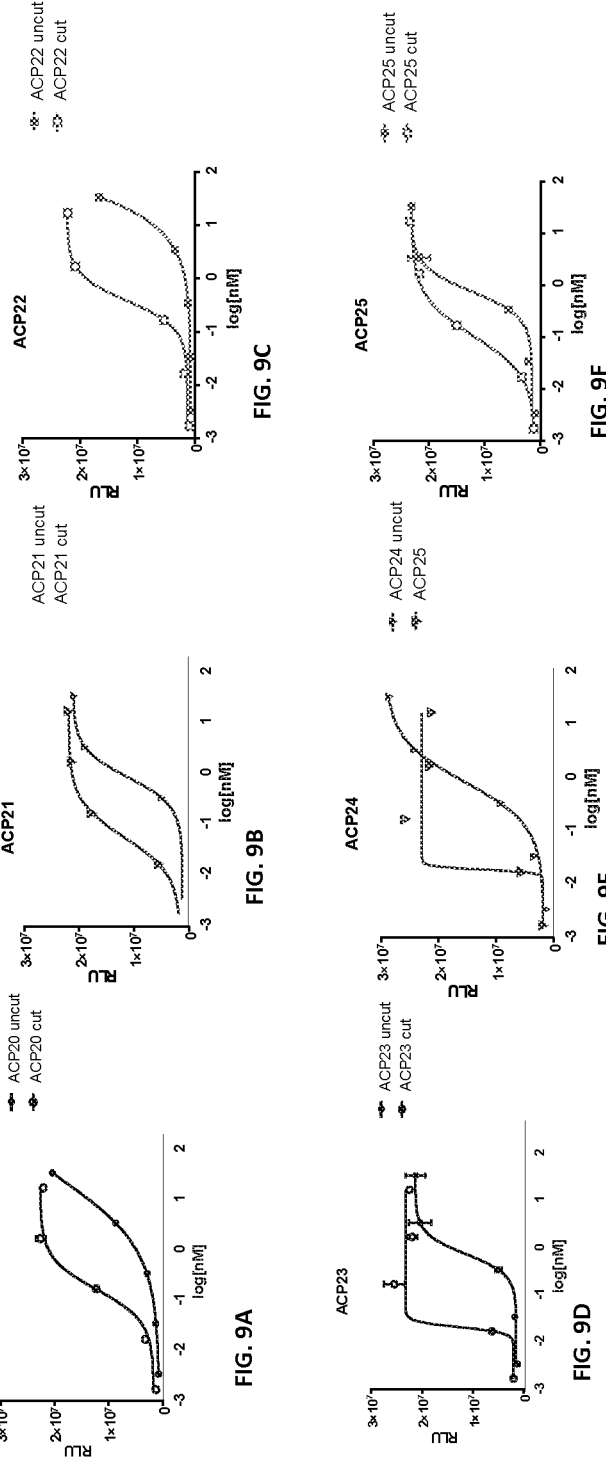
FIGS. 9A-9Z are a series of graphs showing activity of exemplary IL-2 fusion proteins in IL-2 dependent cytotoxic T lymphocyte cell line CTLL-2. Each graph shows results of the IL-2 proliferation assay as quantified by CellTiter-Glo (Promega) luminescence-based cell viability assay. Both uncleaved and MMP9 protease cleaved versions of the fusion protein were used in each assay.
Figures 9T, 9U, 9V, 9W, 9X:
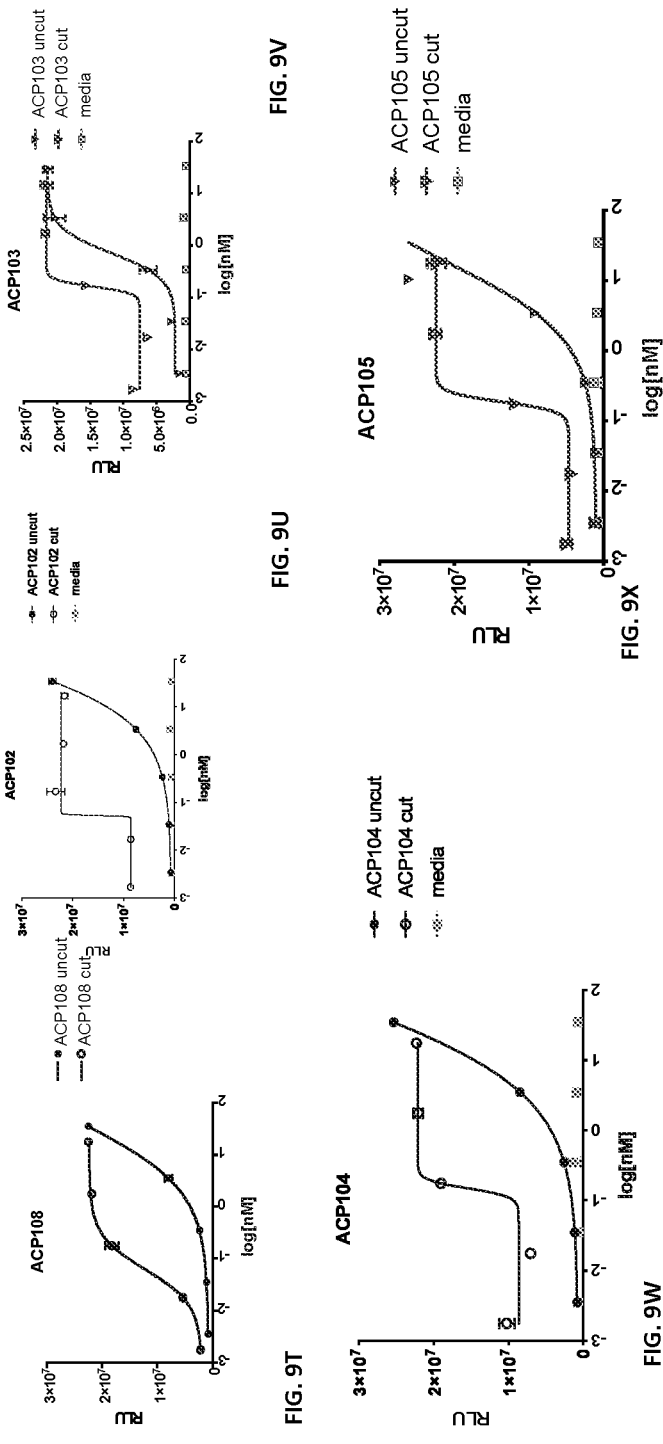
Figures 9Y, 9Z:
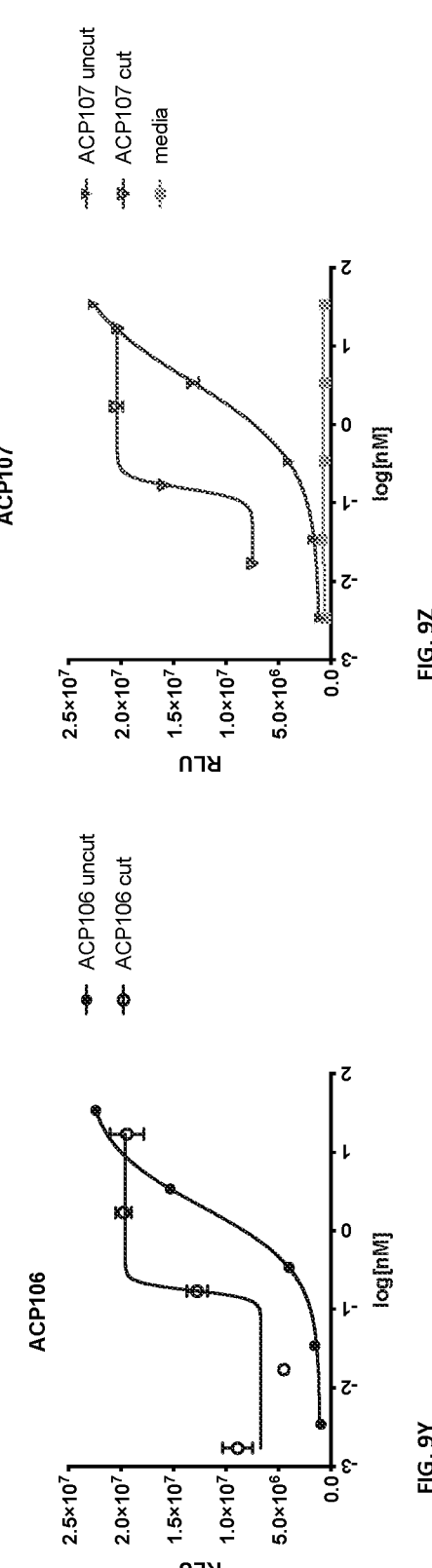
Figure 10:
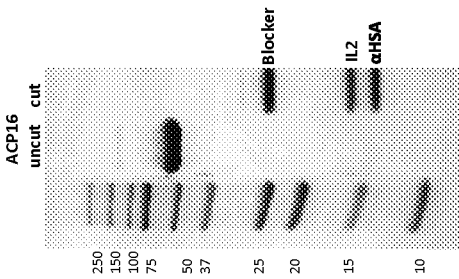
FIG. 10 shows results of protein cleavage assay. Fusion protein ACP16 was run on an SDS-PAGE gel in both cleaved and uncleaved form. As can be seen in the gel, cleavage was complete.
Figure 11B:
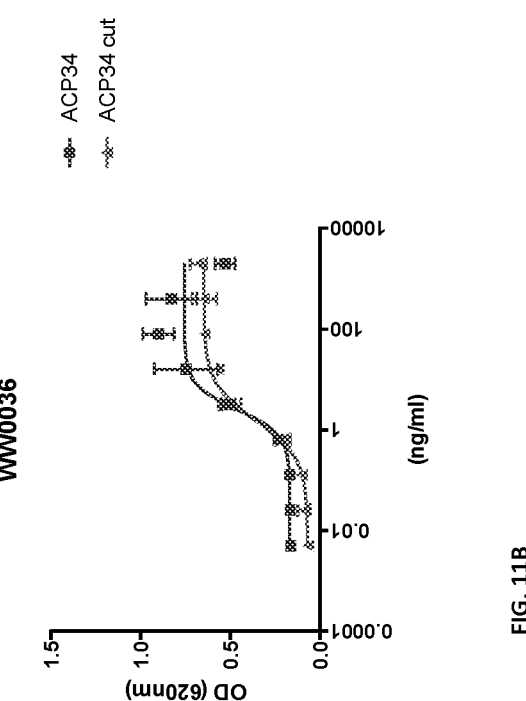
FIGS. 11A-11B are graphs depicting results from a HEK-Blue IL-12 reporter assay performed on human p40/murine p35 IL12 fusion proteins before and after protease cleavage. Constructs ACP35 (FIG. 11A) and ACP34 (FIG. 111B) were tested. Analysis was performed based on quantification of Secreted Alkaline Phosphatase (SEAP) activity using the reagent QUANTI-Blue® (InvivoGen). Results confirm that IL12 protein fusion proteins are active.
Figure 11A:
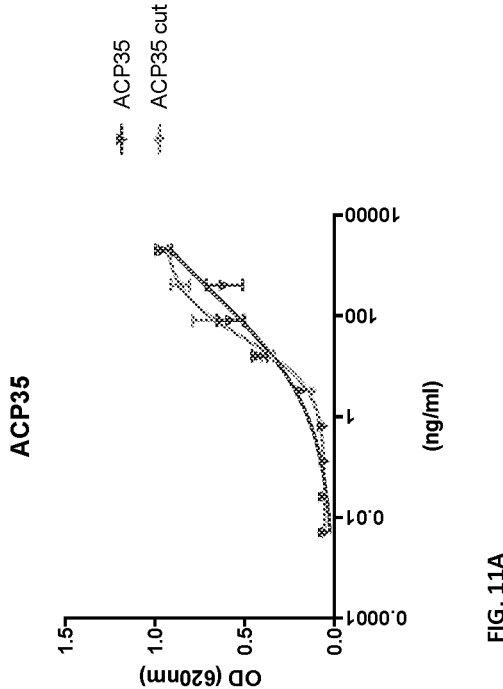
Figure 12F:
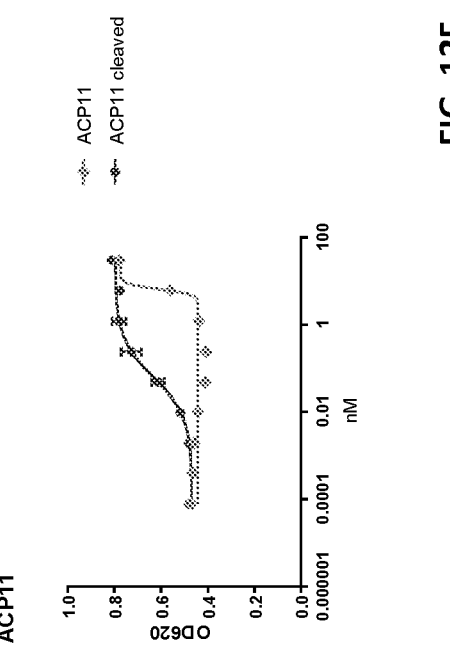
Figure 12E:
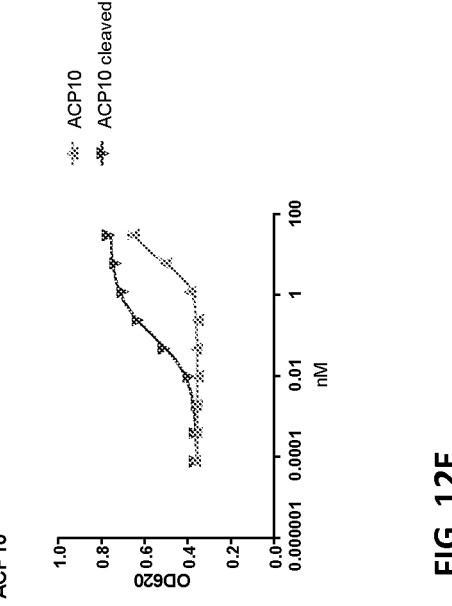
Figure 13:
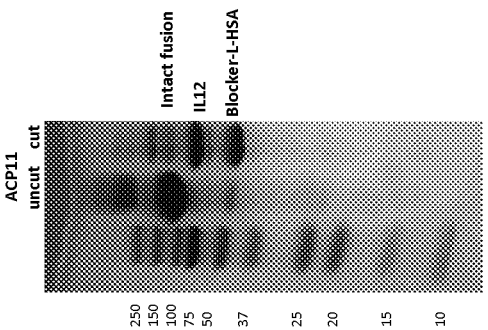
FIG. 13 shows results of protein cleavage assay. Fusion protein ACP11 was run on an SDS-PAGE gel in both cleaved and uncleaved form. As can be seen in the gel, cleavage was complete.
Figures 25A, 25B:
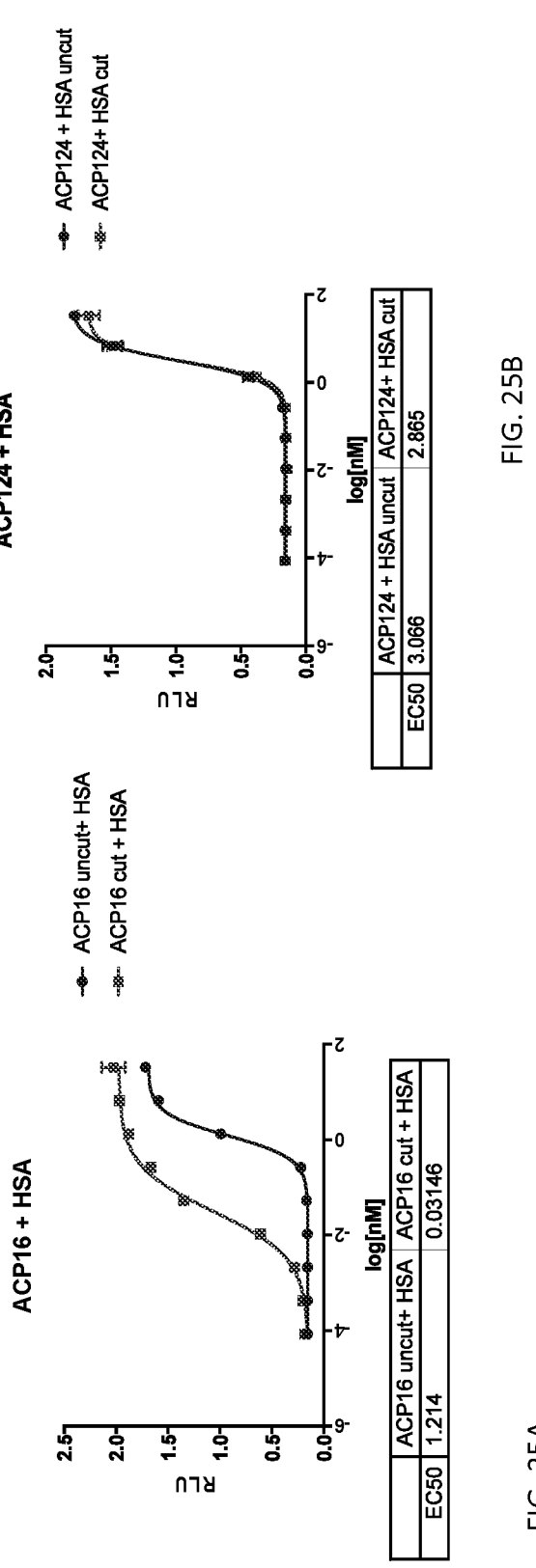
FIGS. 25A and 25B are two graphs showing analysis of ACP16 (FIG. 25A) and ACP124 (FIG. 25B) in a HEKBlue IL-2 reporter assay in the presence of HSA. Circles depict the activity of the uncut polypeptide, squares depict activity of the cut polypeptide.
Figure 26A:
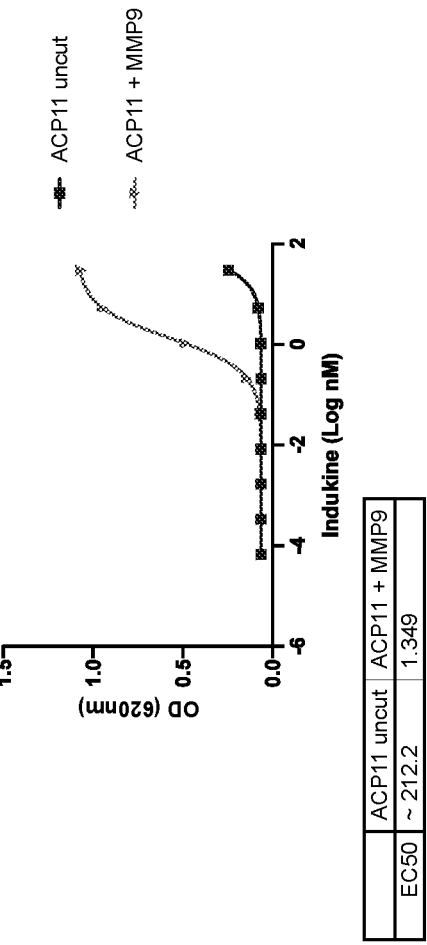
FIGS. 26A-26C are a series of graphs showing activity of fusion proteins in an HEKBlue IL-12 reporter assay.
Figure 26B:
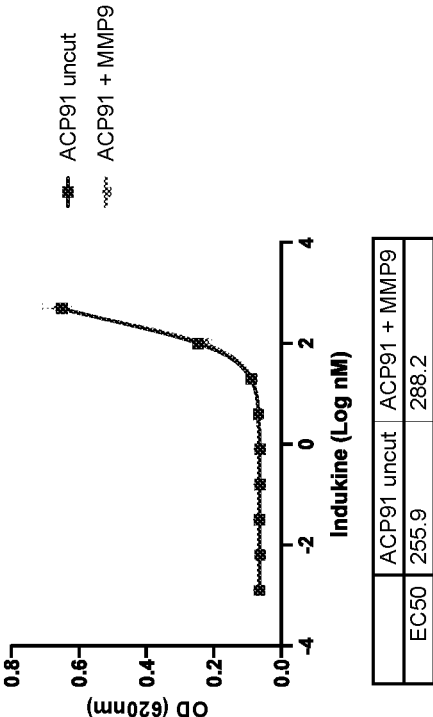
Figure 26C:
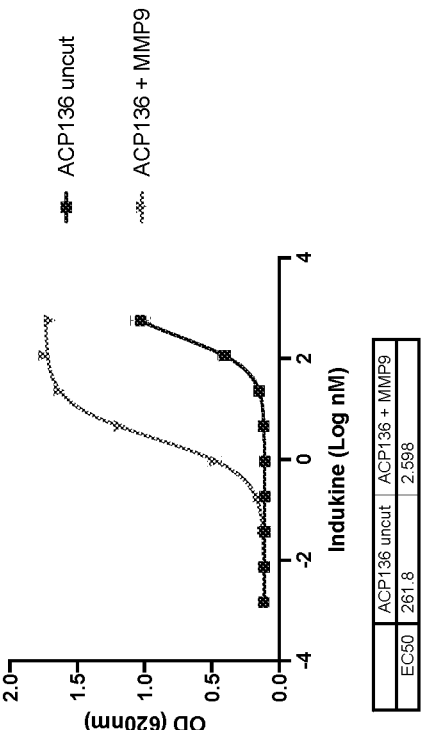
Figures 27B, 27C:
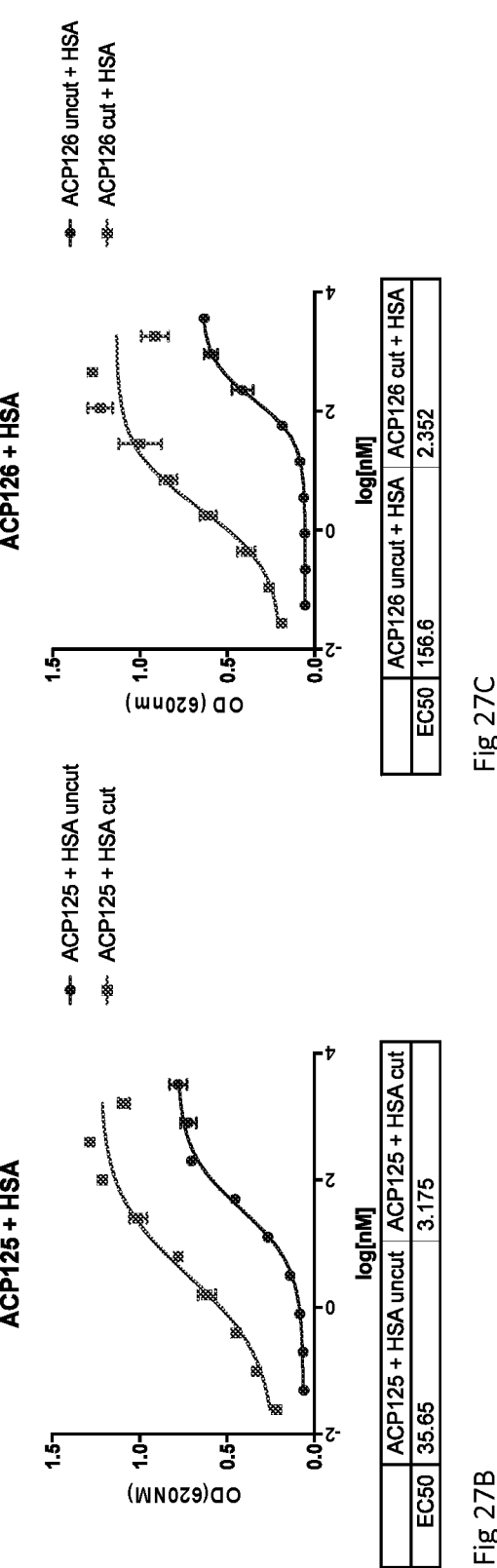
Figure 28F:
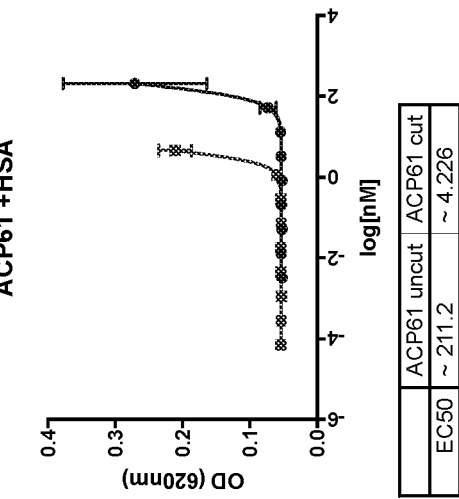
FIGS. 28A-28N are a series of graphs depicting the activity of ACP56 (FIG. 28A), ACP57 (FIG. 28B) ACP58 (FIG. 28C), ACP59 (FIG. 28D), ACP60 (FIG. 28E), ACP61+HSA (FIG. 28F), ACP30+HSA (FIG. 28G), ACP73 (FIG. 28H), ACP70+HSA (FIG. 28I), ACP71 (FIG. 28J), ACP72 (FIG. 28K), ACP 73 (FIG. 28L), ACP74 (FIG. 28M), and ACP75 (FIG. 28N) in a B16 IFNγ reporter assay. Each fusion was tested for its activity when cut (squares) and uncut (circles).
Figure 28G:
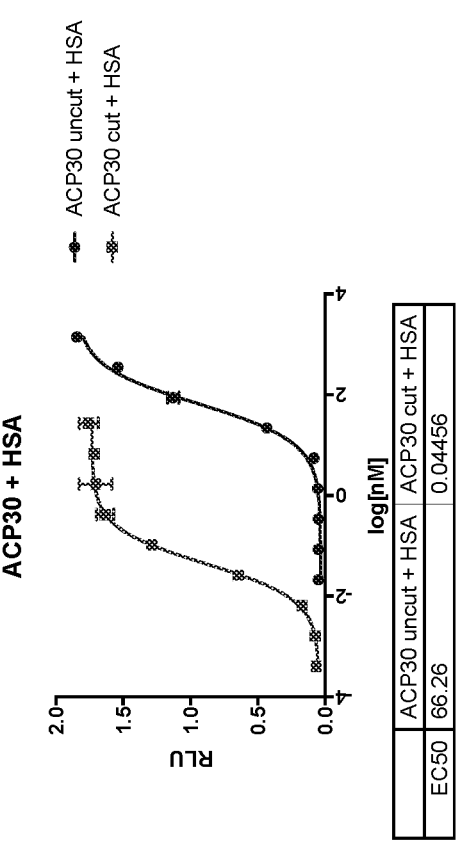
Figure 28H:
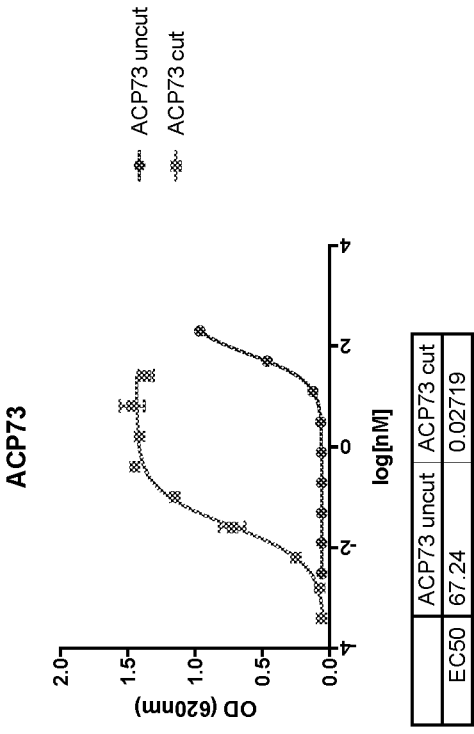
Figure 28I:
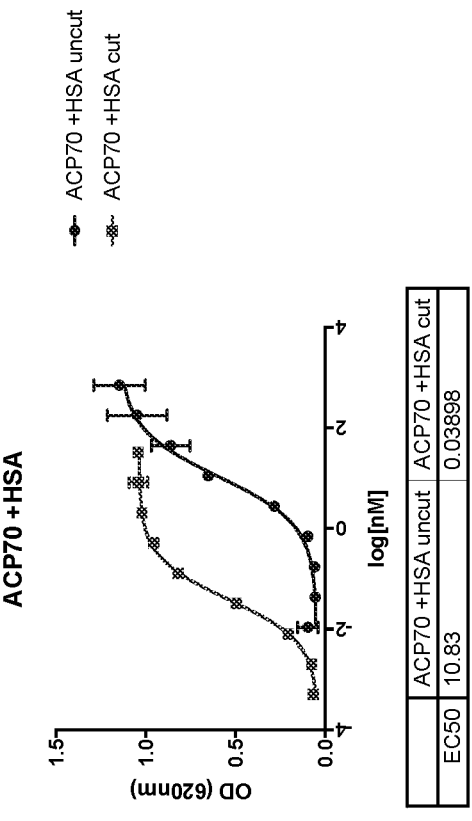
Figure 28J:
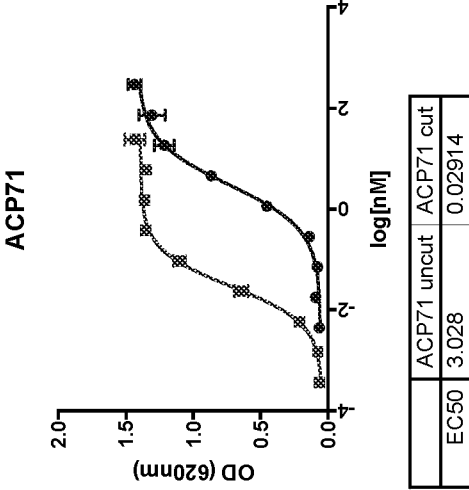
Figure 28K:
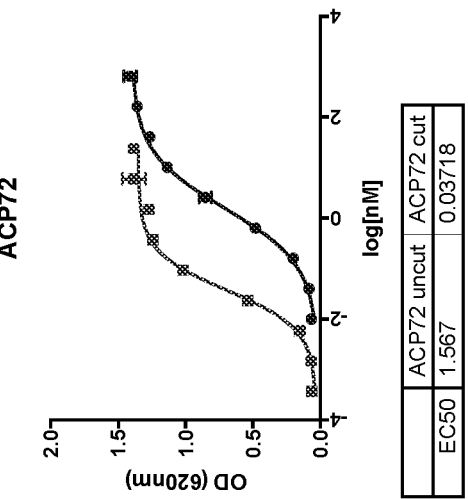
Figure 28L:
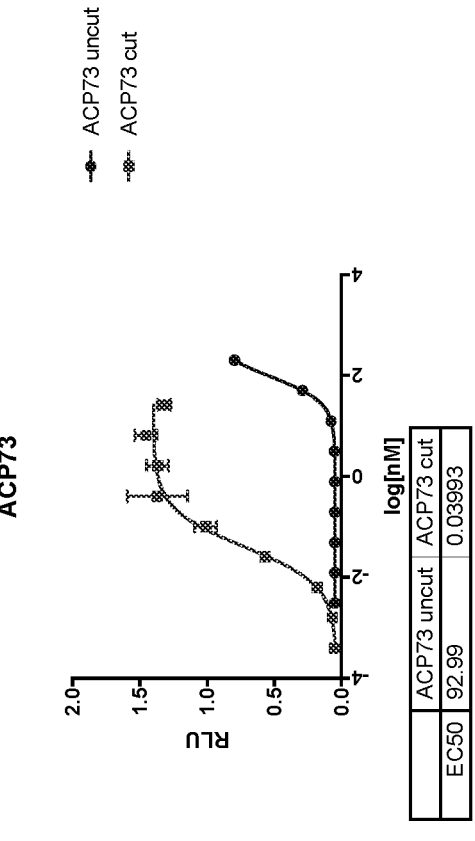
Figure 31A:
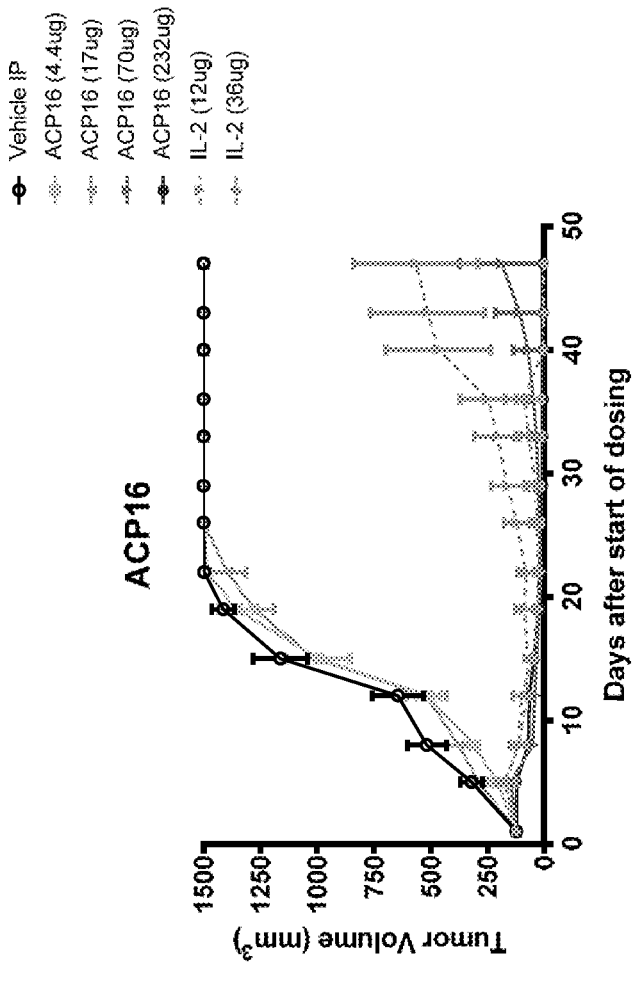
FIG. 31A-31C are three graphs showing results of analyzing ACP16 and ACP124 in a tumor xenograft model.
Figure 31B:
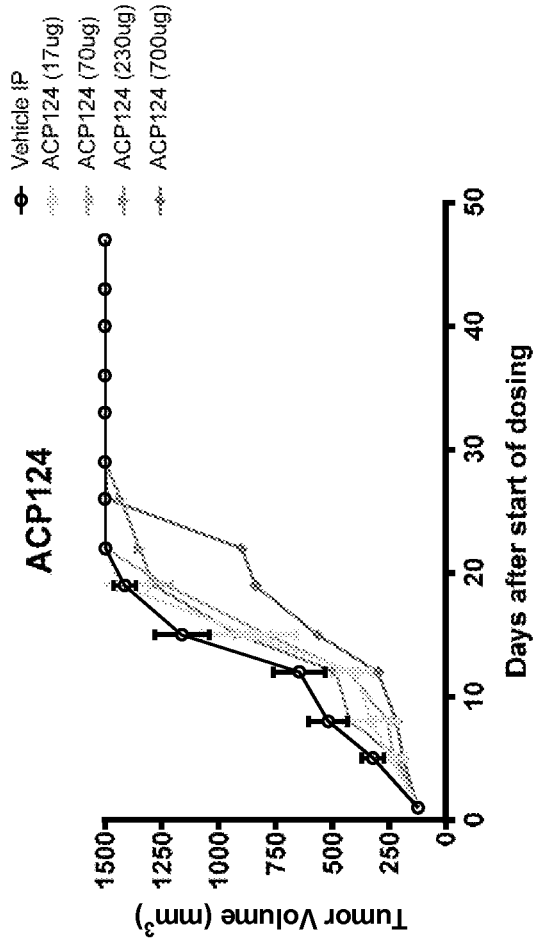
Figure 31C:
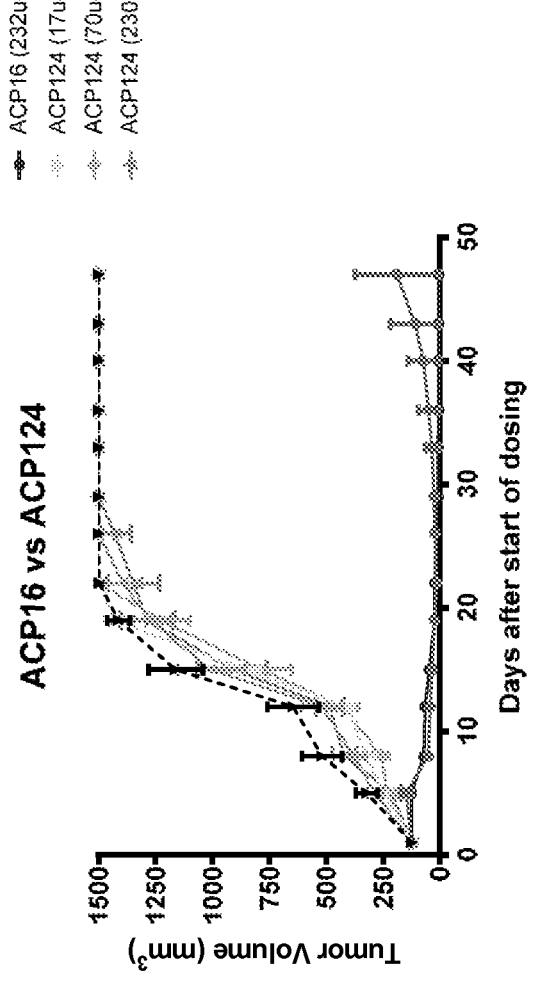
Figure 32B:
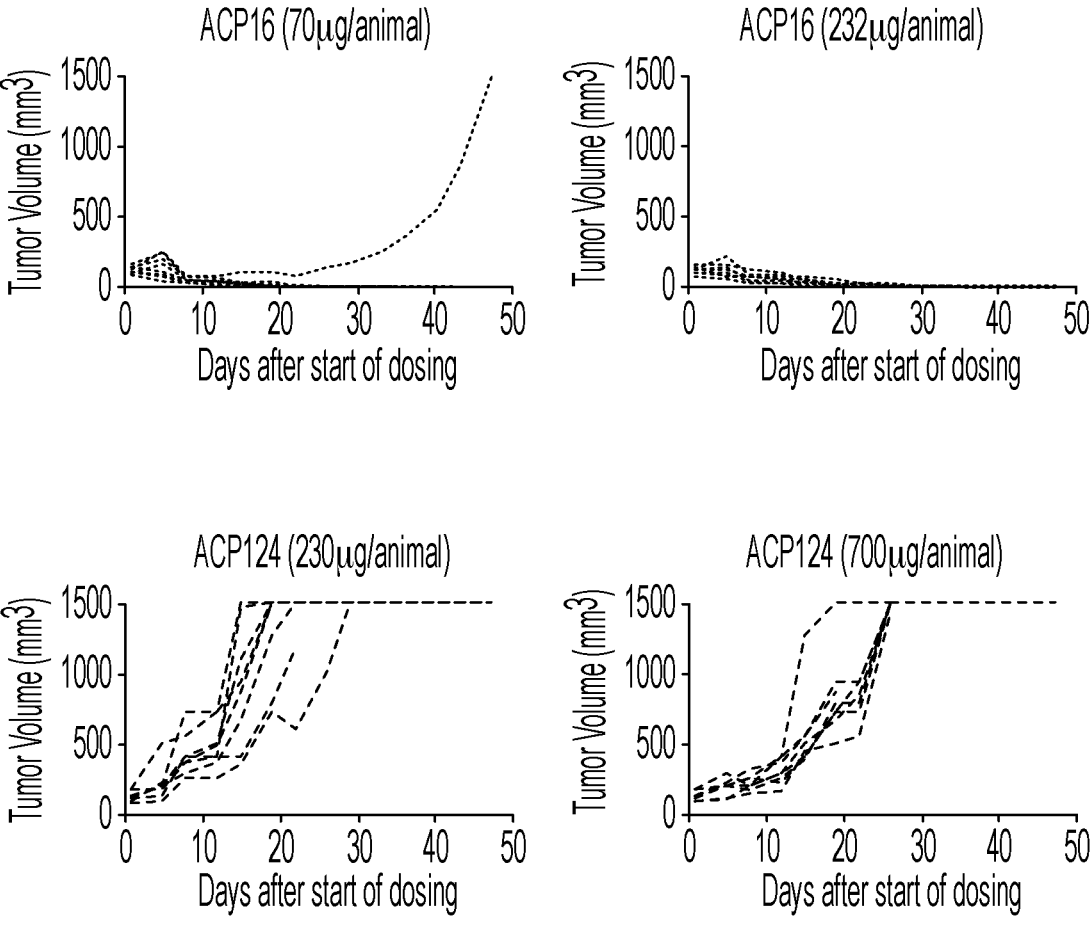
FIGS. 32B-32C are a series of spaghetti plots showing activity of fusion proteins in an MC38 mouse xenograft model corresponding to the data shown in FIG. 31. Each line in the plots is a single mouse.
Figure 32C:
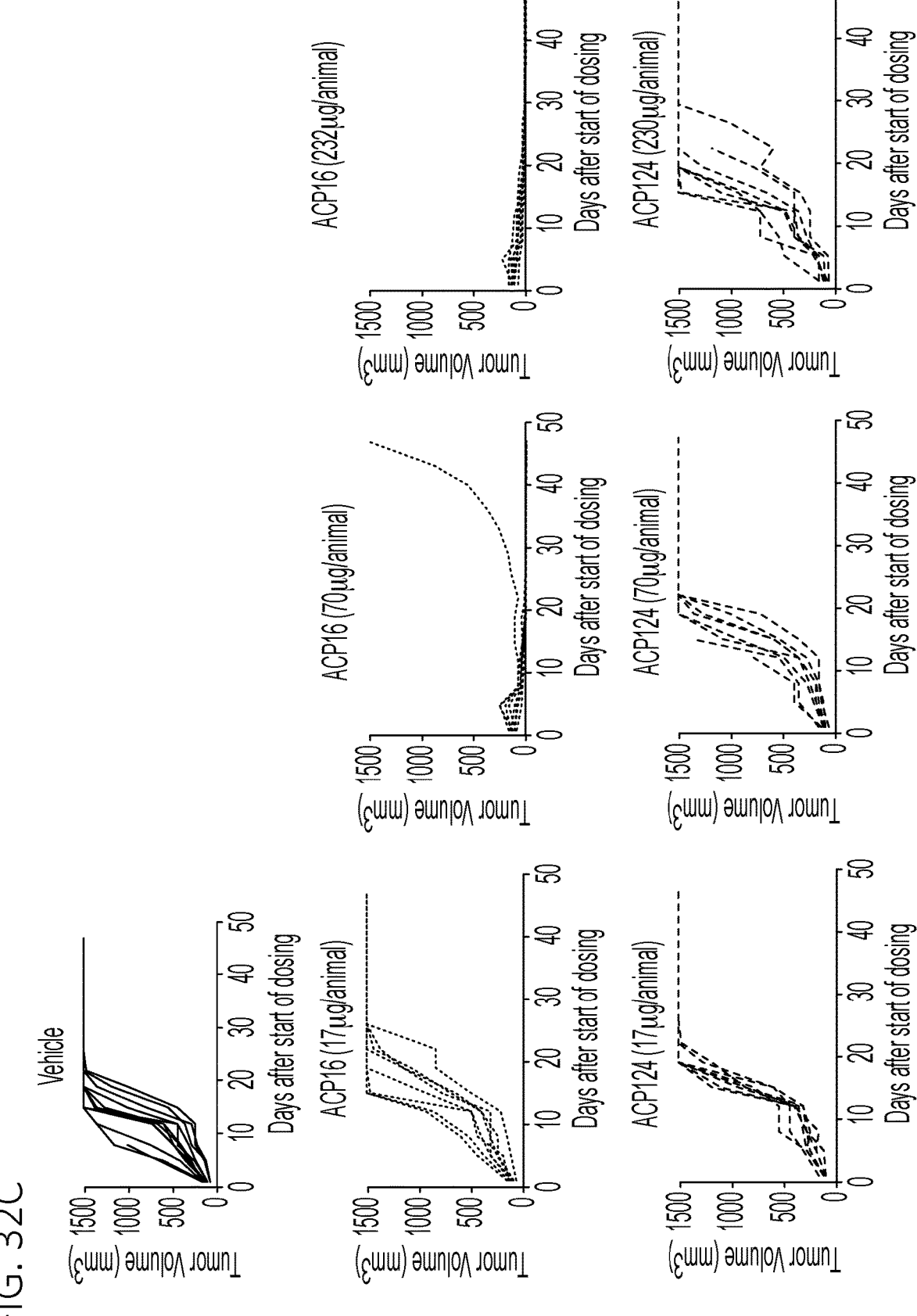

CTLL2 cells (ATCC) were plated in suspension at a concentration of 500,000 cells/well in culture media with or without 40 mg/ml human serum albumin (HSA) and stimulated with a dilution series of recombinant hIL2 or activatable hIL2 for 72 hours at 37° C. and 5% $CO_2$. Activity of uncleaved and cleaved activatable hIL2 was tested. Cleaved activatable hIL2 was generated by incubation with active MMP9. Cell activity was assessed using a CellTiter-Glo (Promega) luminescence-based cell viability assay. Results are shown in FIGS. 8, 9, and 25.

Example 4: Protease Cleavage of the
IL-2/IL-2Rα/IL-2Rγ Chimeric Polypeptide Results
in Increased Accessibility to Antibodies and
Biologically Active IL-2 Mutein The IL-2 mutein fusion proteins are biochemically characterized before and after cleavage with a protease, e.g., PSA. Immunoblot analyses will show that the fusion proteins can be cleaved by PSA and that there is an increase in intensity of the predicted low molecular weight cleavage product of approximately 20 kDa reactive with an anti-IL-2 antibody after treatment of the samples with PSA. The degree of cleavage is dependent upon the amount of PSA as well as the time of incubation. Interestingly, when the fusion protein is analyzed before and after PSA treatment by ELISA, it was found that the apparent amount of IL-2 is increased after PSA cleavage. In this experiment, there is an approximately 2 or 4-fold increase in the apparent amount of IL-2 detected using this sandwich ELISA depending on the construct, suggesting that the antibody binding is partially hindered in the intact fusion protein. Aliquots of the same samples are also analyzed after PSA treatment using the CTLL-2 cell line that requires IL-2 for growth and survival and the viability of cells can be ascertained using the colorimetric MTT assay. In this assay, the more a supernatant can be diluted, the more biologically active IL-2 it contains, and there is an increase in the amount of biologically active IL-2 after PSA cleavage. The amount of IL-2 mutein increase will suggest that after PSA cleavage there is an increase in the predicted low molecular weight cleavage fragment of approximately 20 kDa reactive with an anti-IL-2 antibody, an increase in antibody accessibility, and most importantly, an increase in the amount of biologically active IL-2 mutein.

Example 5. In Vivo Delivery of a Protease
Activated Fusion Protein Results in Decreased
Tumor Growth The chimeric polypeptide is examined to determine if it could have biological effects in vivo. For these experiments a system is used in which tumor cells injected intraperitoneally rapidly and preferentially attach and grow initially on the milky spots, a series of organized immune aggregates found on the omentum (Gerber et al., Am. J. Pathol. 169: 1739-52 (2006)). This system offers a convenient way to examine the effects of fusion protein treatment on tumor growth since fusion proteins can be delivered intraperitoneally multiple times and tumor growth can be analyzed by examining the dissociated omental cells. For these experiments, the Colon 38 cell line, a rapidly growing tumor cell line that expresses both MMP2 and MMP9 in vitro, may be used. The omental tissue normally expresses a relatively small amount of MMP2 and MMP9, but, when Colon 38 tumor is present on the omentum, MMP levels increase. Using this tumor model, the ability of IL-2 mutein fusion proteins to affect tumor growth is examined. Colon 38 cells are injected intraperitoneally, allowed to attach and grow for 1 day, and then treated daily with fusion protein interaperitoneally. At day 7, the animals are sacrificed and the omenta examined for tumor growth using flow cytometry and by a colony-forming assay.

Example 6: Construction of an Exemplary Activatable IL2 Protein Targeting CD20 Generation of an Activatable IL2 Domain An IL-2 polypeptide capable of binding to CD20 polypeptide present in a tumor or on a tumor cell is produced as follows. A nucleic acid is produced that contains nucleic acid sequences: (1) encoding an IFNγ polypeptide sequence and (2) one or more polypeptide linkers. Activatable interleukin plasmid constructs can have optional Flag, His or other affinity tags, and are electroporated into HEK293 or other suitable human or mammalian cell lines and purified. Validation assays include T cell activation assays using T cells responsive to IFNγ stimulation in the presence of a protease. Generation of a scFv CD20 Binding Domain CD20 is one of the cell surface proteins present on B-lymphocytes. CD20 antigen is found in normal and malignant pre-B and mature B lymphocytes, including those in over 90% of B-cell non-Hodgkin's lymphomas (NHL). The antigen is absent in hematopoietic stem cells, activated B lymphocytes (plasma cells) and normal tissue. As such, several antibodies mostly of murine origin have been described: 1F5, 2B8/C2B8, 2H7, and 1H4.

Human or humanized anti-CD20 antibodies are therefore used to generate scFv sequences for CD20 binding domains of an activatable interleukin protein. DNA sequences coding for human or humanized VL and VH domains are obtained, and the codons for the constructs are, optionally, optimized for expression in cells from *Homo sapiens*. The order in which the VL and VH domains appear in the scFv is varied (i.e., VL-VH, or VH-VL orientation), and three copies of the "G4S" (SEQ ID NO.: 449) or "G$_4$S" (SEQ ID NO.: 449) subunit (G$_4$S)$_3$ (SEQ ID NO.: 452) connect the variable domains to create the scFv domain. Anti-CD20 scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD20-expressing cells. Cloning of DNA Expression Constructs Encoding the Activatable IL2 Protein The activatable IL2 construct with protease cleavage site domains are used to construct an activatable interleukin protein in combination with an anti-CD20 scFv domain and a serum half-life extension element (e.g., a HSA binding peptide or VH domain). For expression of an activatable interleukin protein in CHO cells, coding sequences of all protein domains are cloned into a mammalian expression vector system. In brief, gene sequences encoding the activatable interleukin domain, serum half-life extension element, and CD20 binding domain along with peptide linkers L1 and L2 are separately synthesized and subcloned. The resulting constructs are then ligated together in the order of CD20 binding domain-L1-IL2 subunit 1-L2-protease cleavage domain-L3-IL2 subunit 2-L4-anti-CD20 scFv-L5-serum half-life extension element to yield a final construct. All expression constructs are designed to contain coding sequences for an N-terminal signal peptide and a C-terminal hexahistidine (6×His)-tag (SEQ ID NO. 354) to facilitate protein secretion and purification, respectively. Expression of Activatable IL2 Proteins in Stably Transfected CHO Cells A CHO cell expression system (Flp-In®, Life Technologies), a derivative of CHO-K1 Chinese Hamster ovary cells (ATCC, CCL-61) (Kao and Puck, Proc. Natl. Acad Sci USA 1968; 60(4):1275-81), is used. Adherent cells are subcultured according to standard cell culture protocols provided by Life Technologies.

For adaption to growth in suspension, cells are detached from tissue culture flasks and placed in serum-free medium. Suspension-adapted cells are cryopreserved in medium with 10% DMSO.

Recombinant CHO cell lines stably expressing secreted activatable interleukin proteins are generated by transfection of suspension-adapted cells. During selection with the antibiotic Hygromycin B viable cell densities are measured twice a week, and cells are centrifuged and resuspended in fresh selection medium at a maximal density of $0.1 \times 10^6$ viable cells/mL. Cell pools stably expressing activatable interleukin proteins are recovered after 2-3 weeks of selection at which point cells are transferred to standard culture medium in shake flasks. Expression of recombinant secreted proteins is confirmed by performing protein gel electrophoresis or flow cytometry. Stable cell pools are cryopreserved in DMSO containing medium.

Activatable IL2 proteins are produced in 10-day fed-batch cultures of stably transfected CHO cell lines by secretion into the cell culture supernatant. Cell culture supernatants are harvested after 10 days at culture viabilities of typically >75%. Samples are collected from the production cultures every other day and cell density and viability are assessed. On day of harvest, cell culture supernatants are cleared by centrifugation and vacuum filtration before further use.

Protein expression titers and product integrity in cell culture supernatants are analyzed by SDS-PAGE. Purification of Activatable IL2 Proteins Activatable IL2 proteins are purified from CHO cell culture supernatants in a two-step procedure. The constructs are subjected to affinity chromatography in a first step followed by preparative size exclusion chromatography (SEC) on Superdex 200 in a second step. Samples are buffer-exchanged and concentrated by ultrafiltration to a typical concentration of >1 mg/mL. Purity and homogeneity (typically >90%) of final samples are assessed by SDS PAGE under reducing and non-reducing conditions, followed by immunoblotting using an anti-HSA or anti idiotype antibody as well as by analytical SEC, respectively. Purified proteins are stored at aliquots at −80° C. until use.

Example 7: Determination of Antigen Affinity by Flow Cytometry

The activatable interleukin proteins of Example 6 are tested for their binding affinities to human CD20$^+$ cells and cynomolgus CD20$^+$ cells.

CD20$^+$ cells are incubated with 100 μL of serial dilutions of the activatable interleukin proteins of Example 1 and at least one protease. After washing three times with FACS buffer the cells are incubated with 0.1 mL of 10 μg/mL mouse monoclonal anti-idiotype antibody in the same buffer for 45 min on ice. After a second washing cycle, the cells are incubated with 0.1 mL of 15 μg/mL FITC-conjugated goat anti-mouse IgG antibodies under the same conditions as before. As a control, cells are incubated with the anti-His IgG followed by the FITC-conjugated goat anti-mouse IgG antibodies without the activatable IL2 proteins. The cells were then washed again and resuspended in 0.2 mL of FACS buffer containing 2 µg/mL propidium iodide (PI) in order to exclude dead cells. The fluorescence of $1\times10^4$ living cells is measured using a Beckman-Coulter FC500 MPL flow cytometer using the MXP software (Beckman-Coulter, Krefeld, Germany) or a Millipore Guava EasyCyte flow cytometer using the Incyte software (Merck Millipore, Schwalbach, Germany). Mean fluorescence intensities of the cell samples are calculated using CXP software (Beckman-Coulter, Krefeld, Germany) or Incyte software (Merck Millipore, Schwalbach, Germany). After subtracting the fluorescence intensity values of the cells stained with the secondary and tertiary reagents alone the values are then used for calculation of the $K_D$ values with the equation for one-site binding (hyperbola) of the GraphPad Prism (version 6.00 for Windows, GraphPad Software, La Jolla California USA).

CD20 binding and crossreactivity are assessed on the human CD20$^+$ tumor cell lines. The $K_D$ ratio of crossreactivity is calculated using the $K_D$ values determined on the CHO cell lines expressing either recombinant human or recombinant cynomolgus antigens.

Example 8: Cytotoxicity Assay

The activatable interleukin protein of Example 6 is evaluated in vitro on its mediation of immune response to CD20$^+$ target cells.

Fluorescence labeled CD20$^+$ REC-1 cells (a Mantle cell lymphoma cell line, ATCC CRL-3004) are incubated with isolated PBMC of random donors or CB15 T-cells (standardized T-cell line) as effector cells in the presence of the activatable IL2 protein of Example 5 and at least one protease. After incubation for 4 h at 37° C. in a humidified incubator, the release of the fluorescent dye from the target cells into the supernatant is determined in a spectrofluorimeter. Target cells incubated without the activatable IL2 protein of Example land target cells totally lysed by the addition of saponin at the end of the incubation serve as negative and positive controls, respectively.

Based on the measured remaining living target cells, the percentage of specific cell lysis is calculated according to the following formula: [1-(number of living targets$_{(sample)}$/number of living targets$_{(spontaneous)}$]×100%. Sigmoidal dose response curves and EC$_{50}$ values are calculated by non-linear regression/4-parameter logistic fit using the GraphPad Software. The lysis values obtained for a given antibody concentration are used to calculate sigmoidal dose-response curves by 4 parameter logistic fit analysis using the Prism software.

Example 9: Pharmacokinetics of Activatable Interleukin Proteins

The activatable interleukin protein of Example 6 is evaluated for half-time elimination in animal studies.

The activatable IL2 protein is administered to cynomolgus monkeys as a 0.5 mg/kg bolus injection into the saphenous vein. Another cynomolgus monkey group receives a comparable IL2 construct in size, but lacking a serum half-life extension element. A third and fourth group receive an IL2 construct with serum half-life extension element and a cytokine with CD20 and serum half-life extension elements respectively, and both comparable in size to the activatable interleukin protein. Each test group consists of 5 monkeys. Serum samples are taken at indicated time points, serially diluted, and the concentration of the proteins is determined using a binding ELISA to CD20.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-\alpha t}+Be^{-\beta t}$, where c(t) is the plasma concentration at time t, A and B are intercepts on the Y-axis, and a and 3 are the apparent first-order rate constants for the distribution and elimination phases, respectively. The α-phase is the initial phase of the clearance and reflects distribution of the protein into all extracellular fluid of the animal, whereas the second or β-phase portion of the decay curve represents true plasma clearance. Methods for fitting such equations are well known in the art. For example, $A=D/V(\alpha-k21)/(\alpha-\beta)$, $B=D/V(\beta-k21)/(\alpha-\beta)$, and α and β (for α>β) are roots of the quadratic equation: $r^2+(k12+k21+k10)r+k21k10=0$ using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time profiles are made using KaleidaGraph (KaleidaGraph™ V. 3.09 Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif.). Pharmacokinetic parameters are computed as described in Ritschel W A and Kearns G L, 1999, IN: *Handbook Of Basic Pharmacokinetics Including Clinical Applications,* 5th edition, American Pharmaceutical Assoc., Washington, D.C.

It is expected that the activatable interleukin protein of Example 5 has improved pharmacokinetic parameters such as an increase in elimination half-time as compared to proteins lacking a serum half-life extension element.

Example 10: Xenograft Tumor Model

The activatable IL2 protein of Example 6 is evaluated in a xenograft model.

Female immune-deficient NOD/scid mice are sub-lethally irradiated (2 Gy) and subcutaneously inoculated with $4\times10^6$ Ramos RA1 cells into the right dorsal flank. When tumors reach 100 to 200 mm³, animals are allocated into 3 treatment groups. Groups 2 and 3 (8 animals each) are intraperitoneally injected with $1.5\times10^7$ activated human T-cells. Three days later, animals from Group 3 are subsequently treated with a total of 9 intravenous doses of 50 µg activatable interleukin protein of Example 1 (qd×9d). Groups 1 and 2 are only treated with vehicle. Body weight and tumor volume are determined for 30 days.

It is expected that animals treated with the activatable interleukin protein of Example 5 have a statistically significant delay in tumor growth in comparison to the respective vehicle-treated control group.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 11: Mouse IFNγ WEHI Cell Survival Assay

WEHI279 cells (ATCC) were plated in suspension at a concentration of 25,000 cells/well in culture media with or without 1.5% human serum albumin (HSA) and stimulated with a dilution series of recombinant mIFNγ or inducible mIFNγ for 72 hours at 37° C. and 5% $CO_2$. Activity of uncleaved and cleaved inducible mIFNγ was tested. Cleaved inducible mIFNg was generated by incubation with active MMP9. Cell survival was assessed using a CellTiter-Glo (Promega) luminescence-based cell viability assay. The EC50 values for cleaved inducible mIFNg molecules were at least 100× more potent than un-cleaved inducible mIFNg molecules. As shown in FIGS. 16A-16F, greater inducibility was seen in assays wherein the culture media contained human serum albumin.

Example 12: Mouse IFNγ B16 Reporter and Mouse IFNα/β B16 Reporter Cell Assays B16-Blue IFNγ cells (InvivoGen) were plated at a concentration of 75,000 cells/well in culture media with or without 1.5% human serum albumin (HSA) and stimulated with a dilution series of recombinant mIFNγ or inducible mIFNγ for 24 hours at 37° C. and 5% $CO_2$. Activity of uncleaved and cleaved inducible mIFNγ was tested. Cleaved inducible mIFNγ was generated by incubation with active MMP9. Supernatants were harvested, and SEAP activation was assessed by adding QUANTI-Blue Reagent (InvivoGen), incubating at 37° C. for 2 hours, and measuring absorbance at 620 nm. Results are shown in FIGS. 17, 19, 22, 23, and 28. This experiment was repeated with for IFNα fusion proteins using B16-Blue IFNα/β cells. The EC50 values for cleaved inducible mIFNα molecules were at least 100× more potent than un-cleaved inducible mIFNα molecules.

Example 13. In Vivo Delivery of a Protease Activated Fusion Protein Results in Decreased Tumor Growth The chimeric polypeptide is examined to determine if it could have biological effects in vivo. For these experiments a system is used in which tumor cells injected intraperitoneally rapidly and preferentially attach and grow initially on the milky spots, a series of organized immune aggregates found on the omentum (Gerber et al., Am. J. Pathol. 169: 1739-52 (2006)). This system offers a convenient way to examine the effects of fusion protein treatment on tumor growth since fusion proteins can be delivered intraperitoneally multiple times and tumor growth can be analyzed by examining the dissociated omental cells. For these experiments, the Colon 38 cell line, a rapidly growing tumor cell line that expresses both MMP2 and MMP9 in vitro, may be used. The omental tissue normally expresses a relatively small amount of MMP2 and MMP9, but, when Colon 38 tumor is present on the omentum, MMP levels increase. Using this tumor model, the ability of IFN fusion proteins to affect tumor growth is examined. Colon 38 cells are injected intraperitoneally, allowed to attach and grow for 1 day, and then treated daily with fusion protein interaperitoneally. At day 7, the animals are sacrificed and the omenta examined for tumor growth using flow cytometry and by a colony-forming assay.

Example 13b: The Chimeric Polypeptide was Examined to Determine its Biological Effects In Vivo The MC38 cell line, a rapidly growing colon adenocarcinoma cell line that expresses MMP9 in vitro, was used. Using this tumor model, the ability of IFNγ fusion proteins to affect tumor growth was examined. MC38 cells were injected subcutaneously, allowed to grow for 10-14 days, and then treated with fusion protein twice weekly intraperitoneally for a total of four doses, at the levels shown in FIGS. 21A-21D. As a comparator, wild-type mIFNγ was administered at the dose levels indicated, twice daily for 2 weeks on a 5 day on/2 day off schedule (10 total doses). Tumor growth and body weight were monitored approximately twice per week for two weeks.

Example 14: Construction of an Exemplary IFNγ Protein Targeting CD20

Generation of an Activatable Cytokine Domain

An IFNγ polypeptide capable of binding to CD20 polypeptide present in a tumor or on a tumor cell is produced as follows. A nucleic acid is produced that contains nucleic acid sequences: (1) encoding an IFNγ polypeptide sequence and (2) one or more polypeptide linkers. Activatable IFNγ plasmid constructs can have optional Flag, His or other affinity tags, and are electroporated into HEK293 or other suitable human or mammalian cell lines and purified. Validation assays include T cell activation assays using T cells responsive to IFNγ stimulation in the presence of a protease.

Generation of a scFv CD20 Binding Domain

CD20 is one of the cell surface proteins present on B-lymphocytes. CD20 antigen is found in normal and malignant pre-B and mature B lymphocytes, including those in over 90% of B-cell non-Hodgkin's lymphomas (NHL). The antigen is absent in hematopoietic stem cells, activated B lymphocytes (plasma cells) and normal tissue. As such, several antibodies mostly of murine origin have been described: 1F5, 2B8/C2B8, 2H7, and 1H4.

Human or humanized anti-CD20 antibodies are therefore used to generate scFv sequences for CD20 binding domains of an activatable IFNγ protein. DNA sequences coding for human or humanized VL and VH domains are obtained, and the codons for the constructs are, optionally, optimized for expression in cells from *Homo sapiens*. The order in which the VL and VH domains appear in the scFv is varied (i.e., VL-VH, or VH-VL orientation), and three copies of the "G4S" (SEQ ID NO.: 449) or "$G_4S$" (SEQ ID NO.: 449) subunit $(G_4S)_3$ (SEQ ID NO.: 452) connect the variable domains to create the scFv domain. Anti-CD20 scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD20-expressing cells.

Cloning of DNA Expression Constructs Encoding the Activatable IFNγ Protein

Figure 14:
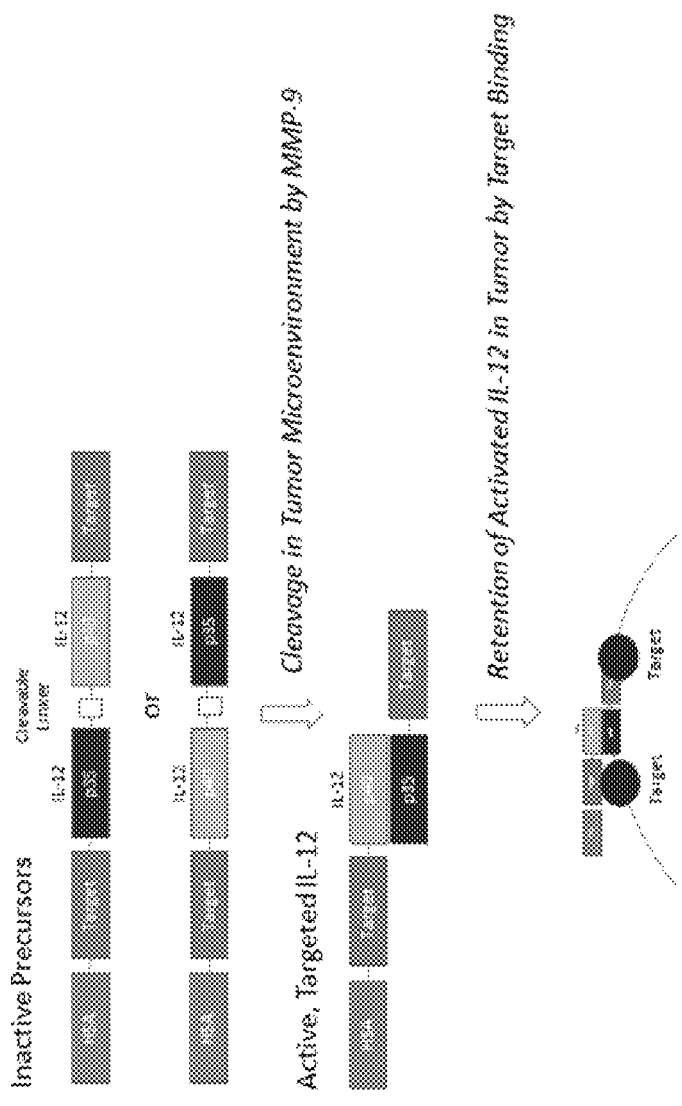
FIG. 14 is a schematic which depicts a non-limiting example of an inducible cytokine protein, wherein the construct is activated upon protease cleavage of a linker attached between two subunits of the cytokine.
Figure 16A:
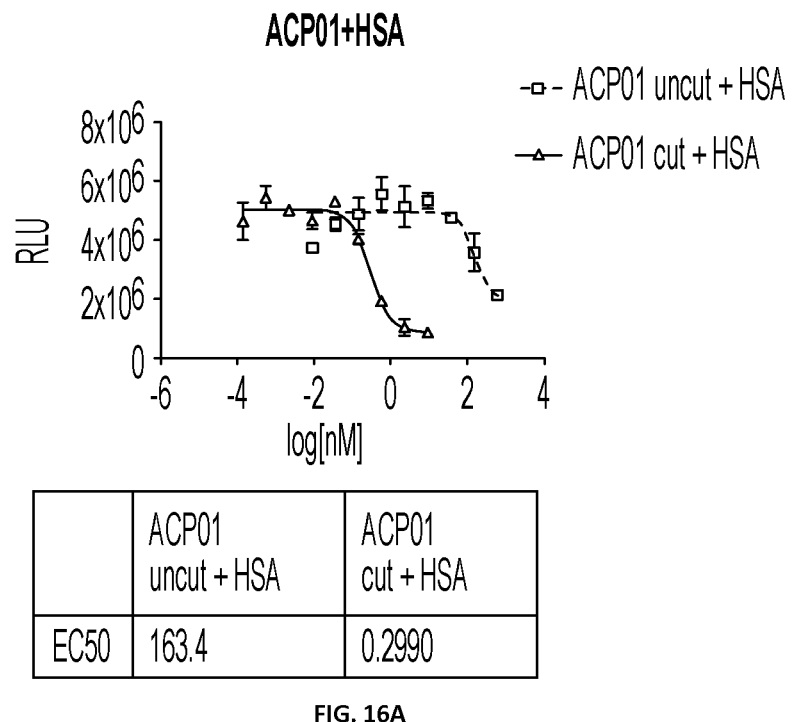
FIGS. 16A-16F are a series of graphs showing activity of exemplary IFNγ fusion proteins compared to activity of mouse IFNγ control using WEHI 279 cell survival assay. Each assay was performed with medium containing HSA (+HSA) or not containing HSA (−HSA). Each fusion protein comprises an anti-HSA binder, and both uncleaved and MMP9 protease cleaved versions of the fusion protein were used in each assay.
Figure 16B:
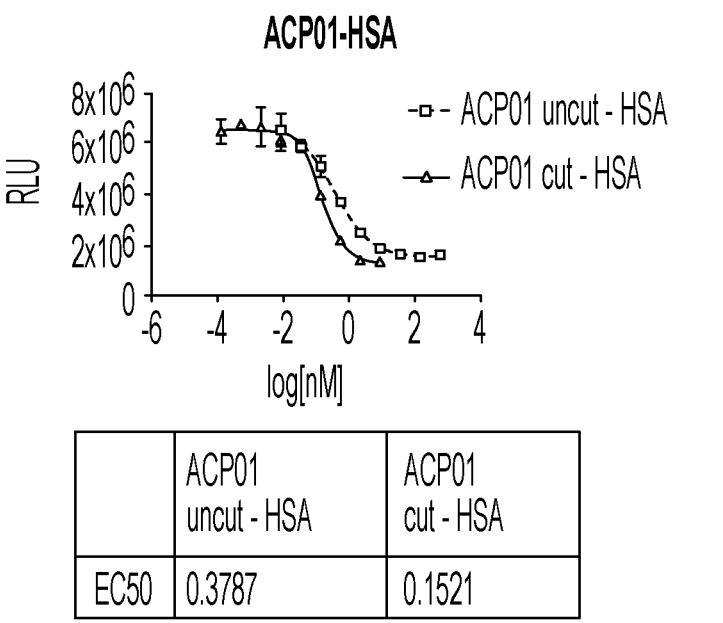
Figure 16C:
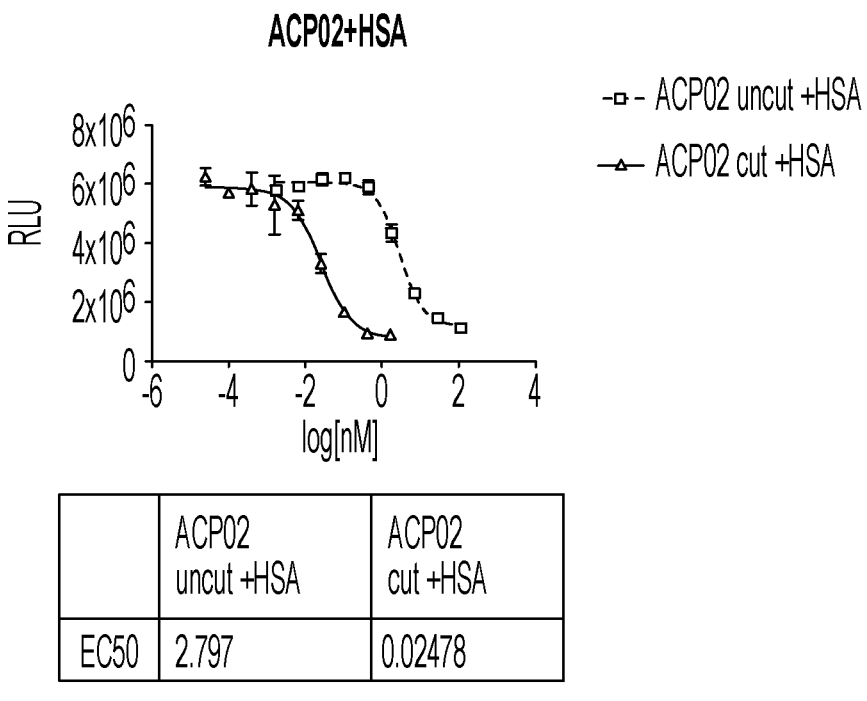
Figure 16D:
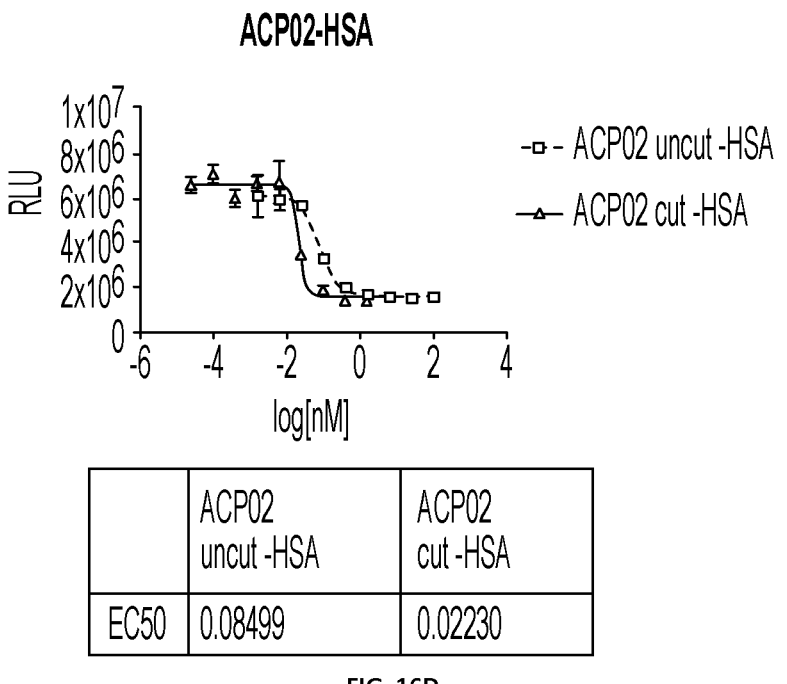
Figure 16E:
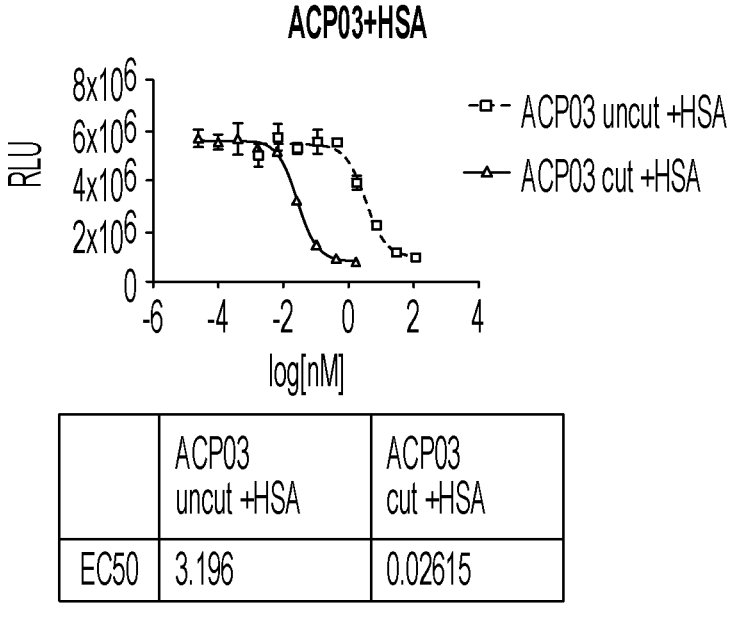
Figure 16F:
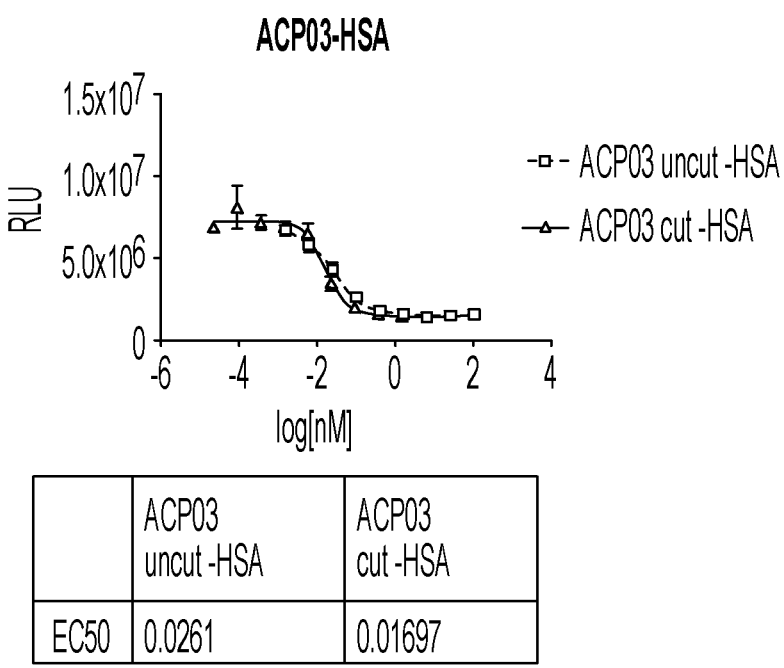
Figure 17E:
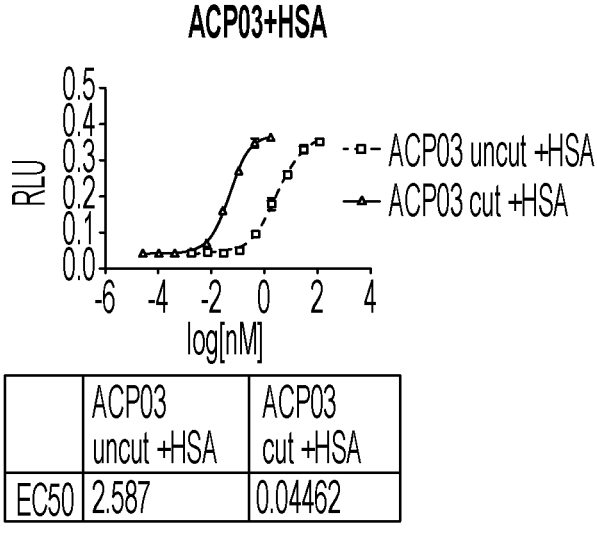
Figure 17F:
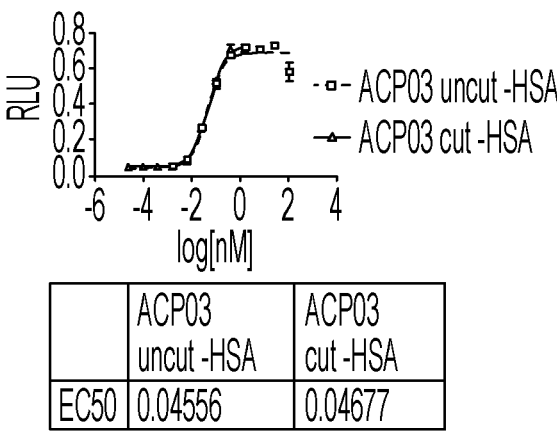
Figure 18B:
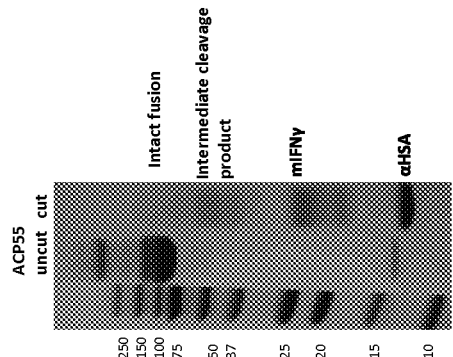
FIGS. 18A-18B show results of protein cleavage assay, as described in Example 2. Two constructs, ACP31 (IFN-α fusion protein.
Figure 18A:
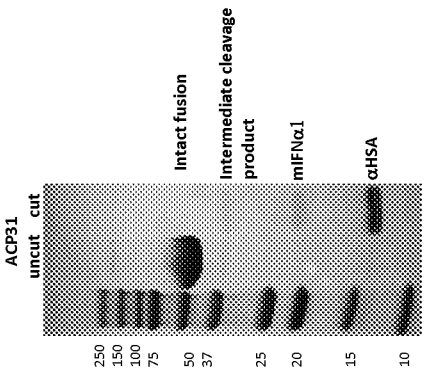
Figures 19A, 19B:
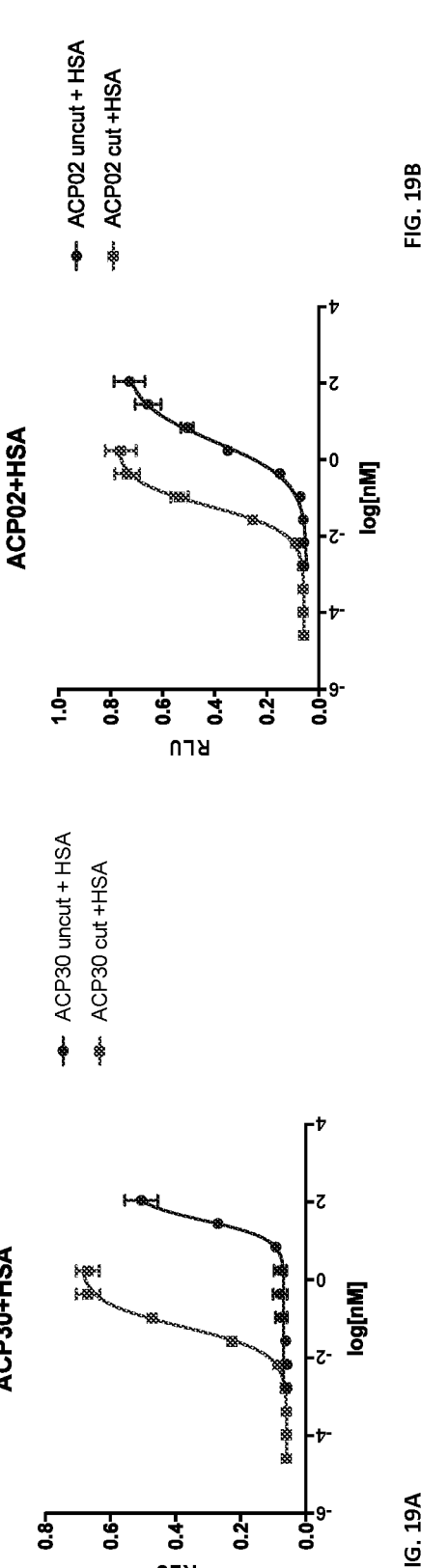
FIGS. 19A-19B are a series of graphs (FIGS. 19A and 19B) showing activity of exemplary IFNγ fusion proteins before and after protease cleavage using B16 reporter assay. Each assay was performed with culture medium containing HSA, and each fusion protein comprises an anti-HSA binder. Both uncleaved and MMP9 protease cleaved versions of the fusion protein were used in each assay.
Figure 20B:
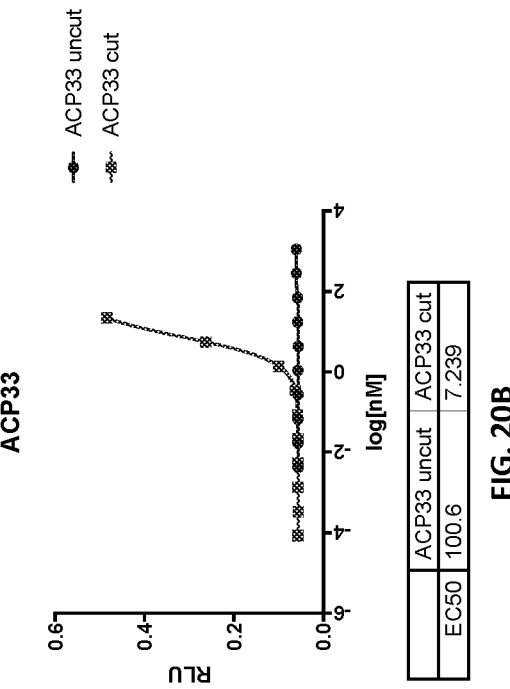
FIGS. 20A-20B are a series of graphs (FIG. 20A and FIG. 20B) showing activity of exemplary IFNα fusion proteins before and after cleavage using a B16 reporter assay. Each assay was performed with medium containing HSA, and each fusion protein comprises an anti-HSA binder. Both uncleaved and MMP9 protease cleaved versions of the fusion protein were used in each assay.
Figure 20A:
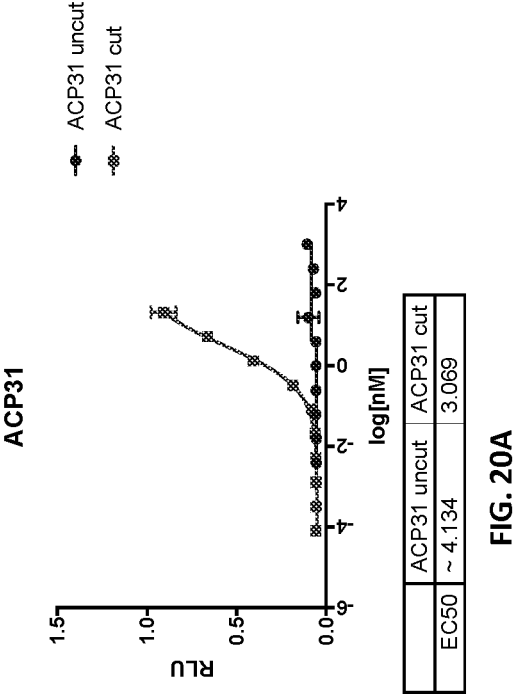
Figure 21A:
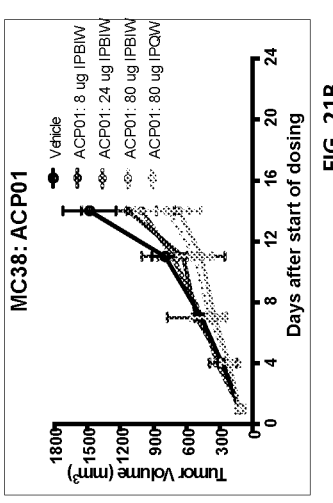
FIGS. 21A-21D are a series of graphs depicting the results of tumor growth studies using the MC38 cell line.
Figure 21B:
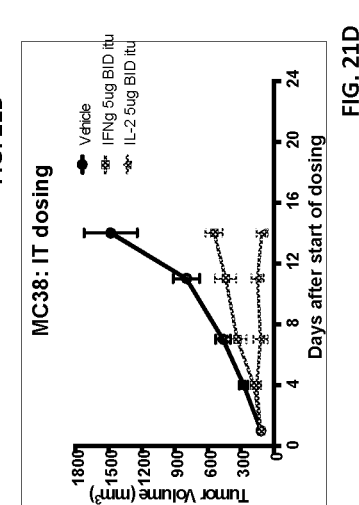
Figure 21C:
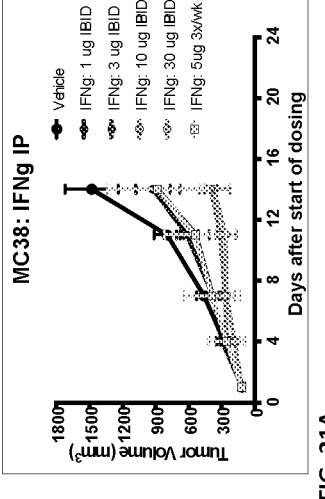
Figure 21D:
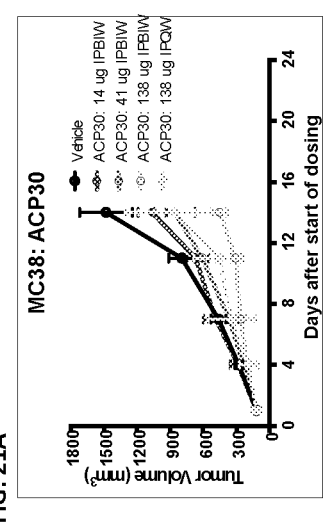
Figure 23B:
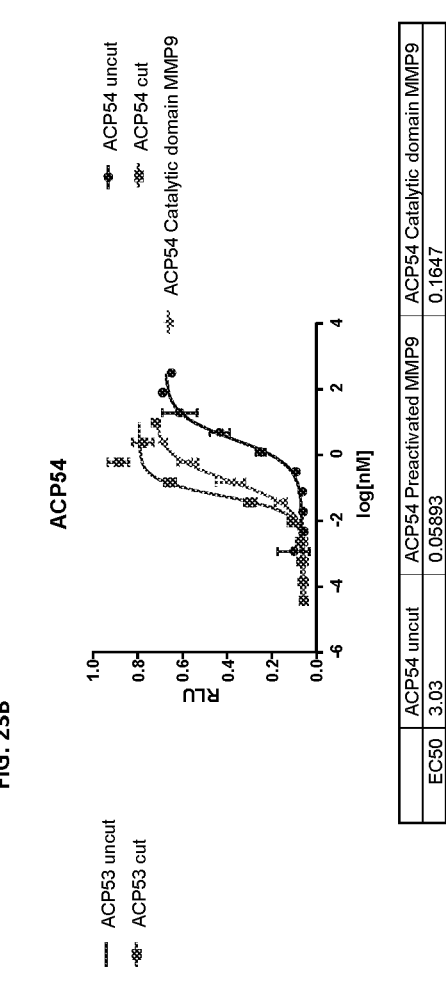
FIGS. 23A-23B are a series of graphs showing activity of exemplary IFNγ fusion proteins (ACP53 and ACP54) cleaved by MMP9 protease compared to activity of uncleaved fusion proteins using B16 reporter assay. Each fusion protein comprises IFNγ directly fused to albumin.
Figure 23A:
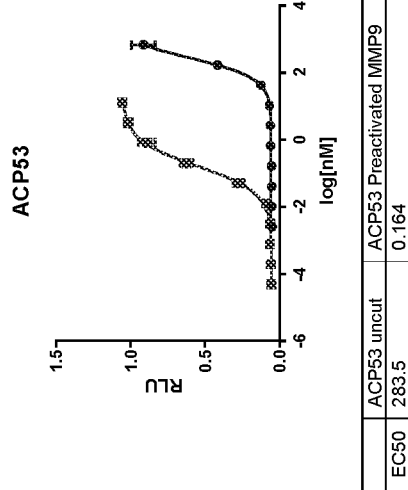
Figure 24A:
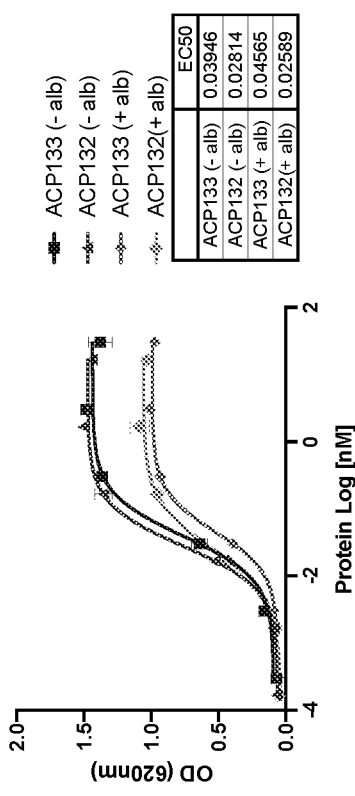
Figure 24C:
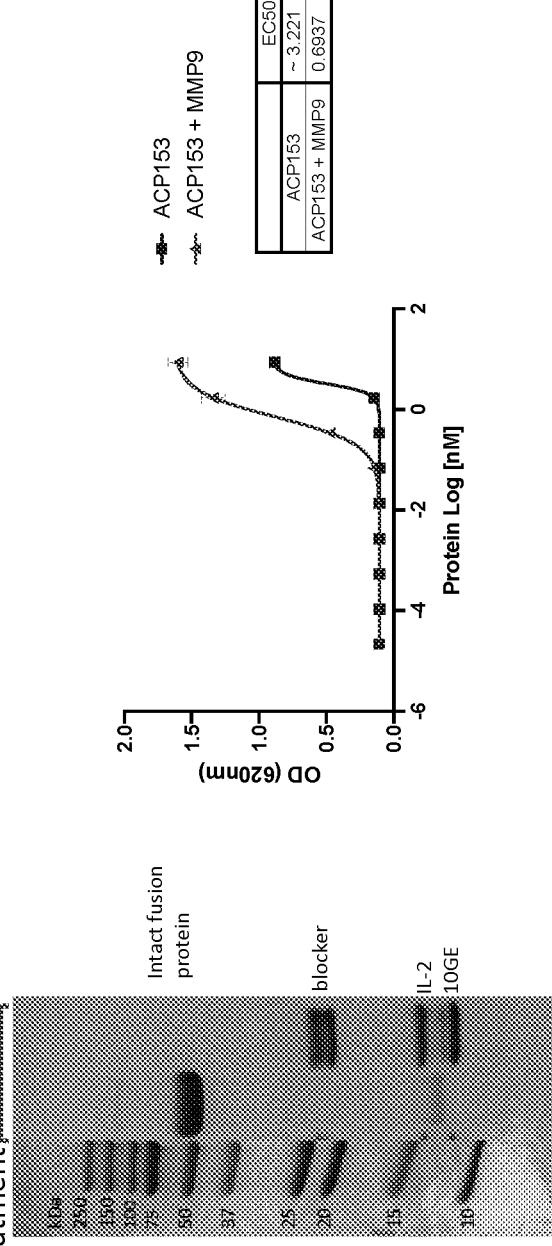
Figure 24D:
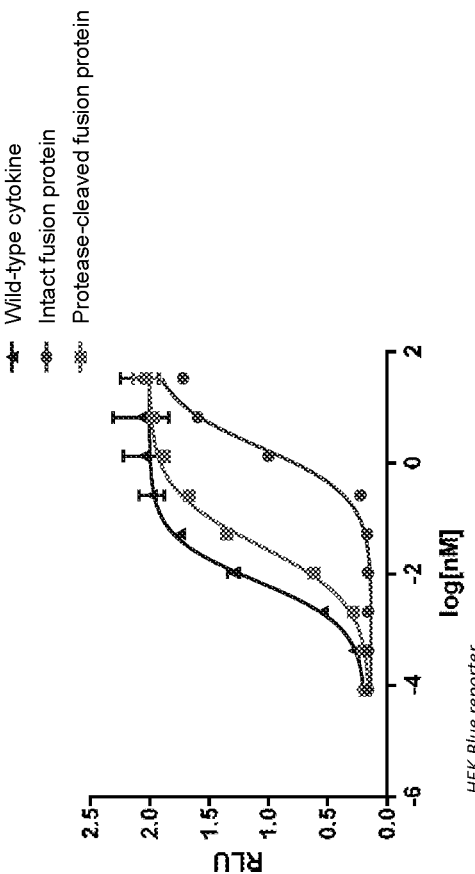

The activatable IFNγ construct with protease cleavage site domains are used to construct an activatable IFNγ protein in combination with an anti-CD20 scFv domain and a serum half-life extension element (e.g., a HSA binding peptide or VH domain), with the domains organized as shown in FIG. 14. For expression of an activatable IFNγ protein in CHO cells, coding sequences of all protein domains are cloned into a mammalian expression vector system. In brief, gene sequences encoding the activatable IFNγ domain, serum half-life extension element, and CD20 binding domain along with peptide linkers L1 and L2 are separately synthesized and subcloned. The resulting constructs are then ligated together in the order of CD20 binding domain-L1-IFNγ subunit 1-L2-protease cleavage domain-L3-IFNγ subunit2-L4-anti-CD20 scFv-L5-serum half-life extension element to yield a final construct. All expression constructs are designed to contain coding sequences for an N-terminal signal peptide and a C-terminal hexahistidine (6×His)-tag (SEQ ID NO.: 354) to facilitate protein secretion and purification, respectively.

Expression of Activatable IFNγ Proteins in Stably Transfected CHO Cells

A CHO cell expression system (Flp-In®, Life Technologies), a derivative of CHO-K1 Chinese Hamster ovary cells (ATCC, CCL-61) (Kao and Puck, Proc. Natl. Acad Sci USA 1968; 60(4):1275-81), is used. Adherent cells are subcultured according to standard cell culture protocols provided by Life Technologies.

For adaption to growth in suspension, cells are detached from tissue culture flasks and placed in serum-free medium. Suspension-adapted cells are cryopreserved in medium with 10% DMSO.

Recombinant CHO cell lines stably expressing secreted activatable IFNγ proteins are generated by transfection of suspension-adapted cells. During selection with the antibiotic Hygromycin B viable cell densities are measured twice a week, and cells are centrifuged and resuspended in fresh selection medium at a maximal density of $0.1 \times 10^6$ viable cells/mL. Cell pools stably expressing activatable IFNγ proteins are recovered after 2-3 weeks of selection at which point cells are transferred to standard culture medium in shake flasks. Expression of recombinant secreted proteins is confirmed by performing protein gel electrophoresis or flow cytometry. Stable cell pools are cryopreserved in DMSO containing medium.

Activatable IFNγ proteins are produced in 10-day fed-batch cultures of stably transfected CHO cell lines by secretion into the cell culture supernatant. Cell culture supernatants are harvested after 10 days at culture viabilities of typically >75%. Samples are collected from the production cultures every other day and cell density and viability are assessed. On day of harvest, cell culture supernatants are cleared by centrifugation and vacuum filtration before further use.

Protein expression titers and product integrity in cell culture supernatants are analyzed by SDS-PAGE.

Purification of Activatable IFNγ Proteins

Activatable IFNγ proteins are purified from CHO cell culture supernatants in a two-step procedure. The constructs are subjected to affinity chromatography in a first step followed by preparative size exclusion chromatography (SEC) on Superdex 200 in a second step. Samples are buffer-exchanged and concentrated by ultrafiltration to a typical concentration of >1 mg/mL. Purity and homogeneity (typically >90%) of final samples are assessed by SDS PAGE under reducing and non-reducing conditions, followed by immunoblotting using an anti-HSA or anti idiotype antibody as well as by analytical SEC, respectively. Purified proteins are stored at aliquots at −80° C. until use.

Example 15: Determination of Antigen Affinity by Flow Cytometry

The activatable IFNγ proteins of Example 1 are tested for their binding affinities to human $CD20^+$ cells and cynomolgus $CD20^+$ cells.

$CD20^+$ cells are incubated with 100 μL of serial dilutions of the activatable IFNγ proteins of Example 1 and at least one protease. After washing three times with FACS buffer the cells are incubated with 0.1 mL of 10 μg/mL mouse monoclonal anti-idiotype antibody in the same buffer for 45 min on ice. After a second washing cycle, the cells are incubated with 0.1 mL of 15 μg/mL FITC-conjugated goat anti-mouse IgG antibodies under the same conditions as before. As a control, cells are incubated with the anti-His IgG followed by the FITC-conjugated goat anti-mouse IgG antibodies without the activatable IFNγ proteins. The cells were then washed again and resuspended in 0.2 mL of FACS buffer containing 2 μg/mL propidium iodide (PI) in order to exclude dead cells. The fluorescence of $1 \times 10^4$ living cells is measured using a Beckman-Coulter FC500 MPL flow cytometer using the MXP software (Beckman-Coulter, Krefeld, Germany) or a Millipore Guava EasyCyte flow cytometer using the Incyte software (Merck Millipore, Schwalbach, Germany). Mean fluorescence intensities of the cell samples are calculated using CXP software (Beckman-Coulter, Krefeld, Germany) or Incyte software (Merck Millipore, Schwalbach, Germany). After subtracting the fluorescence intensity values of the cells stained with the secondary and tertiary reagents alone the values are then used for calculation of the $K_D$ values with the equation for one-site binding (hyperbola) of the GraphPad Prism (version 6.00 for Windows, GraphPad Software, La Jolla California USA).

CD20 binding and crossreactivity are assessed on the human $CD20^+$ tumor cell lines. The $K_D$ ratio of crossreactivity is calculated using the $K_D$ values determined on the CHO cell lines expressing either recombinant human or recombinant cynomolgus antigens.

Example 16: Cytotoxicity Assay

The activatable IFNγ protein of Example 5 is evaluated in vitro on its mediation of immune response to $CD20^+$ target cells.

Fluorescence labeled $CD20^+$ REC-1 cells (a Mantle cell lymphoma cell line, ATCC CRL-3004) are incubated with isolated PBMC of random donors or CB15 T-cells (standardized T-cell line) as effector cells in the presence of the activatable IFNγ protein of Example 5 and at least one protease. After incubation for 4 h at 37° C. in a humidified incubator, the release of the fluorescent dye from the target cells into the supernatant is determined in a spectrofluorimeter. Target cells incubated without the activatable IFNγ protein of Example 5 and target cells totally lysed by the addition of saponin at the end of the incubation serve as negative and positive controls, respectively.

Based on the measured remaining living target cells, the percentage of specific cell lysis is calculated according to the following formula: [1−(number of living targets$_{(sample)}$/number of living targets$_{(spontaneous)}$]×100%. Sigmoidal dose response curves and $EC_{50}$ values are calculated by nonlinear regression/4-parameter logistic fit using the GraphPad Software. The lysis values obtained for a given antibody concentration are used to calculate sigmoidal dose-response curves by 4 parameter logistic fit analysis using the Prism software.

Example 17: Pharmacokinetics of Activatable IFNγ Proteins

The activatable IFNγ protein of Example 5 is evaluated for half-time elimination in animal studies.

The activatable IFNγ protein is administered to cynomolgus monkeys as a 0.5 mg/kg bolus injection into the saphenous vein. Another cynomolgus monkey group receives a comparable cytokine in size, but lacking a serum half-life extension element. A third and fourth group receive a cytokine with serum half-life extension elements and a cytokine with CD20 and serum half-life extension elements respectively, and both comparable in size to the activatable IFNγ protein. Each test group consists of 5 monkeys. Serum samples are taken at indicated time points, serially diluted, and the concentration of the proteins is determined using a binding ELISA to CD20.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-\alpha t}+Be^{-\beta t}$, where c(t) is the plasma concentration at time t, A and B are intercepts on the Y-axis, and a and 3 are the apparent first-order rate constants for the distribution and elimination phases, respectively. The α-phase is the initial phase of the clearance and reflects distribution of the protein into all extracellular fluid of the animal, whereas the second or β-phase portion of the decay curve represents true plasma clearance. Methods for fitting such equations are well known in the art. For example, $A=D/V(\alpha-k21)/(\alpha-\beta)$, $B=D/V(\beta-k21)/(\alpha-\beta)$, and α and β (for α>β) are roots of the quadratic equation: $r^2+(k12+k21+k10)r+k21k10=0$ using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time profiles are made using KaleidaGraph (KaleidaGraph™ V. 3.09 Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif.). Pharmacokinetic parameters are computed as described in Ritschel W A and Kearns G L, 1999, IN: *Handbook Of Basic Pharmacokinetics Including Clinical Applications*, 5th edition, American Pharmaceutical Assoc., Washington, D.C.

It is expected that the activatable IFNγ protein of Example 5 has improved pharmacokinetic parameters such as an increase in elimination half-time as compared to proteins lacking a serum half-life extension element.

Example 18: Xenograft Tumor Model

The activatable IFNγ protein of Example 5 is evaluated in a xenograft model.

Female immune-deficient NOD/scid mice are sub-lethally irradiated (2 Gy) and subcutaneously inoculated with $4\times10^6$ Ramos RA1 cells into the right dorsal flank. When tumors reach 100 to 200 mm³, animals are allocated into 3 treatment groups. Groups 2 and 3 (8 animals each) are intraperitoneally injected with $1.5\times10^7$ activated human T-cells. Three days later, animals from Group 3 are subsequently treated with a total of 9 intravenous doses of 50 µg activatable IFNγ protein of Example 5 (qd×9d). Groups 1 and 2 are only treated with vehicle. Body weight and tumor volume are determined for 30 days.

It is expected that animals treated with the activatable IFNγ protein of Example 5 have a statistically significant delay in tumor growth in comparison to the respective vehicle-treated control group.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 19: HEK-Blue Assay

HEK-Blue IL12 cells (InvivoGen) were plated in suspension at a concentration of 250,000 cells/well in culture media with or without 40 mg/ml human serum albumin (HSA) and stimulated with a dilution series of recombinant hIL12, chimeric IL12 (mouse p35/human p40) or activatable hIL12 for 24 hours at 37° C. and 5% $CO_2$. Activity of uncleaved and cleaved activatable hIL12 was tested. Cleaved inducible hIL12 was generated by incubation with active MMP9. IL12 activity was assessed by quantification of Secreted Alkaline Phosphatase (SEAP) activity using the reagent QUANTI-Blue (InvivoGen), a colorimetric based assay. Results are shown in FIGS. 11, 12, 15, and 26.

HEK-Blue IL2 cells (InvivoGen) were plated in suspension at a concentration of 50,000 cells/well in culture media with or without 15-40 mg/ml human serum albumin (HSA) and stimulated with a dilution series of recombinant hIL2 or activatable hIL2 for 24 hours at 37 C and 5% $CO_2$. Activity of uncleaved and cleaved activatable hIL2 was tested. Cleaved inducible hIL2 was generated by incubation with active MMP9. IL12 activity was assessed by quantification of Secreted Alkaline Phosphatase (SEAP) activity using the reagent QUANTI-Blue (InvivoGen), a colorimetric based assay. Results are shown in FIGS. 24A-24D.

Example 20: Splenocyte T-Blast Assay

T-Blasts were induced from murine splenocytes with a 6-day incubation with PHA and a 24 hr incubation with recombinant hIL12. Tblasts were then plated in suspension at a concentration of 200,000 cells/well in culture media with or without 40 mg/ml human serum albumin (HSA) and stimulated with a dilution series of recombinant hIL12 or chimeric IL12 (mouse p35/human p40) or mouse IL12 for 72 hours at 37° C. and 5% $CO_2$. Activity of uncleaved and cleaved IL12 fusion proteins was tested. Cleaved inducible hIL12 was generated by incubation with active MMP9. IL12 activity was assessed by downstream quantification of IFNγ production using a mIFNγ alpha ELISA.

Example 21: In Vivo Delivery of a Protease Activated Fusion Protein Results in Decreased Tumor Growth The chimeric polypeptide is examined to determine if it could have biological effects in vivo. For these experiments a system is used in which tumor cells injected intraperitoneally rapidly and preferentially attach and grow initially on the milky spots, a series of organized immune aggregates found on the omentum (Gerber et al., Am. J. Pathol. 169: 1739-52 (2006)). This system offers a convenient way to examine the effects of fusion protein treatment on tumor growth since fusion proteins can be delivered intraperitoneally multiple times and tumor growth can be analyzed by examining the dissociated omental cells. For these experiments, the Colon 38 cell line, a rapidly growing tumor cell line that expresses both MMP2 and MMP9 in vitro, may be used. The omental tissue normally expresses a relatively small amount of MMP2 and MMP9, but, when Colon 38 tumor is present on the omentum, MMP levels increase. Using this tumor model, the ability of IL-2 mutein fusion proteins to affect tumor growth is examined. Colon 38 cells are injected intraperitoneally, allowed to attach and grow for 1 day, and then treated daily with fusion protein interaperitoneally. At day 7, the animals are sacrificed and the omenta examined for tumor growth using flow cytometry and by a colony-forming assay.

Example 22: Construction of an Exemplary Activatable Interleukin Protein Targeting CD20

Generation of an Activatable Interleukin Domain

The human IL-12p35 chain canonical sequence is Uniprot Accession No. P29459. The human IL-12p40 chain canonical sequence is Uniprot Accession No. P29460. IL-12p35 and IL-12p40 are cloned into an expression construct. A protease cleavage site is included between the IL-12p35 and IL-12p40 domains. An IL-12 polypeptide capable of binding to CD20 polypeptide present in a tumor or on a tumor cell is produced as follows. A nucleic acid is produced that contains nucleic acid sequences: (1) encoding an IFNγ polypeptide sequence and (2) one or more polypeptide linkers. Activatable interleukin plasmid constructs can have optional Flag, His or other affinity tags, and are electroporated into HEK293 or other suitable human or mammalian cell lines and purified. Validation assays include T cell activation assays using T cells responsive to IL-12 stimulation in the presence of a protease.
Generation of a scFv CD20 Binding Domain CD20 is one of the cell surface proteins present on B-lymphocytes. CD20 antigen is found in normal and malignant pre-B and mature B lymphocytes, including those in over 90% of B-cell non-Hodgkin's lymphomas (NHL). The antigen is absent in hematopoietic stem cells, activated B lymphocytes (plasma cells) and normal tissue. As such, several antibodies mostly of murine origin have been described: 1F5, 2B8/C2B8, 2H7, and 1H4.

Human or humanized anti-CD20 antibodies are therefore used to generate scFv sequences for CD20 binding domains of an activatable interleukin protein. DNA sequences coding for human or humanized VL and VH domains are obtained, and the codons for the constructs are, optionally, optimized for expression in cells from *Homo sapiens*. The order in which the VL and VH domains appear in the scFv is varied (i.e., VL-VH, or VH-VL orientation), and three copies of the "G4S" (SEQ ID NO.: 449) or "$G_4S$" (SEQ ID NO.: 449) subunit $(G_4S)_3$ (SEQ ID NO.: 452) connect the variable domains to create the scFv domain. Anti-CD20 scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of CD20-expressing cells.
Cloning of DNA Expression Constructs Encoding the Activatable Interleukin Protein The activatable interleukin construct with protease cleavage site domains are used to construct an activatable interleukin protein in combination with an anti-CD20 scFv domain and a serum half-life extension element (e.g., a HSA binding peptide or VH domain). For expression of an activatable interleukin protein in CHO cells, coding sequences of all protein domains are cloned into a mammalian expression vector system. In brief, gene sequences encoding the activatable interleukin domain, serum half-life extension element, and CD20 binding domain along with peptide linkers L1 and L2 are separately synthesized and subcloned. The resulting constructs are then ligated together in the order of CD20 binding domain-L1-IL-12p35-L2-protease cleavage domain-L3-IL-12p40-L4-anti-CD20 scFv-L5-serum half-life extension element to yield a final construct. All expression constructs are designed to contain coding sequences for an N-terminal signal peptide and a C-terminal hexahistidine (6×His)-tag (SEQ ID NO.: 354) to facilitate protein secretion and purification, respectively.
Expression of Activatable Interleukin Proteins in Stably Transfected CHO Cells A CHO cell expression system (Flp-In®, Life Technologies), a derivative of CHO-K1 Chinese Hamster ovary cells (ATCC, CCL-61) (Kao and Puck, Proc. Natl. Acad Sci USA 1968; 60(4):1275-81), is used. Adherent cells are subcultured according to standard cell culture protocols provided by Life Technologies.

For adaption to growth in suspension, cells are detached from tissue culture flasks and placed in serum-free medium. Suspension-adapted cells are cryopreserved in medium with 10% DMSO.

Recombinant CHO cell lines stably expressing secreted activatable interleukin proteins are generated by transfection of suspension-adapted cells. During selection with the antibiotic Hygromycin B viable cell densities are measured twice a week, and cells are centrifuged and resuspended in fresh selection medium at a maximal density of $0.1 \times 10^6$ viable cells/mL. Cell pools stably expressing activatable interleukin proteins are recovered after 2-3 weeks of selection at which point cells are transferred to standard culture medium in shake flasks. Expression of recombinant secreted proteins is confirmed by performing protein gel electrophoresis or flow cytometry. Stable cell pools are cryopreserved in DMSO containing medium.

Activatable interleukin proteins are produced in 10-day fed-batch cultures of stably transfected CHO cell lines by secretion into the cell culture supernatant. Cell culture supernatants are harvested after 10 days at culture viabilities of typically >75%. Samples are collected from the production cultures every other day and cell density and viability are assessed. On day of harvest, cell culture supernatants are cleared by centrifugation and vacuum filtration before further use.

Protein expression titers and product integrity in cell culture supernatants are analyzed by SDS-PAGE.

Purification of Activatable Interleukin Proteins

Activatable interleukin proteins are purified from CHO cell culture supernatants in a two-step procedure. The constructs are subjected to affinity chromatography in a first step followed by preparative size exclusion chromatography (SEC) on Superdex 200 in a second step. Samples are buffer-exchanged and concentrated by ultrafiltration to a typical concentration of >1 mg/mL. Purity and homogeneity (typically >90%) of final samples are assessed by SDS PAGE under reducing and non-reducing conditions, followed by immunoblotting using an anti-HSA or anti idiotype antibody as well as by analytical SEC, respectively. Purified proteins are stored at aliquots at −80° C. until use.

Example 23: Determination of Antigen Affinity by Flow Cytometry

The activatable interleukin proteins of Example 5 are tested for their binding affinities to human CD20$^+$ cells and cynomolgus CD20$^+$ cells.

CD20$^+$ cells are incubated with 100 µL of serial dilutions of the activatable interleukin proteins of Example 5 and at least one protease. After washing three times with FACS buffer the cells are incubated with 0.1 mL of 10 µg/mL mouse monoclonal anti-idiotype antibody in the same buffer for 45 min on ice. After a second washing cycle, the cells are incubated with 0.1 mL of 15 µg/mL FITC-conjugated goat anti-mouse IgG antibodies under the same conditions as before. As a control, cells are incubated with the anti-His IgG followed by the FITC-conjugated goat anti-mouse IgG antibodies without the activatable interleukin proteins. The cells were then washed again and resuspended in 0.2 mL of FACS buffer containing 2 µg/mL propidium iodide (PI) in order to exclude dead cells. The fluorescence of $1 \times 10^4$ living cells is measured using a Beckman-Coulter FC500 MPL flow cytometer using the MXP software (Beckman-Coulter, Krefeld, Germany) or a Millipore Guava EasyCyte flow cytometer using the Incyte software (Merck Millipore, Schwalbach, Germany). Mean fluorescence intensities of the cell samples are calculated using CXP software (Beckman-Coulter, Krefeld, Germany) or Incyte software (Merck Millipore, Schwalbach, Germany). After subtracting the fluorescence intensity values of the cells stained with the secondary and tertiary reagents alone the values are then used for calculation of the $K_D$ values with the equation for one-site binding (hyperbola) of the GraphPad Prism (version 6.00 for Windows, GraphPad Software, La Jolla California USA).

CD20 binding and crossreactivity are assessed on the human CD20$^+$ tumor cell lines. The $K_D$ ratio of crossreactivity is calculated using the $K_D$ values determined on the CHO cell lines expressing either recombinant human or recombinant cynomolgus antigens.

Example 24: Cytotoxicity Assay

The activatable interleukin protein of Example 5 is evaluated in vitro on its mediation of immune response to CD20$^+$ target cells.

Fluorescence labeled CD20$^+$ REC-1 cells (a Mantle cell lymphoma cell line, ATCC CRL-3004) are incubated with isolated PBMC of random donors or CB15 T-cells (standardized T-cell line) as effector cells in the presence of the activatable interleukin protein of Example 5 and at least one protease. After incubation for 4 h at 37° C. in a humidified incubator, the release of the fluorescent dye from the target cells into the supernatant is determined in a spectrofluorimeter. Target cells incubated without the activatable interleukin protein of Example 5 and target cells totally lysed by the addition of saponin at the end of the incubation serve as negative and positive controls, respectively.

Based on the measured remaining living target cells, the percentage of specific cell lysis is calculated according to the following formula: [1-(number of living targets$_{(sample)}$/number of living targets$_{(spontaneous)}$)]×100%. Sigmoidal dose response curves and $EC_{50}$ values are calculated by nonlinear regression/4-parameter logistic fit using the GraphPad Software. The lysis values obtained for a given antibody concentration are used to calculate sigmoidal dose-response curves by 4 parameter logistic fit analysis using the Prism software.

Example 25: Pharmacokinetics of Activatable Interleukin Proteins

The activatable interleukin protein of Example 5 is evaluated for half-time elimination in animal studies.

The activatable interleukin protein is administered to cynomolgus monkeys as a 0.5 mg/kg bolus injection into the saphenous vein. Another cynomolgus monkey group receives a comparable cytokine in size, but lacking a serum half-life extension element. A third and fourth group receive a cytokine with serum half-life extension elements and a cytokine with CD20 and serum half-life extension elements respectively, and both comparable in size to the activatable interleukin protein. Each test group consists of 5 monkeys. Serum samples are taken at indicated time points, serially diluted, and the concentration of the proteins is determined using a binding ELISA to CD20.

Pharmacokinetic analysis is performed using the test article plasma concentrations. Group mean plasma data for each test article conforms to a multi-exponential profile when plotted against the time post-dosing. The data are fit by a standard two-compartment model with bolus input and first-order rate constants for distribution and elimination phases. The general equation for the best fit of the data for i.v. administration is: $c(t)=Ae^{-\alpha t}+Be^{-\beta t}$, where c(t) is the plasma concentration at time t, A and B are intercepts on the Y-axis, and a and 3 are the apparent first-order rate constants for the distribution and elimination phases, respectively. The α-phase is the initial phase of the clearance and reflects distribution of the protein into all extracellular fluid of the animal, whereas the second or β-phase portion of the decay curve represents true plasma clearance. Methods for fitting such equations are well known in the art. For example, A=D/V(α−k21)/(α−β), B=D/V(β−k21)/(α−β), and α and β (for α>β) are roots of the quadratic equation: $r^2+(k12+k21+k10)r+k21k10=0$ using estimated parameters of V=volume of distribution, k10=elimination rate, k12=transfer rate from compartment 1 to compartment 2 and k21=transfer rate from compartment 2 to compartment 1, and D=the administered dose.

Data analysis: Graphs of concentration versus time profiles are made using KaleidaGraph (KaleidaGraph™ V. 3.09 Copyright 1986-1997. Synergy Software. Reading, Pa.). Values reported as less than reportable (LTR) are not included in the PK analysis and are not represented graphically. Pharmacokinetic parameters are determined by compartmental analysis using WinNonlin software (WinNonlin® Professional V. 3.1 WinNonlin™ Copyright 1998-1999. Pharsight Corporation. Mountain View, Calif.). Pharmacokinetic parameters are computed as described in Ritschel W A and Kearns G L, 1999, IN: *Handbook Of Basic Pharmacokinetics Including Clinical Applications,* 5th edition, American Pharmaceutical Assoc., Washington, D.C.

It is expected that the activatable interleukin protein of Example 5 has improved pharmacokinetic parameters such as an increase in elimination half-time as compared to proteins lacking a serum half-life extension element.

Example 26: Xenograft Tumor Model

The activatable interleukin protein of Example 5 is evaluated in a xenograft model.

Female immune-deficient NOD/scid mice are sub-lethally irradiated (2 Gy) and subcutaneously inoculated with $4 \times 10^6$ Ramos RA1 cells into the right dorsal flank. When tumors reach 100 to 200 mm$^3$, animals are allocated into 3 treatment groups. Groups 2 and 3 (8 animals each) are intraperitoneally injected with $1.5 \times 10^7$ activated human T-cells. Three days later, animals from Group 3 are subsequently treated with a total of 9 intravenous doses of 50 μg activatable interleukin protein of Example 5 (qd×9d). Groups 1 and 2 are only treated with vehicle. Body weight and tumor volume are determined for 30 days.

It is expected that animals treated with the activatable interleukin protein of Example 5 have a statistically significant delay in tumor growth in comparison to the respective vehicle-treated control group.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 27: MC38 Experiments

The MC38 cell line, a rapidly growing colon adenocarcinoma cell line that expresses MMP9 in vitro, was used. Using this tumor model, the ability of fusion proteins to affect tumor growth was examined.

Example 27a: MC38 IL-2POC

Agents and Treatment:

| Gr. | N | Agent | Formulation dose | Route | Schedule |
|---|---|---|---|---|---|
| 1# | 10 | Vehicle | — | ip | biwk x 3 |
| 2 | 7 | ACP16 | 700 μg/animal | ip | biwk x 3 |

-continued

| Gr. | N | Agent | Formulation dose | Route | Schedule |
|---|---|---|---|---|---|
| 3 | 7 | ACP16 | 230 μg/animal | ip | biwk x 3 |
| 4 | 7 | ACP16 | 70 μg/animal | ip | biwk x 3 |
| 5 | 7 | ACP16 | 55 ug/animal | ip | biwk x 3 |
| 6 | 7 | ACP16 | 17 μg/animal | ip | biwk x 3 |
| 7 | 7 | ACP132 | 361 μg/animal | ip | biwk x 3 |
| 8 | 7 | ACP132 | 119 μg/animal | ip | biwk x 3 |
| 9 | 7 | ACP132 | 36 μg/animal | ip | biwk x 3 |
| 10 | 7 | ACP132 | 28 μg/animal | ip | biwk x 3 |
| 11 | 7 | ACP132 | 9 μg/animal | ip | biwk x 3 |
| 12 | 7 | ACP21 | 540 μg/animal | ip | biwk x 3 |
| 13 | 7 | ACP21 | 177 μg/animal | ip | biwk x 3 |
| 14 | 7 | ACP21 | 54 μg/animal | ip | biwk x 3 |
| 15 | 7 | ACP21 | 42 μg/animal | ip | biwk x 3 |
| 16 | 7 | ACP21 | 13 μg/animal | ip | biwk x 3 |
| # | —ControlGroup | | | | |

Procedures:

Mice were anaesthetized with isoflurane for implant of cells to reduce the ulcerations. 308 CR female C57BL/6 mice were set up with $5 \times 10^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm$^3$ and begin treatment. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >0% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm$^3$ or 45 days, whichever comes first. Responders were followed longer. When the endpoint was reached, the animals are to be euthanized.

Figure 35B:
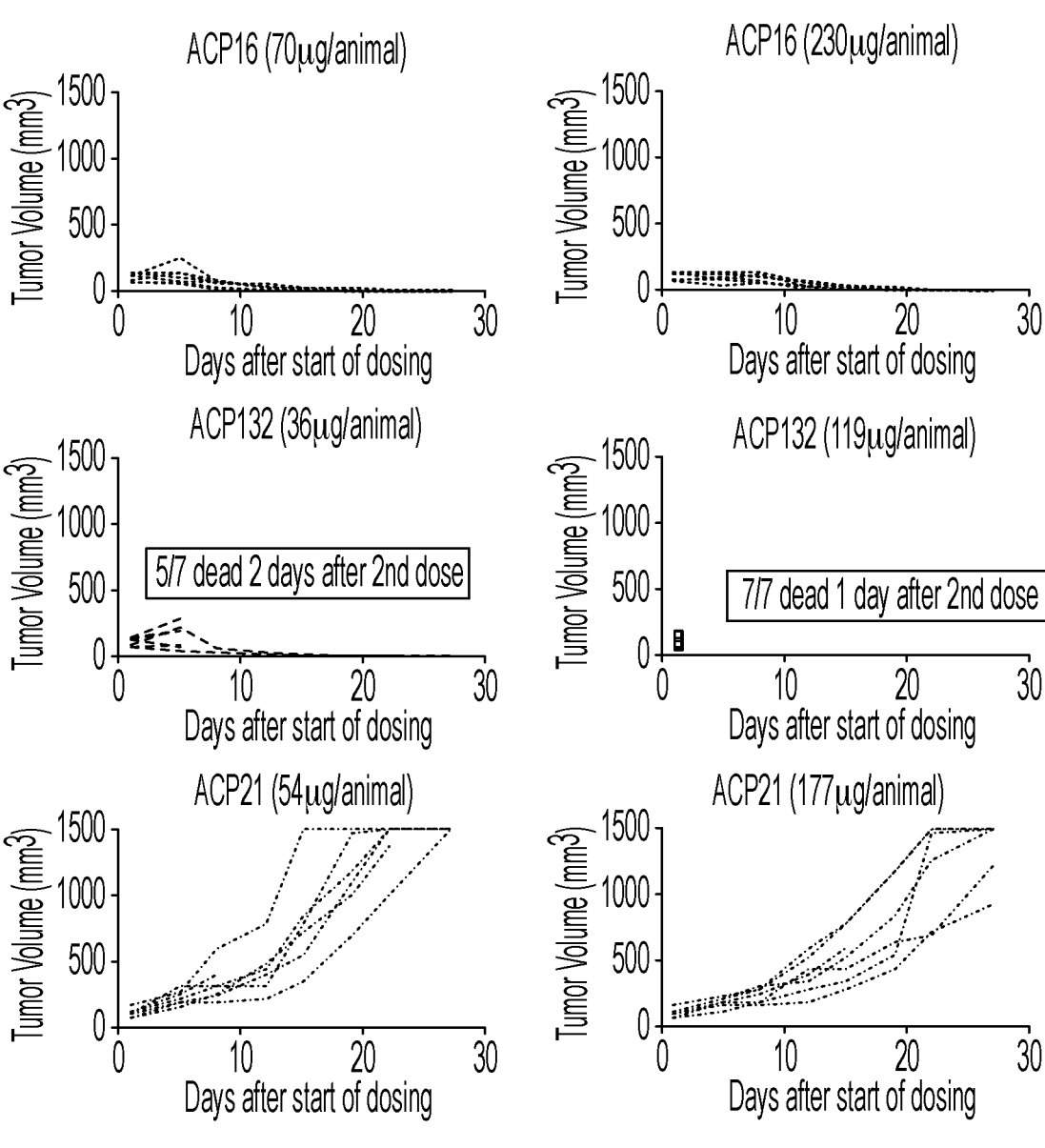
Figure 42A:
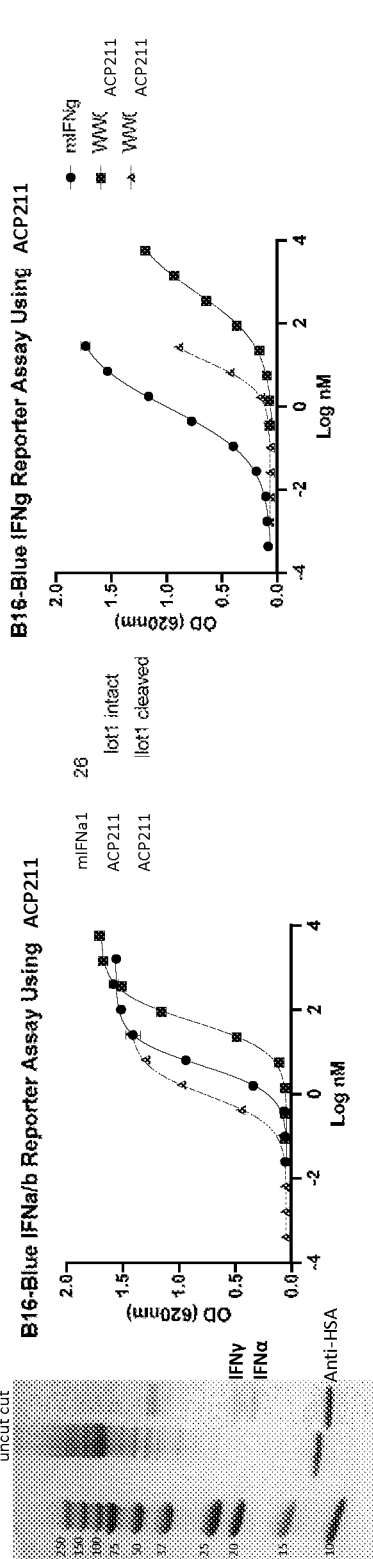
Figure 42C:
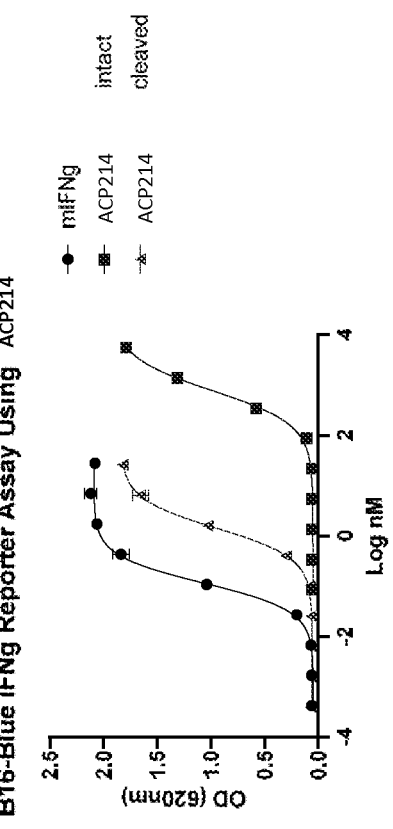
Figure 42D:
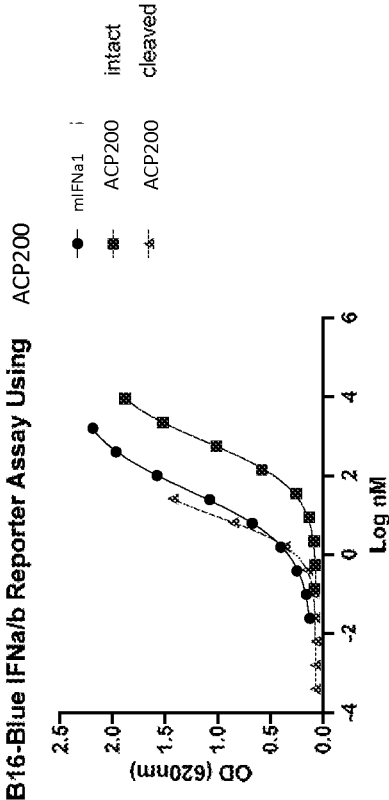
Figure 42E:
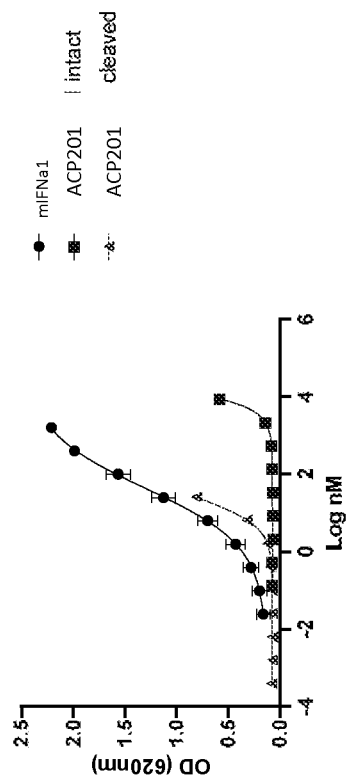
Figure 44A:
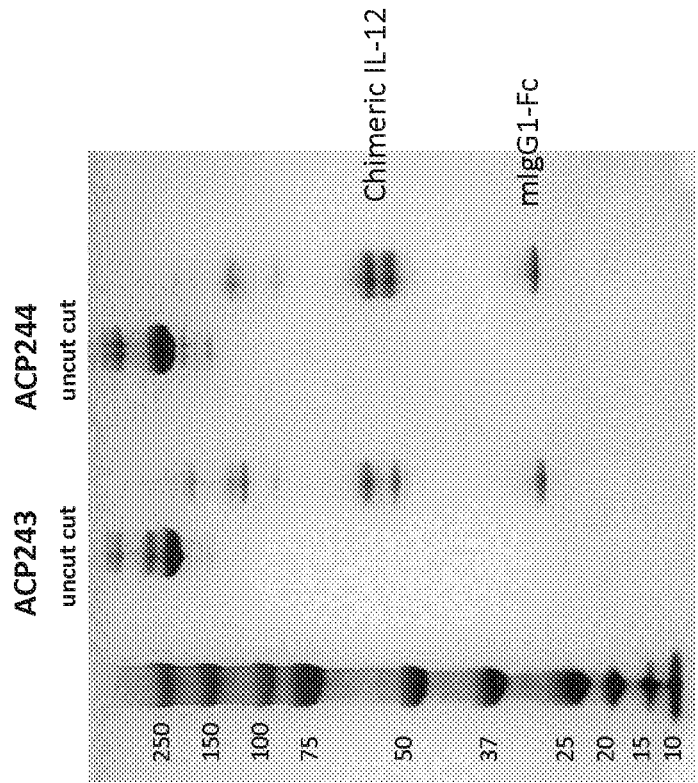
Figure 45B:
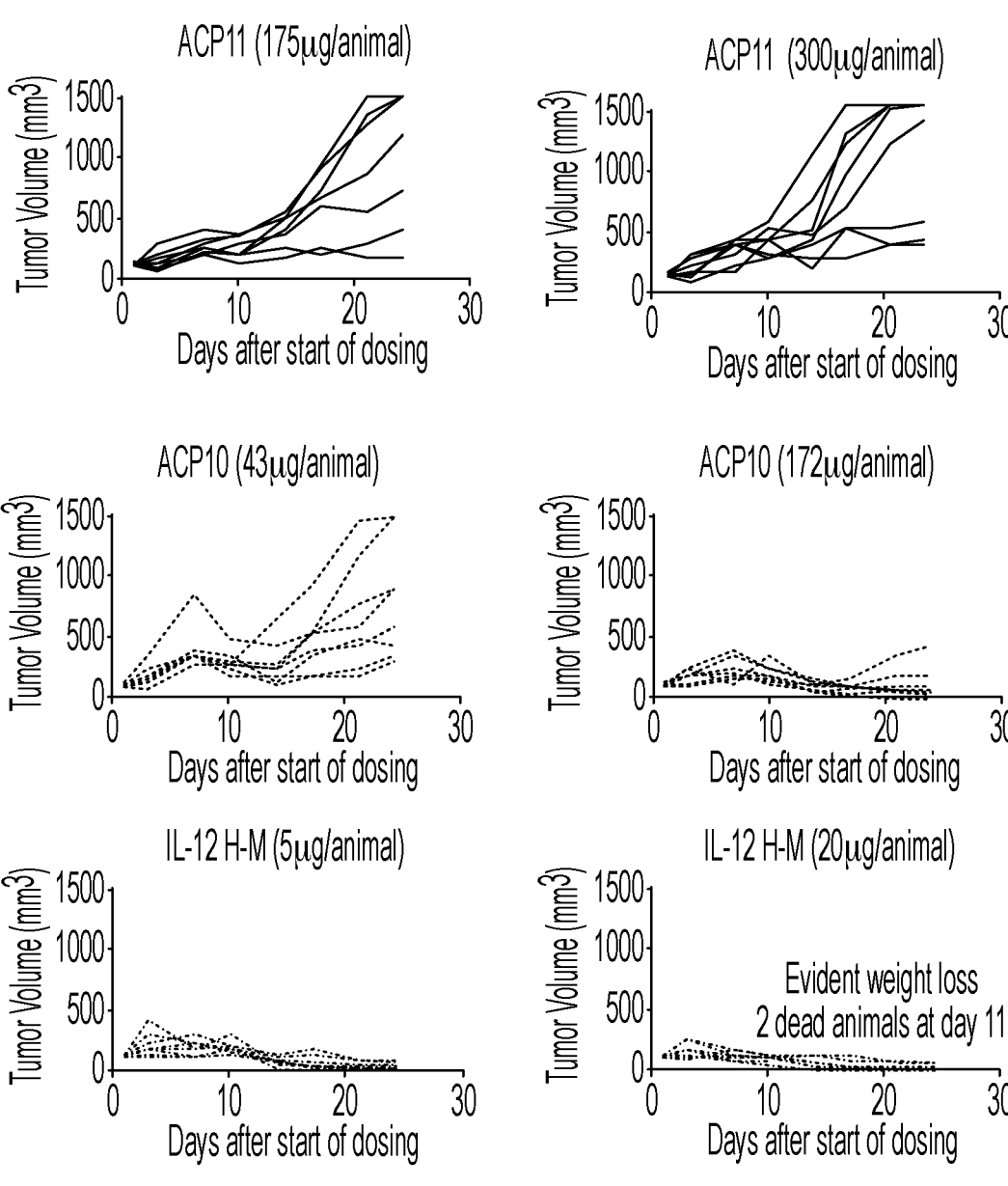
Figure 46A:
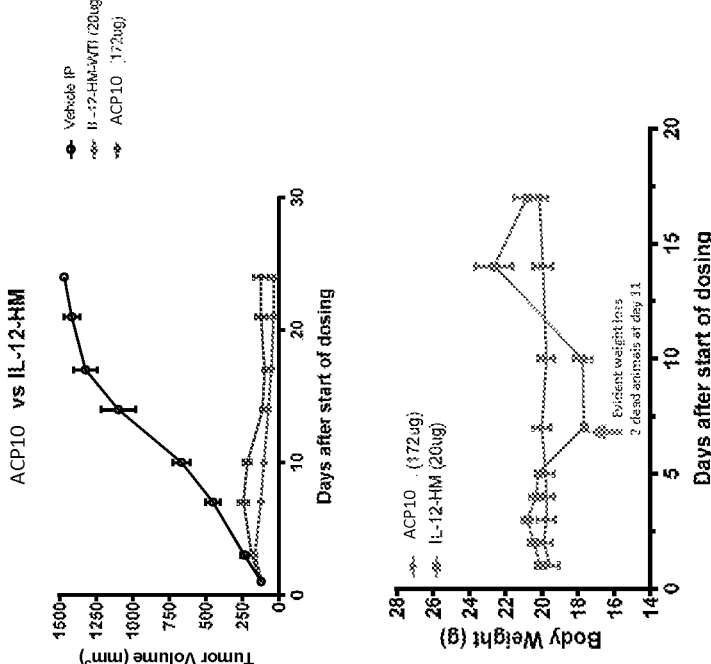
Figure 46B:
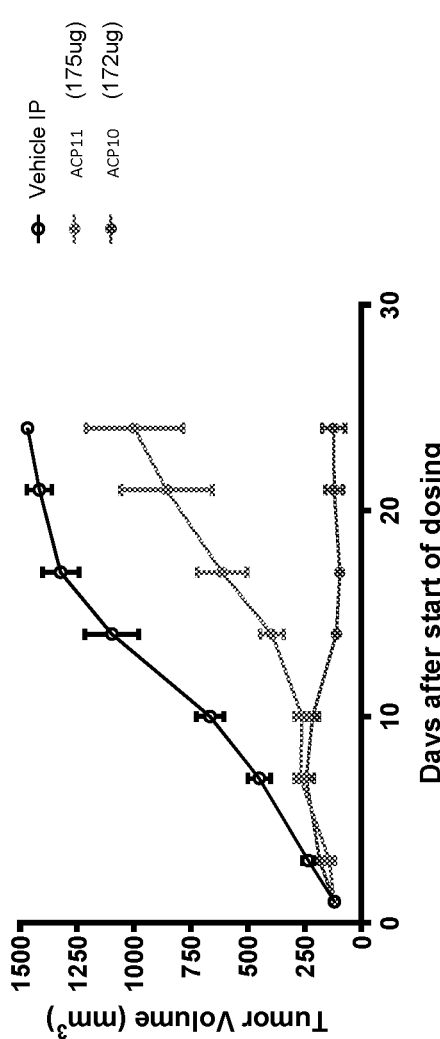
Figure 46C:
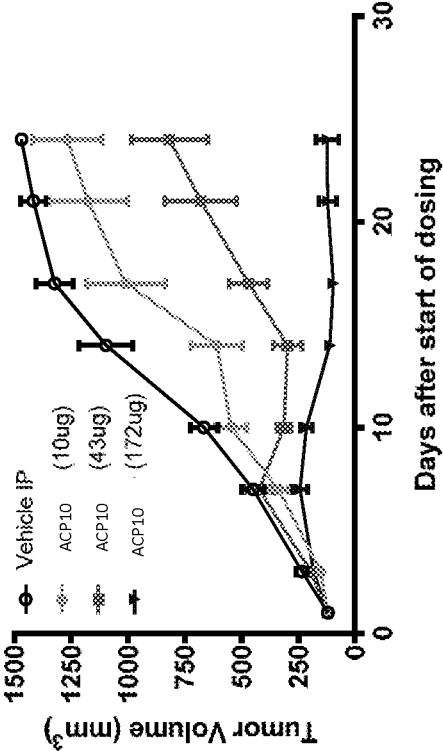
Figure 46D:
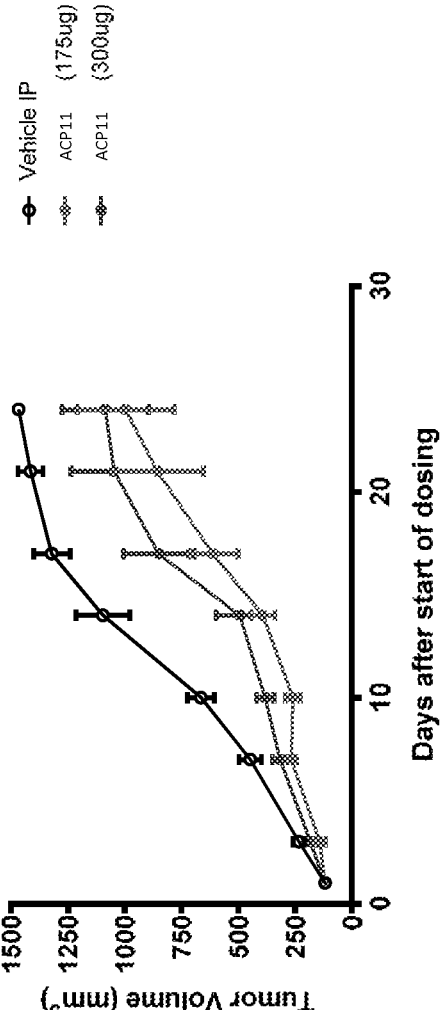
Figure 47B:
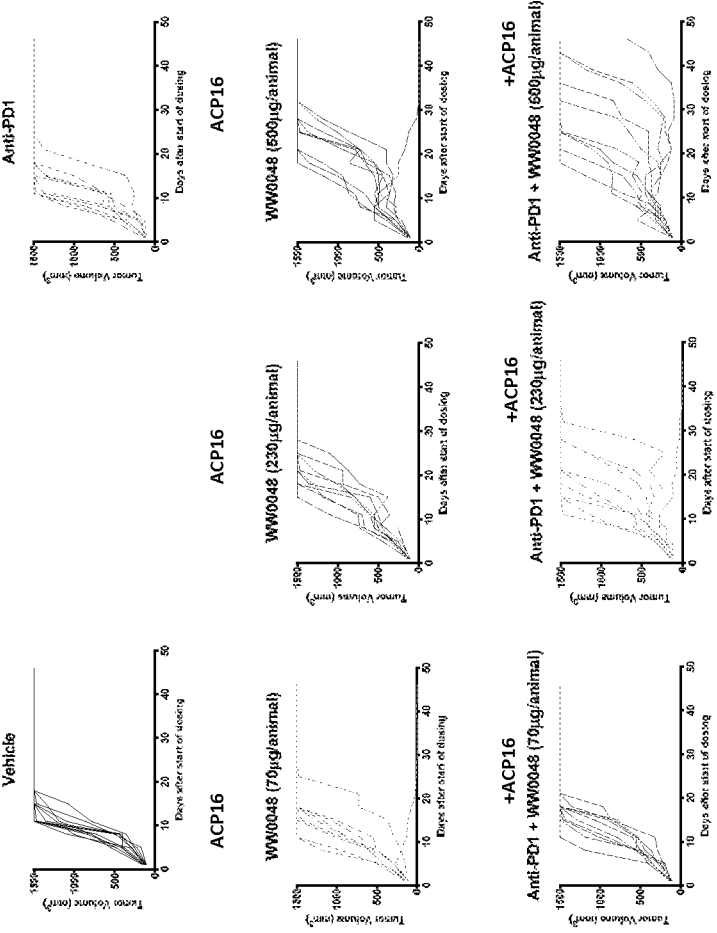
Figure 47C:
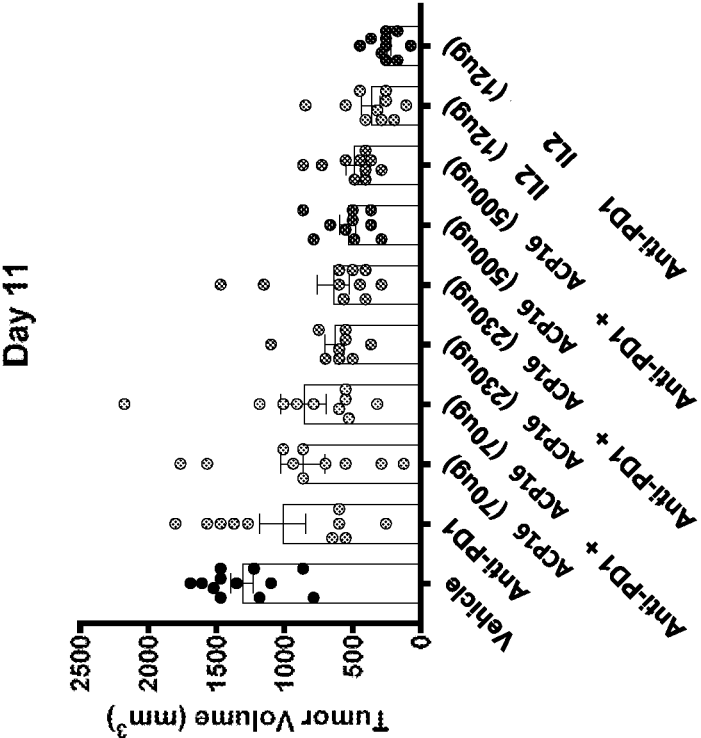
Figure 47D:
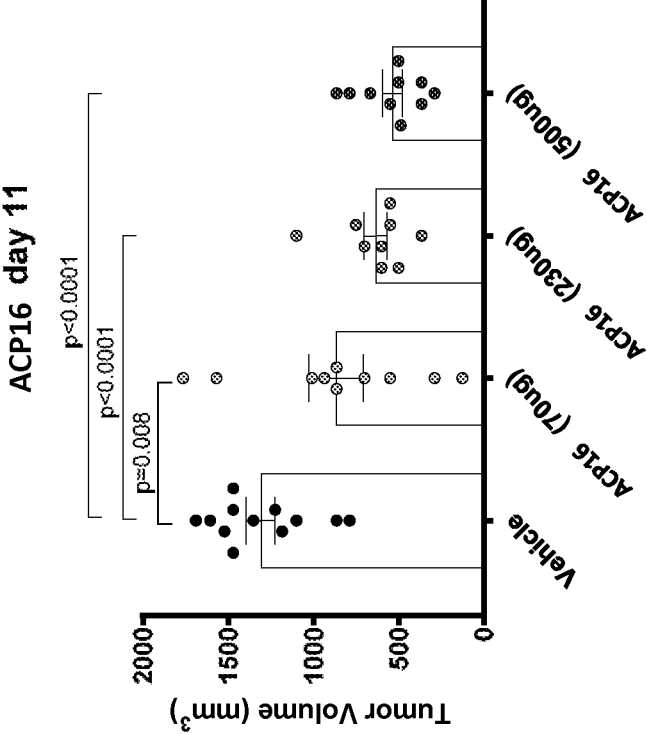
Figure 48A:
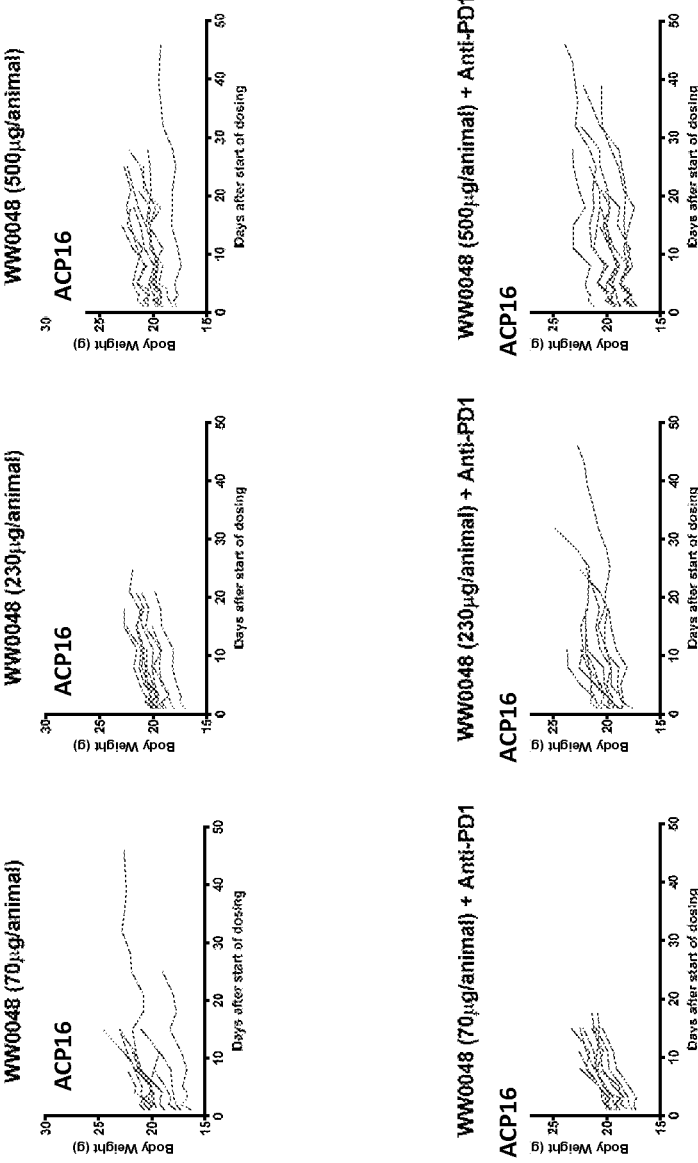
Figure 48B:
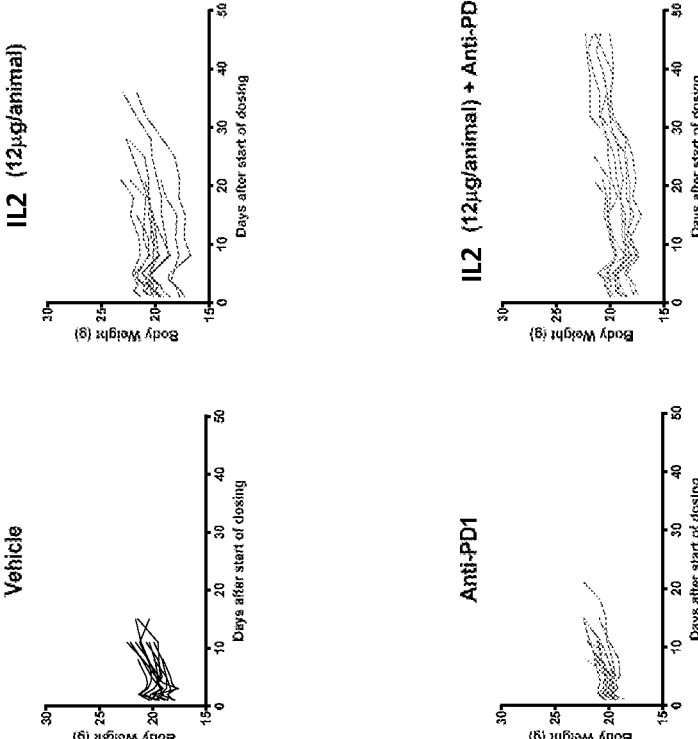
Figure 49A:
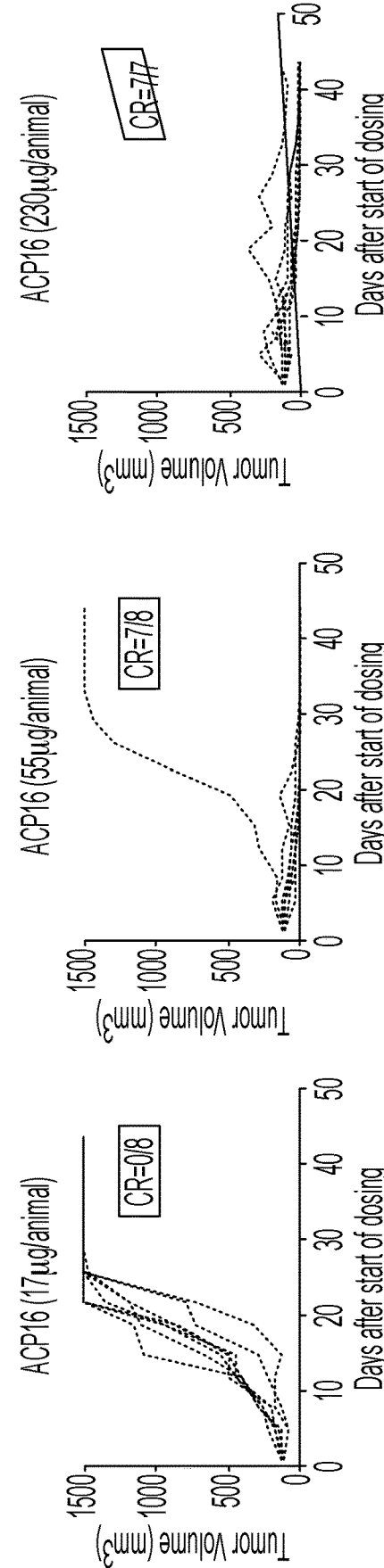
Figure 49B:
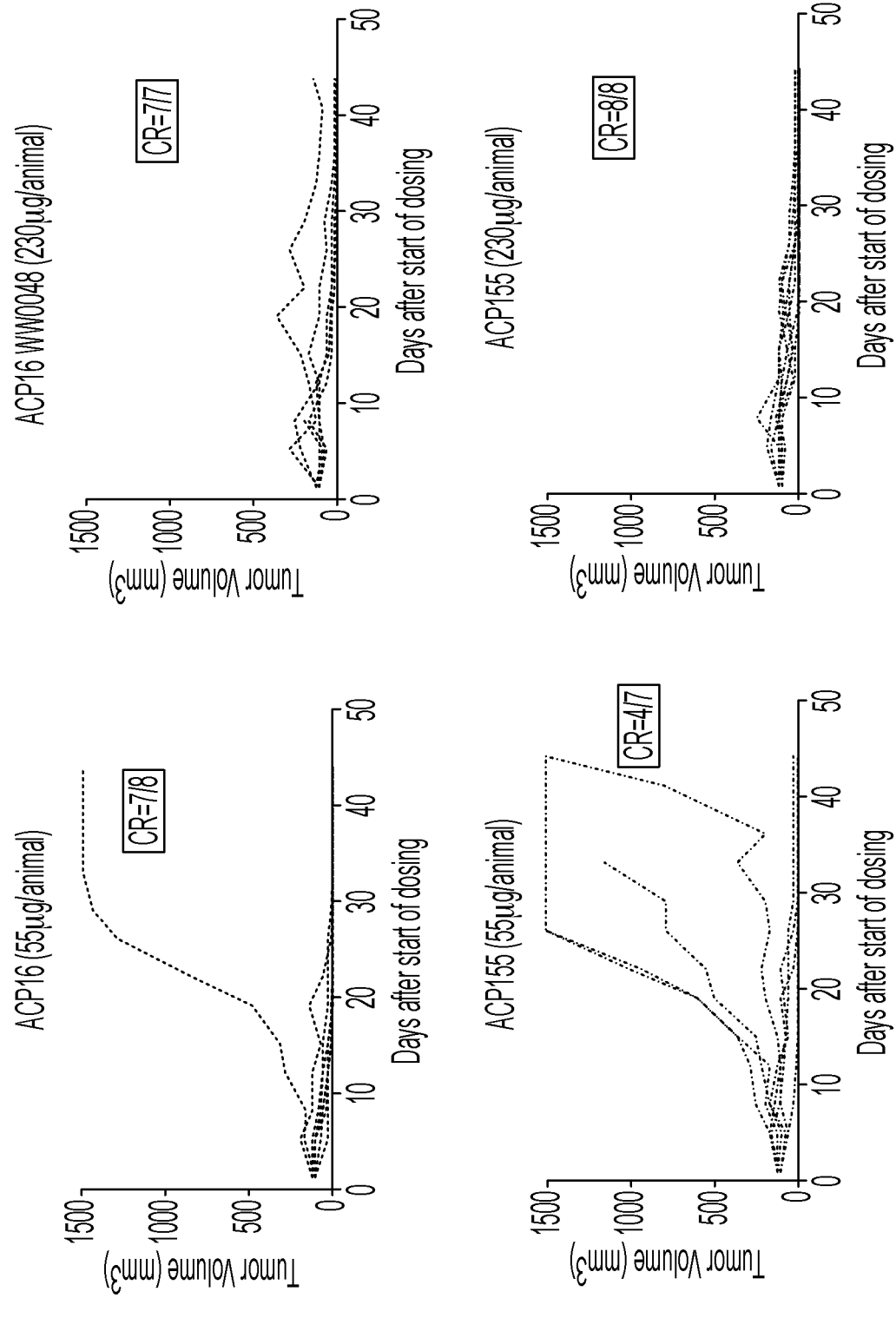
Figure 49C:
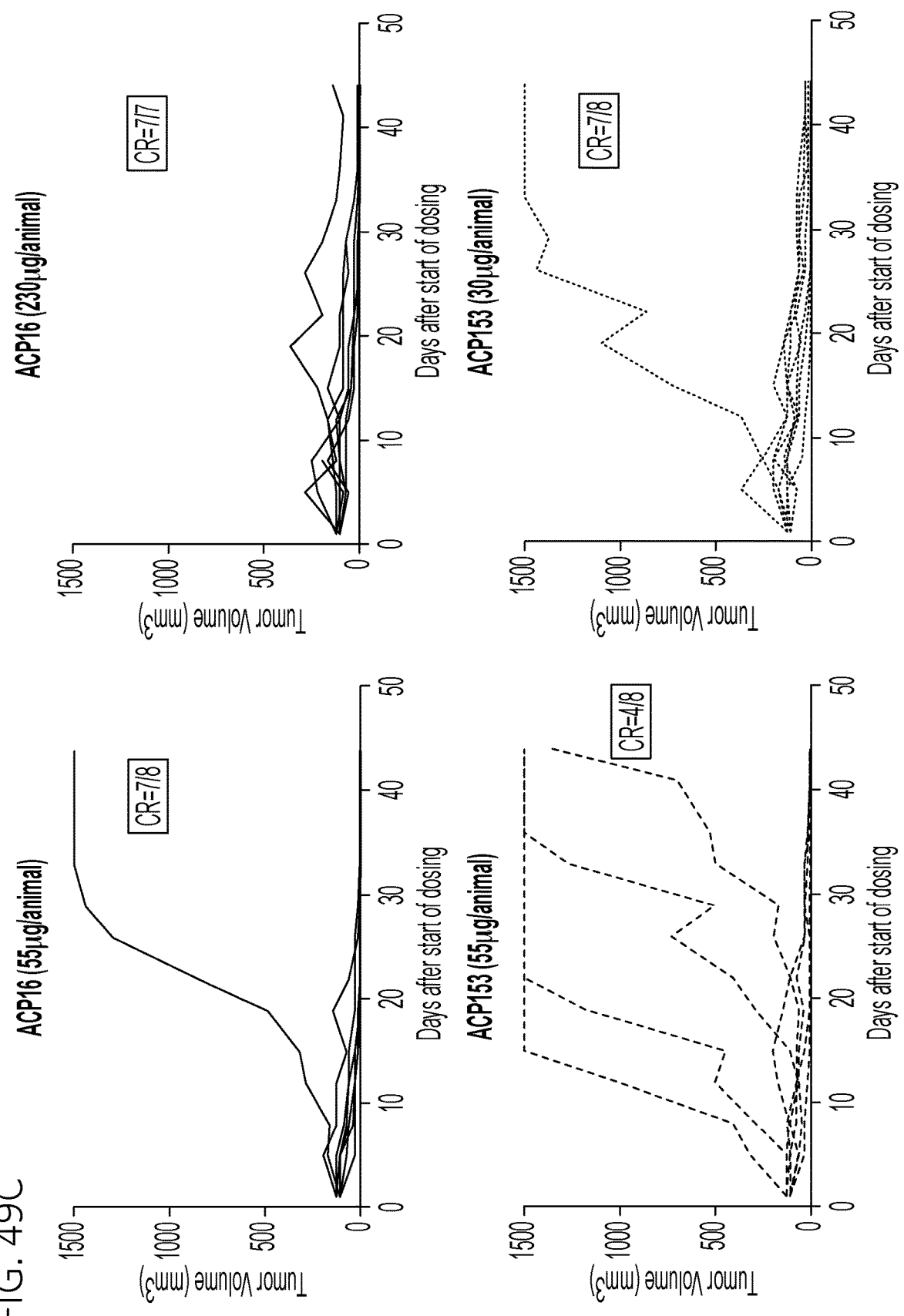
Figure 49D:
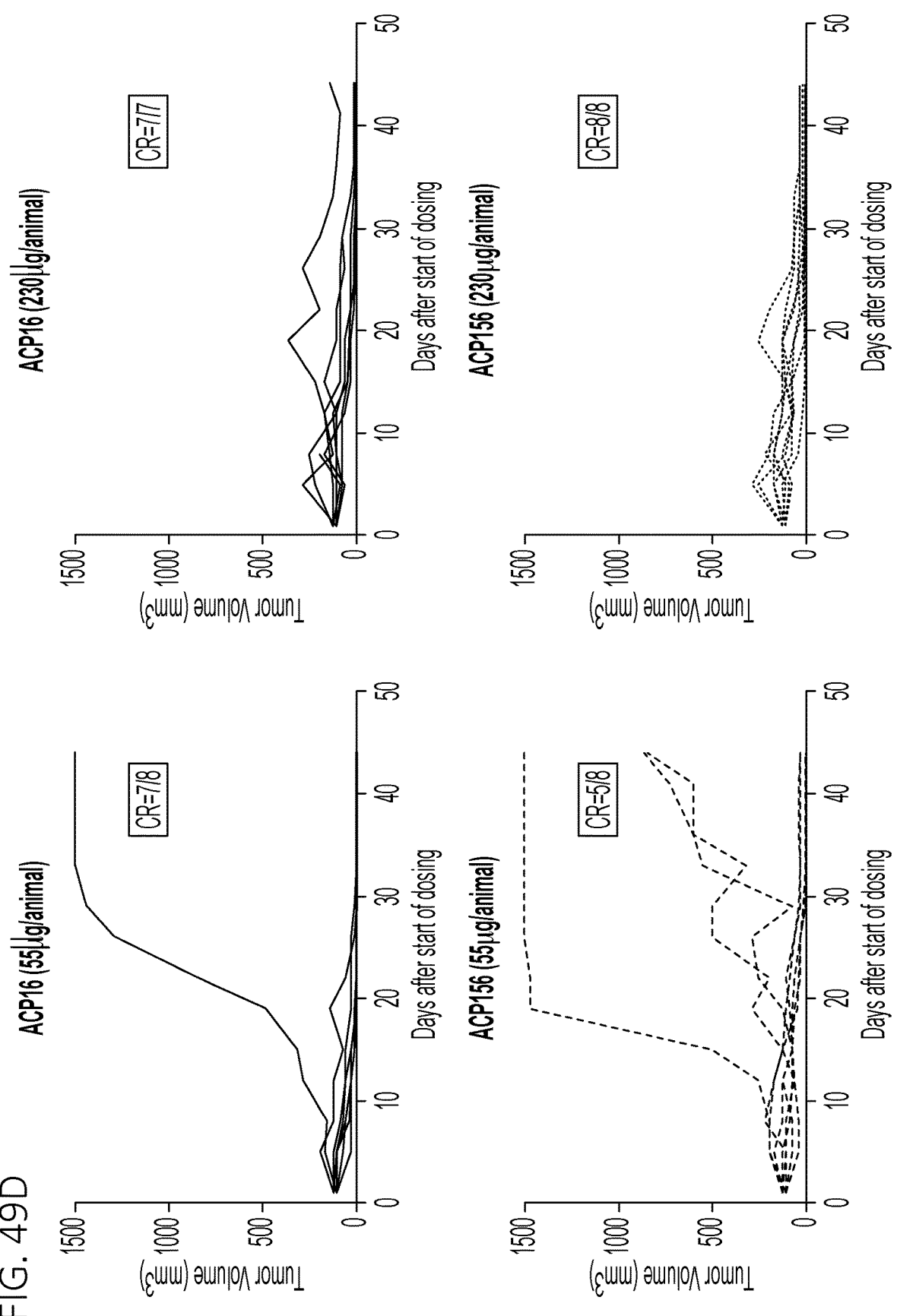
Figure 49E:
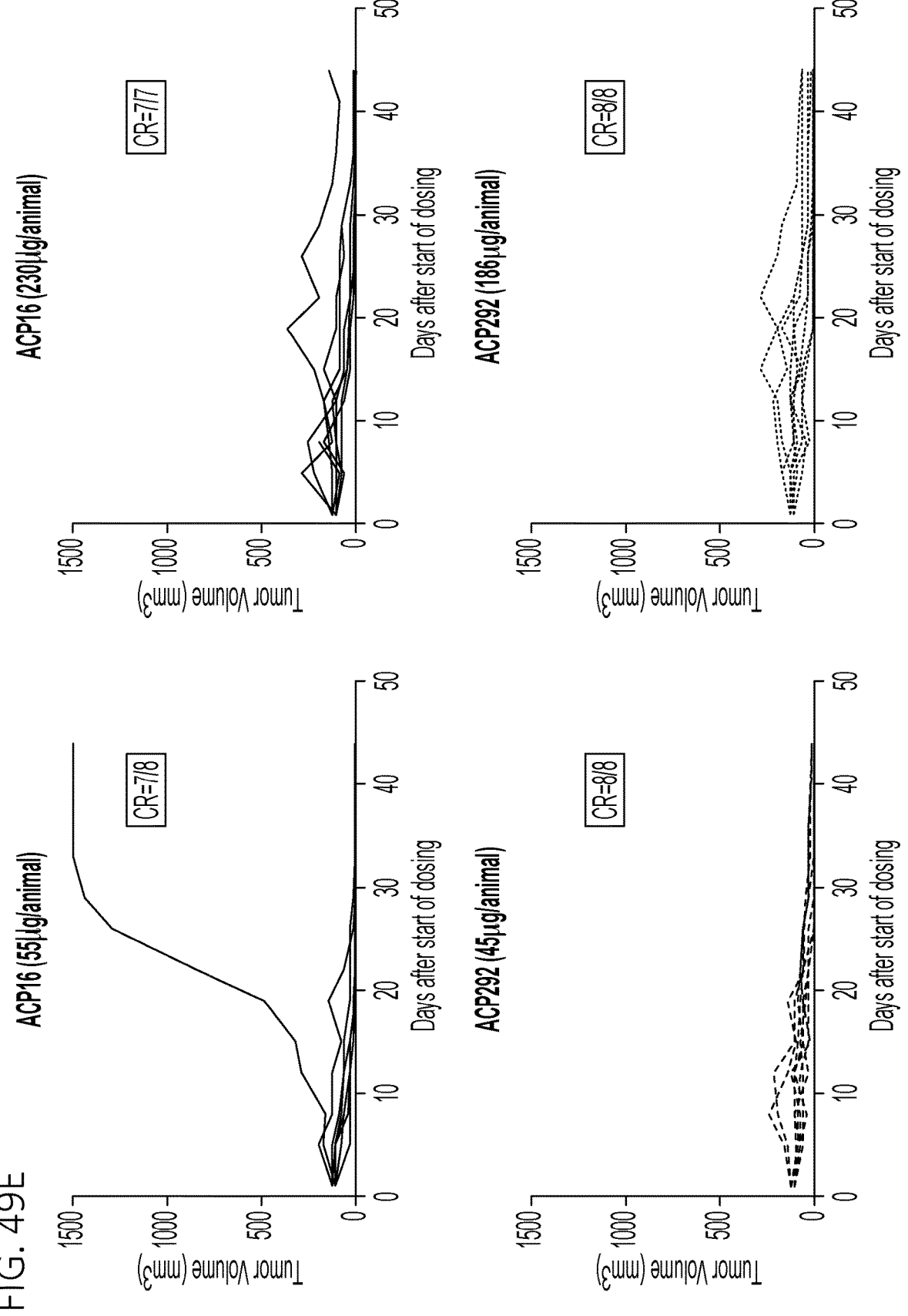
Figure 49F:
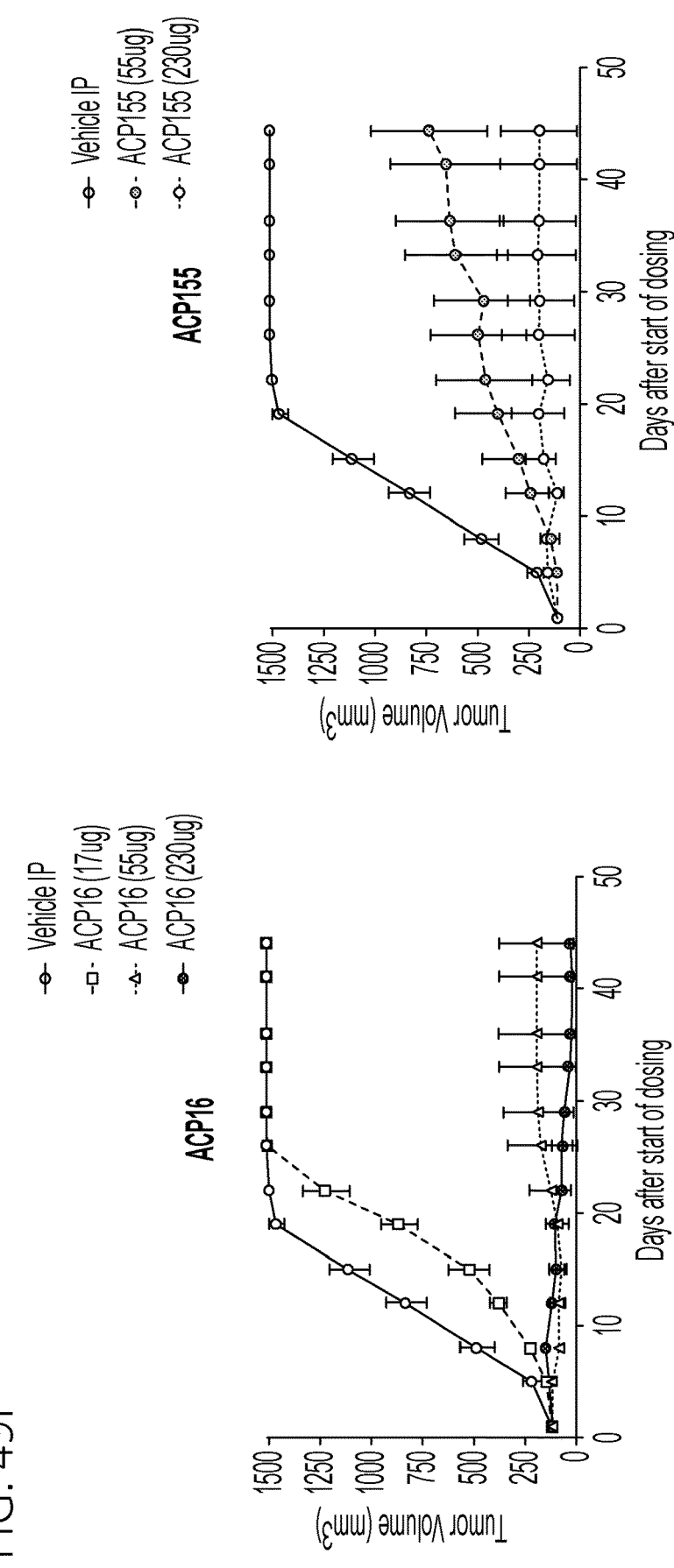
Figure 49F:
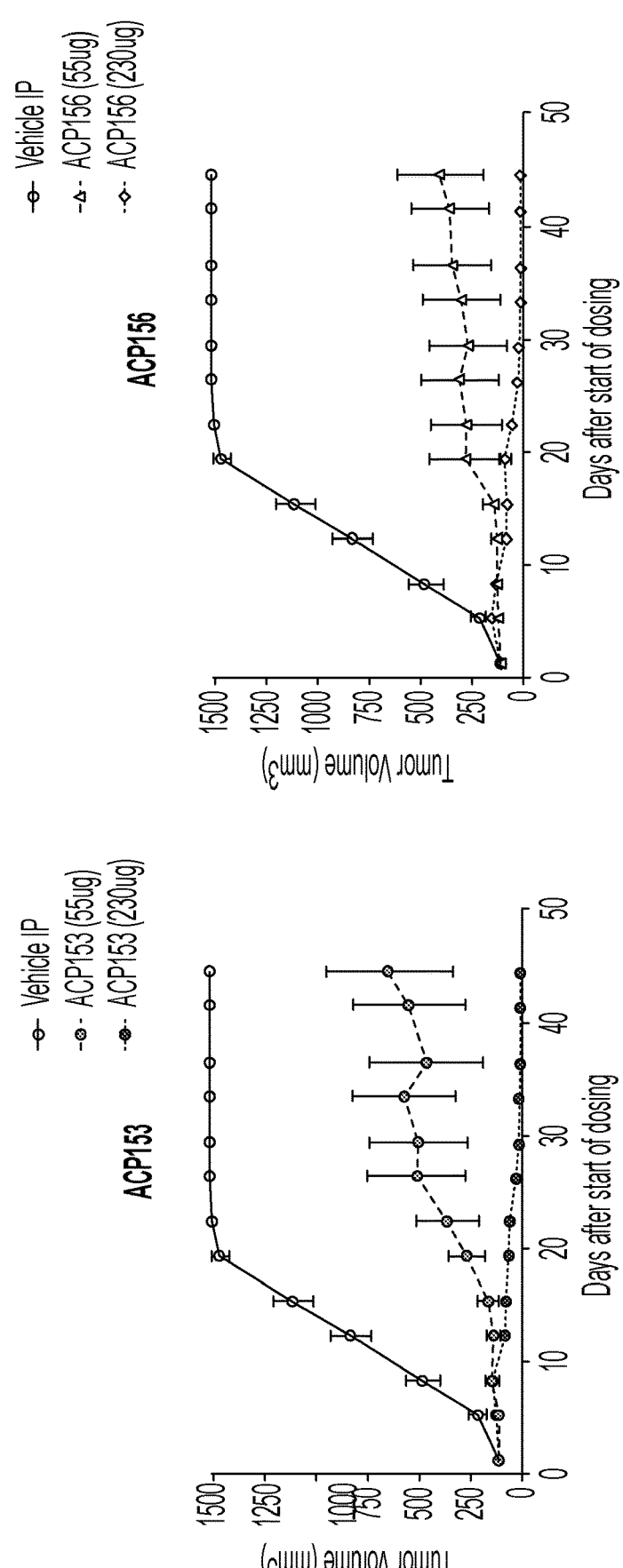
Figure 49G:
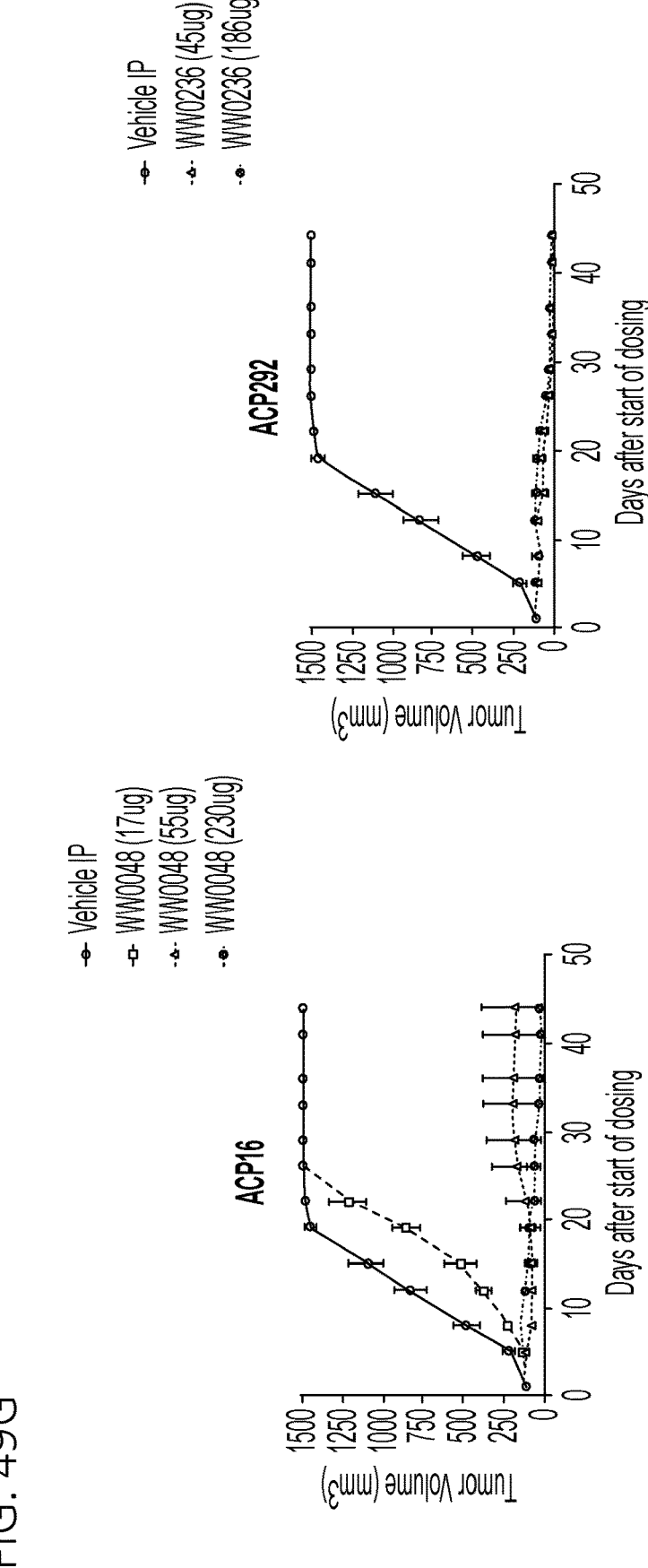
Figure 49H:
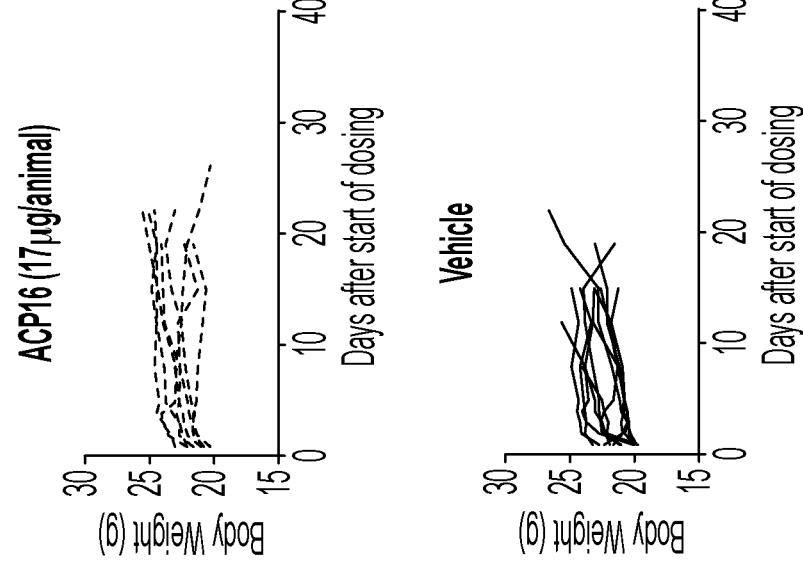
Figure 49H:
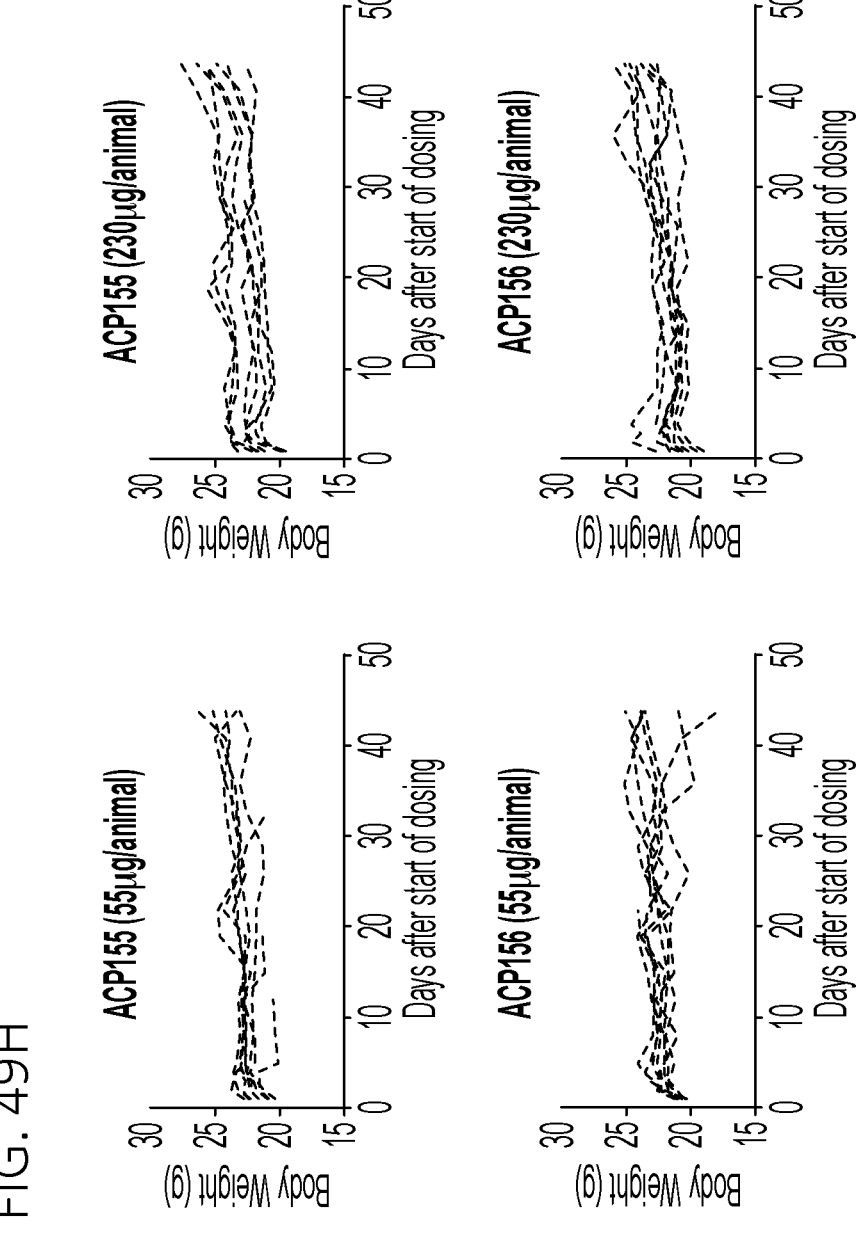
Figure 49I:
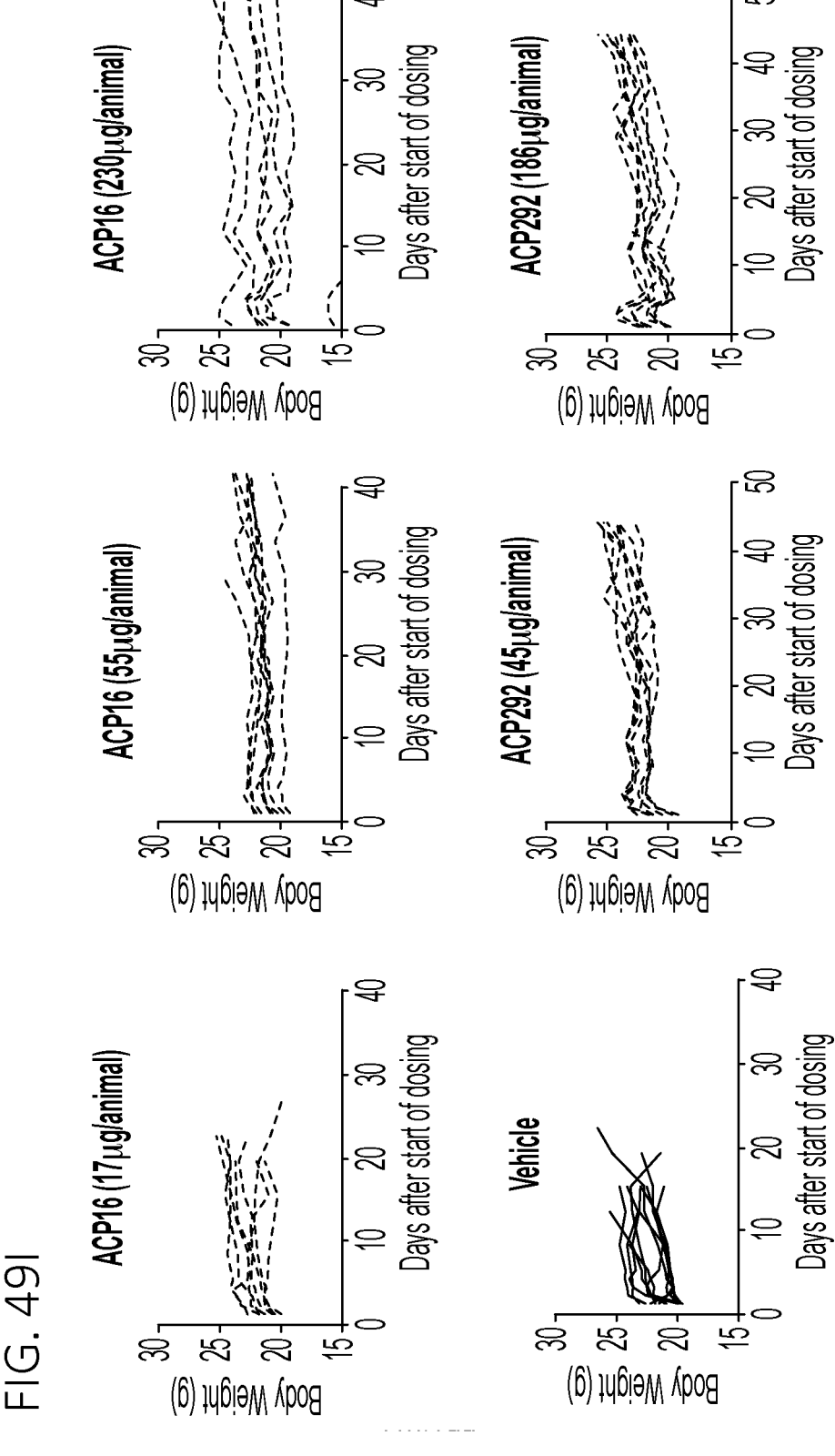

Results are shown in FIG. 35.

Example 27b: MC38 IL-2 POC. Treatment with ACP16, ACP124 and ACP132

Agents and Treatment:

| Gr. | N | Agent | Formulation dose | Route | Schedule |
|---|---|---|---|---|---|
| 1# | 12 | Vehicle | — | ip | biwk x 2 |
| 2 | 8 | ACP16 | 4.4 μg/animal | ip | biwk x 2 |
| 3 | 8 | ACP16 | 17 μg/animal | ip | biwk x 2 |
| 4 | 8 | ACP16 | 70 μg/animal | ip | biwk x 2 |
| 5 | 8 | ACP16 | 232 μg/animal | ip | biwk x 2 |
| 6 | 8 | ACP130 | 19 μg/animal | ip | biwk x 2 |
| 7 | 8 | ACP130 | 45 μg/animal | ip | biwk x 2 |
| 8 | 8 | ACP130 | 180 μg/animal | ip | biwk x 2 |

-continued

| Gr. | N | Agent | Formulation dose | Route | Schedule |
|---|---|---|---|---|---|
| 9 | 8 | ACP130 | 600 µg/animal | ip | biwk x 1 |
| 12 | 8 | ACP124 | 17 µg/animal | ip | biwk x 2 |
| 13 | 8 | ACP124 | 70 µg/animal | ip | biwk x 2 |
| 14 | 8 | ACP124 | 230 µg/animal | ip | biwk x 2 |
| 15 | 8 | ACP124 | 700 µg/animal | ip | biwk x 2 |
| 16 | 8 | IL-2-WTI | 12 µg/animal | ip | bid x 5 then 2-day pause then bid x 5 then 2-day pause |
| 17 | 8 | IL-2-WTI | 36 µg/animal | ip | bid x 5 then 2-day pause then bid x 5 then 2-day pause |
| # | −Control Group | | | | |

Procedures:

Mice were anaesthetized with isoflurane for implant of cells to reduce the ulcerations. 308 CR female C57BL/6 mice were set up with 5×10$^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm$^3$ and begin treatment. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm$^3$ or 45 days, whichever comes first. Responders were followed longer. When the endpoint was reached, the animals are to be euthanized.

Results are shown in FIGS. 31A-31C and FIGS. 32B-32C. Survival curves are shown in FIGS. 34A-34D.

Example 27c: MC38 IFNα and IL-12

Agents and Treatment:

| Gr. | N | Agent | Formulation dose | Route | Schedule |
|---|---|---|---|---|---|
| 1# | 12 | Vehicle | — | ip | biwk x 3 |
| 2 | 8 | ACP11 | 17.5 µg/animal | ip | biwk x 3 |
| 3 | 8 | ACP11 | 175 µg/animal | ip | biwk x 3 |
| 4 | 8 | ACP11 | 525 µg/animal | ip | biwk x 3 |
| 5 | 8 | ACP31 | 33 µg/animal | ip | biwk x 3 |
| 6 | 8 | ACP31 | 110 µg/animal | ip | biwk x 3 |
| 7 | 8 | ACP31 | 330 µg/animal | ip | biwk x 3 |
| 8 | 8 | ACP131 | 1 µg/animal | ip | bid x 5 then 2-day pause then bid x 5 then 2-day pause |
| 9 | 8 | ACP131 | 10 µg/animal | ip | bid x 5 then 2-day pause then bid x 5 then 2-day pause |
| 10 | 8 | ACP131 | 30 µg/animal | ip | bid x 5 then 2-day pause then bid x 5 then 2-day pause |
| 11 | 8 | mIFNa1-WTI | 1 µg/animal | ip | bid x 5 then 2-day pause then bid x 5 then 2-day pause |
| 12 | 8 | mIFNa1-WTI | 10 µg/animal | ip | bid x 5 then 2-day pause then bid x 5 then 2-day pause |
| 13 | 8 | IL-12-HM-WTI | 2 µg/animal | ip | bid x 5 then 2-day pause then bid x 5 then 2-day pause |
| 14 | 8 | IL-12-HM-WTI | 10 µg/animal | ip | bid x 5 then 2-day pause then bid x 5 then 2-day pause |
| 15 | 8 | ACP131 | 5 µg/animal | itu | bid x 5 then 2-day pause then bid x 5 then 2-day pause |
| # | −Control Group | | | | |

Procedures:

Mice were anaesthetized with isoflurane for implant of cells to reduce the ulcerations. 308 CR female C57BL/6 mice were set up with 5×10$^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm$^3$ and begin treatment. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm³ or 45 days, whichever comes first. Responders were followed longer. When the endpoint was reached, the animals are to be euthanized. Results are show in in FIGS. 29A-29B, and 30A-30F.

Example 27d: Treatment with ACP16, ACP132, and ACP21

Agents and Treatment:

| Gr. | N | Agent | Formulation dose | Route | Schedule |
|---|---|---|---|---|---|
| 1# | 10 | Vehicle | — | ip | biwk x 2 |
| 2 | 7 | ACP16 | 17 µg/animal | ip | biwk x 2 |
| 3 | 7 | ACP16 | 55 µg/animal | ip | biwk x 2 |
| 4 | 7 | ACP16 | 70 µg/animal | ip | biwk x 2 |
| 5 | 7 | ACP16 | 230 µg/animal | ip | biwk x 2 |
| 6 | 7 | ACP132 | 9 µg/animal | ip | biwk x 2 |
| 7 | 7 | ACP132 | 28 µg/animal | ip | biwk x 1 |
| 8 | 7 | ACP132 | 36 µg/animal | ip | biwk x 1 |
| 9 | 7 | ACP132 | 119 µg/animal | ip | biwk x 1 |
| 10 | 7 | ACP21 | 13 µg/animal | ip | biwk x 2 |
| 11 | 7 | ACP21 | 42 µg/animal | ip | biwk x 2 |
| 12 | 7 | ACP21 | 54 µg/animal | ip | biwk x 2 |
| 13 | 7 | ACP21 | 177 µg/animal | ip | biwk x 2 |

72 observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm³ or 45 days, whichever comes first. Responders were followed longer. When the endpoint was reached, the animals are to be euthanized. Results are shown in FIG. 35.

Example 27e: MC38 Rechallenge

Cured mice (ACP16-treated) from Example 27b were rechallenged with tumor implantation to determine whether anti-tumor memory had been established from the initial treatments.

Agents and Treatment:

| Gr. | N | Agent | Formulation dose | Route | Schedule |
|---|---|---|---|---|---|
| 1# | 33 | No Treatment | — | — | — |
| 2 | 7 | ACP16 | 70 µg/animal | ip | (ACP16 biwkx2) |
| 3 | 8 | ACP16 | 232 µg/animal | ip | (ACP16 biwkx2) |
| 5 | 5 | IL-2-WTI | 12 µg/animal | ip | (IL-2-WTI bid x 5 then 2-day pause then bid x 5 then 2-day pause) |
| 6 | 7 | IL-2-WTI | 36 µg/animal | ip | (IL-2-WTI bid x 5 then 2-day pause then bid x 5 then 2-day pause) |
| # | –Control Group | | | | |

Figure 33:
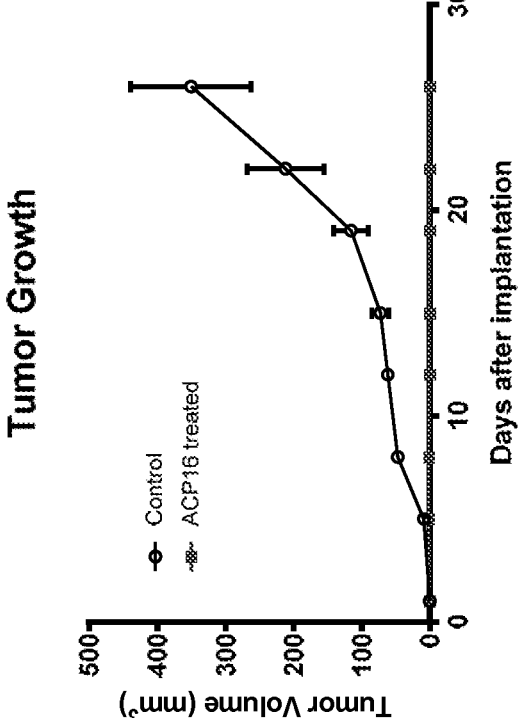
FIG. 33 is a graph showing tumor volume over time in a mouse xenograft model showing tumor growth in control mice (open circles) and AP16-treated mice (squares).
Figure 34A:
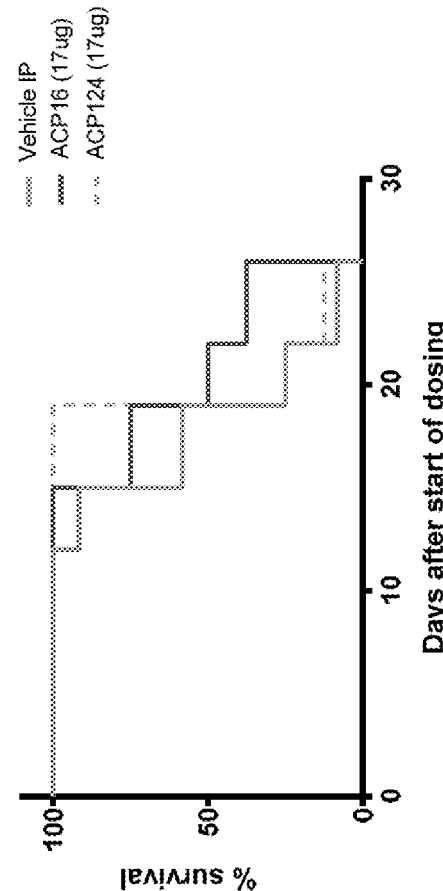
FIGS. 34A-34D are a series of survival plots showing survival of mice over time after treatment with cleavable fusion proteins.
Figure 34B:
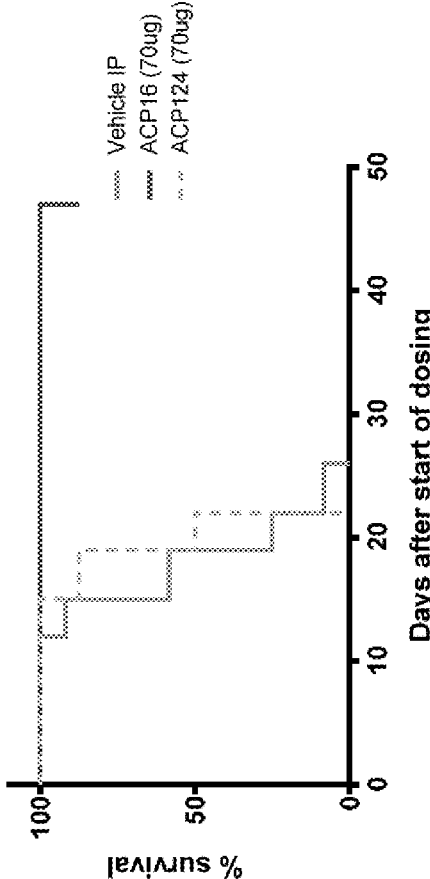
Figure 34C:
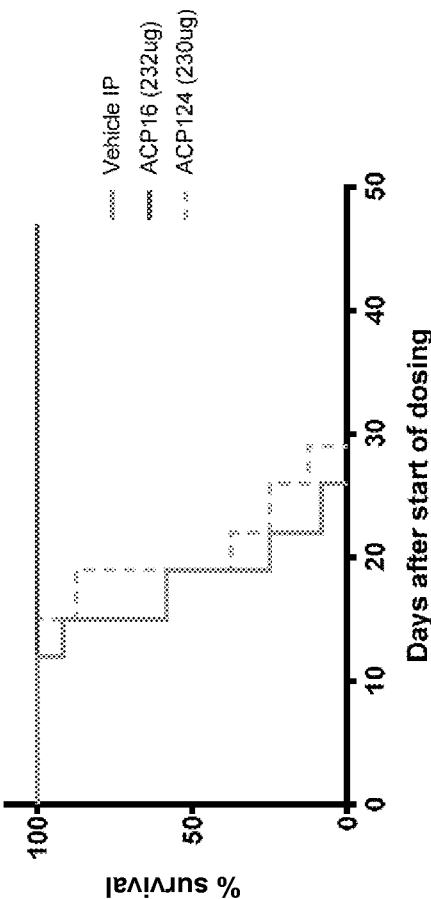
Figure 34D:
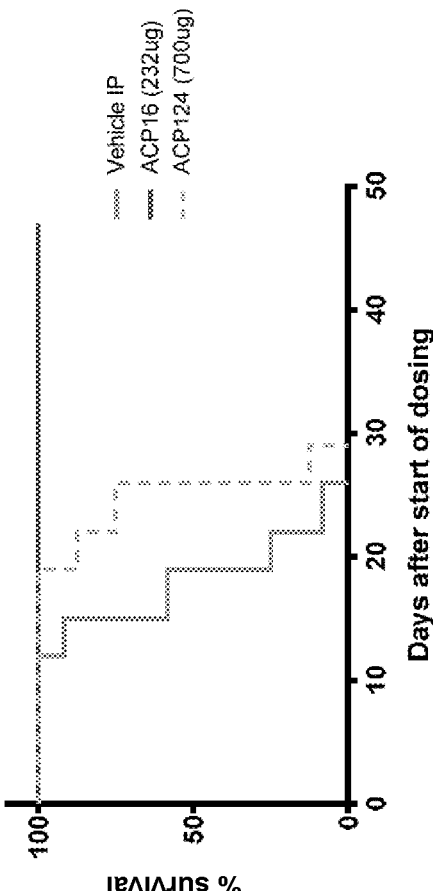

Procedures:

Mice were anaesthetized with isoflurane for implant of cells to reduce the ulcerations. CR female C57BL/6 mice were set up with 5×10⁵ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm³ and begin treatment. ACP16 was dosed at 17, 55, 70, or 230 µg/animal; ACP132 was dosed at 9, 28, 36, or 119 ug/animal; ACP21 was dosed at 13, 42, 54, or 177 µg/animal. Body weights were taken at initiation and then biweekly to the end. Caliper measurements were taken biweekly to the end. Any adverse reactions were to be reported immediately. Any individual animal with a single Procedures:

Mice were anaesthetized with isoflurane for implant of cells to reduce the ulcerations. This portion of the study began on the day of implant (Day 1). Group 1 consisted of 33 CR female C57BL/6 mice set up with 5×10⁵ MC38 tumor cells in 0% Matrigel subcutaneously in the flank. Groups 2-6 consisted of 33 CR female C57BL/6 mice set up with 5×10⁵ MC38 tumor cells in 0% Matrigel sc in the left flank. The tumors from the previous MC38 experiment (Example 27b) were implanted in the right flank of each animal. Cell Injection Volume was 0.1 mL/mouse. Age of control mice at initiation was 14 to 17 weeks. These mice were age matched to mice from the previous MC38 experiment (Example 27b). No dosing of active agent occurred during rechallenge. Body Weights were take biweekly until end, as were caliper measurements. Any adverse reactions or death were reported immediately. Any individual animal with a single observation of >than 30% body weight loss or three consecutive measurements of >25% body weight loss was euthanized. Endpoint was tumor growth delay (TGD). Animals were monitored individually. The endpoint of the experiment was a tumor volume of 1000 mm$^3$ or 45 days, whichever comes first. Responders were followed longer when possible. When the endpoint is reached, the animals were euthanized. Results are shown in FIG. 33.

Example 27f: Treatment with ACP10, ACP11

Agents and Treatment:

| Gr. | N | Agent | Formulation dose | Route | Schedule |
|---|---|---|---|---|---|
| 1# | 12 | Vehicle | — | ip | biwk x 2 |
| 2 | 8 | ACP11 | 175 µg/animal | ip | biwk x 2 |
| 3 | 8 | ACP11 | 300 µg/animal | ip | biwk x 2 |
| 4 | 8 | ACP10 | 5 µg/animal | ip | biwk x 2 |
| 5 | 8 | ACP10 | 10 µg/animal | ip | biwk x 2 |
| 6 | 8 | ACP10 | 43 µg/animal | ip | biwk x 2 |
| 7 | 8 | ACP10 | 43 µg/animal | ip | qwk x 2 |
| 8 | 8 | ACP10 | 172 µg/animal | ip | biwk x 2 |
| 9 | 8 | IL-I2-HM-WTI | 5 µg/animal | ip | bid for 5 days first day 1 dose then 2-day pause then bid for 5 days first day 1 dose then 2-day pause |
| 10 | 8 | IL-12-HM-WTI | 20 µg/animal | ip | bid for 5 days first day 1 dose then 2-day pause then bid for 5 days first day 1 dose then 2-day pause |

Procedures:

Mice were anaesthetized with isoflurane for implant of cells to reduce the ulcerations. CR female C57BL/6 mice were set up with 5×10$^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm$^3$ and begin treatment. ACP11 was dosed at 175 or 300 jig/animal; ACP10 was dosed at 5, 10, 43, or 172 ug/animal; IL-12-HM-WTI was dosed at 5 or 20 ug/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm$^3$ or 45 days, whichever comes first. Responders were followed longer. When the endpoint was reached, the animals are to be euthanized. Results are shown in FIG. 45 and FIGS. 46A-46D.

Example 27g: Treatment with ACP16, APC153, ACP155, ACP156 and ACP292

| Gr. | N | Agent | Formulation dose | Route | Schedule |
|---|---|---|---|---|---|
| 1# | 12 | Vehicle | — | ip | biwk x 2 |
| 2 | 8 | ACP16 | 17 µg/animal | ip | biwk x 2 |
| 3 | 8 | ACP16 | 55 µg/animal | ip | biwk x 2 |
| 4 | 8 | ACP16 | 230 µg/animal | ip | biwk x 2 |
| 5 | 8 | ACP155 | 55 µg/animal | ip | biwk x 2 |
| 6 | 8 | ACP155 | 230 µg/animal | ip | biwk x 2 |

-continued

Agents and Treatment:

| Gr. | N | Agent | Formulation dose | Route | Schedule |
|---|---|---|---|---|---|
| 7 | 8 | ACP153 | 55 µg/animal | ip | biwk x 2 |
| 8 | 8 | ACP153 | 230 µg/animal | ip | biwk x 2 |
| 9 | 8 | ACP156 | 55 µg/animal | ip | biwk x 2 |
| 10 | 8 | ACP156 | 230 µg/animal | ip | biwk x 2 |
| 11 | 8 | ACP292 | 45 µg/animal | ip | biwk x 2 |
| 12 | 8 | ACP292 | 186 µg/animal | ip | biwk x 2 |

Procedures:

Mice were anaesthetized with isoflurane for implant of cells to reduce the ulcerations. CR female C57BL/6 mice were set up with 5×10$^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm$^3$ and begin treatment. ACP16 was dosed at 17, 55 or 230 µg/animal; ACP153, ACP155 and ACP156 were dosed at 55 or 230 µg/animal; ACP292 was dosed at 45 or 186 µg/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm$^3$ or 45 days, whichever comes first. Responders were followed longer. When the endpoint was reached, the animals are to be euthanized. Results are shown in FIGS. 49A-49I.

Example 27h: Treatment with ACP16, APC302 and ACP314

Agents and Treatment:

| Gr. | N | Agent | Formulation dose | Route | Schedule |
|---|---|---|---|---|---|
| 1[#] | 12 | Vehicle | — | ip | biwk x 2 |
| 2 | 9 | ACP16 | 55 µg/animal | ip | biwk x 2 |
| 3 | 9 | ACP16 | 230 µg/animal | ip | biwk x 2 |
| 4 | 9 | ACP302 | 33 µg/animal | ip | biwk x 2 |
| 5 | 9 | ACP302 | 106 µg/animal | ip | biwk x 2 |
| 6 | 9 | ACP302 | 442 µg/animal | ip | biwk x 2 |
| 7 | 9 | ACP302 | 1,344 µg/animal | ip | biwk x 2 |
| 8 | 9 | ACP314 | 21 µg/animal | ip | biwk x 2 |
| 9 | 9 | ACP314 | 68 µg/animal | ip | biwk x 2 |
| 10 | 9 | ACP314 | 283 µg/animal | ip | biwk x 2 |
| 11 | 9 | ACP314 | 861 µg/animal | ip | biwk x 2 |

Figure 50A:
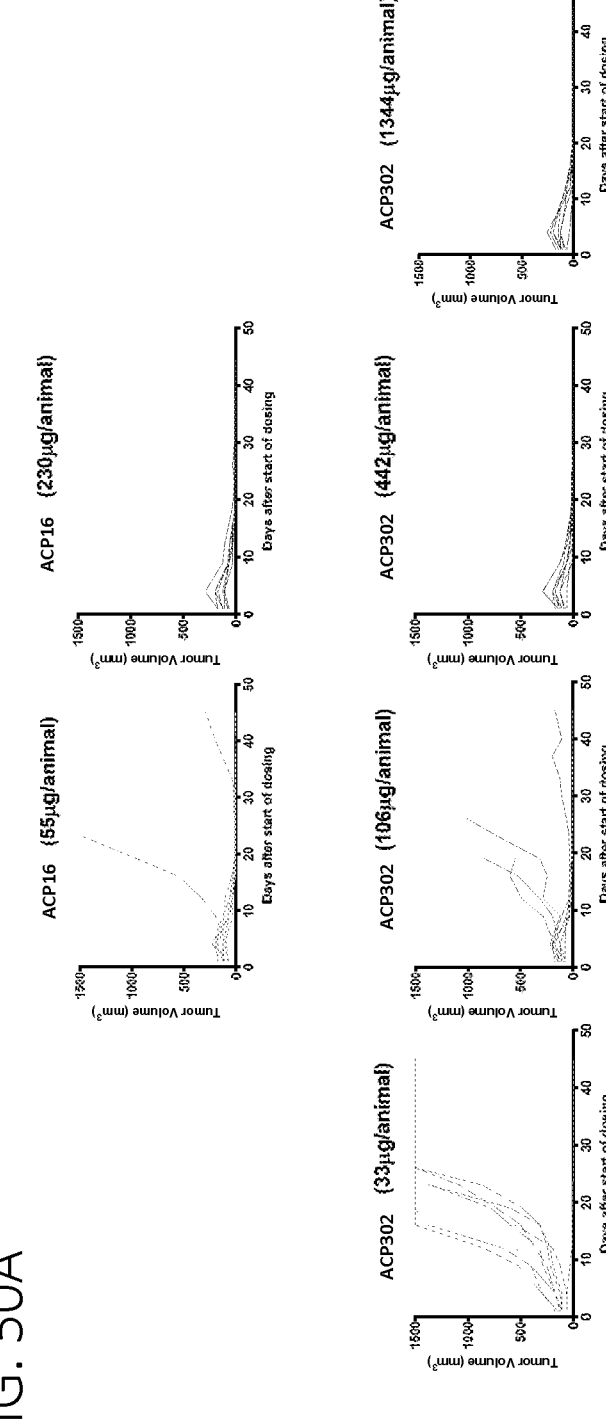
Figure 50B:
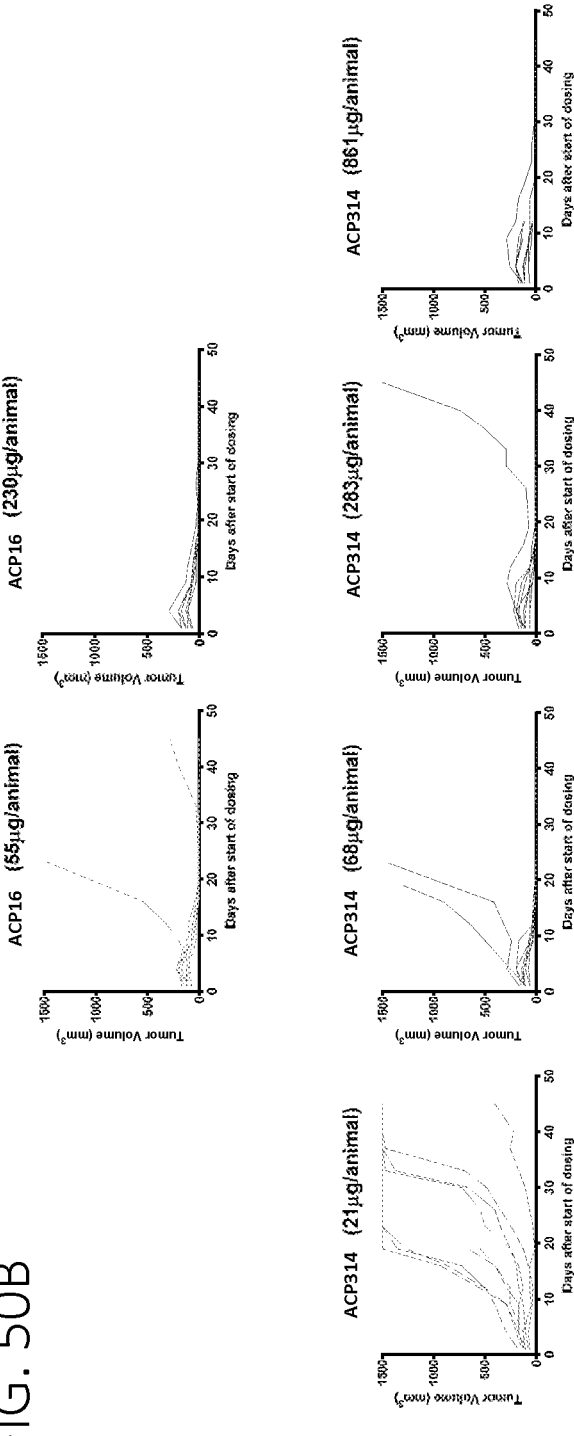

Procedures:

Mice were anaesthetized with isoflurane for implant of cells to reduce the ulcerations. CR female C57BL/6 mice were set up with 5×10$^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm$^3$ and begin treatment. ACP16 was dosed at 55 or 230 µg/animal; ACP302 was dosed at 33, 106, 442 or 1344 ug/animal; ACP314 was dosed at 21, 68, 283 or 861 µg/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm$^3$ or 45 days, whichever comes first. Responders were followed longer. When the endpoint was reached, the animals are to be euthanized. Results are shown in FIG. 50A and FIG. 50B.

Example 27i: Treatment with ACP339

Agents and Treatment:

| Gr. | N | Agent | Formulation dose | Route | Schedule |
|---|---|---|---|---|---|
| 1[#] | 12 | Vehicle | — | ip | biwk x 2 |
| 2 | 9 | ACP339 | 55 µg/animal | ip | biwk x 2 |
| 3 | 9 | ACP339 | 230 µg/animal | ip | biwk x 2 |
| 4 | 9 | ACP339 | 700 µg/animal | ip | biwk x 2 |

Figure 51A:
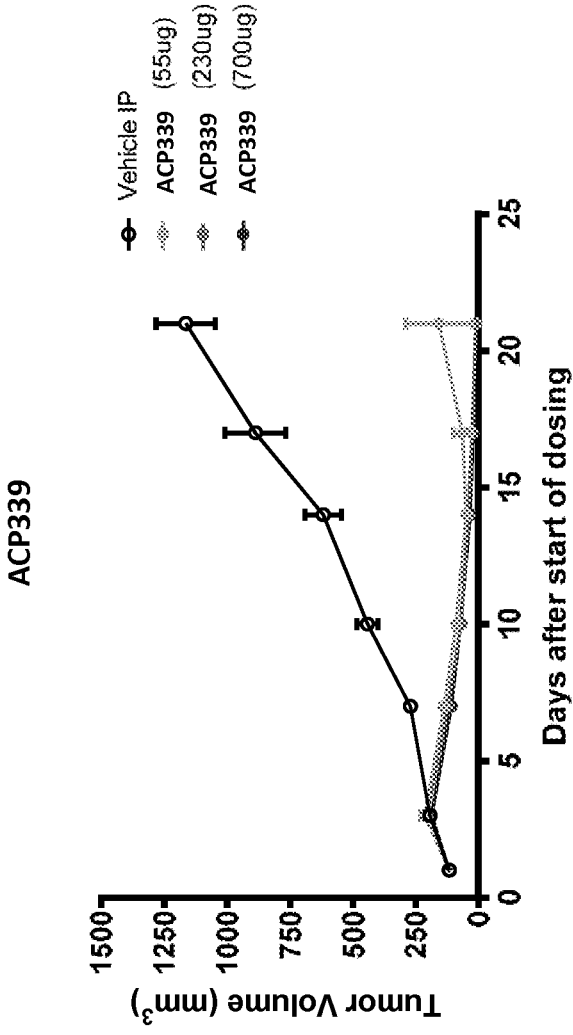
Figure 51B:
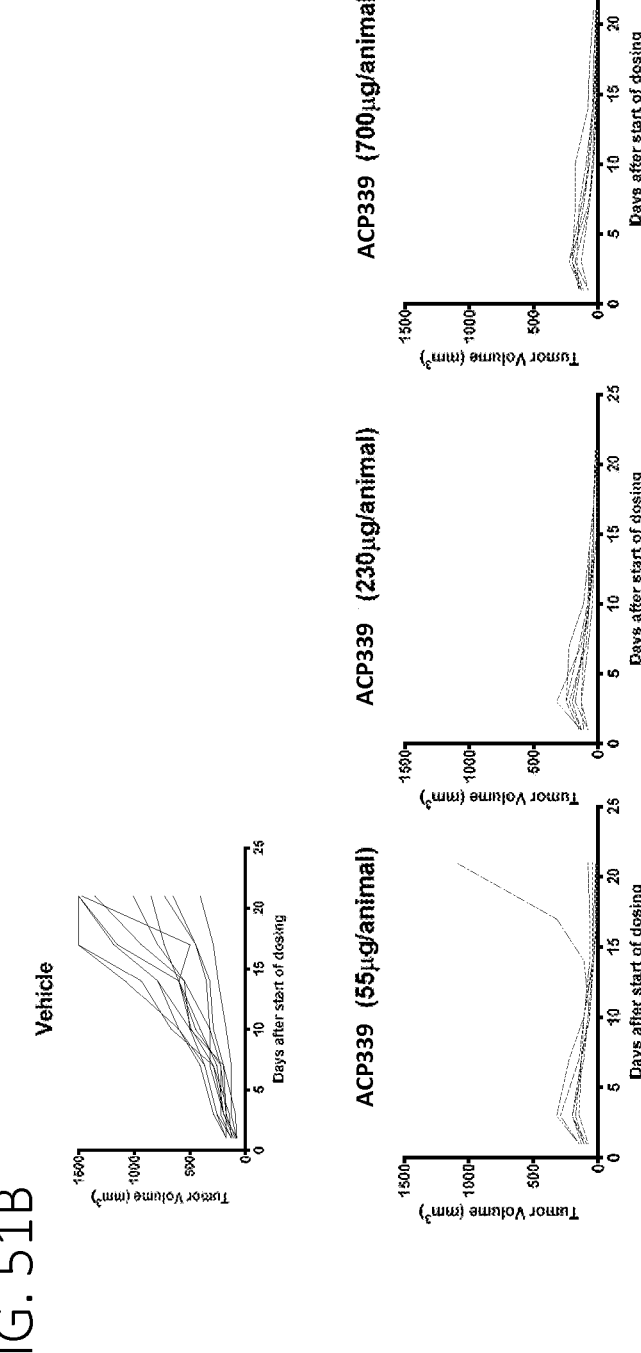
Figure 51C:
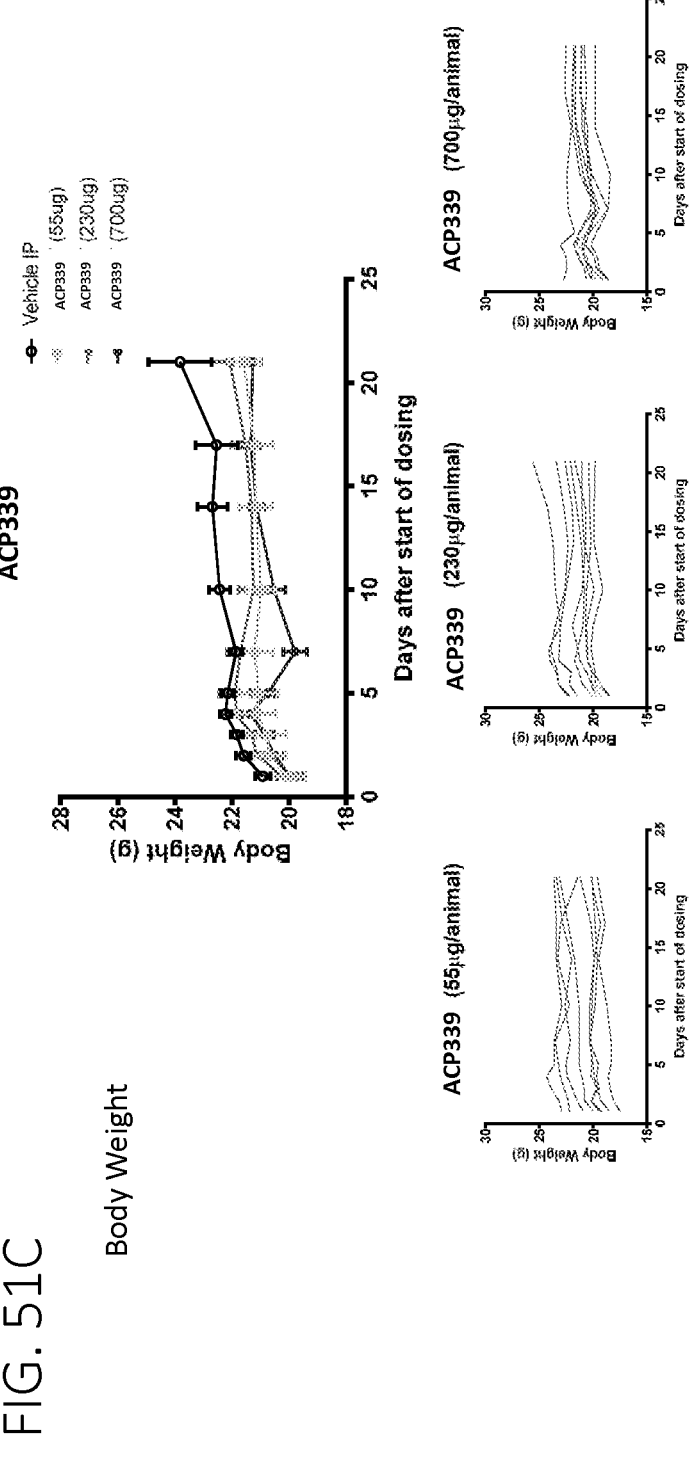
Figure 52D:
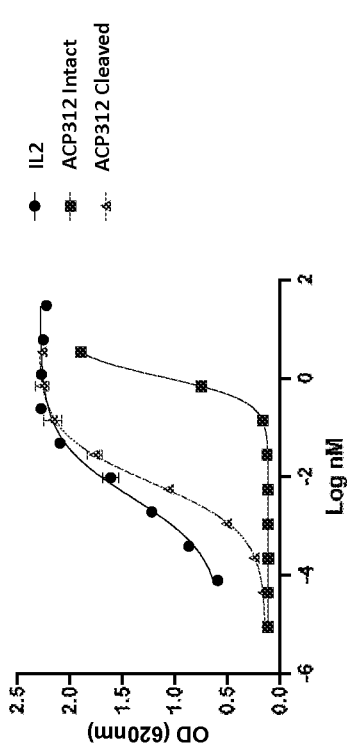
FIGS. 52A-52N, 53A, 53B depict the activity of cytokine fusion proteins constructs.
Figure 52F:
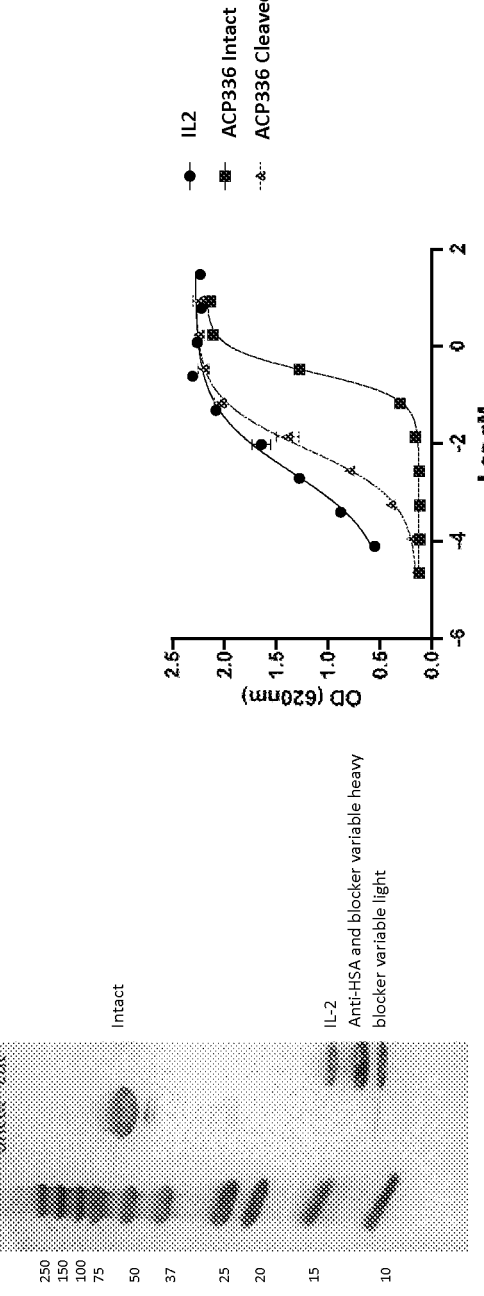
Figure 52G:
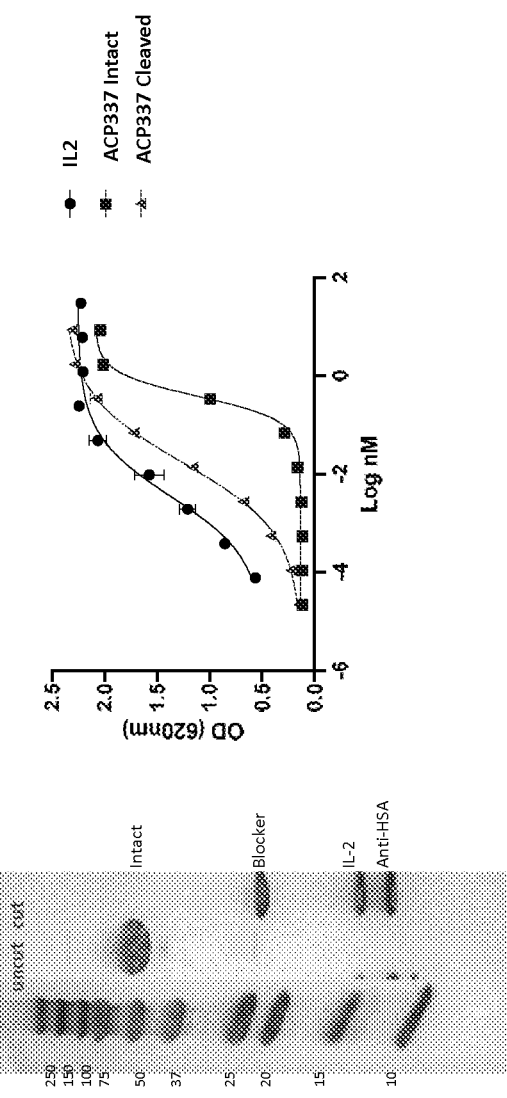
Figure 52H:
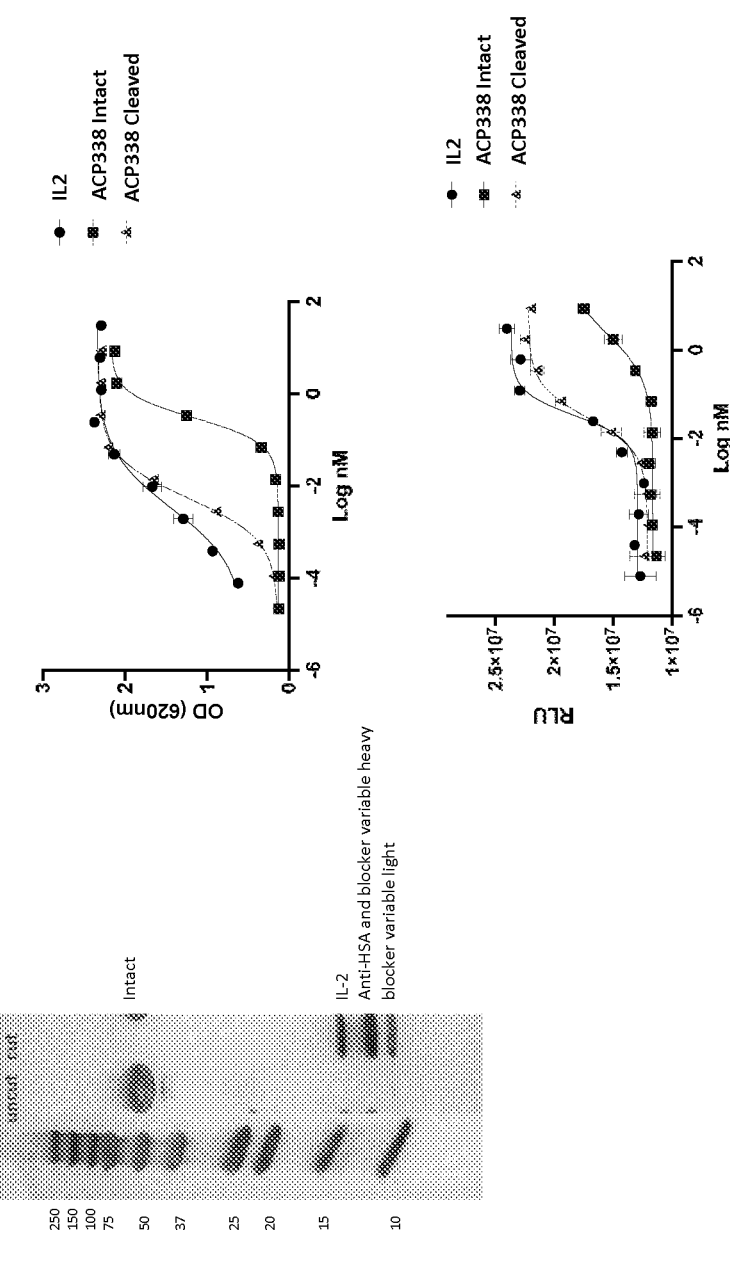
Figure 52I:
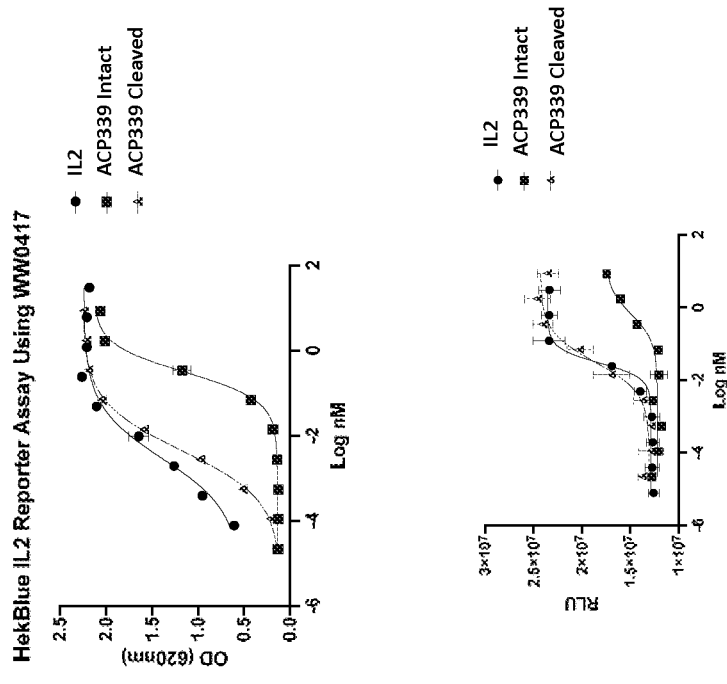
Figure 52J:
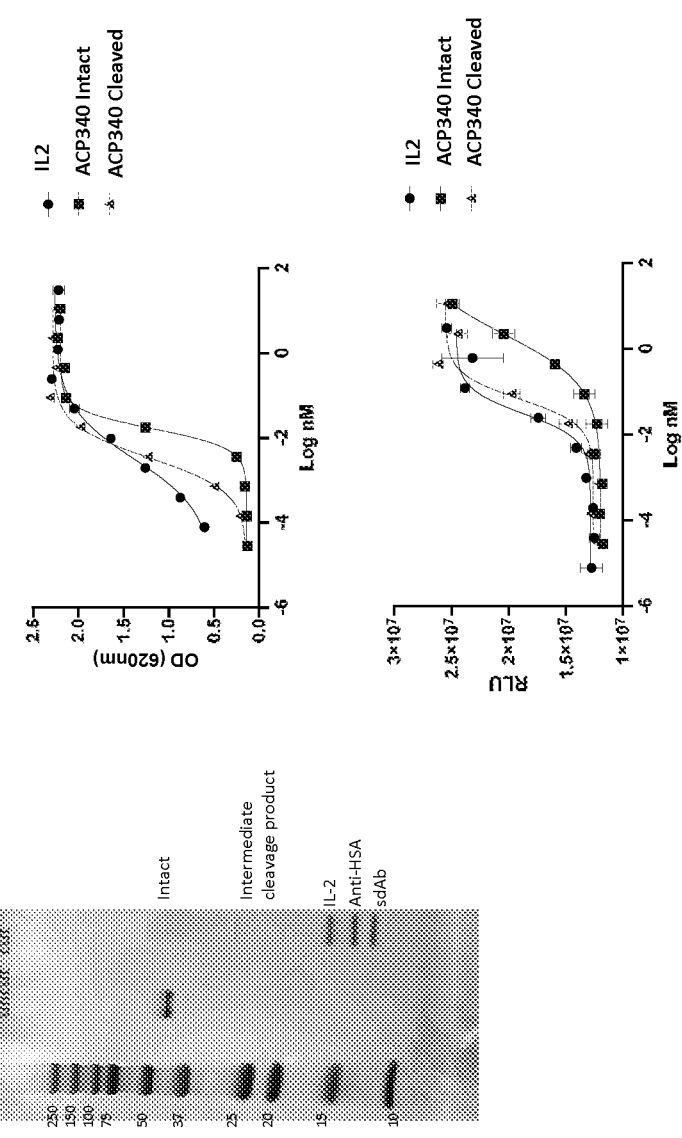
Figure 52M:
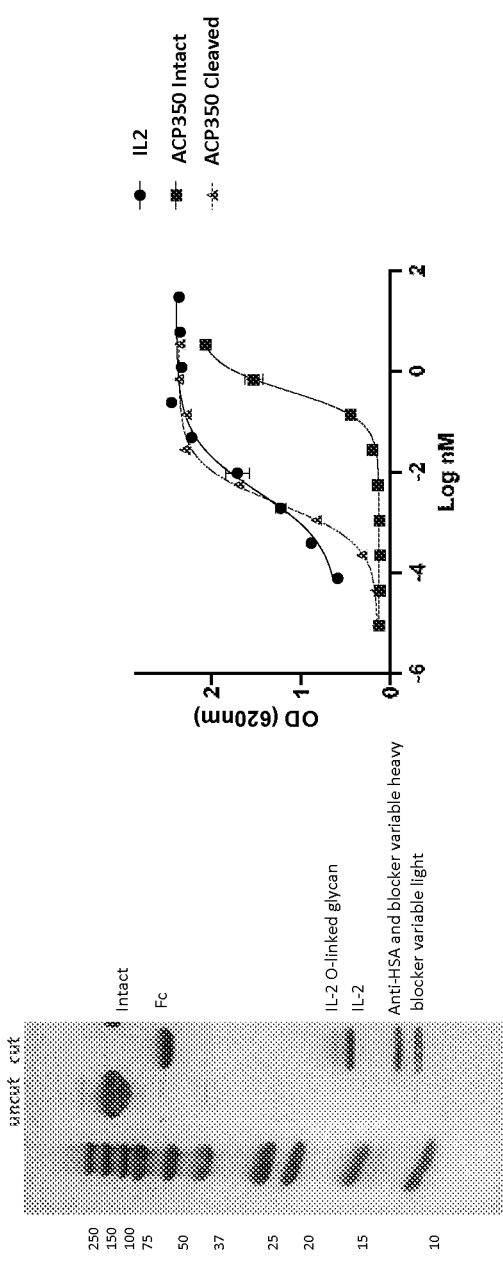
Figure 53A:
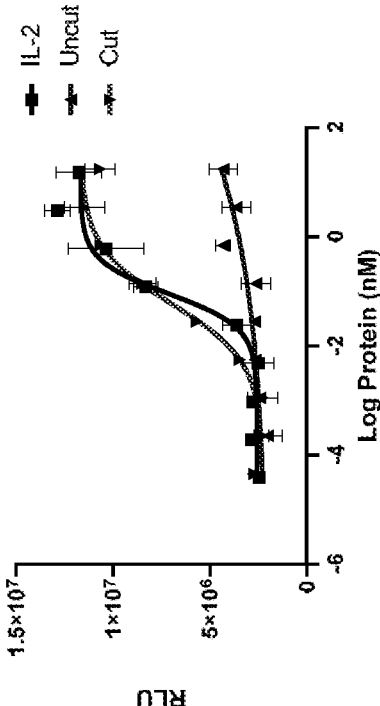
Figure 53B:
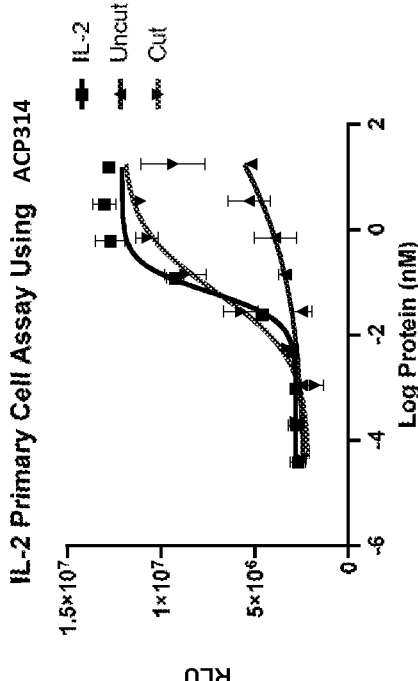
Figure 54C:
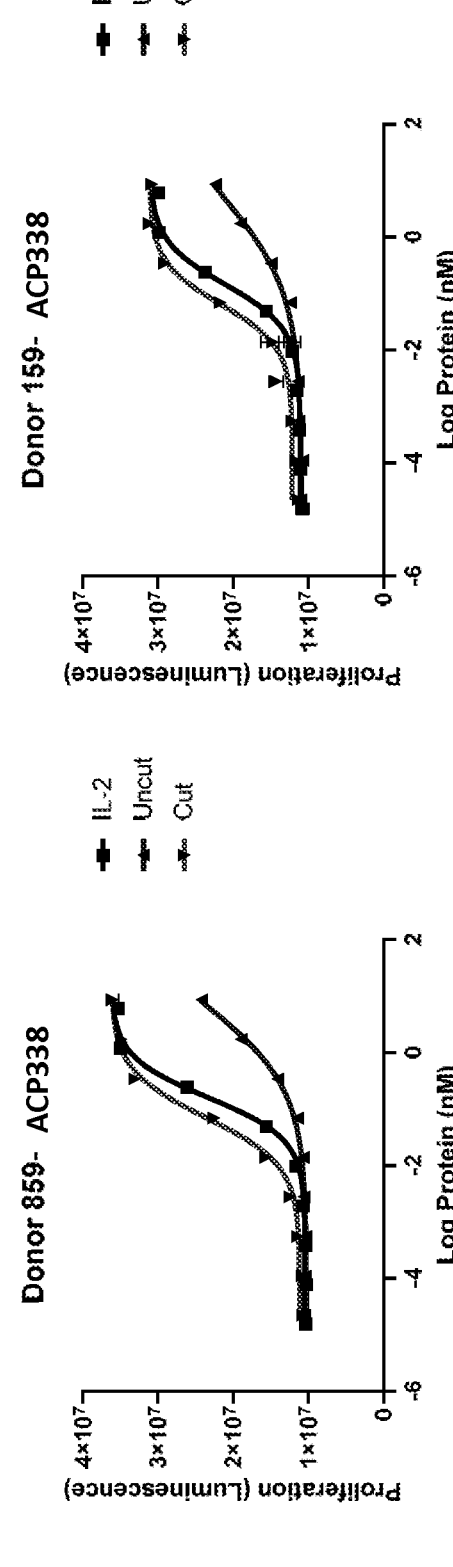
FIG. 54A-54N shows the results of proliferation assays comparing cut protein, uncut protein, and IL2 as a control.
Figure 54E:
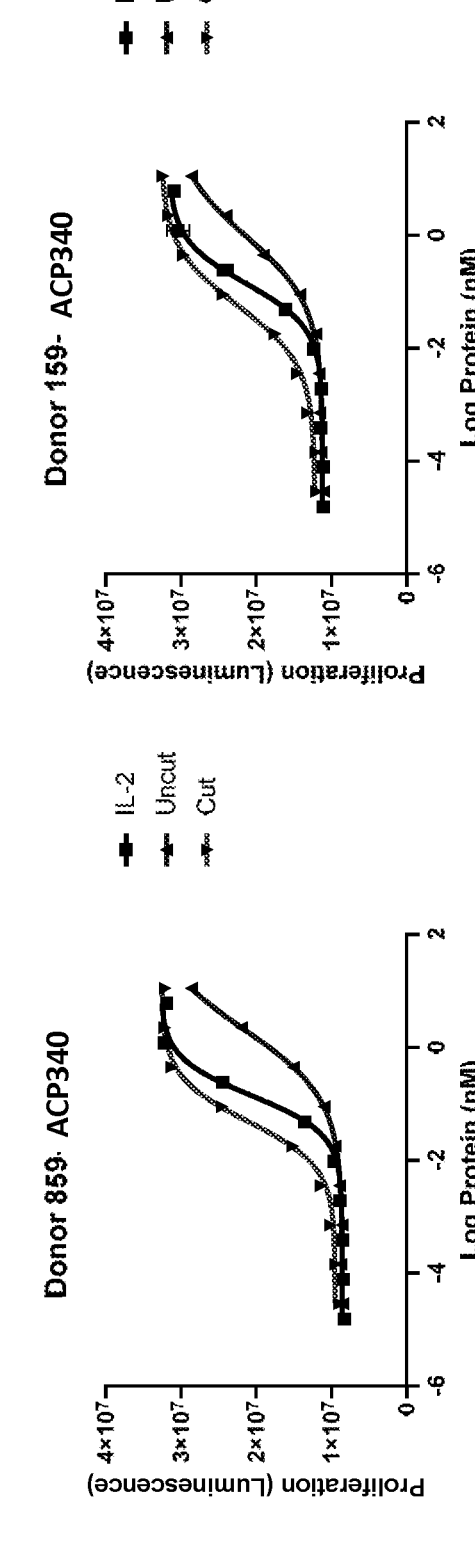
Figure 54G:
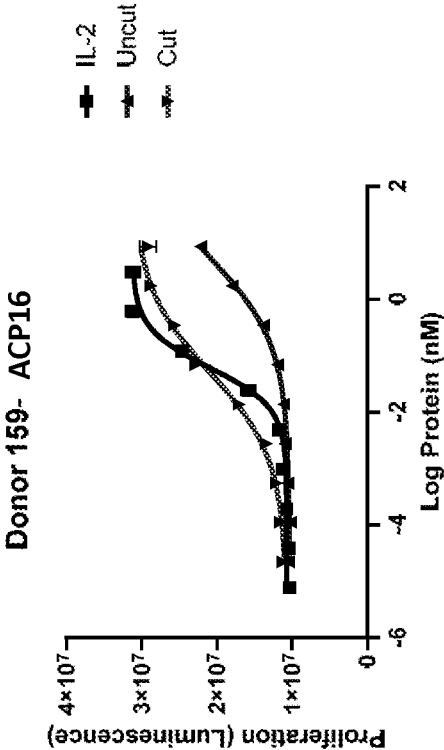
Figure 54H:
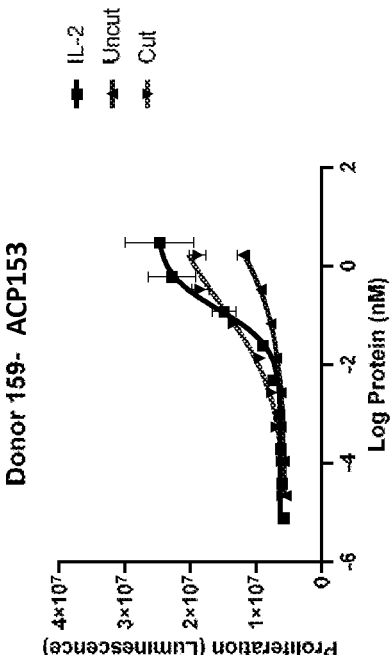
Figure 54I:
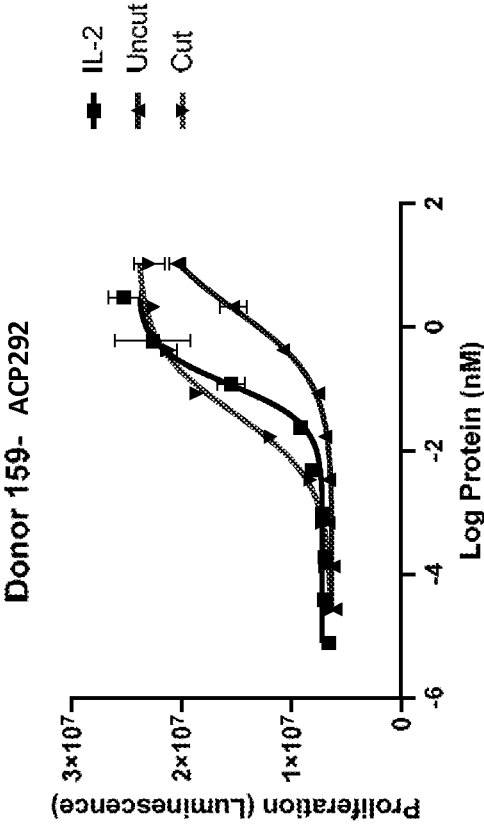
Figure 54J:
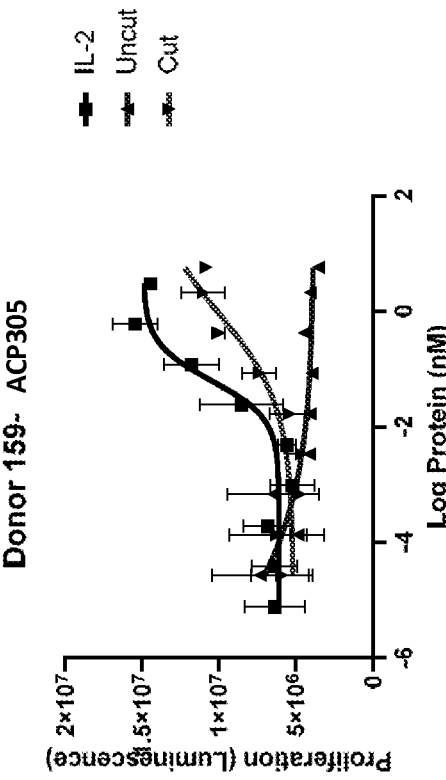
Figure 54K:
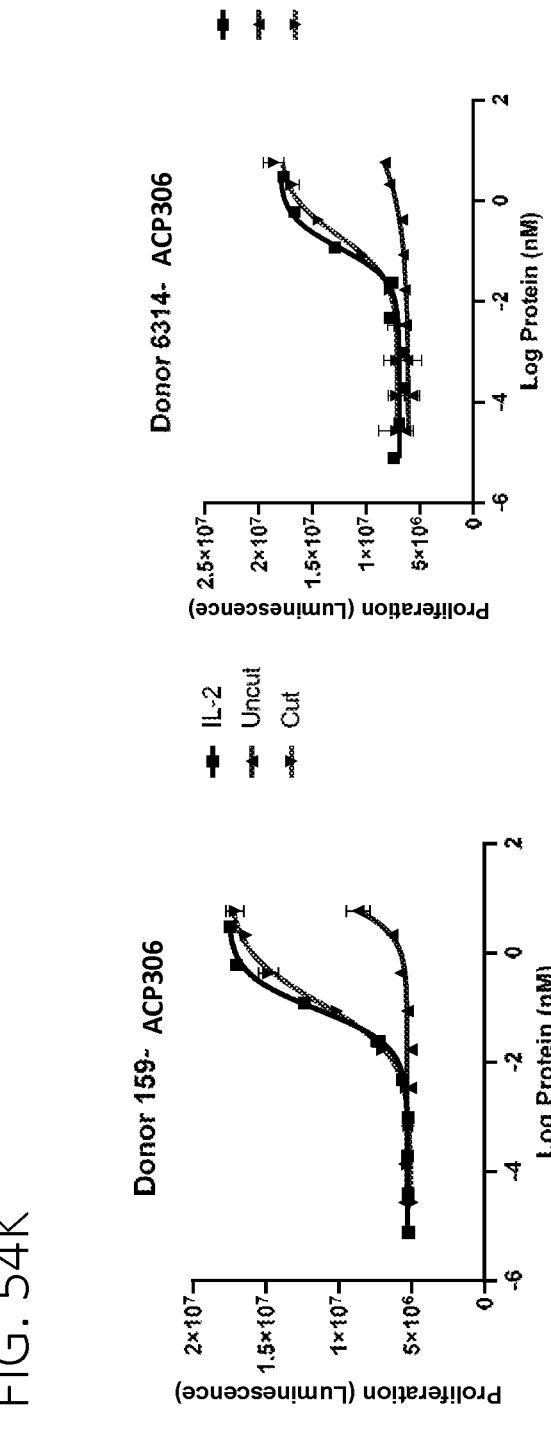
Figure 54L:
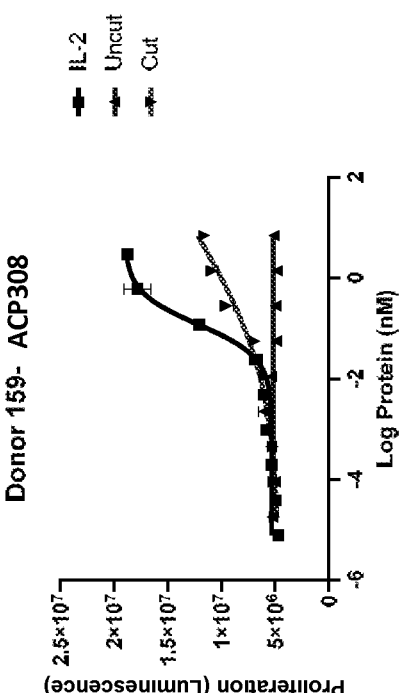
Figure 54M:
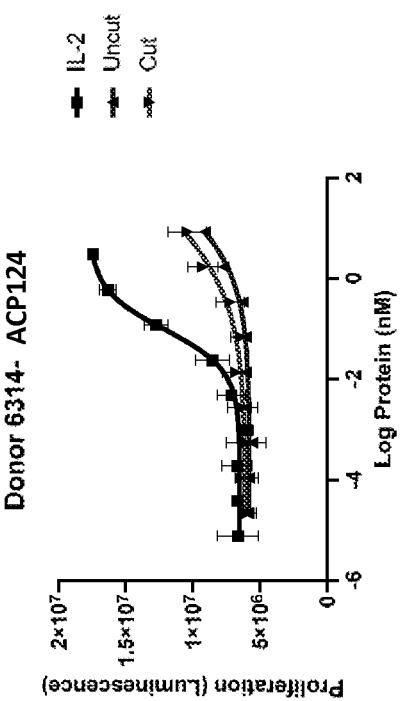
Figure 54N:
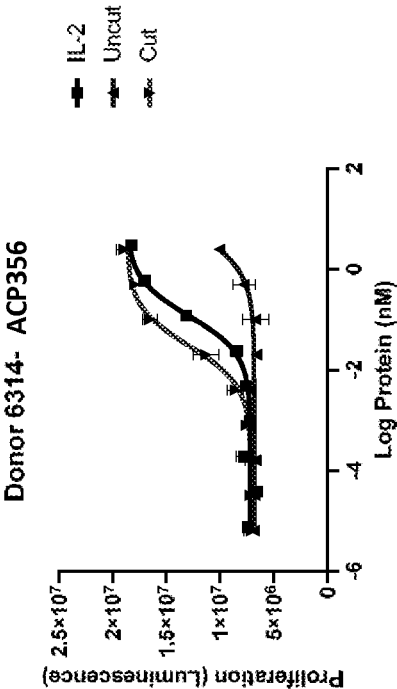
Figure 55A:
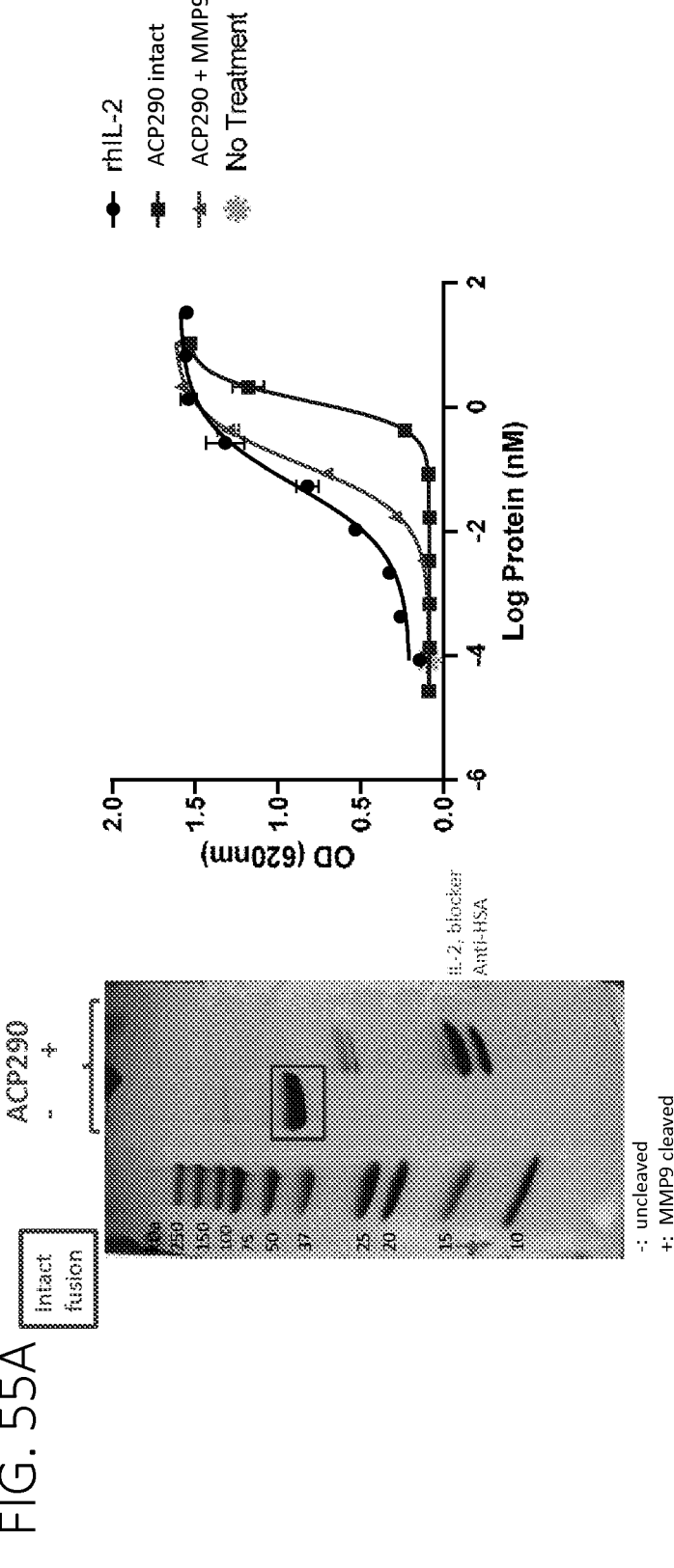
FIGS. 55A-55N shows the results of HekBlue IL2 reporter assays comparing activity of constructs with and without protease cleavage; IL-2 is included as a control.
Figure 55B:
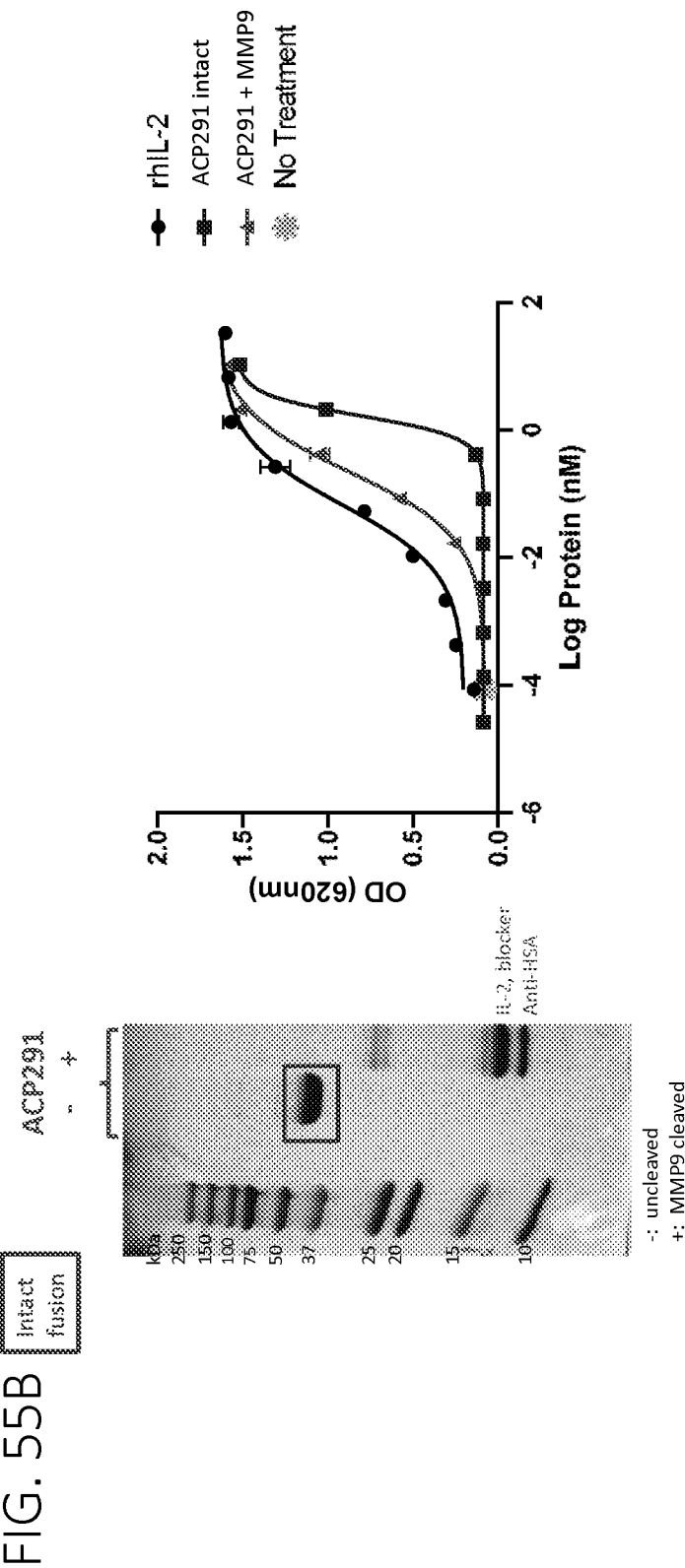
Figure 55C:
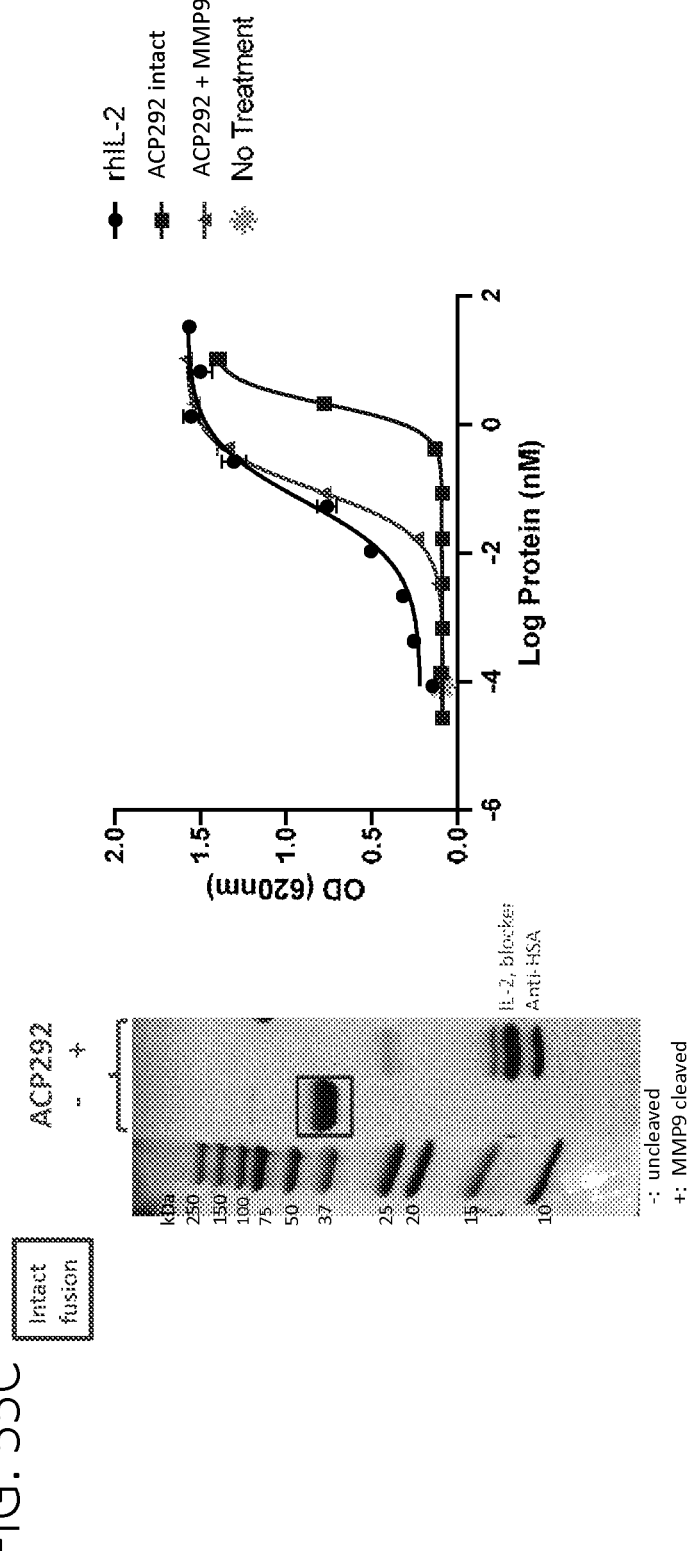
Figure 55D:
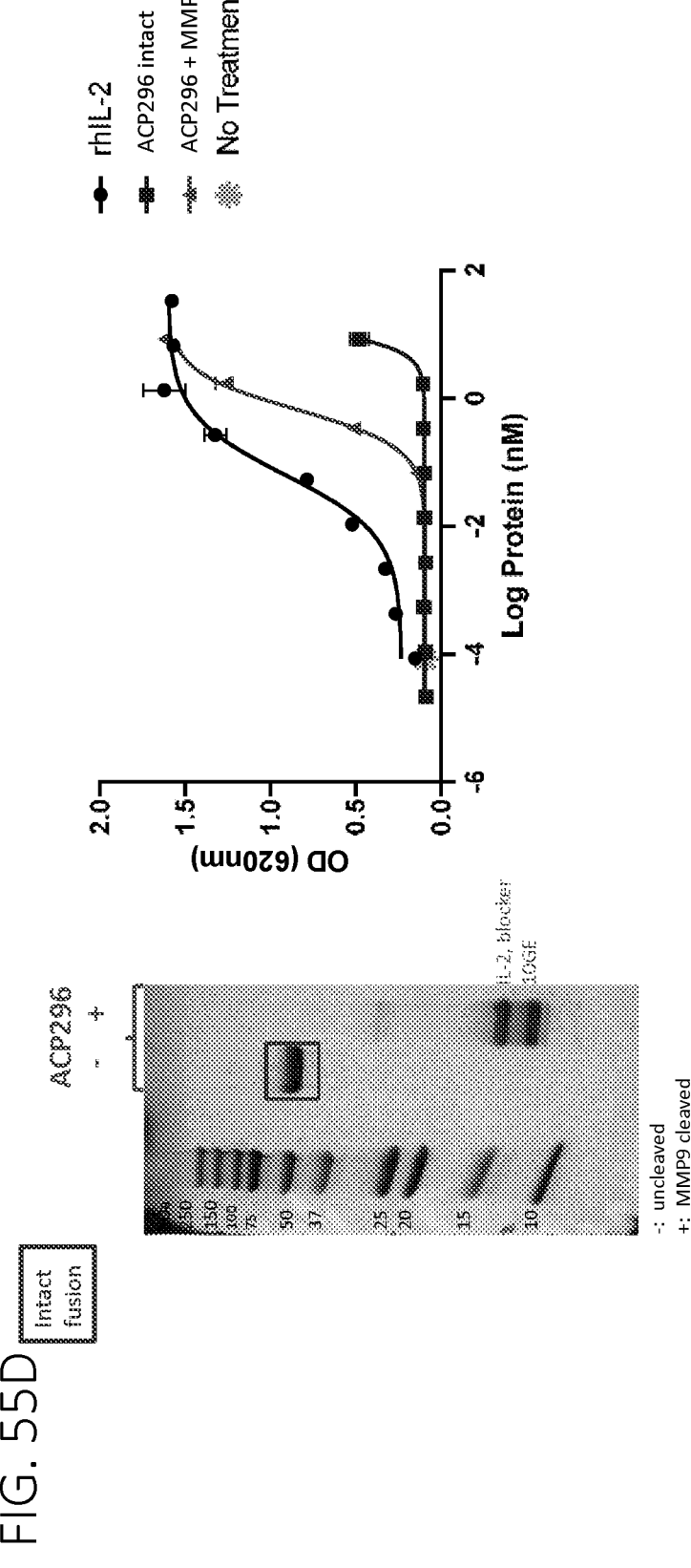
Figure 55E:
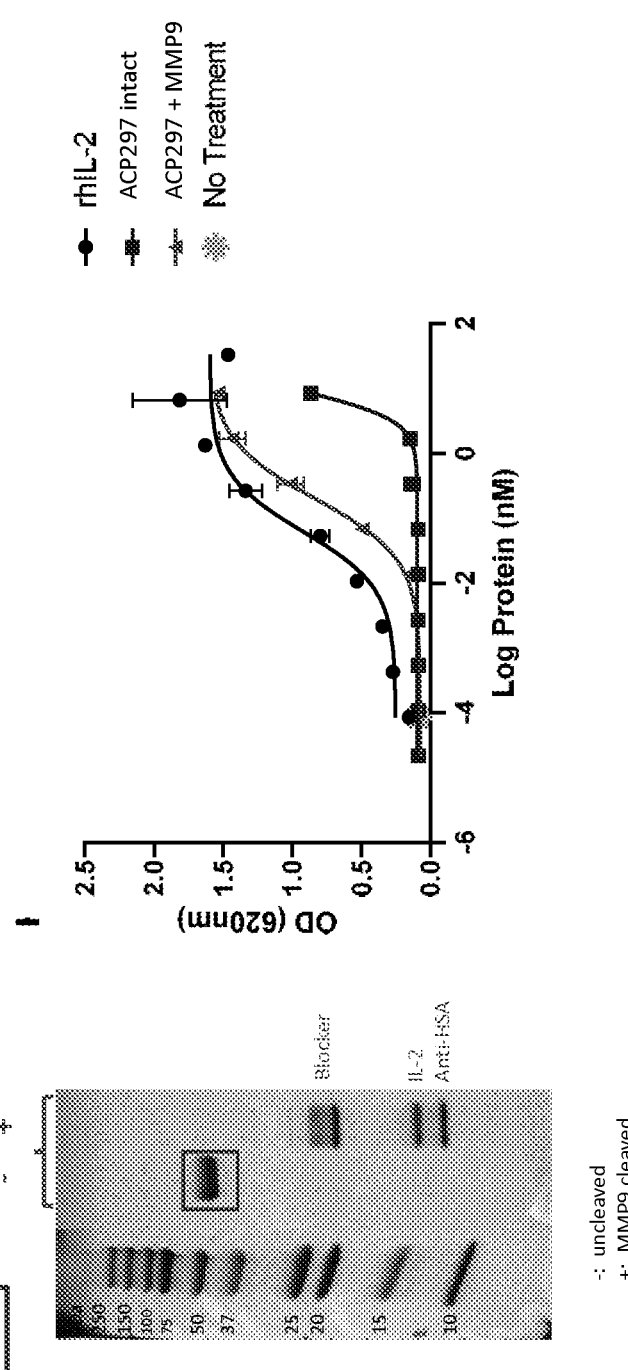
Figure 55F:
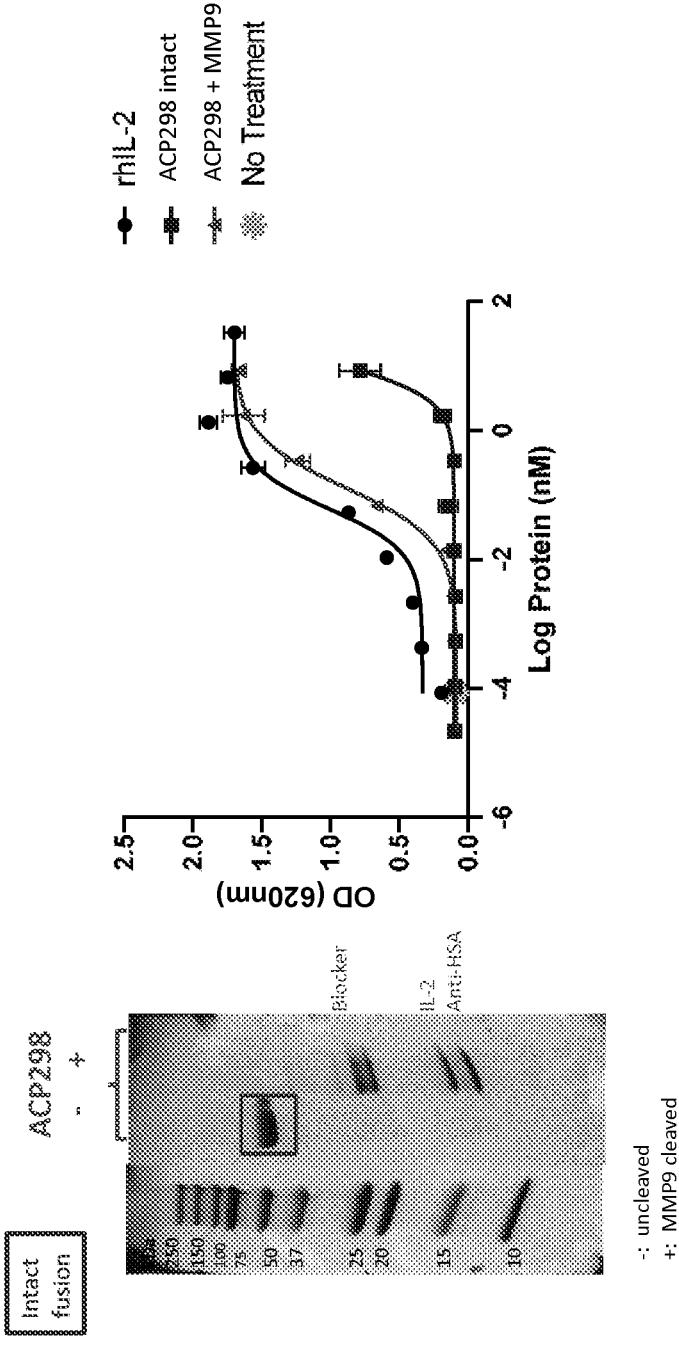
Figure 55H:
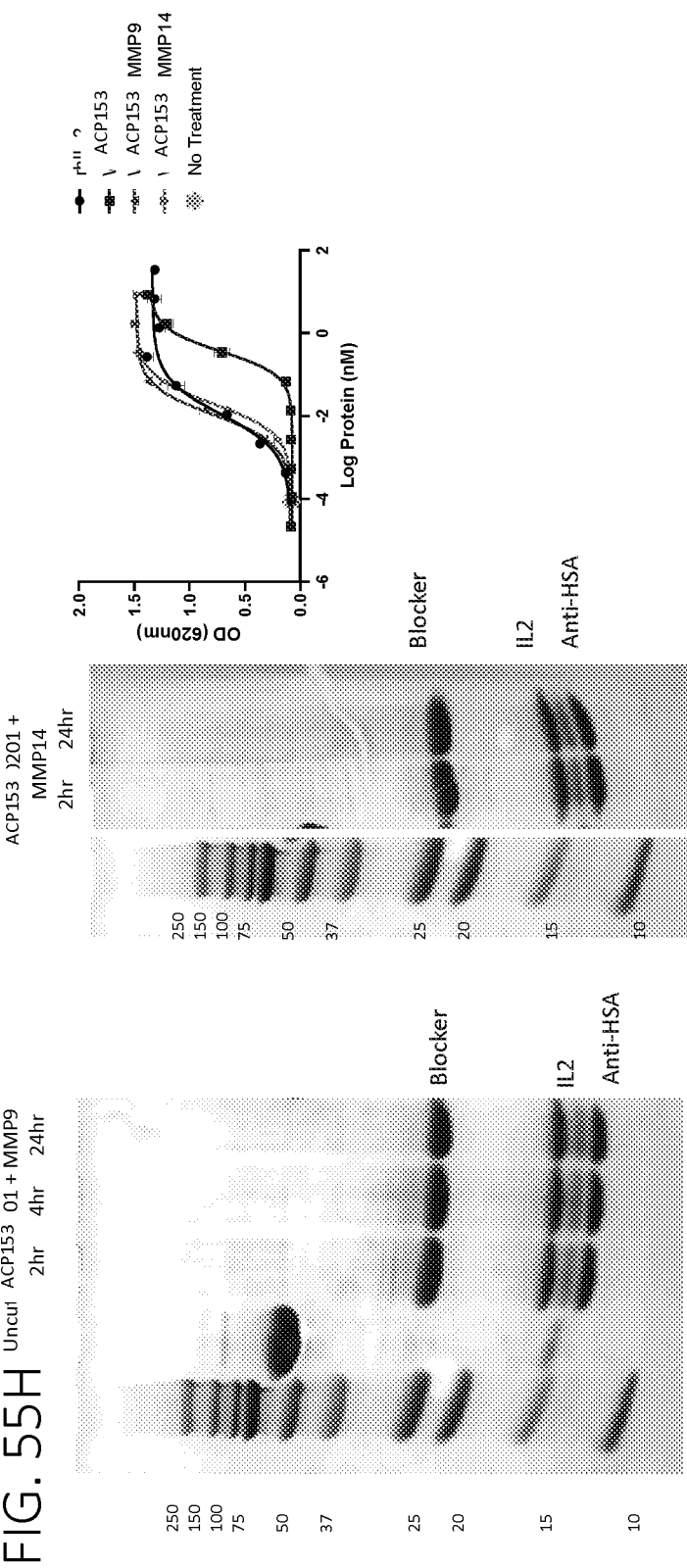
Figure 55I:
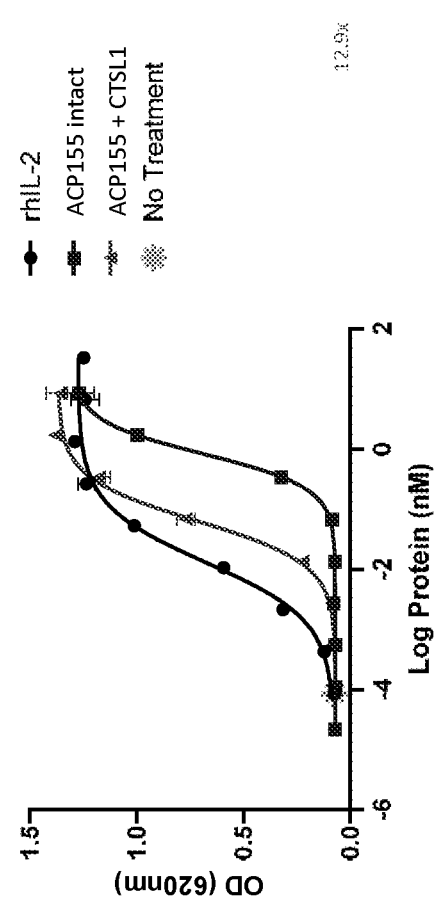
Figure 55J:
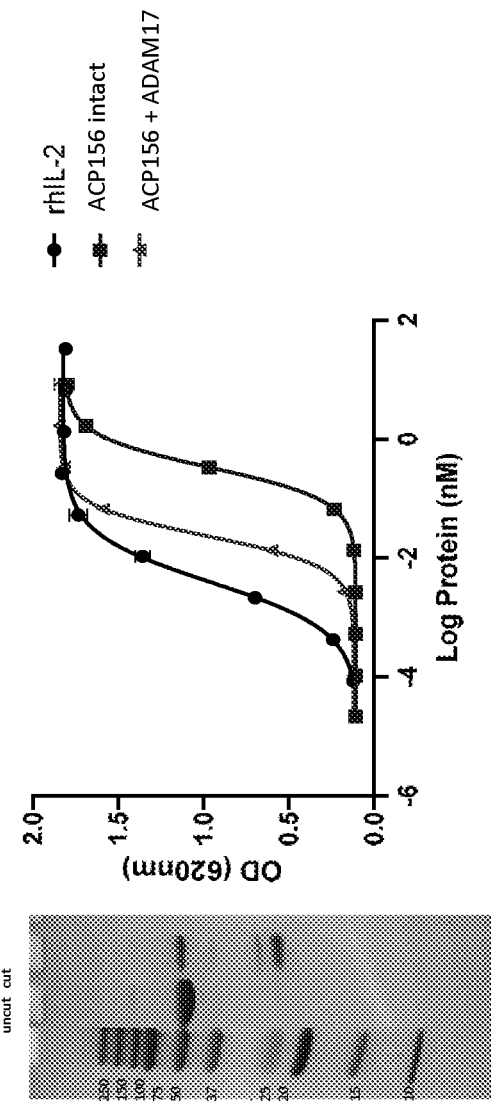
Figure 55L:
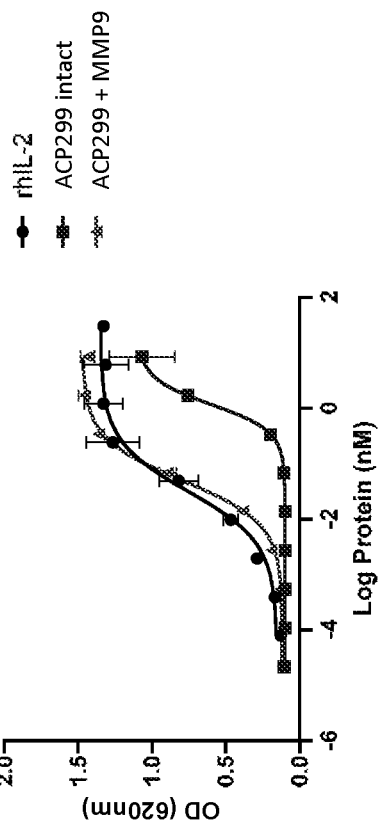
Figure 55N:
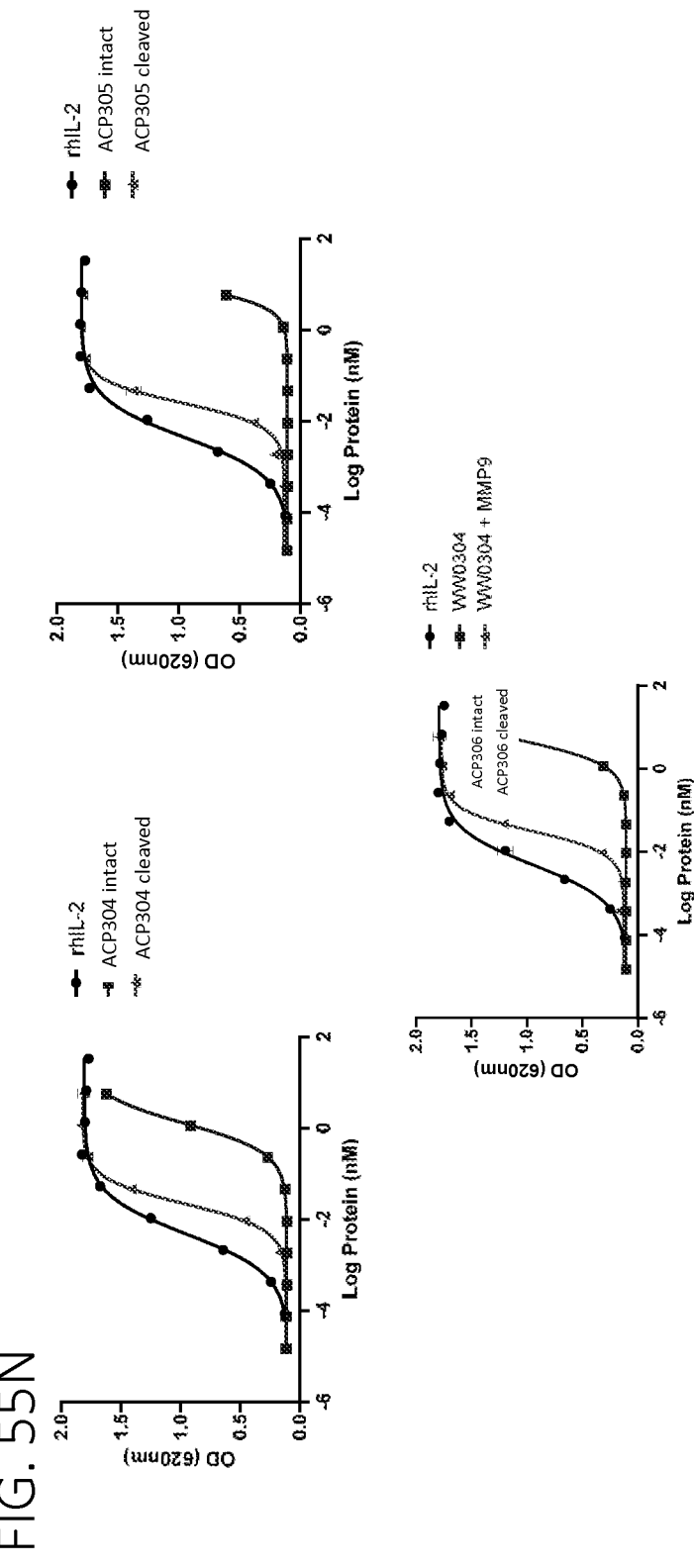
Figure 57A:
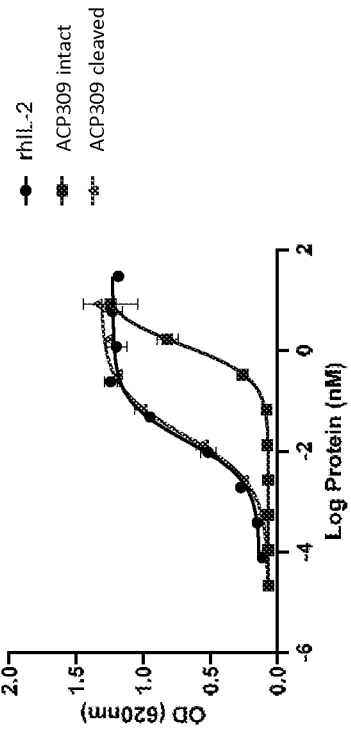
Figure 57B:
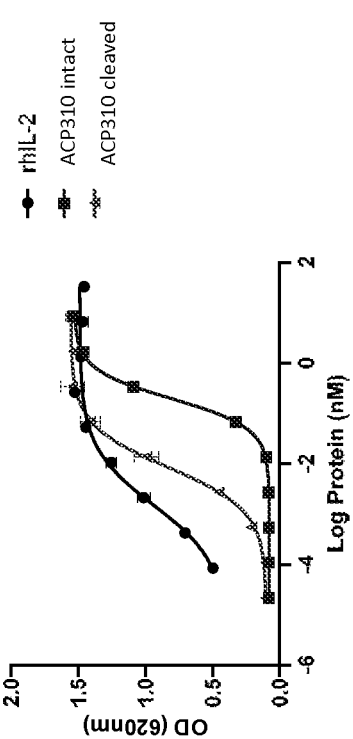
Figure 57C:
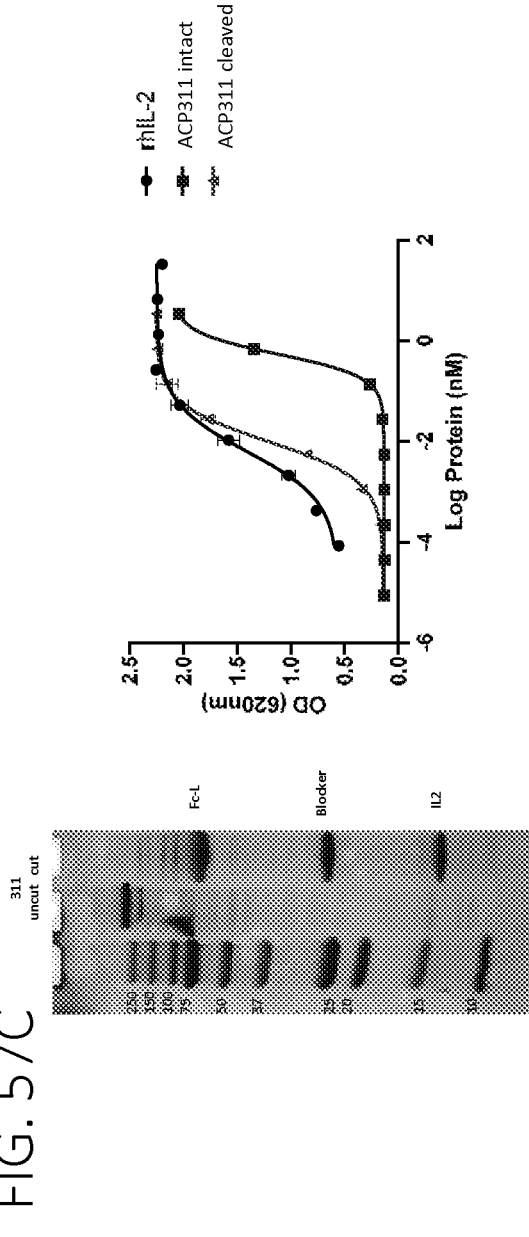
Figure 58:
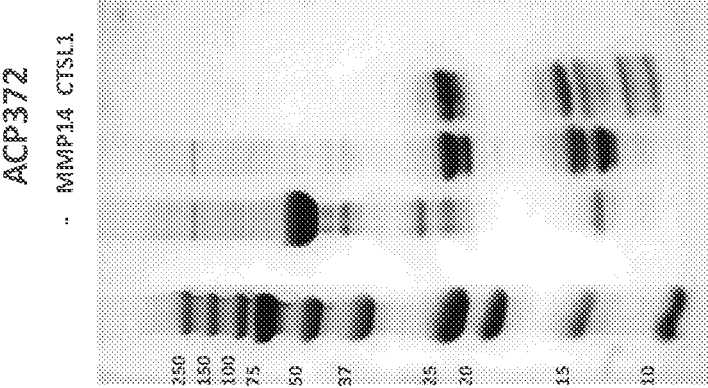
Figure 59M:
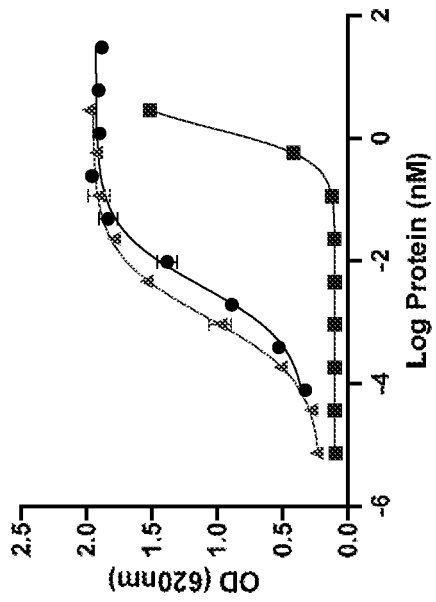
Figure 59T:
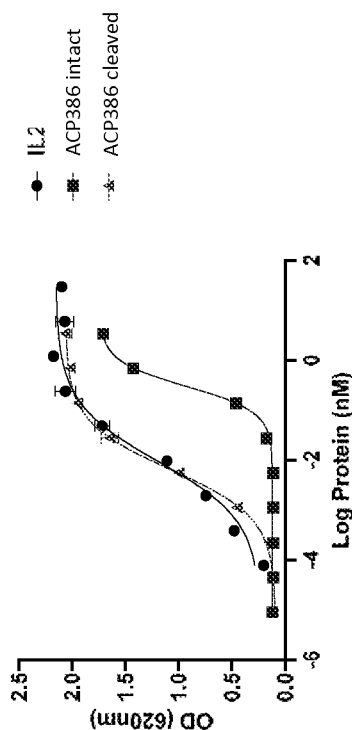

Procedures:

Mice were anaesthetized with isoflurane for implant of cells to reduce the ulcerations. CR female C57BL/6 mice were set up with 5×10$^5$ MC38 tumor cells in 0% Matrigel sc in flank. Cell Injection Volume was 0.1 mL/mouse. Mouse age at start date was 8 to 12 weeks. Pair matches were performed when tumors reach an average size of 100-150 mm$^3$ and begin treatment. ACP339 was dosed at 55, 230 or 700 µg/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm$^3$ or 45 days, whichever comes first. Responders were followed longer. When the endpoint was reached, the animals are to be euthanized. Results are shown in FIGS. 51A-51C.

Example 28: CT26 Experiments

The CT26 cell line, a rapidly growing colon adenocarcinoma cell line that expresses MMP9 in vitro, was used. Using this tumor model, the ability of fusion proteins to affect tumor growth was examined.

Example 28a: Treatment with ACP16 Alone or in Combination with Anti-PD1 Antibody Agents and Treatment:

| Gr. | N | Agent | Formulation dose | Route | Schedule |
|---|---|---|---|---|---|
| 1[#] | 12 | vehicle 1// vehicle 2 | na// na | ip//ip | days 1, 4, 8, 11// days 3, 6, 10, 13 |
| 2 | 10 | vehicle 1// ACP16 | na// 70 µg/animal | ip//ip | days 1, 4, 8, 11// days 3, 6, 10, 13 |
| 3 | 10 | vehicle 1// ACP16 | na// 232 µg/animal | ip//ip | days 1, 4, 8, 11// days 3, 6, 10, 13 |

-continued

| Gr. | N | Agent | Formulation dose | Route | Schedule |
|---|---|---|---|---|---|
| 4 | 10 | vehicle 1// ACP16 | na// 500 μg/animal | ip//ip | days 1, 4, 8, 11// days 3, 6, 10, 13 |
| 5 | 10 | anti-PD-1 RMP1-14// vehicle 2 | 200 μg/animal// na | ip//ip | days 1, 4, 8, 11// days 3, 6, 10, 13 |
| 6 | 10 | anti-PD-1 RMP1-14// ACP16 | 200 μg/animal// 70 μg/animal | ip//ip | days 1, 4, 8, 11// days 3, 6, 10, 13 |
| 7 | 10 | anti-PD-1 RMP1-14// ACP16 | 200 μg/animal// 232 μg/animal | ip//ip | days 1, 4, 8, 11// days 3, 6, 10, 13 |
| 8 | 10 | anti-PD-1 RMP1-14// ACP 16 | 200 μg/animal// 500 μg/animal | ip//ip | days 1, 4, 8, 11// days 3, 6, 10, 13 |
| 9 | 10 | vehicle 1// IL-2 | na// 12 μg/animal | ip//ip | days 1, 4, 8, 11// bid x 5 first day 1 dose per week x 2 |
| 10 | 10 | anti-PD-1 RMP1-14// IL-2 | 200 μg/animal// 12 μg/animal | ip//ip | days 1, 4, 8, 11// bid x 5 first day 1 dose per week x 2 |

Procedures:

Mice were anaesthetized with isoflurane for implant of cells to reduce the ulcerations. CR female BALB/c mice were set up with 3×10⁵ CT26 tumor cells in 0% Matrigel sc in flank. Cell Injection Volume was 0.1 mL/mouse. Mouse age at start date was 8 to 12 weeks. Pair matches were performed when tumors reach an average size of 100-150 mm³ and begin treatment. ACP16 was dosed at 70, 230 or 500 jig/animal with or without anti-PD-1 antibody (RMP1-14) at 200 jig/animal. Body weights were taken at initiation and then biweekly to the end. Caliper measurements were taken biweekly to the end. Any adverse reactions were to be reported immediately. Any individual animal with a single observation of >than 30% body weight loss or three consecutive measurements of >25% body weight loss was euthanized. Any group with a mean body weight loss of >20% or >10% mortality stopped dosing; the group was not euthanized and recovery is allowed. Within a group with >20% weight loss, individuals hitting the individual body weight loss endpoint were euthanized. If the group treatment related body weight loss is recovered to within 10% of the original weights, dosing resumed at a lower dose or less frequent dosing schedule. Exceptions to non-treatment body weight % recovery were allowed on a case-by-case basis. Endpoint was tumor growth delay (TGD). Animals were monitored individually. The endpoint of the experiment was a tumor volume of 1500 mm³ or 45 days, whichever comes first. Responders were followed longer. When the endpoint was reached, the animals are to be euthanized. Results are shown in FIGS. 47A-47D and FIGS. 48A-48B.

Example 29. Human Tblast ASSAY

Pre-stimulated T cells (T-blasts) were used to assess the activity of inducible IL-2 fusion proteins. T-Blasts were induced from human PBMCs with a 3-day incubation with PHA. Tblasts were then plated in suspension at a concentration of 50,000 or 75,000 cells/well in X-VIVO culture media (containing human serum albumin) and stimulated with a dilution series of recombinant IL-2 fusion proteins or human IL-2 for 72 hours at 37° C. and 5% $CO_2$. Activity of uncleaved and cleaved IL-2 fusion proteins was tested. Cleaved inducible IL-2 was generated by incubation with active MMP9. IL-2 activity was assessed measuring proliferation with CellTiter-Glo.

Sample fusion protein constructs are detailed in Table 3. In table 3, "L" is an abbreviation of "linker", and "cleav. link." is an abbreviation of "cleavable linker". Other abbreviations "mIFNg" indicates mouse interferon gamma (IFNg); "hAlbumin" indicates human serum albumin (HSA); "mAlbumin" indicates mouse serum albumin.

TABLE 3

| Construct Name | Construct Description |
|---|---|
| | CONSTRUCT PERMUTATION TABLE ("6xHis" disclosed as SEQ ID NO: 354) |
| ACP01 | (anti-HSA)-(cleav. link.)-mouse IFNg-(cleav. link.)-(anti-HSA)-6xHis |
| ACP02 | (anti-HSA)-(cleav. link.)-mouse IFNg-(cleav. link.)-mouse IFNg-(cleav. link.)-(anti-HSA)-6xHis |
| ACP03 | (anti-HSA)-(cleav. link.)-mouse IFNg-mouse IFNg-(cleav. link.)-(anti-HSA)-6xHis |
| ACP50 | (anti-EpCAM)-(anti-HSA)-(cleav. link.)-mouse IFNg-mouse IFNg-(cleav. link.)-(anti-HSA)-6xHis |
| ACP51 | (anti-EpCAM)-Linker-(anti-HSA)-(cleav. link.)-mIFNg-(cleav. link.)-(anti-HSA)-6xHis |
| ACP52 | (anti-HSA)-(cleav. link.)-mIFNg-(cleav. link.)-(anti-HSA)-Linker-(anti-EpCAM)-6xHis |
| ACP53 | mAlbumin-(cleav. link.)-mIFNg-(cleav. link.)-mAlbumin-6xHis |
| ACP54 | mAlbumin-(cleav. link.)-mIFNg-Linker-mIFNg-(cleav. link.)-mAlbumin-6xHis |
| ACP30 | (anti-HSA)-(cleav. link.)-mouse IFNg-(cleav. link.)-(anti-HSA)-(cleav. link.)-mouse IFNg-(cleav. link.)-(anti-HSA)-6xHis |
| ACP55 | (anti-HSA)-(cleav. link.)-mouse IFNg-(cleav. link.)-(anti-HSA)-(cleav. link.)-mouse IFNg-(cleav. link.)-(anti-HSA)-6xHis-C-tag |
| ACP56 | (anti-FOLR1)-Linker-(anti-HSA)-(cleav. link.)-mIFNg-(cleav. link.)-(anti-HSA)-6xHis |
| ACP57 | (anti-HSA)-(cleav. link.)-mIFNg-(cleav. link.)-(anti-HSA)-Linker-(anti-FOLR1)-6xHis |

TABLE 3-continued

CONSTRUCT PERMUTATION TABLE ("6xHis" disclosed as SEQ ID NO: 354)

| Construct Name | Construct Description |
|---|---|
| ACP58 | (anti-HSA)-(cleav. link.)-mIFNg-(cleav. link.)-mIFNg-(cleav. link.)-(anti-HSA)-Linker-(anti-EpCAM)-6xHis |
| ACP59 | (anti-FOLR1)-Linker-(anti-HSA)-(cleav. link.)-mIFNg-(cleav. link.)-mIFNg-(cleav. link.)-(anti-HSA)-6xHis |
| ACP60 | (anti-HSA)-(cleav. link.)-mIFNg-(cleav. link.)-mIFNg-(cleav. link.)-(anti-HSA)-Linker-(anti-FOLR1)-6xHis |
| ACP61 | (anti-HSA)-(cleav. link.)-mIFNg-(cleav. link.)-mIFNg-(cleav. link.)-(anti-HSA)-Linker-FN(CGS-2)-6xHis |
| ACP63 | anti-FN CGS-2 scFv (Vh/Vl)-6xHis |
| ACP69 | (anti-HSA)-(cleav. link.)-mouse IFNg-(cleav. link.)-(anti-HSA)-(cleav. link.)-mouse IFNg |
| ACP70 | mouse IFNg-(cleav. link.)-(anti-HSA)-(cleav. link.)-mouse IFNg-(cleav. link.)-(anti-HSA) |
| ACP71 | mouse IFNg-(cleav. link.)-mAlbumin-(cleav. link.)-mouse IFNg-(cleav. link.)-mAlbumin |
| ACP72 | mAlbumin-(cleav. link.)-mouse IFNg-(cleav. link.)-mAlbumin-(cleav. link.)-mouse IFNg |
| ACP73 | mAlbumin-(cleav. link.)-mouse IFNg-(cleav. link.)-mAlbumin-(cleav. link.)-mouse IFNg-(cleav. link.)-mAlbumin |
| ACP74 | mAlbumin-(cleav. link.)-mouse IFNg-(cleav. link.)-5mer linker-mAlbumin-5mer linker-(cleav. link.)-mouse IFNg-(cleav. link.)-mAlbumin |
| ACP75 | mAlbumin-(cleav. link.)-mouse IFNg-(cleav. link.)-10mer linker-mAlbumin-10mer linker-(cleav. link.)-mouse IFNg-(cleav. link.)-mAlbumin |
| ACP78 | (anti-HSA)-Linker-mouse_IFNg-Linker-(anti-HSA)-Linker-mouse_IFNg-Linker-(anti-HSA)_(non-cleavable_control) |
| ACP134 | Anti-HSA-(cleav. link.)-mouse_IFNg-(cleav. link.)-anti-HSA-(cleav. link.)-mouse_IFNg-(cleav. link.)-anti-HSA-L-anti-FOLR1 |
| ACP135 | Anti-FOLR1-L-HSA-(cleav. link.)-mouse_IFNg-(cleav. link.)-HSA-(cleav. link.)-mouse_IFNg-(cleav. link.)-HSA |
| ACP04 | human p40-murine p35-6xHis |
| ACP05 | human p40-human p35-6xHis |
| ACP34 | mouse p35-(cleav. link.)-mouse p40-6xHis |
| ACP35 | mouse p35-GS-(cleav. link.)-GS-mouse p40-6xHis |
| ACP36 | (anti-HSA)-(Cleav. Linker)-mouse p40-mouse p35-(Cleav. Linker)-(anti-HSA)-6xHis |
| ACP37 | (anti-EpCAM)-(anti-HSA)-(Cleav. Linker)-mouse p40-mouse p35-(Cleav. Linker)-(anti-HSA)-6xHis |
| ACP79 | (anti-EpCAM)-Linker-(anti-HSA)-(cleav. link.)-mIL12-(cleav. link.)-(Anti-HSA)-6xHis |
| ACP80 | (anti-HSA)-(cleav. link.)-mIL12-(cleav. link.)-(anti-HSA)-Linker-(anti-EpCAM)-6xHis |
| ACP06 | Blocker12-Linker-(cleav. link.)-human p40-Linker-mouse p35-(cleav. link.)-(anti-HSA)-6xHis |
| ACP07 | Blocker12-Linker-(cleav. link.)-human p40-Linker-mouse p35-(cleav. link.)-(anti-HSA)-Linker-(anti-FOLR1)-6xHis |
| ACP08 | (anti-FOLR1)-Linker-Blocker12-Linker-(cleav. link.)-human p40-Linker-mouse p35-(cleav. link.)-(anti-HSA)-6xHis |
| ACP09 | (anti-HSA)-Linker-Blocker12-Linker-(cleav. link.)-human p40-Linker-mouse p35-6xHis |
| ACP10 | (anti-HSA)-(cleav. link.)-human p40-L-mouse p35-(cleav. link.)-Linker-Blocker12-6xHis |
| ACP11 | Human_p40-Linker-mouse_p35-(cleav. link.)-Linker-Blocker12-Linker-(anti-HSA)-6xHis |
| ACP91 | human_p40-Linker-mouse_p35-Linker-Linker-Blocker-Linker-(anti-HSA)_(non-cleavable control) |
| ACP136 | human p40-L-mouse p35-(cleav. link.)-Blocker |
| ACP138 | human_p40-L-mouse_p35-(cleav. link.)-Blocker-L-(anti-HSA)-L-FOLR1 |
| ACP139 | Anti-FOLR1-L-human_p40-L-mouse_p35-(cleav. link.)-Blocker12-L-(anti-HSA) |
| ACP140 | Anti-FOLR1-(cleav. link.)-human_p40-L-mouse_p35-(cleav. link.)-Blocker12-L-(anti-HSA) |
| ACP12 | (anti-EpCAM)-IL2-(cleav. link.)-(anti-HSA)-blocker2-6xHis |
| ACP13 | (anti-EpCAM)-Blocker2-(anti-HSA)-(cleav. link.)-IL2-6xHis |
| ACP14 | Blocker2-Linker-(cleav. link.)-IL2- (cleav. link.)-(anti-HSA)-6xHis |
| ACP15 | Blocker2-Linker-(anti-HSA)-Linker-(cleav. link.)- IL2 -6xHis |
| ACP16 | IL2-(cleav. link.)-(anti-HSA)-Linker-(cleav. link.)-Blocker2-6xHis |
| ACP17 | (anti-EpCAM)-Linker-IL2-(cleav. link.)-(anti-HSA)-Linker-(cleav. link.)-Blocker2-6xHis |
| ACP18 | (anti-EpCAM)-Linker-IL2-(clcav. link.)-(anti-HSA)-Linker-vh(cleav. link.)vl-6xHis |
| ACP19 | IL2-(cleav. link.)-Linker-Blocker2-Linker-(anti-HSA)-Linker-(anti-EpCAM) -6xHis |
| ACP20 | IL2-(cleav. link.)-Blocker2-6xHis |
| ACP21 | IL2-(cleav. link.)-Linker-Blocker2-6xHis |
| ACP22 | IL2-(cleav. link.)-Linker-blocker-(cleav. link.)-(anti-HSA)-Linker-(anti-EpCAM)-6xHis |
| ACP23 | (anti-FOLR1)-(cleav. link.)-Blocker2-Linker-(cleav. link.)-(anti-HSA)-(cleav. link.)-IL2-6xHis |
| ACP24 | (Blocker2)-(cleav. link.)-(IL2)-6xHis |
| ACP25 | Blocker2-Linker-(cleav. link.)-IL2-6xHis |
| ACP26 | (anti-EpCAM)-Linker-IL2-(cleav. link.)-(anti-HSA)-Linker-blocker(NARA1 Vh/Vl) |
| ACP27 | (anti-EpCAM)-Linker-IL2-(cleav. link.)-(anti-HSA)-Linker-blocker(NARA1 Vl/Vh) |
| ACP28 | IL2-(cleav. link.)-Linker-Blocker2-(NARA1 Vh/Vl)-Linker-(anti-HSA)-Linker-(anti-EpCAM) |
| ACP29 | IL2-(cleav. link.)-Linker-Blocker2-(NARA1 Vl/Vh)-Linker-(anti-HSA)-Linker-(anti-EpCAM) |
| ACP38 | IL2-(cleav. link.)-blocker-(anti-HSA)-(anti-EpCAM)-6xHis |

TABLE 3-continued

CONSTRUCT PERMUTATION TABLE ("6xHis" disclosed as SEQ ID NO: 354)

| Construct Name | Construct Description |
| --- | --- |
| ACP39 | (anti-EpCAM)-(cleav. link.)-(anti-HSA)-(cleav. link.)-Blocker2-(cleav. link.)-IL-2-6xHis |
| ACP40 | CD25ecd-Linker-(cleav. link.)-IL2-6xHis |
| ACP41 | IL2-(cleav. link.)-Linker-CD25ecd-6xHis |
| ACP42 | (anti-HSA)-Linker-CD25ecd-Linker-(cleav. link.)-IL2-6xHis |
| ACP43 | IL2-(cleav. link.)-Linker-CD25ecd-Linker-(anti-HSA)-6xHis |
| ACP44 | IL2-(cleav. link.)-Linker-CD25ecd-(cleav. link.)-(anti-HSA)-6xHis |
| ACP45 | (anti-HSA)-(cleav. link.)-Blocker2-Linker-(cleav. link.)-IL2-6xHis |
| ACP46 | IL2-(cleav. link.)-linkerL-vh(cleav. link.)vl-Linker-(anti-HSA)-L-(anti-EpCAM)-6xHis |
| ACP47 | (anti-EpCAM)-Linker-IL2-(Cleavable Linker)-(anti-HSA)-Linker-Blocker2-6xHis |
| ACP48 | IL2-(cleav. link.)-Blocker2-Linker-(anti-HSA)-6xHis |
| ACP49 | IL2-(cleav. link.)-Linker-Blocker2-Linker-(anti-HSA)-6xHis |
| ACP92 | (anti-HSA)-(16mer Cleav. Link.)-IL2-(16mer Cleav. Link.)-(anti-HSA)-6XHis |
| ACP93 | (anti-EpCAM)-(anti-HSA)-(anti-EpCAM)-Blocker2-(cleav. link.)-IL2-6xHis |
| ACP94 | (anti-EpCAM)-(anti-HSA)-Blocker2-(cleav. link.)-IL2-6xHis |
| ACP95 | (anti-EpCAM)-(anti-HSA)-(cleav. link.)-IL2-6xHis |
| ACP96 | (anti-EpCAM)-(16mer cleav. link.)-IL2-(16mer cleav. link.)-(anti-HSA) |
| ACP97 | (anti-EpCAM)-(anti-HSA)-(cleav. link.)-IL2-(cleav. link.)-(anti-HSA)-6xHis |
| ACP99 | (anti-EpCAM)-Linker-IL2-(cleav. link.)-(anti-HSA)-6xHis |
| ACP100 | (anti-EpCAM)-Linker-IL2-6xHis |
| ACP101 | IL2-(cleav. link.)-(anti-HSA)-6xHis |
| ACP102 | (anti-EpCAM)-(cleav. link.)-IL2-(cleav. link.)-(anti-HSA)-Linker-blocker-6xHis |
| ACP103 | IL2-(cleav. link.)-Linker-Blocker2-Linker-(anti-HSA)-Linker-(antiI-FOLR1)-6xHis |
| ACP104 | (anti-FOLR1)-IL2-(cleav. link.)-(anti-HSA)-Linker-Blocker2-6xHis |
| ACP105 | Blocker2-Linker-(cleav. link.)-IL2-(cleav. link.)-(anti-HSA)-Linker-(anti-FOLR1)-6xHis |
| ACP106 | (anti-FOLR1)-Linker-(anti-HSA)-(cleav. link.)-blocker-Linker-(cleav. link.)-IL2 -6xHis |
| ACP107 | Blocker2-Linker-(anti-HSA)-(cleav. link.)-IL2-Linker-(anti-FOLR1)-6xHis |
| ACP108 | (anti-EpCAM)-IL2-(Dually cleav. link.)-(anti-HSA)-Linker-blocker-6xHis |
| ACP117 | anti-FN CGS-2 scFv (Vh/Vl)-6xHis |
| ACP118 | NARA1 Vh/Vl non-cleavable |
| ACP119 | NARA1 Vh/Vl cleavable |
| ACP120 | NARA1 Vl/Vh non-cleavable |
| ACP121 | NARA1 Vl/Vh cleavable |
| ACP124 | IL2-Linker-(anti-HSA)-Linker-Linker-blocker_(non-cleavable_control) |
| ACP132 | IL2-L-HSA |
| ACP141 | IL2-L-human_Albumin |
| ACP142 | IL2-(cleav. link.)-human_Albumin |
| ACP144 | IL2-(cleav. link.)-HSA-(cleav.-link.)blocker-L-(anti-FOLR1) |
| ACP145 | Anti-FOLR1-L-IL2-(cleav. link.)-HSA-Linker-(cleav. link.)-blocker2 |
| ACP146 | Anti-FOLR1-(cleav. link)-IL2-(cleav. link.)-HSA-Linker-(cleav. link.)-blocker2 |
| ACP133 | IL2-6x His |
| ACP147 | IL2-(cleav. Linker)-(anti-HSA)-Linker-(cleav. link.)-blocker2-L-(anti-EpCAM) |
| ACP148 | (anti-EpCAM)-L-IL2-(cleav. link.)-(anti-HSA)-L-(cleav. Linker)-blocker2 |
| ACP149 | (anti-EpCAM)-(cleav. link.)-IL2-(cleav. Linker)-(anti-HSA)-L-(cleav. Linker)-blocker2 |
| ACP31 | (anti-HSA)-(cleav. link.)-mIFNa1-(cleav. link.)-(anti-HSA) |
| ACP32 | (anti-HSA)-(cleav. link.)-mIFNa1(N + C trunc)-(cleav. link.)-(anti-HSA) |
| ACP33 | (anti-HSA)-(cleav. link.)-mIFNa1(C trunc)-(cleav. link.)-(anti-HSA) |
| ACP131 | mIFNa1 |
| ACP125 | Anti-HSA-(cleav. link.)-mIFNa1 |
| ACP126 | mIFNa1-(cleav. link.)-(anti-HSA) |
| ACP127 | Mouse_Albumin-(cleav. Link.)-mIFNa1-(cleav link)-mouse_Albumin |
| ACP128 | Mouse_Albumin-(cleav. link.)-mIFNa1 |
| ACP129 | mIFNa1-(cleav. link.)-mAlb |
| ACP150 | (Anti-FOLR1)-L-(anti-HSA)-(cleav. Link.)-mIFNa1-(cleav. Link.)-(anti-HSA) |
| ACP151 | Anti-FOLR1-L-(anti-HSA)-(cleav. Link.)-mIFNa1-(cleav. Link.)-(anti-HSA)-L-(anti-FLOR1) |
| ACP152 | (anti-HSA)-L-mIFNa1-L-(anti-HSA)_(non-cleavable_control) |
| ACP153 | IL2-(cleav. link.)-(anti-HSA)-linker(cleav. link.)-blocker2 |
| ACP154 | IL2-(cleav. link.)-(anti-HSA)-linker(cleav. link.)-blocker2 |
| ACP155 | IL2-(cleav. link.)-(anti-HSA)-linker(cleav. link.)-blocker2 |
| ACP156 | IL2-(cleav. link.)-(anti-HSA)-linker(cleav. link.)-blocker2 |
| ACP157 | IL2-(cleav. link.)-(anti-HSA)-linker(cleav. link.)-blocker2 |
| ACP200 | mAlb(D3)-X-mouse-IFNa-X-mAlb(D3)_(X = MMP9-M) |
| ACP201 | mAlb(D1-L-D3)-X-mouse-IFNa-X-mAlb(D1-L-D3)_(X = MMP9-M) |
| ACP202 | HSA-X-mIFNa1-X-HSA_(X = MMP9-M + 17aa) |
| ACP203 | HSA-X-mIFNa1-X-HSA_(X = MMP14-1) |
| ACP204 | HSA-X-mIFNa1-X-HSA_(X = CTSL1-1) |
| ACP205 | HSA-X-mIFNa1-X-HSA_(X = ADAM17-2) |
| ACP206 | HSA-X-Human_IFNA2b-X-HSA_(X = MMP14-1) |
| ACP207 | HSA-X-Human_IFNA2b-X-HSA_(X = CTSL1-1) |
| ACP208 | HSA-X-Human_IFNA2b-X-HSA_(X = ADAM17-2) |
| ACP211 | HSA-X-mouse-IFNg-X-IFNa-X-mouse-IFNg-X-HSA_(X = MMP9-M) |
| ACP213 | mAlb(D3)-X-mouse-IFNg-X-mAlb(D3)-X-mouse-IFNg-X-mAlb(D3)_(X = MMP9-M) |
| ACP214 | mAlb(D1-L-D3)-X-mouse-IFNg-X-mAlb(D1-L-D3)-X-mouse-IFNg-X-mAlb(D1-L-D3)_(X = MMP9-M) |
| ACP215 | HSA-X-mouse-IFNg-X-HSA-X-mouse-IFNg-X-HSA_(X = MMP9-M + 17aa) |

TABLE 3-continued

CONSTRUCT PERMUTATION TABLE ("6xHis" disclosed as SEQ ID NO: 354)

| Construct Name | Construct Description |
|---|---|
| ACP240 | HSA-L-human_p40-L-mouse_p35-LL-Blocker_(non-cleavable; Blocker = briakinumab_Vl/Vh) |
| ACP241 | mAlb-X-human_p40-L-mouse_p35-XL-Blocker_(X = MMP9-M; Blocker = briakinumab_Vl/Vh) |
| ACP242 | human_p40-L-mouse_p35-XL-Blocker-X-mAlb_(X = MMP9-M; Blocker = briakinumab_Vl/Vh) |
| ACP243 | mIgG1_Fc-X-human_p40-L-mouse_p35-XL-Blocker_(X = MMP9-M; Blocker = briakinumab_Vl/Vh) |
| ACP244 | human_p40-L-mouse_p35-XL-Blocker-X-mIgG1_Fc_(X = MMP9-M; Blocker = briakinumab_Vl/Vh) |
| ACP245 | HSA-X-human_p40-L-mouse_p35-XL-Blocker(cleavable)_(X = MMP9-M; Blocker = briakinumab_Vl-X-Vh) |
| ACP247 | HSA-X-human_p40-L-mouse_p35-XL-Blocker_(Blocker = 3CYT5; X = MMP9-M) |
| ACP284 | HSA-X-mouse_p35-XL-Blocker_(Blocker = briakinumab_Vl/Vh; X = MMP9-M) |
| ACP285 | HSA-X-human_p40_C199S-L-mouse_p35 C92S-XL-Blocker_(Blocker = briakinumab_Vl/Vh; X = MMP9-M) |
| ACP286 | HSA-X-human p40-L(4xG4S (SEQ ID NO: 453))-mouse p35-XL-Blocker_(Blocker = briakinumab_Vl/Vh; X = MMP9-M) |
| ACP287 | HSA-X-human_p40_mouse_p35-XL-Blocker_(Blocker = briakinumab_Vl/Vh_VH44-VL100_disulfide; X = MMP9-M) |
| ACP288 | HSA-X-human_p40_mouse_p35-XL-Blocker_(Blocker = briakinumab_Vl/Vh_VH105-VL43_disulfide; X = MMP9-M) |
| ACP289 | Geneart_WW0048_IL2-X-HSA-LX-blocker_Fusion_protein-6xHis |
| ACP290 | IL2-X-HSA-LX-blocker_(X = MMP9-M; Blocker = 3TOW69) |
| ACP291 | IL2-X-HSA-LX-blocker_(X = MMP9-M; Blocker = 3TOW85) |
| ACP292 | IL2-X-HSA-LX-blocker_(X = MMP9-M; Blocker = 2TOW91) |
| ACP296 | IL2-X-HSA-LX-blocker(cleavable)_(X = MMP9-M; Blocker = MT204_Vh-X-Vl) |
| ACP297 | IL2-X-HSA-LX-blocker(A46L)_(X = MMP9-M; Blocker = MT204_Vh/Vl) |
| ACP298 | IL2-X-HSA-LX-blocker(A46G)_(X = MMP9-M; Blocker = MT204_Vh/Vl) |
| ACP299 | IL2(Cysl45Ser)-X-HSA-LX-blocker_(X = MMP9-M; Blocker = MT204_Vh/Vl) |
| ACP300 | IL2-X-hAlb-LX-blocker_(X = MMP9-M; Blocker = MT204_Vh/Vl) |
| ACP302 | IL2-X-mAlb-LX-blocker_(X = MMP9-M; Blocker = MT204_Vh/Vl) |
| ACP303 | mAlb-X-IL2(Nterm-41)-X-mALB_(X = MMP9-M) |
| ACP304 | IL2-X-HSA-LX-blocker-XL-CD25ecd_(X = MMP9-M; Blocker = MT204_Vh/Vl) |
| ACP305 | CD25ecd-LX-IL2-X-HSA-LX-blocker_(X = MMP9-M; Blocker = MT204_Vh/Vl) |
| ACP306 | IL2-XL-CD25ecd-X-HSA-LX-blocker_(X = MMP9-M; Blocker = MT204_Vh/Vl) |
| ACP309 | IL2-X-HSA-LX-blocker(A46S)_(X = MMP9-M; Blocker = MT204_Vh/Vl) |
| ACP310 | IL2-X-HSA-LX-blocker(QAPRL_FR2)_(X = MMP9-M; Blocker = MT204_Vh/Vl) |
| ACP311 | IL2-X-IgG4_Fc(S228P)-LX-Blocker_(X = MMP9-M; Blocker = MT204_Vh/Vl) |
| ACP312 | IgG4_Fc(S228P)-X-IL2-LX-Blocker_(X = MMP9-M; Blocker = MT204_Vh/Vl) |
| ACP313 | IL2-XL-Blocker-X-IgG4_Fc(S228P)_(X = MMP9-M; Blocker = MT204_Vh/Vl) |
| ACP314 | mIgG1_Fc-X-IL2-LX-Blocker_(X = MMP9-M; Blocker = MT204_Vh/Vl) |
| ACP336 | IL2-X-anti-HSA-LX-blocker_(Blocker = VHVL.F2.high.A02_Vh-X-Vl_A46S; X = MMP14-1) |
| ACP337 | IL2-X-anti-HSA-LX-blocker_(Blocker = VHVL.F2.high.A02_Vh/Vl_A46S; X = MMP14-1) |
| ACP338 | IL2-X-anti-HSA-LX-blocker_(Blocker = VHVL.F2.high.F03_Vh-X-Vl; X = MMP14-1) |
| ACP339 | IL2-X-anti-HSA-LX-blocker_(Blocker = VHVL.F2.high.F03_Vh/Vl; X = MMP14-1) |
| ACP340 | IL2-X-anti-HSA-LX-blocker_(Blocker = Hu2TOW91_B; X = MMP14-1) |
| ACP341 | IL2-X-anti-HSA-LX-blocker_(Blocker = Hu3TOW85_A; X = MMP14-1) |
| ACP342 | CD25ecd_C213S-LX-IL2-X-anti-HSA-LX-blocker_(Blocker = VHVL.F2.high.A02_Vh-X-Vl_A46S; X = MMP14-1) |
| ACP343 | CD25ecd_C213S-LX-IL2-X-anti-HSA-LX-blocker_(Blocker = VHVL.F2.high.A02_Vh/Vl_A46S; X = MMP14-1) |
| ACP344 | CD25ecd_C213S-LX-IL2-X-anti-HSA-LX-blocker_(Blocker = VHVL.F2.high.F03_Vh-X-Vl; X = MMP14-1) |
| ACP345 | CD25ecd_C213S-LX-IL2-X-anti-HSA-LX-blocker_(Blocker = VHVL.F2.high.F03_Vh/Vl; X = MMP14-1) |
| ACP346 | CD25ecd_C213S-LX-IL2-X-anti-HSA-LX-blocker_(Blocker = Hu2TOW91_B; X = MMP14-1) |
| ACP347 | CD25ecd_C213S-LX-IL2-X-anti-HSA-LX-blocker_(Blocker = Hu3TOW85_A; X = MMP14-1) |
| ACP348 | IgG4_Fc(S228P)-X-IL2-LX-Blocker_(Blocker = VHVL.F2.high.A02_Vh-X-Vl_A46S; X = MMP14-1) |
| ACP349 | IgG4_Fc(S228P)-X-IL2-LX-Blocker_(Blocker = VHVL.F2.high.A02_Vh\Vl_A46S; X = MMP14-1) |
| ACP350 | IgG4_Fc(S228P)-X-IL2-LX-Blocker_(Blocker = VHVL.F2.high.F03_Vh-X-Vl; X = MMP14-1) |
| ACP351 | IgG4_Fc(S228P)-X-IL2-LX-Blocker (Blocker = VHVL.F2.high.F03_Vh\Vl; X = MMP14-1) |

TABLE 3-continued

| Construct Name | Construct Description |
|---|---|
| | CONSTRUCT PERMUTATION TABLE ("6xHis" disclosed as SEQ ID NO: 354) |
| ACP352 | IgG4_Fc(S228P)-X-IL2-LX-Blocker_(Blocker = Hu2TOW91_B; X = MMP14-1) |
| ACP353 | IgG4_Fc(S228P)-X-IL2-LX-Blocker_(Blocker = Hu3TOW85_A; X = MMP14-1) |
| ACP354 | IgG4_Fc(S228P)-X-CD25ecd_C213S-LX-IL2-LX-Blocker_(Blocker = VHVL.F2.high.A02_Vh-X-Vl_A46S; X = MMP14-1) |
| ACP355 | IgG4_Fc(S228P)-X-CD25ecd_C213S-LX-IL2-LX-Blocker_(Blocker = VHVL.F2.high.A02_Vh\Vl_A46S; X = MMP14-1) |
| ACP356 | IgG4_Fc(S228P)-X-CD25ecd_C213S-LX-IL2-LX-Blocker_(Blocker = VHVL.F2.high.F03_Vh-X-Vl; X = MMP14-1) |
| ACP357 | IgG4_Fc(S228P)-X-CD25ecd_C213S-LX-IL2-LX-Blocker_(Blocker = VHVL.F2.high.F03_Vh\Vl; X = MMP14-1) |
| ACP358 | IgG4_Fc(S228P)-X-CD25ecd_C213S-LX-IL2-LX-Blocker_(Blocker = Hu2TOW91_B; X = MMP14-1) |
| ACP359 | IgG4_Fc(S228P)-X-CD25ecd_C213S-LX-IL2-LX-Blocker_(Blocker = Hu3TOW85_A; X = MMP14-1) |
| ACP371 | IL2-X-anti-HSA-LX-blocker_(Blocker = MT204_Vh/Vl_VH44-VL100_disulfide; X = MMP14-1) |
| ACP372 | IL2-X-anti-HSA-LX-blocker_(Blocker = MT204_Vh/Vl_VH105-VL43_disulfide; X = MMP14-1) |
| ACP373 | IL2-X-anti-HSA-LX-blocker_(Blocker = VHVL.F2.high.A02_Vh/Vl_VH44-VL100_disulfide; X = MMP14-1) |
| ACP374 | IL2-X-anti-HSA-LX-blocker_(Blocker = VHVL.F2.high.A02_Vh/Vl_VH105-VL43_disulfide; X = MMP14-1) |
| ACP375 | IL2-X-anti-HSA-LX-blocker_(Blocker = VHVL.F2.high.F03_Vh/Vl_VH44-VL100_disulfide; X = MMP14-1) |
| ACP376 | IL2-X-anti-HSA-LX-blocker_(Blocker = VHVL.F2.high.F03_Vh/Vl_VH105-VL43_disulfideX = MMP14-1) |
| ACP377 | IL2-X-anti-HSA-LX-blocker_(Blocker = Hu2TOW91_A; X = MMP14-1) |
| ACP378 | IL2-X-anti-HSA-LX-Heavy_blocker_Fab_(Blocker = MT204_VH-CH1; X = MMP14-1) |
| ACP379 | IgG4_Fc(S228P)-X-IL2-LX-Heavy_blocker_Fab_(Blocker = MT204_VH-CH1; X = MMP14-1) |
| ACP383 | IgG4_Fc(S228P)-X-IL2-LX-blocker_(Blocker = MT204_Vh/Vl_VH44-VL100_disulfide; X = MMP14-1) |
| ACP384 | IgG4_Fc(S228P)-X-IL2-LX-blocker_(Blocker = MT204_Vh/Vl_VH105-VL43_disulfide; X = MMP14-1) |
| ACP385 | IgG4_Fc(S228P)-X-IL2-LX-blocker_(Blocker = VHVL.F2.high.A02_Vh/Vl_VH44-VL100_disulfide; X = MMP14-1) |
| ACP386 | IgG4_Fc(S228P)-X-IL2-LX-blocker_(Blocker = VHVL.F2.high.A02_Vh/Vl_VH105-VL43_disulfide; X = MMP14-1) |
| ACP387 | IgG4_Fc(S228P)-X-IL2-LX-blocker_(Blocker = VHVL.F2.high.F03_Vh/Vl_VH44-VL100_disulfide; X = MMP14-1) |
| ACP388 | IgG4_Fc(S228P)-X-IL2-LX-blocker_(Blocker = VHVL.F2.high.F03_Vh/Vl_VH105-VL43_disulfide; X = MMP14-1) |
| ACP389 | IgG4_Fc(S228P)-X-IL2-LX-blocker_(Blocker = Hu2TOW91_A; X = MMP14-1) |
| ACP390 | IL2-X-anti-HSA-LX-blocker_(Blocker = VHVL.F2.high.A02_Vh/Vl_A46S_VH44-VL100_disulfide; X = MMP14-1) |
| ACP391 | IgG4_Fc(S228P)-X-IL2-LX-blocker_(Blocker = VHVL.F2.high.A02_Vh/Vl_A46S_VH44-VL100_disulfide; X = MMP14-1) |
| ACP392 | IL2-XL-CD25ecd_C213S-X-HSA-LX-blocker_(Blocker = VHVL.F2.high.A02_Vh_G44C_Vl_A46S_G100C; X = MMP14-1) |
| ACP393 | IL2-XL-CD25ecd_C213S-X-HSA-LX-blocker_(Blocker = VHVL.F2.high.A02_Vh_Q105C_Vl_A43C; X = MMP14-1) |
| ACP394 | IL2-XL-CD25ecd_C213S-X-HSA-LX-blocker_(Blocker = VHVL.F2.high.F03_Vh_G44C_Vl_G100C; X = MMP14-1) |
| ACP395 | IL2-XL-CD25ecd_C213S-X-HSA-LX-blocker_(Blocker = VHVL.F2.high.F03_Vh_Q105C_Vl_A43C; X = MMP14-1) |
| ACP396 | IL2-XL-CD25ecd_C213S-X-HSA-LX-blocker_(Blocker = Hu2TOW91_A; X = MMP14-1) |
| ACP397 | IL2-XL-CD25ecd_C213S-X-HSA-LX-blocker_(Blocker = Hu2TOW91_B; X = MMP14-1) |
| ACP398 | IL2-XL-CD25ecd_C213S-X-HSA-LX-Heavy_blocker_Fab_(Blocker = MT204_VH-CH1; X = MMP14-1) |
| ACP399 | Blocker-XL-HSA-X-IL2(Nterm-41)-X-HSA)_(Blocker = VHVL.F2.high.A02_Vh_G44C_Vl_A46S_G100C; X = MMP14-1) |
| ACP400 | Blocker-XL-HSA-X-IL2(Nterm-41)-X-HSA_(Blocker = VHVL.F2.high.A02_Vh_Q105C_Vl_A43C; X = MMP14-1) |
| ACP401 | Blocker-XL-HSA-X-IL2(Nterm-41)-X-HSA_(Blocker = VHVL.F2.high.F03_Vh_G44C_Vl_G100C; X = MMP14-1) |
| ACP402 | Blocker-XL-HSA-X-IL2(Nterm-41)-X-HSA_(Blocker = VHVL.F2.high.F03_Vh_Q105C_Vl_A43C; X = MMP14-1) |
| ACP403 | Blocker-XL-HSA-X-IL2(Nterm-41)-X-HSA_(Blocker = Hu2TOW91_A; X = MMP14-1) |
| ACP404 | Blocker-XL-HSA-X-IL2(Nterm-41)-X-HSA_(Blocker = Hu2TOW91_B; X = MMP14-1) |
| ACP405 | Heavy_Blocker_Fab-XL-HSA-X-IL2(Nterm-41)-X-HSA_(Blocker = MT204_VH-CH1; X = MMP14-1) |
| ACP406 | mIgG1_Fc(S228P)-X-IL2-LX-Heavy_blocker_Fab_(Blocker = MT204_VH-CH1; X = MMP14-1) |
| ACP407 | mIgG1_Fc(S228P)-X-IL2-LX-blocker_(Blocker = VHVL.F2.high.A02_Vh/Vl_VH44-VL100_disulfide; X = MMP14-1) |
| ACP408 | mIgG1_Fc(S228P)-X-IL2-LX-blocker_(Blocker = VHVL.F2.high.A02_Vh/Vl_A46S_VH44-VL100_disulfide; X = MMP14-1) |

TABLE 3-continued

| Construct Name | Construct Description |
|---|---|
| | CONSTRUCT PERMUTATION TABLE ("6xHis" disclosed as SEQ ID NO: 354) |
| ACP409 | mIgG1_Fc(S228P)-X-IL2-LX-blocker_(Blocker = VHVL.F2.high.A02_Vh/Vl_VH105-VL43_disulfidel; X = MMP14-1) |
| ACP410 | mIgG1_Fc(S228P)-X-IL2-LX-blocker_(Blocker = VHVL.F2.high.F03_Vh/Vl_VH44-VL100_disulfidel; X = MMP14-1) |
| ACP411 | mIgG1_Fc(S228P)-X-IL2-LX-blocker_(Blocker = VHVL.F2.high.F03_Vh/Vl_VH105-VL43_disulfidel; X = MMP14-1) |
| ACP412 | mIgG1_Fc(S228P)-X-IL2-LX-blocker_(Blocker = Hu2TOW91_A; X = MMP14-1) |
| ACP413 | CD25_213S-L-Kappa_blocker_Fab_(Blocker = VHVL.F2.high.A02_A46S_Kappa) |
| ACP414 | CD25_213S-L-Kappa_blocker_Fab_(Blocker = VHVL.F2.high.F03_Kappa) |
| ACP415 | IL2-XL-blocker-L-CD25_213S-X-HSA_Blocker = VHVL.F2.high.A02_Vh_G44C_Vl_A46S_G100C; X = MMP14-1) |
| ACP416 | IL2-XL-blocker-L-CD25_213S-X-HSA_(Blocker = VHVL.F2.high.A02_Vh_Q105C_Vl_A43C; X = MMP14-1) |
| ACP417 | IL2-XL-blocker-L-CD25_213S-X-HSA_(Blocker = VHVL.F2.high.F03_Vh_G44C_Vl_G100C; X = MMP14-1) |
| ACP418 | IL2-XL-blocker-L-CD25_213S-X-HSA_(Blocker = VHVL.F2.high.F03_Vh_Q105C_Vl_A43C; X = MMP14-1) |
| ACP419 | IL2-XL-blocker-L-CD25_213S-X-HSA_(Blocker = Hu2TOW91_A; X = MMP14-1) |
| ACP420 | IL2-XL-blocker-L-CD25_213S-X-HSA_(Blocker = Hu2TOW91_B; X = MMP14-1) |
| ACP421 | HSA-X-blocker-L-CD25_213S-LX-IL2_(Blocker = VHVL.F2.high.A02_Vh_G44C_Vl_A46S_G100C; X = MMP14-1) |
| ACP422 | HSA-X-blocker-L-CD25_213S-LX-IL2_(Blocker = VHVL.F2.high.A02_Vh_Q105C_Vl_A43C; X = MMP14-1) |
| ACP423 | HSA-X-blocker-L-CD25_213S-LX-IL2_(Blocker = VHVL.F2.high.F03_Vh_G44C_Vl_G100C; X = MMP14-1) |
| ACP424 | HSA-X-blocker-L-CD25_213S-LX-IL2_(Blocker = VHVL.F2.high.F03_Vh_Q105C_Vl_A43C; X = MMP14-1) |
| ACP425 | HSA-X-blocker-L-CD25_213S-LX-IL2_(Blocker = Hu2TOW91_A; X = MMP14-1) |
| ACP426 | HSA-X-blocker-L-CD25_213S-LX-IL2_(Blocker = Hu2TOW91_B; X = MMP14-1) |
| ACP427 | IL2-X-anti-HSA-LX-Blocker1-L-Blocker2_(Blocker1 = VHVL.F2.high.A02_Vh_G44C_Vl_A46S_G100C, Blocker2 = Hu2TOW91_A; X = MMP14-1) |
| ACP428 | IL2-X-anti-HSA-LX-Blocker1-L-Blocker2_(Blocker1 = VHVL.F2.high.A02_Vh_Q105C_Vl_A43C, Blocker2 = Hu2TOW91_A; X = MMP14-1) |
| ACP429 | IL2-X-anti-HSA-LX-Blocker1-L-Blocker2_(Blocker1 = VHVL.F2.high.F03_Vh_G44C_Vl_G100C, Blocker2 = Hu2TOW91_A; X = MMP14-1) |
| ACP430 | IL2-X-anti-HSA-LX-Blocker1-L-Blocker2_(Blocker1 = VHVL.F2.high.F03_Vh_Q105C_Vl_A43C, Blocker2 = Hu2TOW91_A; X = MMP14-1) |
| ACP431 | IL2-X-anti-HSA-LX-Blocker1-L-Blocker2_(Blocker1 = VHVL.F2.high.A02_Vh_G44C_Vl_A46S_G100C, Blocker2 = Hu2TOW91_B; X = MMP14-1) |
| ACP432 | IL2-X-anti-HSA-LX-Blocker1-L-Blocker2_(Blocker1 = VHVL.F2.high.A02_Vh_Q105C_Vl_A43C, Blocker2 = Hu2TOW91_B; X = MMP14-1) |
| ACP433 | IL2-X-anti-HSA-LX-Blocker1-L-Blocker2_(Blocker1 = VHVL.F2.high.F03_Vh_G44C_Vl_G100C, Blocker2 = Hu2TOW91_B; X = MMP14-1) |
| ACP434 | IL2-X-anti-HSA-LX-Blocker1-L-Blocker2_(Blocker1 = VHVL.F2.high.F03_Vh_Q105C_Vl_A43C, Blocker2 = Hu2TOW91_B; X = MMP14-1) |
| ACP439 | IL2-X-anti-HSA-LX-blocker_(Blocker = VHVL.F2.high.C07_Vh/Vl; X = MMP14-1) |
| ACP440 | IL2-X-anti-HSA-LX-blocker_(Blocker = VHVL.F2.high.C07_Vh/Vl_A46S; X = MMP14-1) |
| ACP441 | IL2-X-anti-HSA-LX-blocker_(Blocker = VHVL.F2.high.C07_Vh/Vl_A46L; X = MMP14-1) |
| ACP442 | IL2-X-anti-HSA-LX-blocker_(Blocker = VHVL.F2.high.C07_Vh/Vl_A46S_VH44-VL100_disulfide; X = MMP14-1) |
| ACP443 | IL2-X-anti-HSA-LX-blocker_(Blocker = VHVL.F2.high.C07_Vh/Vl_A46L_VH44-VL100_disulfide; X = MMP14-1) |
| ACP444 | IL2-X-anti-HSA-LX-blocker_(Blocker = VHVL.F2.high.C07_Vh/Vl_VH105-VL43_disulfide; X = MMP14-1) |
| ACP445 | IL2-X-anti-HSA-LX-blocker_(Blocker = VHVL.F2.high.A02_Vh-X-Vl_A46L; X = MMP14-1) |
| ACP446 | IL2-X-anti-HSA-LX-blocker_(Blocker = VHVL.F2.high.A02_Vh/Vl_A46L; X = MMP14-1) |
| ACP447 | IL2-X-anti-HSA-LX-blocker_(Blocker = VHVL.F2.high.A02_Vh/Vl_A46L_VH44-VL100_disulfide; X = MMP14-1) |
| ACP451 | IL2-X-anti-HSA-LX-blocker_(Blocker = VHVL.F2.high.A02_Vh/Vl_A46S; X = CTSL1-1) |
| ACP452 | IL2-X-anti-HSA-LX-blocker_(Blocker = VHVL.F2.high.F03_Vh/Vl; X = CTSL1-1) |
| ACP453 | IL2-X-anti-HSA-LX-blocker_(Blocker = VHVL.F2.high.A02_Vh/Vl_A46S_VH44-VL100_disulfide; X = CTSL1-1) |

TABLE 3-continued

CONSTRUCT PERMUTATION TABLE ("6xHis" disclosed as SEQ ID NO: 354)

| Construct Name | Construct Description |
| --- | --- |
| ACP454 | IL2-X-anti-HSA-LX-blocker_(Blocker = VHVL.F2.high.A02_Vh/Vl_VH105-VL43_disulfidel; X = CTSL1-1) |
| ACP455 | IL2-X-anti-HSA-LX-blocker_(Blocker = VHVL.F2.high.F03_Vh/Vl_VH44-VL100_disulfide; X = CTSL1-1) |
| ACP456 | IL2-X-anti-HSA-LX-blocker_(Blocker = VHVL.F2.high.F03_Vh/Vl_VH105-VL43_disulfideX = CTSL 1-1) |
| ACP457 | IL2-X-anti-HSA-LX-Heavy_blocker_Fab_(Blocker = MT204_VH-CH1; X = CTSL1-1) |
| ACP458 | IgG4_Fc(S228P)-X-IL2-LX-Heavy_blocker_Fab_(Blocker = MT204_VH-CH1; X = CTSL1-1) |
| ACP459 | IgG4_Fc(S228P)-X-IL2-LX-Blocker_(Blocker = VHVL.F2.high.A02_Vh\Vl_A46S; X = CTSL1-1) |
| ACP460 | IgG4_Fc(S228P)-X-IL2-LX-Blocker_(Blocker = VHVL.F2.high.F03_Vh\Vl; X = CTSL1-1) |
| ACP461 | IgG4_Fc(S228P)-X-IL2-LX-blocker_(Blocker = VHVL.F2.high.A02_Vh/Vl_A46S_VH44-VL100_disulfide; X = CTSL1-1) |
| ACP462 | IgG4_Fc(S228P)-X-IL2-LX-blocker_(Blocker = VHVL.F2.high.A02_Vh/Vl_VH105-VL43_disulfidel; X = CTSL1-1) |
| ACP463 | IgG4_Fc(S228P)-X-IL2-LX-blocker_(Blocker = VHVL.F2.high.F03_Vh/Vl_VH44-VL100_disulfidel; X = CTSL1-1) |
| ACP464 | IgG4_Fc(S228P)-X-IL2-LX-blocker_(Blocker = VHVL.F2.high.F03_Vh/Vl_VH105-VL43_disulfidel; X = CTSL1-1) |
| ACP465 | mIgG1_Fc-X-IL2-LX-Blocker_(Blocker = VHVL.F2.high.A02_Vh\Vl_A46S; X = CTSL1-1) |
| ACP466 | mIgG1_Fc-X-IL2-LX-Blocker_(Blocker = VHVL.F2.high.F03_Vh\Vl; X = CTSL1-1) |
| ACP467 | mIgG1_Fc-X-IL2-LX-blocker_(Blocker = VHVL.F2.high.A02_Vh/Vl_A46S_VH44-VL100_disulfide; X = CTSL1-1) |
| ACP468 | mIgG1_Fc-X-IL2-LX-blocker_(Blocker = VHVL.F2.high.A02_Vh/Vl_VH105-VL43_disulfidel; X = CTSL1-1) |
| ACP469 | mIgG1_Fc-X-IL2-LX-blocker_(Blocker = VHVL.F2.high.F03_Vh/Vl_VH44-VL100_disulfidel; X = CTSL1-1) |
| ACP470 | mIgG1_Fc-X-IL2-LX-blocker_(Blocker = VHVL.F2.high.F03_Vh/Vl_VH105-VL43_disulfidel; X = CTSL1-1) |
| ACP471 | mIgG1_Fc-X-IL2-LX-Heavy_blocker_Fab_(Blocker = MT204_VH-CH1; X = CTSL1-1) |

SEQUENCE TABLE

| SEQ ID NO. | Name | Sequence |
|---|---|---|
| 1 | Human IL-2 | MYRMQLLSCI ALSLALVTNS APTSSSTKKT QLQLEHLLLD LQMILNGINN YKNPKLTRML TFKFYMPKKA TELKHLQCLE EELKPLEEVL NLAQSKNFHL RPRDLISNIN VIVLELKGSE TTFMCEYADE TATIVEFLNR WITFCQSIISTLT |
| 2 | Human serum albumin | MKWVTFISLL FLFSSAYSRG VFRRDAHKSE VAHRFKDLGE ENFKALVLIA FAQYLQQCPF EDHVKLVNEV TEFAKTCVAD ESAENCDKSL HTLFGDKLCT VATLRETYGE MADCCAKQEP ERNECFLQHK DDNPNLPRLV RPEVDVMCTA FHDNEETFLK KYLYEIARRH PYFYAPELLF FAKRYKAAFT ECCQAADKAA CLLPKLDELR DEGKASSAKQ GLKCASLQKF GERAFKAWAV ARLSQRFPKA EFAEVSKLVT DLTKVHTECC HGDLLECADD RADLAKYICE NQDSISSKLK ECCEKPLLEK SHCIAEVEND EMPADLPSLA ADFVGSKDVC KNYAEAKDVF LGMFLYEYAR RHPDYSVVLL LRLAKTYETT LEKCCAAADP HECYAKVFDE FKPLVEEPQN LIKQNCELFE QLGEYKFQNA LLVRYTKKVP QVSTPTLVEV SRNLGKVGSK CCKHPEAKRM PCAEDCLSVF LNQLCVLHEK TPVSDRVTKC CTESLVNGRPCFSALEVDETYVPKEFNAETFTFHADICTLSEKERQIKKQTALV ELVKHK PKATKEQLKAVMDDFAAFVEKCCKADDKET CFAEEGKKLVAASQAALGL |
| 45 | ACP12 (IL2 fusion protein) | QVQLQESGGGLVQAGGSLRLSCAASGRIFSIDIMSWYRQAPGKQRELVARITRG GTISYDDSVKGRFTISRDNAKNTVYLQMNSLKPEDTGVYYCNALYGTDYWGKG TQVTVSSggggsggggsggggsaptssstkktqlqlehlllqmilnginnyknpkltrmltfkfympkkatelkhlq cleeelkpleevlnlaqsknfhlrprdlisninvivlelkgsettfmceyadetativeflnrwritfcgsiistltSGGPGPAG MKGLPGSEVQLVESGGGLVQPGNSLRLSCAASGFTFSKFGMSWVRQAPGKGLE WVSSISGSGRDTLYAESVKGRFTISRDNAKTTLYLQMNSLRPEDTAVYYCTIGGS LSVSSQGTLVTVSSggggsggggsggggsEVQLVESGGGLVQPGGSLRLSCAASGFTFS SYTLAWVRQAPGKGLEWVAAIDSSSYTYSPDTVRGRFTISRDNAKNSLYLQMNS LRAEDTAVYYCARDSNWDALDYWGQGTTVTVSSGGGGSGGGGSGGGGSDIQM TQSPSSLSASVGDRVTITCKASQNVGTNVGWYQQKPGKAPKALIYSASFRYSGV PSRFSGSGSGTDFTLTISSLQPEDFATYYCQQYYTYPYTFGGGTKVEIKHHHHHH |
| 46 | ACP13 (IL2 fusion protein) | QVQLQESGGGLVQAGGSLRLSCAASGRIFSIDIMSWYRQAPGKQRELVARITRG GTISYDDSVKGRFTISRDNAKNTVYLQMNSLKPEDTGVYYCNALYGTDYWGKG TQVTVSSggggsggggsggggsEVQLVESGGGLVQPGGSLRLSCAASGFTFSSYTLAW VRQAPGKGLEWVAAIDSSSYTYSPDTVRGRFTISRDNAKNSLYLQMNSLRAEDT AVYYCARDSNWDALDYWGQGTTVTVSSGGGGSGGGGSGGGGSDIQMTQSPSS LSASVGDRVTITCKASQNVGTNVGWYQQKPGKAPKALIYSASFRYSGVPSRFSG SGSGTDFTLTISSLQPEDFATYYCQQYYTYPYTFGGGTKVEIKggggsggggsggggsE VQLVESGGGLVQPGNSLRLSCAASGFTFSKFGMSWVRQAPGKGLEWVSSISGSG RDTLYAESVKGRFTISRDNAKTTLYLQMNSLRPEDTAVYYCTIGGSLSVSSQGTL VTVSSSGGPGAGMKGLPGSaptssstktqlqlehlllqmilnginnyknpkltrmltfkfympkkatel khlqcleeelkpleevlnlaqsknfhlrprdlisninvivlelkgsettfmceyadetativeflnrwitfcqsiistltHHHHH H |
| 47 | ACP14 (IL2 fusion protein) | EVQLVESGGGLVQPGGSLRLSCAASGFTFSSYTLAWVRQAPGKGLEWVAAIDSS SYTYSPDTVRGRFTISRDNAKNSLYLQMNSLRAEDTAVYYCARDSNWDALDYW GQGTTVTVSSGGGGSGGGGSGGGGSDIQMTQSPSSLSASVGDRVTITCKASQNV GTNVGWYQQKPGKAPKALIYSASFRYSGVPSRFSGSGSGTDFTLTISSLQPEDFA |

-continued

SEQUENCE TABLE

| SEQ ID NO. | Name | Sequence |
|---|---|---|
| | | TYYCQQYYTYPYTFGGGTKVEIKggggsgggsgggsgggsgggsgggsgggsSGGPGPAGM<br>KGLPGSaptssstkktqlqlehllldlqmilnginnyknpkltrmltfkfympkkatelkhlqcleeelkpleevlnlaqsk<br>nfhlrpdlisninivivlelkgsettfmceyadetativeflnrwitfcqsiisltsGGPGPAGMKGLPGSEVQL<br>VESGGGLVQPGNSLRLSCAASGFTFSKFGMSWVRQAPGKGLEWVSSISGSGRDT<br>LYAESVKGRFTISRDNAKTTLYLQMNSLRPEDTAVYYCTIGGSLSVSSQGTLVTV<br>SSHHHHHH |
| 48 | ACP15<br>(IL2<br>fusion<br>protein) | EVQLVESGGGLVQPGGSLRLSCAASGFTFSSYTLAWRQAPGKGLEWVAAIDSS<br>SYTYSPDTVRGRFTISRDNAKNSLYLQMNSLRAEDTAVYYCARDSNWDALDYW<br>GQGTTVTVSSGGGGSGGGGSGGGGSDIQMTQSPSSLSASVGDRVTITCKASQNV<br>GTNVGWYQQKPGKAPKALIYSASFRYSGVPSRFSGSGSGTDFTLTISSLQPEDFA<br>TYYCQQYYTYPYTFGGGTKVEIKggggsgggsgggsgggsgggsgggsgggsEVQLVESGG<br>GLVQPGNSLRLSCAASGFTFSKFGMSWVRQAPGKGLEWVSSISGSGRDTLYAES<br>VKGRFTISRDNAKTTLYLQMNSLRPEDTAVYYCTIGGSLSVSSQGTLVTVSSgggg<br>sgggsggggSGGPGPAGMKGLPGSaptssstkktqlqlehllldlqmilnginnyknpkltrmltfkfympk<br>katelkhlqcleeelkpleevlnlaqsknfhlrpdlisninivivlelkgsettfmceyadetativeflnrwitfcqsiisltHH<br>HHHH |
| 49 | ACP16<br>(IL2<br>fusion<br>protein) | aptssstkktqlqlehllldlqmilnginnyknpkltrmltfkfympkkatelkhlqcleeelkpleevlnlaqsknfhlrprdli<br>sninivivlelkgsettfmceyadetativeflnrwitfcqsiisltsGGPGPAGMKGLPGSEVQLVESGGG<br>LVQPGNSLRLSCAASGFTFSKFGMSWVRQAPGKGLEWVSSISGSGRDTLYAESV<br>KGRFTISRDNAKTTLYLQMNSLRPEDTAVYYCTIGGSLSVSSQGTLVTVSSggggsg<br>ggggsgggsggggsgggsSGGPGPAGMKGLPGSEVQLVESGGGLVQPGGSLRLS<br>CAASGFTFSSYTLAWVRQAPGKGLEWVAAIDSSSYTYSPDTVRGRFTISRDNAK<br>NSLYLQMNSLRAEDTAVYYCARDSNWDALDYWGQGTTVTVSSGGGGSGGGGS<br>GGGGSDIQMTQSPSSLSASVGDRVTITCKASQNVGTNVGWYQQKPGKAPKALIY<br>SASFRYSGVPSRFSGSGSGTDFTLTISSLQPEDFATYYCQQYYTYPYTFGGGTKV<br>EIKHHHHHH |
| 50 | ACP17<br>(IL2<br>fusion<br>protein) | QVQLQESGGGLVQAGGSLRLSCAASGRIFSIDIMSWYRQAPGKQRELVARITRG<br>GTISYDDSVKGRFTISRDNAKNTVYLQMNSLKPEDTGVYYCNALYGTDYWGKG<br>TQVTVSSggggsgggsggggsaptssstkktqlqlehllldlqmilnginnyknpkltrmltfkfympkkatelkhlq<br>cleeelkpleevlnlaqsknfhlrpdlisninivivlelkgsettfmceyadetativeflnrwitfcqsiisltsGGPGPAG<br>MKGLPGSEVQLVESGGGLVQPGNSLRLSCAASGFTFSKFGMSWVRQAPGKGLE<br>WVSSISGSGRDTLYAESVKGRFTISRDNAKTTLYLQMNSLRPEDTAVYYCTIGGS<br>LSVSSQGTLVTVSSggggsgggsggggsgggsggggsSGGPGPAGMKGLPGSEVQ<br>LVESGGGLVQPGGSLRLSCAASGFTFSSYTLAWVRQAPGKGLEWVAAIDSSSYT<br>YSPDTVRGRFTISRDNAKNSLYLQMNSLRAEDTAVYYCARDSNWDALDYWGQ<br>GTTVTVSSGGGGSGGGGSGGGGSDIQMTQSPSSLSASVGDRVTITCKASQNVGT<br>NVGWYQQKPGKAPKALIYSASFRYSGVPSRFSGSGSGTDFTLTISSLQPEDFATY<br>YCQQYYTYPYTFGGGTKVEIKHHHHHH |
| 51 | ACP18<br>(IL2<br>fusion<br>protein) | QVQLQESGGGLVQAGGSLRLSCAASGRIFSIDIMSWYRQAPGKQRELVARITRG<br>GTISYDDSVKGRFTISRDNAKNTVYLQMNSLKPEDTGVYYCNALYGTDYWGKG<br>TQVTVSSggggsgggsggggsaptssstkktqlqlehllldlqmilnginnyknpkltrmltfkfympkkatelkhlq<br>cleeelkpleevlnlaqsknfhlrpdlisninivivlelkgsettfmceyadetativeflnrwitfcqsiisltsGGPGPAG<br>MKGLPGSEVQLVESGGGLVQPGNSLRLSCAASGFTFSKFGMSWVRQAPGKGLE<br>WVSSISGSGRDTLYAESVKGRFTISRDNAKTTLYLQMNSLRPEDTAVYYCTIGGS |

-continued

SEQUENCE TABLE

| SEQ ID NO. | Name | Sequence |
| --- | --- | --- |
| 52 | ACP19 (IL2 fusion protein) | LSVSSQGTLVTVSSgggggggggggggggggggggggggggggggggggEVQLVESGGGLVQPGGSLR<br>LSCAASGFTFSSYTLAWVRQAPGKGLEWVAAIDSSYTYSPDTVRGRFTISRDNA<br>KNSLYLQMNSLRAEDTAVYYCARDSNWDALDYWGQGTTVTVSSsggpgpagmkgl<br>pgsDIQMTQSPSSLSASVGDRVTITCKASQNVGTNVGWYQQKPGKAPKALIYSAS<br>FRYSGVPSRFSGSGSGTDFTLTISSLQPEDFATYYCQQYYTYPYTFGGGTKVEIKH<br>HHHHH |
| 53 | ACP20 (IL2 fusion protein) | aptssstkktqlqlehllldlqmilnginnyknpkltrmltfkfympkkatelkhlqcleeelkpleevlnlaqsknfhlrprdli<br>sninivivlelkgsettfmceyadetativeflnrwitfcqsiisltsGGPGPAGMKGLPGSgggggggggggggggs<br>gggggggggggggsEVQLVESGGGLVQPGGSLRLSCAASGFTFSSYTLAWVRQAPGK<br>GLEWVAAIDSSYTYSPDTVRGRFTISRDNAKNSLYLQMNSLRAEDTAVYYCAR<br>DSNWDALDYWGQGTTVTVSSGGGGSGGGGSGGGGSDIQMTQSPSSLSASVGDR<br>VTITCKASQNVGTNVGWYQQKPGKAPKALIYSASFRYSGVPSRFSGSGSGTDFT<br>LTISSLQPEDFATYYCQQYYTYPYTFGGGTKVEIKgggsgggggggggsEVQLVESGG<br>GLVQPGNSLRLSCAASGFTFSKFGMSWVRQAPGKGLEWVSSISGSGRDTLYAES<br>VKGRFTISRDNAKTTLYLQMNSLRPEDTAVYYCTIGGSLSVSSQGTLVTVSSgggg<br>sgggggggggsQVQLQESGGGLVQAGGSLRLSCAASGRIFSIDIMSWYRQAPGKQRE<br>LVARITRGGTISYDDSVKGRFTISRDNAKNTVYLQMNSLKPEDTGVYYCNALYG<br>TDYWGKGTQVTVSSHHHHHH** |
| 54 | ACP21 (IL2 fusion protein) | aptssstkktqlqlehllldlqmilnginnyknpkltrmltfkfympkkatelkhlqcleeelkpleevlnlaqsknfhlrprdli<br>sninivivlelkgsettfmceyadetativeflnrwitfcqsiisltsGGPGPAGMKGLPGSgggggggggggggggs<br>gggggggggggggsEVQLVESGGGLVQPGGSLRLSCAASGFTFSSYTLAWVRQAPGK<br>GLEWVAAIDSSYTYSPDTVRGRFTISRDNAKNSLYLQMNSLRAEDTAVYYCAR<br>DSNWDALDYWGQGTTVTVSSGGGGSGGGGSGGGGSDIQMTQSPSSLSASVGDR<br>VTITCKASQNVGTNVGWYQQKPGKAPKALIYSASFRYSGVPSRFSGSGSGTDFT<br>LTISSLQPEDFATYYCQQYYTYPYTFGGGTKVEIKHHHHHH |
| 55 | ACP22 (IL2 fusion protein) | aptssstkktqlqlehllldlqmilnginnyknpkltrmltfkfympkkatelkhlqcleeelkpleevlnlaqsknfhlrprdli<br>sninivivlelkgsettfmceyadetativeflnrwitfcqsiisltsGGPGPAGMKGLPGSgggggggggggggggs<br>gggggggggggggsEVQLVESGGGLVQPGGSLRLSCAASGFTFSSYTLAWVRQAPGK<br>GLEWVAAIDSSYTYSPDTVRGRFTISRDNAKNSLYLQMNSLRAEDTAVYYCAR<br>DSNWDALDYWGQGTTVTVSSGGGGSGGGGSGGGGSDIQMTQSPSSLSASVGDR<br>VTITCKASQNVGTNVGWYQQKPGKAPKALIYSASFRYSGVPSRFSGSGSGTDFT<br>LTISSLQPEDFATYYCQQYYTYPYTFGGGTKVEIKSSGGPAGMKGLPGSEVQL<br>VESGGGLVQPGNSLRLSCAASGFTFSKFGMSWVRQAPGKGLEWVSSISGSGRDT<br>LYAESVKGRFTISRDNAKTTLYLQMNSLRPEDTAVYYCTIGGSLSVSSQGTLVTV<br>SSggggsgggggggggsQVQLQESGGGLVQAGGSLRLSCAASGRIFSIDIMSWYRQAPG<br>KQRELVARITRGGTISYDDSVKGRFTISRDNAKNTVYLQMNSLKPEDTGVYYCN<br>ALYGTDYWGKGTQVTVSSHHHHHH |

-continued

SEQUENCE TABLE

| SEQ ID NO. | Name | Sequence |
|---|---|---|
| 56 | ACP23 (IL2 fusion protein) | QVQLQESGGGLAQAGGSLSLSCAASGFTVSNSVMAWYRQTPGKQREFVAIINSV GSTNYADSVKGRFTISRDNAKNTVVLQMNNLKPEDTAVYVCNRNFDRIYWGQG TQVTVSSSGGPGPAGMKGLPGSEVQLVESGGGLVQPGGSLRLSCAASGFTFSSY TLAWVRQAPGKGLEWVAAIDSSYTYSPDTVRGRFTISRDNAKNSLYLQMNSLR AEDTAVYYCARDSNWDALDYWGQGTTVTVSSGGGSGGGSGGGSDIQMT QSPSSLSASVGDRVTITCKASQNVGTNVGVYQQKPGKAPKALIYSASFRYSGVP SRFSGSGSGTDFTLTISSLQPEDFATYYCQQYTTYPYTFGGGTKVEIKgggsgggs gggsgggsgggsgggsgggsSGGPGPAGMKGLPGSEVQLVESGGGLVQPGNSLRLSCAA SGFTFSKFGMSWVRQAPGKGLEWVSSISGGSGRDTIYAESVKGRFTISRDNAKTT LYLQMNSLRPEDTAVYYCTIGGSLSLVSSSQGTLVTVSSSGGPGPAGMKGLPGSapts ssstktqlqehlldlqmilnginnyknpkltrmltfkfympkkatelkhlqcleeelkpleevlnlaqsknfhlrprdlisnin vivlelkgsettfmceyadetativeflnrwitfcqsiistlthHHHH |
| 57 | ACP24 (IL2 fusion protein) | EVQLVESGGGLVQPGGSLRLSCAASGFTFSSYTLAWVRQAPGKGLEWVAAIDSS SYTYSPDTVRGRFTISRDNAKNSLYLQMNSLRAEDTAVYYCARDSNWDALDYW GQGTTVTVSSGGGSGGGSGGGSDIQMTQSPSSLSASVGDRVTITCKASQNV GTNVGWYQQKPGKAPKALIYSASFRYSGVPSRFSGSGSGTDFTLTISSLQPEDFA TYYCQQYTTYPYTFGGGTKVEIKSGGPGPAGMKGLPGSaptssstktqlqlehlldlqmiln ginnyknpkltrmltfkfympkkatelkhlqcleeelkpleevlnlaqsknfhlrprdlisninvivlelkgsettfmceyade tativeflnrwitfcqsiistlthHHHH |
| 58 | ACP25 (IL2 fusion protein) | EVQLVESGGGLVQPGGSLRLSCAASGFTFSSYTLAWVRQAPGKGLEWVAAIDSS SYTYSPDTVRGRFTISRDNAKNSLYLQMNSLRAEDTAVYYCARDSNWDALDYW GQGTTVTVSSGGGSGGGSGGGSDIQMTQSPSSLSASVGDRVTITCKASQNV GTNVGWYQQKPGKAPKALIYSASFRYSGVPSRFSGSGSGTDFTLTISSLQPEDFA TYYCQQYTTYPYTFGGGTKVEIKgggsgggsgggsgggsgggsgggsgggSGGPGPAGM KGLPGSaptssstktqlqlehlldlqmilnginnyknpkltrmltfkfympkkatelkhlqcleeelkpleevlnlaqsk nfhlrprdlisninvivlelkgsettfmceyadetativeflnrwitfcqsiistlthHHHH |
| 59 | ACP26 (IL2 fusion protein) | QVQLQESGGGLVQAGGSLRLSCAASGRIFSIDIMSWYRQAPGKQRELVARITRG GTISYDDSVKGRFTISRDNAKNTVVLQMNSLKPEDTGVYYCNALYGTDYWGKG TQVTVSSgggsgggsgggsgggsaptssstktqlqlehlldlqmilnginnyknpkltrmltfkfympkkatelkhlq cleeelkpleevlnlaqsknfhlrprdlisninvivlelkgsettfmceyadetativeflnrwitfcqsiistltSGGPGPAG MKGLPGSEVQLVESGGGLVQPGNSLRLSCAASGFTFSKFGMSWVRQAPGKGLE WVSS1SGGSGRDTLYAESVKGRFTISRDNAKTTLYLQMNSLRPEDTAVYYCTIGGS LSVSSQGTLVTVSSgggsgggsgggsgggsgggsgggsQVQLQQSGAELVRPGTSVKVSCKASG YAFTNYLIEWVKQRPGQGLEWIGVINPSGGTNYNEKFKGKATLTADKSSSTAY MQLSSLTSDDSAVFYCARWRGDGYYAYFDVWGAGTTVTVSSgggsgggsgggsgggs DIVLTQSPASLAVSLGQRATISCKASQSVDYDGDSYMNWYQQKPGQPPKLLIYA ASNLESGIPARFSGSGSGTDFTLNIHPVEEEDAATYYCQQSNEDPYTFGGGTKLEI KHHHHHEPEA |
| 60 | ACP27 (IL2 fusion protein) | QVQLQESGGGLVQAGGSLRLSCAASGRIFSIDIMSWYRQAPGKQRELVARITRG GTISYDDSVKGRFTISRDNAKNTVVLQMNSLKPEDTGVYYCNALYGTDYWGKG TQVTVSSgggsgggsgggsgggsaptssstktqlqlehlldlqmilnginnyknpkltrmltfkfympkkatelkhlq cleeelkpleevlnlaqsknfhlrprdlisninvivlelkgsettfmceyadetativeflnrwitfcqsiistltSGGPGPAG MKGLPGSEVQLVESGGGLVQPGNSLRLSCAASGFTFSKFGMSWVRQAPGKGLE |

-continued

SEQUENCE TABLE

| SEQ ID NO. | Name | Sequence |
|---|---|---|
| | | WVSSISGSGRDTLYAESVKGRFTISRDNAKTTLYLQMNSLRPEDTAVYYCTIGGS<br>LSVSSQGTLVTVSSggsggsggsggsggsggsDIVLTQSPASLAVSLGQRATISCKASQ<br>SVDYDGDSYMNWYQQKPGQPPKLLIYAASNLESGIPARFSGSGSGTDFTLNIHPV<br>EEEDAATYYCQQSNEDPYTFGGGTKLEIKgggsggsggsggsggsggsgggsQVQLQQSGAELVRP<br>GTSVKVSCKASGYAFTNYLIEWVKQRPGQGLEWIGVINPGSGGTNYNEKFKGK<br>ATLTADKSSSTAYMQLSSLTSDDSAVYFCARWRGDGYYAYFDVWGAGTTVTV<br>SSHHHHHHEPEA |
| 61 | ACP28 (IL2 fusion protein) | aptsstktqlqlehlldlqmilnginnykmpkltrmltfkfympkkatelkhlqcleeelkpleevlnlaqsknfhlrprdli<br>sninivlelkgsettfmceyadetaiveflnrwitfcqsiistltSGGPGPAGMKGLPGSgggsggsggsggggs<br>ggggsggggsQVQLQQSGAELVRPGTSVKVSCKASGYAFTNYLIEWVKQRPGQGLE<br>WIGVINPGSGGTNYNEKFKGKATLTADKSSSTAYMQLSSLTSDDSAVYFCARWR<br>GDGYYAYFDVWGAGTTVTVSSgggsggsggggsDIVLTQSPASLAVSLGQRATIS<br>CKASQSVDYDGDSYMNWYQQKPGQPPKLLIYAASNLESGIPARFSGSGSGTDFT<br>LNIHPVEEEDAATYYCQQSNEDPYTFGGGTKLEIKgggsggsggsggsggsgEVQLVESGG<br>GLVQPGNSLRLSCAASGFTFSKFGMSWVRQAPGKGLEWVSSISGSGRDTLYAES<br>VKGRFTISRDNAKTTLYLQMNSLRPEDTAVYYCTIGGSLSVSSQGTLVTVSSgggg<br>ggggsggggsQVQLQESGGGLVQAGGSLRLSCAASGRIFSIDIMSWYRQAPGKQRE<br>LVARITRGGTISYDDSVKGRFTISRDNAKNTVYLQMNSLKPEDTGVYYCNALYG<br>TDYWGKGTQVTVSSHHHHHHEPEA |
| 62 | ACP29 (IL2 fusion protein) | aptsstktqlqlehlldlqmilnginnykmpkltrmltfkfympkkatelkhlqcleeelkpleevlnlaqsknfhlrprdli<br>sninivlelkgsettfmceyadetaiveflnrwitfcqsiistltSGGPGPAGMKGLPGSgggsggsggsggggs<br>ggggsggggsDIVLTQSPASLAVSLGQRATISCKASQSVDYDGDSYMNWYQQKPGQ<br>PPKLLIYAASNLESGIPARFSGSGSGTDFTLNIHPVEEEDAATYYCQQSNEDPYTF<br>GGGTKLEIKgggsggsggsggsggsgQVQLQQSGAELVRPGTSVKVSCKASGYAFTNYLI<br>EWVKQRPGQGLEWIGVINPGSGGTNYNEKFKGKATLTADKSSSTAYMQLSSLTS<br>DDSAVYFCARWRGDGYYAYFDVWGAGTTVTVSSgggsggsggggsEVQLVESG<br>GGLVQPGNSLRLSCAASGFTFSKFGMSWVRQAPGKGLEWVSSISGSGRDTLYAE<br>SVKGRFTISRDNAKTTLYLQMNSLRPEDTAVYYCTIGGSLSVSSQGTLVTVSSggg<br>ggggsggggsQVQLQESGGGLVQAGGSLRLSCAASGRIFSIDIMSWYRQAPGKQR<br>ELVARITRGGTISYDDSVKGRFTISRDNAKNTVYLQMNSLKPEDTGVYYCNALY<br>GTDYWGKGTQVTVSSHHHHHHEPEA |
| 63 | IL2Ra | $\phantom{}$10$\phantom{xxxxx}$20$\phantom{xxxxx}$30$\phantom{xxxxx}$40$\phantom{xxxxx}$50<br>MDSYLLMWGL LTFIMVPGCQ AELCDDDPPE IPHATFKAMA YKEGTMLNCE<br>$\phantom{}$60$\phantom{xxxxx}$70$\phantom{xxxxx}$80$\phantom{xxxxx}$90$\phantom{xxxxx}$100<br>CKRGFRRIKS GSLYMLCTGN SSHSSWDNQC QCTSSATRNT TKQVTPQPEE<br>$\phantom{}$110$\phantom{xxxx}$120$\phantom{xxxx}$130$\phantom{xxxx}$140$\phantom{xxxx}$150<br>QKERKTTEMQ SPMQPVDQAS LPGHCREPPP WENEATERIY HFVVQQMVYY<br>$\phantom{}$160$\phantom{xxxx}$170$\phantom{xxxx}$180$\phantom{xxxx}$190$\phantom{xxxx}$200<br>QCVQGYRALH RGPAESVCKM THGKTRWTQP QLICTGEMET SQFPGEEKPQ<br>$\phantom{}$210$\phantom{xxxx}$220$\phantom{xxxx}$230$\phantom{xxxx}$240$\phantom{xxxx}$250<br>ASPEGRPESE TSCLVTTTDF QIQTEMAATM ETSIFTTEYQ VAVAGCVFLL<br>$\phantom{}$260$\phantom{xxxx}$270<br>ISVLLLSGLT WQRRQRKSRR TI |

-continued

SEQUENCE TABLE

| SEQ ID NO. | Name | Sequence |
|---|---|---|

64   IL2Rb

```
            10          20          30          40          50
      MAAPALSWRL  PLILILLPLA  TSWASAAVNG  TSQFTCFYNS  RANISCVWSQ
            60          70          80          90         100
      DGALQDTSCQ  VHAWPDRRRW  NQTCELLPVS  QASWACNLIL  GAPDSQKLTT
           110         120         130         140         150
      VDIVTLRVLC  REGVRWRVMA  IQDFKPFENL  RLMAPISLQV  VHVETHRCNI
           160         170         180         190         200
      SWEISQASHY  FERHLEFEAR  TLSPGHTWEE  APLLTLKQKQ  EWICLETLTP
           210         220         230         240         250
      DTQYEFQVRV  KPLQGEFTTW  SPWSQPLAFR  TKPAALGKDT  IPWLGHLLVG
           260         270         280         290         300
      LSGAFGFIIL  VYLLINCRNT  GPWLKKVLKC  NTPDPSKFFS  QLSSHGGDV
           310         320         330         340         350
      QKWLSSPFPS  SSFSPGGLAP  EISPLEVLER  DKVTQLLLQQ  DKVPEPASLS
           360         370         380         390         400
      SNHSLTSCFT  NQGYFFHLP   DALEIEACQV  YFTYDPYSEE  DPDEGVAGAP
           410         420         430         440         450
      TGSSPQPLQP  LSGEDDAYCT  FPSRDDLLLF  SPSLLGGPSP  PSTAPGGSGA
           460         470         480         490         500
      GEERMPPSLQ  ERVPRDWDPQ  PLGPPTPGVP  DLVDFQPPPE  LVLREAGEEV
           510         520         530         540         550
      PDAGPREGVS  FPWSRPPGQG  EPRALNARLP  LNTDAYLSLQ  ELQGQDPTHL
      V
```

65   IL2Rg

```
            10          20          30          40          50
      MLKPSLPFTS  LLFLQLPLLG  VGLNTTILTP  NGNEDTTADF  FLTTMPTDSL
            60          70          80          90         100
      SVSTLPLPEV  QCFVFNVEYM  NCTWNSSSEP  QPTNLTLHYW  YKNSDNDKVQ
           110         120         130         140         150
      KCSHYLFSEE  ITSGCQLQKK  EIHLYQTFVV  QLQDPREPRR  QATQMLKLQN
           160         170         180         190         200
      LVIPWAPENL  TLHKLSESQL  ELNWNNRFLN  HCLEHLVQYR  TDWDHSWTEQ
           210         220         230         240         250
      SVDYRHKFSL  PSVDGQKRYT  FRVRSRFNPL  CGSAQHWSEW  SHPIHWGSNT
           260         270         280         290         300
      SKENPFLFAL  EAVVISVGSM  GLIISLLCVY  FWLERTMPRI  PTLKNLEDLV
           310         320         330         340         350
      TEYHGNFSAW  SGVSKGLAES  LQPDYSERLC  LVSEIPPKGG  ALGEGPGASP
           360
      CNQHSPYWAP  PCYTLKPET
```

66   ACP04 (human p40/murine p35 IL12)

```
      iwelkkdvyvveldwypdapgemvvltcdtpeedgitwtldqssevlgsgktliqvkefgdaggytchkggevlshslll
      lhkhedgiwstdilkdqkepknktflrceaknysgrftcwlttistdltfsvksrgssdpgvtcgaatlsaervrgdnkey
      eysvecqedsacpaaeeslpievmvdavhklkyentyssffirdiikpdppknilqlkplknsrqvevsweypdtwstphs
      yfslfcvqvggkskrekdrvftdktsatvicrknasisvraqdryysswsewasvpcsgggsgggsgggsrvipv
      sgparclsgsrnllkttddmvktareklkhysctaedidhedlitrdqtstlktclplelhknesclatretssttrgsclppqktslm
```

-continued

SEQUENCE TABLE

| SEQ ID NO. | Name | Sequence |
|---|---|---|
|  | fusion protein) | mtlclgsiyedlkmyqtefqainaalqnhnhqqiildkgmlvaidelmqslnhngetlrqkppvgeadpyrvkmklcillh<br>afstrvtlnrymgylssaHHHHHH |
| 67 | ACP05 (human p40/murine p35 IL12 fusion protein) | iwelkkdvyvveldwypdapgemvvltcdtpeedgitwtldqssevlgsgktltiqvkefgdagqytchkggevlshslll<br>lhktedgiwstdilkdqkepknktflrceaknysgrftcwlttistdltsvkssrgssdpqgvtcgaatlsaervrqdnkey<br>eysvecqedsacpaaeeslpievmvdavhklkyenytssffirdiikpdppknlqlkplknsrqvevsweypdtwstphs<br>yfsltfcvqvgqskrekkdrvftdktsatvicrknasisvraqdryyssswewasvpcsgggsgggsggggsrnlpv<br>atpdpgmfpclhhsqnllravsnmlqkarqtlefypctseeidhedikdktstveaclpleltknesclnsretsfitngsclas<br>rktsfmmaiclssiyedlkmyqvefktmmakllmdpkrqfifldqnmlavidelmqalnfnsetypqkssleepdfyktki<br>klcillhafrirravtidrvmsylnasHHHHHH |
| 68 | ACP06 (human p40/murine p35 IL12 fusion protein) | QSVLTQPPSVSGAPGQRVTISCSGSRSNIGSNTVKWYQQLPGTAPKLLIYYNDQR<br>PSGVPDRFSGSKSGTSASLAITGLQAEDEADYYCQSYDRYTHPALLFGTGTKVT<br>VLGggsgggsgggsgggsQVQLVESGGGVVQPGRSLRLSCAASGFTFSSYGMHWVRQA<br>PGKGLEWVAFIRYDGSNKYYADSVKGRFTISRDNSKNTLYLQMNSLRAEDTAV<br>YYCKTHGSHDNWGQGTMVTVSSggggsgggsgggsgggsgggsgggsSGGPGPAG<br>MKGLPGSiwelkkdvyvveldwypdapgemvvltcdtpeedgitwtldqssevlgsgktltiqvkefgdagqytch<br>kggevlshslllhkkedgiwstdilkdqkepknktflrceaknysgrftcwlttistdltsvkssrgssdpqgvtcgaatls<br>aervrqdnkeyeysvecqedsacpaaeeslpievmvdavhklkyenytssffirdiikpdppknlqlkplknsrqvevsw<br>eypdtwstphsyfsltfcvqvgqskrekkdrvftdktsatvicrknasisvraqdryyssswewasvpcsgggsgggg<br>sgggsgggsrvipvsgparclsqsmllkttddmvktareklkhysctaedidhedltrdqstlktclplelhknesclatretsttr<br>gscIppqktslmmtlclgsiyedlkmyqtefqainaalqnhnhqqiildkgmlvaidelmqslnhngetlrqkppvgead<br>pyrvkmklcillhafstrvtlnrvmgylssaSGGPGPAGMKGLPGSEVQLVESGGGLVQPGNSL<br>RLSCAASGFTFSKFGMSWVRQAPGKGLEWVSSISGSGRDTLYAESVKGRFTISR<br>DNAKTTLYLQMNSLRPEDTAVYYCTIGGSLSVSSQGTLVTVSSHHHHHEPEA |
| 69 | ACP07 (human p40/murine p35 IL12 fusion protein) | QSVLTQPPSVSGAPGQRVTISCSGSRSNIGSNTVKWYQQLPGTAPKLLIYYNDQR<br>PSGVPDRFSGSKSGTSASLAITGLQAEDEADYYCQSYDRYTHPALLFGTGTKVT<br>VLGggsgggsgggsgggsQVQLVESGGGVVQPGRSLRLSCAASGFTFSSYGMHWVRQA<br>PGKGLEWVAFIRYDGSNKYYADSVKGRFTISRDNSKNTLYLQMNSLRAEDTAV<br>YYCKTHGSHDNWGQGTMVTVSSggggsgggsgggsgggsgggsgggsSGGPGPAG<br>MKGLPGSiwelkkdvyvveldwypdapgemvvltcdtpeedgitwtldqssevlgsgktltiqvkefgdagqytch<br>kggevlshslllhkkedgiwstdilkdqkepknktflrceaknysgrftcwlttistdltsvkssrgssdpqgvtcgaatls<br>aervrqdnkeyeysvecqedsacpaaeeslpievmvdavhklkyenytssffirdiikpdppknlqlkplknsrqvevsw<br>eypdtwstphsyfsltfcvqvgqskrekkdrvftdktsatvicrknasisvraqdryyssswewasvpcsgggsgggg<br>sgggsgggsrnllktddmvktareklkhysctaedidhedltrdqstlktclplelhknesclatretsttr<br>gscIppqktslmmtlclgsiyedlkmyqtefqainaalqnhnhqqiildkgmlvaidelmqslnhngetlrqkppvgead<br>pyrvkmklcillhafstrvtlnrvmgylssaSGGPGPAGMKGLPGSEVQLVESGGGLVQPGNSL<br>RLSCAASGFTFSKFGMSWVRQAPGKGLEWVSSISGSGRDTLYAESVKGRFTISR<br>DNAKTTLYLQMNSLRPEDTAVYYCTIGGSLSVSSQGTLVTVSSggggsgggsgggsgggsgggs<br>QVQLQESGGGLAQAGGSLSLSCAASGFTVSNSVMAWYRQTPGKQREFVAIINSV<br>GSTNYADSVKGRFTISRDNAKNTVYLQMNLKPEDTAVVCNRNFDRIYWGQG<br>TQVTVSSHHHHHEPEA |
| 70 | ACP08 (human p40/murine p35 | QVQLQESGGGLAQAGGSLSLSCAASGFTVSNSVMAWYRQTPGKQREFVAIINSV<br>GSTNYADSVKGRFTISRDNAKNTVYLQMNLKPEDTAVVCNRNFDRIYWGQG<br>TQVTVSSggggsgggsgggsgggsQSVLTQPPSVSGAPGQRVTISCSGSRSNIGSNTVKWY<br>QQLPGTAPKLLIYYNDQRPSGVPDRFSGSKSGTSASLAITGLQAEDEADYYCQSY |

-continued

SEQUENCE TABLE

| SEQ ID NO. | Name | Sequence |
|---|---|---|
| | IL12 fusion protein | DRYTHPALLFGTGTKVTVLgggsggggsggggsggggsQVQLVESGGGVVQPGRSLRLSCAA<br>SGFTFSSYGMHWVRQAPGKGLEWVAFIRYDGSNKYYADSVKGRFTISRDNSKN<br>TLYLQMNSLRAEDTAVYYCKTHGSHDNWGQGTMVTVSSggggsggggsggggsggggs<br>ggggsggggsSGGPGPAGMKGLPGSiwelkkdvyvveldwypdapgemvvltcdtpeedgitwtldqsse<br>vlgsgktltiqvkefgdagytchkggevlshslllllhkkedgiwstdilkdqkepknktflrceaknysgrftcvwltistdl<br>tfsvkssrgssdpqgvtcgaatlsaervrgdnkeyeysvecqedsacpaaeeslpievmdavhklkyenytssffirdiik<br>pdppknlqlkplknsrqvevsweypdtwstphsyfsltfcvqvgkskrekkdrvftdktsatvicrknasisvraqdryys<br>sswsewasvpcsgggsggggsggggsrvipvsgparclsqsrnllkttddmvktareklkhysctaedidheditrdqtst<br>lktclplelhknesclatretssttrgsclppqktslmmtlclgsiyedlkmyqtefgainaalqmhnhqqiildkgmlvaidel<br>mqslnhngetlrqkppvgeadpyrvkmklcillhafstrvvtinrvmgylssaSGGPGPAGMKGLPGSEVQ<br>LVESGGGLVQPGNSLRLSCAASGFTFSSKFGMSWVRQAPGKGLEWVSSISGSGRD<br>TLYAESVKGRFTISRDNAKTTLYLQMNSLRPEDTAVYYCTIGGSLSVSSQGTLVT<br>VSSHHHHHHEPEA |
| 71 | ACP09 (human p40/murine p35 IL12 fusion protein) | EVQLVESGGGLVQPGNSLRLSCAASGFTFSKFGMSWVRQAPGKGLEWVSSISGS<br>GRDTLYAESVKGRFTISRDNAKTTLYLQMNSLRPEDTAVYYCTIGGSLSVSSQGT<br>LVTVSSggggsggggsggggsQSVLTQPPSVSGAPGQRVTISCSGSRSNIGSNTVKWYQ<br>QLPGTAPKLLIYYNDQRPSGVPDRPSGSKSGTSASLAITGLQAEDEADYYCQSYD<br>RYTHPALLFGTGTKVTVLgggsggggsggggsQVQLVESGGGVVQPGRSLRLSCAAS<br>GFTFSSYGMHWVRQAPGKGLEWVAFIRYDGSNKYYADSVKGRFTISRDNSKNT<br>LYLQMNSLRAEDTAVYYCKTHGSHDNWGQGTMVTVSSggggsggggsggggsggggs<br>ggggsggggsSGGPGPAGMKGLPGSiwelkkdvyvveldwypdapgemvvltcdtpeedgitwtldqssevl<br>gsgktltiqvkefgdagytchkggevlshslllllhkkedgiwstdilkdqkepknktflrceaknysgrftcvwltistdltf<br>svkssrgssdpqgvtcgaatlsaervrgdnkeyeysvecqedsacpaaeeslpievmdavhklkyenytssffirdiikpd<br>ppknlqlkplknsrqvevsweypdtwstphsyfsltfcvqvgkskrekkdrvftdktsatvicrknasisvraqdryysss<br>wsewasvpcsgggsggggsggggsrvipvsgparclsqsrnllkttddmvktareklkhysctaedidheditrdqtstlk<br>tclplelhknesclatretssttrgsclppqktslmmtlclgsiyedlkmyqtefgainaalqmhnhqqiildkgmlvaidelm<br>qslnhngetlrqkppvgeadpyrvkmklcillhafstrvvtinrvmgylssaHHHHHHEPEA |
| 72 | ACP10 (human p40/murine p35 IL12 fusion protein) | EVQLVESGGGLVQPGNSLRLSCAASGFTFSKFGMSWVRQAPGKGLEWVSSISGS<br>GRDTLYAESVKGRFTISRDNAKTTLYLQMNSLRPEDTAVYYCTIGGSLSVSSQGT<br>LVTVSSSGGPGPAGMKGLPGSiwelkkdvyvveldwypdapgemvvltcdtpeedgitwtldqssevlg<br>sgktltiqvkefgdagytchkggevlshslllllhkkedgiwstdilkdqkepknktflrceaknysgrftcvwltistdltfs<br>vkssrgssdpqgvtcgaatlsaervrgdnkeyeysvecqedsacpaaeeslpievmdavhklkyenytssffirdiikpd<br>ppknlqlkplknsrqvevsweypdtwstphsyfsltfcvqvgkskrekkdrvftdktsatvicrknasisvraqdryysss<br>wsewasvpcsgggsggggsggggsrvipvsgparclsqsrnllkttddmvktareklkhysctaedidheditrdqtstlk<br>tclplelhknesclatretssttrgsclppqktslmmtlclgsiyedlkmyqtefgainaalqmhnhqqiildkgmlvaidelm<br>qslnhngetlrqkppvgeadpyrvkmklcillhafstrvvtinrvmgylssaSGGPGPAGMKGLPGSggggsg<br>gggggsggggsggggsQVQLVESGGGVVQPGRSLRLSCAA<br>SGFTFSSYGMHWVRQAPGKGLEWVAFIRYDGSNKYYADSVKGRFTISRDNSKN<br>TLYLQMNSLRAEDTAVYYCKTHGSHDNWGQGTMVTVSSHHHHHHEPEA |
| 73 | ACP11 (human p40/murine p35 | iwelkkdvyvveldwypdapgemvvltcdtpeedgitwtldqssevlgsgktltiqvkefgdagytchkggevlshslll<br>lhkkedgiwstdilkdqkepknktflrceaknysgrftcvwltistdltfsvkssrgssdpqgvtcgaatlsaervrgdnkey<br>eysvecqedsacpaaeeslpievmdavhklkyenytssffirdiikpdppknlqlkplknsrqvevsweypdtwstphs<br>yfsltfcvqvgkskrekkdrvftdktsatvicrknasisvraqdryysssswsewasvpcsgggsggggsggggsrvipv |

-continued

SEQUENCE TABLE

| SEQ ID NO. | Name | Sequence |
|---|---|---|

73 | IL12 fusion protein) | sgparclsgsrnllkttddmvktareklkhysctaedidheditrdqtstlktclplelhknesclatretssttrgsclppqktslm
mtlclgsiyedlkmhyqtefgainaalqnhnhqqiildkgmlvaidelmqslnhngetlrqkppvgeadpyrvkmklcillh
afstryvtlnrvmgylssaGGPGAGMKGLPGSggggsggggsggggsggggsggggsggggsggggsQSVLT
QPPSVSGAPGQRVTISCSGSRSNIGSNTVKWYQQLPGTAPKWYNDQRPSGVP
DRFSGSKSGTSASLAITGLQAEDEADYYCQSYDRYTHPALLFGTKVTVLgggggs
ggggsggggsQVQLVESGGGVVQPGRSLRLSCAASGFTFSSYGMHWVRQAPGKGLE
WVAFIRYDGSNKYYADSVKGRFTISRDNSKNTLYLQMNSLRAEDTAVYYCKTH
GSHDNWGQGTMVTVSSggggsggggsggggsggggsEVQLVESGGGLVQPGNSLRLSCAASG
FTFSKFGMSWVRQAPGKGLEWVSSISGSGRDTLYAESVKGRFTISRDNAKTTLY
LQMNSLRPEDTAVYYCTIGGSLSVSSQGTLVTVSSHEIREIHHEPEA |

74 | IL12 p40 human (Uniprot Accession No. P29460) | MCHQQLVISW FSLVFLASPL VAIWELKKDY YVVELDWYPD APGEMVLTC
      10        20        30        40        50
DTPEEDGITW TLDQSSEVLG SGKTLTIQVK EFGDAQYTC HKGGEVLSHS
      60        70        80        90        100
LLLLHKKEDG IWSTDILKDQ KEPKNKTFLR CEAKNYSGRF TCWWLTTIST
      110      120      130      140      150
DLTFSVKSSR GSSDPQGVTC GAATLSAERV RGDNKEYEYS VECQEDSACP
      160      170      180      190      200
AAEESLPIEV MVDAVHKLKY ENYTSSFFIR DIIKPDPPKN LQLKPLKNSR
      210      220      230      240      250
QVEVSWEYPD TWSTPHSYFS LTFCVQVQGK SKREKKDRVF TDKTSATVIC
      260      270      280      290      300
RKNASISVRA QDRYYSSSWS EWASVPCS
      310      320 |

75 | IL12 p35 mouse (Uniprot Accession No. P43431) | MCQSRYLLFL ATLALLNHLS LARVIPVSGP ARCLSQSRNL LKTTDDMVKT
      10        20        30        40        50
AREKLKHYSC TAEDIDHEDI TRDQTSTLKT CLPLELHKNE SCLATRETSS
      60        70        80        90        100
TTRGSCLPPQ KTSLMMTLCL GSIYEDLKMY QTEFQAINAA LQNHNHQQII
      110      120      130      140     150
LDKGMLVAID ELMQSLNHNG ETLRQKPPVG EADPYRVKMK LCILLHAFST
      160      170      180      190     200
RVVTINRVMG YLSSA
      210 |

76 | IL12Rb-2 | MAHTPRGCSL AFMFIITELL IKAKIDACKR GDVTVKPSHY ILLGSIYNIT
      10        20        30        40        50
CSLFPROGCF HYSRRNKLIL YKFDRRINEH HGHSLNSQVT GLPLGTTLFV
      60        70        80        90        100
CKLACINSDE IQICGAFIFV GVAREQRQNL SCIQKGEQGT VACTQERGRD
      110      120      130      140     150
IHLYTEYTOQ LSGPKNLTWQ KQCKDIYCDY LDFGINLTPE SPESQFTAKY
      160      170      180      190     200
TAYMELGSES SLPSTFTFLD IVRPLPFWDI RIKFQKASVS RCTLYWRDEG
      210      220      230      240     250
      260      270      280      290      300 |

-continued

SEQUENCE TABLE

| SEQ ID NO. | Name | Sequence |
|---|---|---|
| | | LVLLNRLRYR PSNSRLWNMV NVTKAKGRHD LLDLKPFTEY EFQISSKLHL |
| | | 310       320       330       340       350 |
| | | YKGSWSDWSE SLPAQTPEEE PTGMLDVWYM KRHIDYSRQQ ISLFWWQLSV |
| | | 360       370       380       390       400 |
| | | SEARGKILHY QVTLQELTGG KAMTQNITGH ISWTIVIRRT GNWAVAVSAA |
| | | 410       420       430       440       450 |
| | | NSKGSLPTR INIMNLCEAG LLAPRQVSAN SEGMDNILVI KQPPRKDRSA |
| | | 460       470       480       490       500 |
| | | VQEVVENRE LHPGGDIQYR LNWLRSRPYN VSALISENIK SYICYEIRVY |
| | | 510       520       530       540       550 |
| | | ALSGDQGGCS SILGNSKHKA PLSGPHINAI IEEKGSILIS WNSIRVQEQM |
| | | 560       570       580       590       600 |
| | | GCLLHYRIYW KERDSNSQPQ LCEIPYRYSQ NSHPINSLQP RVIYVLWMTA |
| | | 610       620       630       640       650 |
| | | LTAAGESSHG NEREECLQGK ANWMAFVARS ICIAIIMVGI FSTHYFQQKV |
| | | 660       670       680       690       700 |
| | | FVLLAALRPQ WCSREIPDPA NSICAKKYPI AEEKTQLPLQ RLLIDWPTPE |
| | | 710       720       730       740       750 |
| | | DPEPLVISEV LHQVIPVFRH PPCSNWPQRE KGIQGHQASE KDMMHSASSR |
| | | 760       770       780       790       800 |
| | | PPPRALQAES PQLVDLYKVL ESRGSDPKRE NPACPWTVLR AGDLPTHDGY |
| | | 810       820       830       840       850 |
| | | LPSNIDDLPS HEAPLADSLE ELEPQHISLS VFPSSSLHPL TFSCGDKLTL |
| | | 860 |
| | | DQLKMRCDSL ML |
| 77 | IL12Rb-1 | MEPLVTWVVP LLFLFLLSRQ GAACRISECC FQDPPYPDAD SGSASGPRDL |
| | | 10       20       30       40       50 |
| | | RCYRISSDRY ECSWQYEGPT AGVSHFLRCC LSSGRCCYFA AGSATRLQFS |
| | | 60       70       80       90       100 |
| | | DQAGVSVLYT VTLWVESWAR NQTEKSPEVT LQLYNSVKYE PPLGDIKVSK |
| | | 110       120       130       140       150 |
| | | LAGQLRMEWE TPDNQVGAEV QFRHRIPSSP WKLGDCGPQD DDTESCLCPL |
| | | 160       170       180       190       200 |
| | | EMNVAQEFQL RRRQLGSQGS SWSKWSSPVC VPPENPPQPQ VRFSVEQLGQ |
| | | 210       220       230       240       250 |
| | | DGRRRLILKE QPTQLELPEG CQGLAPGTEV TYRLQLHMLS CPCKAKATRT |
| | | 260       270       280       290       300 |
| | | LHLGKMPYLS GAAYNVAVIS SNQFGPGLNQ TWHTPADTHT EPVALNISVG |
| | | 310       320       330       340       350 |
| | | INGTTMYWPA RAQSMTYCIE WQPVGQDGGL ATCSLTAPQD PDPAGMATYS |
| | | 360       370       380       390       400 |
| | | WSRESGAMGQ EKCYYITIFA SAHPEKLTLW STVLSTYHFG GNASAAGTPH |
| | | 410       420       430       440       450 |
| | | HVSVKNHSLD SVSVDWAPSL LSTCPGVLKE YVVRCRDEDS KQVSEHPVQP |
| | | 460       470       480       490       500 |
| | | TETQVTLSGL RAGVAYTVQV RADTAWLRGV WSQPQRPSIE VQVSDWLIFF |
| | | 510       520       530       540       550 |

-continued

SEQUENCE TABLE

```
                          560        570        580        590        600
                   ASLGSFLSIL LVGVLGYLGL NRAARHLCPP LPTPCASSAI EFPGGKETWQ
                          610        620        630        640        650
                   WINPVDFQEE ASLQEALVVE MSWDKGERTE PLEKTELPEG APELALDTEL
                          660
                   SLEDGDRCKA KM
```

| SEQ ID NO. | Name | Sequence |
|---|---|---|
| 78 | IL-12 p35 human (Uniprot accession no. P29459) | 10 20 30 40 50<br>MCHQQLVISW FSLVFLASPL VAIWELKDV YVVELDWYPD APGEMVVLTC<br>60 70 80 90 100<br>DTPEEDGITW TLDQSSEVLG SGKTLTIQVK EFPGDAGQYTC HKGGEVLSHS<br>110 120 130 140 150<br>LLLLHKKEDG IWSTDILKDQ KEPKNKTFLR CEAKNYSGRF TCWWLTTIST<br>160 170 180 190 200<br>DLTFSVKSSR GSSDPQGVTC GAATLSAERV RGDNKEYEYS VECQEDSACP<br>210 220 230 240 250<br>AAEESLPIEV MVDAVHKLKY ENYTSSFFIR DIIKPDPPKN LQLKPLKNSR<br>260 270 280 290 300<br>QVEVSWEYPD TWSTPHSYFS LTFCVQVQGK SKREKKDRVF TDKTSATVIC<br>310 320<br>RKNASISVRA QDRYYSSSWS EWASVPCS |
| 79 | IL-12 p40 mouse (Uniprot accession no. P43432) | 10 20 30 40 50<br>MCPQKLTISW FAIVLLVSPL MAMWELEKDV YVVEVDWTPD APGETVNLTC<br>60 70 80 90 100<br>DTPEEDGITW TSDQRHGVIG SGKTLTITVK EFLDAGQYTC HKGGETLSHS<br>110 120 130 140 150<br>HLLLHKKENG IWSTEILKNF KNKTFLKCEA PNYSGRPTCS WLVQRNMDLK<br>160 170 180 190 200<br>FNIKSSSSSP DSRAVTCGMA SLSAEKVTLD QRDYEKYSVS CQEDVTCPTA<br>210 220 230 240 250<br>EETLPIELAL EARQQNKYEN YSTSFFIRDI IKPDPPKNLQ MKPLKNSQVE<br>260 270 280 290 300<br>VSWEYPDSWS TPHSYFSLKF FVRIQRKKEK MKETEEGCNQ KGAFLVEKTS<br>310 320 330<br>TEVQCKGGNV CVQAQDRYYN SSCSKWACVP CRVRS |
| 80 | ACP01 (mouse IFNg fusion protein) | EVQLVESGGGLVQPGNSLRLSCAASGFTFSKFGMSWVRQAPGKGLEWVSSISGS<br>GRDTLYAESVKGRFTISRDNAKTTLYLQMNSLRPEDTAVYYCTIGGSLSVSSQGT<br>LVTVSSSGPGPAGMKGLPGShgtvieslsnnyfnssgidveekslfldiwrnwqkdgdmkilqsqiisf<br>ylrlfevlkdnqaisnnisvieshlittfsnskakkdafmsiakfevnnpqvqrqafnelirvvhqllpesslrkrkrsrcSG<br>GPGPAGMKGLPGSEVQLVESGGGLVQPGNSLRLSCAASGFTFSKFGMSWVRQA<br>PGKGLEWVSSISGSGRDTLYAESVKGRFTISRDNAKTTLYLQMNSLRPEDTAVY<br>YCTIGGSLSVSSQGTLVTVSSHHHHHH |
| 81 | ACP02 (mouse IFNg) | EVQLVESGGGLVQPGNSLRLSCAASGFTFSKFGMSWVRQAPGKGLEWVSSISGS<br>GRDTLYAESVKGRFTISRDNAKTTLYLQMNSLRPEDTAVYYCTIGGSLSVSSQGT<br>LVTVSSSGGPGPAGMKGLPGShgtvieslnnyfnssgidveekslfldiwrnwqkdgdmkilqsqiisf |

-continued

SEQUENCE TABLE

| SEQ ID NO. | Name | Sequence |
|---|---|---|
| | fusion protein) | ylrlfevlkdnqaisnnisvieshlittffsnskakkdafmsiakfevnnpqvqrgafnelirvvhqllpesslrkrkrsrcSG<br>GPGPAGMKGLPGShgtviesleslnnyfnssgidveekslfldiwrnwqkdgdmkilqsqiisfylrlfevlkdnq<br>aismnisvieshlittffsnskakkdafmsiakfevnnpqvqrgafnelirvvhqllpesslrkrkrsrcSGGPGPAGM<br>KGLPGSEVQLVESGGGLVQPGNSLRLSCAASGFTFSKFGMSWVRQAPGKGLEW<br>VSSISGSGRDTLYAESVKGRFTISRDNAKTTLYLQMNSLRPEDTAVYYCTIGGSL<br>SVSSQGTLVTVSSHHHHHH |
| 82 | ACP03 (mouse IFNg fusion protein) | EVQLVESGGGLVQPGNSLRLSCAASGFTFSKFGMSWVRQAPGKGLEWVSSISGS<br>GRDTLYAESVKGRFTISRDNAKTTLYLQMNSLRPEDTAVYYCTIGGSLSVSSQGT<br>LVTVSSSGGPGPAGMKGLPGShgtviesleslnnyfnssgidveekslfldiwrnwqkdgdmkilqsqiisf<br>ylrlfevlkdnqaisnnisvieshlittffsnskakkdafmsiakfevnnpqvqrgafnelirvvhqllpesslrkrkrsrcggg<br>gsgggggggshgtviesleslnnyfnssgidveekslfldiwrnwqkdgdmkilqsqiisfylrlfevlkdnqaisnnisv<br>ieshlittffsnskakkdafmsiakfevnnpqvqrgafnelirvvhqllpesslrkrkrsrcSGGPGPAGMKGLPGS<br>EVQLVESGGGLVQPGNSLRLSCAASGFTFSKFGMSWVRQAPGKGLEWVSSISGS<br>GRDTLYAESVKGRFTISRDNAKTTLYLQMNSLRPEDTAVYYCTIGGSLSVSSQGT<br>LVTVSSHHHHHH |
| 83 | Human IFN-g (Uniprot Accession No. P01579) | 10     20     30     40     50<br>MKYTSYILAF QLCIVLGSLG CYCQDPYVKE AENLKKYFNA GHSDVADNGT<br>60     70     80     90     100<br>LFLGLIKNWK EESDRKIMQS QIVSFYFKLF KNFKDDQSIQ KSVETIKEDM<br>110    120    130    140    150<br>NVKFFNSNKK KRDDFEKLTN YSVTDLNVQR KAIHELIQVM AELSPAAKTG<br>160<br>KRKRSQMLFR GRRASQ |
| 84 | Mouse IFN-g (Uniprot Accession No. P01580) | 10     20     30     40     50<br>MNATHCILAL QLFLMAVSGC YCHGTVIESL ESLNNYFNSS GIDVEEKSLF<br>60     70     80     90     100<br>LDIWRNWQKD GDMKILQSQI ISFYLRLFEV LKDNQAISNN ISVIESHLIT<br>110    120    130    140    150<br>TFFSNSKAKK DAFMSIAKFE VNNPQVQRQA FNELIRVVHQ LLPESSLRKR<br>KRSRC |
| 85 | ACP30 (mouse IFNg fusion protein) | mdmrvpaqllglllwlrgarcEVQLVESGGGLVQPGNSLRLSCAASGFTFSKFGMSWVRQ<br>APGKGLEWVSSISGSGRDTLYAESVKGRFTISRDNAKTTLYLQMNSLRPEDTAV<br>YYCTIGGSLSVSSQGTLVTVSSSGGPGPAGMKGLPGShgtviesleslnnyfnssgidveekslfl<br>diwrnwqkdgdmkilqsqiisfylrlfevlkdnqaisnnisvieshlittffsnskakkdafmsiakfevnnpqvqrgafnel<br>irvvhqllpesslrkrkrsrcSGGPGPAGMKGLPGSEVQLVESGGGLVQPGNSLRLSCAASG<br>FTFSKFGMSWVRQAPGKGLEWVSSISGSGRDTLYAESVKGRFTISRDNAKTTLY<br>LQMNSLRPEDTAVYYCTIGGSLSVSSQGTLVTVSSSGGPGPAGMKGLPGShgtvies<br>leslnnyfnssgidveekslfldiwrnwqkdgdmkilqsqiisfylrlfevlkdnqaisnnisvieshlittffsnskakkdaf<br>msiakfevnnpqvqrgafnelirvvhqllpesslrkrkrsrcSGGPGPAGMKGLPGSEVQLVESGGGL<br>VQPGNSLRLSCAASGFTFSKFGMSWVRQAPGKGLEWVSSISGSGRDTLYAESVK<br>GRFTISRDNAKTTLYLQMNSLRPEDTAVYYCTIGGSLSVSSQGTLVTVSSHHHHH<br>H |

-continued

SEQUENCE TABLE

| SEQ ID NO. | Name | Sequence |
|---|---|---|
| 86 | ACP31 (mouse IFNα1 fusion protein) | EVQLVESGGGLVQPGNSLRLSCAASGFTFSKFGMSWVRQAPGKGLEWVSSISGS GRDTLYAESVKGRFTISRDNAKTTLYLQMNSLRPEDTAVYYCTIGGSLSVSSQGT LVTVSSSGGPGPAGMKGLPGScdlpqthnlrnkraltllvqmrrlsplsclkdrkdfgfpqekvdaqqikka qaipvlseltqqilniftskdssaawnttlldsfcndlhqqlndlqgclmqqvgvqefpltqedallavrkyfhritvylrekkh spcawevvraevwralsssanvlgrlreekSGGPGPAGMKGLPGSEVQLVESGGGLVQPGNSLR LSCAASGFTFSKFGMSWVRQAPGKGLEWVSSISGSGRDTLYAESVKGRFTISRD NAKTTLYLQMNSLRPEDTAVYYCTIGGSLSVSSQGTLVTVSSHHHHHHEPEA |
| 87 | ACP32 (mouse IFNα1 fusion protein) | EVQLVESGGGLVQPGNSLRLSCAASGFTFSKFGMSWVRQAPGKGLEWVSSISGS GRDTLYAESVKGRFTISRDNAKTTLYLQMNSLRPEDTAVYYCTIGGSLSVSSQGT LVTVSSSGGPGPAGMKGLPGScdlpqthnlrnkraltllvqmrrlsplsclkdrkdfgfpqekvdaqqikka qaipvlseltqqilniftskdssaawnttlldsfcndlhqqlndlqgclmqqvgvqefpltqedallavrkyfhritvylrekkh spcawevvraevwralsssanvSGGPGPAGMKGLPGSEVQLVESGGGLVQPGNSLRLSCA ASGFTFSKFGMSWVRQAPGKGLEWVSSISGSGRDTLYAESVKGRFTISRDNAKT TLYLQMNSLRPEDTAVYYCTIGGSLSVSSQGTLVTVSSHHHHHHEPEA |
| 88 | IFNgR1 | MALLFLLPLV MQGVSRAEMG TADLGPSSVP TPINVTIESY NMNPIVYWEY 50<br>QIMPQVPVFT VEVKNYGVKN SEWIDACINI SHHYCNISDH VGDPSNSLWV 100<br>RVKARVGQKE SAYAKSEBFA YCRDGKIGPP KLDIRKEEKQ IMIDIFHPSV 150<br>FVNGDEQEVD YDPEITCYIR VINVYVRMNG SEIQYKILTQ KEDDCDEIQC 200<br>QLAIPVSSLN SQYCVSAEGV LHVWGVTTEK SKEVCITIFN SSIKGSLWIP 250<br>VVAALLLFLV LSLVFICFYI EKINPLKEKS IILPKSLISV VRSATLETKP 300<br>ESKYVSLITS YQPFSLEKEV VCEEPLSPAT VPGMHIEDNP GKVEHTEELS 350<br>SIIEVVTIEE NIPDVVPGSH LTPIERESSS PLSSNQSEPG SIALNSYHSR 400<br>NCSESDHSRN GPDTDSSCLE SHSSLSDSEP PPNNKGEIKT EGQELITVIK 450<br>APTSFGYDKP HVLVDLLVDD SGKESLIGYR PTEDSKEFS 480 |
| 89 | IFNgR2 | MRPTLLWSLL LLLGVFAAAA AAPPDPLSQL PAPQHPKIRL YNAEQVLSWE 50<br>PVALSNSTRP VVYQVQFKYT DSKWFIADIM SIGVNCTQIT ATECDETAAS 100<br>PSAGFPMDFN VTLRLRAELG ALHSAWTMP WFQHYRNVTV GPPENIEVTP 150<br>GEGSLIIRFS SPPDIADTST ARFCYYVHYW EKGGIQQVKG PFRSNSISLD 200<br>NLKPSRVYCL QVQAQLLNNK SNIFRVGHLS NISCYETMAD ASTELQQVIT 250 |

-continued

SEQUENCE TABLE

| SEQ ID NO. | Name | Sequence |
|---|---|---|

260    270    280    290    300
310    320    330

| | | |
|---|---|---|
| 90 | ACP51 Mouse IFG fusion protein | ISVGTFSLLS WLAGACFFLV LKYRGLIKYW FHTPPSIPLQ IEEYLKDPTQ<br>PILEALDKDS SPKDDVWDSV SIISFPEKEQ EDVLQTL |
| 91 | ACP52 Mouse IFG fusion protein | QVQLQESGGGLVQAGGSLRLSCAASGRIFSIDIMSWYRQAPGKQRELVARITRG<br>GTISYDDSVKGRFTISRDNAKNTVLQMNSLKPEDTGVYYCNALYGTDYWGKG<br>TQVTVSSggsgggsgggsgggsgggsEVQLVESGGGLVQPGNSLRLSCAASGFTFSKFPGMSW<br>VRQAPGKGLEWVSSISGSGRDTLYAESVKGRFTISRDNAKTTLYLQMNSLRPED<br>TAVYYCTIGGSLSVSSQGTLVTVSSSGGPGPAGMKGLPGShgtviesleslnmyfnssgidve<br>ekslfldiwrnwqkdgdmkilqsqiisfylrlfevlkdnqaisnnisvieshlittffsnskakkdafmsiakfevmpqvqr<br>qafnelirvvhqllpesslrkrkrsrcSGGPGPAGMKGLPGSEVQLVESGGGLVQPGNSLRLSC<br>AASGFTFSKFPGMSWVRQAPGKGLEWVSSISGSGRDTLYAESVKGRFTISRDNAK<br>TTLYLQMNSLRPEDTAVYYCTIGGSLSVSSQGTLVTVSSHHHHHH |
| 92 | ACP53 Mouse IFG fusion protein | EVQLVESGGGLVQPGNSLRLSCAASGFTFSKFPGMSWVRQAPGKGLEWVSSISGS<br>GRDTLYAESVKGRFTISRDNAKTTLYLQMNSLRPEDTAVYYCTIGGSLSVSSISGS<br>LVTVSSSGGPGPAGMKGLPGShgtviesleslnmyfnssgidveekslfldiwrnwqkdgdmkilqsqiisf<br>ylrlfevlkdnqaisnnisvieshlittffsnskakkdafmsiakfevmpqvqrqafnelirvvhqllpesslrkrkrsrcSG<br>GPGPAGMKGLPGSEVQLVESGGGLVQPGNSLRLSCAASGFTFSKFPGMSWVRQA<br>PGKGLEWVSSISGSGRDTLYAESVKGRFTISRDNAKTTLYLQMNSLRPEDTAVY<br>YCTIGGSLSVSSQGTLVTVSSSGGPGPAGMKGLPGSEVQLVESGGGLVQPGNSL<br>RLSCAASGFTFSKFPGMSWVRQAPGKGLEWVSSISGSGRDTLYAESVKGRFTISR<br>DNAKTTLYLQMNSLRPEDTAVYYCTIGGSLSVSSQGTLVTVSSggsgggsgggsgggs<br>QVQLQESGGGLVQAGGSLRLSCAASGRIFSIDIMSWYRQAPGKQRELVARITRG<br>GTISYDDSVKGRFTISRDNAKNTVLQMNSLKPEDTGVYYCNALYGTDYWGKG<br>TQVTVSSHHHHHH |
| | | eahkseiahryndlgeqhfkglvliafsgylqkcsydehaklvgevtdfaktcvadesaancdkslhtlfgdklcaipnlren<br>ygeladcctkqepemecflqhkddnpslppferpeaeamctsfkenpttfmghylhevarrhpyfya<br>ltqccaeaadkescltpkldgvketalvssvrqrmkcssmqfgerafkawavarlsgtfpnadfaeitklatdltkvnkecc<br>hgdllecaddraelakymcenqatisskltqtccdkpllkkahclsevehdtmpadlpaiaadfvedqev<br>gtflyeysrrhpdydysyslllrlakkyeatlekccaeanppacygtvlaefqplveepknlvktncdlyeklgeygfqnailvry<br>tqkapqvstptiveaarnlgrvgtkccotlpedqrlpcvedylsailnrvcllhektpvsehvtkccsgslverrpcfsaltvdety<br>vpkefkaetftfhsdictlpekekgikkqtalaelvkhhpkataeqlktvmddfaqfldtcckaadkdtcfstegpnlvtrckd<br>alasGGPGPAGMKGLPGShgtvieslesinmyfnssgidveekslfldiwrnwqkdgdmkilqsqiisfylrlfev<br>lkdnqaisnnisvieshlittffsnskakkdafmsiakfevmpqvqrqafnelirvvhqllpesslrkrkrsrcSGGPGPA<br>GMKGLPGSeahkseiahryndlgeqhfkglvliafsgylqkcsydehaklvgevtdfaktcvadesaancdkslhtlf<br>gdklcaipnlrenygeladcctkqepemecflqhkddnpslppferpeaeamctsfkenpttfmghylhevarrhpyfya<br>pellyyaeqyneiltqccaeaadkescltpkldgvkekalvssvrqrmkcssmqfgerafkawavarlsgtfpnadfaeitk<br>latdltkvnkecchgdllecaddraelakymcenqatisskltqtccdkpllkahclsevehdtmpadlpaiaadfvedqev<br>cknyaeakdvflgtflyeysrrhpdydysyslllrlakkyeatlekccaeanppacygtvlaefqplveepknlvktncdlyekl<br>geygfqnailvrytqkapqvstptiveaarnlgrvgtkccotlpcvedylsailnrycllhektpvsehvtkccsgslve<br>rrpcfsaltvdetyvpkefkaetftfhsdictlpekekglkkqtalaelvkhhpkataeqlktvmddfaqfldtcckaadkdtc<br>fstegpnlvtrckdalaHHHHHH |
| 93 | ACP54 Mouse | eahkseiahryndlgeqhfkglvliafsgylqkcsydehaklvgevtdfaktcvadesaancdkslhtlfgdklcaipnlren<br>ygeladcctkqepemecflqhkddnpslppferpeaeamctsfkenpttfmghylhevarrhpyfyapellyyaeqynei |

-continued

SEQUENCE TABLE

| SEQ ID NO. | Name | Sequence |
|---|---|---|

| | IFG fusion protein | ltqccaeadkescltpkldgvkekalvssvrqrmkcssmqkfgerafkawavarlsqtfpnadfaeitklatdltkvnkecc hgdllecaddraelakymcenqatissklqtccdkpllkkahclsevehdtmpadlpaiaadfvedqevcknyaeakdvfl gtflyeysrrhpdyavslllrlakkyeatlekccaeanppacygtvlaefqplveepknlvktncdlyeklgeygfqnailvry tqkapqvstptlveaarnlgrvgtkcctlpedqrlpcvedylsailnrvcllhektpvsehvtkccgslverrpcfsaltvdety vpkefkaetftfhsdictlpekekqikkqtalaelvkhkpkataeqlktvmddfaqfldtcckaadkdtcfstegpnlvtrckd alaSGGPGAGMKGLPGShgtviesleslnnyfnssgidveekslfldiwrnwqkdgdmkilqsqiisfylrlfev lkdnqaismnisvieshlittffsnskakkdafmsiakfevnmpqvrqafnelirvvhqllpesslrkrkrsrcggggsgggg sggggshgtviesleslnnyfnssgidveekslfldiwrnwqkdgdmkilqsqiisfylrlfevlkdnqaismnisvieshlitt ffsnskakkdafmsiakfevnmpqvrqafnelirvvhqllpesslrkrkrsrcSGGPGAGMKGLPGSeahkse iahryndlgeqhfkglvliafsqylqkcsydehaklvqevtdfaktcvadesaancdkslhtlfgdklcaipnlrenygelad cctkqepernecflqhkddnpslpfferpeaemctsfkenpttfmghylhevarrhpyfyapellyyaeqyneiltqccae adkescltpkldgvkekalvssvrqrmkcssmqkfgerafkawavarlsqtfpnadfaeitklatdltkvnkecchgdllec addraelakymcenqatissklqtccdkpllkkahclsevehdtmpadlpaiaadfvedqevcknyaeakdvlgtflyey srrhpdysysllllrlakkyeatlekccaeanppacygtvlaefqplveepknlvktncdlyeklgeygfqnailvrytqkapq vstptlveaarnlgrvgtkcctlpedqrlpcvedylsailnrvcllhektpvsehvtkccgslverrpcfsaltvdetyvpkefk aetftfhsdictlpekekqikkqtalaelvkhkpkataeqlktvmddfaqfldtccckaadkdtcfstegpnlvtrckdalaHH HHHH |

| 94 | ACP50 Mouse IFG fusion protein | mdmrvpaqllgllllwlrgarcQVQLQESGGGLVQAGGSLRLSCAASGRIFSIDIMSWVRQA PGKQRELVARITRGGTISYDDSVKGRFTISRDNAKNTVYLQMNSLKPEDTGVYY CNALYGTDYWGKGTQVTVSSgggsgggsgggsggggsEVQLVESGGGLVQPGNSLRLSC AASGFTFSKFGMSWVRQAPGKGLEWVSSISGSGRDTLYAESVKGRFTISRDNAK TTLYLQMNSLRPEDTAVYYCTIGGSLSVSSQGTLVTVSSSGGPGAGMKGLPGSh gtviesleslnnyfnssgidveekslfldiwrnwqkdgdmkilqsqiisfylrlfevlkdnqaismnisvieshlittffsnskak kdafmsiakfevnmpqvrqafnelirvvhqllpesslrkrkrsrcgggsggggsggggshgtviesleslnnyfnssgid veekslfldiwrnwqkdgdmkilqsqiisfylrlfevlkdnqaismnisvieshlittffsnskakkdafmsiakfevnmpqv qrqafnelirvvhqllpesslrkrkrsrcSGGPGAGMKGLPGSEVQLVESGGGLVQPGNSLRLS CAASGFTFSKFGMSWVRQAPGKGLEWVSSISGSGRDTLYAESVKGRFTISRDNA KTTLYLQMNSLRPEDTAVYYCTIGGSLSVSSQGTLVTVSSHHHHHH |

| 95 | ACP55 Mouse IFG fusion protein | mdmrvpaqllgllllwlrgarcEVQLVESGGGLVQPGNSLRLSCAASGFTFSKFGMSWVRQ APGKGLEWVSISGGGRDTLYAESVKGRFTISRDNAKTTLYLQMNSLRPEDTAV YYCTIGGSLSVSSQGTLVTVSSGGPGAGMKGLPGShgtviesleslnnyfnssgidveeksl fl diwrnwqkdgdmkilqsqiisfylrlfevlkdnqaismnisvieshlittffsnskakdafmsiakfevnmpqvqrqafnel irvvhqllpesslrkrkrsrcSGGPGAGMKGLPGSEVQLVESGGGLVQPGNSLRLSCAASG FTFSKFGMSWVRQAPGKGLEWVSSISGSGRDTLYAESVKGRFTISRDNAKTTLY LQMNSLRPEDTAVYYCTIGGSLSVSSQGTLVTVSSGGPGAGMKGLPGShgtvies leslnnyfnssgidveekslfldiwrnwqkdgdmkilqsqiisfylrlfevlkdnqaismnisvieshlittffsnskakkdaf msiakfevnmpqvrqafnelirvvhqllpesslrkrkrsrcSGGPGAGMKGLPGSEVQLVESGGGL VQPGNSLRLSCAASGFTFSKFGMSWVRQAPGKGLEWVSSISGSGRDTLYAESVK GRFTISRDNAKTTLYLQMNSLRPEDTAVYYCTIGGSLSVSSQGTLVTVSSHHHHH H |

| 96 | ACP56 Mouse IFG fusion protein | mdmrvpaqllgllllwlrgarcQVQLQESGGGLAQAGGSLSLSCAASGFTVSNSVMAWYR QTPGKQREFVAIINSVGSTNYADSVKGRFTISRDNAKNTVYLQMNNLKPEDTAV YVCNRNFDRIYWGQGTQVTVSSgggsgggsggggsEVQLVESGGGLVQPGNSLRLS CAASGFTFSKFGMSWVRQAPGKGLEWVSSISGSGRDTLYAESVKGRFTISRDNA KTTLYLQMNSLRPEDTAVYYCTIGGSLSVSSQGTIVTVSSSGGPGAGMKGLPG |

-continued

SEQUENCE TABLE

| SEQ ID NO. | Name | Sequence |
|---|---|---|
| 97 | ACP57 Mouse IFG fusion protein | Shgtvieslesinmyfnssgidveekslfldiwrnwqkdgdmkilqsqiisfylrlfevlkdnqaismnisvieshlittffsnsk akkdafmsiakfevnnpqvgrqafnelirvvhqllpesslrkrkrsrcSGGPGAGMKGLPGSEVQLVES GGGLVQPGNSLRLSCAASGFTFSKFGMSWVRQAPGKGLEWVSSISGSGRDTLYA ESVKGRFTISRDNAKTTLYLQMNSLRPEDTAVYYCTIGGSLVSSQGTLVTVSSH HHHHHEPEA |
| 98 | ACP58 Mouse IFG fusion protein | mdmrvpaqllgllllwlrgarcEVQLVESGGGLVQPGNSLRLSCAASGFTFSKFGMSWVRQ APGKGLEWVSSISGSGRDTLYAESVKGRFTISRDNAKTTLYLQMNSLRPEDTAV YYCTIGGSLSVSSQGTLVTVSSGGPPAGMKGLPGShgtvieslesinnyfnssgidveekslfl diwrnwqkdgdmkilqsqiisfylrlfevlkdnqaismnisvieshlittffsnskakkdafmsiakfevnnpqvgrqafnel irvvhqllpesslrkrkrsrcSGGPGAGMKGLPGSEVQLVESGGGLVQPGNSLRLSCAASG FTFSKFGMSWVRQAPGKGLEWVSSISGSGRDTLYAESVKGRFTISRDNAKTTLY LQMNSLRPEDTAVYYCTIGGSLSVSSQGTLVTVSSgggsgggsgggsgggsQVQLQESG GGLAQAGGSLSLSCAASGFTVSNSVMAWRQTPGKQREFVAIINSVGSTNYADS VKGRFTISRDNAKNTVYLQMNNLKPEDTAVYVCNRNFDRIYWGQGTQVTVSSH HHHHHEPEA |
| 99 | ACP59 Mouse IFG fusion protein | mdmrvpaqllgllllwlrgarcEVQLVESGGGLVQPGNSLRLSCAASGFTFSKFGMSWVRQ APGKGLEWVSSISGSGRDTLYAESVKGRFTISRDNAKTTLYLQMNSLRPEDTAV YYCTIGGSLSVSSQGTLVTVSSgggsgggsgggsgggsEVQLVESGGGLVQPGNSLRLS CAASGFTFSKFGMSWVRQAPGKGLEWVSSISGSGRDTLYAESVKGRFTISRDNA KTTLYLQMNSLRPEDTAVYYCTIGGSLSVSSQGTLVTVSSGGPGAGMKGLPG Shgtvieslesinmyfnssgidveekslfldiwrnwqkdgdmkilqsqiisfylrlfevlkdnqaismnisvieshlittffsnsk akkdafmsiakfevnnpqvgrqafnelirvvhqllpesslrkrkrsrcSGGPGAGMKGLPGShgtvieslesin nyfnssgidveekslfldiwrnwqkdgdmkilqsqiisfylrlfevlkdnqaismnisvieshlittffsnskakkdafmsiak fevnnpqvgrqafnelirvvhqllpesslrkrkrsrcSGGPGAGMKGLPGSEVQLVESGGGLVQPG NSLRLSCAASGFTFSKFGMSWVRQAPGKGLEWVSSISGSGRDTLYAESVKGRFTI SRDNAKTTLYLQMNSLRPEDTAVYYCTIGGSLSVSSQGTLVTVSSHHHHHHEPE A |
| 100 | ACP60 Mouse IFG fusion protein | mdmrvpaqllgllllwlrgarcEVQLVESGGGLVQPGNSLRLSCAASGFTFSKFGMSWVRQ APGKGLEWVSSISGSGRDTLYAESVKGRFTISRDNAKTTLYLQMNSLRPEDTAV YYCTIGGSLSVSSQGTLVTVSSGGPGAGMKGLPGShgtvieslesinnyfnssgidveekslfl diwrnwqkdgdmkilqsqiisfylrlfevlkdnqaismnisvieshlittffsnskakkdafmsiakfevnnpqvgrqafnel irvvhqllpesslrkrkrsrcSGGPGAGMKGLPGSEVQLVESGGGLVQPGNSLRLSCAASG mkilqsqiisfylrlfevlkdnqaismnisvieshlittffsnskakkdafmsiakfevnnpqvgrqafnelirvvhqllpesslr |

-continued

SEQUENCE TABLE

| SEQ ID NO. | Name | Sequence |
|---|---|---|

101  ACP61 Mouse IFG fusion protein krkrsrcSGGPGPAGMKGLPGSEVQLVESGGGLVQPGNSLRLSCAASGFTFSKFGMS
WVRQAPGKGLEWVSSISGSGRDTLYAESVKGRFTISRDNAKTTLYLQMNSLRPE
DTAVYYCTIGGSLSVSSQGTLVTVSSgggsgggsgggsgggsQVQLQESGGGLAQAGGS
LSLSCAASGFTVSNSVMAWYRQTPGKQREFVAIINSVGSTNYADSVKGRFTISRD
NAKNTVYLQMNNLKPEDTAVYVCNRNFDRIYWGQGTQVTVSSHHHHHHEPEA 102  ACP63 Anti-FN CGS-2 scFv mdmrvpaqllglllwlrgarcEVQLVESGGGLVQPGNSLRLSCAASGFTFSKFGMSWVRQ
APGKGLEWVSSISGSGRDTLYAESVKGRFTISRDNAKTTLYLQMNSLRPEDTAV
YYCTIGGSLSVSSQGTLVTVSSgggsgggsgggsgggsEVQLVESGGGLVQPGGSL
diwrnwqkdgdmkilqsqiisfylrlfevlkdngaisnnisvieshlittffsnskakkdafmsiakfevnnpqvqrqafnel
irvvhqllpesslrkrkrsrcSGGPGPAGMKGLPGSEVQLVESGGGLVQPGNSLRLSCAASG
FTFSKFGMSWVRQAPGKGLEWVSSISGSGRDTLYAESVKGRFTISRDNAKTTLY
LQMNSLRPEDTAVYYCTIGGSLSVSSQGTLVTVSSgggsgggsgggsgggsEVQLVESGGGLVQPGGSL
RLSCAASGFTFSSYAMSWVRQAPGKGLEWVSAISGSGSTYYADSVKGRFTISR
DNSKNTLYLQMNSLRAEDTAVYYCARGVGAFRPYRKHEWGQGTLVTVSRgggg
sgggsgggsgggssSELTQDPAVSVALGQTVRITCQGDSLRSYYASWYQQKPGQAPVLV
IYGKNNRPSGIPDRFSGSSSGNTASLTTTGAQAEDEADYYCNSSPFEHNLVVFGG
GTKLTVLHHHHHHEPEA 103  ACP69 Mouse IFG fusion protein mdmrvpaqllglllwlrgarcEVQLVESGGGLVQPGNSLRLSCAASGFTFSKFGMSWVRQ
APGKGLEWVSSISGSGRDTLYAESVKGRFTISRDNAKTTLYLQMNSLRPEDTAV
YYCTIGGSLSVSSQGTLVTVSSgggsgggsgggsgggsEVQLVESGGGLVQPGGSL
diwrnwqkdgdmkilqsqiisfylrlfevlkdngaisnnisvieshlittffsnskakkdafmsiakfevnnpqvqrqafnel
irvvhqllpesslrkrkrsrcSGGPGPAGMKGLPGSEVQLVESGGGLVQPGNSLRLSCAASG
FTFSKFGMSWVRQAPGKGLEWVSSISGSGRDTLYAESVKGRFTISRDNAKTTLY
LQMNSLRPEDTAVYYCTIGGSLSVSSQGTLVTVSSGGPGPAGMKGLPGShgtvies
leslnnyfnssgidveekslfldiwrnwqkdgdmkilqsqiisfylrlfevlkdngaisnnisvieshlittffsnskakkdaf
msiakfevnnpqvqrqafnelirvvhqllpesslrkrkrsrcHHHHHHEPEA 104  ACP70 Mouse IFG fusion protein mdmrvpaqllglllwlrgarchgtvieslesnnyfnssgidveekslfldiwrnwqkdgdmkilqsqiisfylrlfevlkd
ngaisnnisvieshlittffsnskakkdafmsiakfevnnpqvqrqafnelirvvhqllpesslrkrkrsrcSGGPGPAG
MKGLPGSEVQLVESGGGLVQPGNSLRLSCAASGFTFSKFGMSWVRQAPGKGLE
WVSSISGSGRDTLYAESVKGRFTISRDNAKTTLYLQMNSLRPEDTAVYYCTIGGS
LSVSSQGTLVTVSSQGTLVTVSSgggsgggsgggsgggsEVQLVESGGGLVQPGNSLRLSCAASGFTFSKFGM
dmkilqsqiisfylrlfevlkdngaisnnisvieshlittffsnskakkdafmsiakfevnnpqvqrqafnelirvvhqllpessl
rkrkrsrcSGGPGPAGMKGLPGSEVQLVESGGGLVQPGNSLRLSCAASGFTFSKFGM
SWVRQAPGKGLEWVSSISGSGRDTLYAESVKGRFTISRDNAKTTLYLQMNSLRP
EDTAVYYCTIGGSLSVSSQGTLVTVSSHHHHHHEPEA -continued

SEQUENCE TABLE

| SEQ ID NO. | Name | Sequence |
|---|---|---|
| 105 | ACP71 Mouse IFG fusion protein | mdmrvpaqlglglllllwlrgarchgtviesleslnnyfnssgidveekslfldiwrnwqkdgdmkilgsqiisfylrlfevlkd<br>ngaisnnisvieshlittffsnskakkdafmsiakfevnnpqvqrqafnelirvvhqllpesslrkrksrcSGGPGPAG<br>MKGLPGSEAHKSEIAHRYNDLGEQHFKGLVLIAFSQYLQKCSYDEHAKLVQEVT<br>DFAKTCVADESAANCDKSLHTLFGDKLCAIPNLRENYGELADCCTKQEPERNEC<br>FLQHKDDNPSLPPFERPEAEAMCTSFKENPTTFMGHYLHEVARRHPYFYAPELL<br>YYAEQYNEILTQCCAEADKESCLTPKLDGVKEKALVSSVRQRMKCSSMQKFGE<br>RAFKAWAVARLSQTFPNADFAEITKLATDLTKVNKECCHGDLLECADDRAELA<br>KYMCENQATISSKLQTCCDKPLLKKAHCLSEVEHDTMPADLPAIAADFVEDQEV<br>CKNYAEAKDVFLGTFLYEYSRRHPDYSVSLLLRLAKKYEATLEKCCAEANPPAC<br>YGTVLAEFQPLVEEPKNLVKTNCDLYEKLGEYGFQNAILVRYTQKAPQVSTPTL<br>VEAARNLGRVGTKCCTLPEDQRLPCVEDYLSAILNRVCLLHEKTPVSEHVTKCC<br>SGSLVERRPCFSALTVDETYVPKEFKAETTFHSDICTLPEKEKQIKKQTALAELIV<br>KHKPKATAEQLKTVMDDFAQFLDTCCKAADKDTCFSTEGPNLVTRCKDALASG<br>GPGPAGMKGLPGShgtviesleslnnyfnssgidveekslfldiwrnwqkdgdmkilgsqiisfylrlfevlkdnq<br>aismnisvieshlittffsnskakkdafmsiakfevnnpqvqrqafnelirvvhqllpesslrkrksrcSGGPGPAGM<br>KGLPGSEAHKSEIAHRYNDLGEQHFKGLVLIAFSQYLQKCSYDEHAKLVQEVTD<br>FAKTCVADESAANCDKSLHTLFGDKLCAIPNLRENYGELADCCTKQEPERNECF<br>LQHKDDNPSLPPFERPEAEAMCTSFKENPTTFMGHYLHEVARRHPYFYAPELLY<br>YAEQYNEILTQCCAEADKESCLTPKLDGVKEKALVSSVRQRMKCSSMQKFGER<br>AFKAWAVARLSQTFPNADFAEITKLATDLTKVNKECCHGDLLECADDRAELAK<br>YMCENQATISSKLQTCCDKPLLKKAHCLSEVEHDTMPADLPAIAADFVEDQEVC<br>KNYAEAKDVFLGTFLYEYSRRHPDYSVSLLLRLAKKYEATLEKCCAEANPPACY<br>GTVLAEFQPLVEEPKNLVKTNCDLYEKLGEYGFQNAILVRYTQKAPQVSTPTLV<br>EAARNLGRVGTKCCTLPEDQRLPCVEDYLSAILNRVCLLHEKTPVSEHVTKCCS<br>GSLVERRPCFSALTVDETYVPKEFKAETTFHSDICTLPEKEKQIKKQTALAELVK<br>HKPKATAEQLKTVMDDFAQFLDTCCKAADKDTCFSTEGPNLVTRCKDALAHHH<br>HHHEPEA |
| 106 | ACP72 Mouse IFG fusion protein | mdmrvpaqlglglllllwlrgarcEAHKSEIAHRYNDLGEQHFKGLVLIAFSQYLQKCSYDEHA<br>KLVQEVTDFAKTCVADESAANCDKSLHTLFGDKLCAIPNLRENYGELADCCTK<br>QEPERNECFLQHKDDNPSLPPFERPEAEAMCTSFKENPTTFMGHYLHEVARRHP<br>YFYAPELLYYAEQYNEILTQCCAEADKESCLTPKLDGVKEKALVSSVRQRMKCS<br>SMQKFGERAFKAWAVARLSQTFPNADFAEITKLATDLTKVNKECCHGDLLECA<br>DDRAELAKYMCENQATISSKLQTCCDKPLLKKAHCLSEVEHDTMPADLPAIAAD<br>FVEDQEVCKNYAEAKDVFLGTFLYEYSRRHPDYSVSLLLRLAKKYEATLEKCCA<br>EANPPACYGTVLAEFQPLVEEPKNLVKTNCDLYEKLGEYGFQNAILVRYTQKAP<br>QVSTPTLVEAARNLGRVGTKCCTLPEDQRLPCVEDYLSAILNRVCLLHEKTPVSE<br>HVTKCCSGSLVERRPCFSALTVDETYVPKEFKAETTFHSDICTLPEKEKQIKKQT<br>ALAELVKHKPKATAEQLKTVMDDFAQFLDTCCKAADKDTCFSTEGPNLVTRCK<br>DALASGGPGPAGMKGLPGShgtviesleslnnyfnssgidveekslfldiwrnwqkdgdmkilgsqiisfylr<br>lfevlkdnqaismnisvieshlittffsnskakkdafmsiakfevnnpqvqrqafnelirvvhqllpesslrkrksrcSGGP<br>GPAGMKGLPGSEAHKSEIAHRYNDLGEQHFKGLVLIAFSQYLQKCSYDEHAKLV<br>QEVTDFAKTCVADESAANCDKSLHTLFGDKLCAIPNLRENYGELADCCTKQEPE<br>RNECFLQHKDDNPSLPPFERPEAEAMCTSFKENPTTFMGHYLHEVARRHPYFYA<br>PELLYYAEQYNEILTQCCAEADKESCLTPKLDGVKEKALVSSVRQRMKCSSMQ<br>KFGERAFKAWAVARLSQTFPNADFAEITKLATDLTKVNKECCHGDLLECADDR<br>AELAKYMCENQATISSKLQTCCDKPLLKKAHCLSEVEHDTMPADLPAIAADFVE |

-continued

SEQUENCE TABLE

| SEQ ID NO. | Name | Sequence |
|---|---|---|

107  ACP73 Mouse IFG fusion protein

DQEVCKNYABAKDVFLGTFLYEYSRRHPDYSVSLLLRLAKKYEATLEKCCAEA
NPPACYGTVLAEFQPLVEEPKNLVKTNCDLYEKLGEYGFQNAILVRYTQKAPQV
STPTLVEAARNLGRVGTKCCTLPEDQRLPCVEDYLSAILNRVCLLHEKTPVSEHV
TKCCSGSLVERRPCFSALTVDETVPKEFKAEFTFHSDICTLPEKEKQIKKQTAL
AELVKHKPKATAEQLKTVMDDFAQFLDTCCKAADKDTCFSTEGPNLVTRCKDA
LASGGPGAGMKGLPGShgtvieeslnnyfnssgidveekslfldiwrnwqkdgdmkilqsqiisfylrlfe
vlkdnqaisnnisvieshlittffsnskakkdafmsiakfevnnpqvrqgafnelirvvhqllpesslrkrkrsrcHHHHH
HEPEA mdmrvpaqlglglll1wlrgarcEAHKSEIAHRYNDLGEQHFKGLVLIAFSQYLQKCSYDEHA
KLVQEVTDFAKTCVADESAANCDKSLHTLFGDKLCAIPNLRENYGELADCCTK
QEPERNECFLQHKDDNPSLPPFERPEAEAMCTSFKENPTTFMGHYLHEVARRHP
YFYAPELLYYAEQYNEILTQCCAEADKESCLTPKLDGVKEKALVSSVRQRMKCS
SMQKFGERAPKAWAVARLSQTFPNADFAEITKLATDLTKVNKECCHGDLLECA
DDRAELAKYMCENQATISSKLQTCCDKPLLKKAHCLSEVEHDTMPADLPAIAAD
FVEDQEVCKNYAEAKDVFLGTFLYEYSRRHPDYSVSLLLRLAKKYEATLEKCCA
EANPPACYGTVLAEFQPLVEEPKNLVKTNCDLYEKLGEYGFQNAILVRYTQKAP
QVSTPTLVEAARNLGRVGTKCCTLPEDQRLPCVEDYLSAILNRVCLLHEKTPVSE
HVTKCCSGSLVERRPCFSALTVDETYVPKEFKAEFTFHSDICTLPEKEKQIKKQT
ALAELVKHKPKATAEQLKTVMDDFAQFLDTCCKAADKDTCFSTEGPNLVTRCK
DALASGGPGAGMKGLPGShgtvieeslnnyfnssgidveekslfldiwrnwqkdgdmkilqsqiisfylr
lfevlkdnqaisnnisvieshlittffsnskakkdafmsiakfevnnpqvrqgafnelirvvhqllpesslrkrkrsrcSGGP
GPAGMKGLPGSEAHKSEIAHRYNDLGEQHFKGLVLIAFSQYLQKCSYDEHAKLV
QEVTDFAKTCVADESAANCDKSLHTLFGDKLCAIPNLRENYGELADCCTKQEPE
RNECFLQHKDDNPSLPPFERPEAEAMCTSFKENPTTFMGHYLHEVARRHPYFYA
PELLYYAEQYNEILTQCCAEADKESCLTPKLDGVKEKALVSSVRQRMKCSSMQ
KFGERAFKAWAVARLSQTFPNADFAEITKLATDLTKVNKECCHGDLLECADDR
AELAKYMCENQATISSKLQTCCDKPLLKKAHCLSEVEHDTMPADLPAIAADFVE
DQEVCKNYAEAKDVFLGTFLYEYSRRHPDYSVSLLLRLAKKYEATLEKCCAEA
NPPACYGTVLAEFQPLVEEPKNLVKTNCDLYEKLGEYGFQNAILVRYTQKAPQV
STPTLVEAARNLGRVGTKCCTLPEDQRLPCVEDYLSAILNRVCLLHEKTPVSEHV
TKCCSGSLVERRPCFSALTVDETYVPKEFKAEFTFHSDICTLPEKEKQIKKQTAL
AELVKHKPKATAEQLKTVMDDFAQFLDTCCKAADKDTCFSTEGPNLVTRCKDA
LASGGPGAGMKGLPGShgtvieeslnnyfnssgidveekslfldiwrnwqkdgdmkilqsqiisfylrlfe
vlkdnqaisnnisvieshlittffsnskakkdafmsiakfevnnpqvrqgafnelirvvhqllpesslrkrkrsrcSGGPGP
AGMKGLPGSEAHKSEIAHRYNDLGEQHFKGLVLIAFSQYLQKCSYDEHAKLVQ
EVTDFAKTCVADESAANCDKSLHTLFGDKLCAIPNLRENYGELADCCTKQEPER
NECFLQHKDDNPSLPPFERPEAEAMCTSFKENPTTFMGHYLHEVARRHPYFYAP
ELLYYAEQYNEILTQCCAEADKESCLTPKLDGVKEKALVSSVRQRMKCSSMQK
FGERAFKAWAVARLSQTFPNADFAEITKLATDLTKVNKECCHGDLLECADDRA
ELAKYMCENQATISSKLQTCCDKPLLKKAHCLSEVEHDTMPADLPAIAADFVED
QEVCKNYAEAKDVFLGTFLYEYSRRHPDYSVSLLLRLAKKYEATLEKCCAEANP
PACYGTVLAEFQPLVEEPKNLVKTNCDLYEKLGEYGFQNAILVRYTQKAPQVST
PTLVEAARNLGRVGTKCCTLPEDQRLPCVEDYLSAILNRVCLLHEKTPVSEHVT
KCCSGSLVERRPCFSALTVDETYVPKEFKAEFTFHSDICTLPEKEKQIKKQTALA
ELVKHKPKATAEQLKTVMDDFAQFLDTCCKAADKDTCFSTEGPNLVTRCKDAL
AHHHHHHEPEA -continued

SEQUENCE TABLE

| SEQ ID NO. | Name | Sequence |
|---|---|---|
| 108 | ACP74 Mouse IFG fusion protein | mdmrvpaqllglll1wlrgarcEAHKSEIAHRYNDLGEQHFKGLVLIAFSQYLQKCCSYDEHA<br>KLVQEVTDFAKTCVADESAANCDKSLHTLFGDKLCAIPNLRENYGELADCCTK<br>QEPERNECFLQHKDDNPSLPPFERPEAEAMCTSFKENPTTFMGHYLHEVARRHP<br>YFYAPELLYYAEQYNEILTQCCAEADKESCLTPKLDGVKEKALVSSVRQRMKCS<br>SMQKFGERAFKAWAVARLSQTFPNADFAEITKLATDLTKVNKECCHGDLLECA<br>DDRAELAKYMCENQATISSKLQTCCDKPLLKKAHCLSEVEHDTMPADLPAIAAD<br>FVEDQEVCKNYAEAKDVFLGTFLYEYSRRHPDYSVSLLLRLAKKYEATLEKCCA<br>EANPPACYGTVLAEFQPLVEEPKNLVKTNCDLYEKLGEYGFQNAILVRYTQKAP<br>QVSTPTLVEAARNLGRVGTKCCTLPEDQRLPCVEDYLSAILNRVCLLHEKTPVSE<br>HVTKCCSGSLVERRPCFSALTVDETYVPKEFKAETTFHSDICTLPEKEKQIKKQT<br>ALAELVKHKPKATAEQLKTVMDDFAQFLDTCCKAADKDTCFSTEGPNLVTRCK<br>DALASGGPGPAGMKGLPGShgtviesleslnnyfnssgidveekslfldiwrnwqkdgdmkilq<br>lfevlkdnqaismnisvieshlittffsnskakkdafmsiakfevnnpqvqrqafnelirvvhqllpesslrkrksrcSGGP<br>GPAGMKGLPGSgggsEAHKSEIAHRYNDLGEQHFKGLVLIAFSQYLQKCCSYDEH<br>AKLVQEVTDFAKTCVADESAANCDKSLHTLFGDKLCAIPNLRENYGELADCCT<br>KQEPERNECFLQHKDDNPSLPPFERPEAEAMCTSFKENPTTFMGHYLHEVARRH<br>PYFYAPELLYYAEQYNEILTQCCAEADKESCLTPKLDGVKEKALVSSVRQRMKC<br>SSMQKFGERAFKAWAVARLSQTFPNADFAEITKLATDLTKVNKECCHGDLLEC<br>ADDRAELAKYMCENQATISSKLQTCCDKPLLKKAHCLSEVEHDTMPADLPAIAA<br>DFVEDQEVCKNYAEAKDVFLGTFLYEYSRRHPDYSVSLLLRLAKKYEATLEKCC<br>AEANPPACYGTVLAEFQPLVEEPKNLVKTNCDLYEKLGEYGFQNAILVRYTQKA<br>PQVSTPTLVEAARNLGRVGTKCCTLPEDQRLPCVEDYLSAILNRVCLLHEKTPVS<br>EHVTKCCSGSLVERRPCFSALTVDETYVPKEFKAETTFHSDICTLPEKEKQIKKQ<br>TALAELVKHKPKATAEQLKTVMDDFAQFLDTCCKAADKDTCFSTEGPNLVTRC<br>KDALAggggsSGGPGPAGMKGLPGShgtviesleslmnyfnssgidveekslfldiwrnwqkdgdmkilq<br>sqiisfylrlfevlkdnqaismnisvieshlittffsnskakkdafmsiakfevnnpqvqrqafnelirvvhqllpesslrkrksr<br>cSGGPGPAGMKGLPGSEAHKSEIAHRYNDLGEQHFKGLVLIAFSQYLQKCCSYDE<br>HAKLVQEVTDFAKTCVADESAANCDKSLHTLFGDKLCAIPNLRENYGELADCC<br>TKQEPERNECFLQHKDDNPSLPPFERPEAEAMCTSFKENPTTFMGHYLHEVARR<br>HPYFYAPELLYYAEQYNEILTQCCAEADKESCLTPKLDGVKEKALVSSVRQRMK<br>CSSMQKFGERAFKAWAVARLSQTFPNADFAEITKLATDLTKVNKECCHGDLLE<br>CADDRAELAKYMCENQATISSKLQTCCDKPLLKKAHCLSEVEHDTMPADLPAIA<br>ADFVEDQEVCKNYAEAKDVFLGTFLYEYSRRHPDYSVSLLLRLAKKYEATLEK<br>CCAEANPPACYGTVLAEFQPLVEEPKNLVKTNCDLYEKLGEYGFQNAILVRYTQ<br>KAPQVSTPTLVEAARNLGRVGTKCCTLPEDQRLPCVEDYLSAILNRVCLLHEKTP<br>VSEHVTKCCSGSLVERRPCFSALTVDETYVPKEFKAETTFHSDICTLPEKEKQIK<br>KQTALAELVKHKPKATAEQLKTVMDDFAQFLDTCCKAADKDTCFSTEGPNLVT<br>RCKDALAHHHHHHEPEA |
| 109 | ACP75 Mouse IFG fusion protein | mdmrvpaqllglll1wlrgarcEAHKSEIAHRYNDLGEQHFKGLVLIAFSQYLQKCCSYDEHA<br>KLVQEVTDFAKTCVADESAANCDKSLHTLFGDKLCAIPNLRENYGELADCCTK<br>QEPERNECFLQHKDDNPSLPPFERPEAEAMCTSFKENPTTFMGHYLHEVARRHP<br>YFYAPELLYYAEQYNEILTQCCAEADKESCLTPKLDGVKEKALVSSVRQRMKCS<br>SMQKFGERAFKAWAVARLSQTFPNADFAEITKLATDLTKVNKECCHGDLLECA<br>DDRAELAKYMCENQATISSKLQTCCDKPLLKKAHCLSEVEHDTMPADLPAIAAD<br>FVEDQEVCKNYAEAKDVFLGTFLYEYSRRHPDYSVSLLLRLAKKYEATLEKCCA<br>EANPPACYGTVLAEFQPLVEEPKNLVKTNCDLYEKLGEYGFQNAILVRYTQKAP<br>QVSTPTLVEAARNLGRVGTKCCTLPEDQRLPCVEDYLSAILNRVCLLHEKTPVSE |

-continued

SEQUENCE TABLE

| SEQ ID NO. | Name | Sequence |
|---|---|---|
| | | HVTKCCSGSLVERRPCFSALTVDETYVPKEFKAEFTFHSDICTLPEKEKQIKKQT<br>ALAELVKHKPKATAEQLKTVMDDFAQFLDTCCKAADKDTCFSTEGPNLVTRCK<br>DALASGGPGPAGMKGLPGShgtvieslesLnnyfnssgidveeksLfLdiwrnwqkdgqmkiLqsqiisfyLr<br>LfevLkdnqaismnisvieshLittffsnskakkdafmsiakfevnnpqvqrqafneLirvvhqLLpessLrkrksrccSGGP<br>GPAGMKGLPGSggggsggggsEAHKSEIAHRYNDLGEQHFKGLVLIAFSQYLQKCSY<br>DEHAKLVQEVTDFAKTCVADESAANCDKSLHTLFGDKLCAIPNLRENYGELAD<br>CCTKQEPERNECFLQHKDDNPSLPPFERPEAEAMCTSFKENPTTFMGHYLHEVA<br>RRHPYFYAPELLYYAEQYNEILTQCCAEADKESCLTPKLDGVKEKALVSSVRQR<br>MKCSSMQKFGERAFKAWAVARLSQTFPNADFAEITKLATDLTKVNKECCHGDL<br>LECADDRAELALAKYMCENQATISSKLQTCCDKPLLKKAHCLSEVEHDTMPADLP<br>AIAADFVEDGEVCKNYAEAKDVFLGTFLYEYSRRHPDYSVSLLLRLAKKYEATL<br>EKCCAEANPPACYGTVLAEFQPLVEEPKNLVKTNCDLYEKLGEYGFQNAILVRY<br>TQKAPQVSTPTLVEAARNLGRVGTKCCTLPEDQRLPCVEDYLSAILNRVCLLHE<br>KTPVSEHVTKCCCSGSLVERRPCFSALTVDETYVPKEFKAEFTFHSDICTLPEKEK<br>QIKKQTALALELVKHKPKATAEQLKTVMDDFAQFLDTCCKAADKDTCFSTEGPN<br>LVTRCKDALAggggsggggsSGGPGPAGMKGLPGShgtvieslesLnnyfnssgidveeksLfLdiwrn<br>wqkdgqmkiLqsqiisfyLrLfevLkdnqaismnisvieshLittffsnskakkdafmsiakfevnnpqvqrqafneLirvvh<br>qLLpessLrkrksrccSGGPGPAGMKGLPGSEAHKSEIAHRYNDLGEQHFKGLVLIAFSQY<br>LQKCSYDEHAKLVQEVTDFAKTCVADESAANCDKSLHTLFGDKLCAIPNLREN<br>YGELADCCTKQEPERNECFLQHKDDNPSLPPFERPEAEAMCTSFKENPTTFMGH<br>YLHEVARRHPYFYAPELLYYAEQYNEILTQCCAEADKESCLTPKLDGVKEKALV<br>SSVRQRMKCSSMQKFGERAFKAWAVARLSQTFPNADFAEITKLATDLTKVNKE<br>CCHGDLLECADDRAELALAKYMCENQATISSKLQTCCDKPLLKKAHCLSEVEHDT<br>MPADLPAIAADFVEDGEVCKNYAEAKDVFLGTFLYEYSRRHPDYSVSLLLRLAK<br>KYEATLEKCCAEANPPACYGTVLAEFQPLVEEPKNLVKTNCDLYEKLGEYGFQ<br>NAILVRYTQKAPQVSTPTLVEAARNLGRVGTKCCTLPEDQRLPCVEDYLSAILNR<br>VCLLHEKTPVSEHVTKCCCSGSLVERRPCFSALTVDETYVPKEFKAETFTFHSDICT<br>LPEKEKQIKKQTALAELVKHKPKATAEQLKTVMDDFAQFLDTCCKAADKDTCF<br>STEGPNLVTRCKDALAHHHHHHEPEA |
| 110 | ACP78<br>Mouse<br>IFG<br>fusion<br>protein | mdmrvpaqLLgLLLLwLrgarcEVQLVESGGGLVQPGNSLRLSCAASGFTFSKFGMSWVRQ<br>APGKGLEWVSSISGSGRDTLYAESVKGRFTISRDNAKTTLYLQMNSLRPEDTAV<br>YYCTIGGSLSVSSQGTLVTVSSggggsggggsggggsggggshgtvieslesLnnyfnssgidveeksLfLdiwrn<br>wqkdgqmkiLqsqiisfyLrLfevLkdnqaismnisvieshLittffsnskakkdafmsiakfevnnpqvqrqafneLirvvh<br>qLLpessLrkrksrcggggsggggsggggsggggsEVQLVESGGGLVQPGNSLRLSCAASGFTFSKFGM<br>SWVRQAPGKGLEWVSSISGSGRDTLYAESVKGRFTISRDNAKTTLYLQMNSLRP<br>EDTAVYYCTIGGSLSVSSQGTLVTVSSggggsggggsggggsggggsggggshgtvieslesLnnyfnssgidveeksL<br>fLdiwrnwqkdgqmkiLqsqiisfyLrLfevLkdnqaisnnisvieshLittffsnskakkdafmsiakfevnnpqvqrqafn<br>eLirvvhqLLpessLrkrksrcggggsggggsggggsggggsEVQLVESGGGLVQPGNSLRLSCAASGFTFS<br>KFGMSWVRQAPGKGLEWVSSISGSGRDTLYAESVKGRFTISRDNAKTTLYLQM<br>NSLRPEDTAVYYCTIGGSLSVSSQGTLVTVSSHHEIHRHEPEA |
| 111 | ACP134<br>Mouse<br>IFG<br>fuision<br>protein | mdmrvpaqLLgLLLLwLrgarcEVQLVESGGGLVQPGNSLRLSCAASGFTFSKFGMSWVRQ<br>APGKGLEWVSSISGSGRDTLYAESVKGRFTISRDNAKTTLYLQMNSLRPEDTAV<br>YYCTIGGSLSVSSQGTLVTVSSGGPGPAGMKGLPGShgtvieslesLnnyfnssgidveeksLfL<br>diwrnwqkdgqmkiLqsqiisfyLrLfevLkdnqaisnnisvieshLittffsnskakkdafmsiakfevnnpqvqrqafneL<br>irvvhqLLpessLrkrksrcSGGPGPAGMKGLPGSEVQLVESGGGLVQPGNSLRLSCAASG<br>FTFSKFGMSWVRQAPGKGLEWVSSISGSGRDTLYAESVKGRFTISRDNAKTTLY |

-continued

SEQUENCE TABLE

| SEQ ID NO. | Name | Sequence |
|---|---|---|
| 112 | ACP135 Mouse IFG fusion protein | LQMNSLRPEDTAVYYCTIGGSLSVSSQGTLVTVSSSGGPGAGMKGLPGShgtvies<br>leslnnyfnssgidveekslfldiwrnwqkdgdmkilgsqiisfylrlfevlkdnqaismnisvieshlittffsnskakkdaf<br>msiakfevnnpqvqrqafnelirvvhqllpesslrkrkrsrcSGGPGAGMKGLPGSEVQLVESGGGL<br>VQPGNSLRLSCAASGFTFSKFGMSWVRQAPGKGLEWVSSISGSGRDTLYAESVK<br>GRFTISRDNAKTTLYLQMNSLRPEDTAVYYCTIGGSLSVSSQGTLVTVSSggggsgg<br>ggggggsQVQLQESGGGLAQAGGSLSLSCAASGFTVSNSVMAWYRQTPGKQREF<br>VAIINSVGSTNYADSVKGRFTISRDNAKNTVYLQMNNLKPEDTAVYVCNRNFDR<br>IYWGQGTQVTVSSHHHHHHEPEA |
| 113 | ACP34 Mouse IL-12 fusion protein | mdmrvpaqllgllllwlrgarcQVQLQESGGGLAQAGGSLSLSCAASGFTVSNSVMAWYR<br>QTPGKQREFVAIINSVGSTNYADSVKGRFTISRDNAKNTVYLQMNNLKPEDTAV<br>YVCNRNFDRIYWGQGTQVTVSSggggsgggggggsEVQLVESGGGLVQPGNSLRLS<br>CAASGFTFSKFGMSWVRQAPGKGLEWVSSISGSGRDTLYAESVKGRFTISRDNA<br>KTTLYLQMNSLRPEDTAVYYCTIGGSLSVSSQGTLVTVSSSGGPGAGMKGLPG<br>Shgtvieslsnnyfnssgidveekslfldiwrnwqkdgdmkilgsqiisfylrlfevlkdnqaismnisvieshlittffsnsk<br>akkdafmsiakfevnnpqvqrqafnelirvvhqllpesslrkrkrsrcSGGPGAGMKGLPGSEVQLVES<br>GGGLVQPGNSLRLSCAASGFTFSKFGMSWVRQAPGKGLEWVSSISGSGRDTLYA<br>ESVKGRFTISRDNAKTTLYLQMNSLRPEDTAVYYCTIGGSLSVSSQGTLVTVSSS<br>GGPGAGMKGLPGShgtvieslsnnyfnssgidveekslfldiwrnwqkdgdmkilgsqiisfylrlfevlkdn<br>qaismnisvieshlittffsnskakkdafmsiakfevnnpqvqrqafnelirvvhqllpesslrkrkrsrcSGGPGAGM<br>KGLPGSEVQLVESGGGLVQPGNSLRLSCAASGFTFSKFGMSWVRQAPGKGLEW<br>VSSISGSGRDTLYAESVKGRFTISRDNAKTTLYLQMNSLRPEDTAVYYCTIGGSL<br>SVSSQGTLVTVSSHHHHHHEPEA |
| 114 | ACP35 Mouse IL-12 fusion protein | mdmrvpaqllgllllwlrgarcrrvipvsgparclsqsrnllkttddmvktarelkhysctaedidheditrdqtstlktclplel<br>hknesclatretssttrgsclppqdtslmmtlcigsiyedlkmyqtefgainaalqnhhqqiildkgmlvaidelmqsinhn<br>getlrqkppvgeadpyrvkmklcillhafstrvvtinrvmgylssaggggsgggggsgggggsSGGPGAGMKGLPGSmwelekdyvv<br>evdwtpdapgetvnltcdtpeeddiitwtsdqrhgviggskt1titvkefldaggytchkggetlshshllhkkengiwsteil<br>knfknktflkceapnysgrftcswlvqrnmdlkfniksssspdsravtcgmaslsaekvtldqrdyekysvscqedvtcpt<br>aeetlpielalearqqnkyenystsffirdiilkpdppknlqmkplknsqvqevsweypdswstphsyfslkffvriqrkkek<br>mketeegcnqkgaflvektstevqckggnvcvqaqdryynsscskwacvpcrvrsHHHHHH |
| 115 | ACP36 Mouse IL-12 fusion protein | mdmrvpaqllgllllwlrgarcrrvipvsgparclsqsrnllkttddmvktarelkhysctaedidheditrdqtstlktclplel<br>hknesclatretsstrgsclppqdtslmmtlcigsiyedlkmyqtefgainaalqnhhqqiildkgmlvaidelmqsinhn<br>getlrqkppvgeadpyrvkmklcillhafstrvvtinrvmgylssaggggsgggggsgggggsSGGPGAGMKGLP<br>GSggggsgggggsgggsmwelekdyvvevdwtpdapgetvnltcdtpeeddiitwtsdqrhgviggktltitvkefld<br>aggytchkggetlshshllhkkengiwsteilknfknktflkceapnysgrftcswlvqrnmdlkfniksssspdsravtc<br>gmaslsaekvtldqrdyekysvscqedvtcptaeetlpielalearqqnkyenystsffirdiilkpdppknlqmkplknsqv<br>evsweypdswstphsyfslkffvriqrkkekmketeegcnqkgaflvektstevqckggnvcvqaqdryynsscskwac<br>vpcrvrsHHHHH |
| 116 | ACP36 Mouse IL-12 fusion protein | mdmrvpaqllgllllwlrgarcEVQLVESGGGLVQPGNSLRLSCAASGFTFSKFGMSWVRQ<br>APGKGLEWVSSISGSGRDTLYAESVKGRFTISRDNAKTTLYLQMNSLRPEDTAV<br>YYCTIGGSLSVSSQGTLVTVSSSGGPGAGMKGLPGSmwelekdyvvevdwtpdapgetv<br>nltcdtpeeddiitwtsdqrhgviggktltitvkefldaggytchkggetlshshllhkkengiwsteilknfknktflkceap<br>nysgrftcswlvqrnmdlkfniksssspdsravtcgmaslsaekvtldqrdyekysvscqedvtcptaeetlpielalearq<br>qnkyenystsffirdiilkpdppknlqmkplknsqvevsweypdswstphsyfslkffvriqrkkekmketeegcnqkga<br>flvektstevqckggnvcvqaqdryynsscskwacvpcrvrsggggsgggggsgggggsrvipvsgparclsqsrnllkttdd |

-continued

SEQUENCE TABLE

| SEQ ID NO. | Name | Sequence |
|---|---|---|
| | | mvktareklkhysctaedidheditrdqtstlktclplelhknesclatretssttrgsclppqdtslmmtlclgsiyedlkmyqt |
| | | efgainaalqnhnhqqiildkgmlvaidelmqslnhngetlrqkppvgeadpyrvkmklcillhafstrvvtinrvmgylss |
| | | aSGGPGPAGMKGLPGSEVQLVESGGGLVQPGNSLRLSCAASGFTFSKFGMSWVR |
| | | QAPGKGLEWVSSISGSGRDTLYAESVKGRFTISRDNAKTTLYLQMNSLRPEDTA |
| | | VYYCTIGGSLSVSSQGTLVTVSSHHHHH |
| 116 | ACP37 Mouse IL-12 fusion protein | mdmrvpaqllglll1wlrgarcQVQLQESGGGLVQAGGSLRLSCAASGRIFSIDIMSWYRQA |
| | | PGKQRELVARITRGGTISYDDSVKGRFTISRDNAKNTVLQMNSLKPEDTGVYY |
| | | CNALYGTDYWGKGTQVTVSSggggsggggsgggsgggsEVQLVESGGGLVQPGNSLRLSC |
| | | AASGFTFSKFGMSWVRQAPGKGLEWVSSISGSGRDTLYAESVKGRFTISRDNAK |
| | | TTLYLQMNSLRPEDTAVYYCTIGGSLSVSSQGTLVTVSSGGPGAGMKGLPGS |
| | | mwelekdvyvvevdwtpdapgetvnltcdtpeedditwtsdqrhgvigsgktltitvkefldaggytchkggetlshshll1 |
| | | hkkengiwsteilknfknktflkceapnysgrftcswlvqrnmdlkfnikssspdsravtcgmaslsaekvtldqrdyek |
| | | ysvscqedvtcptaeetlpielalearqqnkyenystsffirdliikpdppknlqmkplknsqveyswypdswstphsyfsl |
| | | kffvriqrkkekmketeegcnqkgaflvektstevgckgqvcvqaqdryynsscskwacvpcrvrsgggsgggsg |
| | | gggsrvipvsgparclsqsrnlkttddmvktareklkhysctaedidheditrdqtstlktclplelhknesclatretssttrgsc |
| | | lppqdtslmmtlclgsiyedlkmyqtefgainaalqnhnhqqiildkgmlvaidelmqslnhngetlrqkppvgeadpyr |
| | | vkmklcillhafstrvvtinrvmgylssaSGGPGPAGMKGLPGSEVQLVESGGGLVQPGNSLRL |
| | | SCAASGFTFSKFGMSWVRQAPGKGLEWVSSISGSGRDTLYAESVKGRFTISRDN |
| | | AKTTLYLQMNSLRPEDTAVYYCTIGGSLSVSSQGTLVTVSSHHHHHH |
| 117 | ACP79 Mouse IL-12 fusion protein | mdmrvpaqllglll1wlrgarcQVQLQESGGGLVQAGGSLRLSCAASGRIFSIDIMSWYRQA |
| | | PGKQRELVARITRGGTISYDDSVKGRFTISRDNAKNTVLQMNSLKPEDTGVYY |
| | | CNALYGTDYWGKGTQVTVSSggggsggggsgggsgggsEVQLVESGGGLVQPGNSLRLSC |
| | | AASGFTFSKFGMSWVRQAPGKGLEWVSSISGSGRDTLYAESVKGRFTISRDNAK |
| | | TTLYLQMNSLRPEDTAVYYCTIGGSLSVSSQGTLVTVSSGGPGAGMKGLPGS |
| | | mwelekdvyvvevdwtpdapgetvnltcdtpeedditwtsdqrhgvigsgktltityefldaggytchkggetlshshll1 |
| | | hkkengiwsteilknfknktflkceapnysgrftcswlvqrnmdlkfnikssspdsravtcgmaslsaekvtldqrdyek |
| | | ysvscqedvtcptaeetlpielalearqqnkyenystsffirdliikpdppknlqmkplknsqvevswypdswstphsyfsl |
| | | kffvriqrkkekmketeegcnqkgaflvektstevgckgqvcvqaqdryynsscskwacvpcrvrsgggsgggsg |
| | | gggsrvipvsgparclsqsrnlkttddmvktareklkhysctaedidheditrdqtstlktclplelhknesclatretssttrgsc |
| | | lppqdtslmmtlclgsiyedlkmyqtefgainaalqnhnhqqiildkgmlvaidelmqslnhngetlrqkppvgeadpyr |
| | | vkmklcillhafstrvvtinrvmgylssaSGGPGPAGMKGLPGSEVQLVESGGGLVQPGNSLRL |
| | | SCAASGFTFSKFGMSWVRQAPGKGLEWVSSISGSGRDTLYAESVKGRFTISRDN |
| | | AKTTLYLQMNSLRPEDTAVYYCTIGGSLSVSSQGTLVTVSSHHHHHH |
| 118 | ACP80 Mouse IL-12 fusion protein | mdmrvpaqllglll1wlrgarcEVQLVESGGGLVQPGNSLRLSCAASGFTFSKFGMSWVRQ |
| | | APGKGLEWVSSISGSGRDTLYAESVKGRFTISRDNAKTTLYLQMNSLRPEDTAV |
| | | YYCTIGGSLSVSSQGTLVTVSSGGPGAGMKGLPGSmwelekdvyvvevdwtpdapgetv |
| | | nltcdtpeedditwtsdqrhgviggsktltitvkefldaggytchkggetlshshll1hkkengiwsteilknfknktflkceap |
| | | nysgrftcswlvqrnmdlkfnikssspdsravtcgmaslsaekvtldqrdyekysvscqedvtcptaeetlpielalearq |
| | | qnkyenystsffirdliikpdppknlqmkplknsqvevsweypdswstphsyfslkffvriqrkkekmketeegcnqkga |
| | | flvektstevgckgqvcvqaqdryynsscskwacvpcrvrsgggsgggsgggsrvipvsgparclsqsrnllkttdd |
| | | mvktareklkhysctaedidheditrdqtstlktclplelhknesclatretssttrgsclppqdtslmmtlclgsiyedlkmyqt |
| | | efgainaalqnhnhqqiildkgmlvaidelmqslnhngetlrqkppvgeadpyrvkmklcillhafstrvvtinrvmgylss |
| | | aSGGPGPAGMKGLPGSEVQLVESGGGLVQPGNSLRLSCAASGFTFSKFGMSWVR |
| | | QAPGKGLEWVSSISGSGRDTLYAESVKGRFTISRDNAKTTLYLQMNSLRPEDTA |
| | | VYYCTIGGSLSVSSQGTLVTVSSggggsggggsgggsgggsQVQLQESGGGLVQAGGSLRLS |

-continued

SEQUENCE TABLE

| SEQ ID NO. | Name | Sequence |
|---|---|---|
| 119 | ACP91 Chimeric IL-12 fusion protein | CAASGRIFSIDIMSWVRQAPGKQRELVARITRGGTISYDDSVKGRFTISRDNAKN TVYLQMNSLKPEDTGVYYCNALYGTDYWGKGTQVTVSSHHHHHH<br><br>mdmrvpaqllglllllwlrgarciwelkkdvyvveldwypdapgemvltcdtpeedgitwtldqssevlgsgktltiqvke fgdagqytchkggevlshslllllhkkedgiwstdilkdqkepknktflrceaknysgrftcwlttistdltfsvksrgssdp qgvtcgaatlsaervrgdnkeyeysvecqedsacpaaeeslpievmvdavhklkyenytssffirdiikpdppknlqlkplk nsrqvevsweypdtwstphyfsltfcvqvqgkskrekkdrvfdktsatvicrknasisvraqdryyssswswasvpcs gggggggggggsrvipvsgparclsqsrnllkttddmvktareklkhysctaedidheditrdqtslktclplehknes clatretssttrgsclppqktslmmtlclgsiyedlkmyqtefqainaalqnhhqqilldkgmlvaidelmqslnhngetlrq kppvgeadpyrvkmklclllhafstrvvtlnrvmgylssaggggsggggsggggsggggsggggsggggsggggsggg gsgggggsQSVLTQPPSVSGAPGQRVTISCGSRSNIGSNTVKWYQQLPGTAPKLLIY YNDQRPSGVPDRFSGSKSGTSASLAITGLQAEDEADYYCQSYDRYTHPALLFGT GTKVTVLgggsggggsggggsggggsQVQLVESGGGVVQPGRSLRLSCAASGFTFSSYGMH WVRQAPGKGLEWVAFIRYDGSNKYYADSVKGRFTISRDNSKNTLYLQMNSLRA EDTAVYYCKTHGSHDNWGQGTMVTVSSggggsggggsggggsEVQLVESGGGLVQP GNSLRLSCAASGFTFSKFGMSWVRQAPGKGLEWVSSISGSGRDTLYAESVKGRF TISRDNAKTTLYLQMNSLRPEDTAVYYCTIGGSLSVSSQGTLVTVSSHHHHHEP EA |
| 120 | ACP136 Chimeric IL-12 fusion protein | mdmrvpaqllglllllwlrgarciwelkkdvyvveldwypdapgemvltcdtpeedgitwtldqssevlgsgktltiqvke fgdagqytchkggevlshslllllhkkedgiwstdilkdqkepknktflrceaknysgrftcwlttistdltfsvksrgssdp qgvtcgaatlsaervrgdnkeyeysvecqedsacpaaeeslpievmvdavhklkyenytssffirdiikpdppknlqlkplk nsrqvevsweypdtwstphyfsltfcvqvqgkskrekkdrvfdktsatvicrknasisvraqdryyssswewasvpcs gggggggggggsrvipvsgparclsqsrnllkttddmvktareklkhysctaedidheditrdqtslktclplehknes clatretssttrgsclppqktslmmtlclgsiyedlkmyqtefqainaalqnhhqqilldkgmlvaidelmqslnhngetlrq kppvgeadpyrvkmklclllhafstrvvtlnrvmgylssaSGGPGAGMKGLPGSgggsggggsggggsggg gsggggsggggsQSVLTQPPSVSGAPGQRVTISCGSRSNIGSNTVKWYQQLPGTAP KLLIYYNDQRPSGVPDRFSGSKSGTSASLAITGLQAEDEADYYCQSYDRYTHPAL LFGTGTKVTVLgggsggggsggggsggggsQVQLVESGGGVVQPGRSLRLSCAASGFTFSSY GMHWVRQAPGKGLEWVAFIRYDGSNKYYADSVKGRFTISRDNSKNTLYLQMN SLRAEDTAVYYCKTHGSHDNWGQGTMVTVSSHHREIREIHEPEA |
| 121 | ACP138 Chimeric IL-12 fusion protein | mdmrvpaqllglllllwlrgarciwelkkdvyvveldwypdapgemvltcdtpeedgitwtldqssevlgsgktltiqvke fgdagqytchkggevlshslllllhkkedgiwstdilkdqkepknktflrceaknysgrftcwlttistdltfsvksrgssdp qgvtcgaatlsaervrgdnkeyeysvecqedsacpaaeeslpievmvdavhklkyenytssffirdiikpdppknlqlkplk nsrqvevsweypdtwstphyfsltfcvqvqgkskrekkdrvfdktsatvicrknasisvraqdryyssswewasvpcs gggggggggggsrvipvsgparclsqsrnllkttddmvktareklkhysctaedidheditrdqtslktclplehknes clatretssttrgsclppqktslmmtlclgsiyedlkmyqtefqainaalqnhhqqilldkgmlvaidelmqslnhngetlrq kppvgeadpyrvkmklclllhafstrvvtlnrvmgylssaSGGPGAGMKGLPGSgggsggggsggggsggg gsggggsggggsQSVLTQPPSVSGAPGQRVTISCGSRSNIGSNTVKWYQQLPGTAP KLLIYYNDQRPSGVPDRFSGSKSGTSASLAITGLQAEDEADYYCQSYDRYTHPAL LFGTGTKVTVLgggsggggsggggsggggsQVQLVESGGGVVQPGRSLRLSCAASGFTFSSY GMHWVRQAPGKGLEWVAFIRYDGSNKYYADSVKGRFTISRDNSKNTLYLQMN SLRAEDTAVYYCKTHGSHDNWGQGTMVTVSSggggsggggsggggsEVQLVESGGGL VQPGNSLRLSCAASGFTFSKFGMSWVRQAPGKGLEWVSSISGSGRDTLYAESVK GRFTISRDNAKTTLYLQMNSLRPEDTAVYYCTIGGSLSVSSQGTLVTVSSggggsgg gggsggggsQVQLQESGGGLAQAGGSLSLSCAASGFTVSNSVMAWVRQTPGKQREF |

-continued

SEQUENCE TABLE

| SEQ ID NO. | Name | Sequence |
|---|---|---|
| | | VAIINSVGSTNYADSVKGRFTISRDNAKNTVYLQMNNLKPEDTAVYVCNRNFDR IYWGQGTQVTVSSHEIREIHHEPEA |
| 122 | ACP139 Chimeric IL-12 fusion protein | mdmrvpaqllgllllwlrgarcQVQLQESGGGLAQAGGSLSLSCAASGFTVSNSVMAWYR QTPGKQREFVAIINSVGSTNYADSVKGRFTISRDNAKNTVYLQMNNLKPEDTAV YVCNRNFDRIYWGQGTQVTVSSGgggsgggsgggssiwelkkdvyvveldwpdapgemvltcd tpeedgitwtldqssevlgsgktltiqvkefgdagqytchkggevlshslllhkkedgiwstdilkdqkepknktflrceakn ysgrftcwwltistdltfsvksrgssdpggvtcgaatlsaervrgdnkeyeysvecqedsacpaaeeslpievmvdavhkl kyenytssffirdiikpdppknlqlkplknsrqvevsweypdtwstphsyfsltfcvqvggkskrekkdrvftdktsatvicr knasisvraqdryyssswsewasvpcsgggsgggsgggsgggsrvipvsgparclsqsrnllkttddmvktarelkhysct aedidhedltrdqtstlktclplelhknesclatretsstrgsclppqktslmmtlclgsiyedlkmyqtefgainaalqnhnhq qiildkgmlvaidelmqslnhhgetlrqkppvgeadpyrvkmklcillhafstrvvtlnrvmgylssaSGGPGPAGM KGLPGSgggsgggsgggsgggsgggsgggsgggsQSVLTQPPSVSGAPGQRVTISCSGSRS NIGSNTVKWYQQLPGTAPKLLIYNDQRPSGVPDRFSGSKSGTSASLAITGLQAE DEADYCQSYDRYTHPALLFGTKVTVLgggsgggsgggggsQVQLVESGGGGVQ PGRSLRLSCAASGFTFSSYGMHWVRQAPGKGLEWVAFIRYDGSNKYYADSVKG RFTISRDNSKNTLYLQMNSLRAEDTAVYYCKTHGSHDNWGQGTMVTVSSgggs gggsgggsgggsEVQLVESGGGLVQPGNSLRLSCAASGFTFSKFGMSWVRQAPGKGLE WVSSISGSGRDTLYAESVKGRFTISRDNAKTTLYLQMNSLRPEDTAVYYCTIGGS LSVSSQGTLVTVSSHHHHHHEA |
| 123 | ACP140 Chimeric IL-12 fusion protein | mdmrvpaqllgllllwlrgarcQVQLQESGGGLAQAGGSLSLSCAASGFTVSNSVMAWYR QTPGKQREFVAIINSVGSTNYADSVKGRFTISRDNAKNTVYLQMNNLKPEDTAV YVCNRNFDRIYWGQGTQVTVSSGGPGPAGMKGLPGSiwelkkdvyvveldwpdapge mvltcdtpeedgitwtldqssevlgsgktltiqvkefgdagqytchkggevlshslllhkkedgiwstdilkdqkepknkt flrceaknysgrftcwwltistdltfsvksrgssdpggvtcgaatlsaervrgdnkeyeysvecqedsacpaaeeslpiev mvdavhklkyenytssffirdiikpdppknlqlkplknsrqvevsweypdtwstphsyfsltfcvqvggkskrekkdrvft dktsatvicrknasisvraqdryyssswsewasvpcsgggsgggsgggsgggsgggsrvipvsgparclsqsrnllkttddmvkta reklkhysctaedidhedltrdqtstlktclplelhknesclatretsstrgsclppqktslmmtlclgsiyedlkmyqtefqain aalqnhnhqqiildkgmlvaidelmqslnhhgetlrqkppvgeadpyrvkmklcillhafstrvvtlnrvmgylssaSGG PGPAGMKGLPGSgggsgggsgggsgggsgggsgggsgggsgggsgggsQSVLTQPPSVSGAPGQRVTIS CSGSRSNIGSNTVKWYQQLPGTAPKLLIYNDQRPSGVPDRFSGSKSGTSASLAI TGLQAEDEADYCQSYDRYTHPALLFGTKVTVLgggsgggsgggggsQVQLVES GGGVVQPGRSLRLSCAASGFTFSSYGMHWVRQAPGKGLEWVAFIRYDGSNKY YADSVKGRFTISRDNSKNTLYLQMNSLRAEDTAVYYCKTHGSHDNWGQGTMV TVSSgggsgggsgggsgggsEVQLVESGGGLVQPGNSLRLSCAASGFTFSKFGMSWVRQ APGKGLEWVSSISGSGRDTLYAESVKGRFTISRDNAKTTLYLQMNSLRPEDTAV YYCTIGGSLSVSSQGTLVTVSSHHHHHHEPEA |
| 124 | ACP38 IL-2 fusion protein | mdmrvpaqllgllllwlrgarcaptsssktktqlqlehllldlqmilnginnyknpkltrmltfkfympkkatelkhlqcleee lkpleevlnlaqsknfhlrprdllsninivlelkgsettfmceyadetativeflnrwitfcqsiistltSGGPGPAGMK GLPGSEVQLVESGGGLVQPGGSLRLSCAASGFTFSSYTLAWVRQAPGKGLEWV AAIDSSSYYTYSPDTVRGRFTISRDNAKNSLYLQMNSLRAEDTAVYYCARDSNWD ALDTWGQGTTVTVSSGGGSGGGGSDIQMTQSPSSLSASVGDRVTITCK ASQNVGTNVGWYQQKPGKAPKALIYSASFRYSGVPSRFSGSGSTDFTLTISSLQ PEDFATYYCQQYYTYPYTFGGGTKVEIKgggsgggsgggsgggsgggsEVQLVESGGGLVQPG NSLRLSCAASGFTFSKFGMSWVRQAPGKGLEWVSSISGSGRDTLYAESVKGRFTI SRDNAKTTLYLQMNSLRPEDTAVYYCTIGGSLSVSSQGTLVTVSSgggsgggsgggsgggsgggg |

-continued

SEQUENCE TABLE

| SEQ ID NO. | Name | Sequence |
|---|---|---|
| 125 | ACP39 IL-2 fusion protein | gsQVLQESGGGLVQAGGSLRLSCAASGRIFSIDIMSWYRQAPGKQRELVARITR GGTISYDDSVKGRFTISRDNAKNTVYLQMNSLKPEDTGVYYCNALYGTDYWGK GTQVTVSSHHHHHH |
| 126 | ACP40 IL-2 fusion protein | mdmrvpaqlglllllwlrgarcQVLQESGGGLVQAGGSLRLSCAASGRIFSIDIMSWYRQA PGKQRELVARITRGGTISYDDSVKGRFTISRDNAKNTVYLQMNSLKPEDTGVYY CNALYGTDYWGKGTQVTVSSGGPGAGMKGLPGSEVQLVESGGGLVQPGNSL RLSCAASGFTFSKFPGMSWVRQAPGKGLEWVSSISGSGRDTLYAESVKGRFTISR DNAKTTLYLQMNSLRPEDTAVYYCTIGGSLSVSSQGTLVTVSSGGPGPAGMKG LPGSEVQLVESGGGLVQPGGSLRLSCAASGFTFSSYTLAWVRQAPGKGLEWVA AIDSSYTYSPDTVRGRFTISRDNAKNSLYLQMNSLRAEDTAVYYCARDSNWDA LDYWGQGTTVTVSSGGGGSGGGGSGGGGSDIQMTQSPSSLSASVGDRVTITCKA SQNVGTNVGWYQQKPGKAPKALIYSASFRYSGVPSRFSSGSGTDFTLTISSLQP EDFATYYCQQYTTYPTFGGGTKVEIKSGGPGPAGMKGLPGSaptsssktkktqlqlehlld lqmilnginnyknpkltrmltffympkkatelkhlqcleeelkpleevlnlaqsknfhlrprdlisninivivlelkgsettfm ceyadetativeflnrwitfcqsiistltHHHHHH** |
| 127 | ACP41 IL-2 fusion protein | mdmrvpaqlglllllwlrgarcaptsssktkktqlqlehlldlqmilnginnyknpkltrmltfkfympkkatelkhlqclee lkpleevlnlaqsknfhlrprdlisninivivlelkgsettfmceyadetativeflnrwitfcqsiistltSGGPGPAGMK GLPGSggggsggggsggggsggggsggggselcddppeiphatfkamaykegtmlnceckrgfrriksgs lymlctgnsshsswdnqcqctssatrnttkqvtpqlictgemetsqfpgeekpqaspegrpesets clvtttdfqiqtemaatmetsiftteyqggggsggggsSGGPGPAGMKGLPGSaptsssktkktqlqlehlld lqmilnginnyknpkltrmltfkfympkkatelkhlqcleeelkpleevlnlaqsknfhlrprdli sninivivlelkgsettfmceyadetativeflnrwitfcqsiistltHHHHHH |
| 128 | ACP42 IL-2 fusion protein | mdmrvpaqlglllllwlrgarcEVQLVESGGGLVQPGNSLRLSCAASGFTFSKFGMSWVRQ APGKGLEWVSSISGSGRDTLYAESVKGRFTISRDNAKTTLYLQMNSLRPEDTAV YYCTIGGSLSVSSQGTLVTVSSggggsggggsggggsggggselcddppeiphatfkamaykegtmlnceckr gfrriksgslymlctgnsshsswdnqcqctssatrnttkqvtpqpeedkerkttemqspmqpvdqaslpghcrepppwen eateriyhfvvgqmvyyqcvqgyyralhrgpaesvckmthgktrwtqpqlictgemetsqfpgeekpqaspegrpesets clvtttdfqiqtemaatmetsiftteyqggggsggggsggggsggggsggggsSGGPGPAGMKGLPGS aptsssktkktqlqlehlldlqmilnginnyknpkltrmltfkfympkkatelkhlqcleeelkpleevlnlaqsknfhlrprdli sninivivlelkgsettfmceyadetativeflnrwitfcqsiistltHHHHHH |
| 129 | ACP43 IL-2 fusion protein | mdmrvpaqlglllllwlrgarcaptsssktkktqlqlehlldlqmilnginnyknpkltrmltfkfympkkatelkhlqcleee lkpleevlnlaqsknfhlrprdlisninivivlelkgsettfmceyadetativeflnrwitfcqsiistltSGGPGPAGMK GLPGSggggsggggsggggsggggsggggselcddppeiphatfkamaykegtmlnceckrgfrriksgs lymlctgnsshsswdnqcqctssatrnttkqvtpqpeedkerktemqspmqpvdqaslpghcrepppwenmeateriyhf vvgqmvyyqcvqgyyralhrgpaesvckmthgktrwtqpqlictgemetsqfpgeekpqaspegrpesetsclvtttdfqi qtemaatmetsiftteyqggggsggggsggggsggggsggggsEVQLVESGGGLVQPGNSLRLSCAASGFTFSKF GMSWVRQAPGKGLEWVSSISGSGRDTLYAESVKGRFTISRDNAKTTLYLQMNS LRPEDTAVYYCTIGGSLSVSSQGTLVTVSSHHHHHH |

-continued

SEQUENCE TABLE

| SEQ ID NO. | Name | Sequence |
|---|---|---|
| 130 | ACP44 IL-2 fusion protein | mdmrvpaqlglglllllwlrgarcaptssstkktqlqlehlldlqmilnginnyknpkltrmltfkfympkkatelkhlqcleee lkpleevlnlaqsknflrprdlisninvivlelkgsettfmceyadetativeflnrwitfcqsiistltSGGPGPAGMK GLPGSggggsggggsggggsggggsggggselcddppeiphatfkamaykegtmlnceckrgfrriksgs lymlctgnsshsswdnqcqctssatrntkqvtpqeeqkerkttemqsppmqpvdqaslpghcreppwneateriyhf vvgqmvyyqcvqgyralhrgpaesvckmthgktrwtqpqlictgemetsqfpgeekpqaspegrpesetsclvttdfqi qtemaatmesiftteyqSGGPGPAGMKGLPGSEVQLVESGGGLVQPGNSLRLSCAASGF TFSKFGMSWVRQAPGKGLEWVSSISGSGRDTLYAESVKGRFTISRDNAKTTLYL QMNSLRPEDTAVYYCTIGGSLSVSSQGTLVTVSSFIRREIREI |
| 131 | ACP45 IL-2 fusion protein | mdmrvpaqlglglllllwlrgarcEVQLVESGGGLVQPGNSLRLSCAASGFTFSKFGMSWVRQ APGKGLEWVSSISGSGRDTLYAESVKGRFTISRDNAKTTLYLQMNSLRPEDTAV YYCTIGGSLSVSSQGTLVTVSSGGPGPAGMKGLPGSEVQLVESGGGLVQPGGS LRLSCAASGFTFSSYTLAWVRQAPGKGLEWVAAIDSSSYTYSPDTVRGRFTISRD NAKNSLYLQMNSLRAEDTAVYYCARDSNWDALDYWGQGTTVTVSSGGGSG GGGSGGGGSDIQMTQSPSSLSASVGDRVTITCKASQNVGTNVGWYQQKPGKAP KALIYSASFRYSGVPSRFSGSGSGTDFTLTISSLQPEDFATYYCQQYYTYPYTPGG GTKVEIKggggsggggsggggsggggsggggsSGGPGPAGMKGLPGSaptssstkktqlqlehl lldlqmilnginnyknpkltrmltfkfympkkatelkhlqcleeelkpleevlnlaqsknflrprdlisninvivlelkgsettf mceyadetativeflnrwitfcqsiistltHHHHHH |
| 132 | ACP46 IL-2 fusion protein | mdmrvpaqlglglllllwlrgarcaptssstkktqlqlehlldlqmilnginnyknpkltrmltfkfympkkatelkhlqcleee lkpleevlnlaqsknflrprdlisninvivlelkgsettfmceyadetativeflnrwitfcqsiistltSGGPGPAGMK GLPGSggggsggggsggggsggggsggggsEVQLVESGGGLVQPGGSLRLSCAASGF TFSSYTLAWVRQAPGKGLEWVAAIDSSSYTYSPDTVRGRFTISRDNAKNSLYLQ MNSLRAEDTAVYYCARDSNWDALDYWGQGTTVTVSSsggsgpgagmkgipgsDIQMT QSPSSLSASVGDRVTITCKASQNVGTNVGWYQQKPGKAPKALIYSASFRYSGVP SRFSGSGSGTDFTLTISSLQPEDFATYYCQQYYTYPYTPGGGTKVEIKggggsggggs ggggsEVQLVESGGGLVQPGNSLRLSCAASGFTFSKFGMSWVRQAPGKGLEWVSS ISGSGRDTLYAESVKGRFTISRDNAKTTLYLQMNSLRPEDTAVYYCTIGGSLSVS SQGTLVTVSSggggsggggsggggsQVQLQESGGGLVQAGGSLRLSCAASGRIFSIDIM SWYRQAPGKQRELVARITRGGTISYDDSVKGRFTISRDNAKNTVLQMNSLKPE DTGVYYCNALYGTDYWGKGTQVTVSSHHHHHH |
| 133 | ACP47 IL-2 fusion protein | mdmrvpaqlglglllllwlrgarcQVQLQESGGGLVQAGGSLRLSCAASGRIFSIDIMSWVRQA PGKQRELVARITRGGTISYDDSVKGRFTISRDNAKNTVLQMNSLKPEDTGVYY CNALYGTDYWGKGTQVTVSSggggsggggsggggsaptssstkktqlqlehlldlqmilnginnyknpk ltrmltfkfympkkatelkhlqcleeelkpleevlnlaqsknflrprdlisninvivlelkgsettfmceyadetativeflnrw itfcqsiistltSGGPGPAGMKGLPGSEVQLVESGGGLVQPGNSLRLSCAASGFTFSKFG MSWVRQAPGKGLEWVSSISGSGRDTLYAESVKGRFTISRDNAKTTLYLQMNSLR PEDTAVYYCTIGGSLSVSSQGTLVTVSSggggsggggsggggsggggsggggsEVQLV ESGGGLVQPGGSLRLSCAASGFTFSSYTLAWVRQAPGKGLEWVAAIDSSSYTYS PDTVRGRFTISRDNAKNSLYLQMNSLRAEDTAVYYCARDSNWDALDYWGQGT TVTVSSGGGSGGGGSGGGGSDIQMTQSPSSLSASVGDRVTITCKASQNVGTNV GWYQQKPGKAPKALIYSASFRYSGVPSRFSGSGSGTDFTLTISSLQPEDFATYYC QQYYTYPYTPGGGTKVEIKHHHHHH |

-continued

SEQUENCE TABLE

| SEQ ID NO. | Name | Sequence |
|---|---|---|
| 134 | ACP48 IL-2 fusion protein | mdmrvpaqllglllllwlrgarcaptssstkktqlqlehllldlqmilnginnyknpkltrmltfkfympkkatelkhlqcleee lkpleevlnlaqsknfhlrprdlisninvivlelkgsettfmceyadetativeflnrwitfcqsiistltsGGPGPAGMK GLPGSEVQLVESGGGLVQPGGSLRLSCAASGFTFSSYTLAWRQAPGKGLEWV AAIDSSYTYSPDTVRGRFTISRDNAKNSLYLQMNSLRAEDTAVYYCARDSNWD ALDYWGQGTTVTVSSGGGGSGGGGSGGGGSDIQMTQSPSSLSASVGDRVTITCK ASQNVGTNVGWYQQKPGKAPKALIYSASFRYSGVPSRFSGSGSGTDFTLTISSLQ PEDFATYYCQQYTYPYTPGGGTKVEIKggggsgggggsggggsEVQLVESGGGLVQPG NSLRLSCAASGFTFSKFGMSWVRQAPGKGLEWVSSISGSGRDTLYAESVKGRFTI SRDNAKTTLYLQMNSLRPEDTAVYYCTIGGSLSVSSQGTLVTVSSHHHHHH |
| 135 | ACP49 IL-2 fusion protein | mdmrvpaqllglllllwlrgarcaptssstkktqlqlehllldlqmilnginnyknpkltrmltfkfympkkatelkhlqcleee lkpleevlnlaqsknfhlrprdlisninvivlelkgsettfmceyadetativeflnrwitfcqsiistltsGGPGPAGMK GLPGSggggsggggsggggsggggsEVQLVESGGGLVQPGGSLRLSCAASGF TFSSYTLAWRQAPGKGLEWVAAIDSSYTYSPDTVRGRFTISRDNAKNSLYLQ MNSLRAEDTAVYYCARDSNWDALDYWGQGTTVTVSSGGGGSGGGGS DIQMTQSPSSLSASVGDRVTITCKASQNVGTNVGWYQQKPGKAPKALIYSASFR YSGVPSRFSGSGSGTDFTLTISSLQPEDFATYYCQQYTYPYTPGGGTKVEIKggg ggggsggggsEVQLVESGGGLVQPGNSLRLSCAASGFTFSKFGMSWVRQAPGKGL EWVSSISGSGRDTLYAESVKGRFTISRDNAKTTLYLQMNSLRPEDTAVYYCTIGG SLSVSSQGTLVTVSSHHHHHH |
| 136 | ACP92 IL-2 fusion protein | mdmrvpaqllglllllwlrgarcEVQLVESGGGLVQPGNSLRLSCAASGFTFSKFGMSWVRQ APGKGLEWVSSISGSGRDTLYAESVKGRFTISRDNAKTTLYLQMNSLRPEDTAV YYCTIGGSLSVSSQGTLVTVSSGGPGPAGMKGLPGSaptssstkktqlqlehllldlqmilngin nyknpkltrmltfkfympkkatelkhlqcleeelkpleevlnlaqsknfhlrprdlisninvivlelkgsettfmceyadetati veflnrwitfcqsiistltsGGPGPAGMKGLPGSEVQLVESGGGLVQPGNSLRLSCAASGFT FSKFGMSWVRQAPGKGLEWVSSISGSGRDTLYAESVKGRFTISRDNAKTTLYLQ MNSLRPEDTAVYYCTIGGSLSVSSQGTLVTVSSHHHHHH |
| 137 | ACP93 IL-2 fusion protein | mdmrvpaqllglllllwlrgarcQVQLQESGGGLVQAGGSLRLSCAASGRIFSIDIMSWYRQA PGKQRELVARITRGGTISYDDSVKGRFTISRDNAKNTVYLQMNSLKPEDTGVYY CNALYGTDYWGKGTQVTVSSgsgsgsgsgsgsgsEVQLVESGGGLVQPGNSLRLSC AASGFTFSKFGMSWVRQAPGKGLEWVSSISGSGRDTLYAESVKGRFTISRDNAK TTLYLQMNSLRPEDTAVYYCTIGGSLSVSSQGTLVTVSSgsgsgsgsgsgsgsgsQVQLQ ESGGGLVQAGGSLRLSCAASGRIFSIDIMSWYRQAPGKQRELVARITRGGTISYD DSVKGRFTISRDNAKNTVYLQMNSLKPEDTGVYYCNALYGTDYWGKGTQVTV SSgsgsgsgsgsgsgsgsEVQLVESGGGLVQPGGSLRLSCAASGFTFSSYTLAWVRQAP GKGLEWVAAIDSSSYTYSPDTVRGRFTISRDNAKNSLYLQMNSLRAEDTAVYYC ARDSNWDALDYWGQGTTVTVSSGGGGSGGGGSGGGGSDIQMTQSPSSLSASVG DRVTITCKASQNVGTNVGWYQQKPGKAPKALIYSASFRYSGVPSRFSGSGSGTD FTLTISSLQPEDFATYYCQQYTYPYTPGGGTKVEIKSGGPGPAGMKGLPGSaptss stktktqlqlehllldlqmilnginnyknpkltrmltfkfympkkatelkhlqcleeelkpleevlnlaqsknfhlrprdlisnin vivlelkgsettfmceyadetativeflnrwitfcqsiistltHHHHHH |
| 138 | ACP94 IL-2 fusion | mdmrvpaqllglllllwlrgarcQVQLQESGGGLVQAGGSLRLSCAASGRIFSIDIMSWYRQA PGKQRELVARITRGGTISYDDSVKGRFTISRDNAKNTVYLQMNSLKPEDTGVYY CNALYGTDYWGKGTQVTVSSgsgsgsgsgsgsgsgsEVQLVESGGGLVQPGNSLRLSC |

-continued

SEQUENCE TABLE

| SEQ ID NO. | Name | Sequence |
|---|---|---|
| | protein | AASGFTFSKFGMSWVRQAPGKGLEWVSSISGSGRDTLYAESVKGRFTISRDNAK<br>TTLYLQMNSLRPEDTAVYYCTIGGSLSVSSQGTLVTVSSgsgsgsgsgsgsEVQLV<br>ESGGGLVQPGGSLRLSCAASGFTFSSYTLAWVRQAPGKGLEWVAAIDSSSYTYS<br>PDTVRGRFTISRDNAKNSLYLQMNSLRAEDTAVYYCARDSNWDALDYWGQGT<br>TVTVSSGGGGSGGGGSGGGGSDIQMTQSPSSLSASVGDRVTITCKASQNVGTNV<br>GWYQQKPGKAPKALIYSASFRYSGVPSRFSGSGSGTDFTLTISSLQPEDFATYYC<br>QQYYTYPYTPGGGTKVEIKSGPPAGMKGLPGSaptssstkktqlqlehlldlqmilnginnyk<br>npkltrmlafympkkatelkhlqcleeelkpleevlnlaqsknfhlrprdlisninvivlelkgsettfmceyadetativefl<br>nrwitfcqsiistltHHHHHH |
| 139 | ACP95<br>IL-2<br>fusion<br>protein | mdmrvpaqllglllwlrgarcQVQLQESGGGLVQAGGSLRLSCAASGRIFSIDIMSWYRQA<br>PGKQRELVARITRGGTISYDDSVKGRFTISRDNAKNTVYLQMNSLKPEDTGVYY<br>CNALYGTDYWGKGTQVTVSSgsgsgsgsgsgsgsEVQLVESGGGLVQPGNSLRLSC<br>AASGFTFSKFGMSWVRQAPGKGLEWVSSISGSGRDTLYAESVKGRFTISRDNAK<br>TTLYLQMNSLRPEDTAVYYCTIGGSLSVSSQGTLVTVSSGGPAGMKGLPGSa<br>ptssstkktqlqlehlldlqmilnginnyknpkltrmltfkfympkkatelkhlqcleeelkpleevlnlaqsknfhlrprdlis<br>ninvivlelkgsettfmceyadetativeflnrwitfcqsiistltHHHHHH |
| 140 | ACP96<br>IL-2<br>fusion<br>protein | mdmrvpaqllglllwlrgarcQVQLQESGGGLVQAGGSLRLSCAASGRIFSIDIMSWYRQA<br>PGKQRELVARITRGGTISYDDSVKGRFTISRDNAKNTVYLQMNSLKPEDTGVYY<br>CNALYGTDYWGKGTQVTVSSGGPGAGMKGLPGSaptssstkktqlqlehlldlqmilngin<br>nyknpkltrmltfkfympkkatelkhlqcleeelkpleevlnlaqsknfhlrprdlisninvivlelkgsettfmceyadetati<br>veflnrwitfcqsiistltSGGPGAGMKGLPGSEVQLVESGGGLVQPGNSLRLSCAASGFT<br>FSKFGMSWVRQAPGKGLEWVSSISGSGRDTLYAESVKGRFTISRDNAKTTLYLQ<br>MNSLRPEDTAVYYCTIGGSLSVSSQGTLVTVSSHHHHHH |
| 141 | ACP97<br>IL-2<br>fusion<br>protein | mdmrvpaqllglllwlrgarcQVQLQESGGGLVQAGGSLRLSCAASGRIFSIDIMSWYRQA<br>PGKQRELVARITRGGTISYDDSVKGRFTISRDNAKNTVYLQMNSLKPEDTGVYY<br>CNALYGTDYWGKGTQVTVSSgsgsgsgsgsgsgsgsgsEVQLVESGGGLVQPGNSLRLSC<br>AASGFTFSKFGMSWVRQAPGKGLEWVSSISGSGRDTLYAESVKGRFTISRDNAK<br>TTLYLQMNSLRPEDTAVYYCTIGGSLSVSSQGTLVTVSSGGPAGMKGLPGSa<br>ptssstkktqlqlehlldlqmilnginnyknpkltrmltfkfympkkatelkhlqcleeelkpleevlnlaqsknfhlrprdlis<br>ninvivlelkgsettfmceyadetativeflnrwitfcqsiistltSGGPGAGMKGLPGSEVQLVESGGGL<br>VQPGNSLRLSCAASGFTFSKFGMSWVRQAPGKGLEWVSSISGSGRDTLYAESVK<br>GRFTISRDNAKTTLYLQMNSLRPEDTAVYYCTIGGSLSVSSQGTLVTVSSHHHH<br>H |
| 142 | ACP99<br>IL-2<br>fusion<br>protein | mdmrvpaqllglllwlrgarcQVQLQESGGGLVQAGGSLRLSCAASGRIFSIDIMSWYRQA<br>PGKQRELVARITRGGTISYDDSVKGRFTISRDNAKNTVYLQMNSLKPEDTGVYY<br>CNALYGTDYWGKGTQVTVSSgggsgggsgggsgaptssstkktqlqlehlldlqmilnginnyknpk<br>ltrmltfkfympkkatelkhlqcleeelkpleevlnlaqsknfhlrprdlisninvivlelkgsettfmceyadetativeflnrw<br>itfcqsiistltSGGPGAGMKGLPGSEVQLVESGGGLVQPGNSLRLSCAASGFTFSKFG<br>MSWVRQAPGKGLEWVSSISGSGRDTLYAESVKGRFTISRDNAKTTLYLQMNSLR<br>PEDTAVYYCTIGGSLSVSSQGTLVTVSSHHHHHH |
| 143 | ACP100<br>IL-2<br>fusion | mdmrvpaqllglllwlrgarcQVQLQESGGGLVQAGGSLRLSCAASGRIFSIDIMSWYRQA<br>PGKQRELVARITRGGTISYDDSVKGRFTISRDNAKNTVYLQMNSLKPEDTGVYY<br>CNALYGTDYWGKGTQVTVSSgggsgggsgggsgaptssstkktqlqlehlldlqmilnginnyknpk |

-continued

SEQUENCE TABLE

| SEQ ID NO. | Name | Sequence |
|---|---|---|
| | protein | ltrmltfkfympkkatelkhlqcleeelkpleevlnlaqsknfhlrprdlisninvivlelkgsettfmceyadetativeflnrw<br>tfcqsiistltHHHHHH |
| 144 | ACP101<br>IL-2<br>fusion<br>protein | mdmrvpaqllglllwlrgarcaptssstkktqlqlehllldlqmilnginnyknpkltrmltfkfympkkatelkhlqcleee<br>lkpleevlnlaqsknfhlrprdlisninvivlelkgsettfmceyadetativeflnrwitfcqsiistltSGGPGPAGMK<br>GLPGSEVQLVESGGGLVQPGNSLRLSCAASGFTFSSKFGMSWVRQAPGKGLEWV<br>SSISGSGRDTLYAESVKGRFTISRDNAKTTLYLQMNSLRPEDTAVYYCTIGGSLS<br>VSSQGTLVTVSSHHHHHH |
| 145 | ACP102<br>IL-2<br>fusion<br>protein | mdmrvpaqllglllwlrgarcQVQLQESGGGLVQAGGSLRLSCAASGRIFSIDIMSWYRQA<br>PGKQRELVARITRGGTISYDDSVKGRFTISRDNAKNTVYLQMNSLKPEDTGVYY<br>CNALYGTDYWGKGTQVTVSSSGPGPAGMKGLPGSaptssstkktqlqlehllldlqmilngin<br>nyknpkltrmltfkfympkkatelkhlqcleeelkpleevlnlaqsknfhlrprdlisninvivlelkgsettfmceyadetati<br>veflnrwitfcqsiistltSGGPGPAGMKGLPGSEVQLVESGGGLVQPGNSLRLSCAASGFT<br>FSSKFGMSWVRQAPGKGLEWVSSISGSGRDTLYAESVKGRFTISRDNAKTLYLQ<br>MNSLRPEDTAVYYCTIGGSLSVSSQGTLVTVSSggggsgggsgggsggggsgggsgggs<br>EVQLVESGGGLVQPGGSLRLSCAASGFTFSSYTLAWVRQAPGKGLEWVAAIDSS<br>SYTYSPDTVRGRFTISRDNAKNSLYLQMNSLRAEDTAVYYCARDSNWDALDYW<br>GQGTTVTVSSGGGGSGGGGSGGGGSDIQMTQSPSSLSASVGDRVTITCKASQNV<br>GTNVGWYQQKPGKAPKALIYSASFRYSGVPSRFSGSGSGTDFTLTISSLQPEDFA<br>TYYCQQYYTYPYTPGGGTKVEIKHHHHHH |
| 146 | ACP103<br>IL-2<br>fusion<br>protein | mdmrvpaqllglllwlrgarcaptssstkktqlqlehllldlqmilnginnyknpkltrmltfkfympkkatelkhlqcleee<br>lkpleevlnlaqsknfhlrprdlisninvivlelkgsettfmceyadetativeflnrwitfcqsiistltSGGPGPAGMK<br>GLPGSggggsgggsgggsggggsgggsgggsEVQLVESGGGLVQPGGSLRLSCAASGF<br>TFSSYTLAWVRQAPGKGLEWVAAIDSSSYTYSPDTVRGRFTISRDNAKNSLYLQ<br>MNSLRAEDTAVYYCARDSNWDALDYWGQGTTVTVSSGGGGSGGGGSGGGGS<br>DIQMTQSPSSLSASVGDRVTITCKASQNVGTNVGWYQQKPGKAPKALIYSASFR<br>YSGVPSRFSGSGSGTDFTLTISSLQPEDFATYYCQQYYTYPYTPGGGTKVEIKggg<br>gsgggsggggsEVQLVESGGGLVQPGNSLRLSCAASGFTFSSKFGMSWVRQAPGKGL<br>EWVSSISGSGRDTLYAESVKGRFTISRDNAKTTLYLQMNSLRPEDTAVYYCTIGG<br>SLSVSSQGTLVTVSSggggsgggsgggsggggsgggsEVQLQESGGGLAQAGGSLSLSCAASGFTV<br>SNSVMAWYRQTPGKQREFVAIINSVGSTNYADSVKGRFTISRDNAKNTVYLQM<br>NNLKPEDTAVYVCNRNFDRIYWGQGTQVTVSSHHHHHH |
| 147 | ACP104<br>IL-2<br>fusion<br>protein | mdmrvpaqllglllwlrgarcQVQLQESGGGLAQAGGSLSLSCAASGFTVSNSVMAWYR<br>QTPGKQREFVAIINSVGSTNYADSVKGRFTISRDNAKNTVYLQMNNLKPEDTAV<br>YVCNRNFDRIYWGQGTQVTVSSaptssstkktqlqlehllldlqmilnginnyknpkltrmltfkfympkk<br>atelkhlqcleeelkpleevlnlaqsknfhlrprdlisninvivlelkgsettfmceyadetativeflnrwitfcqsiistltSGG<br>PGPAGMKGLPGSEVQLVESGGGLVQPGNSLRLSCAASGFTFSSKFGMSWVRQAP<br>GKGLEWVSSISGSGRDTLYAESVKGRFTISRDNAKTTLYLQMNSLRPEDTAVYY<br>CTIGGSLSVSSQGTLVTVSSggggsgggsgggsggggsgggsgggsEVQLVESGGGLVQ<br>PGGSLRLSCAASGFTFSSYTLAWVRQAPGKGLEWVAAIDSSSYTYSPDTVRGRF<br>TISRDNAKNSLYLQMNSLRAEDTAVYYCARDSNWDALDYWGQGTTVTVSSGG<br>GGSGGGGSGGGGSDIQMTQSPSSLSASVGDRVTITCKASQNVGTNVGWYQQKP<br>GKAPKALIYSASFRYSGVPSRFSGSGSGTDFTLTISSLQPEDFATYYCQQYYTYPY<br>TPGGGTKVEIKHHHHHH |

-continued

SEQUENCE TABLE

| SEQ ID NO. | Name | Sequence |
|---|---|---|
| 148 | ACP105 IL-2 fusion protein | mdmrvpaqllglllllwlrgarcEVQLVESGGGLVQPGGSLRLSCAASGFTFSSYTLAWRQ APGKGLEWVAAIDSSSYTYSPDTVRGRFTISRDNAKNSLYLQMNSLRAEDTAVY YCARDSNWDALDYWGQGTTVTVSSGGGSGGGGSGGGGSDIQMTQSPSSLSAS VGDRVTITCKASQNVGTNVGWYQQKPGKAPKALIYSASFRYSGVPSRFSGSGSG TDFTLTISSLQPEDFATYYCQQYYTYPYTFGGGTKVEIKggggsggggsggggsggggsgg ggsggggsggGGPPAGMKGLPGsaptssstkktqlehllldlqmilnginnyknpkltrmltfkfympkkate lkhlqcleeelkpleevlnlaqsknflhlprdlisninvivlelkgsettfmceyadetativeflnrwitfcgsiistltSGGPG PAGMKGLPGsEVQLVESGGGLVQPGNSLRLSCAASGFTFSKFGMSWVRQAPGK GLEWVSSISGSGRDTLYAESVKGRFTISRDNAKTTLYLQMNSLRPEDTAVYYCTI GGSLSVSSQGTLVTVSSgggsggggsgggsgggQVQLQESGGGLAQAGGSLSLSCAASG FTVSNSVMAWYRQTPGKQREFVAIINSVGSTNYADSVKGRFTISRDNAKNTVYL QMNNLKPEDTAVYVCNRNFDRIYWGQGTQVTVSSHHHHHH |
| 149 | ACP106 IL-2 fusion protein | mdmrvpaqllglllllwlrgarcQVQLQESGGGLAQAGGSLSLSCAASGFTVSNSVMAWYR QTPGKQREFVAIINSVGSTNYADSVKGRFTISRDNAKNTVYLQMNNLKPEDTAV YVCNRNFDRIYWGQGTQVTVSSgggsggggsggggsggggsEVQLVESGGGLVQPGNSLRLS CAASGFTFSKFGMSWVRQAPGKGLEWVSSISGSGRDTLYAESVKGRFTISRDNA KTTLYLQMNSLRPEDTAVYYCTIGGSLSVSSQGTLVTVSSGGGTLVTVSSGGPGPAGMKGLPG SEVQLVESGGGLVQPGGSLRLSCAASGFTFSSYTLAWVRQAPGKGLEWVAAIDS SSYTYSPDTVRGRFTISRDNAKNSLYLQMNSLRAEDTAVYYCARDSNWDALDY WGQGTTVTVSSGGGSGGGGSGGGGSDIQMTQSPSSLASVGDRVTITCKASQN VGTNVGWYQQKPGKAPKALIYSASFRYSGVPSRFSGSGSGTDFTLTISSLQPEDF ATYYCQQYYTYPYTFGGGTKVEIKggggsggggsggggsggggsggggsggggsSGGPGPAG MKGLPGSaptssstkktqlqlehllldlqmilnginnyknpkltrmltfkfympkkatelkhlqcleeelkpleevlnlaq sknflhrprdlisninvivlelkgsettfmceyadetativeflnrwitfcgsiistltHHHHHH |
| 150 | ACP107 IL-2 fusion protein | mdmrvpaqllglllllwlrgarcEVQLVESGGGLVQPGGSLRLSCAASGFTFSSYTLAWRQ APGKGLEWVAAIDSSSYTYSPDTVRGRFTISRDNAKNSLYLQMNSLRAEDTAVY YCARDSNWDALDYWGQGTTVTVSSGGGSGGGGSGGGGSDIQMTQSPSSLSAS VGDRVTITCKASQNVGTNVGWYQQKPGKAPKALIYSASFRYSGVPSRFSGSGSG TDFTLTISSLQPEDFATYYCQQYYTYPYTFGGGTKVEIKggggsggggsggggsggggsgg ggsggggsgggggEVQLVESGGGLVQPGNSLRLSCAASGFTFSKFGMSWVRQAPGKGLEW VSSISGSGRDTLYAESVKGRFTISRDNAKTTLYLQMNSLRPEDTAVYYCTIGGSL SVSSQGTLVTVSSGGPGPAGMKGLPGsaptssstkktqlqlehllldlqmilnginnyknpkltrmltf kfympkkatelkhlqcleeelkpleevlnlaqsknflhlprdlisninvivlelkgsettfmceyadetativeflnrwitfcgsi istltgggsggggsggggsgggQVQLQESGGGLAQAGGSLSLSCAASGFTVSNSVMAWYRQT PGKQREFVAIINSVGSTNYADSVKGRFTISRDNAKNTVYLQMNNLKPEDTAVYV CNRNFDRIYWGQGTQVTVSSHHHHHH |
| 151 | ACP108 IL-2 fusion protein | mdmrvpaqllglllllwlrgarcQVQLQESGGGLVQAGGSLRLSCAASGRIFSIDIMSWYRQA PGKQRELVARITRGGTISYDDSVKGRFTISRDNAKNTVYLQMNSLKPEDTGVYY CNALYGTDYWGKGTQVTVSSggggsggggsaptssstkktqlqlehllldlqmilnginnyknpk ltrmltfkfympkkatelkhlqcleeelkpleevlnlaqsknflhlrprdlisninvivlelkgsettfmceyadetativeflnrw itfcgsiistltSGGPGPAGMKGLPGsrgetgpaaPGSEVQLVESGGGLVQPGNSLRLSCAAS GFTFSKFGMSWVRQAPGKGLEWVSSISGSGRDTLYAESVKGRFTISRDNAKTTL YLQMNSLRPEDTAVYYCTIGGSLSVSSQGTLVTVSSgggsggggsggggsggggsggggsgg gggsEVQLVESGGGLVQPGGSLRLSCAASGFTFSSYTLAWVRQAPGKGLEWVAAI DSSSYTYSPDTVRGRFTISRDNAKNSLYLQMNSLRAEDTAVYYCARDSNWDAL |

-continued

SEQUENCE TABLE

| SEQ ID NO. | Name | Sequence |
|---|---|---|
| 152 | ACP117 Anti-FN CGS-2 scFv | DYWQGGTTVTVSSGGGGSGGGGSGGGGSGGGGSDIQMTQSPSSLSASVGDRVTITCKAS QNVGTNVGWYQQKPGKAPKALIYSASFRYSGVPSRFSGSGSGTDFTLTISSLQPE DFATYYCQQYYTYPYTYPFGGGTKVEIKHHHHHH |
| 153 | ACP118 NARA1 Vh/V1 non-cleavable | mdmrvpaqllglllllwlrgarcEVQLVESGGGLVQPGGSLRLSCAASGFTFSSYAMSWVRQ APGKGLEWVSAISGSGSTYYADSVKGRFTISRDNSKNTLYLQMNSLRAEDTAV YYCARGVGAPRYRKHEWGQGTLVTVSRsggsgsgsgsgsgssSELTQDPAVSVAL GQTVRITCQGDSLRSYYASWYQQKPGQAPVLVIYGKNNRPSGIPDRFSGSSSGNT ASLTTTGAQAEDEADYYCNSSPFEHNLVVFGGGTKLTVLHHHHHEPEA |
| 154 | ACP119 NARA1 Vh/V1 cleavable | mdmrvpaqllglllllwlrgarcQVQLQQSGAELVRPGTSVKVSCKASGYAFTNYLIEWVKQ RPGQGLEWIGVINPGSGTNYNEKFKGKATLTADKSSSTAYMQLSSLTSDDSAV YFCARWRGDGYYAYFDVWGAGTTVTVSSggsgsgsgsgsgsDIVLTQSPASLAVS LGQRATISCKASQSVDYDGDSYMNWYQQKPGQPPKLLIYAASNLESGIPARFSG SGSGTDFTLNIHPVEEEDAATYYCQQSNEDPYTFGGGTKLEIKHHHHHEPEA |
| 155 | ACP120 NARA1 V1/Vh non-cleavable | mdmrvpaqllglllllwlrgarcDIVLTQSPASLAVSLGQRATISCKASQSVDYDGDSYMNW YQQKPGQPPKLLIYAASNLESGIPARFSGSGSGTDFTLNIHPVEEEDAATYYCQQS NEDPYTFGGGTKLEIKggsgsgsgsgsgsQVQLQQSGAELVRPGTSVKVSCKASGY AFTNYLIEWVKQRPGQGLEWIGVINPGSGTNYNEKFKGKATLTADKSSSTAYM QLSSLTSDDSAVYFCARWRGDGYYAYFDVWGAGTTVTVSSHHHHHEPEA |
| 156 | ACP121 NARA1 V1/Vh cleavable | mdmrvpaqllglllllwlrgarcDIVLTQSPASLAVSLGQRATISCKASQSVDYDGDSYMNW YQQKPGQPPKLLIYAASNLESGIPARFSGSGSGTDFTLNIHPVEEEDAATYYCQQS NEDPYTFGGGTKLEIKSGGPGPAGMKGLPGSQVQLQQSGAELVRPGTSVKVSCK ASGYAFTNYLIEWVKQRPGQGLEWIGVINPGSGTNYNEKFKGKATLTADKSSS TAYMQLSSLTSDDSAVYFCARWRGDGYYAYFDVWGAGTTVTVSSHHHHHEP EA |
| 157 | ACP124 IL-2 fusion protein | mdmrvpaqllglllllwlrgarcaptssstkktqlqlehllldlqmilnginnyknpkltrmltfkfympkkatelkhlqcleee lkpleevlnlaqsknfhlrprdliseninvivlelkgsettfmceyadetativeflnrwitfcqsiistltgggsgsggsgggs EVQLVESGGGLVQPGNSLRLSCAASGFTFSKFGMSWVRQAPGKGLEWVSISGS GRDTLYAESVKGRFTISRDNAKTTLYLQMNSLRPDTAVYYCTIGGSLSVSSQGT LVTVSSHHHHHHEPEA |
| 158 | ACP132 IL-2 fusion protein | mdmrvpaqllglllllwlrgarcaptssstkktqlqlehllldlqmilnginnyknpkltrmltfkfympkkatelkhlqcleee lkpleevlnlaqsknfhlrprdliseninvivlelkgsettfmceyadetativeflnrwitfcqsiistltgggsgsggsgggs dahksevahrfkdigeenfkalvliafadylqqcpfedhvklvnevtefaktcvadesaencdkslhtlfgdklctvatlrety gemadccakqepernecflqhkddnpnlprlvrpevdvmctafhdneetflkkylyeiarrhpyfyapellffakrykaaft eccgaadkaacllpkldeIrdegktassakfqrlkcaslqkfgeraflkawavarlsqrfpkaefaevsklvtdltkvhtecchgdl lecaddradlakyicenqdsisslkeccekpllekshciaevendempadlpslaadfvesrkdvcknyaeakdvflgmfl |

-continued

SEQUENCE TABLE

| SEQ ID NO. | Name | Sequence |
| --- | --- | --- |
| 159 | ACP141 IL-2 fusion protein | yeyarrhpdysvvlllrlaktyettlekccaaadphecyakvfdefkplveepqnlikqncelfeqlgeykfqnallvrytkkv pqvstplvevsrnlgkvgskcchpeakrmpcaedylsvvlnqlcvlhektpvsdrvtkcctesl vnrpcfsalevdety vpkefnaettfhadict lsekerqikkqtalvelvkhkpka tkeqlkavmddfaafvekcckaddketcfaeegkklvaas qaalglHHHHHEPEA |
| 160 | ACP142 IL-2 fusion protein | mdmrvpaqlglllllwlrgarcaptssstkktqlqlehllldlqmilnginnyknpkltrmltfkfympkkatelkhlqcleee lkpleevlnlaqsknfhlrprdlisninivlvelkgsettfmceyadetativeflnrwitfcqsiistltgggsgggsgggsgggs dahksevahrfkdlgeenfkalvliafaqylqqcpfedhvklvnevtefaktcvadesaencdkslhtlfgdklctvatlrety gemadccakqepernecflqhkddnpnlprlvrpevdvmctafhdneetflkkylyeiarrhpyfyapellfakrykaaft eccqaadkaacllpkldelrdegkassakqrlkcasslqfgerafkawavarlsqrfpkaefaevsklvtdltkvhtecchgdl lecaddradlakyicenqdsisskleccekpllekshciaevendempadlpslaadfvreskdvcknyaeakdvflgmfl yeyarrhpdysvvlllrlaktyettlekccaaadphecyakvfdefkplveepqnlikqncelfeqlgeykfqnallvrytkkv pqvstplvevsrnlgkvgskcchpeakrmpcaedylsvvlnqlcvlhektpvsdrvtkcctesl vnrpcfsalevdety vpkefnaettfhadict lsekerqikkqtalvelvkhkpka tkeqlkavmddfaafvekcckaddketcfaeegkklvaas qaalglHHHHHEPEA |
| 161 | ACP144 IL-2 fusion protein | mdmrvpaqlglllllwlrgarcaptssstkktqlqlehllldlqmilnginnyknpkltrmltfkfympkkatelkhlqcleee lkpleevlnlaqsknfhlrprdlisninivlvelkgsettfmceyadetativeflnrwitfcqsiistltsGGPGAGMK GLPGSdahksevahrfkdlgeenfkalvliafaqylqqcpfednvklvnevtefaktcvadesaencdkslhtlfgdklct vatlretygemadccakqepernecflqhkddnpnlprlvrpevdvmctafhdneetflkkylyeiarrhpyfyapellffa krykaaftecqqaadkaacllpkldelrdegkassakqrlkcaslqkfgerafkawavarlsqrfpkaefaevsklvtdltkvh tecchgdllecaddradlakyicenqdsisskleccekpllekshciaevendempadlpslaadfvreskdvcknyaeak dvflgmflyeyarrhpdysvvlllrlaktyettlekccaaadphecyakvfdefkplveepqnlikqncelfeqlgeykfqna llvrytkkvpqvstplvevsrnlgkvgskcchpeakrmpcaedylsvvlnqlcvlhektpvsdrvtkcctesl vnrrpcfs alevdetyvpkefnaettfhadictlsekerqikkqtalvelvkhkpkatkeqlkavmddfaafvekcckaddketcfaee gkklvaasqaalglHHHHHEPEA |
| 162 | ACP145 IL-2 fusion protein | mdmrvpaqlglllllwlrgarcQVQLQESGGGLAQAGGSLSLSCAASGFTVSNSVMAWR QTPGKQREFVAIINSVGSTNYADSVKGRFTISRDNAKNTVYLQMNNLKPEDTAV YVCNRNFDRIYWGQGTQVTVSSgggsgggsgggsaptssstkktqlqlehllldlqmilnginnyknpkltrmltfkfympkkatelkhlqcleeelkpleevlnlaqsknfhlrprdlisninivlvelkgsettfmceyadetativeflnrwitfcqsiistltsGGPGAGMKGLPGSEVQLVPGGSLRLSCAASGFTFSSYTLAWVRQAPGKGLEWVAAIDSSSYTYSFGMSWVRQAPGKGLEWVSSISGSGRDTLYAESVKGRFTISRDNAKTTLYLQMNSLRPEDTAVYYCTIGGSLSVSSQGTLVPGGSLRLSCAASGFTVSNSVMAWRQTPGKQREFVAI INSVGSTNYADSVKGRFTISRDNAKNTVYLQMNNLKPEDTAVYVCNRNFDRIYWGQGTQVTVSSSGG PGPAGMKGLPGSEVQLVESSGGGLVQPGGSLRLSCAASGFTFSSYTLAWVRQAPG |

-continued

SEQUENCE TABLE

| SEQ ID NO. | Name | Sequence |
|---|---|---|
| 163 | ACP146 IL-2 fusion protein | KGLEWVAAIDSSSYTYSPDTVRGRFTISRDNAKNSLYLQMNSLRAEDTAVYYCA RDSNWDALDYWGQGTTVTVSSGGGGSGGGGSDIQMTQSPSSLSASVGD RVTITCKASQNVGTNVGWYQQKPGKAPKALIYSASFRYSGVPSRPSGSGSGTDF TLTISSLQPEDFATYYCQQYYTYPYTFGGGTKVEIKHHHHHHEPEA |
| 164 | ACP133 IL-2-6xHis ("6xHis" disclosed as SEQ ID NO.: 354) | mdmrvpaqllglllllwlrgarcQVQLQESGGGLAQAGGSLSLSCAASGFTVSNSVMAWYR QTPGKQREFVAIINSVGSTNYADSVKGRFTISRDNAKNTVYLQMNNLKPDTAV YVCNRNFDRIYWGQGTQVTVSSGGPGPAGMKGLPGSaptsssttktqlqlehlldlqmilng innyknpkltrmltfkfympkkatelkhlqcleeelkpleevlnlaqsknfhlrprdlisninvivlelkgsettfmceyadeta tiveflnrwitfcqsiistltSGGPGPAGMKGLPGSEVQLVESGGGLVQPGNSLRLSCAASGF TFSFKPGMSWVRQAPGKGLEWVSSIGSGRDTLYAESVKGRFTISRDNAKTTLYL QMNSLRPEDTAVYYCTIGGSLSVSSQGTLTVTVSSgggsggggsggggsggggsggggsgggg gsSGGPGPAGMKGLPGSEVQLVESGGGLVQPGGSLRLSCAASGFTFSSYTLAWV RQAPGKGLEWVAAIDSSSYTYSPDTVRGRFTISRDNAKNSLYLQMNSLRAEDTA VYYCARDSNWDALDYWGQGTTVTVSSGGGGSGGGGSDIQMTQSPSSL SASVGDRVTITCKASQNVGTNVGWYQQKPGKAPKALIYSASFRYSGVPSRFSGS GSGTDFTLTISSLQPEDFATYYCQQYYTYPYTFGGGTKVEIKHHHHHHEPEA |
| 164 | | mdmrvpaqllglllllwlrgarcaptsssttktqlqlehlldlqmilnginnyknpkltrmltfkfympkkatelkhlqcleee lkpleevlnlaqsknfhlrprdlisninvivlelkgsettfmceyadetativeflnrwitfcqsiistltHHHHHH |
| 165 | ACP147 IL-2 fusion protein | mdmrvpaqllglllllwlrgarcaptsssttktqlqlehlldlqmilnginnyknpkltrmltfkfympkkatelkhlqcleee lkpleevlnlaqsknfhlrprdlisninvivlelkgsettfmceyadetativeflnrwitfcqsiistltSGGPGPAGMK GLPGSEVQLVESGGGLVQPGNSLRLSCAASGFTFSKFGMSWVRQAPGKGLEWV SSIGSGRDTLYAESVKGRFTISRDNAKTTLYLQMNSLRPEDTAVYYCTIGGSLS VSSQGTLVTVSSgggsggggsggggsggggsggggsSGGPGPAGMKGLPGSEVQLV ESGGGLVQPGGSLRLSCAASGFTFSSYTLAWVRQAPGKGLEWVAAIDSSSYTYS PDTVRGRFTISRDNAKNSLYLQMNSLRAEDTAVYYCARDSNWDALDYWGQGT TVTVSSGGGGSGGGGSGGGGSDIQMTQSPSSLSASVGDRVTITCKASQNVGTNV GWYQQKPGKAPKALIYSASFRYSGVPSRFSGSGSGTDFTLTISSLQPEDFATYYC QQYYTYPYTFGGGTKVEIKggggsggggsggggsQVQLQESGGGLVQAGGSLRLSCA ASGRIFSIDIMSWYRQAPGKQRELVARITRGGTISYDDSVKGRFTISRDNAKNTV YLQMNSLKPEDTGVYYCNALYGTDYWGKGTQVTVSSHHHHHHEPEA |
| 166 | ACP148 IL-2 fusion protein | mdmrvpaqllglllllwlrgarcQVQLQESGGGLVQAGGSLRLSCAASGRIFSIDIMSWYRQA PGKQRELVARITRGGTISYDDSVKGRFTISRDNAKNTVYLQMNSLKPEDTGVYY CNALYGTDYWGKGTQVTVSSgggsggggsggggsaptsssttktqlqlehlldlqmilnginnyknpk ltrmltfkfympkkatelkhlqcleeelkpleevlnlaqsknfhlrprdlisninvivlelkgsettfmceyadetativeflnrw itfcqsiistltSGGPGPAGMKGLPGSEVQLVESGGGLVQPGNSLRLSCAASGFTFSKFG MSWVRQAPGKGLEWVSSIGSGRDTLYAESVKGRFTISRDNAKTTLYLQMNSLR PEDTAVYYCTIGGSLSVSSQGTLVTVSSgggsggggsggggsggggsggggsSGGPG PAGMKGLPGSEVQLVESGGGLVQPGGSLRLSCAASGFTFSSYTLAWVRQAPGK |

-continued

SEQUENCE TABLE

| SEQ ID NO. | Name | Sequence |
|---|---|---|

167 ACP149 IL-2 fusion protein

GLEWVAAIDSSSYYSPDTVRGRFTISRDNAKNSLYLQMNSLRAEDTAVYYCAR
DSNWDALDYWGQGTTVTVSSGGGGSGGGGSGGGGSDIQMTQSPSSLSASVGDR
VTITCKASQNVGTNVGWYQQKPGKAPKALIYSASFRYSGVPSRFSGSGSGTDFT
LTISSLQPEDFATYYCQQYYTYPTFGGGTKVEIKHHHHHHEPEA

168 ACP33 Mouse IFNα-fusion protein mdmrvpaqllglllllwlrgarcQVQLQESGGGLVQAGGSLRLSCAASGRIFSIDIMSWVRQA
PGKQRELVARITRGGTISYDDSVKGRFTISRDNAKNTVYLQMNSLKPEDTGVYY
CNALYGTDYWGKGTQVTVSSSGPGAGMKGLPGSaptssstkktqlqlehllldlqmilngin
nykmpkltrmltfkfympkkatelkhlqcleeelkpleevlnlaqsknfhlrprdlisninvivlelkgsettfmceyadetati
veflnrwitfcqsiistlsSGGPGAGMKGLPGSEVQLVESGGGLVQPGNSLRLSCAASGFT
FSKFGMSWVRQAPGKGLEWVSSISGSGRDTLYAESVKGRFTISRDNAKTTLYLQ
MNSLRPEDTAVYYCTIGGSLSVSSQGTLVTVSSggggsggggsggggsggggsggggs
SGGPGPAGMKGLPGSEVQLVESGGGLVQPGGSLRLSCAASGFTFSSYTLAWVRQ
APGKGLEWVAAIDSSSYYSPDTVRGRFTISRDNAKNSLYLQMNSLRAEDTAVY
YCARDSNWDALDYWGQGTTVTVSSGGGSGGGGSGGGGSDIQMTQSPSSLSAS
VGDRVTITCKASQNVGTNVGWYQQKPGKAPKALIYSASFRYSGVPSRFSGSGSG
TDFTLTISSLQPEDFATYYCQQYYTYPTFGGGTKVEIKHHHHHHEPEA 169 ACP131 Mouse IFNα mdmrvpaqllglllllwlrgarcEVQLVESGGGLVQPGNSLRLSCAASGFTFSKFGMSWVRQ
APGKGLEWVSSISGSGRDTLYAESVKGRFTISRDNAKTTLYLQMNSLRPEDTAV
YYCTIGGSLSVSSQGTLVTVSSSGPGAGMKGLPGScdlpqthnlrnkraltllvqmrrlsplsc
lkdrkdfgfpqekvdaqqikkaqaipvlseltqqilniftskdssaawnttlldsfcndlhqqindlqgclmqqvgvqefplt
qedallavrkyfhritvylrekkhspcawevvraevvralsssanvSGGPGAGMKGLPGSEVQLVESG
GGLVQPGNSLRLSCAASGFTFSKFGMSWVRQAPGKGLEWVSSISGSGRDTLYAE
SVKGRFTISRDNAKTTLYLQMNSLRPEDTAVYYCTIGGSLSVSSQGTLVTVSSHH
HHHHEPEA 170 ACP125 Mouse IFNα-fusion protein mdmrvpaqllglllllwlrgarcEVQLVESGGGLVQPGNSLRLSCAASGFTFSKFGMSWVRQ
APGKGLEWVSSISGSGRDTLYAESVKGRFTISRDNAKTTLYLQMNSLRPEDTAV
YYCTIGGSLSVSSQGTLVTVSSSGPGAGMKGLPGScdlpqthnlrnkraltllvqmrrlsplsc
lkdrkdfgfpqekvdaqqikkaqaipvlseltqqilniftskdssaawnttlldsfcndlhqqindlqgclmqqvgvqefplt
qedallavrkyfhritvylrekkhspcawevvraevvralsssanvlgrlreekHHHHHHEPEA 171 ACP126 Mouse IFNα-fusion protein mdmrvpaqllglllllwlrgarccdlpqthnlrnkraltllvqmrrlsplsclkdrkdfgfpqekvdaqqikkaqaipvlseltq
qilniftskdssaawnttlldsfcndlhqqindlqgclmqqvgvqefpltqedallavrkyfhritvylrekkhspcawevvr
aevvralsssanvlgrlreeksSGGPGPAGMKGLPGSEVQLVESGGGLVQPGNSLRLSCAAS
GFTFSKFGMSWVRQAPGKGLEWVSSISGSGRDTLYAESVKGRFTISRDNAKTTL
YLQMNSLRPEDTAVYYCTIGGSLSVSSQGTLVTVSSHHHHHHEPEA 172 ACP127 Mouse IFNα-fusion protein mdmrvpaqllglllllwlrgarcEAHKSEIAHRYNDLGEQHFKGLVLIAFSQYLQKCSYDEHA
KLVQEVTDFAKTCVADESAANCDKSLHTLFGDKLCAIPNLRENYGELADCCTK
QEPERNECFLQHKDDNPSLPPFERPEAEAMCTSFKENPTTFMGHYLHEVARRHP
YFYAPELLYAEQYNEILTQCCAEADKESCLTPKLDGVKEKALVSSVRQRMKCS
SMQKFGERAFKAWAVARLSQTFPNADFAEITKLATDLTKVNKECCHGDLLECA
DDRAELAKIMCENQATISSKLQTCCDKPLLKKAHCLSEVEHDTMPADLPAIAAD -continued

SEQUENCE TABLE

| SEQ ID NO. | Name | Sequence |
|---|---|---|
| | | FVEDQEVCKNYAEAKDVFLGTFLYEYSRRHPDYSVSLLLRLAKKYEATLEKCCA |
| | | EANPPACYGTVLAEFQPLVEEPKNLVKTNCDLYEKLGEYGFQNAILVRYTQKAP |
| | | QVSTPTLVEAARNLGRVGTKCCTLPEDQRLPCVEDYLSAILNRVCLLHEKTPVSE |
| | | HVTKCCSGSLVERRPCFSALTVDETYVPKEFKAETFTFHSDICTLPEKEKQIKKQT |
| | | ALAELVKHKPKATAEQLKTVMDDFAQFLDTCCKAADKDTCFSTEGPNLVTRCK |
| | | DALASGGPAGMKGLPGScdlpqthnlrnkraltllvqmrrlsplsclkdrkdfgfpqekvdaqqikkaqai |
| | | pvlseltqqilniftskdssaawnttlldsfcndlhqqlndlqgclmqqvgvqefpltqedallavrkyfhritvylrekkhspc |
| | | awevvraevwralsssanvlgrlreeksSGGPGPAGMKGLPGSEAHKSEIAHRYNDLGEQHFKG |
| | | LVLIAFSQYLQKCSYDEHAKLVQEVTDFAKTCVADESAANCDKSLHTLFGDKLC |
| | | AIPNLRENYGELADCCTKQEPERNECFLQHKDDNPSLPPFERPEAEAMCTSFKEN |
| | | PTTFMGHYLHEVARRHPYFYAPELLYYAEQYNEILTQCCAEADKESCLITPKLDG |
| | | VKEKALVSSVRQRMKCSSMQKFGERAFKAWAVARLSQTFPNADFAEITKLLATD |
| | | LTKVNKECCHGDLLECADDRAELAKYMCENQATISSKLQTCCDKPLLKKAHCL |
| | | SEVEHDTMPADLPAIAADFVEDQEVCKNYAEAKDVFLGTFLYEYSRRHPDYSVS |
| | | LLLRLAKKYEATLEKCCAEANPPACYGTVLAEFQPLVEEPKNLVKTNCDLYEKL |
| | | GEYGFQNAILVRYTQKAPQVSTPTLVEAARNLGRVGTKCCTLPEDQRLPCVEDY |
| | | LSAILNRVCLLHEKTPVSEHVTKCCSGSLVERRPCFSALTVDETYVPKEFKAETFT |
| | | FHSDICTLPEKEKQIKKQTALAEILVKHKPKATAEQLKTVMDDFAQFLDTCCKAA |
| | | DKDTCFSTEGPNLVTRCKDALAHHHHHHPEA |
| 173 | ACP128 Mouse IFNa- fusion protein | mdmrvpaqllglllllwlrgarcEAHKSEIAHRYNDLGEQHFKGLVLLIAFSQYLQKCSYDEHA |
| | | KLVQEVTDFAKTCVADESAANCDKSLHTLFGDKLCAIPNLRENYGELADCCTK |
| | | QEPERNECFLQHKDDNPSLPPFERPEAEAMCTSFKENPTTFMGHYLHEVARRHP |
| | | YFYAPELLYYAEQYNEILTQCCAEADKESCLTPKLDGVKEKALVSSVRQRMKCS |
| | | SMQKFGERAFKAWAVARLSQTFPNADFAEITKLATDLTKVNKECCHGDLLECA |
| | | DDRAELAKYMCENQATISSKLQTCCDKPLLKKAHCLSEVEHDTMPADLPAIAAD |
| | | FVEDQEVCKNYAEAKDVFLGTFLYEYSRRHPDYSVSLLLRLAKKYEATLEKCCA |
| | | EANPPACYGTVLAEFQPLVEEPKNLVKTNCDLYEKLGEYGFQNAILVRYTQKAP |
| | | QVSTPTLVEAARNLGRVGTKCCTLPEDQRLPCVEDYLSAILNRVCLLHEKTPVSE |
| | | HVTKCCSGSLVERRPCFSALTVDETYVPKEFKAETFTFHSDICTLPEKEKQIKKQT |
| | | ALAELVKHKPKATAEQLKTVMDDFAQFLDTCCKAADKDTCFSTEGPNLVTRCK |
| | | DALASGGPAGMKGLPGScdlpqthnlrnkraltllvqmrrlsplsclkdrkdfgfpqekvdaqqikkaqai |
| | | pvlseltqqilniftskdssaawnttlldsfcndlhqqlndlqgclmqqvgvqefpltqedallavrkyfhritvylrekkhspc |
| | | awevvraevwralsssanvlgrlreekHHHHHHPEA |
| 174 | ACP129 Mouse IFNa- fusion protein | mdmrvpaqllglllllwlrgarccdlpqthnlrnkraltllvqmrrlsplsclkdrkdfgfpqekvdaqqikkaqaipvlseltq |
| | | qilniftskdssaawnttlldsfcndlhqqlndlqgclmqqvgvqefpltqedallavrkyfhritvylrekkhspcawevvr |
| | | aevwralsssanvlgrlreeksSGGPGPAGMKGLPGSEAHKSEIAHRYNDLGEQHFKGLVLI |
| | | AFSQYLQKCSYDEHAKLVQEVTDFAKTCVADESAANCDKSLHTLFGDKLCAIPN |
| | | LRENYGELADCCTKQEPERNECFLQHKDDNPSLPPFERPEAEAMCTSFKENPTTF |
| | | MGHYLHEVARRHPYFYAPELLYYAEQYNEILTQCCAEADKESCLTPKLDGVKE |
| | | KALVSSVRQRMKCSSMQKFGERAFKAWAVARLSQTFPNADFAEITKLATDLTK |
| | | VNKECCHGDLLECADDRAELAKYMCENQATISSKLQTCCDKPLLKKAHCLSEV |
| | | EHDTMPADLPAIAADFVEDQEVCKNYAEAKDVFLGTFLYEYSRRHPDYSVSLLL |
| | | RLAKKYEATLEKCCAEANPPACYGTVLAEFQPLVEEPKNLVKTNCDLYEKLGE |
| | | YGFQNAILVRYTQKAPQVSTPTLVEAARNLGRVGTKCCTLPEDQRLPCVEDYLS |
| | | AILNRVCLLHEKTPVSEHVTKCCSGSLVERRPCFSALTVDETYVPKEFKAETFTF |

-continued

SEQUENCE TABLE

| SEQ ID NO. | Name | Sequence |
|---|---|---|
| 175 | ACP150 Mouse IFNa- fusion protein | HSDICTLPEKEKQIKKQTALAELVKHKPATAEQLKTVMDDFAQFLDTCCKAAD KDTCFSTEGPNLVTRCKDALAHHHHHEPEA |
| 176 | ACP151 Mouse IFNa- fusion protein | mdmrvpaqllgllllwlrgarcQVQLQESGGGLAQAGGSLSLSCAASGFTVSNSVMAWYR QTPGKQREFVAIINSVGSTNYADSVKGRFTISRDNAKNTVYLQMNLKPEDTAV YVCNRNFDRIYWGQGTQVTVSSgggsgggsgggggsEVQLVESGGGLVQPGNSLRLS CAASGFTSKFGMSWVRQAPGKGLEWVSSISGSGRDTLYAESVKGRFTISRDNA KTTLYLQMNSLRPEDTAVYYCTIGGSLVSSQGTLVTVSSSGPGPAGMKGLPG Scdlpqthnlrnkraltllvqmrrlsplsclkdrkdfgfpqekvdaqqilkkapipvlseltqqilniftskdssaawnttlldsf cndlhqlndlqgclmqqvgvqefpltqedallavrkyfhritvylrekkhspcawevvraewvralsssanvlgrlreekS GGPGPAGMKGLPGSEVQLVESGGGLVQPGNSLRLSCAASGFTFSKFGMSWVRQ APGKGLEWVSSISGSGRDTLYAESVKGRFTISRDNAKTTLYLQMNSLRPEDTAV YYCTIGGSLSVSSQGTLVTVSSHHHHHEPEA |
| 177 | ACP152 Mouse IFNa- fusion protein | mdmrvpaqllgllllwlrgarcEVQLVESGGGLVQPGNSLRLSCAASGFTFSKFGMSWVRQ APGKGLEWVSSISGSGRDTLYAESVKGRFTISRDNAKTTLYLQMNSLRPEDTAV YYCTIGGSLSVSSQGTLVTVSSgggsgggsgggggsEVQLVESGGGLVQPGNSLRLSCAASGFTFSKFGMSWVRQ APGKGLEWVSSISGSGRDTLYAESVKGRFTISRDNAKTTLYLQMNSLRPEDTAV YYCTIGGSLSVSSQGTLVTVSSgggsgggsgggggscdlpqthnlrnkraltllvqmrrlsplsc gfpqekvdaqqilkkapipvlseltqqilniftskdssaawnttlldsfcndlhqlndlqgclmqqvgvqefpltqedalla vrkyfhritvylrekkhspcawevvraewvralsssanvlgrlreekgggsgggsgggggsggggsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSHHHHHH EPEA |
| 178 | ACP153 (IL-2 Conju- gate) | mdmrvpaqllgllllwlrgarcaptssstkktqlqlehlldlqmilnginnyknpkltrmltfkfympkkatelkhlqcleee lkpleevlnlaqsknfhlrprdlisninvivlelkgsettfmceyadetativeflnrwitfcqsiistltsgpGPAGLYAQ pgsEVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVSSQ GTLVTVSSgggsgggsgggggsggggssggsggpGPAGLYAQpgsEVQLVESGGGL VQPGSLRLSCAASGFTFSSYTLAWVRQAPGKGLEWVAAIDSSSYTYSPDTVRG RFTISRDNAKNSLYLQMNSLRAEDTAVYYCARDSNWDALDYWGQGTTVTVSS GGGSGGGSGGGGSDIQMTQSPSSLSASVGDRVTITCKASQNVGTNVGWYQQ KPGKAPKALIYSASFRYSGVPSRFSGSGSGTDFTLTISSLQPEDFATYYCQQYYTY PYTFGGGTKVEIKHHHHHEPEA |
| 179 | ACP154 (IL-2 Conju- | mdmrvpaqllgllllwlrgarcaptssstkktqlqlehlldlqmilnginnyknpkltrmltfkfympkkatelkhlqcleee lkpleevlnlaqsknfhlrprdlisninvivlelkgsettfmceyadetativeflnrwitfcqsiistltsggpPGGPAGIGp gsEVQLVESGGGLVQPGNSLRLSCAASGFTFSKFGMSWVRQAPGKGLEWVSSIS |

-continued

SEQUENCE TABLE

| SEQ ID NO. | Name | Sequence |
|---|---|---|
| | gate) | GSGRDTLYAESVKGRFTISRDNAKTTLYLQMNSLRPEDTAVYYCTIGGSLSVSSQ GTLVTVSSgggsgggsgggsgggsgggsgggsgggsgggsgggPGGPAGIGpgsEVQLVESGGGLV QPGGSLRLSCAASGFTFSSYTLAWVRQAPGKGLEWVAAIDSSSYTYSPDTVRGR FTISRDNAKNSLYLQMNSLRAEDTAVYYCARDSNWDALDYWGQGTTVTVSSG GGGSGGGGSGGGGSDIQMTQSPSSLSASVGDRVTITCKASQNVGTNVGWYQQK PGKAPKALIYSASFRYSGVPSRFSGSGSGTDFTLTISSLQPEDFATYYCQQYYTYP YTFGGGTKVEIKHHHHHHEPEA |
| 180 | ACP155 (IL-2 Conju- gate) | mdmrvpaqllglllllwlrgarcaptsssttkktqlqlehllldlqmilnginnyknpkltrmltfkfympkkatelkhlqcleee lkpleevlnlaqsknfhlrprdlisninivlvlelkgsettfmceyadetativeflnrwitfcqgsiistltsggpALFKSSFPp gsEVQLVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSLSVSSQ GTLVTVSSgggsgggsgggsgggsgggsgggsgggsgggsgggPALFKSSFPpgsEVQLVESGGGLV QPGGSLRLSCAASGFTFSSYTLAWVRQAPGKGLEWVAAIDSSSYTYSPDTVRGR FTISRDNAKNSLYLQMNSLRAEDTAVYYCARDSNWDALDYWGQGTTVTVSSG GGGSGGGGSGGGGSDIQMTQSPSSLSASVGDRVTITCKASQNVGTNVGWYQQK PGKAPKALIYSASFRYSGVPSRFSGSGSGTDFTLTISSLQPEDFATYYCQQYYTYP YTFGGGTKVEIKHHHHHHEPEA |
| 181 | ACP156 (IL-2 Conju- gate) | mdmrvpaqllglllllwlrgarcaptsssttkktqlqlehllldlqmilnginnyknpkltrmltfkfympkkatelkhlqcleee lkpleevlnlaqsknfhlrprdlisninivlvlelkgsettfmceyadetativeflnrwitfcqgsiistltsggpPLAQKLKS SpgsEVQLVESGGGLVQPGNSLRLSCAASGFTFSKFGMSWVRQAPGKGLEWVSSI SGSGRDTLYAESVKGRFTISRDNAKTTLYLQMNSLRPEDTAVYYCTIGGSLSVSS QGTLVTVSSgggsgggsgggsgggsgggsgggsgggsgggsgggsgggPLAQKLKSSpgsEVQLVESGG GLVQPGGSLRLSCAASGFTFSSYTLAWVRQAPGKGLEWVAAIDSSSYTYSPDTV RGRFTISRDNAKNSLYLQMNSLRAEDTAVYYCARDSNWDALDYWGQGTTVTV SSGGGGSGGGGSGGGGSDIQMTQSPSSLSASVGDRVTITCKASQNVGTNVGWY QQKPGKAPKALIYSASFRYSGVPSRFSGSGSGTDFTLTISSLQPEDFATYYCQQYY TYPYTFGGGTKVEIKHHHHHHEPEA |
| 182 | ACP157 (IL-2 Conju- gate) | mdmrvpaqllglllllwlrgarcaptsssttkktqlqlehllldlqmilnginnyknpkltrmltfkfympkkatelkhlqcleee lkpleevlnlaqsknfhlrprdlisninivlvlelkgsettfmceyadetativeflnrwitfcqgsiistltsggpPGGPAGIGa lfkssfpPLAQKLKSSpgsEVQLVESGGGLVQPGNSLRLSCAASGFTFSKFGMSWVR QAPGKGLEWVSSISGSGRDTLYAESVKGRFTISRDNAKTTLYLQMNSLRPEDTA VYYCTIGGSLSVSSQGTLVTVSSgggsgggsgggsgggsgggsgggsgggsgggsgggPGGPAGI GalfkssfpPLAQKLKSSpgsEVQLVESGGGLVQPGGSLRLSCAASGFTFSSYTLAWV RQAPGKGLEWVAAIDSSSYTYSPDTVRGRFTISRDNAKNSLYLQMNSLRAEDTA VYYCARDSNWDALDYWGQGTTVTVSSGGGGSGGGGSGGGGSDIQMTQSPSSL SASVGDRVTITCKASQNVGTNVGWYQQKPGKAPKALIYSASFRYSGVPSRFSGS GSGTDFTLTISSLQPEDFATYYCQQYYTYPYTFGGGTKVEIKHHHHHHEPEA |
| 183 | | Place Hold |
| 184 | | Place Hold |
| 185 | | Place Hold |
| 186 | | Place Hold |

-continued

SEQUENCE TABLE

| SEQ ID NO. | Name | Sequence |
|---|---|---|
| 187 | | Place Hold |
| 188 | | Place Hold |
| 189 | | Place Hold |
| 190 | | Place Hold |
| 191 | Blocker 2 (IL2 blocker) | mdmrvpaqllgllllwlrgarcEVQLVESGGGLVQPGGSLRLSCAASGFTFSSYTLAWVRQ APGKGLEWVAAIDSSYTYSPDTVRGRFTISRDNAKNSLYLQMNSLRAEDTAVY YCARDSNWDALDYWGQGTTVTVSSggggsggggsggggsDIQMTQSPSSLSASVGDR VTITCKASQNVGTNVGWYQQKPGKAPKALIYSASFRYSGVPSRFSGSGSGTDFT LTIISSLQPEDFATYYCQQYYTYPYTFGGGTKVEIKHHHHHH |
| 192 | Blocker 12 (IL-12 blocker) | mdmrvpaqllgllllwlrgarcQSVLTQPPSVSGAPGQRVTISCCGSRSNIGSNTVKWYQQL PGTAPKWYNDQRPSGVPDRFSGSKSGTSASLAITGLQAEDEADYYCQSYDRY THPALLFGTGTKVTVLggggsggggsggggsQVQLVESGGGVVQPGRSLRLSCAASGF TFSSYGMHWVRQAPGKGLEWVAFIRYDGSNKYYADSVKGRFTISRDNSKNTLY LQMNSLRAEDTAVYYCKTHGSHDNWGQGTMVTVSSHHHHHH |
| 193 | Human_FNA2b_I | cdlpqthslgsrrtlmllaqmrrislfsclkdrhdfgfpqeefgnqfqkaetipvlhemiqqifnlfstkdssaawdetlldkfy telyqglndleacviqgvgvtetplmkedsilavrkyfqritlylkekkyspcawevvraeimrsflstnlqeslrskeHHH HHH** |
| 194 | ACP239-geneart | iwelkkdvyyveldwypdapgemvvltcdtpeedgitwtldqssevlgsgktliqvkefgdaqqytchkggevlshsllll hkkedgiwstdilkdqkepknktflrceaknysgrftcwltistdltfsvkssrgssdpqgytcgaatlsaervrgdnkey eysvecqedacpaaees1pievmvdavhklkyenytssffirdiikpdppkniqlkplknsrqvevsweypdtwstphs yfsltfcvqvggkskrekkdrvfdktsatvicrknasisvraqdryysswewasvpcsgggsggggsggggsrvipvsg parclsqsrnllkttddmvktareklkhysctaedidheditrdqtstlktclplelhknesclatretssttrgsclppqktslm mtlclgsiyedlkmyqtefqainaalqnhnhqqiildkgmlvaidelmqslnhnqetlrqkppvgeadpyrvkmklcillh afstrvvtinrvmgylssahhhhh |
| 195 | 3CYT5_sdAb | QVQLQESGGGLVQAGGSLRLSCAASGRTFSSVYDMGWFRQAPGKDREFVARITESARNTRYADSV RGRFTISRDNAKNTVYLQMNLELEDAAVYYCAADPQTVVGTPDYWGQGTQVTVSSAAAYPYD VPDYGSHHHHHH |
| 196 | ACP248 | QSVLTQPPSVSGAPGQRVTISCtGSsSNIGSNTVKWYQQLPGTAPKLLIYgN DQRPSGVPDRFSGSKSGTSASLAITGLQAEDEADYYCQSYDRYTHPAyvF GTGTKVTVLggggsggggsggggsQVQLVESGGGVVQPGRSLRLSCAASGFTFS SYGMHWVRQAPGKGLEWVAFIRYDGSNKYYADSVKGRFTISRDNSKNT LYLQMNSLRAEDTAVYYCKTHGSHDNWGQGTMVTVSSHHHHHH |
| 197 | ACP249 | QSVLTQPPSVSGAPGQRVTISCtGSsSNIGSNTVKWYQQLPGTAPKLLIYYNDQRP SGVPDRFSGSKSGTSASLAITGLQAEDEADYYCQSYDRYTHPAyvFGTGTKVTVL ggggsggggsggggsQVQLVESGGGVVQPGRSLRLSCAASGFTFSSYGMHWVRQAPG KGLEWVAFIRYDGSNKYYADSVKGRFTISRDNSKNTLYLQMNSLRAEDTAVYY CKTHGSHDNWGQGTMVTVSSHHHHHH |

-continued

SEQUENCE TABLE

| SEQ ID NO. | Name | Sequence |
|---|---|---|
| 198 | ACP250 | QSVLTQPPSVSGAPGQRVTISCSGSRSNIGSNTVKWYQQLPGTAPKLLIYYNDQR PSGVPDRFSGSKSGTSASLAITGLQAEDEADYYCQSYDRYTHPALLFGTGTKVT VLgggsggggsggggsQVQLVESGGGVVQPGRSLRLSCAASGFTFSSYaMHWVRQAP GKGLEWVAViSYDGSNKYYADSVKGRFTISRDNSKNTLYLQMNSLRAEDTAVY YCArHGSHDNWGQGTMVTVSSHHHHHH |
| 199 | ACP251 | QSVLTQPPSVSGAPGQRVTISCSGSRSNIGSNTVKWYQQLPGTAPKLLIYYNDQR PSGVPDRFSGSKSGTSASLAITGLQAEDEADYYCQSYDRYTHPALLFGTGTKVT VLgggsggggsggggsQVQLVESGGGVVQPGRSLRLSCAASGFTFSSYGMHWVRQA PGKGLEWVAFIRYeGSNKYYADSVKGRFTISRDNSKNTLYLQMNSLRAEDTAVY YCKTHGSHDNWGQGTMVTVSSHHHHHH |
| 200 | ACP252 | QSVLTQPPSVSGAPGQRVTISCSGSRSNIGSNTVKWYQQLPGTAPKLLIYYNDQR PSGVPDRFSGSKSGTSASLAITGLQAEDEADYYCQSYDRYTHPALLFGTGTKVT VLgggsggggsggggsQVQLVESGGGVVQPGRSLRLSCAASGFTFSSYGMHWVRQA PGKGLEWVAFIRYDGSNKYYAeSVKGRFTISRDNSKNTLYLQMNSLRAEDTAVY YCKTHGSHDNWGQGTMVTVSSHHHHHH |
| 201 | ACP253 | QSVLTQPPSVSGAPGQRVTISCSGSRSNIGSqTVKWYQQLPGTAPKLLIYYNDQR PSGVPDRFSGSKSGTSASLAITGLQAEDEADYYCQSYeRYTHPALLFGTGTKVTV LgggsggggsggggsQVQLVESGGGVVQPGRSLRLSCAASGFTFSSYGMHWVRQAP GKGLEWVAFIRYDGSNKYYADSVKGRFTISRDNSKNTLYLQMNSLRAEDTAVY YCKTHGSHDNWGQGTMVTVSSHHHHHH |
| 202 | ACP254 | QSVLTQPPSVSGAPGQRVTISCSGSRSNIGSqTVKWYQQLPGTAPKLLIYYNDQR PSGVPDRFSGSKSGTSASLAITGLQAEDEADYYCQSYsRYTHPALLFGTGTKVTV LgggsggggsggggsQVQLVESGGGVVQPGRSLRLSCAASGFTFSSYGMHWVRQAP GKGLEWVAFIRYDGSNKYYADSVKGRFTISRDNSKNTLYLQMNSLRAEDTAVY YCKTHGSHDNWGQGTMVTVSSHHHHHH |
| 203 | ACP255 | QSVLTQPPSVSGAPGQRVTISCSGSeSNIGSNTVKWYQQLPGTAPKLLIYYNDQR PSGVPDRFSGSKSGTSASLAITGLQAEDEADYYCQSYDRYTHPALLFGTGTKVT VLgggsggggsggggsQVQLVESGGGVVQPGRSLRLSCAASGFTFSSYGMHWVRQA PGKGLEWVAFIRYDGSNKYYADSVKGRFTISRDNSKNTLYLQMNSLRAEDTAV YYCKTHGSHDNWGQGTMVTVSSHHHHHH |
| 204 | ACP256 | QSVLTQPPSVSGAPGQRVTISCSGSsSNIGSNTVKWYQQLPGTAPKLLIYYNDQRP SGVPDRFSGSKSGTSASLAITGLQAEDEADYYCQSYDRYTHPALLFGTGTKVTV LgggsggggsggggsQVQLVESGGGVVQPGRSLRLSCAASGFTFSSYGMHWVRQAP GKGLEWVAFIRYDGSNKYYADSVKGRFTISRDNSKNTLYLQMNSLRAEDTAVY YCKTHGSHDNWGQGTMVTVSSHHHHHH |
| 205 | ACP257 | QSVLTQPPSVSGAPGQRVTISCSGSRSNIGdNTVKWYQQLPGTAPKLLIYYNDQR PSGVPDRFSGSKSGTSASLAITGLQAEDEADYYCQSYDRYTHPALLFGTGTKVT VLgggsggggsggggsQVQLVESGGGVVQPGRSLRLSCAASGFTFSSYGMHWVRQA PGKGLEWVAFIRYDGSNKYYADSVKGRFTISRDNSKNTLYLQMNSLRAEDTAV YYCKTHGSHDNWGQGTMVTVSSHHHHHH |

-continued

SEQUENCE TABLE

| SEQ ID NO. | Name | Sequence |
|---|---|---|
| 206 | ACP258 | QSVLTQPPSVSGAPGQRVTISCSGSRSNIGeNTVKWYQQLPGTAPKLLIYYNDQR PSGVPDRFSGSKSGTSASLAITGLQAEDEADYYCQSYDRYTHPALLFGTGTKVT VLgggsgggsgggsgggsQVQLVESGGGVVQPGRSLRLSCAASGFTFSSYGMHWVRQA PGKGLEWVAFIRYDGSNKYYADSVKGRFTISRDNSKNTLYLQMNSLRAEDTAV YYCKTHGSHDNWGQGTMVTVSSHHHHHH |
| 207 | ACP259 | QSVLTQPPSVSGAPGQRVTISCSGSRSNIGSdTVKWYQQLPGTAPKLLIYYNDQR PSGVPDRFSGSKSGTSASLAITGLQAEDEADYYCQSYDRYTHPALLFGTGTKVT VLgggsgggsgggsgggsQVQLVESGGGVVQPGRSLRLSCAASGFTFSSYGMHWVRQA PGKGLEWVAFIRYDGSNKYYADSVKGRFTISRDNSKNTLYLQMNSLRAEDTAV YYCKTHGSHDNWGQGTMVTVSSHHHHHH |
| 208 | ACP260 | QSVLTQPPSVSGAPGQRVTISCSGSRSNIGSeTVKWYQQLPGTAPKLLIYYNDQRP SGVPDRFSGSKSGTSASLAITGLQAEDEADYYCQSYDRYTHPALLFGTGTKVTV LgggsgggsgggsgggsQVQLVESGGGVVQPGRSLRLSCAASGFTFSSYGMHWVRQAP GKGLEWVAFIRYDGSNKYYADSVKGRFTISRDNSKNTLYLQMNSLRAEDTAVY YCKTHGSHDNWGQGTMVTVSSHHHHHH |
| 209 | ACP261 | QSVLTQPPSVSGAPGQRVTISCSGSRSNIGSNdVKWYQQLPGTAPKLLIYYNDQR PSGVPDRFSGSKSGTSASLAITGLQAEDEADYYCQSYDRYTHPALLFGTGTKVT VLgggsgggsgggsgggsQVQLVESGGGVVQPGRSLRLSCAASGFTFSSYGMHWVRQA PGKGLEWVAFIRYDGSNKYYADSVKGRFTISRDNSKNTLYLQMNSLRAEDTAV YYCKTHGSHDNWGQGTMVTVSSHHHHHH |
| 210 | ACP262 | QSVLTQPPSVSGAPGQRVTISCSGSRSNIGSNTVdWYQQLPGTAPKLLIYYNDQR PSGVPDRFSGSKSGTSASLAITGLQAEDEADYYCQSYDRYTHPALLFGTGTKVT VLgggsgggsgggsgggsQVQLVESGGGVVQPGRSLRLSCAASGFTFSSYGMHWVRQA PGKGLEWVAFIRYDGSNKYYADSVKGRFTISRDNSKNTLYLQMNSLRAEDTAV YYCKTHGSHDNWGQGTMVTVSSHHHHHH |
| 211 | ACP263 | QSVLTQPPSVSGAPGQRVTISCSGSRSNIGSNTVeWYQQLPGTAPKLLIYYNDQRP SGVPDRFSGSKSGTSASLAITGLQAEDEADYYCQSYDRYTHPALLFGTGTKVTV LgggsgggsgggsgggsQVQLVESGGGVVQPGRSLRLSCAASGFTFSSYGMHWVRQAP GKGLEWVAFIRYDGSNKYYADSVKGRFTISRDNSKNTLYLQMNSLRAEDTAVY YCKTHGSHDNWGQGTMVTVSSHHHHHH |
| 212 | ACP264 | QSVLTQPPSVSGAPGQRVTISCSGSRSNIGSNTVKWYQQLPGTAPKLLIYYNDQd PSGVPDRFSGSKSGTSASLAITGLQAEDEADYYCQSYDRYTHPALLFGTGTKVT VLgggsgggsgggsgggsQVQLVESGGGVVQPGRSLRLSCAASGFTFSSYGMHWVRQA PGKGLEWVAFIRYDGSNKYYADSVKGRFTISRDNSKNTLYLQMNSLRAEDTAV YYCKTHGSHDNWGQGTMVTVSSHHHHHH |
| 213 | ACP265 | QSVLTQPPSVSGAPGQRVTISCSGSRSNIGSNTVKWYQQLPGTAPKLLIYYNDQe PSGVPDRFSGSKSGTSASLAITGLQAEDEADYYCQSYDRYTHPALLFGTGTKVT VLgggsgggsgggsgggsQVQLVESGGGVVQPGRSLRLSCAASGFTFSSYGMHWVRQA PGKGLEWVAFIRYDGSNKYYADSVKGRFTISRDNSKNTLYLQMNSLRAEDTAV YYCKTHGSHDNWGQGTMVTVSSHHHHHH |

-continued

SEQUENCE TABLE

| SEQ ID NO. | Name | Sequence |
|---|---|---|
| 214 | ACP266 | QSVLTQPPSVSGAPGQRVTISCSGSRSNIGSNTVKWYQQLPGTAPKLLIYYNDQR PdGVPDRFSGSKSGTSASLAITGLQAEDEADYYCQSYDRYTHPALLFGTGTKVTV LgggsgggsgggsggggsQVQLVESGGGVVQPGRSLRLSCAASGFTFSSYGMHWVRQAP GKGLEWVAFIRYDGSNKYYADSVKGRFTISRDNSKNTLYLQMNSLRAEDTAVY YCKTHGSHDNWGQGTMVTVSSHHHHHH |
| 215 | ACP267 | QSVLTQPPSVSGAPGQRVTISCSGSRSNIGSNTVKWYQQLPGTAPKLLIYYNDQR PSGVPDRFSGSKSGTSASLAITGLQAEDEADYYCQSYDeYTHPALLFGTGTKVTV LgggsgggsgggsggggsQVQLVESGGGVVQPGRSLRLSCAASGFTFSSYGMHWVRQAP GKGLEWVAFIRYDGSNKYYADSVKGRFTISRDNSKNTLYLQMNSLRAEDTAVY YCKTHGSHDNWGQGTMVTVSSHHHHHH |
| 216 | ACP268 | QSVLTQPPSVSGAPGQRVTISCSGSRSNIGSNTVKWYQQLPGTAPKLLIYYNDQR PSGVPDRFSGSKSGTSASLAITGLQAEDEADYYCQSYDRYTdPALLFGTGTKVTV LgggsgggsgggsggggsQVQLVESGGGVVQPGRSLRLSCAASGFTFSSYGMHWVRQAP GKGLEWVAFIRYDGSNKYYADSVKGRFTISRDNSKNTLYLQMNSLRAEDTAVY YCKTHGSHDNWGQGTMVTVSSHHHHHH |
| 217 | ACP269 | QSVLTQPPSVSGAPGQRVTISCSGSeSNIGSNTVKWYQQLPGTAPKLLIYYNDQeP SGVPDRFSGSKSGTSASLAITGLQAEDEADYYCQSYDeYTHPALLFGTGTKVTVL gggsgggsgggsggggsQVQLVESGGGVVQPGRSLRLSCAASGFTFSSYGMHWVRQAPG KGLEWVAFIRYDGSNKYYADSVKGRFTISRDNSKNTLYLQMNSLRAEDTAVYY CKTHGSHDNWGQGTMVTVSSHHHHHH |
| 218 | ACP270 | QSVLTQPPSVSGAPGQRVTISCSGSeSNIGSNdVKWYQQLPGTAPKLLIYYNDQRP SGVPDRFSGSKSGTSASLAITGLQAEDEADYYCQSYDRYTHPALLFGTGTKVTV LgggsgggsgggsggggsQVQLVESGGGVVQPGRSLRLSCAASGFTFSSYGMHWVRQAP GKGLEWVAFIRYDGSNKYYADSVKGRFTISRDNSKNTLYLQMNSLRAEDTAVY YCKTHGSHDNWGQGTMVTVSSHHHHHH |
| 219 | ACP271 | QSVLTQPPSVSGAPGQRVTISCSGSRSNIGSNTVKWYQQLPGTAPKLLIYYNDQR PSGVPDRFSGSKSGTSASLAITGLQAEDEADYYCQSYDRYTHPALLFGTGTKVT VLgggsgggsgggsggggsQVQLVESGGGVVQPGRSLRLSCAASGFTFeSYGMHWVRQA PGKGLEWVAFIRYDGSNKYYADSVKGRFTISRDNSKNTLYLQMNSLRAEDTAV YYCKTHGSHDNWGQGTMVTVSSHHHHHH |
| 220 | ACP272 | QSVLTQPPSVSGAPGQRVTISCSGSRSNIGSNTVKWYQQLPGTAPKLLIYYNDQR PSGVPDRFSGSKSGTSASLAITGLQAEDEADYYCQSYDRYTHPALLFGTGTKVT VLgggsgggsgggsggggsQVQLVESGGGVVQPGRSLRLSCAASGFTFSeYGMHWVRQA PGKGLEWVAFIRYDGSNKYYADSVKGRFTISRDNSKNTLYLQMNSLRAEDTAV YYCKTHGSHDNWGQGTMVTVSSHHHHHH |
| 221 | ACP273 | QSVLTQPPSVSGAPGQRVTISCSGSRSNIGSNTVKWYQQLPGTAPKLLIYYNDQR PSGVPDRFSGSKSGTSASLAITGLQAEDEADYYCQSYDRYTHPALLFGTGTKVT VLgggsgggsgggsggggsQVQLVESGGGVVQPGRSLRLSCAASGFTFSdYGMHWVRQA PGKGLEWVAFIRYDGSNKYYADSVKGRFTISRDNSKNTLYLQMNSLRAEDTAV YYCKTHGSHDNWGQGTMVTVSSHHHHHH |

-continued

SEQUENCE TABLE

| SEQ ID NO. | Name | Sequence |
|---|---|---|
| 222 | ACP274 | QSVLTQPPSVSGAPGQRVTISCSGSRSNIGSNTVKWYQQLPGTAPKLLIYYNDQR<br>PSGVPDRFSGSKSGTSASLAITGLQAEDEADYYCQSYDRYTHPALLFGTGTKVT<br>VLgggsgggsgggsggggsQVQLVESGGGVVQPGRSLRLSCAASGFTFSSYGMHWVRQA<br>PGKGLEWVAFIeYDGSNKYYADSVKGRFTISRDNSKNTLYLQMNSLRAEDTAVY<br>YCKTHGSHDNWGQGTMVTVSSHHHHHH |
| 223 | ACP275 | QSVLTQPPSVSGAPGQRVTISCSGSRSNIGSNTVKWYQQLPGTAPKLLIYYNDQR<br>PSGVPDRFSGSKSGTSASLAITGLQAEDEADYYCQSYDRYTHPALLFGTGTKVT<br>VLgggsgggsgggsggggsQVQLVESGGGVVQPGRSLRLSCAASGFTFSSYGMHWVRQA<br>PGKGLEWVAFIdYDGSNKYYADSVKGRFTISRDNSKNTLYLQMNSLRAEDTAV<br>YYCKTHGSHDNWGQGTMVTVSSHHHHHH |
| 224 | ACP276 | QSVLTQPPSVSGAPGQRVTISCSGSRSNIGSNTVKWYQQLPGTAPKLLIYYNDQR<br>PSGVPDRFSGSKSGTSASLAITGLQAEDEADYYCQSYDRYTHPALLFGTGTKVT<br>VLgggsgggsgggsggggsQVQLVESGGGVVQPGRSLRLSCAASGFTFSSYGMHWVRQA<br>PGKGLEWVAFIRYDGSNdYYADSVKGRFTISRDNSKNTLYLQMNSLRAEDTAVY<br>YCKTHGSHDNWGQGTMVTVSSHHHHHH |
| 225 | ACP277 | QSVLTQPPSVSGAPGQRVTISCSGSRSNIGSNTVKWYQQLPGTAPKLLIYYNDQR<br>PSGVPDRFSGSKSGTSASLAITGLQAEDEADYYCQSYDRYTHPALLFGTGTKVT<br>VLgggsgggsgggsggggsQVQLVESGGGVVQPGRSLRLSCAASGFTFSSYGMHWVRQA<br>PGKGLEWVAFIRYDGSNeYYADSVKGRFTISRDNSKNTLYLQMNSLRAEDTAVY<br>YCKTHGSHDNWGQGTMVTVSSHEIHHHH |
| 226 | ACP278 | QSVLTQPPSVSGAPGQRVTISCSGSRSNIGSNTVKWYQQLPGTAPKLLIYYNDQR<br>PSGVPDRFSGSKSGTSASLAITGLQAEDEADYYCQSYDRYTHPALLFGTGTKVT<br>VLgggsgggsgggsggggsQVQLVESGGGVVQPGRSLRLSCAASGFTFSSYGMHWVRQA<br>PGKGLEWVAFIRYDGSNKYYADSVeGRFTISRDNSKNTLYLQMNSLRAEDTAVY<br>YCKTHGSHDNWGQGTMVTVSSHHHHHH |
| 227 | ACP279 | QSVLTQPPSVSGAPGQRVTISCSGSRSNIGSNTVKWYQQLPGTAPKLLIYYNDQR<br>PSGVPDRFSGSKSGTSASLAITGLQAEDEADYYCQSYDRYTHPALLFGTGTKVT<br>VLgggsgggsgggsggggsQVQLVESGGGVVQPGRSLRLSCAASGFTFSSYGMHWVRQA<br>PGKGLEWVAFIRYDGSNKYYADSVKGRFTISRDNSKNTLYLQMNSLRAEDTAV<br>YYCKTHGSeDNWGQGTMVTVSSHHHHHH |
| 228 | ACP280 | QSVLTQPPSVSGAPGQRVTISCSGSRSNIGSNTVKWYQQLPGTAPKLLIYYNDQR<br>PSGVPDRFSGSKSGTSASLAITGLQAEDEADYYCQSYDRYTHPALLFGTGTKVT<br>VLgggsgggsgggsggggsQVQLVESGGGVVQPGRSLRLSCAASGFTFSSYGMHWVRQA<br>PGKGLEWVAFIeYDGSNKYYADSVKGRFTISRDNSKNTLYLQMNSLRAEDTAVY<br>YCKTHGSHDNWGQGTMVTVSSHHHHHH |
| 229 | ACP281 | QSVLTQPPSVSGAPGQRVTISCSGSRSNIGSNTVKWYQQLPGTAPKLLIYYNDQR<br>PSGVPDRFSGSKSGTSASLAITGLQAEDEADYYCQSYDRYTHPALLFGTGTKVT<br>VLgggsgggsgggsggggsQVQLVESGGGVVQPGRSLRLSCAASGFTFSSYGMHWVRQA<br>PGKGLEWVAFIeYDGSNKYYADSVeGRFTISRDNSKNTLYLQMNSLRAEDTAVY<br>YCKTHGSeDNWGQGTMVTVSSHHHHHH |

-continued

SEQUENCE TABLE

| SEQ ID NO. | Name | Sequence |
|---|---|---|
| 230 | ACP282 | QSVLTQPPSVSGAPGQRVTISCSGSRSNIGSNTVKWYQQLPGTAPKLLIYYNDQR PSGVPDRFSGSKSGTSASLAITGLQAEDEADYYCQSYDRYTHPALLFGTGTKVT VLggggggggggggggggggQVQLVESGGGVVQPGRSLRLSCAASGFTFSSYGMHWVRQA PGKGLEWVAPIRYDGSNKYYADSVKGRFTISRDNSKNTLYLQMNSLRAEDTAV YYCKTHGSHDNWGQGTMVTVSSHEIREIHH |
| 231 | ACP283 | iwelkkdvyveldwypdapgemvvltcdtpeedgitwtldqssevlgsgtltiqvkefgdaqgytchkggevlshslll lhkkedgiwstdilkdqkepknktflrceakmysgrftcwlttistdltfsvkssrgssdpgqvtcqaatlsaervrgdnkey eysvecqedsacpaaeeslpievmvdavhklkyenytssffirdiikpdppknlqlkplknsrqvevsweyppdtwstphs yfsltfcvqvggkskrekkdrvftdktsatvicrknasisvraqdryysswsewasvpcs |
| 232 | 3TOW6 9sdAb | QVQLQESGGGGLVQTGGSLRLSCTTSGTIFSGYTMGWYRQAPGEQRELVA VISGGGDTNYADSVKGRFTISRDNTKDTMVLQMNSLKPEDTAVYYCYSR EVTPPWKLYWGQGTQVTVSSAAAYPYDVPDYGSHHHHHH |
| 233 | 3TOW85 sdAb | QVQLQESGGGGLVQRGGSLRLSCAASERIFSTDVMGWYRQAAEKQRELVAVVSA RGTTNYLDAVKGRFTISRDNARNTILTLQMNDLKPEDTASYYCVRETTSPWRIY WGQGTQVTVSSAAAYPYDVPDYGSHHHHHH |
| 234 | 2TOW91 sdAb | QVQLQESGGGGLVQAGGSLRLSCAASGSIFSANAMGWYRQAPGKQRELVAVISS GGSTNYADSVKGRFTISRDNAKNTVYLQMNSLKPEDTAVYYCMYSGSYYYTPN DYWGQGTQVTVSSAAAYPYDVPDYGSHHHHHH |
| 235 | ACP301 | evqlvesgggglvqpggslrlscaasgftfssytlawvrqapgkglewvaaidssvtvspdtvrgrftisrdnakns lylqmnslraedtavyycardsnwdaldywgqgtvtvssggggsgggggsdiqmtqspsslsasvgdr vtitckasqnvgtnvgwyqqkpgkapkallysasfrysgvpsrfsgsggsgtdfltisslqpedfatyycqqyvtv pytfgggtkveikhhhhhh |
| 236 | Hu2TOW91 A | evqllesgggglvqpggslrlscaasGSIFSANAMGwYrqapgkgleLvAVISSGGSTNYAD SVKGrftisrdnskntVylqmnslraedtavyycMYSGSYYYTPNDYwgqgtlvtvssAAAY PYDVPDYGSHHHHHH** |
| 237 | Hu2TOW91 B | evqllesgggglvqpggslrlscaasGSIFSANAMGwYrqapgkgleLvAVISSGGSTNYADSVKGrft isrdnskntVylqmnslraedtavyycMYSGSYYYTPNDYwgqgtlvtvssAAAYPYDVPDYGSH HHHHH** |
| 238 | Hu2TOW91 C | evqllesgggglvqpggslrlscaasGSIFSANAMGwvrqapgkglewvsVISSGGSTNYADSVKGrftis rdnskntlylqmnslraedtavyycMYSGSYYYTPNDYwgqgtlvtvssAAAYPYDVPDYGSHHH HHH** |
| 239 | Hu2TOW91 D | QvqllesgggglvpggslrlscaasGSIFSANAMGwYrqapgkgReLvAVISSGGSTNYADSVKG rftisrdnskntVylqmnslraedtavyycMYSGSYYYTPNDYwgqgtlvtvssAAAYPYDVPDYGS HHHHHH** |
| 240 | HE_LM_ 2TOW91 | evqllesgggglVqpggslrlscaasgSIfsANamGwYrqapgkgReLvAVissgggstNyadsvkgrftisrdnsknt VylqmnslraedtavyycMYSGSYYYTPNDYwgqgtlvtvssAAAYPYDVPDYGSHHHHHH ** |

-continued

SEQUENCE TABLE

| SEQ ID NO. | Name | Sequence |
|---|---|---|
| 241 | HE_L_ 2TOW91 | QvqllesggglvqAggslrlscaasgSIfsANamGwYrqapgkQReLvAVissggstNyadsvkgrftisrdnsk ntVylqmnslraedtavyyCMYSGSYYTPNDYwgggtlvtvssAAAYPVDPDYGSHHHHH H** |
| 242 | Hu3TOW85_ A | evqllesggglvqpggslrlscaasERIFSTDVMGwYrqapgkQReLvAVVsARGTTNYLDAVKG rftisrdnsknt1ylqmnslraedtavyyCYVRETTSPWRIYwgggtlvtvssAAAYPYDVPDYGSHH HHHH** |
| 243 | Hu3TOW85_ B | evqllesggglvqpggslrlscaasERIFSTDVMGwYrqapgkgleLvAVVsARGTTNYLDAVKGrf tisrdnskntlylqmnslraedtavyyCYVRETTSPWRIYwgggtlvtvssAAAYPYDVPDYGSHHH HHH** |
| 244 | Hu3TOW85_ C | evqllesggglvqpggslrlscaasERIFSTDVMGwvrqapgkglewvsVVSARGTTNYLDAVKGrft isrdnskntlylqmnslraedtavyyCYVRETTSPWRIYwgggtlvtvssAAAYPYDVPDYGSHHH HHH** |
| 245 | Hu3TOW85_ D | QvqllesggglvqpggslrlscaasERIFSTDVMGwYrqapgkQReLvAVVsARGTTNYLDAVK GrftisrdnskntlylqmnslraedtavyyCYVRETTSPWRIYwgggtlvtvssAAAYPYDVPDYGSH HHHHH** |
| 246 | HE_LM_ 3TOW85 | evqllesggglvqpggslrlscaasERIfsTDVmGwYrqapgkgReLvAVVsARgTtNyLdsvkgrftisrdn skntlylqmnslraedtavyyCYVRETTSPWRIYwgggtlvtvssAAAYPYDVPDYGSHHHHHH* * |
| 247 | HE_L_ 3TOW85 | QvqllesggglvqEggslrlscaasERIfsTDVmGwYrqaAgkQReLvAVVsARgTtNyLdAvkgrftis rdnskntlylqmnslraedtaSyycYVRETTSPWRIYwgggtlvtvssAAAYPYDVPDYGSHHHHH H** |
| 248 | HE_LM_ R45_L3TOW85 | evqllesggglvqpggslrlscaasERIfsTDVmGwYrqapgkgleLvAVVsARgTtNyLdsvkgrftisrdns kntlylqmnslraedtavyyCYVRETTSPWRIYwgggtlvtvssAAAYPYDVPDYGSHHHHHH** |
| 249 | Hu3TOW69_ A | evqllesggglvqpggslrlscaTsGTIFSGYTMGwYrqapgkQReLvAVISGGGDTNYADSVKG rftisrdnskDtMylqmnslraedtavyyCYSREVTPPWKLYwgggtlvtvssAAAYPYDVPDYGSH HHHHH** |
| 250 | Hu3TOW69_ B | evqllesggglvqpggslrlscaTsGTIFSGYTMGwYrqapgkgleLvAVISGGGDTNYADSVKGrf tisrdnskDtMylqmnslraedtavyyCYSREVTPPWKLYwgggtlvtvssAAAYPYDVPDYGSHH HHHH** |
| 251 | Hu3TOW69_ C | evqllesggglvqpggslrlscaasGTIFSGYTMGwvrqapgkglewvsVISGGGDTNYADSVKGrfti srdnskntlylqmnslraedtavyyCYSREVTPPWKLYwgggtlvtvssAAAYPYDVPDYGSHHH HHH** |
| 252 | Hu3TOW69_ D | QvqllesggglvqpggslrlscaTsGTIFSGYTMGwYrqapgkQReLvAVISGGGDTNYADSVK GrftisrdnskntlylqmnslraedtavyyCYSREVTPPWKLYwgggtlvtvssAAAYPYDVPDYGS HHHHHH** |

-continued

SEQUENCE TABLE

| SEQ ID NO. | Name | Sequence |
|---|---|---|
| 253 | Hu3TOW69_E | evqllesgggglvqpggslrlscaTsgTIFSGYTmGwYrqapgkqReLvAVISGGGDTNYADSVKG rftisrdnskntMylqmnslraedtavyyCYSREVTPPWKLYwgggtlvtvssAAAYPYDVPDYGSH HHHHH** |
| 254 | HE_LM_3TOW69 | evqllesgggglvqpggslrlscaTsgTIfsGYTmGwYrqapgkgReLvAVisGggDtNyadsvkgrftisrdnsk ntMylqmnslraedtavyyCYSREVTPPWKLYwgggtlvtvssAAAYPYDVPDYGSHHHHHH* |
| 255 | HE_L_3TOW69 | QvqllesgggglvqfTggslrlscaTsgTIfsGYTmGwYrqapgkqReLvAVisGggDtNyadsvkgrftisrdn skDtMylqmnslraedtavyyCYSREVTPPWKLYwgggtlvtvssAAAYPYDVPDYGSHHHHH H** |
| 256 | HE_LM_R45L_3TOW69 | evqllesgggglvqpggslrlscaTsgTIfsGYTmGwYrqapgkgleLvAVisGggDtNyadsvkgrftisrdnsk ntMylqmnslraedtavyyCYSREVTPPWKLYwgggtlvtvssAAAYPYDVPDYGSHHHHH* |
| 257 | ACP363 | EVQLVESGGGLVQPGGSLRLSCAASGFTFSSYTLAWVRQAPGKGLEWVA AIDSSSYTYSPDTVRGRFTISRDNAKNSLYLQMNSLRAEDTAVYYCARDS NWDALDYWGQGTTVTVSSggggsggggsggggsDIQMTQSPSSLSASVGDRVT ITCKAREKLWSAVAWYQQKPGKAPKALIYSASFRYSGVPSRFSGSGSGTD FTLTISSLQPEDFATYYCQQYYTYPTFGGGTKVEIKHHHHHH |
| 258 | ACP364 | EVQLVESGGGLVQPGGSLRLSCAASGFTFSSYTLAWVRQAPGKGLEWVAAIDSS SYTYSPDTVRGRFTISRDNAKNSLYLQMNSLRAEDTAVYYCARDSNWDALDYW GQGTTVTVSSggggsggggsggggsDIQMTQSPSSLSASVGDRVTITCKAREKLWSAV AWYQQKPGKAPKsLIYSASFRYSGVPSRFSGSGSGTDFTLTISSLQPEDFATYYCQ QYYTYPTFGGGTKVEIKHHHHHH |
| 259 | ACP367 | EVQLVESGGGLVQPGGSLRLSCAASGFTFSSYTLAWVRQAPGKGLEWVA AIDSSSYTYSPDTVRGRFTISRDNAKNSLYLQMNSLRAEDTAVYYCARDS NWDALDYWGQGTTVTVSSggggsggggsggggsDIQMTQSPSSLSASVGDRVT ITCKVTEKVWGNVAWYQQKPGKAPISLIYSPSLRKSGVPSRFSGSGSGTD FTLTISSLQPEDFATYYCQQYYTYPTFGGGTKVEIKHHHHHH |
| 260 | ACP369 | EVQLVESGGGLVQPGGSLRLSCAASGFTFSSYTLAWVRQAPGKGLEWVA AIDSSSYTYSPDTVRGRFTISRDNAKNSLYLQMNSLRAEDTAVYYCARDS NWDALDYWGQGTTVTVSSggggsggggsggggsDIQMTQSPSSLSASVGDRVT ITCKSSEKLWANVAWYQQKPGKAPKALIYSASFRYSGVPSRFSGSGSGTD FTLTISSLQPEDFATYYCQQYYTYPTFGGGTKVEIKHHHHHH |
| 261 | ACP370 | EVQLVESGGGLVQPGGSLRLSCAASGFTFSSYTLAWVRQAPGKGLEWVAAIDSS SYTYSPDTVRGRFTISRDNAKNSLYLQMNSLRAEDTAVYYCARDSNWDALDYW GQGTTVTVSSggggsggggsggggsDIQMTQSPSSLSASVGDRVTITCKSSEKLWANVA WYQQKPGKAPKsLIYSASFRYSGVPSRFSGSGSGTDFTLTISSLQPEDFATYYCQQ YYTYPTFGGGTKVEIKHHHHHH |
| 262 | ACP380 | DIQMTQSPSSLSASVGDRVTITCKASQNVGTNVGWYQQKPGKAPKALIY SASFRYSGVPSRFSGSGSGTDFTLTISSLQPEDFATYYCQQYYTYPYTFGG |

-continued

SEQUENCE TABLE

| SEQ ID NO. | Name | Sequence |
|---|---|---|
| 263 | ACP381 | GTKVEIKrtvaapsvfifppsdeqlksgtasvvellmnfypreakvqwkvdnalqsgnsqesvteqdskdst yslsstltlskadyekhkvyacevthqglsspvtksfnrgec |
| 264 | ACP382 | DIQMTQSPSSLSASVGDRVTITCKAREKLWSAVAWYQQKPGKAPKsLIYSASFR YSGVPSRFSGSGSGTDFTLTISSLQPEDFATYYCQQYYTYPYTFGGGTKVEIKrtvaa psvfifppsdeqlksgtasvvcllnnfypreakvqwkvdnalqsgnsqesvteqdskdstyslsstltlskadyekhkvyac evthqglsspvtksfnrgec |
| 265 | ACP435 | DIQMTQSPSSLSASVGDRVTITCKVTEKVWGNVAWYQQKPGKAPISLIYSPSLRK SGVPSRFSGSGSGTDFTLTISSLQPEDFATYYCQQYYTYPYTFGGGTKVEIKrtvaap svfifppsdeqlksgtasvvcllnnfypreakvqwkvdnalqsgnsqesvteqdskdstyslssthlskadyekhkvyace vthqglsspvtksfnrgec |
| 266 | ACP436 | DIQMTQSPSSLSASVGDRVTITCKAREKLWSAVAWYQQKPGKAPKsLIYS ASFRYSGVPSRFSGSGSGTDFTLTISSLQPEDFATYYCQQYYTYPYTFGGG TKVEIKrtvaapsvfifppsdeqlksgtasvvcllnfypreakvqwkvdnalqsgnsqesvteqdskdsty slsstltlskadyekhkvyacevthqglsspvtksfnrgecggggsggggsggggsggggsggggsev qllesgglvqpggslrlscaasgsifsanamgwyrqapgkqrelvavissggstnyadsvkgrftisrdnskntv ylqmnslraedtavyycmysgsyyytpndywggqtlvtvss** |
| 267 | ACP437 | DIQMTQSPSSLSASVGDRVTITCKVTEKVWGNVAWYQQKPGKAPISLIYSPSLRK SGVPSRFSGSGSGTDFTLTISSLQPEDFATYYCQQYYTYPYTFGGGTKVEIKrtvaap svfifppsdeqlksgtasvvcllnnfypreakvqwkvdnalqsgnsqesvteqdskdstyslsstthlskadyekhkvyac evthqglsspvtksfnrgecggggsggggsggggsggggsggggsevqllesgglvqpggslrlscaasgsifsa namgwyrqapgkglelvavissggstnyadsvkgrftisrdnskntvylqmnslraedtavyycmysgsyyytpndyw gggtlvtvss** |
| 268 | ACP438 | DIQMTQSPSSLSASVGDRVTITCKVTEKVWGNVAWYQQKPGKAPISLIYSPSLRK SGVPSRFSGSGSGTDFTLTISSLQPEDFATYYCQQYYTYPYTFGGGTKVEIKrtvaap svfifppsdeqlksgtasvvcllnnfypreakvqwkvdnalqsgnsqesvteqdskdstyslsstltlskadyekhkvyace vthqglsspvtksfnrgecggggsggggsggggsggggsggggsevqllesgglvqpggslrlscaasgsifsan amgwyrqapgkglelvavissggstnyadsvkgrftisrdnskntvylqmnslraedtavyycmysgsyyytpndywg gggtlvtvss** |
| 269 | ACP448 | DIQMTQSPSSLSASVGDRVTITCKSSEKLWANVAWYQQKPGKAPKsLIYS ASFRYSGVPSRFSGSGSGTDFTLTISSLQPEDFATYYCQQYYTYPYTFGGG TKVEIKrtvaapsvfifppsdeqlksgtasvvcllnnfypreakvqwkvdnalqsgnsqesvteqdskdsty slsstltlskadyekhkvyaceythqglsspvtksfnrgec** |
| 270 | ACP449 | DIQMTQSPSSLSASVGDRVTITCKSSEKLWANVAWYQQKPGKAPKLLIYSASFR YSGVPSRFSGSGSGTDFTLTISSLQPEDFATYYCQQYYTYPYTFGGGTKVEIKrtvaa |

-continued

SEQUENCE TABLE

| SEQ ID NO. | Name | Sequence |
|---|---|---|
| 271 | ACP450 | psvfifppsdeqlksgtasvvclinnfypreakvgwkvdnalqsgnsqesvteqdskdstyslsstltlskadyekhkvyac evthglsspvtksfnrgec** |
| | | DIQMTQSPSSLSASVGDRVTITCKAREKLWSAVAWYQQKPGKAPKLLIYSASFR YSGVPSRFSGSGSGTDFTLTISSLQPEDFATYYCQQYYTYPYTFGGGTKVEIKrtvaa psvfifppsdeqlksgtasvvclinnfypreakvgwkvdnalqsgnsqesvteqdskdstyslsstltlskadyekhkvyac evthglsspvtksfnrgec** |
| 272 | ACP439 | aptssstkktqlqlehllldlqmilnginnykmpkltrmltfkfympkkatelkhlqcleeelkpleevlnlaqsknf hlrpdlisninivlelkgsettfmceyadetativeflnrwitfcqsiistltsggpGPAGLYAQpgsEVQ LVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSL SVSSQGTLVTVSSggggsggggsggggsggggsggggsggggsggggsggggsggggsgpGPAGLYAQpgsEV QLVESGGGLVQPGGSLRLSCAASGFTFSSYTLAWVRQAPGKGLEWVAAI DSSSYTYSPDTVRGRFTISRDNAKNSLYLQMNSLRAEDTAVYYCARDSN WDALDYWGQGTTVTVSSGGGGSGGGGSGGGGSDIQMTQSPSSLSASVG DRVTITCKSSEKLWANVAWYQQKPGKAPKALIYSASFRYSGVPSRFSGSG SGTDFTLTISSLQPEDFATYYCQQYYTYPYTFGGGTKVEIK |
| 273 | ACP440 | aptssstkktqlqlehllldlqmilnginnyknpkltrmltfkfympkkatelkhlqcleeelkpleevlnlaqsknfhlrpdli sninivlelkgsettfmceyadetativeflnrwitfcqsiistltsggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSggggsgggg ggggsggggsggggsggggsggggsggggsggpGPAGLYAQpgsEVQLVESGGGLVQPGGSLRLSCAAS GFTFSSYTLAWVRQAPGKGLEWVAAIDSSSYTYSPDTVRGRFTISRDNAKNSLY LQMNSLRAEDTAVYYCARDSNWDALDYWGQGTTVTVSSGGGGSGGGGSGGGG GSDIQMTQSPSSLSASVGDRVTITCKSSEKLWANVAWYQQKPGKAPKsLIYSASF RYSGVPSRFSGSGSGTDFTLTISSLQPEDFATYYCQQYYTYPYTFGGGTKVEIK |
| 274 | ACP441 | aptssstkktqlqlehllldlqmilnginnyknpkltrmltfkfympkkatelkhlqcleeelkpleevlnlaqsknfhlrpdli sninivlelkgsettfmceyadetativeflnrwitfcqsiistltsggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSggggsgggg ggggsggggsggggsggggsggggsggggsggpGPAGLYAQpgsEVQLVESGGGLVQPGGSLRLSCAAS GFTFSSYTLAWVRQAPGKGLEWVAAIDSSSYTYSPDTVRGRFTISRDNAKNSLY LQMNSLRAEDTAVYYCARDSNWDALDYWGQGTTVTVSSGGGGSGGGGSGGGG GSDIQMTQSPSSLSASVGDRVTITCKSSEKLWANVAWYQQKPGKAPKLLIYSAS FRYSGVPSRFSGSGSGTDFTLTISSLQPEDFATYYCQQYYTYPYTFGGGTKVEIK |
| 275 | ACP442 | aptssstkktqlqlehllldlqmilnginnyknpkltrmltfkfympkkatelkhlqcleeelkpleevlnlaqsknfhlrpdli sninivlelkgsettfmceyadetativeflnrwitfcqsiistltsggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSggggsgggg ggggsggggsggggsggggsggggsggggsggpGPAGLYAQpgsEVQLVESGGGLVQPGGSLRLSCAAS GFTFSSYTLAWVRQAPGKcLEWVAAIDSSSYTYSPDTVRGRFTISRDNAKNSLYL QMNSLRAEDTAVYYCARDSNWDALDYWGQGTTVTVSSGGGGSGGGGSGGGGG SDIQMTQSPSSLSASVGDRVTITCKSSEKLWANVAWYQQKPGKAPKsLIYSASFR YSGVPSRFSGSGSGTDFTLTISSLQPEDFATYYCQQYYTYPYTFGcGTKVEIK |

-continued

SEQUENCE TABLE

| SEQ ID NO. | Name | Sequence |
|---|---|---|
| 276 | ACP443 | aptssstktqlqlehlldlqmilnginnykmpkltrmltkfympkkatelkhlqcleeelkpleevlnlaqsknfhlrprdli sninivlelkgsettfmceyadetativeflnrwitfcqsiislt sggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSgggsgggg sggggsggggsggggsggggsggpGPAGLYAQpgsEVQLVESGGGLVQPGGSLRLSCAAS GFTFSSYTLAWVRQAPGKcLEWVAAIDSSYTYSPDTVRGRFTISRDNAKNSLYL QMNSLRAEDTAVYYCARDSNWDALDYWGQGTTVTVSSGGGGSGGGGSGGGG SDIQMTQSPSSLSASVGDRVTITCKSSEKLWANVAWYQQKPGKAPKLLIYSASFR YSGVPSRFSGSGSGTDFTLTISSLQPEDFATYYCQQYYTYPYTFGCGTKVEIK |
| 277 | ACP444 | aptssstktqlqlehlldlqmilnginnykmpkltrmltkfympkkatelkhlqcleeelkpleevlnlaqsknfhlrprdli sninivlelkgsettfmceyadetativeflnrwitfcqsiislt sggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSgggsgggg sggggsggggsggggsggggsggpGPAGLYAQpgsEVQLVESGGGLVQPGGSLRLSCAAS GFTFSSYTLAWVRQAPGKGLEWVAAIDSSYTYSPDTVRGRFTISRDNAKNSLY LQMNSLRAEDTAVYYCARDSNWDALDYWGcGTTVTVSSGGGGSGGGGSGGGG SDIQMTQSPSSLSASVGDRVTITCKSSEKLWANVAWYQQKPGKcPKALIYSASFR YSGVPSRFSGSGSGTDFTLTISSLQPEDFATYYCQQYYTYPYTFGGGTKVEIK |
| 278 | ACP445 | aptssstktqlqlehlldlqmilnginnykmpkltrmltkfympkkatelkhlqcleeelkpleevlnlaqsknfhlrprdli sninivlelkgsettfmceyadetativeflnrwitfcqsiislt sggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSgggsgggg sggggsggggsggggsggggsggpGPAGLYAQpgsEVQLVESGGGLVQPGGSLRLSCAAS GFTFSSYTLAWVRQAPGKGLEWVAAIDSSYTYSPDTVRGRFTISRDNAKNSLY LQMNSLRAEDTAVYYCARDSNWDALDYWGcGTTVTVSSgggpGPAGLYAQpgsD IQMTQSPSSLSASVGDRVTITCKAREKLWSAVAWYQQKPGKAPKWYSASFRY SGVPSRFSGSGSGTDFTLTISSLQPEDFATYYCQQYYTYPYTFGGGTKVEIK |
| 279 | ACP446 | aptssstktqlqlehlldlqmilnginnykmpkltrmltkfympkkatelkhlqcleeelkpleevlnlaqsknfhlrprdli sninivlelkgsettfmceyadetativeflnrwitfcqsiislt sggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSgggsgggg sggggsggggsggggsggggsggpGPAGLYAQpgsEVQLVESGGGLVQPGGSLRLSCAAS GFTFSSYTLAWVRQAPGKGLEWVAAIDSSYTYSPDTVRGRFTISRDNAKNSLY LQMNSLRAEDTAVYYCARDSNWDALDYWGcGTTVTVSSGGGGSGGGGSGGGG GSDIQMTQSPSSLSASVGDRFTLTISSLQPEDFATYYCQQYYTYPYTFGGGTKVEIK |
| 280 | ACP447 | aptssstktqlqlehlldlqmilnginnykmpkltrmltkfympkkatelkhlqcleeelkpleevlnlaqsknfhlrprdli sninivlelkgsettfmceyadetativeflnrwitfcqsiislt sggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSgggsgggg sggggsggggsggggsggggsggpGPAGLYAQpgsEVQLVESGGGLVQPGGSLRLSCAAS GFTFSSYTLAWVRQAPGKcLEWVAAIDSSYTYSPDTVRGRFTISRDNAKNSLYL QMNSLRAEDTAVYYCARDSNWDALDYWGQGTTVTVSSGGGGSGGGGSGGGG |

-continued

SEQUENCE TABLE

| SEQ ID NO. | Name | Sequence |
|---|---|---|
| 281 | ACP451 | SDIQMTQSPSSLSASVGDRVTITCKAREKLWSAVAWYQQKPGKAPKLLIYSASF<br>RYSGVPSRFSGSGSGTDFTLTISSLQPEDFATYYCQQYYTYPYTFGcGTKVEIK |
| 282 | ACP452 | aptsstktqlqlehlldlqmilnginnyknpkltrmltfldympkkatelkhlqcleeelkpleevlnlagsknf<br>hlrpdlisninvivlelkgsettfmceyadetativeflnrwitfcqsiistltsggpALFKSSFPpgsEVQL<br>VESGGGLVQPGNSLRLSCAASGFTFSKFGMSWVRQAPGKGLEWVSSISG<br>SGRDTLYAESVKGRFTISRDNAKTLYLQMNSLRPEDTAVYYCTIGGSLS<br>VSSQGTLVTVSSgggsgsgggsgsgggsgsgggsgsgggsgsgggpALFKSSFPpgsEVQL<br>VESGGGLVQPGGSLRLSCAASGFTFSSYTLAWRQAPGKGLEWVAAIDS<br>SSYTYSPDTVRGRFTISRDNAKNSLYLQMNSLRAEDTAVYYCARDSNWD<br>ALDYWGQGTTVTVSSGGGGSGGGGSGGGGSDIQMTQSPSSLSASVGDRV<br>TITCKAREKLWSAVAWYQQKPGKAPKsLIYSASFRYSGVPSRFSGSGSGT<br>DFTLTISSLQPEDFATYYCQQYYTYPYTFGGGTKVEIK** |
| 283 | ACP453 | aptsstktqlqlehlldlqmilnginnyknpkltrmltfkfympkkatelkhlqcleeelkpleevlnlagsknfhlrpdli<br>sninvivlelkgsettfmceyadetativeflnrwitfcqsiistltsggpALFKSSFPpgsEVQLVESGGGLVQ<br>PGNSLRLSCAASGFTFSKFGMSWVRQAPGKGLEWVSSISGSGRDTLYAESVKGR<br>FTISRDNAKTTLYLQMNSLRPEDTAVYYCTIGGSLSVSSQGTLVTVSSgggsgsgggs<br>gggsgsgggsgsgggsgsgggpALFKSSFPpgsEVQLVESGGGLVQPGGSLRLSCAASGF<br>TFSSYTLAWRQAPGKcLEWVAAIDSSSYTYSPDTVRGRFTISRDNAKNSLYLQ<br>MNSLRAEDTAVYYCARDSNWDALDYWGQGTTVTVSSGGGGSGGGGSGGGGS<br>DIQMTQSPSSLSASVGDRVTITCKAREKLWSAVAWYQQKPGKAPKsLIYSASFR<br>YSGVPSRFSGSGSGTDFTLTISSLQPEDFATYYCQQYYTYPYTFGcGTKVEIK** |
| 284 | ACP454 | aptsstktqlqlehlldlqmilnginnyknpkltrmltfkfympkkatelkhlqcleeelkpleevlnlagsknfhlrpdli<br>sninvivlelkgsettfmceyadetativeflnrwitfcqsiistltsggpALFKSSFPpgsEVQLVESGGGLVQ<br>PGNSLRLSCAASGFTFSKFGMSWVRQAPGKGLEWVSSISGSGRDTLYAESVKGR<br>FTISRDNAKTTLYLQMNSLRPEDTAVYYCTIGGSLSVSSQGTLVTVSSgggsgsgggs<br>gggsgsgggsgsgggsgsgggpALFKSSFPpgsEVQLVESGGGLVQPGGSLRLSCAASGF<br>TFSSYTLAWRQAPGKGLEWVAAIDSSSYTYSPDTVRGRFTISRDNAKNSLYLQ<br>MNSLRAEDTAVYYCARDSNWDALDYWGcGTTVTVSSGGGGSGGGGSGGGGSD<br>IQMTQSPSSLSASVGDRVTITCKAREKLWSAVAWYQQKPGKcPKALIYSASFRYS<br>GVPSRFSGSGSGTDFTLTISSLQPEDFATYYCQQYYTYPYTFGGGTKVEIK** |
| 285 | ACP455 | aptsstktqlqlehlldlqmilnginnyknpkltrmltfkfympkkatelkhlqcleeelkpleevlnlagsknfhlrpdli<br>sninvivlelkgsettfmceyadetativeflnrwitfcqsiistltsggpALFKSSFPpgsEVQLVESGGGLVQ<br>PGNSLRLSCAASGFTFSKFGMSWVRQAPGKGLEWVSSISGSGRDTLYAESVKGR<br>FTISRDNAKTTLYLQMNSLRPEDTAVYYCTIGGSLSVSSQGTLVTVSSgggsgsgggs |

-continued

SEQUENCE TABLE

| SEQ ID NO. | Name | Sequence |
|---|---|---|
| 441 | ACP456 | gggsgggggsgggsggsgggsggsgggpALFKSSFPpgsEVQLVESGGGLVQPGGSLRLSCAASGF<br>TFSSYTLAWVRQAPGKcLEWVAAIDSSYTYSPDTVRGRFTISRDNAKNSLYLQ<br>MNSLRAEDTAVYYCARDSNWDALDYWGQGTTVTVSSGGGGSGGGGS<br>DIQMTQSPSSLSASVGDRVTITCKVTEKVWGNVAWYQQKPGKAPISLIYSPSLRK<br>SGVPSRFSGSGSGTDFTLTISSLQPEDFATYYCQQYYTYPYTFGcGTKVEIK** |
| 286 | ACP457 | aptssstktqlqlehlldlqmilnginnykmpkltrmltfkfympkkatelkhlqcleeelkpleevlnlaqsknfhlrprdli<br>sninivlelkgsettfmceyadetativeflnrwitfcqsiistltsggpALFKSSFPpgsEVQLVESGGGLVQ<br>PGNSLRLSCAASGFTFSKFGMSWVRQAPGKGLEWVSSISGSGRDTLYAESVKGR<br>FTISRDNAKTTLYLQMNSLRPEDTAVYYCTIGGSLSVSSQGTLVTVSSggggsgggs<br>gggsgggsgggsgggsgggsgggpALFKSSFPpgsEVQLVESGGGLVQPGGSLRLSCAASGF<br>TFSSYTLAWVRQAPGKGLEWVAAIDSSYTYSPDTVRGRFTISRDNAKNSLYLQ<br>MNSLRAEDTAVYYCARDSNWDALDYWGcGTTVTVSSGGGGSGGGGSGGGGSD<br>IQMTQSPSSLSASVGDRVTITCKVTEKVWGNVAWYQQKPGKcPISLIYSPSLRKS<br>GVPSRFSGSGSGTDFTLTISSLQPEDFATYYCQQYYTYPYTFGGGTKVEIK** |
| 287 | ACP458 | aptssstktqlqlehlldlqmilnginnykmpkltrmltfkfympkkatelkhlqcleeelkpleevlnlaqsknfhlrprdli<br>sninivlelkgsettfmceyadetativeflnrwitfcqsiistltsggpALFKSSFPpgsEVQLVESGGGLVQ<br>PGNSLRLSCAASGFTFSKFGMSWVRQAPGKGLEWVSSISGSGRDTLYAESVKGR<br>FTISRDNAKTTLYLQMNSLRPEDTAVYYCTIGGSLSVSSQGTLVTVSSggggsgggs<br>gggsgggsgggsgggsgggsgggpALFKSSFPpgsEVQLVESGGGLVQPGGSLRLSCAASGF<br>TFSSYTLAWVRQAPGKGLEWVAAIDSSYTYSPDTVRGRFTISRDNAKNSLYLQ<br>MNSLRAEDTAVYYCARDSNWDALDYWGcGTTVTVSSastkgpsvfplapsskstsggtaalg<br>clvkdyfpepvtvswnsgaltsgvhtfpavlqssglyslssvvtvpsslgtqtyicnvnhkpsntkvdkrvepksc** |
| 288 | ACP459 | eskygppcppcpapeflggpsvflfppkpkdtlmisrtpevtcvvvdvsqedpevqfnwyvdgvevhnaktkpreeqf<br>nstyrvvsvltvlhqdwlngkeykckvsnkglpssiektiskaksgprepqvytlppsqeemtknqvsltclvkgfypsdi<br>avewesngpennyktppvldsdgsfflysrltvdksrwqegnvfscsvmhealhnhytqkslslslgksggpALFK<br>SSFPgsaptssstktqlqlehlldlqmilnginnyknpkltrmltfkfympkkatelkhlqcleeelkpleevlnlaqsk<br>nfhlrprdlisninivlelkgsettfmceyadetativeflnrwitfcqsiistltgggsgggsgggsgggsgggsgggsgg<br>ggssggpALFK SSFPpgsEVQLVESGGGLVQPGGSLRLSCAASGFTFSSYTLAWVRQ<br>APGKGLEWVAAIDSSYTYSPDTVRGRFTISRDNAKNSLYLQMNSLRAEDTAVY<br>YCARDSNWDALDYWGQGTTVTVSSastkgpsvflplapsskstsggtaalgclvkdyfpepvtvswnsg<br>altsgvhtfpavlqssglyslssvvtvpsslgtqtyicnvnhkpsntkvdkrvepksc** |
| 289 | ACP460 | eskygppcppcpapeflggpsvflfppkpkdtlmisrtpevtcvvvdvsqedpevqfnwyvdgvevhnaktkpreeqf<br>nstyrvvsvltvlhqdwlngkeykckvsnkglpssiektiskaksgprepqvytlppsqeemtknqvsltclvkgfypsdi<br>avewesngpennyktppvldsdgsfflysrltvdksrwqegnvfscsvmhealhnhytqkslslslgksggpALFK<br>SSFPgsaptssstktqlqlehlldlqmilnginnyknpkltrmltfkfympkkatelkhlqcleeelkpleevlnlaqsk<br>nfhlrprdlisninivlelkgsettfmceyadetativeflnrwitfcqsiistltgggsgggsgggsgggsgggsgggsgg<br>ggssggpALFKSSFPpgsEVQLVESGGGLVQPGGSLRLSCAASGFTFSSYTLAWVRQ<br>APGKGLEWVAAIDSSYTYSPDTVRGRFTISRDNAKNSLYLQMNSLRAEDTAVY<br>YCARDSNWDALDYWGQGTTVTVSSASWYQQKPGKAPKsLIYSASPRYSGVPSRFSGSGSG<br>TDFTLTISSLQPEDFATYYCQQYYTYPYTFGGGTKVEIK** |
| 289 | ACP460 | eskygppcppcpapeflggpsvflfppkpkdtlmisrtpevtcvvvdvsqedpevqfnwyvdgvevhnaktkpreeqf<br>nstyrvvsvltvlhqdwlngkeykckvsnkglpssiektiskaksgprepqvytlppsqeemtknqvsltclvkgfypsdi |

-continued

SEQUENCE TABLE

| SEQ ID NO. | Name | Sequence |
|---|---|---|

290  ACP461 avewesngpennykttppvldsdgsfflysrltvdksrwgegnvfscsvmhealhnhytqkslslslgksggpALFK
SSFPpgsaptsssstkktqlqlehllldlqmilnginnyknpkltrmltfkfymppkkatelkhlqcleeelkpleevlnlaqsk
nfhlrprdlisnlnnivivlelkgsettfmceyadetativeflnrwitfcqsiislsltsggsggsggsggsggsgggggsggsgg
ggsggpALFKSSFPpgsEVQLVESGGGLVQPGGSLRLSCAASGFTFSSYTLAWVRQ
APGKGLEWVAAIDSSSYTYSPDTVRGRFTISRDNAKNSLYLQMNSLRAEDTAVY
YCARDSNWDALDYWGQGTTVTVSSGGGSGGGGSGGGGSDIQMTQSPSSLSAS
VGDRVTITCKAREKlWSAVAWYQQKPGKAPKsLIYSASFRYSGVPSRFSGSGSG
TDFTLTISSLQPEDFATYYCQQYYTYPYTFGGGTKVEIK**

291  ACP462 eskyppcppcpapeflggpsvflfppkpkdtlmisrtpevtcvvvdvsqedpevqfnwyvdgvevhnaktkpreeqf
nstyrvvsvltvlhqdwlngkeykckvsnkglpssiektiskakgqprepqvytlppsqeemtknqvsltclvkgfypsdi
avewesngpennykttppvldsdgsfflysrltvdksrwgegnvfscsvmhealhnhytqkslslslgksggpALFK
SSFPpgsaptsssstkktqlqlehllldlqmilnginnyknpkltrmltfkfymppkkatelkhlqcleeelkpleevlnlaqsk
nfhlrprdlisnlnnivivlelkgsettfmceyadetativeflnrwitfcqsiislsltsggsggsggsggsggsgggggsggsgg
ggsggpALFKSSFPpgsEVQLVESGGGLVQPGGSLRLSCAASGFTFSSYTLAWVRQ
APGKGLEWVAAIDSSSYTYSPDTVRGRFTISRDNAKNSLYLQMNSLRAEDTAVY
YCARDSNWDALDYWGQGTTVTVSSGGGSGGGGSGGGGSDIQMTQSPSSLSAS
VGDRVTITCKAREKlWSAVAWYQQKPGKAPKcPKALIYSASFRYSGVPSRFSGSGSG
TDFTLTISSLQPEDFATYYCQQYYTYPYTFGcGTKVEIK**

292  ACP463 eskyppcppcpapeflggpsvflfppkpkdtlmisrtpevtcvvvdvsqedpevqfnwyvdgvevhnaktkpreeqf
nstyrvvsvltvlhqdwlngkeykckvsnkglpssiektiskakgqprepqvytlppsqeemtknqvsltclvkgfypsdi
avewesngpennykttppvldsdgsfflysrltvdksrwgegnvfscsvmhealhnhytqkslslslgksggpALFK
SSFPpgsaptsssstkktqlqlehllldlqmilnginnyknpkltrmltfkfymppkkatelkhlqcleeelkpleevlnlaqsk
nfhlrprdlisnlnnivivlelkgsettfmceyadetativeflnrwitfcqsiislsltsggsggsggsggsggsgggggsggsgg
ggsggpALFKSSFPpgsEVQLVESGGGLVQPGGSLRLSCAASGFTFSSYTLAWVRQ
APGKGLEWVAAIDSSSYTYSPDTVRGRFTISRDNAKNSLYLQMNSLRAEDTAVY
YCARDSNWDALDYWGQGTTVTVSSGGGSGGGGSGGGGSDIQMTQSPSSLSAS
VGDRVTITCKVTEKVWGNVAWYQQKPGKAPISLIYSPSLRKSGVPSRFSGSGSG
TDFTLTISSLQPEDFATYYCQQYYTYPYTFGcGTKVEIK**

293  ACP464 eskyppcppcpapeflggpsvflfppkpkdtlmisrtpevtcvvvdvsqedpevqfnwyvdgvevhnaktkpreeqf
nstyrvvsvltvlhqdwlngkeykckvsnkglpssiektiskakgqprepqvytlppsqeemtknqvsltclvkgfypsdi
avewesngpennykttppvldsdgsfflysrltvdksrwgegnvfscsvmhealhnhytqkslslslgksggpALFK
SSFPpgsaptsssstkktqlqlehllldlqmilnginnyknpkltrmltfkfymppkkatelkhlqcleeelkpleevlnlaqsk
nfhlrprdlisnlnnivivlelkgsettfmceyadetativeflnrwitfcqsiislsltsggsggsggsggsggsgggggsggsgg
ggsggpALFKSSFPpgsEVQLVESGGGLVQPGGSLRLSCAASGFTFSSYTLAWVRQ -continued

SEQUENCE TABLE

| SEQ ID NO. | Name | Sequence |
|---|---|---|
| 294 | ACP465 | APGKGLEWVAAIDSSYTYSPDTVRGRFTISRDNAKNSLYLQMNSLRAEDTAVY<br>YCARDSNWDALDYWGcGTTVTVSSGGGSGGGSGGGSDIQMTQSPSSLSAS<br>VGDRVTITCKVTEKVWGNVAWYQQKPGKcPISLIYSPSLRKSGVPSRFSGSGSGT<br>DFTLTISSLQPEDFATYYCQQYYTYPYTFGGGTKVEIK** |
| 295 | ACP466 | vprdcgckpcictypevssvfifppkpkdvltitltpkvtcvvvdiskddpevqfswfvddvevhtaqtqpreeqfnstfrsv<br>selpimhqdwlngkefkcrvnsaafpapiektisktkgrpkapqvytipppkeqmakdkvsltcmitdffpeditvewq<br>wngqpaenykntqpimdtdgsyfvysklnvqksnweagntftcsvlheglhnhhtekslshspgksggpALFKSSF<br>Ppgsaptssstkktqlqlehlildlqmilnginmyknpkltrmltfkfympkkatelkhlqcleeelkpleevlnlaqsknfhlr<br>prdlisninvivlelkgsettfmceyadetativeflnrwitfcqsiistltgsgsggsgggsgggsgggsgggsggg<br>gpALFKSSFPpgsEVQLVESGGGLVQPGGSLRLSCAASGFTFSSYTLAWVRQAPGK<br>GLEWVAAIDSSYTYSPDTVRGRFTISRDNAKNSLYLQMNSLRAEDTAVYYCAR<br>DSNWDALDYWGQGTTVTVSSGGGSGGGSGGGSDIQMTQSPSSLSASVGDR<br>VTITCKAREKLWSAVAWYQQKPGKAPKsLIYSASFRYSGVPSRFSGSGSGTDFTL<br>TISSLQPEDFATYYCQQYYTYPYTFGGGTKVEIK** |
| 296 | ACP467 | vprdcgckpcictypevssvfifppkpkdvltitltpkvtcvvvdiskddpevqfswfvddvevhtaqtqpreeqfnstfrsv<br>selpimhqdwlngkefkcrvnsaafpapiektisktkgrpkapqvytipppkeqmakdkvsltcmitdffpeditvewq<br>wngqpaenykntqpimdtdgsyfvysklnvqksnweagntftcsvlheglhnhhtekslshspgksggpALFKSSF<br>Ppgsaptssstkktqlqlehlildlqmilnginmyknpkltrmltfkfympkkatelkhlqcleeelkpleevlnlaqsknfhlr<br>prdlisninvivlelkgsettfmceyadetativeflnrwitfcqsiistltgsgsggsgggsgggsgggsgggsggg<br>gpALFKSSFPpgsEVQLVESGGGLVQPGGSLRLSCAASGFTFSSYTLAWVRQAPGK<br>cLEWVAAIDSSYTYSPDTVRGRFTISRDNAKNSLYLQMNSLRAEDTAVYYCAR<br>DSNWDALDYWGQGTTVTVSSGGGSGGGSGGGSDIQMTQSPSSLSASVGDR<br>VTITCKAREKLW SAVAWYQQKPGKAPKsLIYSASFRYSGVPSRFSGSGSGTDFTL<br>TISSLQPEDFATYYCQQYYTYPYTFGcGTKVEIK** |
| 297 | ACP468 | vprdcgckpcictypevssvfifppkpkdvltitltpkvtcvvvdiskddpevqfswfvddvevhtaqtqpreeqfnstfrsv<br>selpimhqdwlngkefkcrvnsaafpapiektisktkgrpkapqvytipppkeqmakdkvsltcmitdffpeditvewq<br>wngqpaenykntqpimdtdgsyfvysklnvqksnweagntftcsvlheglhnhhtekslshspgksggpALFKSSF<br>Ppgsaptssstkktqlqlehlildlqmilnginmyknpkltrmltfkfympkkatelkhlqcleeelkpleevlnlaqsknfhlr<br>prdlisninvivlelkgsettfmceyadetativeflnrwitfcqsiistltgsgsggsgggsgggsgggsgggsggg<br>gpALFKSSFPpgsEVQLVESGGGLVQPGGSLRLSCAASGFTFSSYTLAWVRQAPGK<br>GLEWVAAIDSSYTYSPDTVRGRFTISRDNAKNSLYLQMNSLRAEDTAVYYCAR<br>DSNWDALDYWGcGTTVTVSSGGGSGGGSGGGSDIQMTQSPSSLSASVGDR<br>VTITCKAREKLW SAVAWYQQKPGKcPKALIYSASFRYSGVPSRFSGSGSGTDFTL<br>TISSLQPEDFATYYCQQYYTYPYTFGGGTKVEIK** |

-continued

SEQUENCE TABLE

| SEQ ID NO. | Name | Sequence |
|---|---|---|
| 298 | ACP469 | vprdcgckpcictvpevssvfifppkpkdvltitltpkvtcvvvdiskddpevgfswfvddvevhtaqtqpreeqfnstfrsv selpimhqdwlngkefkcrvnsaafpapiektisktkgrpkapqvytipppkeqmakdkvsltcmitdffpeditvewq wngqpaenykntqpimdtdgsyfvysklnvqksnweagntftcsvlheglhnhhteksishspgksggpALFKSSF Ppgsaptssstkktqlqlehlldlqmilnginmyknpkltrmltfkfympkkatelkhlqcleeelkpleevlnlaqsknfhlr prdlisninivivlelkgsettfmceyadetativeflnrwitfcqsiistltggggsggggsggggsggggsggggssg gpALFKSSFPpgsEVQLVESGGGLVQPGGSLRLSCAASGFTFSSYTLAWRQAPGK cLEWVAAIDSSSYTYSPDTVRGRFTISRDNAKNSLYLQMNSLRAEDTAVYYCAR DSNMDALDYWGQGTTVTVSSGGGSGGGGSGGGGSDIQMTQSPSSLSASVGDR VTITCKVTEKVWGNVAWYQQKPGKAPISLIYSPSLRKSGVPSRFSGSGSGTDFTL TISSLQPEDFATYYCQQYYTYPYTFGcGTKVEIK** |
| 299 | ACP470 | vprdcgckpcictvpevssvfifppkpkdvltitltpkvtcvvvdiskddpevgfswfvddvevhtaqtqpreeqfnstfrsv selpimhqdwlngkefkcrvnsaafpapiektisktkgrpkapqvytipppkeqmakdkvsltcmitdffpeditvewq wngqpaenykntqpimdtdgsyfvysklnvqksnweagntftcsvlheglhnhhteksishspgksggpALFKSSF Ppgsaptssstkktqlqlehlldlqmilnginmyknpkltrmltfkfympkkatelkhlqcleeelkpleevlnlaqsknfhlr prdlisninivivlelkgsettfmceyadetativeflnrwitfcqsiistltggggsggggsggggsggggsggggssg gpALFKSSFPpgsEVQLVESGGGLVQPGGSLRLSCAASGFTFSSYTLAWRQAPGK GLEWVAAIDSSSYTYSPDTVRGRFTISRDNAKNSLYLQMNSLRAEDTAVYYCAR DSNMDALDYWGcGTTVTVSSGGGSGGGGSGGGGSDIQMTQSPSSLSASVGDR VTITCKVTEKVWGNVAWYQQKPGKcPISLIYSPSLRKSGVPSRFSGSGSGTDFTLT ISSLQPEDFATYYCQQYYTYPYTFGGGTKVEIK** |
| 300 | ACP471 | mdmrvpaqllgllllwlrgarcvprdcgckpcictvpevssvfifppkpkdvltitltpkvtcvvvdiskddpevgfswfvd dvevhtaqtqpreeqfnstfrsyselpimhqdwlngkefkcrvnsaafpapiektisktkgrpkapqvytipppkeqmak dkvsltcmitdffpeditvewqwngqpaenykntqpimdtdgsyfvysklnvqksnweagntftcsvlheglhnhhtek slshspgksggpALFKSSFPpgsaptssstkktqlqlehlldlqmilnginmyknpkltrmltfkfympkkatelkhlq cleeelkpleevlnlaqsknfhlrprdlisninivivlelkgsettfmceyadetativeflnrwitfcqsiistltggggsggggssg ggggsggggsggggsggggsgpALFKSSFPpgsEVQLVESGGGLVQPGGSLRLSCAASGFT FSSYTLAWRQAPGKGLEWVAAIDSSSYTYSPDTVRGRFTISRDNAKNSLYLQM NSLRAEDTAVYYCARDSNWDALDYWGQGTTVTVSSastkgpsvflpapsskstsggtaalgcl vkdyfpepvtvswnsgaltsgvhtfpavlqssglyslssvvtvpsslgtqtyicnvnhkpsntkvdkrvepksc** |
| 301 | ACP382 | DIQMTQSPSSLSASVGDRVTITCKVTEKVWGNVAWYQQKPGKAPISLIYS PSLRKSGVPSRFSGSGSGTDFTLTISSLQPEDFATYYCQQYYTYPYTFGGG TKVEIKrtvaapsvfifppdeqlksgtasvvcllnnfypreakvqwkvdnalqsgnsqesvteqdskdsty slssthlskadyekhkvyacevthqglsspvtksfnrgec** |
| 302 | ACP383 | eskyyqppcppcpapeflggpsvflfppkpkdtlmisrtpevtcvvvdvsqedpevqfnwyvdgvevhnaktkpreeqf nstyrvvsvltvlhqdwlngkeyfkckvsnkglpssiektiskakgqprepqvylppsqeemtknqvsltclvkgfypsdi avewesngqpennykttppvldsdqsfflysrltvdksrwgenvfscsvmhealhnhytqkslslslgksggpGPAG LYAQpgsaptssstkktqlqlehlldlqmilnginmyknpkltrmltfkfympkkatelkhlqcleeelkpleevlnlaqs knfhlrprdliisninivivlelkgsettfmceyadetativeflnrwitfcqsiistltggggsggggsggggsggggsggggssg gggssggpGPAGLYAQpgsEVQLVESGGGLVQPGGSLRLSCAASGFTFSSYTLAWVR QAPGKcLEWVAAIDSSSYTYSPDTVRGRFTISRDNAKNSLYLQMNSLRAEDTAV YYCARDSNWDALDYWGQGTTVTVSSGGGSGGGGSGGGGSDIQMTQSPSSLS ASVGDRVTITCKASQNVGTNVGWYQQKPGKAPKALIYSASFRYSGVPSRFSGSG SGTDFTLTISSLQPEDFATYYCQQYYTYPYTFGcGTKVEIK** |

-continued

SEQUENCE TABLE

| SEQ ID NO. | Name | Sequence |
|---|---|---|
| 303 | ACP384 | eskygppcppcpapeflggpsvflfppkpkdtlmisrtpevtcvvvdvsqedpevqfnwyvdgvevhnaktkpreeqf<br>nstyrvvsvltvlhqdwlngkeykckvsnkglpssiektiskakgqprepqvytlppsqeemtknqvsltclvkgfypsdi<br>avewesngpennykttppvldsdgsfflysrltvdksrwqegnvfscsvmhealhnhytqkslslgksggpGPAG<br>LYAQpgsaptsssstkktqlqlehllldlqmilnginnyknpkltrmltfkfympkkatelkhlqcleeelkpleevlnlaqs<br>knfhlrprdlisninvivielkgsettfmceyadetativeflnrwitfcqsiistltggggsgggggsggggsgggggsg<br>ggggsggpGPAGLYAQpgsEVQLVESGGGLVQPGGSLRLSCAASGFTFSSYTLAWVR<br>QAPGKGLEWVAAIDSSSYYTYSPDTVRGRFTISRDNAKNSLYLQMNSLRAEDTAV<br>YYCARDSNWDALDYWGcGTTVTVSSGGGSGGGGSGGGGSDIQMTQSPSSLSA<br>SVGDRVTITCKASQNVGTNVGWYQQKPGKcPKALIYSASFRYSGVPSRFSGSGS<br>GTDFTLTIISSLQPEDFATYYCQQYTYPYTFGGGTKVEIK** |
| 304 | ACP385 | eskygppcppcpapeflggpsvflfppkpkdtlmisrtpevtcvvvdvsqedpevqfnwyvdgvevhnaktkpreeqf<br>nstyrvvsvltvlhqdwlngkeykckvsnkglpssiektiskakgqprepqvytlppsqeemtknqvsltclvkgfypsdi<br>avewesngpennykttppvldsdgsfflysrltvdksrwqegnvfscsvmhealhnhytqkslslgksggpGPAG<br>LYAQpgsaptsssstkktqlqlehllldlqmilnginnyknpkltrmltfkfympkkatelkhlqcleeelkpleevlnlaqs<br>knfhlrprdlisninvivielkgsettfmceyadetativeflnrwitfcqsiistltggggsgggggsggggsgggggsg<br>ggggsggpGPAGLYAQpgsEVQLVESGGGLVQPGGSLRLSCAASGFTFSSYTLAWVR<br>QAPGKcLEWVAAIDSSSYYTYSPDTVRGRFTISRDNAKNSLYLQMNSLRAEDTAV<br>YYCARDSNWDALDYWGQGTTVTVSSGGGSGGGGSGGGGSDIQMTQSPSSLS<br>ASVGDRVTITCKAREKLW SAVAWYQQKPGKAPKALIYSASFRYSGVPSRFSGSG<br>SGTDFTLTIISSLQPEDFATYYCQQYTYPYTFGGcGTKVEIK** |
| 305 | ACP386 | eskygppcppcpapeflggpsvflfppkpkdtlmisrtpevtcvvvdvsqedpevqfnwyvdgvevhnaktkpreeqf<br>nstyrvvsvltvlhqdwlngkeykckvsnkglpssiektiskakgqprepqvytlppsqeemtknqvsltclvkgfypsdi<br>avewesngpennykttppvldsdgsfflysrltvdksrwqegnvfscsvmhealhnhytqkslslgksggpGPAG<br>LYAQpgsaptsssstkktqlqlehllldlqmilnginnyknpkltrmltfkfympkkatelkhlqcleeelkpleevlnlaqs<br>knfhlrprdlisninvivielkgsettfmceyadetativeflnrwitfcqsiistltggggsgggggsggggsgggggsg<br>ggggsggpGPAGLYAQpgsEVQLVESGGGLVQPGGSLRLSCAASGFTFSSYTLAWVR<br>QAPGKGLEWVAAIDSSSYYTYSPDTVRGRFTISRDNAKNSLYLQMNSLRAEDTAV<br>YYCARDSNWDALDYWGcGTTVTVSSGGGSGGGGSGGGGSDIQMTQSPSSLSA<br>SVGDRVTITCKAREKLWSAVAWYQQKPGKcPKALIYSASFRYSGVPSRFSGSGS<br>GTDFTLTIISSLQPEDFATYYCQQYTYPYTFGGGTKVEIK** |
| 306 | ACP387 | eskygppcppcpapeflggpsvflfppkpkdtlmisrtpevtcvvvdvsqedpevqfnwyvdgvevhnaktkpreeqf<br>nstyrvvsvltvlhqdwlngkeykckvsnkglpssiektiskakgqprepqvytlppsqeemtknqvsltclvkgfypsdi<br>avewesngpennykttppvldsdgsfflysrltvdksrwqegnvfscsvmhealhnhytqkslslgksggpGPAG<br>LYAQpgsaptsssstkktqlqlehllldlqmilnginnyknpkltrmltfkfympkkatelkhlqcleeelkpleevlnlaqs<br>knfhlrprdlisninvivielkgsettfmceyadetativeflnrwitfcqsiistltggggsgggggsggggsgggggsg<br>ggggsggpGPAGLYAQpgsEVQLVESGGGLVQPGGSLRLSCAASGFTFSSYTLAWVR<br>QAPGKcLEWVAAIDSSSYYTYSPDTVRGRFTISRDNAKNSLYLQMNSLRAEDTAV<br>YYCARDSNWDALDYWGQGTTVTVSSGGGSGGGGSGGGGSDIQMTQSPSSLS<br>ASVGDRVTITCKVTBKVWGNVAWYQQKPGKAPISLLIYSPSLRKSGVPSRFSGSGS<br>GTDFTLTIISSLQPEDFATYYCQQYTYPYTFGGcGTKVEIK** |
| 307 | ACP388 | eskygppcppcpapeflggpsvflfppkpkdtlmisrtpevtcvvvdvsqedpevqfnwyvdgvevhnaktkpreeqf<br>nstyrvvsvltvlhqdwlngkeykckvsnkglpssiektiskakgqprepqvytlppsqeemtknqvsltclvkgfypsdi<br>avewesngpennykttppvldsdgsfflysrltvdksrwqegnvfscsvmhealhnhytqkslslgksggpGPAG |

-continued

SEQUENCE TABLE

| SEQ ID NO. | Name | Sequence |
|---|---|---|
| 308 | | LYAQpgsaptsssttktqlqlehllldlqmilnginnyknpkltrmltfkfympkkatelkhlqcleeelkpleevlnlaqs knfhlrprdlisnninvivlelkgsettfmceyadetativeflnrwitfcqsiistltgggsgsggggsggggsggggsg gggsggpGPAGLYAQpgsEVQLVESGGGlVQPGGSLRLSCAASGFTFSSYTLAWVR QAPGKGLEWVAAIDSSSYTYSPDTVRGRFTISRDNAKNSLYLQMNSLRAEDTAV YYCARDSNWDALDYWGcGTTVTVSSGGGGSGGGGSGGGGSDIQMTQSPSSLSA SVGDRVTITCKVTEKVWGNVAWYQQKPGKCPISLIYSPSLRKSGVPSRRSGSGSG TDFTLTISSLQPEDFATYYCQQYYTPYTPGGGTKVEIK** |
| 309 | ACP389 | eskyqppcppcpapeflggpsvflfppkpkdtlmisrtpevtcyvvdvsqedpevqfnwyvdgvevhnaktkpreeqf nstyrvvsvltvlhqdwlngkeykckvsnkglpssiektiskakgqprepqvytlppsqeemtknqvsltclvkgfypsdi avewesngqpennykttppvldsdgsfflysrltvdkswqegnvfscsvmhealnhhytqksls1sqkssgpGPAG LYAQpgsaptsssttktqlqlehllldlqmilnginnyknpkltrmltfkfympkkatelkhlqcleeelkpleevlnlaqs knfhlrprdlisnninvivlelkgsettfmceyadetativeflnrwitfcqsislsesggggsggggsggggsggggsg gggsggpGPAGLYAQpgsevqllesggglvqpggslrlscaasgsifsanamgwyrqapgkqrelvavissggst nyadsvkgrftisrdnskntvylqmnslraedtavyycmysgsvyytpndywgggtlvtvss** |
| 310 | ACP390 | aptsssttktqlqlehllldlqmilnginnyknpkltrmltfkfympkkatelkhlqcleeelkpleevlnlaqsknfhlrprdli sninivivlelkgsettfmceyadetativeflnrwitfcqsiistltsggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSgggsgggg sggggsgggsgggsgggsggpGPAGLYAQpgsEVQLVESGGGLVQPGGSLRLSCAAS GFTFSSYTLAWVRQAPGKcLEWVAAIDSSSYTYSPDTVRGRFTISRDNAKNSLYL QMNSLRAEDTAVYYCARDSNWDALDYWGQGTTVTVSSGGGGSGGGGSGGGGG SDIQMTQSPSSLSASVGDRVTITCKAREKIWSAVAWYQQKPGKAPKSLIYSASFR YSGVPSRFSGSGSGTDFTLTISSLQPEDFATYYCQQYYTPYTPGcGTKVEIK** |
| 311 | ACP391 | eskyqppcppcpapeflggpsvflfppkpkdtlmisrtpevtcvvvdvsqedpevqfnwyvdgvevhnaktkpreeqf nstyvvvsvltvlhqdwlngkeykckvsnkglpssiektiskakgqprepqvytlppsqeemtknqvsltclvkgfypsdi avewesngqpennykttppvldsdgsfflysrltvdksrwqegnvfscsvmhealnhhytqksls1sqkssgpGPAG LYAQpgsaptsssttktqlqlehllldlqmilnginnyknpkltrmltfkfympkkatelkhlqcleeelkpleevlnlaqs knfhlrprdlisnninvivlelkgsettfmceyadetativeflnrwitfcqsislsesggggsggggsggggsggggsg gggsggpGPAGLYAQpgsEVQLVESGGGlVQPGGSLRLSCAASGFTFSSYTLAWVR QAPGKcLEWVAAIDSSSYTYSPDTVRGRFTISRDNAKNSLYLQMNSLRAEDTAV YYCARDSNWDALDYWGQGTTVTVSSGGGGSGGGGSGGGGSDIQMTQSPSSLS ASVGDRVTITCKAREKLWSAVAWYQQKPGKAPKSLIYSASFRYSGVPSRFSGSG SGTDFTLTISSLQPEDFATYYCQQYYTPYTPGcGTKVEIK** |
| 311 | ACP392 | aptsssttktqlqlehllldlqmilnginnyknpkltrmltfkfympkkatelkhlqcleeelkpleevlnlaqsknfhlrprdli sninivivlelkgsettfmceyadetativeflnrwitfcqsiistltsggpGPAGLYAQpgsEVQLVESGGGsggg sggggsggggselcdddpeiphatfkamaykegtmlnceckrgfrriksgslymlctgnshsswdnqcqctssatr nttkqvtpqeeqkerkttemqspmqpvdqaslpqhcreppweneateriyhfvvgqmvyycvqgyralhrgpae svckmthgktrwtdpqllctgemetsqfpgeekpqaspegrpesetsslvtttdfqiqtemaatmetsifftteyqsggP AGLYAQpgsEVQLVESGGGlVQPGNSLRLSCAASGFTFSKFGMSWVRQAPGKGL EWVSSISGSGRDTLYAESVKGRFTISRDNAKTTLYLQMNSLRPEDTAVYYCTIGG SLSVSSQGTLVTVSSgggsgggggsggggggsggggggsggpGPAGLYAQpgsEVQL VESGGGLVQPGGSLRLSCAASGFTFSSYTLAWVRQAPGKcLEWVAAIDSSSYTY SPDTVRGRFTISRDNAKNSLYLQMNSLRAEDTAVYYCARDSNWDALDYWGQG TTVTVSSGGGGSGGGGSGGGGSDIQMTQSPSSLSASVGDRVTITCKAREKLWSA |

-continued

SEQUENCE TABLE

| SEQ ID NO. | Name | Sequence |
|---|---|---|
| 312 | ACP393 | VAWYQQKPGKGAPKSLIYSASFRYSGVPSRFSGSGSGTDFTLTISSLQPEDFATYYC QQYYTYPYTFGcGTKVEIK** |
| 313 | ACP394 | aptssstktqlqehlldlqmilnginnyknpkltrmltfkfympkkatelkhlqcleeelkpleevlnlaqsknfhlrprdli sninivlelkgsettfmceyadetativeflnrwitfcqsiistltsggpGPAGLYAQpgsgggsgggggsgg ggsgggsgggselcddpeiphatfkamaykegtmlnceckrgfrriksgslymlctgnsshsswdnqcqctssatr nttkqvtpqeeqkerkttemqspmqpvdqaslpghcreppweneateriyhfvvgqmvyyqcvqgyralhrgpae svckmthgktrwtdpqlictgemetsqfpgeekpqaspegrpesetsslvttdfqiqtemaatmetsiftteyqsggpGP AGLYAQpgsEVQLVESGGGLVQPGNSLRLSCAASGFTFSKFGMSWVRQAPGKGL EWVSSISGSGRDTLYAESVKGRFTISRDNAKTTLYLQMNSLRPEDTAVYYCTIGG SLSVSSQGTILVTVSSgggsgggsgggsgggsgggsgggsggpGPAGLYAQpgsEVQL VESGGGLVQPGGSLRLSCAASGFTFSSYTLAWVRQAPGKGLEWVAAIDSSSYTY SPDTVRGRFTISRDNAKNSLYLQMNSLRAEDTAVYYCARDSNWDALDYWGcGT TVTVSSGGGGSGGGGSGGGGSDIQMTQSPSSLSASVGDRVTITCKAREKLWSAV AWYQQKPGKcPKALIYSASFRYSGVPSRFSGSGSGTDFTLTISSLQPEDFATYYCQ QYYTYPYTFGGGTKVEIK** |
| 314 | ACP395 | aptssstktqlqehlldlqmilnginnyknpkltrmltfkfympkkatelkhlqcleeelkpleevlnlaqsknfhlrprdli sninivlelkgsettfmceyadetativeflnrwitfcqsiistltsggpGPAGLYAQpgsgggsgggggsgg ggsgggsgggselcddpeiphatfkamaykegtmlnceckrgfrriksgslymlctgnsshsswdnqcqctssatr nttkqvtpqeeqkerkttemqspmqpvdqaslpghcreppweneateriyhfvvgqmvyyqcvqgyralhrgpae svckmthgktrwtdpqlictgemetsqfpgeekpqaspegrpesetsslvttdfqiqtemaatmetsiftteyqsggpGP AGLYAQpgsEVQLVESGGGLVQPGNSLRLSCAASGFTFSKFGMSWVRQAPGKGL EWVSSISGSGRDTLYAESVKGRFTISRDNAKTTLYLQMNSLRPEDTAVYYCTIGG SLSVSSQGTILVTVSSgggsgggsgggsgggsgggsgggsggpGPAGLYAQpgsEVQL VESGGGLVQPGGSLRLSCAASGFTFSSYTLAWVRQAPGKGLEWVAAIDSSSYTY SPDTVRGRFTISRDNAKNSLYLQMNSLRAEDTAVYYCARDSNWDALDYWGcGT TVTVSSGGGGSGGGGSGGGGSDIQMTQSPSSLSASVGDRVTITCKVTEKVWGNV AWYQQKPGKcPISLLIYSPSLRKSGVPSRFSGSGSGTDFTLTISSLQPEDFATYYCQQ YYTYPYTFGGGTKVEIK** |
| 315 | ACP396 | aptssstktqlqehlldlqmilnginnyknpkltrmltfkfympkkatelkhlqcleeelkpleevlnlaqsknfhlrprdli sninivlelkgsettfmceyadetativeflnrwitfcqsiistltsggpGPAGLYAQpgsgggsgggggsgg ggsgggsgggselcddpeiphatfkamaykegtmlnceckrgfrriksgslymlctgnsshsswdnqcqctssatr |

-continued

SEQUENCE TABLE

| SEQ ID NO. | Name | Sequence |
|---|---|---|
|  |  | nttkqvtpqeeqkerkttemqspmqpvdqaslpghcreppweneateriyhfvvgqmvyyqcvqgyralhrgpae |
|  |  | svckmthgktrwtqpqlictgemetsqfpgeekpqaspegrpesetsSlvttdfqiqtemaatmetsifttteyqsggpGP |
|  |  | AGLYAQpgsEVQLVESGGGLVQPGNSLRLSCAASGFTFSKFGMSWVRQAPGKGL |
|  |  | EWVSSISGSGRDTLYAESVKGRFTISRDNAKTTLYLQMNSLRPEDTAVYYCTIGG |
|  |  | SLSVSSQGTLVTVSSgggsgggggggggggsgggggggsggGPAGLYAQpgsevqlles |
|  |  | ggglvqpggslrlscaasgsifsanamgwyrqapgkqrelvavissggstnyadsvkgrftisrdnskntvylqmnslraed |
|  |  | tavyycmysgsyyYtpndywgqgtlvtvss** |
| 316 | ACP397 | aptssstkktqlqlehlldlqmilnginnykmpkltrmltfkfympkkatelkhlqcleeelkpleevlnlagsknfhlrprdli |
|  |  | sninivilelkgsettfmceyadetativeflnrwitfcqsiistltsggpGPAGLYAQpgsgggggsgggggsgg |
|  |  | gggggggggggselcdddpeiphatfkamaykegtmlnceckrgfrriksgslymlctgnsshsswdnqcqctssatr |
|  |  | nttkqvtpqeeqkerkttemqspmqpvdqaslpghcreppweneateriyhfvvgqmvyyqcvqgyralhrgpae |
|  |  | svckmthgktrwtqpqlictgemetsqfpgeekpqaspegrpesetsSlvttdfqiqtemaatmetsifttteyqsggpGP |
|  |  | AGLYAQpgsEVQLVESGGGLVQPGNSLRLSCAASGFTFSKFGMSWVRQAPGKGL |
|  |  | EWVSSISGSGRDTLYAESVKGRFTISRDNAKTTLYLQMNSLRPEDTAVYYCTIGG |
|  |  | SLSVSSQGTLVTVSSgggsggggggggggggggsggGPAGLYAQpgsevqlles |
|  |  | ggglvqpggslrlscaasgsifsanamgwyrqapgkglelvavissggstnyadsvkgrftisrdnskntvylqmnslraed |
|  |  | tavyycmysgsyyYtpndywgqgtlvtvss** |
| 317 | ACP398 | aptsssstkktqlqlehlldlqmilnginnyknpkltrmltfkfympkkatelkhlqcleeelkpleevlnlagsknfhlrprdli |
|  |  | sninivilelkgsettfmceyadetativeflnrwitfcqsiistltsggpGPAGLYAQpgsgggggsgggggsgg |
|  |  | gggggggggggselcdddpeiphatfkamaykegtmlnceckrgfrriksgslymlctgnsshsswdnqcqctssatr |
|  |  | nttkqvtpqeeqkerkttemqspmqpvdqaslpghcreppweneateriyhfvvgqmvyyqcvqgyralhrgpae |
|  |  | svckmthgktrwtqpqlictgemetsqfpgeekpqaspegrpesetsSlvttdfqiqtemaatmetsifttteyqsggpGP |
|  |  | AGLYAQpgsEVQLVESGGGLVQPGNSLRLSCAASGFTFSKFGMSWVRQAPGKGL |
|  |  | EWVSSISGSGRDTLYAESVKGRFTISRDNAKTTLYLQMNSLRPEDTAVYYCTIGG |
|  |  | SLSVSSQGTLVTVSSgggsgggggggggsgggggggsggGPAGLYAQpgsEVQL |
|  |  | VESGGGLVQPGGSLRLSCAASGFTFSSYTLAWVRQAPGKGLEWVAAIDSSYTY |
|  |  | SPDTVRGRFTISRDNAKNSLYLQMNSLRAEDTAVYYCARDSNWDALDYWGQG |
|  |  | TTVTVSSastkgpsvfplapsskstsggtaalgclvkdyfpepvtvswnsgaltsgvhtfpavlqssglyslsvvtvpss |
|  |  | slgtqtyicnvnhkpsntkvdkrvepksc** |
| 318 | ACP399 | EVQLVESGGGLVQPGGSLRLSCAASGFTFSSYTLAWVRQAPGKCLEWVAAIDSS |
|  |  | SYTYSPDTVRGRFTISRDNAKNSLYLQMNSLRAEDTAVYYCARDSNWDALDYW |
|  |  | GQGTTVTVSSGGGGSGGGGSGGGGSDIQMTQSPSSLSASVGDRVTITCKAREKL |
|  |  | WSAVAWYQQKPGKAPKsLIYSASFRYSGVPSRFSGSGSGTDFTLTISSLQPEDFAT |
|  |  | YYCQQYYTYPYTFGcGTKVEIKsggpGPAGLYAQpsgggggsgggggsggggggsg |
|  |  | gggsEVQLVESGGGLVQPGNSLRLSCAASGFTFSKFGMSWVRQAPGKGLEWVSSI |
|  |  | SGSGRDTLYAESVKGRFTISRDNAKTTLYLQMNSLRPEDTAVYYCTIGGSLSVSS |
|  |  | QGTLVTVSSsggpGPAGLYAQpgstfkfympkkatelkhlqcleeelkpleevlnlagsknfhlrprdlisnin |
|  |  | vivlelkgsettfmceyadetativeflnrwitfcqsiistltcGsssstkktqlqlehlldlqmilnginnyknpkltrmlsggp |
|  |  | GPAGLYAQpgsEVQLVESGGGLVQPGNSLRLSCAASGFTFSKFGMSWVRQAPGK |
|  |  | GLEWVSSISGSGRDTLYAESVKGRFTISRDNAKTTLYLQMNSLRPEDTAVYYCTI |
|  |  | GGSLSVSSQGTLVTVSS** |
| 319 | ACP400 | EVQLVESGGGLVQPGGSLRLSCAASGFTFSSYTLAWVRQAPGKGLEWVAAIDSS |
|  |  | SYTYSPDTVRGRFTISRDNAKNSLYLQMNSLRAEDTAVYYCARDSNWDALDYW |
|  |  | GcGTTVTVSSGGGGSGGGGSGGGGSDIQMTQSPSSLSASVGDRVTITCKAREKL |

-continued

SEQUENCE TABLE

| SEQ ID NO. | Name | Sequence |
|---|---|---|
| | | WSAVAWYQQKPGKcPKALIYSASPRYSGVPSRFSGSGSGTDFTLTISSLQPEDFA<br>TYYCQQYYTYPYTFGGGTKVEIKsggpGPAGLYAQpgsgsggggsgggsgggsggg<br>ssgggsEVQLVESGGGLVQPGNSLRLSCAASGFTFSKFGMSWVRQAPGKGLEWVS<br>SISGSGRDTLYAESVKGRFTISRDNAKTTLYLQMNSLRPEDTAVYYCTIGGSLSV<br>SSQGTLVTVSSsggpGPAGLYAQpgstfkfympkatelkhlqcleeelkpleevlnlaqsknfhlrprdlisn<br>invivlelkgsettfmceyadetativeflnrwitfcqsiistltGGssstkktqlqlehlldlqmilnginnyknpkltrmlsg<br>gpGPAGLYAQpgsEVQLVESGGGLVQPGNSLRLSCAASGFTFSKFGMSWVRQAP<br>GKGLEWVSSISGSGRDTLYAESVKGRFTISRDNAKTTLYLQMNSLRPEDTAVYY<br>CTIGGSLSVSSQGTLVTVSS** |
| 320 | ACP401 | EVQLVESGGGLVQPGGSLRLSCAASGFTFSSYTLAWVRQAPGKcLEWVAAIDSS<br>SYTYSPDTVRGRFTISRDNAKNSLYLQMNSLRAEDTAVYYCARDSNWDALDYW<br>GQGTTVTVSSGGGSGGGGSGGGGSDIQMTQSPSSLSASVGDRVTITCKVTEKV<br>WGNVAWYQQKPGKAPISLIYSPSLRKSGVPSRFSGSGSGTDFTLTISSLQPEDFAT<br>YYCQQYYTYPYTFGccTKVEIKsggpGPAGLYAQpgsgsggggsgggsgggsgggsg<br>gggsEVQLVESGGGLVQPGNSLRLSCAASGFTFSKFGMSWVRQAPGKGLEWVSSI<br>SGSGRDTLYAESVKGRFTISRDNAKTTLYLQMNSLRPEDTAVYYCTIGGSLSVSS<br>QGTLVTVSSsggpGPAGLYAQpgstfkfympkatelkhlqcleeelkpleevlnlaqsknfhlrprdlisnin<br>vivlelkgsettfmceyadetativeflnrwitfcqsiistltGGssstkktqlqlehlldlqmilnginnyknpkhrmlsggp<br>GPAGLYAQpgsEVQLVESGGGLVQPGNSLRLSCAASGFTFSKFGMSWVRQAPGK<br>GLEWVSSISGSGRDTLYAESVKGRFTISRDNAKTTLYLQMNSLRPEDTAVYYCTI<br>GGSLSVSSQGTLVTVSS** |
| 321 | ACP402 | EVQLVESGGGLVQPGGSLRLSCAASGFTFSSYTLAWVRQAPGKGLEWVAAIDSS<br>SYTYSPDTVRGRFTISRDNAKNSLYLQMNSLRAEDTAVYYCARDSNWDALDYW<br>GcGTTVTVSSGGGSGGGGSGGGGSDIQMTQSPSSLSASVGDRVTITCKVTEKV<br>WGNVAWYQQKPGKcPISLIYSPSLRKSGVPSRFSGSGSGTDFTLTISSLQPEDFAT<br>YYCQQYYTYPYTFGGGTKVEIKsggpGPAGLYAQpgsgsggggsgggsgggsgggsg<br>gggsEVQLVESGGGLVQPGNSLRLSCAASGFTFSKFGMSWVRQAPGKGLEWVSS<br>ISGSGRDTLYAESVKGRFTISRDNAKTTLYLQMNSLRPEDTAVYYCTIGGSLSVS<br>SQGTLVTVSSsggpGPAGLYAQpgstfkfympkkatelkhlqcleeelkpleevlnlaqsknfhlrprdlisni<br>nvivlelkgsettfmceyadetativeflnrwitfcqsiistltGGssstkktqlqlehlldlqmilnginnyknpkltrmlsgg<br>pGPAGLYAQpgsEVQLVESGGGLVQPGNSLRLSCAASGFTFSKFGMSWVRQAPG<br>KGLEWVSSISGSGRDTLYAESVKGRFTISRDNAKTTLYLQMNSLRPEDTAVYYC<br>TIGGSLSVSSQGTLVTVSS** |
| 322 | ACP403 | evqllesgggl vqpggslrlscaasgsifsanamgwyrqapgkgrelvavissggstnyadsvkgrftisrdnskntvylqm<br>nslraedtavyycmysgsyytpndywgggtlvtvsssgpGPAGLYAQpgsgsggggsgggsgggsggggsg<br>gggsggggsEVQLVESGGGLVQPGNSLRLSCAASGFTFSKFGMSWVRQAPGKGLE<br>WVSSISGSGRDTLYAESVKGRFTISRDNAKTTLYLQMNSLRPEDTAVYYCTIGGS<br>LSVSSQGTLVTVSSsggpGPAGLYAQpgstfkfympkkatelkhlqcleeelkpleevlnlaqsknfhlrpr<br>dlisninvivlelkgsettfmceyadetativeflnrwitfcqsiistltGGssstkktqlqlehlldlqmilnginnyknpkltr<br>mlsggpGPAGLYAQpgsEVQLVESGGGLVQPGNSLRLSCAASGFTFSKFGMSWVRQ<br>APGKGLEWVSSISGSGRDTLYAESVKGRFTISRDNAKTTLYLQMNSLRPEDTAV<br>YYCTIGGSLSVSSQGTLVTVSS** |
| 323 | ACP404 | evqllesgggl vqpggslrlscaasgsifsanamgwyrqapgkgrelvavissggstnyadsvkgrftisrdnskntvylqm<br>nslraedtavyycmysgsyytpndywgggtlvtvsssgpGPAGLYAQpgsgsggggsgggsgggsggggsg |

-continued

SEQUENCE TABLE

| SEQ ID NO. | Name | Sequence |
|---|---|---|

324  ACP405

```
ggggggggsEVQLVESGGGLVQPGNSLRLSCAASGFTFSKFGMSWVRQAPGKGLE
WVSSISGSGRDTLYAESVKGRFTISRDNAKTTLYLQMNSLRPEDTAVYYCTIGGS
LSVSSQGTLVTVSSsggpGPAGLYAQpgsfkfympkkatelkhlqcleeelkpleevlnlaqsknfhlrpr
dlisninivlelkgsettfmceyadetativeflnrwitfcqsiisltGGssstkktqlqlehlldlqmilnginnykmpkltr
mlsggpGPAGLYAQpgsEVQLVESGGGLVQPGNSLRLSCAASGFTFSKFGMSWVRQ
APGKGLEWVSSISGSGRDTLYAESVKGRFTISRDNAKTTLYLQMNSLRPEDTAV
YYCTIGGSLSVSSQGTLVTVSS**
```

325  ACP406

```
EVQLVESGGGLVQPGGSLRLSCAASGFTFSSYTLAWVRQAPGKGLEWVAAIDSS
SYTYSPDTVRGRFTISRDNAKNSLYLQMNSLRAEDTAVYYCARDSNWDALDYW
GQGTTVTVSSsastkgpsvfplapssksstsggtaalgclvkdyfpepvtvswnsgaltsgvhtfpavlqssglyslssv
vtvpsslgtqtyicnvnhkpsntkvdkrvepkscsggpGPAGLYAQpgsgggggsggggsggggs
sggggsEVQLVESGGGLVQPGNSLRLSCAASGFTFSKFGMSWVRQAPGKGLEWVS
SISGSGRDTLYAESVKGRFTISRDNAKTTLYLQMNSLRPEDTAVYYCTIGGSLSV
SSQGTLVTVSSsggpGPAGLYAQpgstfkfympkkatelkhlqcleeelkpleevlnlaqsknfhlrprdlisn
invlvlelkgsettfmceyadetativeflnrwitfcqsiisltGGssstkktqlqlehlldlqmilnginnykmpkltrmlsg
gpGPAGLYAQpgsEVQLVESGGGLVQPGNSLRLSCAASGFTFSKFGMSWVRQAP
GKGLEWVSSISGSGRDTLYAESVKGRFTISRDNAKTTLYLQMNSLRPEDTAVYY
CTIGGSLSVSSQGTLVTVSS**
```

326  ACP407

```
vprdcgckpcictvpevsvfifppkpkdvltitltpkvtcvvvdiskddpevqfswfvddvevhtaqtqpreeqfnstfrsv
selpimhqdwlngkefkcrvnsaafpapiektisktkgrpkapqvytipppkeqmakdkvsltcmitdffpeditvewq
wngqpaenykntqpimdtdgsyfvysklnvqksnweagntftcsvlheglhnhhtekslshspgksggpGPAGLY
AQpgsaptssstkktqlqlehlldlqmilnginnykmpkltrmltfkfympkkatelkhlqcleeelkpleevlnlaqsknf
hlrprdlisninivlelkgsettfmceyadetativeflnrwitfcqsiisltgggsggggsggggsggggsgggg
ssggpGPAGLYAQpgsEVQLVESGGGLVQPGGSLRLSCAASGFTFSSYTLAWVRQA
PGKGLEWVAAIDSSSYTYSPDTVRGRFTISRDNAKNSLYLQMNSLRAEDTAVYY
CARDSNWDALDYWQGGTTVTVSSaastkgpsvfplapssksstsggtaalgclvkdyfpepvtvswnsgal
tsgvhtfpavlqssglyslssvvtvpsslgtqtyicnvnhkpsntkvdkrvepksc**
```

327  ACP408

```
vprdcgckpcictvpevsvfifppkpkdvltitltpkvtcvvvdiskddpevqfswfvddvevhtaqtqpreeqfnstfrsv
selpimhqdwlngkefkcrvnsaafpapiektisktkgrpkapqvytipppkeqmakdkvsltcmitdffpeditvewq
wngqpaenykntqpimdtdgsyfvysklnvqksnweagntftcsvlheglhnhhtekslshspgksggpGPAGLY
AQpgsaptssstkktqlqlehlldlqmilnginnykmpkltrmltfkfympkkatelkhlqcleeelkpleevlnlaqsknf
hlrprdlisninivlelkgsettfmceyadetativeflnrwitfcqsiisltgggsggggsggggsggggsgggg
ssggpGPAGLYAQpgsEVQLVESGGGLVQPGGSLRLSCAASGFTFSSYTLAWVRQA
PGKcLEWVAAIDSSSYTYSPDTVRGRFTISRDNAKNSLYLQMNSLRAEDTAVYY
```

-continued

SEQUENCE TABLE

| SEQ ID NO. | Name | Sequence |
|---|---|---|
| 328 | ACP409 | CARDSNWDALDYWGQGTTVTVSSGGGGSGGGGSGGGGSDIQMTQSPSSLSASV<br>GDRVTITCKAREKLWSAVAWYQQKPGKAPKsLIIYSASFRYSGVPSRFSGSGSGT<br>DFTLTISSLQPEDFATYYCQQYYTYPYTFGcGTKVEIK** |
| 329 | ACP410 | vprdcgckpcictvpevssvfifppkpkdvltitltpkvtcvvvdiskddpevgfswfvddvevhtaqtqpreeqfnstfrsv<br>selpimhqdvlngkefkcrvnsaafpapiektisktkgrpkapqvytipppkeqmakdkvsltcmitdffpeditvewq<br>wngqpaenykntqpimdtdgsyfvysklnvqksnweagntftcsvlheglhnhhteksIshspksggpGPAGLY<br>AQpgsaptssstktqlqlehlldlqmilnginnyknpkltrmltfkfympkkatelkhlqcleeelkpleevlnlaqsknf<br>hlrpdlisninvivlelkgsettfmceyadetativeflnrwitfcqsiistltgggsgggsgggsgggsgggsgggg<br>ssggpGPAGLYAQpgsEVQLVESGGGLVQPGGSLRLSCAASGFTFSSYTLAWVRQA<br>PGKGLEWVAAIDSSSYTYSPDTVRGRFTISRDNAKNSLYLQMNSLRAEDTAVYY<br>CARDSNWDALDYWGcGTTVTVSSGGGGSGGGGSGGGGSDIQMTQSPSSLSASV<br>GDRVTITCKAREKLWSAVAWYQQKPGKcPKALIYSASFRYSGVPSRFSGSGSGT<br>DFTLTISSLQPEDFATYYCQQYYTYPYTFGGGTKVEIK** |
| 330 | ACP411 | vprdcgckpcictvpevssvfifppkpkdvltitltpkvtcvvvdiskddpevgfswfvddvevhtaqtqpreeqfnstfrsv<br>selpimhqdvlngkefkcrvnsaafpapiektisktkgrpkapqvytipppkeqmakdkvsltcmitdffpeditvewq<br>wngqpaenykntqpimdtdgsyfvysklnvqksnweagntftcsvlheglhnhhteksIshspksggpGPAGLY<br>AQpgsaptssstktqlqlehlldlqmilnginnyknpkltrmltfkfympkkatelkhlqcleeelkpleevlnlaqsknf<br>hlrpdlisninvivlelkgsettfmceyadetativeflnrwitfcqsiistltgggsgggsgggsgggsgggsgggg<br>ssggpGPAGLYAQpgsEVQLVESGGGLVQPGGSLRLSCAASGFTFSSYTLAWVRQA<br>PGKGLEWVAAIDSSSYTYSPDTVRGRFTISRDNAKNSLYLQMNSLRAEDTAVYY<br>CARDSNWDALDYWGcGTTVTVSSGGGGSGGGGSGGGGSDIQMTQSPSSLSASV<br>GDRVTITCKVTEKVWGNVAWYQQKPGKcPISLIYSPSLRKSGVPSRFSGSGSGTD<br>FTLTISSLQPEDFATYYCQQYYTYPYTFGGGTKVEIK** |
| 331 | ACP412 | vprdcgckpcictvpevssvfifppkpkdvltitltpkvtcvvvdiskddpevgfswfvddvevhtaqtqpreeqfnstfrsv<br>selpimhqdvlngkefkcrvnsaafpapiektisktkgrpkapqvytipppkeqmakdkvsltcmitdffpeditvewq<br>wngqpaenykntqpimdtdgsyfvysklnvqksnweagntftcsvlheglhnhhteksIshspksggpGPAGLY<br>AQpgsaptssstktqlqlehlldlqmilnginnyknpkltrmltfkfympkkatelkhlqcleeelkpleevlnlaqsknf<br>hlrpdlisninvivlelkgsettfmceyadetativeflnrwitfcqsiistltgggsgggsgggsgggsgggsgggg<br>ssggpGPAGLYAQpgsevqllessgglvqpggsirlscaasgsifsanamgwyrqapgkgrelvavissggsthya<br>dsvkgrftisrdnskntvylqmnslraedtavyycmysgsyyytpndyvgqgtlvtvss** |
| 332 | ACP413 | elcddqdppeiphatfkamaykegtmlnceckrgfirrikssglymlctgnsshsswdncqctssatrnttkqvtpqpeeqk<br>erkttemqsfpmqpvdqasIpghcrepppweneateriyhfvvgqmvryyqcvqgyralhrgpaesvckmthgktrwtq<br>pqllctgemetsqfpgeekpqaspegrpesetsSlvttdfqiqtemaatmetsifteyqggggsgggsgggsgggggs |

-continued

SEQUENCE TABLE

| SEQ ID NO. | Name | Sequence |
|---|---|---|

333

ACP414

```
ggggggggggsDIQMTQSPSSLSASVGDRVTITCKAREKLmSAVAWYQQKPGKAPKsL
IYSASFRYSGVPSRFSGSGSGTDFTLTISSLQPEDFATYYCQQYYTYPYTFGGGTK
VEIKtvaapsyfifppsdeqlksgtasvvcllnfypreakvqwkydnalqsgnsqesvteqdskdstyslsstltlskad
yekhkvyacevthqglsspvtksfnrgec**
```

334

ACP415

```
elcdddppeiphatfkamaykegtmlnceckrgfririksgslymlctgnshsswdnqcqctssatmttkqvtpqpeeqk
erkttemqspmqpvdqaslpghcreppweneateriyhfvvgqmvyyqcvqgyralhrgpaesyckmthgktrwtq
pqllctgemetsqfpgeekpqaspegrpesetslvttdfqiqtemaatmetsifteyqgsgggsggsggggggggs
ggggggggggsDIQMTQSPSSLSASVGDRVTITCKVTEKVWGNVAWYQQKPGKAPISL
IYSPSLRKSGVPSRFSGSGSGTDFTLTISSLQPEDFATYYCQQYYTYPYTFGGGTK
VEIKtvaapsyfifppsdeqlksgtasvvcllnfypreakvqwkydnalqsgnsqesvteqdskdstyslsstltlskad
yekhkvyacevthqglsspvtksfnrgec**
```

335

ACP416

```
aptssstkktqlqlehlldlqmilnginnykmpkltrmltfkfympkkatelkhlqcleeelkpleevlnlaqsknfhlrprdli
sninivlelkgsettfmceyadetativeflnrwitfcqsiistltsggpGPAGLYAQpgsgggsgggsgggsgggsgg
ggsgggggggsEVQLVESGGGLVQPGGSLRLSCAASGFTFSSYTLAWVRQAPGKcL
EWVAAIDSSSYTYSPDTVRGRFTISRDNAKNSLYLQMNSLRAEDTAVYYCARDS
NWDALDYWGQGTTVTVSSGGGGSGGGGSGGGGSDIQMTQSPSSLSASVGDRVT
ITCKAREKLmSAVAWYQQKPGKAPKsLIYSASFRYSGVPSRFSGSGSGTDFTLTIS
SLQPEDFATYYCQQYYTYPYTFGcGTKVEIKgggsgggsgggsgggsgggsgggsgg
gggsgggsgggsgselcdddppeiphatfkamaykegtmlnceckrgfririksgslymlctgnshsswdnqcqctssatr
nttkqvtpqpeeqkerkttemqspmqpvdqaslpghcreppweneateriyhfvvgqmvyyqcvqgyralhrgpae
svckmthgktrwtqpqllctgemetsqfpgeekpqaspegrpesetslvttdfqiqtemaatmetsifteyqsggpGP
AGLYAQpgsEVQLVESGGGLVQPGNSLRLSCAASGFTFSKFGMSWVRQAPGKGL
EWVSSISGSGRDTLYAESVKGRFTISRDNAKTTLYLQMNSLRPEDTAVYYCTIGG
SLSVSSQGTLVTVSS**
```

336

ACP417

```
aptssstkktqlqlehlldlqmilnginnykmpkltrmltfkfympkkatelkhlqcleeelkpleevlnlaqsknfhlrprdli
sninivlelkgsettfmceyadetativeflnrwitfcqsiislltsggpGPAGLYAQpgsgggsgggsgggsgggsgg
ggsgggggggsEVQLVESGGGLVQPGGSLRLSCAASGFTFSSYTLAWVRQAPGKcL
EWVAAIDSSSYTYSPDTVRGRFTISRDNAKNSLYLQMNSLRAEDTAVYYCARDS
NWDALDYWGQGTTVTVSSGGGGSGGGGSGGGGSDIQMTQSPSSLSASVGDRVT
ITCKVTEKVWGNVAWYQQKPGKAPISLIYSPSLRKSGVPSRFSGSGSGTDFTLTIS
SLQPEDFATYYCQQYYTYPYTFGcGTKVEIKgggsgggsgggsgggsgggsgggsgg
```

-continued

SEQUENCE TABLE

| SEQ ID NO. | Name | Sequence |
|---|---|---|
| 337 | ACP418 | ggsgggsgggsgselcddppeiphatfkamaykegtmlnceckrgfrriksgslymlctgnsshsswdnqcqctssatr nttkqvtpqpeeqkerkttemqspmqpvdqaslpghcreppweneateriyhfvvgqmvyyqcvqgyralhrgpae svckmthgktrwtdpqlictgemetsqfpgeekpqaspegrpesetsslvttdfqiqtemaatmetsiftteyqsggpGP AGLYAQpgsEVQLVESGGGLVQPGNSLRLSCAASGFTFSKFGMSWVRQAPGKGL EWVSSISGSGRDTLYAESVKGRFTISRDNAKTTLYLQMNSLRPEDTAVYYCTIGG SLSVSSQGTLVTVSS** |
| 338 | ACP419 | aptssstkktqlqehlldlqmilnginnyknpkltrmltfkfympkkatelkhlqcleeelkpleevlnlaqsknfhlrprdli sninivlvlelkgsettfmceyadetativeflnrwitfcqsiistltsggpGPAGLYAQpgsgggsgggggsgggsgg ggsggggsggggsEVQLVESGGGLVQPGGSLRLSCAASGFTFSSYTLAWVRQAPGKG LEWVAAIDSSYTYSPDTVRGRFTISRDNAKNSLYLQMNSLRAEDTAVYYCARD SNWDALDYWGcGTTVTVSSGGGSGGGGSGGGGSGGGGSDIQMTQSPSSLSASVGDRV TITCKVTEKVWGNVAWYQQKPGKcPISLLYSPSLRKSGVPSRFSGSGSGTDFTLTI SSLQPEDFATYYCQQYYTYPYTFGGGTKVEIKggggsggggsggggsggggsggggsgggsg ggsgggggsggggselcddpeiphatfkamaykegtmlnceckrgfrriksgslymlctgnsshsswdnqcqctssat rnttkqvtpqpeeqkerkttemqspmqpvdqaslpghcreppweneateriyhfvvgqmvyyqcvqgyralhrgpae svckmthgktrwtdpqlictgemetsqfpgeekpqaspegrpesetsslvttdfqiqtemaatmetsiftteyqsggpGP AGLYAQpgsEVQLVESGGGLVQPGNSLRLSCAASGFTFSKFGMSWVRQAPGKGL EWVSSISGSGRDTLYAESVKGRFTISRDNAKTTLYLQMNSLRPEDTAVYYCTIGG SLSVSSQGTLVTVSS** |
| 339 | ACP420 | aptssstkktqlqehlldlqmilnginnyknpkltrmltfkfympkkatelkhlqcleeelkpleevlnlaqsknfhlrprdli sninivlvlelkgsettfmceyadetativeflnrwitfcqsiistltsggpGPAGLYAQpgsgggsgggsgggsggggsgg ggsggggsggggsevqllesggglvqpggslrlscaasgifsanamgwyrqapgkglelvavissggstnyadsvkgrft isrdnskntvylqmnslraedtavvycmysgsyyytpndywggtlvtvssgggsgggsgggsggggsgggggsg ggsgggggsggggselcddppeiphatfkamaykegtmlnceckrgfrriksgslymlctgnsshsswdnqc qctssatrnttkqvtpqpeeqkerkttemqspmqpvdqaslpghcreppweneateriyhfvvgqmvyyqcvqgyral hrgpaesvckmthgktrwtqpqlictgemetsqfpgeekpqaspegrpesetsslvttdfqiqtemaatmetsiftteyqs ggpGPAGLYAQpgsEVQLVESGGGLVQPGNSLRLSCAASGFTFSKFGMSWVRQAP GKGLEWVSSISGSGRDTLYAESVKGRFTISRDNAKTTLYLQMNSLRPEDTAVYY CTIIGGSLSVSSQGTLVTVSS** |
| 340 | ACP421 | aptssstkktqlqehlldlqmilnginnyknpkltrmltfkfympkkatelkhlqcleeelkpleevlnlaqsknfhlrprdli sninivlvlelkgsettfmceyadetativeflnrwitfcqsiistltsggpGPAGLYAQpgsgggsgggsgggsggggsgg ggsggggsggggsevqllesggglvqpggslrlscaasgifsanamgwyrqapgkglelvavissggstnyadsvkgrft isrdnskntvylqmnslraedtavvycmysgsyyytpndywggtlvtvssgggsgggsgggsggggsgggggsg ggsgggggsggggselcddppeiphatfkamaykegtmlnceckrgfrriksgslymlctgnsshsswdnqc qctssatrnttkqvtpqpeeqkerkttemqspmqpvdqaslpghcreppweneateriyhfvvgqmvyyqcvqgyral hrgpaesvckmthgktrwtqpqlictgemetsqfpgeekpqaspegrpesetsslvttdfqiqtemaatmetsiftteyqs ggpGPAGLYAQpgsEVQLVESGGGLVQPGNSLRLSCAASGFTFSKFGMSWVRQAP GKGLEWVSSISGSGRDTLYAESVKGRFTISRDNAKTTLYLQMNSLRPEDTAVYY CTIIGGSLSVSSQGTLVTVSSA** |
| | ACP421 | EVQLVESGGGLVQPGNSLRLSCAASGFTFSKFGMSWVRQAPGKGLEWVSSISGS GRDTLYAESVKGRFTISRDNAKTTLYLQMNSLRPEDTAVYYCTIGGSLSVSSQGT LVTVSSsggpGPAGLYAQpgsEVQLVESGGGLVQPGGSLRLSCAASGFTFSSYTLA WVRQAPGKcLEWVAAIDSSSYTYSPDTVRGRFTISRDNAKNSLYLQMNSLRAED TAVYYCARDSNWDALDYWGcGTTVTVSSGGGSGGGGSGGGGSDIQMTQSPS |

-continued

SEQUENCE TABLE

| SEQ ID NO. | Name | Sequence |
|---|---|---|
| | | SLSASVGDRVTITCKAREKLWSAVAWYQQKPGKAPKsLIYSASPRYSGVPSRFSG |
| | | SGSGTDFTLTISSLQPEDFATYYCQQYYTYPYTFGcGTKVEIKgggsggggggssgg |
| | | gggsggggsgggggggssggggseldcddppeiphatfkamaykegtmlnceckrgfrriksgslymlctgnss |
| | | hsswdnqcqctssatrnttkqvtpqpeeqkerkttemqspmqpvdqaslpghcreppweneateriyhfvvgqmvyy |
| | | qcvqgyralhrgpaesvckmthgktrwtdpqlictgemetsqfpgeekpqaspegrpesetsSlvttdfqiqtemaatme |
| | | tsiftteyqgggsggggsggggsggggggsgggsggsgggGPAGLYAQpgsaptssstkktqlqehllldlqm |
| | | ilnginnyknpkltrmltfkfympkkatelkhlqcleeelkpleevlnlaqsknfhlrprdlisninivlelkgsettfmceya |
| | | detativeflnrwitfcqgslisltlt** |
| 341 | ACP422 | EVQLVESGGGLVQPGNSLRLsCAASGFTFSKFGMSWVRQAPGKGLEWVSSISGS |
| | | GRDTLYAESVKGRFTISRDNAKTLYLQMNSLRPEDTAVYYCTIGGSLSVSSQGT |
| | | LVTVSSsggpGPAGLYAQpgsEVQLVESGGGLVQPGGSLRLSCAASGFTFSSYTLA |
| | | WVRQAPGKGLEWVAAIDSSSYTYSPDTVRGRFTISRDNAKNSLYLQMNSLRAE |
| | | DTAVYYCARDSNWDALDYWGcGTTVTVSSGGGGSGGGGSGGGGSDIQMTQSP |
| | | SSLSASVGDRVTITCKAREKLW SAVAWYQQKPGKcPKALIYSASFRYSGVPSRFS |
| | | GSGSGTDFTLTISSLQPEDFATYYCQQYYTYPYTFGGGTKVEIKgggsggggggss |
| | | gggsggggsgggggggssggggseldcddppeiphatfkamaykegtmlnceckrgfrriksgslymlctg |
| | | nsshsswdnqcqctssatrnttkqvtpqpeeqkerkttemqspmqpvdqaslpghcreppweneateriyhfvvgqm |
| | | vyyqcvqgyralhrgpaesvckmthgktrwtqpqlictgemetsqfpgeekpqaspegrpesetsSlvttdfqiqtemaa |
| | | tmetsiftteyqgggsggggsggggsggggsgggsggsgggGPAGLYAQpgsaptssstkktqlqehllld |
| | | lqmilnginnyknpkltrmlafympkkatelkhlqcleeelkpleevlnlaqsknfhlrprdlisninivlelkgsettfm |
| | | ceyadetativeflnrwitfcqgsiistlt** |
| 342 | ACP423 | EVQLVESGGGLVQPGNSLRLsCAASGFTFSKFGMSWVRQAPGKGLEWVSSISGS |
| | | GRDTLYAESVKGRFTISRDNAKTLYLQMNSLRPEDTAVYYCTIGGSLSVSSQGT |
| | | LVTVSSsggpGPAGLYAQpgsEVQLVESGGGLVQPGGSLRLSCAASGFTFSSYTLA |
| | | WVRQAPGKGLEWVAAIDSSSYTYSPDTVRGRFTISRDNAKNSLYLQMNSLRAED |
| | | TAVYYCARDSNWDALDYWGQGTTVTVSSGGGGSGGGGSGGGGSDIQMTQSPS |
| | | SLSASVGDRVTITCKVTEKVWGNVAWYQQKPGKAPISLIYSPSLRKSGVPSRFSG |
| | | SGSGTDFTLTISSLQPEDFATYYCQQYYTYPYTFGcGTKVEIKgggsggggggssggg |
| | | hsswdnqcqctssatrnttkqvtpqpeeqkerkttemqspmqpvdqaslpghcreppweneateriyhfvvgqmvyy |
| | | qcvqgyralhrgpaesvckmthgktrwtdpqlictgemetsqfpgeekpqaspegrpesetsSlvttdfqiqtemaatme |
| | | tsiftteyqgggsggggsggggsggggggsgggsggsgggGPAGLYAQpgsaptssstkktqlqehllldlqm |
| | | ilnginnyknpkltrmltfkfympkkatelkhlqcleeelkpleevlnlaqsknfhlrprdlisninivlelkgsettfmceya |
| | | detativeflnrwitfcqgslisltlt** |
| 343 | ACP424 | EVQLVESGGGLVQPGNSLRLsCAASGFTFSKFGMSWVRQAPGKGLEWVSSISGS |
| | | GRDTLYAESVKGRFTISRDNAKTLYLQMNSLRPEDTAVYYCTIGGSLSVSSQGT |
| | | LVTVSSsggpGPAGLYAQpgsEVQLVESGGGLVQPGGSLRLSCAASGFTFSSYTLA |
| | | WVRQAPGKGLEWVAAIDSSSYTYSPDTVRGRFTISRDNAKNSLYLQMNSLRAE |
| | | DTAVYYCARDSNWDALDYWGcGTTVTVSSGGGGSGGGGSGGGGSDIQMTQSP |
| | | SSLSASVGDRVTITCKVTEKVWGNVAWYQQKPGKcPISLLIYSPSLRKSGVPSRFS |
| | | GSGSGTDFTLTISSLQPEDFATYYCQQYYTYPYTFGGGTKVEIKgggsggggggss |
| | | gggsggggsgggggggssggggseldcddppeiphatfkamaykegtmlnceckrgfrriksgslymlctg |
| | | nsshsswdnqcqctssatrnttkqvtpqpeeqkerkttemqspmqpvdqaslpghcreppweneateriyhfvvgqm |
| | | vyyqcvqgyralhrgpaesvckmthgktrwtqpqlictgemetsqfpgeekpqaspegrpesetsSlvttdfqiqtemaa |
| | | tmetsiftteyqgggsggggsggggsggggsgggsggsgggGPAGLYAQpgsaptssstkktqlqehllld |

-continued

SEQUENCE TABLE

| SEQ ID NO. | Name | Sequence |
|---|---|---|
| 344 | Acp425 | lqmilnginnykmpkltrmlafympkkatelkhlqcleeelkpleevlnlaqsknfhlrprdlisninivlvlelkgsettfm<br>ceyadetativeflnrwitfcqsiistlt** |
| 345 | ACP426 | EVQLVESGGGLVQPGNSLRLSCAASGFTFSKFGMSWVRQAPGKGLEWVSSISGS<br>GRDTLYAESVKGRFTISRDNAKTTLYLQMNSLRPEDTAVVYCTIGGSLSVSSQGT<br>LVTVSSsggpGPAGLYAQpgsevqllesgglvqpggslrlscaasgifsanamgwyrqapgkqrelvaviss<br>ggstnyadsvkgrftisrdnskntvylqmnslraedtavyycmysgsvyytpndywgqgtlvtvssggggsggggsggg<br>gsggggsggggsggggsggggsggggselcdddpeiphatfkamaykegtmlnceckrgfrriksgslymlc<br>tgnsshsswdnqcqctssatrnttkqvtpqeeqkerkttemqspmpvdqaslpghcreppweneateriyhfvvgq<br>mvyycvgyralhrgpaesvckmthgktrwtqpqlictgemetsqfpgeekpqaspegrpeetsslvttdfqiqtem<br>aatmetsiftteygggggsggggsggggsggggsggggsggggGPAGLYAQpgsaptssstktqlqlehll<br>ldlqmilnginnyknpkltrmltfkfympkkatelkhlqcleeelkpleevlnlaqsknfhlrprdlisninivlvlelkgsettf<br>mceyadetativeflnrwitfcqsiistlt** |
| 346 | ACP427 | aptssstktqlqlehlldlqmilnginnykmpkltrmltfkfympkkatelkhlqcleeelkpleevlnlaqsknfhlrprdli<br>sninivlelkgsettfmceyadetativeflnrwitfcqsiistltsggpGPAGLYAQpgsEVQLVESGGGLV<br>QPGNSLRLSCAASGFTFSKFGMSWVRQAPGKGLEWVSSISGSGRDTLYAESVKG<br>RFTISRDNAKTTLYLQMNSLRPEDTAVYYCTIGGSLSVSSQGTLVTVSSggggsggggg<br>gggggsggggsggggsggggssggpGPAGLYAQpgsEVQLVESGGGLVQPGGSLRLSCAAS<br>GFTFSSYTLAWVRQAPGKGLEWVAAIDSSSYTYSPDTVRGRFTISRDNAKNSLYL<br>QMNSLRAEDTAVYYCARDSNWDALDYWGCGTTVTVSSGGGSGGGGGSGGGG<br>SDIQMTQSPSSLSASVGDRVTITCKAREKLWSAVAWYQQKPGKAPKsLIYSASFR<br>YSGVPSRFSGSGSGTDFTLTISSLQPEDFATYYCQQYYTYPYTPGcGTKVEIKggg<br>ggggsggggsggggsggggsggggsevqllesgglvqpggslrlscaasgsifsanamgwyrqapgkqrelvaviss<br>ggstnyadsvkgrftisrdnskntvylqmnslraedtavyycmysgsvyytpndywgqgtlvtvss** |
| 347 | ACP428 | aptssstktqlqlehlldlqmilnginnykmpkltrmltfkfympkkatelkhlqcleeelkpleevlnlaqsknfhlrprdli<br>sninivlelkgsettfmceyadetativeflnrwitfcqsiistltsggpGPAGLYAQpgsEVQLVESGGGLV<br>QPGNSLRLSCAASGFTFSKFGMSWVRQAPGKGLEWVSSISGSGRDTLYAESVKG<br>RFTISRDNAKTTLYLQMNSLRPEDTAVYYCTIGGSLSVSSQGTLVTVSSggggsggggg<br>gggggsggggsggggsggggssggpGPAGLYAQpgsEVQLVESGGGLVQPGGSLRLSCAAS<br>GFTFSSYTLAWVRQAPGKGLEWVAAIDSSSYTYSPDTVRGRFTISRDNAKNSLY<br>LQMNSLRAEDTAVYYCARDSNWDALDYWGcGTTVTVSSGGGSGGGGGSGGGGG<br>SDIQMTQSPSSLSASVGDRVTITCKAREKLWSAVAWYQQKPGKcPKALIYSASFR<br>YSGVPSRFSGSGSGTDFTLTISSLQPEDFATYYCQQYYTYPYTPGGGTKVEIKggg<br>gggggsggggsggggsggggsevglrlscaasgsifsanamgwyrqapgkqrelvaviss<br>sgggstnyadsvkgrftisrdnskntvylqmnslraedtavyycmysgsvyytpndywgggtlvtvss** |

-continued

SEQUENCE TABLE

| SEQ ID NO. | Name | Sequence |
|---|---|---|
| 348 | ACP429 | aptssstktqlqlehllidlqmilnginnykmpkltrmltfkfympkkatelkhlqcleeelkpleevlnlaqsknfhlrprdli sninivivlelkgsettfmceyadetativeflnrwitfcqsiistltsggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSgggsgggg sggggsggggsggggsggggsggpGPAGLYAQpgsEVQLVESGGGLVQPGGSLRLSCAAS GFTFSSYTLAWVRQAPGKcLEWVAAIDSSYTYSPDTVRGRFTISRDNAKNSLYL QMNSLRAEDTAVYYCARDSNWDALDYWGcGTTVTVSSGGGSGGGSGGGG SDIQMTQSPSSLSASVGDRVTITCKVTEKVWGNVAWYQQKPGKAPISLIYSPSLR KSGVPSRFSGSGSGTDFTLTISSLQPEDFATYYCQQYYTYPYTFGcGTKVEIKgggg sggggsggggsggggsggggsevqllesggglvqpggslrlscaasgsifsanamgwyrqapgkqrelvaviss gggstnyadsvkgrftisrdnskntvylqmnslraedtavycmysgsyYytpndywgggtlvtvss** |
| 349 | ACP430 | aptssstktqlqlehllidlqmilnginnykmpkltrmltfkfympkkatelkhlqcleeelkpleevlnlaqsknfhlrprdli sninivivlelkgsettfmceyadetativeflnrwitfcqsiistltsggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSgggsgggg sggggsggggsggggsggggsggpGPAGLYAQpgsEVQLVESGGGLVQPGGSLRLSCAAS GFTFSSYTLAWVRQAPGKGLEWVAAIDSSSYTYSPDTVRGRFTISRDNAKNSLY LQMNSLRAEDTAVYYCARDSNWDALDYWGcGTTVTVSSGGGSGGGSGGGG SDIQMTQSPSSLSASVGDRVTITCKVTEKVWGNVAWYQQKPGKcPISLIYSPSLR KSGVPSRFSGSGSGTDFTLTISSLQPEDFATYYCQQYYTYPYTFGGGTKVEIKgggg sggggsggggsggggsggggsevqllesggglvqpggslrlscaasgsifsanamgwyrqapgkqrelvaviss sggstnyadsvkgrftisrdnskntvylqmnslraedtavycmysgsyYytpndywgggtlvtvss** |
| 350 | ACP431 | aptssstktqlqlehllidlqmilnginnykmpkltrmltfkfympkkatelkhlqcleeelkpleevlnlaqsknfhlrprdli sninivivlelkgsettfmceyadetativeflnrwitfcqsiistltsggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSgggsgggg sggggsggggsggggsggggsggpGPAGLYAQpgsEVQLVESGGGLVQPGGSLRLSCAAS GFTFSSYTLAWVRQAPGKcLEWVAAIDSSSYTYSPDTVRGRFTISRDNAKNSLYL QMNSLRAEDTAVYYCARDSNWDALDYWGcGTTVTVSSGGGSGGGSGGGG SDIQMTQSPSSLSASVGDRVTITCKAREKLWSAVAWYQQKPGKAPKsLIIYSASFR YSGVPSRFSGSGSGTDFTLTISSLQPEDFATYYCQQYYTYPYTFGcGTKVEIKgggg sggggsggggsggggsggggsevqllesggglvqpggslrlscaasgsifsanamgwyrqapgkglelvaviss gggstnyadsvkgrftisrdnskntvylqmnslraedtavycmysgsyYytpndywgggtlvtvss** |
| 351 | ACP432 | aptssstktqlqlehllidlqmilnginnykmpkltrmltfkfympkkatelkhlqcleeelkpleevlnlaqsknfhlrprdli sninivivlelkgsettfmceyadetativeflnrwitfcqsiistltsggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSgggsgggg sggggsggggsggggsggggsggpGPAGLYAQpgsEVQLVESGGGLVQPGGSLRLSCAAS GFTFSSYTLAWVRQAPGKGLEWVAAIDSSSYTYSPDTVRGRFTISRDNAKNSLY LQMNSLRAEDTAVYYCARDSNWDALDYWGcGTTVTVSSGGGSGGGSGGGG SDIQMTQSPSSLSASVGDRVTITCKAREKLWSAVAWYQQKPGKcPKALIYSASFR YSGVPSRFSGSGSGTDFTLTISSLQPEDFATYYCQQYYTYPYTFGGGTKVEIKgggg sggggsggggsggggsggggsevqllesggglvqpggslrlscaasgsifsanamgwyrqapgkglelvaviss sggstnyadsvkgrftisrdnskntvylqmnslraedtavycmysgsyYytpndywgggtlvtvss** |

-continued

SEQUENCE TABLE

| SEQ ID NO. | Name | Sequence |
|---|---|---|
| 352 | ACP433 | aptssstktqlqlehlldlqmilnginnykmpkltrmltfkfympkkatelkhlqcleeelkpleevlnlaqsknfhlrprdli sninvivlelkgsettfmceyadetativeflnrwitfcqsiisltsggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSgggsgsggg sggggsgggsgsggggsgsgggsggGPAGLYAQpgsEVQLVESGGGLVQPGGSLRLSCAAS GFTFSSYTLAWVRQAPGKcLEWVAAIDSSSYTYSPDTVRGRFTISRDNAKNSLYL QMNSLRAEDTAVYYCARDSNWDALDYWGQGTTVTVSSGGGGSGGGGSGGGG SDIQMTQSPSSLSASVGDRVTITCKVTEKVWGNVAWYQQKPGKAPISLLYSPSLR KSGVPSRFSGSGSGTDFTLTISSLQPEDFATYYCQQYYTYPTFGcGTKVEIKggg sgggsggsggggsgsggggsgsggsevqllesggrlvqpgglrlscaasgsifsanamgwyrqapgkglelvaviss ggstnyadsvkgrftisrdnskntvylqmnslraedtavycmysgsyYYtpndywgqgtlvtvss** |
| 353 | ACP434 | aptssstktqlqlehlldlqmilnginnykmpkltrmltfkfympkkatelkhlqcleeelkpleevlnlaqsknfhlrprdli sninvivlelkgsettfmceyadetativeflnrwitfcqsiisltsggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSgggsgsggg sggggsgggsgsggggsgsgggsggGPAGLYAQpgsEVQLVESGGGLVQPGGSLRLSCAAS GFTFSSYTLAWVRQAPGKGLEWVAAIDSSSYTYSPDTVRGRFTISRDNAKNSLY LQMNSLRAEDTAVYYCARDSNWDALDYWGcGTTVTVSSGGGGSGGGGSGGGG SDIQMTQSPSSLSASVGDRVTITCKVTEKVWGNVAWYQQKPGKcPISLLYSPSLR KSGVPSRFSGSGSGTDFTLTISSLQPEDFATYYCQQYYTYPTFGGGTKVEIKggg sgggsggsggggsgsggggsgsggsevqllesggrlvqpgglrlscaasgsifsanamgwyrqapgkglelvavis ggstnyadsvkgrftisrdnskntvylqmnslraedtavycmysgsyYYtpndywgqgtlvtvss** |
| 265 | ACP435 | DIQMTQSPSLSASVGDRVTITCKAREKlWSAVAWYQQKPGKAPKsLIYSASFR YSGVPSRFSGSGSGTDFTLTISSLQPEDFATYYCQQYYTYPTFGGGTKVEIKtvaa psvfifppsdeqlkgtasvvcllnnfypreakvqwkvdnalqsnsqevteqdskdstys1sstltlskadyekhkvyac evthglsspvtksfnrgecgggsgsggggsgggsgsggggsgsgggsgggsevqllesgglvqpggsvlrlscaasgsifsa namgWyrqapgkqrelvavissggstnyadsvkgrftisrdnskntvylqmnslraedtavyycmysgsyYYtpndyw gqgtlvtvss** |
| 355 | ACP371 | aptssstktqlqlehlldlqmilnginnykmpkltrmltfldympkkatelkhlqcleeelkpleevlnlaqsknf hlrprdlisninvivlelkgsettfmceyadetativeflnrwitfcqsiisltsggpGPAGLYAQpgsEVQ LVESGGGLVQPGNSLRLSCAASGFTFSKFGMSWVRQAPGKGLEWVSSIS GSGRDTLYAESVKGRFTISRDNAKTTLYLQMNSLRPEDTAVYYCTIGGSL SVSSQGTLVTVSSgggsgsggggsgggsgsggggsgsgggsggGPAGLYAQpgsEV QLVESGGGLVQPGGSLRLSCAASGFTFSSYTLAWVRQAPGKcLEWVAAI DSSSYTYSPDTVRGRFTISRDNAKNSLYLQMNSLRAEDTAVYYCARDSN WDALDYWGQGTTVTVSSGGGGSGGGGSGGGGSDIQMTQSPSSLSASVG DRVTITCKASQNVGTNVGWYQQKPGKAPKALIYSASFRYSGVPSRFSGS GSGTDFTLTISSLQPEDFATYYCQQYYTYPTFGcGTKVEIK** |
| 356 | ACP372 | aptssstktqlqlehlldlqmilnginnykmpkltrmltfkfympkkatelkhlqcleeelkpleevlnlaqsknfhlrprdli sninvivlelkgsettfmceyadetativeflnrwitfcqsiisltsggpGPAGLYAQpgsEVQLVESGGGLV QPGNSLRLSCAASGFTFSKFGMSWVRQAPGKGLEWVSSISGSGRDTLYAESVKG RFTISRDNAKTTLYLQMNSLRPEDTAVYYCTIGGSLSVSSQGTLVTVSSgggsgsggg sggggsgggsgsggggsgsgggsggGPAGLYAQpgsEVQLVESGGGLVQPGGSLRLSCAAS |

-continued

SEQUENCE TABLE

| SEQ ID NO. | Name | Sequence |
|---|---|---|
| 357 | ACP373 | GFTFSSYTLAWVRQAPGKGLEWVAAIDSSSYTYSPDTVRGRFTISRDNAKNSLY<br>LQMNSLRAEDTAVYYCARDSNWDALDYWGcGTTVTVSSGGGSGGGGSGGGG<br>SDIQMTQSPSSLSASVGDRVTITCKASQNVGTNVGWYQQKPGKcPKALIYSASFR<br>YSGVPSRFSGSGSGTDFTLTISSLQPEDFATYYCQQYYTYPYTFGGGTKVEIK** |
| 358 | ACP374 | aptssstktqlqlehlldlqmilnginnykmpkltrmltfkfympkkatelkhlqcleeelkpleevlnlaqsknfhlrprdli<br>sninivivlelkgsettfmceyadetativeflnrwitfcqsiisltsggpGPAGLYAQpgsEVQLVESGGGLV<br>QPGNSLRLSCAASGFTFSKFPGMSWVRQAPGKGLEWVSSISGSGRDTLYAESVKG<br>RFTISRDNAKTTLYLQMNSLRPEDTAVYYCTIGGSLSVSSQGTLVTVSSggggsgggg<br>sggggsggggsggggsggggsggggsggpGPAGLYAQpgsEVQLVESGGGLVQPGGSLRLSCAAS<br>GFTFSSYTLAWVRQAPGKcLEWVAAIDSSSYTYSPDTVRGRFTISRDNAKNSLYL<br>QMNSLRAEDTAVYYCARDSNWDALDYWGcGTTVTVSSGGGSGGGGSGGGG<br>SDIQMTQSPSSLSASVGDRVTITCKAREKLWSAVAWYQQKPGKAPKALIYSASF<br>RYSGVPSRFSGSGSGTDFTLTISSLQPEDFATYYCQQYYTYPYTFGcGTKVEIK** |
| 359 | ACP375 | aptssstktqlqlehlldlqmilnginnykmpkltrmltfkfympkkatelkhlqcleeelkpleevlnlaqsknfhlrprdli<br>sninivivlelkgsettfmceyadetativeflnrwitfcqsiisltsggpGPAGLYAQpgsEVQLVESGGGLV<br>QPGNSLRLSCAASGFTFSKFPGMSWVRQAPGKGLEWVSSISGSGRDTLYAESVKG<br>RFTISRDNAKTTLYLQMNSLRPEDTAVYYCTIGGSLSVSSQGTLVTVSSggggsgggg<br>sggggsggggsggggsggggsggggsggpGPAGLYAQpgsEVQLVESGGGLVQPGGSLRLSCAAS<br>GFTFSSYTLAWVRQAPGKcLEWVAAIDSSSYTYSPDTVRGRFTISRDNAKNSLYL<br>QMNSLRAEDTAVYYCARDSNWDALDYWGcGTTVTVSSGGGSGGGGSGGGG<br>SDIQMTQSPSSLSASVGDRVTITCKVTEKVWGNVAWYQQKPGKAPISLIYSPSLR<br>KSGVPSRFSGSGSGTDFTLTISSLQPEDFATYYCQQYYTYPYTFGcGTKVEIK** |
| 360 | ACP376 | aptssstktqlqlehlldlqmilnginnykmpkltrmltfkfympkkatelkhlqcleeelkpleevlnlaqsknfhlrprdli<br>sninivivlelkgsettfmceyadetativeflnrwitfcqsiisltsggpGPAGLYAQpgsEVQLVESGGGLV<br>QPGNSLRLSCAASGFTFSKFPGMSWVRQAPGKGLEWVSSISGSGRDTLYAESVKG<br>RFTISRDNAKTTLYLQMNSLRPEDTAVYYCTIGGSLSVSSQGTLVTVSSggggsgggg<br>sggggsggggsggggsggggsggggsggpGPAGLYAQpgsEVQLVESGGGLVQPGGSLRLSCAAS<br>GFTFSSYTLAWVRQAPGKGLEWVAAIDSSSYTYSPDTVRGRFTISRDNAKNSLY<br>LQMNSLRAEDTAVYYCARDSNWDALDYWGcGTTVTVSSGGGSGGGGSGGGG<br>SDIQMTQSPSSLSASVGDRVTITCKVTEKVWGNVAWYQQKPGKcPISLIYSPSLR<br>KSGVPSRFSGSGSGTDFTLTISSLQPEDFATYYCQQYYTYPYTFGGGTKVEIK** |
| 361 | ACP377 | aptssstktqlqlehlldlqmilnginnykmpkltrmltfkfympkkatelkhlqcleeelkpleevlnlaqsknfhlrprdli<br>sninivivlelkgsettfmceyadetativeflnrwitfcqsiisltsggpGPAGLYAQpgsEVQLVESGGGLV<br>QPGNSLRLSCAASGFTFSKFPGMSWVRQAPGKGLEWVSSISGSGRDTLYAESVKG |

-continued

SEQUENCE TABLE

| SEQ ID NO. | Name | Sequence |
|---|---|---|
| 362 | ACP378 | RFTISRDNAKTTLYLQMNSLRPEDTAVYYCTIGGSLSVSSQGTLVTVSSggggsggggg<br>ggggsggggsggggsggggsggggsggGPAGLYAQpgsevqllesgglvqpggslrlscaasgslfsanamgwyrq<br>apgkqrelvavissggsthyadsvkgrftisrdnskntvylqmnslraedtavyycmysgsyYYtpndywgqgtlvtvss<br>** |
| 363 | ACP379 | aptssktktqlqlehlldlqmilnginnyknpkltrmltfkfympkkatelkhlqcleeelkpleevlnlaqsknfhlrprdli<br>sninivlelkgsettfmceyadetaivefInrwitfcqsiisltsggpGPAGLYAQpgsEVQLVESGGGLV<br>QPGNSLRLSCAASGFTFSSKFGMSWVRQAPGKGLEWVSSISGSGRDTLYAESVKG<br>RFTISRDNAKTTLYLQMNSLRPEDTAVYYCTIGGSLSVSSQGTLVTVSSggggsggggg<br>ggggsggggsggggsggggsggggsggGPAGLYAQpgsGPAGLYAQpgsEVQLVESGGGLVQPGGSLRLSCAAS<br>GFTFSSYTLAWVRQAPGKGLEWVAAIDSSSYTYSPDTVRGRFTISRDNAKNSLY<br>LQMNSLRAEDTAVYYCARDSNWDALDYWGQGTTVTVSSastkgpsvfplapsskstsggt<br>aalgclvkdyfpepvtvswnsgaltsgvhtfpavlqssglyslssvvtvpssigtqtyicnvnhkpsntkvdkrvepksc*<br>* |
| 364 | ACP368 | EVQLVESGGGLVQPGGSLRLSCAASGFTFSSYTLAWVRQAPGKGLEWVA<br>AIDSSSYTYSPDTVRGRFTISRDNAKNSLYLQMNSLRAEDTAVYYCARDS<br>NWDALDYWGQGTTVTVSSsggpGPAGLYAQpgsDIQMTQSPSSLSASVGD<br>RVTITCKVTEKVWGNVAWYQQKPGKAPISLIYSPSLRKSGVPSRFSGSGS<br>GTDFTLTISSLQPEDFATYYCQQYYTYPYTFGGGTKVEIKHHHHHH |
| 365 | ACP365 | EVQLVESGGGLVQPGGSLRLSCAASGFTFSSYTLAWVRQAPGKGLEWVA<br>AIDSSSYTYSPDTVRGRFTISRDNAKNSLYLQMNSLRAEDTAVYYCARDS<br>NWDALDYWGQGTTVTVSSsggpGPAGLYAQpgsDIQMTQSPSSLSASVGD<br>RVTITCKAREKLWSAVAWYQQKPGKAPKALIYSASFRYSGVPSRFSGSGS<br>GTDFTLTISSLQPEDFATYYCQQYYTYPYTFGGGTKVEIKHHHHHH |
| 366 | ACP366 | EVQLVESGGGLVQPGGSLRLSCAASGFTFSSYTLAWVRQAPGKGLEWVAAIDSS<br>SYTYSPDTVRGRFTISRDNAKNSLYLQMNSLRAEDTAVYYCARDSNWDALDYW<br>GQGTTVTVSSsggpGPAGLYAQpgsDIQMTQSPSSLSASVGDRVTITCKAREKLWS<br>AVAWYQQKPGKAPKSLIYSASFRYSGVPSRFSGSGSGTDFTLTISSLQPEDFATYY<br>CQQYYTYPYTFGGGTKVEIKHHHHHH |
| 367 | ACP284 | EVQLVESGGGLVQPGNSLRLSCAASGFTFSKFGMSWVRQAPGKGLEWVS<br>SISGSGRDTLYAESVKGRFTISRDNAKTTLYLQMNSLRPEDTAVYYCTIG<br>GSLSVSSQGTLVTVSSGGPGPAGMKGLPGSrvipvsgparclsgsrnllkttddmvktar<br>eklkhysctaedidheditrdqtstlktclplelhknesclatretssttrgsclppqktslmmtlclgsiyedlkmyq<br>tefgainaalqnhnhqqilldkgmlvaidelmqslnhngetlrqkppvgeadpyrvkmklcillhafstrvvtlnr |

-continued

SEQUENCE TABLE

| SEQ ID NO. | Name | Sequence |
|---|---|---|

368 vmgylssaSGGPGPAGMKGLPGSggggsggggsggggsggggsggggsggggsQSVLTQP
PSVSGAPGQRVTISCSGSRSNIGSNTVKNYQQLPGTAPKLLIYNDQRPSG
VPDRPSGSKSGTSASLAITGLQAEDEADYYCQSYDRYTHPALLFGTGTKV
TVLggggsggggsggggsgQVLVESGGGVVQPGRSLRLSCAASGFTFSSYGMH
WVRQAPGKGLEWVAFIRYDGSNKYYADSVKGRFTISRDNSKNTLYLQM
NSLRAEDTAVYYCKTHGSHDNWGQGTMVTVSS

ACP285

EVQLVESGGGLVQPGNSLRLSCAASGFTFSKFGMSWVRQAPGKGLEWVSSISGS
GRDTLYAESVKGRFTISRDNAKTTLYLQMNSLRPEDTAVYYCTIGGSLSVSSQGT
LVTVSSSGGPGPAGMKGLPGSiwelkkdvyvveldwypdapgemvltcdtpeedgitwtldqssevlg
sgktltiqvkefgdagqytchkggevlshsllllhkkedgiwstdilkdqkepknktflrceaknysgrftcwwlttistdltfs
vksrsgssdpggvtcgaatlsaervrgdnkeyyesvvecqedsaSpaaeeslpievmvdavhklkyenytssffirdilkpd
ppknlqlkplknsrqvevsweypdtwstphsyfsltfcvqvggkskrekkdrvtfdktsatvicrknasisvraqdryysss
wsewasvpcsggggsggggsggggsggggsrvipvsgparclsqsrnllkttddmvktareklkhysctaedidheditrdqstslk
tclplelhknesslatretsstrrgsclppqktslmmtlclgsiyedlkmyqtefqainaalqnhnhqqilldkgmlvaidelm
qslnhngetlrqkppygeadpyrvkmklcillhafstrvvtinrvmgylssaSGGPGPAGMKGLPGSggggsg
ggggsggggsggggsggggsggggsQSVLTQPPSVSGAPQGRVTISCSGSRSNIGSNTVKWY
QQLPGTAPKLLIYNDQRPSGVPDRPSGSKSGTSASLAITGLQAEDEADYYCQSY
DRYTHPALLFGTGTKVTVLgggsggggsggggsQVLVESGGGVVQPGRSLRLSCAA
SGFTFSSYGMHWVRQAPGKGLEWVAFIRYDGSNKYYADSVKGRFTISRDNSKN
TLYLQMNSLRAEDTAVYYCKTHGSHDNWGQGTMVTVSS

369

ACP286

EVQLVESGGGLVQPGNSLRLSCAASGFTFSKFGMSWVRQAPGKGLEWVSSISGS
GRDTLYAESVKGRFTISRDNAKTTLYLQMNSLRPEDTAVYYCTIGGSLSVSSQGT
LVTVSSSGGPGPAGMKGLPGSiwelkkdvyvveldwypdapgemvltcdtpeedgitwtldqssevlg
sgktltiqvkefgdagqytchkggevlshsllllhkkedgiwstdilkdqkepknktflrceaknysgrftcwwlttistdltfs
vksrsgssdpggvtcgaatlsaervrgdnkeyyesvvecqedsacpaaeeslpievmvdavhklkyenytssffirdilkpd
ppknlqlkplknsrqvevsweypdtwstphsyfsltfcvqvggkskrekkdrvtfdktsatvicrknasisvraqdryysss
wsewasvpcsggggsggggsggggsggggsrvipvsgparclsqsrnllkaddmvktareklkhysctaedidheditr
dqtstlktclplelhknesclatretsstrrgsclppqktslmmtlclgsiyedlkmyqtefqainaalqnhnhqqilldkgmlv
aidelmqslnhngetlrqkppvgeadpyrvkmklcillhafstrvvtinrvmgylssaSGGPGPAGMKGLPGSg
ggggsggggsggggsggggsggggsggggsQVLTQPPSVSGAPGQRVTISCSGSRSNIGSNTV
KWYQQLPGTAPKLLIYNDQRPSGVPDRPSGSKSGTSASLAITGLQAEDEADYY
CQSYDRYTHPALLFGTGTKVTVLgggsggggsggggsggggsQVLVESGGGVVQPGRSLRL
SCAASGFTFSSYGMHWVRQAPGKGLEWVAFIRYDGSNKYYADSVKGRFTISRD
NSKNTLYLQMNSLRAEDTAVYYCKTHGSHDNWGQGTMVTVSS

370

ACP287

EVQLVESGGGLVQPGNSLRLSCAASGFTFSKFGMSWVRQAPGKGLEWVSSISGS
GRDTLYAESVKGRFTISRDNAKTTLYLQMNSLRPEDTAVYYCTIGGSLSVSSQGT
LVTVSSSGGPGPAGMKGLPGSiwelkkdvyvveldwypdapgemvltcdtpeedgitwtldqssevlg
sgktltiqvkefgdagqytchkggevlshsllllhkkedgiwstdilkdqkepknktflrceaknysgrftcwwlttistdltfs
vksrsgssdpggvtcgaatlsaervrgdnkeyyesvvecqedsacpaaeeslpievmvdavhklkyenytssffirdilkpd
ppknlqlkplknsrqvevsweypdtwstphsyfsltfcvqvggkskrekkdrvtfdktsatvicrknasisvraqdryysss
wsewasvpcsggggsggggsggggsggggsrvipvsgparclsqsrnllkttddmvktareklkhysctaedidheditrdqstslk
tclplelhknesclatretsstrrgsclppqktslmmtlclgsiyedlkmyqtefqainaalqnhnhqqilldkgmlvaidelm
qslnhngetlrqkppvgeadpyrvkmklcillhafstrvvtinrvmgylssaSGGPGPAGMKGLPGSggggsg
ggggsggggsggggsggggsggggsQSVLTQPPSVSGAPQGRVTISCSGSRSNIGSNTVKWY
QQLPGTAPKLLIYNDQRPSGVPDRPSGSKSGTSASLAITGLQAEDEADYYCQSY -continued

SEQUENCE TABLE

| SEQ ID NO. | Name | Sequence |
|---|---|---|
| 371 | | DRYTHPALLFGcGTKVTVLgggsgsggsgsggsgsQVQLVESGGGVVQPGRSLRLSCAA SGFTFSSYGMHWVRQAPGKCLEWVAFIRYDGSNKYYADSVKGRFTISRDNSKNT LYLQMNSLRAEDTAVYYCKTHGSHDNWGQGTMVTVSS |
| 371 | ACP288 | EVQLVESGGGLVQPGNSLRLSCAASGFTFSKFGMSWVRQAPGKGLEWVSSISGS GRDTLYAESVKGRFTISRDNAKTTLYLQMNSLRPEDTAVYYCTIGGSLSVSSQGT LVTVSSSGGPAGMKGLPGSiwelkkdvyvveldwypdapgemvvltcdtpeedgitwtldqssevlg sgktltiqvkefgdaqytchkggevlshslllllhkkedgiwstdilkdqkepknktflrceaknysgrftcwvlttistdltfs vkssrgssdpqgvtcgaatlsaervrgdnkeyeysvecqedsacpaaeeslpievmdvavhklkyenytssffilrdiikpd ppknlqlkplknsrqveysweypdtwstphsyfsltfcvqvgqkskrekkdrvfdktsatvicrknasisvraqdryysss wsewasvpcsgsggggsgggggsgrvipvsgsparclsgsrnllkttddmvktareklkhysctaedidheditrdqtstlk tclplelhknesclatretssttrgsclppqkts1mmtlclgsiyedlkmyqtefqainaalqmhnhqqiildkqmlvaidelm qslnhngetlrqkppvgeadpyrvkmklcillhafstrvvtinrvmgylssaSGGPGPAGMKGLPGSGggggsg ggggggggggggggggsgsggggsggggsQSVLTQPPSVSGAPGQRVTISCSGSRSNIGSNTVKWY QQLPGTcPKLLIYNDQRPSGVPDRFSGSKSGTSASLAITGLQAEDEADYYCQSY DRYTHPALLFGTGTKVTVLgggsgsggsgsggggsQVQLVESGGGVVQPGRSLRLSCAA SGFTFSSYGMHWVRQAPGKGLEWVAFIRYDGSNKYYADSVKGRFTISRDNSKN TLYLQMNSLRAEDTAVYYCKTHGSHDNWGcGTMVTVSS |
| 372 | ACP289 | aptssstktqlqlehlldlqmilnginnyknpkltrmltfldympkkatelkhlqcleeelkpleevlnlaqsknf hlrpdlisninvivlelkgsettfmceyadetativeflnrwitfcqsiistltsggpgpagmkglpgsevqlvesg gglvqpgnslrlscaasgftfskfgmswvrqapgkglewvssisgsgrdtlyaesvkgrftisrdnakttlylqmn slrpedtavyyctiggslsvssqgtlvtvssgggsgggsgggsgggsgggsgggsggggsggggsgpgpagmkgl pgsevqlvesgggIvqpgglrlscaasgtfssytlawvrqapgkglewvaaidssvtvspdtvrgrftisrdna knslylqmnslraedtavyyccardsnwdaldywgggttvtvssgggsgggsgggsgggsggggsgggsgslsas vgdrvtitckasqvgtnvgvwyqqkpgkapkaliysasfrysgvpsrfsgsgsgtdftitisslqpedfatyycqq yytypytfgggtkveikhhhhhh |
| 373 | ACP290 | aptssstktqlqlehlldlqmilnginnyknpkltrmltfkfympkkatelkhlqcleeelkpleevlnlaqsknfhlrprdli sninviviviveikgsettfmceyadetativeflnrwitfcqsiistltsggpgpagmkglpgsevqlvesgggIvqpgnslrlsca asgftfskfgmswvrqapgkglewvssisgsgrdtlyaesvkgrftisrdnakttlylqmnslrpedtavyyctiggslsvss gqtlvtvssgggsgggsgggsgggsgggsgggsggggsgpgpagmkglpgQVQLQESGGGLVQTGG SLRLSCTTSGTIFSGYTMGWYRQAPGEQRELVAVISGGDTNYADSVKGRFTISR DNTKDTMYLQMNSLKPEDTAVYYCYSREVTPPWKLYWGQGTVSSAAAYP YDVPDYGSHHHHHH |
| 374 | ACP291 | aptssstktqlqlehlldlqmilnginnyknpkltrmltfkfympkkatelkhlqcleeelkpleevlnlaqsknfhlrprdli sninviviviveikgsettfmceyadetativeflnrwitfcqsiistltsggpgpagmkglpgsevqlvesgggIvqpgnslrlsca asgtfskfgmswvrqapgkglewvssisgsgrdtlyaesvkgrftisrdnakttlylqmnslrpedtavyyctiggslsvss gqtlvtvssgggsgggsgggsgggsgggsgggsggggsgpgpagmkglpgQVQLQESGGGLVQEGG SLRLSCAASERIFSTDVMGWYRQAAEKQRELVAVVSARGTTNYLDAVKGRFTIS RDNARNTLTLQMNDLKPEDTASYYCYVRETTSPWRIYWGQGTQVTVSSAAAYP YDVPDYGSHHHHHH |
| 375 | ACP292 | aptssstktqlqlehlldlqmilnginnyknpkltrmltfkfympkkatelkhlqcleeelkpleevlnlaqsknfhlrprdli sninviviviveikgsettfmceyadetativeflnrwitfcqsiistltsggpgpagmkglpgsevqlvesgggIvqpgnslrlsca asgtfskfgmswvrqapgkglewvssisgsgrdtlyaesvkgrftisrdnakttlylqmnslrpedtavyyctiggslsyss qgtlvtvssgggsgggsgggsgggsgggsgggsggggsgpgpagmkglpgQVQLQESGGGLVQAG |

-continued

SEQUENCE TABLE

| SEQ ID NO. | Name | Sequence |
|---|---|---|
| 376 | ACP296 | GSLRLSCAASGSIFSANAMGWYRQAPGKQRELVAVISSGSTNYADSVKGRFTI<br>SRDNAKNTVYLQMNSLKPEDTAVYYCMYSGSYYTPNDVWGQGTQVTVSSAA<br>AYPYDVPDYGSHHHHHH |
| 377 | Acp297 | aptssstktqlqlehlldlqmilnginnykmpkltrmltfldympkkatelkhlqcleeelkpleevlnlaqsknf<br>hlrprdlisninvivlelkgsettfmceyadetativeflnrwitfcqsiistltSGGPGPAGMKGLPGSE<br>VQLVESGGGLVQPGGNSLRLSCAASGFTFSKFGMSWVRQAPGKGLEWVSS<br>ISGSGRDTLYAESVKGRFTISRDNAKTTLYLQMNSLRPEDTAVYYCTIGG<br>SLSVSSQGTLVTVSSgggsgsggsggggsgsggsggggsgsggsggggsSGGPGPAGMKGLP<br>GSEVQLVESGGGLVQPGGSLRLSCAASGFTFSSYTLAWVRQAPGKGLEW<br>VAAIDSSSYTYSPDTVRGRFTISRDNAKNSLYLQMNSLRAEDTAVYYCAR<br>DSNWDALDYWGQGTTVTVSSSGPGPAGMKGLPGSDIQMTQSPSSLSAS<br>VGDRVTITCKASQNVGTNVGWYQQKPGKAPKALIYSASFRYSGVPSRFS<br>GSGSGTDFTLTISSLQPEDFATYYCQQYYTYPYTPGGGTKVEIKREIREIRREI<br>EPEA** |
| 378 | ACP298 | aptssstktqlqlehlldlqmilnginnykmpkltrmltfkfympkkatelkhlqcleeelkpleevlnlaqsknfhlrprdli<br>sninvivlelkgsettfmceyadetativeflnrwitfcqsiistltSGGPGPAGMKGLPGSEVQLVESGGG<br>LVQPGNSLRLSCAASGFTFSKFGMSWVRQAPGKGLEWVSSISGSGRDTLYAESV<br>KGRFTISRDNAKTTLYLQMNSLRPEDTAVYYCTIGGSLSVSSQGTLVTVSSgggsg<br>gggsgsggsggggsgggsgsggsgggsSGGPGPAGMKGLPGSEVQLVESGGGLVQPGGSLRLS<br>CAASGFTFSSYTLAWVRQAPGKGLEWVAAIDSSSYTYSPDTVRGRFTISRDNAK<br>NSLYLQMNSLRAEDTAVYYCARDSNWDALDYWGQGTTVTVSSGGGSGGGGS<br>GGGGSDIQMTQSPSSLSASVGDRVTITCKASQNVGTNVGWYQQKPGKAPKGLIY<br>SASFRYSGVPSRFSGSGSGTDFTLTISSLQPEDFATYYCQQYYTYPYTPGGGTKV<br>EIKHHHHHHEPEA** |
| 379 | ACp299 | aptssstktqlqlehlldlqmilnginnykmpkltrmltfidympkkatelkhlqcleeelkpleevlnlaqsknfhlrprdli<br>sninvivlelkgsettfmceyadetativeflnrwitfsqsiistltSGGPGPAGMKGLPGSEVQLVESGGG<br>LVQPGNSLRLSCAASGFTFSKFGMSWVRQAPGKGLEWVSSISGSGRDTLYAESV<br>KGRFTISRDNAKTTLYLQMNSLRPEDTAVYYCTIGGSLSVSSQGTLVTVSSgggsg<br>gggsgsggsggggsgggsgsggsgggsSGGPGPAGMKGLPGSEVQLVESGGGLVQPGGSLRLS<br>CAASGFTFSSYTLAWVRQAPGKGLEWVAAIDSSSYTYSPDTVRGRFTISRDNAK<br>NSLYLQMNSLRAEDTAVYYCARDSNWDALDYWGQGTTVTVSSGGGSGGGGS<br>GGGGSDIQMTQSPSSLSASVGDRVTITCKASQNVGTNVGWYQQKPGKAPKALIY<br>SASFRYSGVPSRFSGSGSGTDFTLTISSLQPEDFATYYCQQYYTYPYTPGGGTKV<br>EIKHHHHHHEPEA** |

-continued

SEQUENCE TABLE

| SEQ ID NO. | Name | Sequence |
|---|---|---|
| 380 | ACP300 | aptssţktqlqlehllldlqmilnginnykmpkltrmltfidympkkatelkhlqcleeelkpleevlnlaqsknf<br>hlrpdlisninivlelkgsettmceyadetativeflnrwitfcqsiisltSGGPGPAGMKGLPGSda<br>hksevahrfkdlgeenfkalvliafaqylqgcpfedhvklvnevtefaktcvadesaencdkslhtlfgdklctvat<br>lretygemadccakqepernecfiqhkddnpnlprlvrpevdvmctafhdneetflkkylyelarrhpyfyape<br>llffakrykaaftecqaadkaacllpkldelrdegkassakqrlkcaaslqkfgerafkawavarlsqrfpkaefae<br>vsklvtdltkvhtecchgd1lecaddradlakyicenqdsisslkeccekp1lekshciaevendempadlpsla<br>adfveskdvcknyaeakdvflgmflyeyarrhpdysvvlllrlaktyettlekccaaadphecyakvfdefkplv<br>eepqnlikqncelfeqlgeykfqnallvrytkkvrpqvstptlvevsrnlgkvgskcckhpeakrmpcaedylsv<br>vlnqlcvlhektpvsdrvtkcctes1vnrpcfsalevdetyvpkefnaetftfhadictlsekerqikkqtalvelvk<br>hkpkatkeqlkavmddfaatvekccakddketcfaeegkklvaasqaalglgggsggggsggggsggggs<br> gggggggsSGGPGPAGMKGLPGSEVQLVESGGGLVQPGGSLRLSCAASGF<br>TFSSYTLAWRQAPGKGLEWVAAIDSSSYTYSPDTVRGRFTISRDNAKNS<br>LYLQMNSLRAEDTAVYYCARDSNWDALDYWGQGTTVTVSSGGGSGG<br>GGGSGGGGSDIQMTQSPSSLSASVGDRVTITCKASQNVGTNVGWYQQKPG<br>KAPKALIYSASFRYSGVPSRFSGSGSGTDFTLTISSLQPEDFATYYCQQYY<br>TYPYTFGGGTKVEIKHHHHHHEPEA** |
| 381 | ACP302 | aptssţktqlqlehllldlqmilnginnykmpkltrmltfkfympkkatelkhlqcleeelkpleevlnlaqsknf<br>hlrpdlisninivlelkgsettmceyadetativeflnrwitfcqsiisltSGGPGPAGMKGLPGSE<br>AHKSEIAHRYNDLGEQHFKGLVLLIAFSQYLQKCSYDEHAKLVQEVTDFA<br>KTCVADESAANCDKSLHTLFGDKLCAIPNLRENYGELADCCTKQEPERN<br>ECFLQHKDDNPSLPPFERPEAEAMCTSFKENPTTFMGHYLHEVARRHPYF<br>YAPELLYYABQYNEIITQCCAEADKESCLTPKLDGVKEKALVSSVRQRM<br>KCCSMQKFGERAFKAWAVARLSQTFPNADFAEITKLATDLTKVNKECCH<br>GDLLECADDRAELAKYMCENQATISSKLQTCCDKPLLKKAHCLSEVEHD<br>TMPADLPAIAADFVEDQEVCKNYAEAKDVFLGTFLYEYSRRHPDYSVSL<br>LLRLAKKYEATLEKCCAEANPPACYGTVLAEFQPIVEEPKNLVKTNCDL<br>YEKLGEYGFQNAILVRYTQKAPQVSTPTLVEAARNLGRVGTKCCTLPED<br>QRLPCVEDYLSAILNRVCLLHEKTPVSEHVTKCCSGSLVERRPCFSALTV<br>DETTVPKEFKAEFTFHSDICTLPEKEKQIKKQTALAELVKHKPKATAEQ<br>LKTVMDDFAQFLDTCCKAADKDTCFSTEGNLVTRCKDALAgggsgggggsg<br>gggsgggsgggggsgggsgggsgggsSGGPGPAGMKGLPGSEVQLVESGGGLVQPGGSLRL<br>SCAASGFTFSSYTLAWVRQAPGKGLEWVAAIDSSSYTYSPDTVRGRFTIS<br>RDNAKNSLVLQMNSLRAEDTAVYYCARDSNWDALDYWGQGTTVTVSS<br>GGGGSGGGGSGGGGSDIQMTQSPSSLSASVGDRVTITCKASQNVGTNVG<br>WYQQKPGKAPKALIYSASFRYSGVPSRFSGSGSGTDFTLTISSLQPEDFAT<br>YYCQQYYTYPYTFGGGTKVEIKHHHHHH** |
| 382 | ACP303 | EAHKSEIAHRYNDLGEQHFKGLVLLIAFSQYLQKCSYDEHAKLVQEVTDFAKTCV<br>ADESAANCDKSLHTLFGDKLCAIPNLRENYGELADCCTKQEPERNECFLQHKDD<br>NPSLPPFERPEAEAMCTSFKENPTTFMGHYLHEVARRHPYFYAPELLYYAEQYN<br>EILTQCCAEADKESCLTPKLDGVKEKALVSSVRQRMKCCSSMQKFGERAFKAWA<br>VARLSQTFPNADFAEITKLATDLTKVNKECCHGDLLECADDRAELAKYMCENQ<br>ATISSKLQTCCDKPLLKKAHCLSEVEHDTMPADLPAIAADFVEDQEVCKNYAEA<br>KDVFLGTFLYEYSRRHPDYSVSLLLRLAKKYEATLEKCCAEANPPACYGTVLAE<br>FQPIVEEPKNLVKTNCDLYEKLGEYGFQNAILVRYTQKAPQVSTPTLVEAARNL<br>GRVGTKCCTLPEDQRLPCVEDYLSAILNRVCLLHEKTPVSEHVTKCCSGSLVERR |

-continued

SEQUENCE TABLE

| SEQ ID NO. | Name | Sequence |
|---|---|---|
| 383 | ACP304 | PCFSALTVDETYVPKEFKAETFTHSDICTLPEKEKQIKKQTALAELVKHKPKAT AEQLKTVMDDFAQFLDTCCKAADKDTCFSTEGPNLVTRCKDALASGGPGPAGM KGLPGStfkfympkkatelkhlqcleeelkpleevlnlaqsknfhlrprdlisninivlvlelkgsettfmceyadetativef lnrwitfcqsiistltGssstktqlqehllldlqmilnginnyknpkltrmlSGGPGPAGMKGLPGSEAHK SEIAHRYNDLGEQHFKGLVLIAFSQYLQKCSYDEHAKLVQEVTDFAKTCVADES AANCDKSLHTLFGDKLCAIPNLRENYGELADCCTKQEPERNECFLQHKDDNPSL PPFERPEAEAMCTSPKENPTTFMGHYLHEVARRHYFYAPELLYYAEQYNEILTQ CCAEADKESCLTPKLDGVKEKALVSSVRQRMKCSSMQKFGERAFKAWAVARL SQTFPNADFAEITKLATDLTKVNKECCHGDLLECADDRAELAKYMCENQATISS KLQTCCDKPLLKKAHCLSEVEHDTMPADLPAIAADFVEDQEVCKNYAEAKDVF LGTFLYEYSRRHPDYSVSLLLRLAKKYEATLEKCCAEANPPACYGTVLAEFQPL VEEPKNLVKTNCDLYEKLGEYGFQNAILVRYTQKAPQVSTPTLVEAARNLGRV GTKCCTLPEDQRLPCVEDYLSAILNRVCLLHEKTPVSEHVTKCCSGSLVERRPCF SALTVDETYVPKEFKAETFTHSDICTLPEKEKQIKKQTALAELVKHKPKATAEQ LKTVMDDFAQFLDTCCKAADKDTCFSTEGPNLVTRCKDALAHHHHHH** |
| 384 | ACP305 | aptssstktqlqlehllldlqmilnginnyknpkltrmltfldympkkatelkhlqcleeelkpleevlnlaqsknf hlrprdlisninivlvlelkgsettfmceyadetativeflnrwitfcqsiistltSGGPGPAGMKGLPGSE VQLVESGGGLVQPGNSLRLSCAASGFTFSKFGMSWVRQAPGKGLEWVSS ISGSGRDTLYAESVKGRFTISRDNAKTTLYLQMNSLRPEDTAVYCTIGG SLSVSSQGTLVTVSSgggsgggsgggsgggsgggsgggsgggsggsSGGPGPAGMKGLP GSEVQLVESGGGLVQPGGSLRLSCAASGFTFSSYTLAWRQAPGKGLEW VAAIDSSSYTYSPDTVRGRFTISRDNAKNSLYLQMNSLRAEDTAVYYCAR DSNMDALDYWGQGTTVTVSSGGGSGGGGSGGGGSGDIQMTQSPSSLSA SVGDRVTITCKASQNVGTNVGWYQQKPGKAPKALIYSASFRYSGVPSRF SGSGSGTDFTLTISSLQPEDFATYYCQQYYTYPYTFGGGTKVEIKSGGPGP AGMKGLPGSggsgggsgggsgggsgggsgggsgggsgggselcddppeiphatfkamaykegtml nceeckrgfrriksgslymlctgnsshsswdnqcqctssatrntttkqvtpqeeqk pghcrepppweneateriyhfvvgqmvyycvqgyralhrgpaesvckmthgktrwtqpqlictgemetsq fpgeekpgaspegrpesetsclvttdfqigtemaatmetsifteyqHHHHHH** |
| 385 | ACP306 | elcddppeiphatfkamaykegtmlnceeckrgfrriksgslymlctgnsshsswdnqcqctssatrntttkqvtpqeeqk erkttemqspmqpvdqaslpghcrepppweneateriyhfvvgqmvyqvcvqgyralhrgpaesvckmthgktrwtq pqlictgemetsqfpgeekpgaspegrpesetsclvttdfqigtemaatmetsifteyqggggsgggggsgggggsg gggsgggsSGGPGPAGMKGLPGSaptssstktqlqlehllldlqmilnginnyknpkltrmltfkfympkka telkhlqcleeelkpleevlnlaqsknfhlrprdlisninivlvlelkgsettfmceyadetativeflnrwitfcqsiistltSGGP GPAGMKGLPGSEVQLVESGGGLVQPGNSLRLSCAASGFTFSKFGMSWVRQAPG KGLEWVSSISGSGRDTLYAESVKGRFTISRDNAKTTLYLQMNSLRPEDTAVYYC TIGGSLSVSSQGTLVTVSSgggsgggsgggsgggsgggsgggsgggsggsSGGPGPAGMKGLPG SEVQLVESGGGLVQPGGSLRLSCAASGFTFSSYTLAWRQAPGKGLEWVAAIDS SSYTYSPDTVRGRFTISRDNAKNSLYLQMNSLRAEDTAVYYCARDSNWDALDY WGQGTTVTVSSGGGSGGGGSGGGGSGDIQMTQSPSSLSASVGDRVTITCKASQN VGTNVGWYQQKPGKAPKALIYSASFRYSGVPSRFSGSGSGTDFTLTISSLQPEDF ATYYCQQYYTYPYTFGGGTKVEIKHHHHHH** |
| 385 | ACP306 | aptssstktqlqlehllldlqmilnginnyknpkltrmltfkfympkkatelkhlqcleeelkpleevlnlaqsknfhlrprdli sninivlvlelkgsettfmceyadetativeflnrwitfcqsiistltSGGPGPAGMKGLPGSgggsgggsgggsgggggs gggsgggsgggselcddppeiphatfkamaykegtmlnceeckrgfrriksgslymlctgnsshsswdnqcqctss |

-continued

SEQUENCE TABLE

| SEQ ID NO. | Name | Sequence |
|---|---|---|
| | | atrnttkqvtpqpeeqkerkttemqspmqpvdqaslpghcreppweneateriyhfvvgqmvyyqcvgdyralhrgp<br>aesvckmthgktrwtqpqllctgemetsqfpgeekpqaspegrpesetsclvttdfqiqtemaatmetsiftteyqSGGP<br>GPAGMKGLPGSEVQLVESGGGLVQPGNSLRLSCAASGFTFSKFGMSWVRQAPG<br>KGLEWVSSISGSGRDTLYAESVKGRFTISRDNAKTTLYLQMNSLRPEDTAVYYC<br>TIGGSLSVSSQGTLVTVSSgggsgggggsggggsgggsggggsggggsSGGPGPAGMKGLPG<br>SEVQLVESGGGLVQPGGSLRLSCAASGFTFSSYTLAWVRQAPGKGLEWVAAIDS<br>SSYTYSPDTVRGRFTISRDNAKNSLYLQMNSLRAEDTAVYYCARDSNWDALDY<br>WGQGTTVTVSSGGGGSGGGGSGGGGSDIQMTQSPSSLSASVGDRVTITCKASQN<br>VGTNVGWYQQKPGKAPKALIYSASFRYSGVPSRFSGSGSGTDFTLTISSLQPEDF<br>ATYYCQQYYTYPYTFGGGTKVEIKHHHHHH** |
| 386 | ACP307 | EVQLVESGGGLVQPGNSLRLSCAASGFTFSKFGMSWVRQAPGKGLEWVSSISGS<br>GRDTLYAESVKGRFTISRDNAKTTLYLQMNSLRPEDTAVYYCTIGGSLSVSSQGT<br>LVTVSSSGGPGPAGMKGLPGStfkfympkkatelkhlqcleeelkpleevlnlaqsknfhlrprdlisninvi<br>vlelkgsettfmceyadetativeflnrwitfcqsiistltGGssstktqlqlehllldlqmilnginnyknpkltrmlSGGP<br>GPAGMKGLPGSEVQLVESGGGLVQPGNSLRLSCAASGFTFSKFGMSWVRQAPG<br>KGLEWVSSISGSGRDTLYAESVKGRFTISRDNAKTTLYLQMNSLRPEDTAVYYC<br>TIGGSLSVSSQGTLVTVSSgggsgggggsggggsgggsggggsggggsSGGPGPAGMKGLPG<br>SEVQLVESGGGLVQPGGSLRLSCAASGFTFSSYTLAWVRQAPGKGLEWVAAIDS<br>SSYTYSPDTVRGRFTISRDNAKNSLYLQMNSLRAEDTAVYYCARDSNWDALDY<br>WGQGTTVTVSSGGGGSGGGGSGGGGSDIQMTQSPSSLSASVGDRVTITCKASQN<br>VGTNVGWYQQKPGKAPKALIYSASFRYSGVPSRFSGSGSGTDFTLTISSLQPEDF<br>ATYYCQQYYTYPYTFGGGTKVEIKHHHHHH** |
| 387 | ACP308 | EVQLVESGGGLVQPGGSLRLSCAASGFTFSSYTLAWVRQAPGKGLEWVAAIDSS<br>SYTYSPDTVRGRFTISRDNAKNSLYLQMNSLRAEDTAVYYCARDSNWDALDYW<br>GQGTTVTVSSGGGGSGGGGSGGGGSDIQMTQSPSSLSASVGDRVTITCKASQNV<br>GTNVGWYQQKPGKAPKALIYSASFRYSGVPSRFSGSGSGTDFTLTISSLQPEDFA<br>TYYCQQYYTYPYTFGGGTKVEIKSGGPGPAGMKGLPGSgggsgggsggggsggggsgg<br>gggggggsEVQLVESGGGLVQPGNSLRLSCAASGFTFSKFGMSWVRQAPGKGLE<br>WVSSISGSGRDTLYAESVKGRFTISRDNAKTTLYLQMNSLRPEDTAVYYCTIGGS<br>LSVSSQGTLVTVSSSGGPGPAGMKGLPGStfkfympkkatelkhlqcleeelkpleevlnlaqsknfhl<br>rprdlisninvivlelkgsettfmceyadetativeflnrwitfcqsiistltGGssstktqlqlehllldlqmilnginnyknpk<br>ltrmlSGGPGPAGMKGLPGSEVQLVESGGGLVQPGNSLRLSCAASGFTFSKFGMS<br>WVRQAPGKGLEWVSSISGSGRDTLYAESVKGRFTISRDNAKTTLYLQMNSLRPE<br>DTAVVYCCTIGGSLSVSSQGTLVTVSSHHHHHH** |
| 388 | ACP309 | aptsssktktqlqlehllldlqmilnginnyknpkltrmltfkfympkkatelkhlqcleeelkpleevlnlaqsknfhlrprdli<br>sninivivlelkgsettfmceyadetativeflnrwitfcqsiistltSGGPGPAGMKGLPGSEVQLVESGGG<br>LVQPGNSLRLSCAASGFTFSKFGMSWVRQAPGKGLEWVSSISGSGRDTLYAESV<br>KGRFTISRDNAKTTLYLQMNSLRPEDTAVYYCTIGGSLSVSSQGTLVTVSSgggggsg<br>gggsgggsgggsgggsgggsgggsSGGPGPAGMKGLPGSEVQLVESGGGLVQPGGSLRLS<br>CAASGFTFSSYTLAWVRQAPGKGLEWVAAIDSSSYTYSPDTVRGRFTISRDNAK<br>NSLYLQMNSLRAEDTAVYYCARDSNWDALDYWGQGTTVTVSSGGGGSGGGGS<br>GGGGSDIQMTQSPSSLSASVGDRVTITCKASQNVGTNVGWYQQKPGKAPKSLIY<br>SASFRYSGVPSRFSGSGSGTDFTLTISSLQPEDFATYYCQQYYTYPYTFGGGTKV<br>EIKHHHHHH** |

-continued

SEQUENCE TABLE

| SEQ ID NO. | Name | Sequence |
|---|---|---|
| 389 | ACP310 | aptssstktqlqlehlldlqmilnginnykmpkltrmltfkfympkkatelkhlqcleee1kpleevlnlagsknfhlrprdli<br>sninivlelkgsettfmceyadetativeflnrwitfcqsiistltSGGPGPAGMKGLPGSEVQLVESGG<br>LVQPGNSLRLSCAASGFTFSKFGMSWVRQAPGKGLEWVSSISGSGRDTLYAESV<br>KGRFTISRDNAKTTLYLQMNSLRPEDTAVYYCTIGGSLSVSSQGTLVTVSSgggsg<br>gggsgggsgggsgggsgggsgggsSGGPAGMKGLPGSEVQLVESGGGLVQPGGSLRLS<br>CAASGFTFSSYTLAWVRQAPGKGLEWVAAIDSSYTYSPDTVRGRFTISRDNAK<br>NSLYLQMNSLRAEDTAVYYCARDSNWDALDYWGQGTTVTVSSGGGGSGGGGS<br>GGGGSDIQMTQSPSSLSASVGDRVTITCKASQNVGTNVGWYQQKPGQAPRLLIY<br>SASFRYSGVPSRFSGSGSGTDFTLTISSLQPEDFATYYCQQYYTYPYTFGGGTKV<br>EIKHHHHHH** |
| 390 | ACP311 | aptssstktqlqlehlldlqmilnginnyknpkltrmltfldympkkatelkhlqcleee1kpleevlnlagsknf<br>hlrprdliisninivlvlelkgsettfmceyadetativeflnrwitfcqsiistltSGGPGPAGMKGLPGSes<br>kygpPcpppcpapeflgggpsvflfppkpkdtlmisrtpevtcvvvdvsqedpevqfnwyvdgvevhnaktkpr<br>eeqfnstyrvvsvltvlhqdwlngkeykckvsnkglpssiektiskakgqprepqvytlppsqeemtknqvslt<br>clvkfypsdiaevesngqpennykttppvldsdgsfflysrltvdksrwqegnvfscsvmhealnhhytqk<br>slslslgkggggsgggsgggsgggsgggsgggsSGGPAGMKGLPGSEVQLVESG<br>GGLVQPGGSLRLSCAASGFTFSSYTLAWVRQAPGKGLEWVAAIDSSSYT<br>YSPDTVRGRFTISRDNAKNSLYLQMNSLRAEDTAVYYCARDSNWDALD<br>YWGQGTTVTVSSGGGGSGGGGSGGGGSDIQMTQSPSSLSASVGDRVTIT<br>CKASQNVGTNVGWYQQKPGKAPKALIYSASFRYSGVPSRFSGSGSGTDF<br>TLTISSLQPEDFATYYCQQYYTYPYTFGGGTKVEIKHHHHHH** |
| 391 | ACP312 | eskyppPcpPcpapeflggpsvflfppkpkdtlmisrtpevtcvvvdvsqedpevqfnwyvdgvevhnaktkpreeqf<br>nstyrvvsvltvlhqdwlngkeykckvsnkglpssiektiskakgqprepqvytlppsqeemtknqvsltclvkgfypsdi<br>avewesngqpennykttppvldsdgsfflysrltvdksrwqegnvfscsvmhealnhhytqkslslsgkSGGPGPA<br>GMKGLPGSaptssstktqlqlehlldlqmilnginnyknpkltrmlafympkkatelkhlqcleee1kpleev1nl<br>aqsknfhlrprdlisninivlelkgsettfmceyadetativelnrwitfcqsiistltgggsgggsgggsgggsgggg<br>ggggsSGGPGPAGMKGLPGSEVQLVESGGGLVQPGGSLRLSCAASGFTFSSYTLA<br>WVRQAPGKGLEWVAAIDSSSYTYSPDTVRGRFTISRDNAKNSLYLQMNSLRAE<br>DTAVYYCARDSNWDALDYWGQGTTVTVSSGGGGSGGGGSGGGGSDIQMTQSP<br>SSLSASVGDRVTITCKASQNVGTNVGWYQQKPGKAPKALIYSASFRYSGVPSRF<br>SGSGSGTDFTLTISSLQPEDFATYYCQQYYTYPYTFGGGTKVEIKHHHHHH** |
| 392 | ACP313 | aptssstktqlqlehlldlqmilnginnyknpkltrmltfkfympkkatelkhlqcleee1kpleev1nlagsknfhlrprdli<br>sninivlelkgsettfmceyadetativeflnrwitfcqsiistltSGGPGPAGMKGLPGSgggsgggsgggsgggs<br>gggsgggsgggsEVQLVESGGGLVQPGGSLRLSCAASGFTFSSYTLAWVRQAPGK<br>GLEWVAAIDSSSYTYSPDTVRGRFTISRDNAKNSLYLQMNSLRAEDTAVYYCAR<br>DSNWDALDYWGQGTTVTVSSGGGGSGGGGSGGGGSDIQMTQSPSSLSASVGDR<br>VTITCKASQNVGTNVGWYQQKPGKAPKALIYSASFRYSGVPSRFSGSGSGTDFT<br>LTISSLQPEDFATYYCQQYYTYPYTFGGGTKVEIKSGGPGPAGMKGLPGSeskYgPP<br>cppcpapeflggpsvflfppkpkdtlmisrtpevtcvvvdvsqedpevqfnwyvdgvevhnaktkpreeqfnstyrvvs<br>vltvlhqdwlngkeykckvsnkglpssiektiskakgqprepqvytlppsqeemtknqvsltclvkgfypsdiavewesn<br>gqpennykappvldsdgsfflysrltvdksrwqegnvfscsvmhealnhhytqkslslglkHHHHHH** |
| 393 | ACP314 | vprdcgckpcictvpevssvfifppkpkdvltitltpkvtcvvvdisddpevgfswfvddvevhtagtqpreeq<br>fnstfrsvselpimhqdwlngkefkcrvnsaafpapieltisttkgrpkapqvytipppkeqmakdkvsltcmi<br>tdffpeditvewqwngqpaenykntqpimdtdgsyfvysklnvqksnweagntfcsvlheglnhnhteksls |

-continued

SEQUENCE TABLE

| SEQ ID NO. | Name | Sequence |
|---|---|---|
| | | hspgkSGGPGPAGMKGLPGSaptssstkktqlqlehlldlqmilnginnykmpkltrmltfldympk |
| | | katelkhlqcleeelkpleevlnlaqsknfhlrprdlisninvivlelkgsettfmceyadetativeflnrwitfcqsii |
| | | stltgggsgggsgggsgggsgggsgggsSGGPGPAGMKGLPGSEVQLVESGGG |
| | | LVQPGGSLRLSCAASGFTFSSYTLAWVRQAPGKGLEWVAAIDSSYTYSP |
| | | DTVRGRFTISRDNAKNSLYLQMNSLRAEDTAVYYCARDSNWDALDYWG |
| | | QGTTVTVSSGGSGGSGGSGGSDIQMTQSPSSLSASVGDRVTITCKAS |
| | | QNVGTNVGWYQQKPGKAPKALIYSASFRYSGVPSRFSGSGSGTDFTLTIS |
| | | SLQPEDFATYYCQQYYTYPYTFGGGTKVEIKHHHHHH** |
| 394 | ACP336 | aptssstkktqlqlehlldlqmilnginnykmpkltrmltfldympkkatelkhlqcleeelkpleevlnlaqsknf |
| | | hlrpdlisninvivlelkgsettfmceyadetativeflnrwitfcqsiisltsggpGPAGLYAQpgsEVQ |
| | | LVESGGGLVQPGNSLRLSCAASGFTFSKFGMSWVRQAPGKGLEWVSSIS |
| | | GSGRDTLYAESVKGRFTISRDNAKTTLYLQMNSLRPEDTAVYYCTIGGSL |
| | | SVSSQGTLVTVSSsgggsgggsgggsgggsgggsgggsgggGPAGLYAQpgsEV |
| | | QLVESGGGLVQPGGSLRLSCAASGFTFSSYTLAWVRQAPGKGLEWVAAI |
| | | DSSSYTYSPDTVRGRFTISRDNAKNSLYLQMNSLRAEDTAVYYCARDSN |
| | | WDALDYWGQGTTVTVSSsggpGPAGLYAQpgsDIQMTQSPSSLSASVGDR |
| | | VTITCKAREKLMSAVAWYQQKPGKAPKsLIYSASFRYSGVPSRFSGSGSG |
| | | TDFTLTISSLQPEDFATYYCQQYYTYPYTFGGGTKVEIK** |
| 395 | ACP337 | aptssstkktqlqlehlldlqmilnginnykmpkltrmltfkfympkkatelkhlqcleeelkpleevlnlaqsknfhlrprdli |
| | | sninvivlelkgsettfmceyadetativeflnrwitfcqsiisltsggpGPAGLYAQpgsEVQLVESGGGLV |
| | | QPGNSLRLSCAASGFTFSKFGMSWVRQAPGKGLEWVSSISGSGRDTLYAESVKG |
| | | RFTISRDNAKTTLYLQMNSLRPEDTAVYYCTIGGSLSVSSQGTLVTVSSsgggsgggg |
| | | sgggsgggsgggsgggsgggsgggGPAGLYAQpgsEVQLVESGGGLVQPGGSLRLSCAAS |
| | | GFTFSSYTLAWVRQAPGKGLEWVAAIDSSSYTYSPDTVRGRFTISRDNAKNSLY |
| | | LQMNSLRAEDTAVYYCARDSNWDALDYWGQGTTVTVSSGGSGGSGGSGGG |
| | | GSDIQMTQSPSSLSASVGDRVTITCKAREKLMSAVAWYQQKPGKAPKsLIYSASF |
| | | RYSGVPSRFSGSGSGTDFTLTISSLQPEDFATYYCQQYYTYPYTFGGGTKVEIK** |
| 396 | ACP338 | aptssstkktqlqlehlldlqmilnginnykmpkltrmltfkfympkkatelkhlqcleeelkpleevlnlaqsknfhlrprdli |
| | | sninvivlelkgsettfmceyadetativeflnrwitfcqsiisltsggpGPAGLYAQpgsEVQLVESGGGLV |
| | | QPGNSLRLSCAASGFTFSKFGMSWVRQAPGKGLEWVSSISGSGRDTLYAESVKG |
| | | RFTISRDNAKTTLYLQMNSLRPEDTAVYYCTIGGSLSVSSQGTLVTVSSgggsggggg |
| | | sgggsgggsgggsgggsgggsgggGPAGLYAQpgsEVQLVESGGGLVQPGGSLRLSCAAS |
| | | GFTFSSYTLAWVRQAPGKGLEWVAAIDSSSYTYSPDTVRGRFTISRDNAKNSLY |
| | | LQMNSLRAEDTAVYYCARDSNWDALDYWGQGTTVTVSSsggpGPAGLYAQpgsD |
| | | IQMTQSPSSLSASVGDRVTITCKVTEKVWGNVAWYQQKPGKAPISLIYSPSLRKS |
| | | GVPSRFSGSGSGTDFTLTISSLQPEDFATYYCQQYYTYPYTFGGGTKVEIK** |
| 397 | ACP339 | aptssstkktqlqlehlldlqmilnginnykmpkltrmltfkfympkkatelkhlqcleeelkpleevlnlaqsknfhlrprdli |
| | | sninvivlelkgsettfmceyadetativeflnrwitfcqsiisltsggpGPAGLYAQpgsEVQLVESGGGLV |
| | | QPGNSLRLSCAASGFTFSKFGMSWVRQAPGKGLEWVSSISGSGRDTLYAESVKG |
| | | RFTISRDNAKTTLYLQMNSLRPEDTAVYYCTIGGSLSVSSQGTLVTVSSgggsgggggg |
| | | sgggsgggsgggsgggsgggsgggGPAGLYAQpgsEVQLVESGGGLVQPGGSLRLSCAAS |
| | | GFTFSSYTLAWVRQAPGKGLEWVAAIDSSSYTYSPDTVRGRFTISRDNAKNSLY |
| | | LQMNSLRAEDTAVYYCARDSNWDALDYWGQGTTVTVSSGGSGGSGGSGGG |

-continued

SEQUENCE TABLE

| SEQ ID NO. | Name | Sequence |
|---|---|---|
| 398 | ACP340 | GSDIQMTQSPSSLSASVGDRVTITCKVTEKVWGNVAWYQQKPGKAPISLIYSPSL<br>RKSGVPSRFSGSGSGTDFTLTISSLQPEDFATYYCQQYYTYPYTFGGGTKVEIK** |
| 399 | ACP341 | aptssstktqlqlehlldlqmilnginnyknpkltrmltfkfympkkatelkhlqcleeelkpleevlnlaqsknfhlrprdli<br>sninivlvlelkgsettfmceyadetativeflnrwitfcqsiistltsggpGPAGLYAQpgsEVQLVESGGGLV<br>QPGNSLRLSCAASGFTFSKFGMSWVRQAPGKGLEWVSSISGSGRDTLYAESVKG<br>RFTISRDNAKTTLYLQMNSLRPEDTAVYYCTIGGSLSVSSQGTLVTVSSggggsgggg<br>sggggsggggsggggsggggsgpGPAGLYAQpgsevqllesgglvqpgglrlscaasgsifsanamgwyrq<br>apgkglelvaviusggstnyadsvkgrftisrdnskntvylqmnslraedtavyycmysgsyYYtpndywgqgtlvtvss*<br>* |
| 400 | ACP342 | aptssstktqlqlehlldlqmilnginnyknpkltrmltfkfympkkatelkhlqcleeelkpleevlnlaqsknfhlrprdli<br>sninivlvlelkgsettfmceyadetativeflnrwitfcqsiistltsggpGPAGLYAQpgsEVQLVESGGGLV<br>QPGNSLRLSCAASGFTFSKFGMSWVRQAPGKGLEWVSSISGSGRDTLYAESVKG<br>RFTISRDNAKTTLYLQMNSLRPEDTAVYYCTIGGSLSVSSQGTLVTVSSggggsgggg<br>sggggsggggsggggsggggsggpGPAGLYAQpgsevqllesgglvqpgglrlscaaserifstdvmgwyrq<br>apgkqrelvavvsargttnyldavkgrftisrdnsknt1ylqmnslraedtavyycyvrettspwrlywgqgtlvtvss** |
| | | elcdddppeiphatfkamaykegtmlnceckrgfrriksgslymlctgnsshswdnqcqctssatrnttkqvtpqpeeqk<br>erkttemqspmqpvdqaslpghcrreppweneateriyhfvvgqmvyyqcvqgyralhrgpaesvckmthgktrwtq<br>pqlictgemetsqfpgeekpqaspegrpesetslvttdfqiqtemaatmetsifteyqggggsggggsggggsggggs<br>ggggsggggsggpGPAGLYAQpgsaptssstktqlqlehlldlqmilnginnyknpkltrmltfkfympkkatel<br>khlqcleeelkpleevlnlaqsknfhlrprdlisninivlvlelkgsettfmceyadetativeflnrwitfcqsiistltsggpGP<br>AGLYAQpgsEVQLVESGGGLVQPGNSLRLSCAASGFTFSKFGMSWRQAPGKGL<br>EWVSSISGSGRDTLYAESVKGRFTISRDNAKTTLYLQMNSLRPEDTAVYYCTIGG<br>SLSVSSQGTLVTVSSggggsggggsggggsggggsggggsgggpGPAGLYAQpgsEVQL<br>VESGGGLVQPGGSLRLSCAASGFTFSSYTLAWVRQAPGKGLEWVAAIDSSSYTY<br>SPDTVRGRFTISRDNAKNSLYLQMNSLRAEDTAVYYCARDSNWDALDYWGQG<br>TTVTVSSsgpGPAGLYAQpgsDIQMTQSPSSLSASVGDRVTITCKAREKLWSAVA<br>WYQQKPGKAPKsLIYSASFRYSGVPSRFSGSGSGTDFTLTISSLQPEDFATYYCQQ<br>YYTYPYTFGGGTKVEIK** |
| 401 | ACP343 | elcdddppeiphatfkamaykegtmlnceckrgfrriksgslymlctgnsshswdnqcqctssatrnttkqvtpqpeeqk<br>erkttemqspmqpvdqaslpghcrreppweneateriyhfvvgqmvyyqcvqgyralhrgpaesvckmthgktrwtq<br>pqlictgemetsqfpgeekpqaspegrpesetslvttdfqiqtemaatmetsifteyqggggsggggsggggsggggs<br>ggggsggggsggpGPAGLYAQpgsaptssstktqlqlehlldlqmilnginnyknpkltrmltfkfympkkatel<br>khlqcleeelkpleevlnlaqsknfhlrprdlisninivlvlelkgsettfmceyadetativeflnrwitfcqsiistltsggpGP<br>AGLYAQpgsEVQLVESGGGLVQPGNSLRLSCAASGFTFSKFGMSWRQAPGKGL<br>EWVSSISGSGRDTLYAESVKGRFTISRDNAKTTLYLQMNSLRPEDTAVYYCTIGG<br>SLSVSSQGTLVTVSSggggsggggsggggsggggsggggsgggpGPAGLYAQpgsEVQL<br>VESGGGLVQPGGSLRLSCAASGFTFSSYTLAWVRQAPGKGLEWVAAIDSSSYTY<br>SPDTVRGRFTISRDNAKNSLYLQMNSLRAEDTAVYYCARDSNWDALDYWGQG<br>TTVTVSSGGGGSGGGGSGGGGSDIQMTQSPSSLSASVGDRVTITCKAREKLWSA<br>VAWYQQKPGKAPKsLIYSASFRYSGVPSRFSGSGSGTDFTLTISSLQPEDFATYYC<br>QQYYTYPYTFGGGTKVEIK** |
| 402 | ACP344 | elcdddppeiphatfkamaykegtmlnceckrgfrriksgslymlctgnsshswdnqcqctssatrnttkqvtpqpeeqk<br>erkttemqspmqpvdqaslpghcrreppweneateriyhfvvgqmvyyqcvqgyralhrgpaesvckmthgktrwtq |

-continued

SEQUENCE TABLE

| SEQ ID NO. | Name | Sequence |
|---|---|---|
| 403 | ACP345 | pqlictgemetsqfpgeekpqaspegrpesetslvttdfqiqtemaatmetsifteyqggggsggggsggggsggggs<br>ggggsggggsggpGPAGLYAQpgsaptssstktqlqlehllldlqmilnginnyknpkltrmltfkfympkkatel<br>khlqcleeelkpleevlnlaqsknfhlrpdlisninvivlelkgsettfmceyadetativeflnrwitfcqsiisltsggpGP<br>AGLYAQpgsEVQLVESGGGLVQPGNSLRLSCAASGFTFSKFGMSWVRQAPGKGL<br>EWVSSISGSGRDTLYAESVKGRFTISRDNAKTTLYLQMNSLRPEDTAVYYCTIGG<br>SLSVSSQGTLVTVSSgggggsggggsggggsggggsggggsggpGPAGLYAQpgsEVQL<br>VESGGGLVQPGGSLRLSCAASGFTFSSYTLAWVRQAPGKGLEWVAAIDSSSYTY<br>SPDTVRGRFTISRDNAKNSLYLQMNSLRAEDTAVYYCARDSNWDALDYWGQG<br>TTVTVSSsggpGPAGLYAQpgsDIQMTQSPSSLSASVGDRVTITCKVTEKVWGNVA<br>WYQQKPGKAPISLIYSPSLRKSGVPSRFSGSGSGTDFTLTISSLQPEDFATYYCQQ<br>YYTYPYTFGGGTKVEIK** |
| 404 | ACP346 | elcddppeiphatfkamaykegtmlnceckrgfrririkgslymlctgnsshsswdnqcqctssatrnttkqvtpqpeeqk<br>erkttemqspmqpvdqaslpghcrepppweneateriyhfvvgqmvyyqcvqgyralhrgpaesvckmthgktrwtq<br>pqlictgemetsqfpgeekpqaspegrpesetslvttdfqiqtemaatmetsifteyqggggsggggsggggsggggs<br>ggggsggggsggpGPAGLYAQpgsaptssstktqlqlehllldlqmilnginnyknpkltrmltfkfympkkatel<br>khlqcleeelkpleevlnlaqsknfhlrpdlisninvivlelkgsettfmceyadetativeflnrwitfcqsiisltsggpGP<br>AGLYAQpgsEVQLVESGGGLVQPGNSLRLSCAASGFTFSKFGMSWVRQAPGKGL<br>EWVSSISGSGRDTLYAESVKGRFTISRDNAKTTLYLQMNSLRPEDTAVYYCTIGG<br>SLSVSSQGTLVTVSSgggggsggggsggggsggggsggggsggpGPAGLYAQpgsEVQL<br>VESGGGLVQPGGSLRLSCAASGFTFSSYTLAWVRQAPGKGLEWVAAIDSSSYTY<br>SPDTVRGRFTISRDNAKNSLYLQMNSLRAEDTAVYYCARDSNWDALDYWGQG<br>TTVTVSSgggggsggggsggggsgggGSDIQMTQSPSSLSASVGDRVTITCKVTEKVWGN<br>VAWYQQKPGKAPISLIYSPSLRKSGVPSRFSGSGSGTDFTLTISSLQPEDFATYYC<br>QQYYTYPYTFGGGTKVEIK** |
| 405 | ACP347 | elcddppeiphatfkamaykegtmlnceckrgfrririkgslymlctgnsshsswdnqcqctssatrnttkqvtpqpeeqk<br>erkttemqspmqpvdqaslpghcrepppweneateriyhfvvgqmvyyqcvqgyralhrgpaesvckmthgktrwtq<br>pqlictgemetsqfpgeekpqaspegrpesetslvttdfqiqtemaatmetsifteyqggggsggggsggggsggggs<br>ggggsggggsggpGPAGLYAQpgsaptssstktqlqlehllldlqmilnginnyknpkltrmltfkfympkkatel<br>khlqcleeelkpleevlnlaqsknfhlrpdlisninvivlelkgsettfmceyadetativeflnrwitfcqsiisltsggpGP<br>AGLYAQpgsEVQLVESGGGLVQPGNSLRLSCAASGFTFSKFGMSWVRQAPGKGL<br>EWVSSISGSGRDTLYAESVKGRFTISRDNAKTTLYLQMNSLRPEDTAVYYCTIGG<br>SLSVSSQGTLVTVSSgggggsggggsggggsggggsggggsggpGPAGLYAQpgsevqlles<br>ggglyqpggslrlscaaserifstdvmgwyrqapqkqrelvavvsargttnyldavkqrftisrdnskntlylqmnslraedt<br>avyycyvrettspwriywqggtlvtvss** |

-continued

SEQUENCE TABLE

| SEQ ID NO. | Name | Sequence |
|---|---|---|
| 406 | ACP348 | eskygppcppcpapeflggpsvflfppkpkdtlmisrtpevtcvvvdvsqedpevqfnwyvdgvevhnaktkpreeqf<br>nstyrvvsvltvlhqdwlngkeykckvsnkglpssiektiskakgqprepqvytlppsqeemtknqvsltclvkgfypsdi<br>avewesngqpennykttppvldsdgsfflysrltvdksrwqegnvfscsvmhealnhhytqkslslgksggpGPAG<br>LYAQgsaptssstkktqlqlehllldlqmilnginnyknpkltrmltfkfympkkatelkhlqcleeelkpleevlnlaqs<br>knfhlrprdlisninvivlelkgsettfmceyadetativeflnrwitfcqsiistltgggsggggsggggsggggsg<br>gggsggggpGPAGLYAQpgsEVQLVESGGGlVQPGGSLRLSCAASGFTFSSYTLAWVR<br>QAPGKGLEWVAAIDSSSYTYSPDTVRGRFTISRDNAKNSLYLQMNSLRAEDTAV<br>YYCARDSNWDALDYWGQGTTVTVSSsggpGPAGLYAQpgsDIQMTQSPSSLSASV<br>GDRVTITCKAREKLWSAVAWYQQKPGKAPKsLIYSASFRYSGVPSRFSGSGSGT<br>DFTLTISSLQPEDFATYYCQQYYTYPYTFGGGTKVEIK** |
| 407 | ACP349 | eskygppcppcpapeflggpsvflfppkpkdtlmisrtpevtcvvvdvsqedpevqfnwyvdgvevhnaktkpreeqf<br>nstyrvvsvltvlhqdwlngkeykckvsnkglpssiektiskakgqprepqvytlppsqeemtknqvsltclvkgfypsdi<br>avewesngqpennykttppvldsdgsfflysrltvdksrwqegnvfscsvmhealnhhytqkslslgksggpGPAG<br>LYAQgsaptssstkktqlqlehllldlqmilnginnyknpkltrmltfkfympkkatelkhlqcleeelkpleevlnlaqs<br>knfhlrprdlisninvivlelkgsettfmceyadetativeflnrwitfcqsiistltgggsggggsggggsggggsggggsg<br>gggsggggpGPAGLYAQpgsEVQLVESGGGlVQPGGSLRLSCAASGFTFSSYTLAWVR<br>QAPGKGLEWVAAIDSSSYTYSPDTVRGRFTISRDNAKNSLYLQMNSLRAEDTAV<br>YYCARDSNWDALDYWGQGTTVTVSSGGGSGGGGSGGGGSDIQMTQSPSSLS<br>ASVGDRVTITCKAREKLWSAVAWYQQKPGKAPKsLIYSASFRYSGVPSRFSGSG<br>SGTDFTLTISSLQPEDFATYYCQQYYTYPYTFGGGTKVEIK** |
| 408 | ACP350 | eskygppcppcpapeflggpsvflfppkpkdtlmisrtpevtcvvvdvsqedpevqfnwyvdgvevhnaktkpreeqf<br>nstyrvvsvltvlhqdwlngkeykckvsnkglpssiektiskakgqprepqvytlppsqeemtknqvsltclvkgfypsdi<br>avewesngqpennykttppvldsdgsfflysrltvdksrwqegnvfscsvmhealnhhytqkslslgksggpGPAG<br>LYAQgsaptssstkktqlqlehllldlqmilnginnyknpkltrmltfkfympkkatelkhlqcleeelkpleevlnlaqs<br>knfhlrprdlisninvivlelkgsettfmceyadetativeflnrwitfcqsiistltgggsggggsggggsggggsggggsg<br>gggsggggpGPAGLYAQpgsEVQLVESGGGlVQPGGSLRLSCAASGFTFSSYTLAWVR<br>QAPGKGLEWVAAIDSSSYTYSPDTVRGRFTISRDNAKNSLYLQMNSLRAEDTAV<br>YYCARDSNWDALDYWGQGTTVTVSSsggpGPAGLYAQpgsDIQMTQSPSSLSASV<br>GDRVTITCKVTEKVWGNVAWYQQKPGKAPISLIYSPSLRKSGVPSRFSGSGSG<br>DFTLTISSLQPEDFATYYCQQYYTYPYTFGGGTKVEIK** |
| 409 | ACP351 | eskygppcppcpapeflggpsvflfppkpkdtlmisrtpevtcvvvdvsqedpevqfnwyvdgvevhnaktkpreeqf<br>nstyrvvsvltvlhqdwlngkeykckvsnkglpssiektiskakgqprepqvytlppsqeemtknqvsltclvkgfypsdi<br>avewesngqpennykttppvldsdgsfflysrltvdksrwqegnvfscsvmhealnhhytqkslslgksggpGPAG<br>LYAQgsaptssstkktqlqlehllldlqmilnginnyknpkltrmltfkfympkkatelkhlqcleeelkpleevlnlaqs<br>knfhlrprdlisninvivlelkgsettfmceyadetativeflnrwitfcqsiistltgggsggggsggggsggggsggggsg<br>gggsggggpGPAGLYAQpgsEVQLVESGGGlVQPGGSLRLSCAASGFTFSSYTLAWVR<br>QAPGKGLEWVAAIDSSSYTYSPDTVRGRFTISRDNAKNSLYLQMNSLRAEDTAV<br>YYCARDSNWDALDYWGQGTTVTVSSGGGSGGGGSGGGGSDIQMTQSPSSLS<br>ASVGDRVTITCKVTEKVWGNVAWYQQKPGKAPISLIYSPSLRKSGVPSRFSGSGS<br>GTDFTLTISSLQPEDFATYYCQQYYTYPYTFGGGTKVEIK** |
| 410 | ACP352 | eskygppcppcpapeflggpsvflfppkpkdtlmisrtpevtcvvvdvsqedpevqfnwyvdgvevhnaktkpreeqf<br>nstyrvvsvltvlhqdwlngkeykckvsnkglpssiektiskakgqprepqvytlppsqeemtknqvsltclvkgfypsdi<br>avewesngqpennykttppvldsdgsfflysrltvdksrwqegnvfscsvmhealnhhytqkslslgksggpGPAG<br>LYAQgsaptssstkktqlqlehllldlqmilnginnyknpkltrmltfkfympkkatelkhlqcleeelkpleevlnlaqs |

-continued

SEQUENCE TABLE

| SEQ ID NO. | Name | Sequence |
|---|---|---|
| 411 | ACP353 | knfhlrprdlisninivivlelkgsettfmceyadetativeflnrwitfcqsiistltggggsggggsggggsggggsg<br>gggssggpGPAGLYAQpgsevqllesgggglvqpggslr1scaasgsifsanamgwyrqapgkglelvavissggst<br>nyadsvkgrftisrdnskntvylqmnslraedtavyycmysgsyYytpndywgggtlvtvss** |
| 412 | ACP354 | eskygppcpcpapeflggpsvflfppkpkdtlmisrtpevtcvvvdvsqedpevqfnwyvdgvevhnaktkpreeqf<br>nstyrvvsvltvlhqdwlngkeyhtckvsnkglpssiektiskakgqprepqvytlppsqeemtknqvsltclvkgfypsdi<br>avewesngqpennykttppvldsdgsfflysrltvdksrwqegnvfscsvmhealhnhytqkslslgksggpGPAG<br>LYAQpgsaptssttktqlqlehlldlqmilnginnyknpkltrmltfkfympkkatelkhlqcleeelkpleevlnlaqs<br>knfhlrprdlisninivivlelkgsettfmceyadetativeflnrwitfcqsiistltggggsggggsggggsggggsg<br>gggssggpGPAGLYAQpgsevqllesgggglvqpggslr1scaaserifstdvmgwyrqapgkqprelvavvsargttn<br>yldavkgrftisrdnsknt1ylqmnslraedtavyycyvret spwriywgggtlvtvss** |
| 413 | ACP355 | eskygppcpcpapeflggpsvflfppkpkdtlmisrtpevtcvvvdvsqedpevqfnwyvdgvevhnaktkpreeqf<br>nstyrvvsvltvlhqdwlngkeyhtckvsnkglpssiektiskakgqprepqvytlppsqeemtknqvsltclvkgfypsdi<br>avewesngqpennykttppvldsdgsfflysrltvdksrwqegnvfscsvmhealhnhytqkslslgksggpGPAG<br>LYAQpgselcddappeiphatfkamaykegtmlnceckrgfrriksgslymlctgnsshsswdnqcqctssatmttkq<br>vtpqpeeqkerkttemqspmqpvdqaslpghcreppwneateriyhfvvgqmvyyqcvqgyralhrgpaesvck<br>mthgktrwtcpqliictgemetsqfpgeekpqaspegrpesetslvttdfqiqtemaatmetsifteyqgggsggggsg<br>gggggggsggggsggggsgGPAGLYAQpgsaptssstktqlqlehlldlqmilnginnyknpkltrmltfk<br>fympkkatelkhlqcleeelkpleevlnlaqsknfhlrprdlisninivivlelkgsettfmceyadetativeflnrwitfcqsiis<br>tltgggsgggsggggsggggsggggsggggsggpGPAGLYAQpgsEVQLVESGGGLVQPGGS<br>LRLSCAASGFTFSSYTLAWRQAPGKGLEWVAAIDSSSYTYSSPDTVRGRPTISRD<br>NAKNSLYLQMNSLRAEDTAVYYCARDSNWDALDYWGQGTTVTVSSGGGGSG<br>GGGSGGGGSDIQMTQSPSSLSASVGDRVTITCKAREKLWSAVAWYQQKPGKAP<br>KsLIYSASPRYSGVPSRFSGSGSGTDFTLTISSLQPEDFATYYCQQYYTYPYTPGG<br>GTKVEIK** |
| 414 | ACP356 | eskygppcpcpapeflggpsvflfppkpkdtlmisrtpevtcvvvdvsqedpevqfnwyvdgvevhnaktkpreeqf<br>nstyrvvsvltvlhqdwlngkeyhtckvsnkglpssiektiskakgqprepqvytlppsqeemtknqvsltclvkgfypsdi<br>avewesngqpennykttppvldsdgsfflysrltvdksrwqegnvfscsvmhealhnhytqkslslgksggpGPAG<br>LYAQpgselcddappeiphatfkamaykegtmlnceckrgfrriksgslymlctgnsshsswdnqcqctssatmttkq<br>vtpqpeeqkerkttemqspmqpvdqaslpghcreppwneateriyhfvvgqmvyyqcvqgyralhrgpaesyck<br>mthgktrwtcpqliictgemetsqfpgeekpqaspegrpesetslvttdfqiqtemaatmetsifteyqgggsggggsg |

-continued

SEQUENCE TABLE

| SEQ ID NO. | Name | Sequence |
|---|---|---|

415   ACP357

```
gggsggggsggggsggggsggggsggpGPAGLYAQpgsaptssstkktqlqlehllldlqmilnginmyknpkltrmltfk
fympkkatelkhlqcleeelkpleevlnlaqsknfhlrprdlisninivlvlelkgsettfmceyadetativeflnrwitfcqsiis
tltgggsgggsggggsggggsggggsggggsggpGPAGLYAQpgsEVQLVESGGGLVQPGGS
LRLSCAASGFTFSSYTLAWVRQAPGKGLEWVAAIDSSSYTYSPDTVRGRFTISRD
NAKNSLYLQMNSLRAEDTAVYYCARDSNWDALDYWGQGTTVTVSSsggpGPAG
LYAQpgsDIQMTQSPSSLSASVGDRVTITCKVTEKVWGNVAWYQQKPGKAPISLI
YSPSLRKSGVPSRFSGSGSGTDFTLTISSLQPEDFATYYCQQYYTPYTPGGGTK
VEIK**
```

416   ACP358

```
eskyppcppcpapeflggpsvflfppkpkdtlmisrtpevtcvvvdvsgedpevqfnwyvdgvevhnaktkpreeqf
nstyrvvsvltvlhqdwlngkeykckvsnkglpssiektiskakgqprepqvytlppsqeemtknqvsltclvkgfypsdi
avewesngqpennyktttppvldsdgsfflysrltvdksrwqegnyfscsvmhealhnhytqkslslslgksggpGPAG
LYAQpgselcdddpeiphatfkamaykegtmlnceckrgfrriksgslymlctgnshsswdnqcqctssatrnttkq
vtpqpeeqkerkttemqspmqpvdqaslpqhcreppwenaeteriyhfvvgqmvyyqcvggyralhrgpaesvck
mthgktrwtqpqlictgemetsqfpgeekpqaspegrpeetsslvtttdfqiqtemaatmetsifftteyqgggsggggsg
gggsggggsggggsggggsggggsggpGPAGLYAQpgsaptssstkktqlqlehllldlqmilnginmyknpkltrmltfk
fympkkatelkhlqcleeelkpleevlnlaqsknfhlrprdlisninivlvlelkgsettfmceyadetativeflnrwitfcqsiis
tltgggsgggsggggsggggsggggsggggsggpGPAGLYAQpgsEVQLVESGGGLVQPGGS
LRLSCAASGFTFSSYTLAWVRQAPGKGLEWVAAIDSSSYTYSPDTVRGRFTISRD
NAKNSLYLQMNSLRAEDTAVYYCARDSNWDALDYWGQGTTVTVSSGGGGSG
GGGSGGGGSDIQMTQSPSSLSASVGDRVTITCKVTEKVWGNVAWYQQKPGKAP
ISLIYSPSLRKSGVPSRFSGSGSGTDFTLTISSLQPEDFATYYCQQYYTPYTPGGG
TKVEIK**
```

417   ACP359

```
eskyppcppcpapeflggpsvflfppkpkdtlmisrtpevtcvvvdvsgedpevqfnwyvdgvevhnaktkpreeqf
nstyrvvsvltvlhqdwlngkeykckvsnkglpssiektiskakgqprepqvytlppsqeemtknqvsltclvkgfypsdi
avewesngqpennyktttppvldsdgsfflysrltvdksrwqegnvfscsvmhealhnhytqkslslslgksggpGPAG
LYAQpgselcdddpeiphatfkamaykegtmlnceckrgfrriksgslymlctgnshsswdnqcqctssatrnttkq
vtpqpeeqkerkttemqspmqpvdqaslpqhcreppwenaeteriyhfvvgqmvyyqcvggyralhrgpaesvck
mthgktrwtqpqlictgemetsqfpgeekpqaspegrpeetsslvtttdfqiqtemaatmetsifftteyqgggsggggsg
gggsggggsggggsggggsggggsggpGPAGLYAQpgsaptssstkktqlqlehllldlqmilnginmyknpkltrmltfk
fympkkatelkhlqcleeelkpleevlnlaqsknfhlrprdlisninivlvlelkgsettfmceyadetativeflnrwitfcqsiis
tltgggsgggsggggsggggsggggsggggsggpGPAGLYAQpgsevqllesgglyqpgggslrlscaaserif
stdvmgwyrqapgkqrelvavvsargtnyldavkgrftisrdnskntlylqmnslraedtavycyvrettspwriywgg
gtlvtvss**
```

-continued

SEQUENCE TABLE

| SEQ ID NO. | Name | Sequence |
|---|---|---|
| 418 | ACP360 | EVQLVESGGGLVQPGGSLRLSCAASGFTFSSYTLAWVRQAPGKGLEWVAAIDSS SYTYSPDTVRGRFTISRDNAKNSLYLQMNSLRAEDTAVYYCARDSNWDALDYW GQGTTVTVSSggggggggggggggsDIQMTQSPSSLSASVGDRVTITCKASQNVGTNV GWYQQKPGKAPKSLIYSASFRYSGVPSRFSGSGSGTDFTLTISSLQPEDFATYYCQ QYYTYPYTFGGGTKVEIKHHHHHH** |
| 419 | ACP361 | EVQLVESGGGLVQPGGSLRLSCAASGFTFSSYTLAWVRQAPGKGLEWVAAIDSS SYTYSPDTVRGRFTISRDNAKNSLYLQMNSLRAEDTAVYYCARDSNWDALDYW GQGTTVTVSSsggpGPAGLYAQpgsDIQMTQSPSSLSASVGDRVTITCKASQNVGT NVGWYQQKPGKAPKALIYSASFRYSGVPSRFSGSGSGTDFTLTISSLQPEDFATY YCQQYYTYPYTFGGGTKVEIKHHHHHH** |
| 420 | ACP362 | EVQLVESGGGLVQPGGSLRLSCAASGFTFSSYTLAWVRQAPGKGLEWVAAIDSS SYTYSPDTVRGRFTISRDNAKNSLYLQMNSLRAEDTAVYYCARDSNWDALDYW GQGTTVTVSSsggpGPAGLYAQpgsDIQMTQSPSSLSASVGDRVTITCKASQNVGT NVGWYQQKPGKAPKSLIYSASFRYSGVPSRFSGSGSGTDFTLTISSLQPEDFATYY CQQYYTYPYTFGGGTKVEIKHHHHHH** |
| 421 | ACP200 | lveepknlvktncdlyeklgeygfqnailvryrtqkapqvstptlveaarnlgrvgtkcctlpedqrlpcvedylsail nrvcllhektpvsehvtkccsgslverrpcfsaltvdetyvpkefkaetffhsdictlpekekqikkqtalaelvkh kpkataeqlktvmddfaqfldtcckaadkdtcfstegpnlvtrckdalaSGGPGAGMKGLPGScdlp qthnlrnkraltllvqmrrlsplsclkdrkdfgfpqekvdaqqikkapipvlseltqqilnifstskdssaawnttlld sfcndlhqqlndlgqclmqqvgvqefpltqedallavrkyfhritvylrekkhspcawevvraevvralsssan vlgrlreekSGGPGAGMKGLPGSlveepknlvktncdlyeklgeygfqnailvrytqkapqvstptl veaarnlgrvgtkcctlpedqrlpcvedylsailnrvcllhektpvsehytkccsgslverrpcfsaltvdetyvpke fkaetffhsdictlpekekqikkqtalaelvkhkpkataeqlktvmddfaqfldtcckaadkdtcfstegpnlvtrc kdalaHHHHHH** |
| 422 | ACP201 | eahkseiahryndlgeqhfkglvliafsqylqkcsydehaklvgevtdfaktcvadesaancdkslhtlfgdklcaipnlren ygeladcctkqepernecflqhkddnpslppferpeaeamctsfkenpttfmghylhevarrhpyfyapellyyaeqynei ltqccaeadkescltpkldgykekalvssyrqGGGSGGGGSGGGGSlveepknlvktncdlyeklgeygfqnailvr ytqkapqvstptlveaarnlgrvgtkcctlpedqrlpcvedylsailnrycllhektpvsehvtkccsgslverrpcfsaltvdet yvpkefkaetffhsdictlpekekqikkqtalaelvkhkpkataeqlktvmddfaqfldtcckaadkdtcfstegpnlvtrck dalaSGGPGAGMKGLPGScdlpqthnlmkraltllvqmrrlsplckdrkdfgfpqekvdaqqikkapipvl seltqqilnifstskdssaawnttlldsfcndlhqqlndlgqclmqqvgvqefpltqedallavrkyfhritvylrekkhspcaw evvraevvralsssanvlgrlreekSGGPGAGMKGLPGSeahkseiahryndlgeqhfkglvliafsqylqkcs ydehaklvgevtdfaktcvadesaancdkslhtlfgdklcaipnlrenygeladcctkqepernecflqhkddnpslppfer peaeamctsfkenpttfmghylhevarrhpyfyapellyyaeqyneiltqccaeadkescltpkldgykekalvssyrqG GGSGGGGSGGGGSlveepknlvktncdlyeklgeygfqnailvrytqkapqvstptlveaarnlgrvgtkcctlpedq rlpcvedylsailnrvcllhektpvsehvtkccsgslverrpcfsaltvdetyvpkefkaetffhsdictlpekekqikkqtala elvkhkpkataeqlktvmddfaqfldtcckaadkdtcfstegpnlytrckdalaHHHHHH** |
| 423 | ACP202 | EVQLVESGGGLVQPGNSLRLSCAASGFTFSKFGMSWVRQAPGKGLEWVSSISGS GRDTLYAESVKGRFTISRDNAKTTLYLQMNSLRPEDTAVYYCTIGGSLSVSSQGT LVTVSSggggsggGSGGPGAGMKGLPGSgggsgggsggscdlpqthnlmkraltllvqmrrlsplsclkdrk dfgfpqekvdaqqikkapipvlseltqqilnifstskdssaawnttlldsfcndlhqqlndlgqclmqqvgvqefpltqedall avrkyfhritvylrekkhspcawevvraevvralsssanvlgrlreekgggsgggsgggSGGPGAGMKGLPGSgg ggsgggsEVQLVESGGGLVQPGNSLRLSCAASGFTFSKFGMSWVRQAPGKGLEWV |

-continued

SEQUENCE TABLE

| SEQ ID NO. | Name | Sequence |
|---|---|---|
| 424 | ACP203 | SSISGSGRDTLYAESVKGRFTISRDNAKTTLYLQMNSLRPEDTAVYYCTIGGSLS VSSQGTLVTVSSHHHHHH** |
| 425 | ACP204 | EVQLVESGGGLVQPGNSLRLSCAASGFTFSKFGMSWVRQAPGKGLEWVSSISGS GRDTLYAESVKGRFTISRDNAKTTLYLQMNSLRPEDTAVYYCTIGGSLSVSSQGT LVTVSSsggpGPAGLYAQpgscdlpqthnlrnkraltllvqmrlsplsclkdrkdfgfpqekvdaqqikkaqai pvlseltqqilniftskdssaawnttlldsfcndlhqqlndlggclmqqvqvqefpltqedallavrkyfhritvvlrekkhspc awevvraevwralsssanvlgrlreeksggpPAGLYAQpgsEVQLVESGGGLVQPGNSLRLSCA ASGFTFSKFGMSWVRQAPGKGLEWVSSISGSGRDTLYAESVKGRFTISRDNAKT TLYLQMNSLRPEDTAVYYCTIGGSLSVSSQGTLVTVSS** |
| 426 | ACP205 | EVQLVESGGGLVQPGNSLRLSCAASGFTFSKFGMSWVRQAPGKGLEWVSSISGS GRDTLYAESVKGRFTISRDNAKTTLYLQMNSLRPEDTAVYYCTIGGSLSVSSQGT LVTVSSsggpALFKSSFPpgscdlpqthnlrnkraltllvqmrlsplsclkdrkdfgfpqekvdaqqikkaqaipv lseltqqilniftskdssaawnttlldsfcndlhqqlndlggclmqqvqvqefpltqedallavrkyfhritvylrekkhspcaw evvraevwralsssanvlgrlreeksggpALFKSSFPpgsEVQLVESGGGLVQPGNSLRLSCAAS GFTFSKFGMSWVRQAPGKGLEWVSSISGSGRDTLYAESVKGRFTISRDNAKTTL YLQMNSLRPEDTAVYYCTIGGSLSVSSQGTLVTVSS** |
| 427 | ACP206 | EVQLVESGGGLVQPGNSLRLSCAASGFTFSKFGMSWVRQAPGKGLEWVSSISGS GRDTLYAESVKGRFTISRDNAKTTLYLQMNSLRPEDTAVYYCTIGGSLSVSSQGT LVTVSSsggpPLAQKLKSSpgscdlpqthnlrnkraltllvqmrrlsplsclkdrkdfgfpqekvdaqqikkaqai pvlseltqqilniftskdssaawnttlldsfcndlhqqlndlggclmqqvqvqefpltqedallavrkyfhritvylrekkhspc awevvraevwralsssanvlgrlreeksggpPLAQKLKSSpgsEVQLVESGGGLVQPGNSLRLSC AASGFTFSKFGMSWVRQAPGKGLEWVSSISGSGRDTLYAESVKGRFTISRDNAK TTLYLQMNSLRPEDTAVYYCTIGGSLSVSSQGTLVTVSS** |
| 428 | ACP207 | EVQLVESGGGLVQPGNSLRLSCAASGFTFSKFGMSWVRQAPGKGLEWVSSISGS GRDTLYAESVKGRFTISRDNAKTTLYLQMNSLRPEDTAVYYCTIGGSLSVSSQGT LVTVSSsggpGPAGLYAQpgscdlpqthslgsrrtlmllaqmrislfsclkdrhdfgfpqeefgnqfqkaetipvl hemiqqifnlfstkdssaawdetlldkfytelyqqlndleacviqgvgvtetplmkedsilavrkyfqritlylkekkyspca wevvraeimrfslstnlqeslrskesggpGPAGLYAQpgsEVQLVESGGGLVQPGNSLRLSCAA SGFTFSKFGMSWVRQAPGKGLEWVSSISGSGRDTLYAESVKGRFTISRDNAKTT LYLQMNSLRPEDTAVYYCTIGGSLSVSSQGTLVTVSS** |
| 429 | ACP208 | EVQLVESGGGLVQPGNSLRLSCAASGFTFSKFGMSWVRQAPGKGLEWVSSISGS GRDTLYAESVKGRFTISRDNAKTTLYLQMNSLRPEDTAVYYCTIGGSLSVSSQGT LVTVSSsggpALFKSSFPpgscdlpqthslgsrrtlmllaqmrislfsclkdrhdfgfpqeefgnqfqkaetipvlh emiqqifnlfstkdssaawdetlldkfytelyqqlndleacviqgvgvtetplmkedsilavrkyfqritlylkekkyspcaw evvraeimrfslstnlqeslrskesggpALFKSSFPpgsEVQLVESGGGLVQPGNSLRLSCAASG FTFSKFGMSWVRQAPGKGLEWVSSISGSGRDTLYAESVKGRFTISRDNAKTTLY LQMNSLRPEDTAVYYCTIGGSLSVSSQGTLVTVSS** |
| 429 | ACP208 | EVQLVESGGGLVQPGNSLRLSCAASGFTFSKFGMSWVRQAPGKGLEWVSSISGS GRDTLYAESVKGRFTISRDNAKTTLYLQMNSLRPEDTAVYYCTIGGSLSVSSQGT LVTVSSsggpPLAQKLKSSpgscdlpqthslgsrrtlmllaqmrislfsclkdrhdfgfpqeefgnqfqkaetipv lhemiqqifnlfstkdssaawdetlldkfytelyqqlndleacviqgvgvtetplmkedsilavrkyfqritlylkekkyspca wevvraeimrfslstnlqeslrskesggpPLAQKLKSSpgsEVQLVESGGGLVQPGNSLRLSCAA |

-continued

SEQUENCE TABLE

| SEQ ID NO. | Name | Sequence |
|---|---|---|

430 ACP211

SGFTFSKFGMSWVRQAPGKGLEWVSSISGSGRDTLYAESVKGRFTISRDNAKTT
LYLQMNSLRPEDTAVYYCTIGGSLSVSSQGTLVTVSS**

EVQLVESGGGLVQPGNSLRLSCAASGFTFSKFGMSWVRQAPGKGLEWVS
SISGSGRDTLYAESVKGRFTISRDNAKTTLYLQMNSLRPEDTAVYYCTIG
GSLSVSSQGTLVTVSSSGGPGAGMKGLPGShgtviesleslnnyfnssgidveeksIfldi
wrnwqkdgdmkilqsqiisfylrifevlkdnqaisnnisvieshlittfsnskakkdafmsiakfevnnpqvqr
qafnelirvvhqllpesslrkrkrsrcSGGPGAGMKGLPGScdlpqthnlrnkraltllvqmrrlsplsc
lkdrkdfgfpqekvdaqqikkapipvlseltqqilniftskdssaawntlldsfcndlhqqindlqgclmqqvg
vgefpltqedallavrkyfhrityIrekkhspcawevvraevwralsssanvlgrlreekSGGPGPAGM
KGLPGShgtvieslesInnyfnssgidveeksIfldiwrnwqkdgdmkilqsqiisfylrifevlkdnqaismn
isvieshlittfsnskakkdafmsiakfevnnpqvqrqafnelirvvhqllpesslrkrkrsrcSGGPGPAG
MKGLPGSEVQLVESGGGLVQPGNSLRLSCAASGFTFSKFGMSWVRQAPG
KGLEWVSSISGSGRDTLYAESVKGRFTISRDNAKTTLYLQMNSLRPEDTA
VYYCTIGGSLSVSSQGTLVTVSSSHEIREIREI

431 ACP213 lveepknlvktncdlyeklgeygfqnailvrytqkapqvstplveaarnlgrvgtkcctlpedqrlpcvedylsail
nrvcllhektpvsehvtkccsgslverrpcfsaltvdetyvpkefkaetfthsdictlpekektgikkqtalaelvkh
kpkataeqlktvmddfaqfldtcckaadkdtcfstegpnlvtrckdalaSGGPGAGMKGLPGShgt
vieslesInnyfnssgidveeksIfldiwrnwqkdgdmkilqsqiisfylrlfevlkdnqaisnnisvieshlittffs
nskakkdafmsiakfevnnpqvqrqafnelirvvhqllpesslrkrkrsrcSGGPGAGMKGLPGSlv
eepknlvktncdlyeklgeygfqnailvrytqkapqvstplveaarnlgrvgtkcctlpedqrlpcvedylsailn
rvcllhektpvsehvtkccsgslverrpcfsaltvdetyvpkefkaetfthsdictlpekekqikkqtalaelvkhk
pkataeqlktvmddfaqfldtcckaadkdtcfstegpnlvtrckdalaSGGPGAGMKGLPGShgtvi
eslesInnyfnssgidveeksIfldiwrnwqkdgdmkilqsqiisfylrlfevlkdnqaisnnisvieshlittffsns
kakkdafmsiakfevnnpqvqrqafnelirvvhqllpesslrkrkrsrcSGGPGAGMKGLPGSlvee
pknlvktncdlyeklgeygfqnailvrytqkapqvstplveaarnlgrvgtkcctlpedqrlpcvedylsailnrv
cllhektpvsehvtkccsgslverrpcfsaltvdetyvpkeflcaetfthsdictlpekekqikkqtalaelvkhkpk
ataeqlktvmddfaqfldtcckaadkdtcfstegpnlvtrckdalaHHHHHH**

432 ACP214 eahkseiahryndlgeqhfkglvliafsqylqkcsydehaklyqevtdfaktcvadesaancdkslhtlfgdklcaipnlren
ygeladcctkqepernecflqhkddnpslppferpeaeamctsfkenpttfmghylhevarrhpyfyapellyyaeqynei
ltqccaeadkescltpkldgykekalvssvrqGGGSGGGGSGGGGSlveepknlvktncdlyeklgeygfqnailvr
ytqkapqvstplveaarnlgrvgtkcctlpedqrlpcvedylsailnrvcllhektpvsehvtkccsgslverrpcfsaltvdet
yypkefkaetfthsdictlpekekqikkqtalaelvkhkpkataeqlktvmddfaqfldtcckaadkdtcfstegpnlvtrck
dalaSGGPGPAGMKGLPGshgtviesleslnnyfnssgidveeksIfldiwrnwqkdgdmkilqsqiisfylrlfe
vlkdnqaisnnisvieshlittffsnskakkdafmsiakfevnnpqvqrqafnelirvvhqllpesslrkrkrsrcSGGPGP
AGMKGLPGSeahkseiahryndlgeqhfkglvliafsqylqkcsydehaklyqevtdfaktcvadesaancdkslht
lfgdklcaipnlrenygeladcctkqepernecflqhkddnpslppferpeaeamctsfkenpttfmghylhevarrhpyfy
apellyyaeqyneiltqccaeadkescltpkldgvkekalvssvrqGGGSGGGGSGGGGSlveepknlvktncdly
eklgeygfqnailvrytqkapqvstplveaarnlgrvgtkcctlpedqrlpcvedylsailnrvcllhektpvsehvtkccsgs
lverrpcfsaltvdetyypkefkaetfthsdictlpekekqikkqtalaelvkhkpkataeqlktvmddfaqfldtcckaadk
dtcfstegpnlvtrckdalaSGGPGPAGMKGLPGshgtviesleslnnyfnssgidveeksIfldiwrnwqkdgd
mkilqsqiisfylrlfeylkdnqaisnnisvieshlittffsnskakkdafmsiakfevnnpqvqrqafnelirvvhqllpesslr
krkrsrcSGGPGPAGMKGLPGSeahkseiahryndlgeqhfkglvliafsqylqkcsydehaklyqevtdfaktc
vadesaancdkslhtlfgdklcaipnlrenygeladcctkqepernecflqhkddnpslppferpeaeamctsfkenpttfm
ghylhevarrhpyfyapellyyaeqyneiltqccaeadkescltpkldgvkekalvssvrqGGGSGGGGSGGGGS1
veepknlvktncdlyeklgeygfqnailvrytqkapqvstplveaarnlgrvgtkcctlpedqrlpcvedylsailnrvcllhe -continued

SEQUENCE TABLE

| SEQ ID NO. | Name | Sequence |
|---|---|---|
| 433 | ACP215 | ktpvsehvtkccsglverrpcfsaltvdetyrpkefkaetfthsdictlpekekqikkqtalaelvkhkpkataeqlktvmd<br>dfaqfldtcckaadkdtcfstegpnlvtrckdalaHHHHHH** |
| 433 | ACP215 | EVQLVESGGGLVQPGNSLRLSCAASGFTFSKFGMSWVRQAPGKGLEWVSSISGS<br>GRDTLYAESVKGRFTISRDNAKTTLYLQMNSLRPEDTAVYYCTIGGSLSVSSQGT<br>LVTVSSgggsgggsSGGPGAGMKGLPGSgggsgggshgtvieslesInnyfnssgidveeksIfIdiwr<br>nwqkdgdmkilqsqiisfyIrlfevlkdnqaismnisvieshlittffsnskakkdafmsiakfevmnpqvrqafnelirvv<br>hqllpessIrkrkrsrcgggsgggsSGGPGAGMKGLPGSgggsgggsEVQLVESGGGLVQPGN<br>SLRLSCAASGFTFSKFGMSWVRQAPGKGLEWVSSISGSGRDTLYAESVKGRFTIS<br>RDNAKTTLYLQMNSLRPEDTAVYYCTIGGSLSVSSQGTLVTVSSgggsgggsSGGP<br>GPAGMKGLPGSgggsgggsghgtvieslesInnyfnssgidveeksIfIdiwrnwqkdgdmkilqsqiisfyIrlfe<br>vlkdnqaismnisvieshlittffsnskakkdafmsiakfevmnpqvrqafnelirvvhqllpessIrkrkrsrcgggsgggg<br>SGGPGAGMKGLPGSgggsgggsEVQLVESGGGLVQPGNSLRLSCAASGFTFSKFG<br>MSWVRQAPGKGLEWVSSISGSGRDTLYAESVKGRFTISRDNAKTTLYLQMNSLR<br>PEDTAVYYCTIGGSLSVSSQGTLVTVSSHHHHHH** |
| 434 | ACP240 | EVQLVESGGGLVQPGNSLRLSCAASGFTFSKFGMSWVRQAPGKGLEWVS<br>SISGSGRDTLYAESVKGRFTISRDNAKTTLYLQMNSLRPEDTAVYYCTIG<br>GSLSVSSQGTLVTVSSgggsgggsgggsiwelkdvyvveldwypdapgemvvltcdtpee<br>dgitwtldqssevlgsgktltiqvkefgdagqytchkggevlshslllhkkedgiwstdilkdqkepknktflrce<br>aknysgrftcwwlttistdltfsvkssrgssdpgqvtcgaatlsaerrvrgdnkeyeyvecqedsacpaaeeslpie<br>vmvdavhklkyenytssffirdiikrpdppknlqlkplknsrqvevsweypdtwstphsyfsltfcvqvggkskr<br>ekkdrvftdktsatvicrknasisvraqdryysssweavspcsgggsgggsgggsrvipvsqparclsq<br>srnllkttddmvktareklkhysctaedidhediirdqtstlktclplelhknesclatretsstrgsclppqktslmm<br>tlclgsiyedlkmyqtefqainaalqnhnhqqiildkgmlvaidelmgslnhngetlrqkppvgeadpyrvkm<br>klcillhafstrvvtinrvmgylsaggggsgggsgggsgggsgggsgggsgggsgggsgggsgggsgggsQ<br>SVLTQPPSVSGAPGQRVTISCSGSRSNIGSNTVKHYQQLPGTAPKLLIYYN<br>DQRPSGVPDRFSGSKSGTSASLAITGLQAEDEADYYCQSYDRYTHPALLF<br>GTGTKVTVLgggsgggsgggsgggsgQVQLVESGGVVQPGRSLRLSCAASGFTFS<br>SYGMHWVRQAPGKGLEWVAFIRYDGSNKYADSVKGRFTISRDNSKNT<br>LYLQMNSLRAEDTAVYYCKTHGSHDNWGQGTMVTVSSHRHHHH |
| 435 | ACP241 | EAHKSEIAHRYNDLGEQHFKGLVLIAFSQYLQKCCSYDEHAKLVQEVTDF<br>AKTCVADESAANCDKSLHTLFGDKLCAIPNLRENYGELADCCTKQEPER<br>NECFLQHKDDNPSLPPFERPEAEAMCTSFKENPTTFMGHYLHEVARRHPY<br>FYAPELLYYAEQYNEILTQCCAEADKESCLTPKLDGVKEKALVSSVRQR<br>MKCSSMQKFGERAFKAWAVARLSQTFPNADFAEITKLATDLTKVNKECC<br>HGDLLECADDRAELAKYMCENQATISSKLQTCCDKPLLKKAHCLSEVEH<br>DTIVIPADLPAIAADFVEDQEVCKNYAEAKDVFLGTFLYEYSRRHPDYSVS<br>LLLRLAKKYEATLEKCCAEANPPACYGTVLAEFQPLVEERPKNLVKTNCD<br>LYEKLGEYGFQNAILVRYTQKAPQVSTPTIVEAARNLGRVGTKCCTLPE<br>DQRLPCVEDYLSAILNRVCLLHEKTPVSEHVTKCCSGSLVERRPCFSALT<br>VDETYVPKEFKAEITFTHSDICTLPEKEKQIKKQTALAELVKHKPKATAE<br>QLKTVMDDFAQFLDTCCKAADKDTCFSTEGPNLVTRCKDALASCGPGPA<br>GMKGLPGSiwelkdvyvveldwypdapgemvvltcdtpeedgitwtldqssevlgsgktltiqvkefg<br>daggytchkggevlshslllhkkedgiwstdilkdqkepknktflrceaknysgrftcwwlttistdltfsvkssrg<br>ssdpgqvtcgaatlsaerrvrgdnkeyeyvecqedsacpaaeeslpievmvdavhklkyenytssffirdiikpd<br>ppknlqlkplknsrqvevsweypdtwstphsyfsltfcvqvggkskrekkdrvftdktsatvicrknasisvraq |

-continued

SEQUENCE TABLE

| SEQ ID NO. | Name | Sequence |
|---|---|---|
| | | dryysswsewasvpcsggggsggggsggggsrvipvsgparclsqsrnllktddmvktareklkhysctae |
| | | didhedltrdqtstlktclplelhknesclatretssttrgsclppqktslmmtlclgsiyedlkmyqtefqainaalqn |
| | | hnhqqiildkgmlvaidelmqslnhngetlrqkppvgeadpyrvkmlcillhafstrvvtinrvmgylssaS |
| | | GGPGPAGMKGLPGSggggsggggsggggsggggsggggsggggsgQSVLTQPPSVSGAP |
| | | GQRVTISCSGSRSNIGSNTVKWYQQLPGTAPKLLIYYNDQRPSGVPDRFS |
| | | GSKSGTSASLAITGLQAEDEADYYCQSYDRYTHPALLFGTKVTVLgggg |
| | | sgggsggggsQVQLVESGGGVVQPGRSLRLSCAASGFTFSSYGMHWVRQAP |
| | | GKGLEWVAFIRYDGSNKYADSVKGRFTISRDNSKNTLYLQMNSLRAED |
| | | TAVYYCKTHGSHDNWGQGTMVTVSSHHHHHH** |
| 436 | ACP242 | iwelkkdvyvveldwypdapgemvltcdtpeedgitwtldqssevlgsqktltiqvkefgdagqytchkggevlshsll1 |
| | | lhkkedgiwstdilkdqkepknktflrceaknysgrftcwwlttistdltfsvkssrgssdpqgtvtcgaatlsaervrgdnkey |
| | | eysvecqedsacpaaeeslpievmdavhklkyenytssffirdiikpdppkniqlkpplknsrqvevsweypdtwstphs |
| | | yfsltfcvqvqgkskrekkdrvfdktsatvicrknasisvraqdryysswsewasvpcsggggsggggsggggsrvipv |
| | | sgparclsqsrnllktddmvktareklkhysctaedidheditrdqtstlktclplelhknesclatretssttrgsclppqktslm |
| | | mtlclgsiyedlkmyqtefqainaalqnhnhqqiildkgmlvaidelmqslnhngetlrqkppvgeadpyrvkmlcillh |
| | | afstrvvtinrvmgylssaSGGPGPAGMKGLPGSggggsggggsggggsggggsggggsQSVLT |
| | | QPPSVSGAPGQRVTISCSGSRSNIGSNTVKWYQQLPGTAPKLLIYYNDQRPSGVP |
| | | DRFSGSKSGTSASLAITGLQAEDEADYYCQSYDRYTHPALLFGTKVTVLggggs |
| | | ggggsggggsQVQLVESGGGVVQPGRSLRLSCAASGFTFSSYGMHWVRQAPGKGLE |
| | | WVAFIRYDGSNKYADSVKGRFTISRDNSKNTLYLQMNSLRAEDTAVYYCKTH |
| | | GSHDNWGQGTMVTVSSSGGPGPAGMKGLPGSEAHKSEIAHRYNDLGEQHFKGL |
| | | VLIAFSQYLQKCSYDEHAKLVQEVTDFAKTCVADESAANCDKSLHTLFGDKLC |
| | | AIPNLRENYGELADCCTKQEPERNECFLQHKDDNPSLPPFERPEAEAMCTSFKEN |
| | | PTTFMGHYLHEVARRHPYFYAPELLYYAEQYNEILTQCCAEADKESCLTPKLDG |
| | | VKEKALVSSVRQRMKCSSMQKFGERAFKaWAVARLSQTFPNADFAEITKLATD |
| | | LTKVNKECHGDLLECADDRAELAKYMCENQATISSKLQTCCDKPLLKKAHCL |
| | | SEVEHDTMPADLPAIAADFVEDQEVCKNYAEAKDVFLGTFLYEYSRRHPDYSVS |
| | | LLLRLAKKYEATLEKCCAEANPPACYGTVLAEFQPLVEBPKNLVKTNCDLYEKL |
| | | GEYGFQNALLVRYTQKAPQVSTPLIVEAARNLGRVGTKCCTLPEDQRLPCVEDY |
| | | LSAILNRVCLLHEKTPVSEHVTKCCSGSLVERRPCFSALTVDETYVPKEFKAEITFT |
| | | FHSDICTLPEKEKQIKKQTALAELVKHKPKATAEQLKTVMDDFAQFLDTCCKAA |
| | | DKDTCFSTEGPNLVTRCKDALAHHHHHH** |
| 437 | ACP243 | vprdcgckpcictvpevssvfifppkpkdvltltltpkvtcvvvdiskddpevqfswfvddvevhtaqtqpreeqfnstfrsv |
| | | selpimhqdvlngkefkcrvnsaafpapiektiskfgrpkapqvytippkeqmakdkvsltcmitdfipedtvewq |
| | | wngqpaenykntqpimdtdqsyfvysklnvqksnweagntftcsvlheglnhhtekslshspgkSGGPGPAGM |
| | | KGLPGSiwelkkdvyvveldwypdapgemvltcdtpeedgitwtldqssevlgsqktltiqvkefgdagqytchkg |
| | | gevlshslllhkkedgiwstdilkdqkepknktflrceaknysgrftcwwlttistdltfsvkssrgssdpqgtvtcgaatlsaer |
| | | vrgdnkeyeysvecqedsacpaaeeslpievmdavhklkyenytssffirdiikpdppkniqlkplknsrqvevsweyp |
| | | dtwstphsyfsltfcvqvqgkskrekkdrvfdktsatvicrknasisvraqdryysswsewasvpcsggggsggggsgg |
| | | ggsrvipvsgparclsqsrnllktddmvktareklkhysctaedidheditrdqtstlktclplelhknesclatretssttrgscl |
| | | ppqktslmmtlclgsiyedlkmyqtefqainaalqnhnhqqiildkgmlvaidelmqslnhngetlrqkppvgeadpyrv |
| | | kmklcillhafstrvvtinrvmgylssaSGGPGPAGMKGLPGSggggsggggsggggsggggsggggs |
| | | sQSVLTQPPSVSGAPGQRVTISCSGSRSNIGSNTVKWYQQLPGTAPKLLIYYNDQ |
| | | RPSGVPDRFSGSKSGTSASLAITGLQAEDEADYYCQSYDRYTHPALLFGTGTKVT |
| | | VLggggsggggsggggsggggsQVQLVESGGGVVQPGRSLRLSCAASGFTFSSYGMHWVRQA |

-continued

SEQUENCE TABLE

| SEQ ID NO. | Name | Sequence |
|---|---|---|
| 438 | ACP244 | PGKGLEWVAFIRYDGSNKYYADSVKGRFTISRDNSKNTLYLQMNSLRAEDTAV<br>YYCKTHGSHDNWGQGTMVTVSSHHHHHH** |
| 439 | ACP245 | iwelkkdvyveldwypdapgemvvltcdtpeedgitwtldqssevlgsgktltiqvkefgdaggytchkggevlshslll<br>lhktedgiwstdilkdqkepknktflrceaknysgrftcwwlttistdltfsvksrsgssdpqgvtcgaatlsaervrgdnkey<br>eysvecqedsacpaaeeslpievmvdavhklkyenytssffirdiikpdppknlqlkplknsrqvevsweypdtwstphs<br>yfsltcvqvqgkskrekkdrvftdktsatvicrknasisvraqdyyssswsewasvpcsgggsgggsggggsrvipv<br>sgparclsqsrnllkttddmvktareklkhysctaedidheditrdqstlktclplelhknesclatretssttrgsclppqktslm<br>mtlclgsiyedlkmyqtefqainaalqnhnhqqiilkdkqmlvaidelmqslnhnqetlrqkppygeadpyrvkmklcillh<br>afstrvvtlnrvmgylssaSGGPGAGMKGLPGsgggsgggsgggsgggsgggsgggsgggsgggsQSVLT<br>QPPSVSGAPGQRVTISCSGSRSNIGSNTVKWYQQLPGTAPKLLIYYNDQRPSGVP<br>DRFSGSKSGTSASLAITGLQAEDEADYYCQSYDRYTHPALLFGTGTKVTVLggggs<br>gggsgggsgggsQVQLVESGGGVVQPGRSLRLSCAASGFTFSSYGMHWVRQAPGKGLE<br>WVAFIRYDGSNKYYADSVKGRFTISRDNSKNTLYLQMNSLRAEDTAVYYCKTH<br>GSHDNWGQGTMVTVSSGGPGAGMKGLPGsvprdcgckpcictypevssvfifppkpkdvltit<br>ltpkvtcvvvdiskddpevqfswfvddvevhtaqtqpreeqfnstfrsvselpimhqdwlngkefkcrvnsaafpapiekt<br>isktkgrpkapqvytipppkeqmakdkvsltcmitdffpeditvewqwngqpaenykntqpimdtdgsyfyysklnvq<br>ksnweagnthcsylheglhnhhtekslshspgkHHHHHH** |
| 440 | ACP247 | EVQLVESGGGLVQPGNSLRLSCAASGFTFSKFGMSWVRQAPGKGLEWVS<br>SISGSGRDTLYAESVKGRFTISRDNAKTTLYLQMNSLRPEDTAVYYCTIG<br>GSLSVSSQGTLVTVSSSGGPGPAGMKGLPGSiwelkkdvyvveldwypdapgemvvl<br>tcdtpeedgitwtldqssevlgsgktltiqvkefgdaggytchkggevlshslllllhhkedgiwstdilkdqkepk<br>nktflrceaknysgrftcwwlttistdltsvksrsgssdpqgvtcgaatlsaervrgdnkeyeysvecqedsacpa<br>aeeslpievmvdavhklkyenytssffirdiikpdppknlqlkplknsrqvevsweypdtwstphsyfsltfcvq<br>vggkskrekkdrvftdktsatvicrknasisvraqdryysssewasvpcsgggsgggsgggsgggsrvipvs<br>gparclsqsrnllkttddmvktareklkhysctaedidheditrdqtstlktclplelhknesclatretssttrgsclpp<br>qktslmmtlclgsiyedlkmyqtefqainaalqnhnhqqiildkqmlvaidelmqslnhngetlrqkppygea<br>dpyrvkmklcillhafstrvvtlnrvmgylssaSGGPGAGMKGLPGSgggsgggsgggsgggsggg<br>TAPKLLIYYNDQRPSGVPDRFSGSKSGTSASLAITGLQAEDEADYYCQSY<br>DRYTHPALLFGTGTKVTVLSGGPGAGMKGLPGSQVQLVESGGGVVQP<br>GRSLRLSCAASGFTFSSYGMHWVRQAPGKGLEWVAFIRYDGSNKYYAD<br>SVKGRFTISRDNSKNTLYLQMNSLRAEDTAVYYCKTHGSHDNWGQGTM<br>VTVSSHHHHHH |
| 440 | ACP247 | EVQLVESGGGLVQPGNSLRLSCAASGFTFSKFGMSWVRQAPGKGLEWVS<br>SISGSGRDTLYAESVKGRFTISRDNAKTTLYLQMNSLRPEDTAVYYCTIG<br>GSLSVSSQGTLVTVSSSGGPGPAGMKGLPGSiwelkkdvyvveldwypdapgemvvl<br>tcdtpeedgitwtldqssevlgsgktltiqvkefgdaggytchkggevlshslllllhhkedgiwstdilkdqkepk<br>nktflrceaknysgrftcwwlttistdltsvksrsgssdpqgvtcgaatlsaervrgdnkeyeysvecqedsacpa<br>aeeslpievmvdavhklkyenytssffirdiikpdppknlqlkplknsrqvevsweypdtwstphsyfsltfcvq<br>vggkskrekkdrvftdktsatvicrknasisvraqdryysssewasvpcsgggsgggsgggsgggsrvipvs<br>gparclsqsrnllkttddmvktareklkhysctaedidheditrdqtstlktclplelhknesclatretssttrgsclpp<br>qktslmmtlclgsiyedlkmyqtefqainaalqnhnhqqiildkqmlvaidelmqslnhngetlrqkppygea<br>dpyrvkmklcillhafstrvvtlnrvmgylssaSGGPGAGMKGLPGSgggsgggsgggsgggsggg<br>gsgggsgggsgggsQVQLQESGGGLVQAGGSLRLSCAASGRTFSSVVDMGWFRQ |

-continued

SEQUENCE TABLE

| SEQ ID NO. | Name | Sequence |
|---|---|---|
| | | APGKDREFVARITESARNTRYADSVRGRFTISRDNAKNTVYLQMNNLEL EDAAVYYCAADPQTVVGTPDYWGQGTQVTVSSHHHHHH |

INCORPORATION BY REFERENCE

The entire disclosures of all patent and non-patent publications cited herein are each incorporated by reference in their entireties for all purposes.

OTHER EMBODIMENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

---

The invention claimed is:

1. A conditionally active IL-18 comprising a fusion polypeptide comprising at least one of each of:

a) A human IL-18 polypeptide [A];

b) an IL-18 blocking moiety [D], wherein the IL-18 blocking moiety [D] comprises an antibody or antigen-binding fragment that binds the IL-18 polypeptide, a ligand-binding domain or fragment of a cognate receptor for the IL-18 polypeptide;

c) a half-life extension element [H], wherein the half-life extension element [H] is a human serum albumin, an antigen-binding polypeptide that binds serum albumin, or an immunoglobulin Fc; and d) a protease cleavable polypeptide linker [L];

wherein the conditionally active cytokine has attenuated IL-18 receptor activating activity that is at least about 10-fold less than the IL-18 receptor activating activity of the polypeptide that contains the IL-18 polypeptide that is produced by cleavage of the protease cleavable linker.

2. The conditionally active cytokine of claim 1, wherein the IL-18 blocking moiety [D] is an antibody fragment that binds to the IL-18 polypeptide and the antibody fragment is a single domain antibody, a Fab or scFv that binds the IL-18 polypeptide.

3. The conditionally active cytokine of claim 1, wherein the IL-18 blocking moiety inhibits the cytokine polypeptide from activating its cognate receptor.

4. The conditionally active cytokine comprising of claim 1, wherein the protease cleavable linker comprises a sequence that is capable of being cleaved by a protease selected from the group consisting of a kallikrein, thrombin, chymase, carboxypeptidase A, an elastase, PR-3, granzyme M, a calpain, a matrix metalloproteinase (MMP), an ADAM, a FAP, a plasminogen activator, a cathepsin, a caspase, a tryptase, and a tumor cell surface protease.

5. The conditionally active cytokine of claim 1, wherein the protease cleavable polypeptide linker independently comprises two or more cleavage sites for the same protease, or two or more cleavage sites that are cleaved by different proteases or at least one of the protease-cleavable polypeptides comprises a cleavage site for two or more different proteases.

6. The conditionally active cytokine of claim 1, wherein the protease cleavable polypeptide linker comprises a sequence that is cleaved by cathepsin selected from the group consisting of cathepsin B, cathepsin C, cathepsin D, cathepsin E, cathepsin K, cathepsin L, and cathepsin G.

7. The conditionally active cytokine of claim 1, wherein the protease cleavable polypeptide linker comprises a sequence that is cleaved by a matrix metalloprotease (MMP)

selected from the group consisting of MMP1, MMP2, MMP3, MMP8, MMP9, MMP10, MMP11, MMP12, MMP13, and MMP14.

8. The conditionally active cytokine of claim 1, comprising a fusion polypeptide having the Formula:

[A]-[L1]-[H]-[L2]-[D] or [A]-[L1]-[D]-[L2]-[H] or
[D]-[L2]-[H]-[L1]-[A] or [H]-[L2]-[D]-[L1]-[A]
or [D]-[L1]-[A]-[L1]-[H] or [H]-[L1]-[A]-[L1]-
[D], wherein, L1 is a protease cleavable polypeptide linker, and L2 is a polypeptide linker that is optionally protease cleavable.

9. The conditionally active cytokine of claim 1, wherein the serum half-life of the IL-18 polypeptide that is produced by cleavage of the protease-cleavable linker is comparable to the half-life of naturally occurring IL-18.

10. A nucleic acid encoding the conditionally active cytokine of claim 1.

11. A pharmaceutical composition comprising a non-viral delivery system comprising the nucleic acid of claim 10.

12. A pharmaceutical composition comprising a mammalian cell comprising the conditionally active cytokine of claim 1.

13. A pharmaceutical composition comprising a mammalian cell comprising the nucleic acid of claim 10.

\*   \*   \*   \*   \*

SEQUENCE LISTING

```
Sequence total quantity: 453
SEQ ID NO: 1               moltype = AA  length = 153
FEATURE                    Location/Qualifiers
source                     1..153
                           mol_type = protein
                           organism = Homo sapiens
SEQUENCE: 1
MYRMQLLSCI ALSLALVTNS APTSSSTKKT QLQLEHLLLD LQMILNGINN YKNPKLTRML  60
TFKFYMPKKA TELKHLQCLE EELKPLEEVL NLAQSKNFHL RPRDLISNIN VIVLELKGSE  120
TTFMCEYADE TATIVEFLNR WITFCQSIIS TLT                               153

SEQ ID NO: 2               moltype = AA  length = 609
FEATURE                    Location/Qualifiers
source                     1..609
                           mol_type = protein
                           organism = Homo sapiens
SEQUENCE: 2
MKWVTFISLL FLFSSAYSRG VFRRDAHKSE VAHRFKDLGE ENFKALVLIA FAQYLQQCPF  60
EDHVKLVNEV TEFAKTCVAD ESAENCDKSL HTLFGDKLCT VATLRETYGE MADCCAKQEP  120
ERNECFLQHK DDNPNLPRLV RPEVDVMCTA FHDNEETFLK KYLYEIARRH PYFYAPELLF  180
FAKRYKAAFT ECCQAADKAA CLLPKLDELR DEGKASSAKQ GLKCASLQKF GERAFKAWAV  240
ARLSQRFPKA EFAEVSKLVT DLTKVHTECC HGDLLECADD RADLAKYICE NQDSISSKLK  300
ECCEKPLLEK SHCIAEVEND EMPADLPSLA ADFVGSKDVC KNYAEAKDVF LGMFLYEYAR  360
RHPDYSVVLL LRLAKTYETT LEKCCAAADP HECYAKVFDE FKPLVEEPQN LIKQNCELFE  420
QLGEYKFQNA LLVRYTKKVP QVSTPTLVEV SRNLGKVGSK CCKHPEAKRM PCAEDCLSVF  480
LNQLCVLHEK TPVSDRVTKC CTESLVNGRP CFSALEVDET YVPKEFNAET FTFHADICTL  540
SEKERQIKKQ TALVELVKHK PKATKEQLKA VMDDFAAFVE KCCKADDKET CFAEEGKKLV  600
AASQAALGL                                                         609

SEQ ID NO: 3               moltype = AA  length = 8
FEATURE                    Location/Qualifiers
source                     1..8
                           mol_type = protein
                           note = MMP7 cleavage domain sequence
                           organism = unidentified
SEQUENCE: 3
KRALGLPG                                                           8

SEQ ID NO: 4               moltype = AA  length = 40
FEATURE                    Location/Qualifiers
source                     1..40
                           mol_type = protein
                           note = MMP7 cleavage domain sequence
                           organism = unidentified
SEQUENCE: 4
DEDEDEDEDE DEDEDERPLA LWRSDRDRDR DRDRDRDRDR                        40

SEQ ID NO: 5               moltype =   length =
SEQUENCE: 5
000

SEQ ID NO: 6               moltype = AA  length = 5
FEATURE                    Location/Qualifiers
source                     1..5
                           mol_type = protein
                           note = MMP9 cleavage domain sequence
                           organism = unidentified
SEQUENCE: 6
LEATA                                                              5
```

-continued

```
SEQ ID NO: 7             moltype = AA  length = 10
FEATURE                  Location/Qualifiers
source                   1..10
                         mol_type = protein
                         note = MMP11 cleavage domain sequence
                         organism = unidentified
SEQUENCE: 7
GGAANLVRGG                                                           10

SEQ ID NO: 8             moltype = AA  length = 10
FEATURE                  Location/Qualifiers
source                   1..10
                         mol_type = protein
                         note = MMP14 cleavage domain sequence
                         organism = unidentified
SEQUENCE: 8
SGRIGFLRTA                                                           10

SEQ ID NO: 9             moltype = AA  length = 6
FEATURE                  Location/Qualifiers
source                   1..6
                         mol_type = protein
                         note = MMP cleavage domain sequence
                         organism = unidentified
SEQUENCE: 9
PLGLAG                                                               6

SEQ ID NO: 10            moltype = AA  length = 6
FEATURE                  Location/Qualifiers
VARIANT                  6
                         note = Any amino acid
source                   1..6
                         mol_type = protein
                         note = MMP cleavage domain sequence
                         organism = unidentified
SEQUENCE: 10
PLGLAX                                                               6

SEQ ID NO: 11            moltype = AA  length = 6
FEATURE                  Location/Qualifiers
VARIANT                  4
                         note = s-methyl cysteine
source                   1..6
                         mol_type = protein
                         note = MMP cleavage domain sequence
                         organism = unidentified
SEQUENCE: 11
PLGXAG                                                               6

SEQ ID NO: 12            moltype = AA  length = 8
FEATURE                  Location/Qualifiers
source                   1..8
                         mol_type = protein
                         note = MMP cleavage domain sequence
                         organism = unidentified
SEQUENCE: 12
ESPAYYTA                                                             8

SEQ ID NO: 13            moltype = AA  length = 6
FEATURE                  Location/Qualifiers
source                   1..6
                         mol_type = protein
                         note = MMP cleavage domain sequence
                         organism = unidentified
SEQUENCE: 13
RLQLKL                                                               6

SEQ ID NO: 14            moltype = AA  length = 7
FEATURE                  Location/Qualifiers
source                   1..7
                         mol_type = protein
                         note = MMP cleavage domain sequence
                         organism = unidentified
SEQUENCE: 14
RLQLKAC                                                              7

SEQ ID NO: 15            moltype = AA  length = 7
FEATURE                  Location/Qualifiers
MOD_RES                  3
```

-continued

```
                        note = citrulline
MOD_RES                 5
                        note = homophenylalanine
source                  1..7
                        mol_type = protein
                        note = MMP2, MMP9, MMP14 cleavage domain sequence
                        organism = unidentified
SEQUENCE: 15
EPXGXYL                                                              7

SEQ ID NO: 16           moltype = AA  length = 5
FEATURE                 Location/Qualifiers
source                  1..5
                        mol_type = protein
                        note = Urokinase plasminogen activator (uPA) cleavage
                         domain sequence
                        organism = unidentified
SEQUENCE: 16
SGRSA                                                                5

SEQ ID NO: 17           moltype = AA  length = 4
FEATURE                 Location/Qualifiers
source                  1..4
                        mol_type = protein
                        note = Urokinase plasminogen activator (uPA) cleavage
                         domain sequence
                        organism = unidentified
SEQUENCE: 17
DAFK                                                                 4

SEQ ID NO: 18           moltype = AA  length = 5
FEATURE                 Location/Qualifiers
source                  1..5
                        mol_type = protein
                        note = Urokinase plasminogen activator (uPA) cleavage
                         domain sequence
                        organism = unidentified
SEQUENCE: 18
GGGRR                                                                5

SEQ ID NO: 19           moltype = AA  length = 4
FEATURE                 Location/Qualifiers
source                  1..4
                        mol_type = protein
                        note = Lysosomal Enzyme cleavage domain sequence
                        organism = unidentified
SEQUENCE: 19
GFLG                                                                 4

SEQ ID NO: 20           moltype = AA  length = 4
FEATURE                 Location/Qualifiers
source                  1..4
                        mol_type = protein
                        note = Lysosomal Enzyme cleavage domain sequence
                        organism = unidentified
SEQUENCE: 20
ALAL                                                                 4

SEQ ID NO: 21           moltype =   length =
SEQUENCE: 21
000

SEQ ID NO: 22           moltype =   length =
SEQUENCE: 22
000

SEQ ID NO: 23           moltype = AA  length = 5
FEATURE                 Location/Qualifiers
MOD_RES                 3
                        note = s-ethyl cysteine
source                  1..5
                        mol_type = protein
                        note = Cathepsin D cleavage domain sequence
                        organism = unidentified
SEQUENCE: 23
PIXFF                                                                5

SEQ ID NO: 24           moltype = AA  length = 8
FEATURE                 Location/Qualifiers
```

-continued

```
source                          1..8
                                mol_type = protein
                                note = Cathepsin K cleavage domain sequence
                                organism = unidentified
SEQUENCE: 24
GGPRGLPG                                                                 8

SEQ ID NO: 25                   moltype = AA  length = 6
FEATURE                         Location/Qualifiers
source                          1..6
                                mol_type = protein
                                note = Prostate Specific Antigen cleavage domain sequence
                                organism = unidentified
SEQUENCE: 25
HSSKLQ                                                                   6

SEQ ID NO: 26                   moltype = AA  length = 7
FEATURE                         Location/Qualifiers
source                          1..7
                                mol_type = protein
                                note = Prostate Specific Antigen cleavage domain sequence
                                organism = unidentified
SEQUENCE: 26
HSSKLQL                                                                  7

SEQ ID NO: 27                   moltype = AA  length = 9
FEATURE                         Location/Qualifiers
source                          1..9
                                mol_type = protein
                                note = Prostate Specific Antigen cleavage domain sequence
                                organism = unidentified
SEQUENCE: 27
HSSKLQEDA                                                                9

SEQ ID NO: 28                   moltype = AA  length = 10
FEATURE                         Location/Qualifiers
source                          1..10
                                mol_type = protein
                                note = Herpes Simplex Virus Protease cleavage domain
                                 sequence
                                organism = unidentified
SEQUENCE: 28
LVLASSSFGY                                                               10

SEQ ID NO: 29                   moltype = AA  length = 10
FEATURE                         Location/Qualifiers
source                          1..10
                                mol_type = protein
                                note = HIV Protease cleavage domain sequence
                                organism = unidentified
SEQUENCE: 29
GVSQNYPIVG                                                               10

SEQ ID NO: 30                   moltype = AA  length = 10
FEATURE                         Location/Qualifiers
source                          1..10
                                mol_type = protein
                                note = CMV Protease cleavage domain sequence
                                organism = unidentified
SEQUENCE: 30
GVVQASCRLA                                                               10

SEQ ID NO: 31                   moltype =   length =
SEQUENCE: 31
000

SEQ ID NO: 32                   moltype = AA  length = 6
FEATURE                         Location/Qualifiers
source                          1..6
                                mol_type = protein
                                note = Thrombin cleavage domain sequence
                                organism = unidentified
SEQUENCE: 32
DPRSFL                                                                   6

SEQ ID NO: 33                   moltype = AA  length = 6
FEATURE                         Location/Qualifiers
source                          1..6
                                mol_type = protein
```

-continued

```
                              note = Thrombin cleavage domain sequence
                              organism = unidentified
SEQUENCE: 33
PPRSFL                                                                             6

SEQ ID NO: 34                 moltype = AA   length = 4
FEATURE                       Location/Qualifiers
source                        1..4
                              mol_type = protein
                              note = Caspase-3 cleavage domain sequence
                              organism = unidentified
SEQUENCE: 34
DEVD                                                                               4

SEQ ID NO: 35                 moltype = AA   length = 5
FEATURE                       Location/Qualifiers
source                        1..5
                              mol_type = protein
                              note = Caspase-3 cleavage domain sequence
                              organism = unidentified
SEQUENCE: 35
DEVDP                                                                              5

SEQ ID NO: 36                 moltype = AA   length = 8
FEATURE                       Location/Qualifiers
source                        1..8
                              mol_type = protein
                              note = Caspase-3 cleavage domain sequence
                              organism = unidentified
SEQUENCE: 36
KGSGDVEG                                                                           8

SEQ ID NO: 37                 moltype = AA   length = 6
FEATURE                       Location/Qualifiers
source                        1..6
                              mol_type = protein
                              note = Interleukin 1-beta converting enzyme cleavage domain
                               sequence
                              organism = unidentified
SEQUENCE: 37
GWEHDG                                                                             6

SEQ ID NO: 38                 moltype = AA   length = 7
FEATURE                       Location/Qualifiers
source                        1..7
                              mol_type = protein
                              note = Enterokinase cleavage domain sequence
                              organism = unidentified
SEQUENCE: 38
EDDDDKA                                                                            7

SEQ ID NO: 39                 moltype = AA   length = 9
FEATURE                       Location/Qualifiers
source                        1..9
                              mol_type = protein
                              note = FAP cleavage domain sequence
                              organism = unidentified
SEQUENCE: 39
KQEQNPGST                                                                          9

SEQ ID NO: 40                 moltype = AA   length = 6
FEATURE                       Location/Qualifiers
source                        1..6
                              mol_type = protein
                              note = Kallikrein 2 cleavage domain sequence
                              organism = unidentified
SEQUENCE: 40
GKAFRR                                                                             6

SEQ ID NO: 41                 moltype = AA   length = 4
FEATURE                       Location/Qualifiers
source                        1..4
                              mol_type = protein
                              note = Plasmin cleavage domain sequence
                              organism = unidentified
SEQUENCE: 41
DAFK                                                                               4

SEQ ID NO: 42                 moltype = AA   length = 4
```

```
FEATURE             Location/Qualifiers
source              1..4
                    mol_type = protein
                    note = Plasmin cleavage domain sequence
                    organism = unidentified
SEQUENCE: 42
DVLK                                                                    4

SEQ ID NO: 43       moltype = AA  length = 4
FEATURE             Location/Qualifiers
source              1..4
                    mol_type = protein
                    note = Plasmin cleavage domain sequence
                    organism = unidentified
SEQUENCE: 43
DAFK                                                                    4

SEQ ID NO: 44       moltype = AA  length = 7
FEATURE             Location/Qualifiers
source              1..7
                    mol_type = protein
                    note = TOP cleavage domain sequence
                    organism = unidentified
SEQUENCE: 44
ALLLALL                                                                 7

SEQ ID NO: 45       moltype = AA  length = 652
FEATURE             Location/Qualifiers
source              1..652
                    mol_type = protein
                    organism = synthetic construct
SEQUENCE: 45
QVQLQESGGG LVQAGGSLRL SCAASGRIFS IDIMSWYRQA PGKQRELVAR ITRGGTISYD    60
DSVKGRFTIS RDNAKNTVYL QMNSLKPEDT GVYYCNALYG TDYWGKGTQV TVSSGGGGSG    120
GGGSGGGGSA PTSSSTKKTQ LQLEHLLLDL QMILNGINNY KNPKLTRMLT FKFYMPKKAT    180
ELKHLQCLEE ELKPLEEVLN LAQSKNFHLR PRDLISNINV IVLELKGSET TFMCEYADET    240
ATIVEFLNRW ITFCQSIIST LTSGGPGPAG MKGLPGSEVQ LVESGGGLVQ PGNSLRLSCA    300
ASGFTFSKFG MSWVRQAPGK GLEWVSSISG SGRDTLYAES VKGRFTISRD NAKTTLYLQM    360
NSLRPEDTAV YYCTIGGSLS VSSQGTLVTV SSGGGGSGGG GSGGGGSEVQ LVESGGGLVQ    420
PGGSLRLSCA ASGFTSSYT LAWVRQAPGK GLEWVAAIDS SSYTYSPDTV RGRFTISRDN    480
AKNSLYLQMN SLRAEDTAVY YCARDSNWDA LDYWGQGTTV TVSSGGGGSG GGGSGGGGSD    540
IQMTQSPSSL SASVGDRVTI TCKASQNVGT NVGWYQQKPG KAPKALIYSA SFRYSGVPSR    600
FSGSGSGTDF TLTISSLQPE DFATYYCQQY YTYPYTFGGG TKVEIKHHHH HH            652

SEQ ID NO: 46       moltype = AA  length = 652
FEATURE             Location/Qualifiers
source              1..652
                    mol_type = protein
                    organism = synthetic construct
SEQUENCE: 46
QVQLQESGGG LVQAGGSLRL SCAASGRIFS IDIMSWYRQA PGKQRELVAR ITRGGTISYD    60
DSVKGRFTIS RDNAKNTVYL QMNSLKPEDT GVYYCNALYG TDYWGKGTQV TVSSGGGGSG    120
GGGSGGGGSE VQLVESGGGL VQPGGSLRLS CAASGFTFSS YTLAWVRQAP GKGLEWVAAI    180
DSSSYTYSPD TVRGRFTISR DNAKNSLYLQ MNSLRAEDTA VYYCARDSNW DALDYWGQGT    240
TVTVSSGGGG SGGGGSGGGG SDIQMTQSPS SLSASVGDRV TITCKASQNV GTNVGWYQQK    300
PGKAPKALIY SASFRYSGVP SRFSGSGSGT DFTLTISSLQ PEDFATYYCQ QYYTYPYTFG    360
GGTKVEIKGG GGSGGGGSGG GGSEVQLVES GGGLVQPGNS LRLSCAASGF TFSKFGMSWV    420
RQAPGKGLEW VSSISGSGRD TLYAESVKGR FTISRDNAKT TLYLQMNSLR PEDTAVYYCT    480
IGGSLSVSSQ GTLVTVSSSG GPGPAGMKGL PGSAPTSSST KKTQLQLEHL LLDLQMILNG    540
INNYKNPKLT RMLTFKFYMP KKATELKHLQ CLEEELKPLE EVLNLAQSKN FHLRPRDLIS    600
NINVIVLELK GSETTFMCEY ADETATIVEF LNRWITFCQS IISTLTHHHH HH            652

SEQ ID NO: 47       moltype = AA  length = 553
FEATURE             Location/Qualifiers
source              1..553
                    mol_type = protein
                    organism = synthetic construct
SEQUENCE: 47
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSGGG    120
GSGGGGSGGG GSDIQMTQSP SSLSASVGDR VTITCKASQN VGTNVGWYQQ KPGKAPKALI    180
YSASFRYSGV PSRFSGSGSG TDFTLTISSL QPEDFATYYC QQYYTYPYTF GGGTKVEIKG    240
GGGGSGGGGS GGGGSGGGGS GGPGPAGMKG LPGSAPTSSS TKKTQLQLEH    300
LLLDLQMILN GINNYKNPKL TRMLTFKFYM PKKATELKHL QCLEEELKPL EEVLNLAQSK    360
NFHLRPRDLI SNINVIVLEL KGSETTFMCE YADETATIVE FLNRWITFCQ SIISTLTSGG    420
PGPAGMKGLP GSEVQLVESG GGLVQPGNSL RLSCAASGFT FSKFGMSWVR QAPGKGLEWV    480
SSISGSGRDT LYAESVKGRF TISRDNAKTT LYLQMNSLRP EDTAVYYCTI GGSLSVSSQG    540
TLVTVSSHHH HHH                                                      553
```

```
SEQ ID NO: 48          moltype = AA   length = 553
FEATURE                Location/Qualifiers
source                 1..553
                       mol_type = protein
                       organism = synthetic construct
SEQUENCE: 48
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSGGG   120
GSGGGGSGGG GSDIQMTQSP SSLSASVGDR VTITCKASQN VGTNVGWYQQ KPGKAPKALI   180
YSASFRYSGV PSRFSGSGSG TDFTLTISSL QPEDFATYYC QQYYTYPYTF GGGTKVEIKG   240
GGGSGGGGSG GGGSGGGGSG GGGSGGGGSE VQLVESGGGL VQPGNSLRLS CAASGFTFSK   300
FGMSWVRQAP GKGLEWVSSI SGSGRDTLYA ESVKGRFTIS RDNAKTTLYL QMNSLRPEDT   360
AVYYCTIGGS LSVSSQGTLV TVSSGGGGSG GGGSGGGGSS GGPGPAGMKG LPGSAPTSSS   420
TKKTQLQLEH LLLDLQMILN GINNYKNPKL TRMLTFKFYM PKKATELKHL QCLEEELKPL   480
EEVLNLAQSK NFHLRPRDLI SNINVIVLEL KGSETTFMCE YADETATIVE FLNRWITFCQ   540
SIISTLTHHH HHH                                                     553

SEQ ID NO: 49          moltype = AA   length = 553
FEATURE                Location/Qualifiers
source                 1..553
                       mol_type = protein
                       organism = synthetic construct
SEQUENCE: 49
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GMKGLPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKASQNVG TNVGWYQQKP   480
GKAPKALIYS ASFRYSGVPS RFSGSGSGTD FTLTISSLQP EDFATYYCQQ YYTYPYTFGG   540
GTKVEIKHHH HHH                                                     553

SEQ ID NO: 50          moltype = AA   length = 682
FEATURE                Location/Qualifiers
source                 1..682
                       mol_type = protein
                       organism = synthetic construct
SEQUENCE: 50
QVQLQESGGG LVQAGGSLRL SCAASGRIFS IDIMSWYRQA PGKQRELVAR ITRGGTISYD    60
DSVKGRFTIS RDNAKNTVYL QMNSLKPEDT GVYYCNALYG TDYWGKGTQV TVSSGGGGSG   120
GGGSGGGGSA PTSSSTKKTQ LQLEHLLLDL QMILNGINNY KNPKLTRMLT FKFYMPKKAT   180
ELKHLQCLEE ELKPLEEVLN LAQSKNFHLR PRDLISNINV IVLELKGSET TFMCEYADET   240
ATIVEFLNRW ITFCQSIIST LTSGGPGPAG MKGLPGSEVQ LVESGGGLVQ PGNSLRLSCA   300
ASGFTFSKFG MSWVRQAPGK GLEWVSSISG SGRDTLYAES VKGRFTISRD NAKTTLYLQM   360
NSLRPEDTAV YYCTIGGSLS VSSQGTLVTV SSGGGGSGGG GSGGGGSGGG GGSGGGG     420
GSSGGPGPAG MKGLPGSEVQ LVESGGGLVQ PGGSLRLSCA ASGFTFSSYT LAWVRQAPGK   480
GLEWVAAIDS SSYTYSPDTV RGRFTISRDN AKNSLYLQMN SLRAEDTAVY YCARDSNWDA   540
LDYWGQGTTV TVSSGGGGSG GGGSGGGGSD IQMTQSPSSL SASVGDRVTI TCKASQNVGT   600
NVGWYQQKPG KAPKALIYSA SFRYSGVPSR FSGSGSGTDF TLTISSLQPE DFATYYCQQY   660
YTYPYTFGGG TKVEIKHHHH HH                                           682

SEQ ID NO: 51          moltype = AA   length = 667
FEATURE                Location/Qualifiers
source                 1..667
                       mol_type = protein
                       organism = synthetic construct
SEQUENCE: 51
QVQLQESGGG LVQAGGSLRL SCAASGRIFS IDIMSWYRQA PGKQRELVAR ITRGGTISYD    60
DSVKGRFTIS RDNAKNTVYL QMNSLKPEDT GVYYCNALYG TDYWGKGTQV TVSSGGGGSG   120
GGGSGGGGSA PTSSSTKKTQ LQLEHLLLDL QMILNGINNY KNPKLTRMLT FKFYMPKKAT   180
ELKHLQCLEE ELKPLEEVLN LAQSKNFHLR PRDLISNINV IVLELKGSET TFMCEYADET   240
ATIVEFLNRW ITFCQSIIST LTSGGPGPAG MKGLPGSEVQ LVESGGGLVQ PGNSLRLSCA   300
ASGFTFSKFG MSWVRQAPGK GLEWVSSISG SGRDTLYAES VKGRFTISRD NAKTTLYLQM   360
NSLRPEDTAV YYCTIGGSLS VSSQGTLVTV SSGGGGSGGG GSGGGGSGGG GGSGGGGSGG   420
GSEVQLVESG GGLVQPGGSL RLSCAASGFT FSSYTLAWVR QAPGKGLEWV AAIDSSSYTY   480
SPDTVRGRFT ISRDNAKNSL YLQMNSLRAE DTAVYYCARD SNWDALDYWG QGTTVTVSSS   540
GGPGPAGMKG LPGSDIQMTQ SPSSLSASVG DRVTITCKAS QNVGTNVGWY QQKPGKAPKA   600
LIYSASFRYS GVPSRFSGSG SGTDFTLTIS SLQPEDFATY YCQQYYTYPY TFGGGTKVEI   660
KHHHHHH                                                            667

SEQ ID NO: 52          moltype = AA   length = 682
FEATURE                Location/Qualifiers
source                 1..682
                       mol_type = protein
                       organism = synthetic construct
SEQUENCE: 52
APTSSSTKKT QLQLEHLLLD LQMILNGINN YKNPKLTRML TFKFYMPKKA TELKHLQCLE    60
```

-continued

```
EELKPLEEVL NLAQSKNFHL RPRDLISNIN VIVLELKGSE TTFMCEYADE TATIVEFLNR    120
WITFCQSIIS TLTSGGPGPA GMKGLPGSGG GGSGGGGSGG GGSGGGGSGG GGSGGGGSEV    180
QLVESGGGLV QPGGSLRLSC AASGFTFSSY TLAWVRQAPG KGLEWVAAID SSSYTYSPDT    240
VRGRFTISRD NAKNSLYLQM NSLRAEDTAV YYCARDSNWD ALDYWGQGTT VTVSSGGGGS    300
GGGGSGGGGS DIQMTQSPSS LSASVGDRVT ITCKASQNVG TNVGWYQQKP GKAPKALIYS    360
ASFRYSGVPS RFSGSGSGTD FTLTISSLQP EDFATYYCQQ YYTYPYTFGG GTKVEIKGGG    420
GSGGGGSGGG GSEVQLVESG GGLVQPGNSL RLSCAASGFT FSKFGMSWVR QAPGKGLEWV    480
SSISGSGRDT LYAESVKGRF TISRDNAKTT LYLQMNSLRP EDTAVYYCTI GGSLSVSSQG    540
TLVTVSSGGG GSGGGGSGGG GSQVQLQESG GGLVQAGGSL RLSCAASGRI FSIDIMSWYR    600
QAPGKQRELV ARITRGGTIS YDDSVKGRFT ISRDNAKNTV YLQMNSLKPE DTGVYYCNAL    660
YGTDYWGKGT QVTVSSHHHH HH                                            682

SEQ ID NO: 53            moltype = AA   length = 393
FEATURE                  Location/Qualifiers
source                   1..393
                         mol_type = protein
                         organism = synthetic construct
SEQUENCE: 53
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GMKGLPGSEV QLVESGGGLV QPGGSLRLSC AASGFTFSSY    180
TLAWVRQAPG KGLEWVAAID SSSYTYSPDT VRGRFTISRD NAKNSLYLQM NSLRAEDTAV    240
YYCARDSNWD ALDYWGQGTT VTVSSGGGGS GGGGSGGGGS DIQMTQSPSS LSASVGDRVT    300
ITCKASQNVG TNVGWYQQKP GKAPKALIYS ASFRYSGVPS RFSGSGSGTD FTLTISSLQP    360
EDFATYYCQQ YYTYPYTFGG GTKVEIKHHH HHH                                393

SEQ ID NO: 54            moltype = AA   length = 423
FEATURE                  Location/Qualifiers
source                   1..423
                         mol_type = protein
                         organism = synthetic construct
SEQUENCE: 54
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GMKGLPGSGG GGSGGGGSGG GGSGGGGSGG GGSGGGGSEV    180
QLVESGGGLV QPGGSLRLSC AASGFTFSSY TLAWVRQAPG KGLEWVAAID SSSYTYSPDT    240
VRGRFTISRD NAKNSLYLQM NSLRAEDTAV YYCARDSNWD ALDYWGQGTT VTVSSGGGGS    300
GGGGSGGGGS DIQMTQSPSS LSASVGDRVT ITCKASQNVG TNVGWYQQKP GKAPKALIYS    360
ASFRYSGVPS RFSGSGSGTD FTLTISSLQP EDFATYYCQQ YYTYPYTFGG GTKVEIKHHH    420
HHH                                                                 423

SEQ ID NO: 55            moltype = AA   length = 682
FEATURE                  Location/Qualifiers
source                   1..682
                         mol_type = protein
                         organism = synthetic construct
SEQUENCE: 55
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GMKGLPGSGG GGSGGGGSGG GGSGGGGSGG GGSGGGGSEV    180
QLVESGGGLV QPGGSLRLSC AASGFTFSSY TLAWVRQAPG KGLEWVAAID SSSYTYSPDT    240
VRGRFTISRD NAKNSLYLQM NSLRAEDTAV YYCARDSNWD ALDYWGQGTT VTVSSGGGGS    300
GGGGSGGGGS DIQMTQSPSS LSASVGDRVT ITCKASQNVG TNVGWYQQKP GKAPKALIYS    360
ASFRYSGVPS RFSGSGSGTD FTLTISSLQP EDFATYYCQQ YYTYPYTFGG GTKVEIKSGG    420
PGPAGMKGLP GSEVQLVESG GGLVQPGNSL RLSCAASGFT FSKFGMSWVR QAPGKGLEWV    480
SSISGSGRDT LYAESVKGRF TISRDNAKTT LYLQMNSLRP EDTAVYYCTI GGSLSVSSQG    540
TLVTVSSGGG GSGGGGSGGG GSQVQLQESG GGLVQAGGSL RLSCAASGRI FSIDIMSWYR    600
QAPGKQRELV ARITRGGTIS YDDSVKGRFT ISRDNAKNTV YLQMNSLKPE DTGVYYCNAL    660
YGTDYWGKGT QVTVSSHHHH HH                                            682

SEQ ID NO: 56            moltype = AA   length = 682
FEATURE                  Location/Qualifiers
source                   1..682
                         mol_type = protein
                         organism = synthetic construct
SEQUENCE: 56
QVQLQESGGG LAQAGGSLSL SCAASGFTVS NSVMAWYRQT PGKQREFVAI INSVGSTNYA     60
DSVKGRFTIS RDNAKNTVYL QMNNLKPEDT AVYVCNRNFD RIYWGQGTQV TVSSSGGPGP    120
AGMKGLPGSE VQLVESGGGL VQPGGSLRLS CAASGFTFSS YTLAWVRQAP GKGLEWVAAI    180
DSSSYTYSPD TVRGRFTISR DNAKNSLYLQ MNSLRAEDTA VYYCARDSNW DALDYWGQGT    240
TVTVSSGGGG SGGGGSGGGG SDIQMTQSPS SLSASVGDRV TITCKASQNV GTNVGWYQQK    300
PGKAPKALIY SASFRYSGVP SRFSGSGSGT DFTLTISSLQ PEDFATYYCQ QYYTYPYTFG    360
GGTKVEIKGG GGSGGGGSGG GGSGGGGSGG GGSGGGGSGG GPGPAGMKGL PGSEVQLVES    420
GGGLVQPGNS LRLSCAASGF TFSKFGMSWV RQAPGKGLEW VSSISGSGRD TLYAESVKGR    480
FTISRDNAKT TLYLQMNSLR PEDTAVYYCT IGGSLSVSSQ GTLVTVSSSG GPGPAGMKGL    540
PGSAPTSSST KKTQLQLEHL LLDLQMILNG INNYKNPKLT RMLTFKFYMP KKATELKHLQ    600
CLEEELKPLE EVLNLAQSKN FHLRPRDLIS NINVIVLELK GSETTFMCEY ADETATIVEF    660
LNRWITFCQS IISTLTHHHH HH                                            682
```

-continued

```
SEQ ID NO: 57            moltype = AA   length = 393
FEATURE                  Location/Qualifiers
source                   1..393
                         mol_type = protein
                         organism = synthetic construct
SEQUENCE: 57
EVQLVESGGG LVQPGGSLRL SCAASGFTFS SYTLAWVRQA PGKGLEWVAA IDSSSYTYSP   60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKASQN VGTNVGWYQQ KPGKAPKALI  180
YSASFRYSGV PSRFSGSGSG TDFTLTISSL QPEDFATYYC QQYYTYPYTF GGGTKVEIKS  240
GGPGPAGMKG LPGSAPTSSS TKKTQLQLEH LLLDLQMILN GINNYKNPKL TRMLTFKFYM  300
PKKATELKHL QCLEEELKPL EEVLNLAQSK NFHLRPRDLI SNINVIVLEL KGSETTFMCE  360
YADETATIVE FLNRWITFCQ SIISTLTHHH HHH                              393

SEQ ID NO: 58            moltype = AA   length = 423
FEATURE                  Location/Qualifiers
source                   1..423
                         mol_type = protein
                         organism = synthetic construct
SEQUENCE: 58
EVQLVESGGG LVQPGGSLRL SCAASGFTFS SYTLAWVRQA PGKGLEWVAA IDSSSYTYSP   60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKASQN VGTNVGWYQQ KPGKAPKALI  180
YSASFRYSGV PSRFSGSGSG TDFTLTISSL QPEDFATYYC QQYYTYPYTF GGGTKVEIKG  240
GGGSGGGGSG GGGSGGGGSG GGGSGGGGSS GGPGPAGMKG LPGSAPTSSS TKKTQLQLEH  300
LLLDLQMILN GINNYKNPKL TRMLTFKFYM PKKATELKHL QCLEEELKPL EEVLNLAQSK  360
NFHLRPRDLI SNINVIVLEL KGSETTFMCE YADETATIVE FLNRWITFCQ SIISTLTHHH  420
HHH                                                              423

SEQ ID NO: 59            moltype = AA   length = 669
FEATURE                  Location/Qualifiers
source                   1..669
                         mol_type = protein
                         organism = synthetic construct
SEQUENCE: 59
QVQLQESGGG LVQAGGSLRL SCAASGRIFS IDIMSWYRQA PGKQRELVAR ITRGGTISYD   60
DSVKGRFTIS RDNAKNTVYL QMNSLKPEDT GVYYCNALYG TDYWGKGTQV TVSSGGGGSG  120
GGGSGGGGSA PTSSSTKKTQ LQLEHLLLDL QMILNGINNY KNPKLTRMLT FKFYMPKKAT  180
ELKHLQCLEE ELKPLEEVLN LAQSKNFHLR PRDLISNINV IVLELKGSET TFMCEYADET  240
ATIVEFLNRW ITFCQSIIST LTSGGPGPAG MKGLPGSEVQ LVESGGGLVQ PGNSLRLSCA  300
ASGFTFSKFG MSWVRQAPGK GLEWVSSISG SGRDTLYAES VKGRFTISRD NAKTTLYLQM  360
NSLRPEDTAV YYCTIGGSLS VSSQGTLVTV SSGGGGSGGG GSGGGGSGGG GSQVQLQQSG  420
AELVRPGTSV KVSCKASGYA FTNYLIEWVK QRPGQGLEWI GVINPGSGGT NYNEKFKGKA  480
TLTADKSSST AYMQLSSLTS DDSAVYFCAR WRGDGYYAYF DVWGAGTTVT VSSGGGGSGG  540
GGSGGGGSDI VLTQSPASLA VSLGQRATIS CKASQSVDYD GDSYMNWYQQ KPGQPPKLLI  600
YAASNLESGI PARFSGSGSG TDFTLNIHPV EEEDAATYYC QQSNEDPYTF GGGTKLEIKH  660
HHHHHEPEA                                                        669

SEQ ID NO: 60            moltype = AA   length = 669
FEATURE                  Location/Qualifiers
source                   1..669
                         mol_type = protein
                         organism = synthetic construct
SEQUENCE: 60
QVQLQESGGG LVQAGGSLRL SCAASGRIFS IDIMSWYRQA PGKQRELVAR ITRGGTISYD   60
DSVKGRFTIS RDNAKNTVYL QMNSLKPEDT GVYYCNALYG TDYWGKGTQV TVSSGGGGSG  120
GGGSGGGGSA PTSSSTKKTQ LQLEHLLLDL QMILNGINNY KNPKLTRMLT FKFYMPKKAT  180
ELKHLQCLEE ELKPLEEVLN LAQSKNFHLR PRDLISNINV IVLELKGSET TFMCEYADET  240
ATIVEFLNRW ITFCQSIIST LTSGGPGPAG MKGLPGSEVQ LVESGGGLVQ PGNSLRLSCA  300
ASGFTFSKFG MSWVRQAPGK GLEWVSSISG SGRDTLYAES VKGRFTISRD NAKTTLYLQM  360
NSLRPEDTAV YYCTIGGSLS VSSQGTLVTV SSGGGGSGGG GSGGGGSGGG GSDIVLTQSP  420
ASLAVSLGQR ATISCKASQS VDYDGDSYMN WYQQKPGQPP KLLIYAASNL ESGIPARFSG  480
SGSGTDFTLN IHPVEEEDAA TYYCQQSNED PYTFGGGTKL EIKGGGGSGG GGSGGGGSQV  540
QLQQSGAELV RPGTSVKVSC KASGYAFTNY LIEWVKQRPG QGLEWIGVIN PGSGGTNYNE  600
KFKGKATLTA DKSSSTAYMQ LSSLTSDDSA VYFCARWRGD GYYAYFDVWG AGTTVTVSSH  660
HHHHHEPEA                                                        669

SEQ ID NO: 61            moltype = AA   length = 689
FEATURE                  Location/Qualifiers
source                   1..689
                         mol_type = protein
                         organism = synthetic construct
SEQUENCE: 61
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTSGGPGPA GMKGLPGSGG GGSGGGGSGG GGSGGGGSGG GGSQVQLQQS  180
GAELVRPGTS VKVSCKASGY AFTNYLIEWV KQRPGQGLEW IGVINPGSGG TNYNEKFKGK  240
ATLTADKSSS TAYMQLSSLT SDDSAVYFCA RWRGDGYYAY FDVWGAGTTV TVSSGGGGSG  300
GGGSGGGGSD IVLTQSPASL AVSLGQRATI SCKASQSVDY DGDSYMNWYQ QKPGQPPKLL  360
```

-continued

```
IYAASNLESG IPARFSGSGS GTDFTLNIHP VEEEDAATYY CQQSNEDPYT FGGGTKLEIK    420
GGGGSGGGGS GGGGSEVQLV ESGGGLVQPG NSLRLSCAAS GFTFSKFGMS WVRQAPGKGL    480
EWVSSISGSG RDTLYAESVK GRFTISRDNA KTTLYLQMNS LRPEDTAVYY CTIGGSLSVS    540
SQGTLVTVSS GGGGSGGGGS GGGGSQVQLQ ESGGGLVQAG GSLRLSCAAS GRIFSIDIMS    600
WYRQAPGKQR ELVARITRGG TISYDDSVKG RFTISRDNAK NTVYLQMNSL KPEDTGVYYC    660
NALYGTDYWG KGTQVTVSSH HHHHHEPEA                                      689

SEQ ID NO: 62            moltype = AA  length = 689
FEATURE                  Location/Qualifiers
source                   1..689
                         mol_type = protein
                         organism = synthetic construct
SEQUENCE: 62
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GMKGLPGSGG GGSGGGGSGG GGSGGGGSGG GGSDIVLTQS    180
PASLAVSLGQ RATISCKASQ SVDYDGDSYM NWYQQKPGQP PKLLIYAASN LESGIPARFS    240
GSGSGTDFTL NIHPVEEEDA ATYYCQQSNE DPYTFGGGTK LEIKGGGGSG GGGSGGGGSQ    300
VQLQQSGAEL VRPGTSVKVS CKASGYAFTN YLIEWVKQRP GQGLEWIGVI NPGSGGTNYN    360
EKFKGKATLT ADKSSSTAYM QLSSLTSDDS AVYFCARWRG DGYYAYFDVW GAGTTVTVSS    420
GGGGSGGGGS GGGGSEVQLV ESGGGLVQPG NSLRLSCAAS GFTFSKFGMS WVRQAPGKGL    480
EWVSSISGSG RDTLYAESVK GRFTISRDNA KTTLYLQMNS LRPEDTAVYY CTIGGSLSVS    540
SQGTLVTVSS GGGGSGGGGS GGGGSQVQLQ ESGGGLVQAG GSLRLSCAAS GRIFSIDIMS    600
WYRQAPGKQR ELVARITRGG TISYDDSVKG RFTISRDNAK NTVYLQMNSL KPEDTGVYYC    660
NALYGTDYWG KGTQVTVSSH HHHHHEPEA                                      689

SEQ ID NO: 63            moltype = AA  length = 272
FEATURE                  Location/Qualifiers
source                   1..272
                         mol_type = protein
                         note = IL2Ra sequence
                         organism = unidentified
SEQUENCE: 63
MDSYLLMWGL LTFIMVPGCQ AELCDDDPPE IPHATFKAMA YKEGTMLNCE CKRGFRRIKS    60
GSLYMLCTGN SSHSSWDNQC QCTSSATRNT TKQVTPQPEE QKERKTTEMQ SPMQPVDQAS    120
LPGHCREPPP WENEATERIY HFVVGQMVYY QCVQGYRALH RGPAESVCKM THGKTRWTQP    180
QLICTGEMET SQFPGEEKPQ ASPEGRPESE TSCLVTTTDF QIQTEMAATM ETSIFTTEYQ    240
VAVAGCVFLL ISVLLLSGLT WQRRQRKSRR TI                                  272

SEQ ID NO: 64            moltype = AA  length = 551
FEATURE                  Location/Qualifiers
source                   1..551
                         mol_type = protein
                         note = IL2Rb sequence
                         organism = unidentified
SEQUENCE: 64
MAAPALSWRL PLLILLLPLA TSWASAAVNG TSQFTCFYNS RANISCVWSQ DGALQDTSCQ    60
VHAWPDRRRW NQTCELLPVS QASWACNLIL GAPDSQKLTT VDIVTLRVLC REGVRWRVMA    120
IQDFKPFENL RLMAPISLQV VHVETHRCNI SWEISQASHY FERHLEFEAR TLSPGHTWEE    180
APLLTLKQKQ EWICLETLTP DTQYEFQVRV KPLQGEFTTW SPWSQPLAFR TKPAALGKDT    240
IPWLGHLLVG LSGAFGFIIL VYLLINCRNT GPWLKKVLKC NTPDPSKFFS QLSSEHGGDV    300
QKWLSSPFPS SSFSPGGLAP EISPLEVLER DKVTQLLLQQ DKVPEPASLS SNHSLTSCFT    360
NQGYFFFHLP DALEIEACQV YFTYDPYSEE DPDEGVAGAP TGSSPQPLQP LSGEDDAYCT    420
FPSRDDLLLF SPSLLGGPSP PSTAPGGSGA GEERMPPSLQ ERVPRDWDPQ PLGPPTPGVP    480
DLVDFQPPPE LVLREAGEEV PDAGPREGVS FPWSRPPGQG EFRALNARLP LNTDAYLSLQ    540
ELQGQDPTHL V                                                        551

SEQ ID NO: 65            moltype = AA  length = 369
FEATURE                  Location/Qualifiers
source                   1..369
                         mol_type = protein
                         note = IL2Rg sequence
                         organism = unidentified
SEQUENCE: 65
MLKPSLPFTS LLFLQLPLLG VGLNTTILTP NGNEDTTADF FLTTMPTDSL SVSTLPLPEV    60
QCFVFNVEYM NCTWNSSSEP QPTNLTLHYW YKNSDNDKVQ KCSHYLFSEE ITSGCQLKK    120
EIHLYQTFVV QLQDPREPRR QATQMLKLQN LVIPWAPENL TLHKLSESQL ELNWNNRFLN    180
HCLEHLVQYR TDWDHSWTEQ SVDYRHKFSL PSVDGQKRYT FRVRSRFNPL CGSAQHWSEW    240
SHPIHWGSNT SKENPFLFAL EAVVISVGSM GLIISLLCVY FWLERTMPRI PTLKNLEDLV    300
TEYHGNFSAW SGVSKGLAES LQPDYSERLC LVSEIPPKGG ALGEGPGASP CNQHSPYWAP    360
PCYTLKPET                                                           369

SEQ ID NO: 66            moltype = AA  length = 520
FEATURE                  Location/Qualifiers
source                   1..520
                         mol_type = protein
                         organism = synthetic construct
SEQUENCE: 66
IWELKKDVYV VELDWYPDAP GEMVVLTCDT PEEDGITWTL DQSSEVLGSG KTLTIQVKEF    60
```

```
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSGGGG SGGGGSGGGG SRVIPVSGPA RCLSQSRNLL KTTDDMVKTA REKLKHYSCT   360
AEDIDHEDIT RDQTSTLKTC LPLELHKNES CLATRETSST TRGSCLPPQK TSLMMTLCLG   420
SIYEDLKMYQ TEFQAINAAL QNHNHQQIIL DKGMLVAIDE LMQSLNHNGE TLRQKPPVGE   480
ADPYRVKMKL CILLHAFSTR VVTINRVMGY LSSAHHHHHH                        520

SEQ ID NO: 67            moltype = AA   length = 524
FEATURE                  Location/Qualifiers
source                   1..524
                         mol_type = protein
                         organism = synthetic construct
SEQUENCE: 67
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSGGGG SGGGGSGGGG SRNLPVATPD PGMFPCLHHS QNLLRAVSNM LQKARQTLEF   360
YPCTSEEIDH EDITKDKTST VEACLPLELT KNESCLNSRE TSFITNGSCL ASRKTSFMMA   420
LCLSSIYEDL KMYQVEFKTM NAKLLMDPKR QIFLDQNMLA VIDELMQALN FNSETVPQKS   480
SLEEPDFYKT KIKLCILLHA FRIRAVTIDR VMSYLNASHH HHHH                   524

SEQ ID NO: 68            moltype = AA   length = 940
FEATURE                  Location/Qualifiers
source                   1..940
                         mol_type = protein
                         organism = synthetic construct
SEQUENCE: 68
QSVLTQPPSV SGAPGQRVTI SCSGSRSNIG SNTVKWYQQL PGTAPKLLIY YNDQRPSGVP   60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SGGGGSGGGG SGGGGSGGGG SGGGGSGGGG SSGGPGPAGM KGLPGSIWEL KKDVYVVELD   300
WYPDAPGEMV VLTCDTPEED GITWTLDQSS EVLGSGKTLT IQVKEFGDAG QYTCHKGGEV   360
LSHSLLLLHK KEDGIWSTDI LKDQKEPKNK TFLRCEAKNY SGRFTCWWLT TISTDLTFSV   420
KSSRGSSDPQ GVTCGAATLS AERVRGDNKE YEYSVECQED SACPAAEESL PIEVMVDAVH   480
KLKYENYTSS FFIRDIIKPD PPKNLQLKPL KNSRQVEVSW EYPDTWSTPH SYFSLTFCVQ   540
VQGKSKREKK DRVFTDKTSA TVICRKNASI SVRAQDRYYS SSWSEWASVP CSGGGGSGGG   600
GSGGGGSRVI PVSGPARCLS QSRNLLKTTD DMVKTAREKL KHYSCTAEDI DHEDITRDQT   660
STLKTCLPLE LHKNESCLAT RETSSTTRGS CLPPQKTSLM MTLCLGSIYE DLKMYQTEFQ   720
AINAALQNHN HQQIILDKGM LVAIDELMQS LNHNGETLRQ KPPVGEADPY RVKMKLCILL   780
HAFSTRVVTI NRVMGYLSSA SGGPGPAGMK GLPGSEVQLV ESGGGLVQPG NSLRLSCAAS   840
GFTFSKFGMS WVRQAPGKGL EWVSSISGSG RDTLYAESVK GRFTISRDNA KTTLYLQMNS   900
LRPEDTAVYY CTIGGSLSVS SQGTLVTVSS HHHHHHEPEA                        940

SEQ ID NO: 69            moltype = AA   length = 1069
FEATURE                  Location/Qualifiers
source                   1..1069
                         mol_type = protein
                         organism = synthetic construct
SEQUENCE: 69
QSVLTQPPSV SGAPGQRVTI SCSGSRSNIG SNTVKWYQQL PGTAPKLLIY YNDQRPSGVP   60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SGGGGSGGGG SGGGGSGGGG SGGGGSGGGG SSGGPGPAGM KGLPGSIWEL KKDVYVVELD   300
WYPDAPGEMV VLTCDTPEED GITWTLDQSS EVLGSGKTLT IQVKEFGDAG QYTCHKGGEV   360
LSHSLLLLHK KEDGIWSTDI LKDQKEPKNK TFLRCEAKNY SGRFTCWWLT TISTDLTFSV   420
KSSRGSSDPQ GVTCGAATLS AERVRGDNKE YEYSVECQED SACPAAEESL PIEVMVDAVH   480
KLKYENYTSS FFIRDIIKPD PPKNLQLKPL KNSRQVEVSW EYPDTWSTPH SYFSLTFCVQ   540
VQGKSKREKK DRVFTDKTSA TVICRKNASI SVRAQDRYYS SSWSEWASVP CSGGGGSGGG   600
GSGGGGSRVI PVSGPARCLS QSRNLLKTTD DMVKTAREKL KHYSCTAEDI DHEDITRDQT   660
STLKTCLPLE LHKNESCLAT RETSSTTRGS CLPPQKTSLM MTLCLGSIYE DLKMYQTEFQ   720
AINAALQNHN HQQIILDKGM LVAIDELMQS LNHNGETLRQ KPPVGEADPY RVKMKLCILL   780
HAFSTRVVTI NRVMGYLSSA SGGPGPAGMK GLPGSEVQLV ESGGGLVQPG NSLRLSCAAS   840
GFTFSKFGMS WVRQAPGKGL EWVSSISGSG RDTLYAESVK GRFTISRDNA KTTLYLQMNS   900
LRPEDTAVYY CTIGGSLSVS SQGTLVTVSS GGGGSGGGGS GGGSQVQLQ ESGGGLAQAG   960
GSLSLSCAAS GFTVSNSVMA WYRQTPGKQR EFVAIINSVG STNYADSVKG RFTISRDNAK   1020
NTVYLQMNNL KPEDTAVYVC NRNFDRIYWG QGTQVTVSSH HHHHHEPEA             1069

SEQ ID NO: 70            moltype = AA   length = 1069
FEATURE                  Location/Qualifiers
source                   1..1069
                         mol_type = protein
                         organism = synthetic construct
SEQUENCE: 70
```

-continued

```
QVQLQESGGG LAQAGGSLSL SCAASGFTVS NSVMAWYRQT PGKQREFVAI INSVGSTNYA    60
DSVKGRFTIS RDNAKNTVYL QMNNLKPEDT AVYVCNRNFD RIYWGQGTQV TVSSGGGGSG   120
GGGGSGGGGSQ SVLTQPPSVS GAPGQRVTIS CSGSRSNIGS NTVKWYQQLP GTAPKLLIYY  180
NDQRPSGVPD RFSGSKSGTS ASLAITGLQA EDEADYYCQS YDRYTHPALL FGTGTKVTVL   240
GGGGSGGGGS GGGGSQVQLV ESGGGVVQPG RSLRLSCAAS GFTFSSYGMH WVRQAPGKGL   300
EWVAFIRYDG SNKYYADSVK GRFTISRDNS KNTLYLQMNS LRAEDTAVYY CKTHGSHDNW   360
GQGTMVTVSS GGGGSGGGGS GGGGSGGGGS GGGGSGGGGS SGGPGPAGMK GLPGSIWELK   420
KDVYVVELDW YPDAPGEMVV LTCDTPEEDG ITWTLDQSSE VLGSGKTLTI QVKEFGDAGQ   480
YTCHKGGEVL SHSLLLLHKK EDGIWSTDIL KDQKEPKNKT FLRCEAKNYS GRFTCWWLTT   540
ISTDLTFSVK SSRGSSDPQG VTCGAATLSA ERVRGDNKEY EYSVECQEDS ACPAAEESLP   600
IEVMVDAVHK LKYENYTSSF FIRDIIKPDP PKNLQLKPLK NSRQVEVSWE YPDTWSTPHS   660
YFSLTFCVQV QGKSKREKKD RVFTDKTSAT VICRKNASIS VRAQDRYYSS SWSEWASVPC   720
SGGGGSGGGG SGGGGSRVIP VSGPARCLSQ SRNLLKTTDD MVKTAREKLK HYSCTAEDID   780
HEDITRDQTS TLKTCLPLEL HKNESCLATR ETSSTTRGSC LPPQKTSLMM TLCLGSIYED   840
LKMYQTEFQA INAALQNHNH QQIILDKGML VAIDELMQSL NHNGETLRQK PPVGEADPYR   900
VKMKLCILLH AFSTRVVTIN RVMGYLSSAS GGPGPAGMKG LPGSEVQLVE SGGGLVQPGN   960
SLRLSCAASG FTFSKFGMSW VRQAPGKGLE WVSSISGSGR DTLYAESVKG RFTISRDNAK  1020
TTLYLQMNSL RPEDTAVYYC TIGGSLSVSS QGTLVTVSSH HHHHHEPEA             1069

SEQ ID NO: 71          moltype = AA   length = 940
FEATURE                Location/Qualifiers
source                 1..940
                       mol_type = protein
                       organism = synthetic construct
SEQUENCE: 71
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSGGGGS   120
GGGGSGGGGS QSVLTQPPSV SGAPGQRVTI SCSGSRSNIG SNTVKWYQQL PGTAPKLLIY   180
YNDQRPSGVP DRFSGSKSGT SASLAITGLQ AEDEADYYCQ SYDRYTHPAL LFGTGTKVTV   240
LGGGGSGGGG SGGGGSQVQL VESGGGVVQP GRSLRLSCAA SGFTFSSYGM HWVRQAPGKG   300
LEWVAFIRYD GSNKYYADSV KGRFTISRDN SKNTLYLQMN SLRAEDTAVY YCKTHGSHDN   360
WGQGTMVTVS SGGGGSGGGG SGGGGSGGGG SGGGGSGGGG SSGGPGPAGM KGLPGSIWEL   420
KKDVYVVELD WYPDAPGEMV VLTCDTPEED GITWTLDQSS EVLGSGKTLT IQVKEFGDAG   480
QYTCHKGGEV LSHSLLLLHK KEDGIWSTDI LKDQKEPKNK TFLRCEAKNY SGRFTCWWLT   540
TISTDLTFSV KSSRGSSDPQ GVTCGAATLS AERVRGDNKE YEYSVECQED SACPAAEESL   600
PIEVMVDAVH KLKYENYTSS FFIRDIIKPD PPKNLQLKPL KNSRQVEVSW EYPDTWSTPH   660
SYFSLTFCVQ VQGKSKREKK DRVFTDKTSA TVICRKNASI SVRAQDRYYS SSWSEWASVP   720
CSGGGGSGGG GSGGGGSRVI PVSGPARCLS QSRNLLKTTD DMVKTAREKL KHYSCTAEDI   780
DHEDITRDQT STLKTCLPLE LHKNESCLAT RETSSTTRGS CLPPQKTSLM MTLCLGSIYE   840
DLKMYQTEFQ AINAALQNHN HQQIILDKGM LVAIDELMQS LNHNGETLRQ KPPVGEADPY   900
RVKMKLCILL HAFSTRVVTI NRVMGYLSSA HHHHHHEPEA                        940

SEQ ID NO: 72          moltype = AA   length = 940
FEATURE                Location/Qualifiers
source                 1..940
                       mol_type = protein
                       organism = synthetic construct
SEQUENCE: 72
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGMKGLPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPGP AGMKGLPGSG   660
GGGSGGGGSG GGGSGGGGSG GGGSGGGGSQ SVLTQPPSVS GAPGQRVTIS CSGSRSNIGS   720
NTVKWYQQLP GTAPKLLIYY NDQRPSGVPD RFSGSKSGTS ASLAITGLQA EDEADYYCQS   780
YDRYTHPALL FGTGTKVTVL GGGGSGGGGS GGGGSQVQLV ESGGGVVQPG RSLRLSCAAS   840
GFTFSSYGMH WVRQAPGKGL EWVAFIRYDG SNKYYADSVK GRFTISRDNS KNTLYLQMNS   900
LRAEDTAVYY CKTHGSHDNW GQGTMVTVSS HHHHHHEPEA                        940

SEQ ID NO: 73          moltype = AA   length = 940
FEATURE                Location/Qualifiers
source                 1..940
                       mol_type = protein
                       organism = synthetic construct
SEQUENCE: 73
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSGGGG SGGGGSGGGG SRVIPVSGPA RCLSQSRNLL KTTDDMVKTA REKLKHYSCT   360
AEDIDHEDIT RDQTSTLKTC LPLELHKNES CLATRETSST TRGSCLPPQK TSLMMTLCLG   420
SIYEDLKMYQ TEFQAINAAL QNHNHQQIIL DKGMLVAIDE LMQSLNHNGE TLRQKPPVGE   480
```

-continued

```
ADPYRVKMKL CILLHAFSTR VVTINRVMGY LSSASGGPGP AGMKGLPGSG GGGSGGGGSG   540
GGGSGGGGSG GGGSGGGGSQ SVLTQPPSVS GAPGQRVTIS CSGSRSNIGS NTVKWYQQLP   600
GTAPKLLIYY NDQRPSGVPD RFSGSKSGTS ASLAITGLQA EDEADYYCQS YDRYTHPALL   660
FGTGTKVTVL GGGGSGGGGS GGGGSQVQLV ESGGGVVQPG RSLRLSCAAS GFTFSSYGMH   720
WVRQAPGKGL EWVAFIRYDG SNKYYADSVK GRFTISRDNS KNTLYLQMNS LRAEDTAVYY   780
CKTHGSHDNW GQGTMVTVSS GGGGSGGGGS GGGGSEVQLV ESGGGLVQPG NSLRLSCAAS   840
GFTFSKFGMS WVRQAPGKGL EWVSSISGSG RDTLYAESVK GRFTISRDNA KTTLYLQMNS   900
LRPEDTAVYY CTIGGSLSVS SQGTLVTVSS HHHHHHEPEA                         940

SEQ ID NO: 74          moltype = AA  length = 328
FEATURE                Location/Qualifiers
source                 1..328
                       mol_type = protein
                       organism = Homo sapiens
SEQUENCE: 74
MCHQQLVISW FSLVFLASPL VAIWELKKDV YVVELDWYPD APGEMVVLTC DTPEEDGITW   60
TLDQSSEVLG SGKTLTIQVK EFGDAGQYTC HKGGEVLSHS LLLLHKKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SKREKKDRVF TDKTSATVIC   300
RKNASISVRA QDRYYSSSWS EWASVPCS                                      328

SEQ ID NO: 75          moltype = AA  length = 215
FEATURE                Location/Qualifiers
source                 1..215
                       mol_type = protein
                       organism = Mus musculus
SEQUENCE: 75
MCQSRYLLFL ATLALLNHLS LARVIPVSGP ARCLSQSRNL LKTTDDMVKT AREKLKHYSC   60
TAEDIDHEDI TRDQTSTLKT CLPLELHKNE SCLATRETSS TTRGSCLPPQ KTSLMMTLCL   120
GSIYEDLKMY QTEFQAINAA LQNHNHQQII LDKGMLVAID ELMQSLNHNG ETLRQKPPVG   180
EADPYRVKMK LCILLHAFST RVVTINRVMG YLSSA                              215

SEQ ID NO: 76          moltype = AA  length = 862
FEATURE                Location/Qualifiers
source                 1..862
                       mol_type = protein
                       note = IL12Rb-2 sequence
                       organism = unidentified
SEQUENCE: 76
MAHTFRGCSL AFMFIITWLL IKAKIDACKR GDVTVKPSHV ILLGSTVNIT CSLKPRQGCF   60
HYSRRNKLIL YKFDRRINFH HGHSLNSQVT GLPLGTTLFV CKLACINSDE IQICGAEIFV   120
GVAPEQPQNL SCIQKGEQGT VACTWERGRD THLYTEYTLQ LSGPKNLTWQ KQCKDIYCDY   180
LDFGINLTPE SPESNFTAKV TAVNSLGSSS SLPSTFTFLD IVRPLPPWDI RIKFQKASVS   240
RCTLYWRDEG LVLLNRLRYR PSNSRLWNMV NVTKAKGRHD LLDLKPFTEY EFQISSKLHL   300
YKGSWSDWSE SLRAQTPEEE PTGMLDVWYM KRHIDYSRQQ ISLFWKNLSV SEARGKILHY   360
QVTLQELTGG KAMTQNITGH TSWTTVIPRT GNWAVAVSAN NSKGSSLPTR INIMNLCEAG   420
LLAPRQVSAN SEGMDNILVT WQPPRKDPSA VQEYVVEWRE LHPGGDTQVP LNWLRSRPYN   480
VSALISENIK SYICYEIRVY ALSGDQGGCS SILGNSKHKA PLSGPHINAI TEEKGSILIS   540
WNSIPVQEQM GCLLHYRIYW KERDSNSQPQ LCEIPYRVSQ NSHPINSLQP RVTYVLWMTA   600
LTAAGESSHG NEREFCLQGK ANWMAFVAPS ICIAIIMVGI FSTHYFQQKV FVLLAALRPQ   660
WCSREIPDPA NSTCAKKYPI AEEKTQLPLD RLLIDWPTPE DPEPLVISEV LHQVTPVFRH   720
PPCSNWPQRE KGIQGHQASE KDMMHSASSP PPPRALQAES RQLVDLYKVL ESRGSDPKPE   780
NPACPWTVLP AGDLPTHDGY LPSNIDDLPS HEAPLADSLE ELEPQHISLS VFPSSSLHPL   840
TFSCGDKLTL DQLKMRCDSL ML                                            862

SEQ ID NO: 77          moltype = AA  length = 662
FEATURE                Location/Qualifiers
source                 1..662
                       mol_type = protein
                       note = IL12Rb-1 sequence
                       organism = unidentified
SEQUENCE: 77
MEPLVTWVVP LLFLFLLSRQ GAACRTSECC FQDPPYPDAD SGSASGPRDL RCYRISSDRY   60
ECSWQYEGPT AGVSHFLRCC LSSGRCCYFA AGSATRLQFS DQAGVSVLYT VTLWVESWAR   120
NQTEKSPEVT LQLYNSVKYE PPLGDIKVSK LAGQLRMEWE TPDNQVGAEV QFRHRTPSSP   180
WKLGDCGPQD DDTESCLCPL EMNVAQEFQL RRRQLGSQGS SWSKWSSPVC VPPENPPQPQ   240
VRFSVEQLGQ DGRRRLTLKE QPTQLELPEG CQGLAPGTEV TYRLQLHMLS CPCKAKATRT   300
LHLGKMPYLS GAAYNVAVIS SNQFGPGLNQ TWHIPADTHT EPVALNISVG TNGTTMYWPA   360
RAQSMTYCIE WQPVGQDGGL ATCSLTAPQD PDPAGMATYS WSRESGAMGQ EKCYYITIFA   420
SAHPEKLTLW STVLSTYHFG GNASAAGTPH HVSVKNHSLD SVSVDWAPSL LSTCPGVLKE   480
YVVRCRDEDS KQVSEHPVQP TETQVTLSGL RAGVAYTVQV RADTAWLRGV WSQPQRFSIE   540
VQVSDWLIFF ASLGSFLSIL LVGVLGYLGL NRAARHLCPP LPTPCASSAI EFPGGKETWQ   600
WINPVDFQEE ASLQEALVVE MSWDKGERTE PLEKTELPEG APELALDTEL SLEDGDRCKA   660
KM                                                                 662

SEQ ID NO: 78          moltype = AA  length = 328
FEATURE                Location/Qualifiers
source                 1..328
```

```
                              mol_type = protein
                              organism = Homo sapiens
SEQUENCE: 78
MCHQQLVISW FSLVFLASPL VAIWELKKDV YVVELDWYPD APGEMVVLTC DTPEEDGITW   60
TLDQSSEVLG SGKTLTIQVK EFGDAGQYTC HKGGEVLSHS LLLLHKKEDG IWSTDILKDQ   120
KEPKNKTFLR CEAKNYSGRF TCWWLTTIST DLTFSVKSSR GSSDPQGVTC GAATLSAERV   180
RGDNKEYEYS VECQEDSACP AAEESLPIEV MVDAVHKLKY ENYTSSFFIR DIIKPDPPKN   240
LQLKPLKNSR QVEVSWEYPD TWSTPHSYFS LTFCVQVQGK SKREKKDRVF TDKTSATVIC   300
RKNASISVRA QDRYYSSSWS EWASVPCS                                      328

SEQ ID NO: 79           moltype = AA  length = 335
FEATURE                 Location/Qualifiers
source                  1..335
                        mol_type = protein
                        organism = Mus musculus
SEQUENCE: 79
MCPQKLTISW FAIVLLVSPL MAMWELEKDV YVVEVDWTPD APGETVNLTC DTPEEDDITW   60
TSDQRHGVIG SGKTLTITVK EFLDAGQYTC HKGGETLSHS HLLLLHKKENG IWSTEILKNF  120
KNKTFLKCEA PNYSGRFTCS WLVQRNMDLK FNIKSSSSSP DSRAVTCGMA SLSAEKVTLD   180
QRDYEKYSVS CQEDVTCPTA EETLPIELAL EARQQNKYEN YSTSFFIRDI IKPDPPKNLQ   240
MKPLKNSQVE VSWEYPDSWS TPHSYFSLKF FVRIQRKKEK MKETEEGCNQ KGAFLVEKTS   300
TEVQCKGGNV CVQAQDRYYN SSCSKWACVP CRVRS                              335

SEQ ID NO: 80           moltype = AA  length = 399
FEATURE                 Location/Qualifiers
source                  1..399
                        mol_type = protein
                        organism = synthetic construct
SEQUENCE: 80
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG   120
PAGMKGLPGS HGTVIESLES LNNYFNSSGI DVEEKSLFLD IWRNWQKDGD MKILQSQIIS   180
FYLRLFEVLK DNQAISNNIS VIESHLITTF FSNSKAKKDA FMSIAKFEVN NPQVQRQAFN   240
ELIRVVHQLL PESSLRKRKR SRCSGGPGPA GMKGLPGSEV QLVESGGGLV QPGNSLRLSC   300
AASGFTFSKF GMSWVRQAPG KGLEWVSSIS GSGRDTLYAE SVKGRFTISR DNAKTTLYLQ   360
MNSLRPEDTA VYYCTIGGSL SVSSQGTLVT VSSHHHHHH                          399

SEQ ID NO: 81           moltype = AA  length = 547
FEATURE                 Location/Qualifiers
source                  1..547
                        mol_type = protein
                        organism = synthetic construct
SEQUENCE: 81
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG   120
PAGMKGLPGS HGTVIESLES LNNYFNSSGI DVEEKSLFLD IWRNWQKDGD MKILQSQIIS   180
FYLRLFEVLK DNQAISNNIS VIESHLITTF FSNSKAKKDA FMSIAKFEVN NPQVQRQAFN   240
ELIRVVHQLL PESSLRKRKR SRCSGGPGPA GMKGLPGSHG TVIESLESLN NYFNSSGIDV   300
EEKSLFLDIW RNWQKDGDMK ILQSQIISFY LRLFEVLKDN QAISNNISVI ESHLITTFFS   360
NSKAKKDAFM SIAKFEVNNP QVQRQAFNEL IRVVHQLLPE SSLRKRKRSR CSGGPGPAGM   420
KGLPGSEVQL VESGGGLVQP GNSLRLSCAA SGFTFSKFGM SWVRQAPGKG LEWVSSISGS   480
GRDTLYAESV KGRFTISRDN AKTTLYLQMN SLRPEDTAVY YCTIGGSLSV SSQGTLVTVS   540
SHHHHHH                                                            547

SEQ ID NO: 82           moltype = AA  length = 547
FEATURE                 Location/Qualifiers
source                  1..547
                        mol_type = protein
                        organism = synthetic construct
SEQUENCE: 82
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG   120
PAGMKGLPGS HGTVIESLES LNNYFNSSGI DVEEKSLFLD IWRNWQKDGD MKILQSQIIS   180
FYLRLFEVLK DNQAISNNIS VIESHLITTF FSNSKAKKDA FMSIAKFEVN NPQVQRQAFN   240
ELIRVVHQLL PESSLRKRKR SRCGGGGSGG GGSGGGGSHG TVIESLESLN NYFNSSGIDV   300
EEKSLFLDIW RNWQKDGDMK ILQSQIISFY LRLFEVLKDN QAISNNISVI ESHLITTFFS   360
NSKAKKDAFM SIAKFEVNNP QVQRQAFNEL IRVVHQLLPE SSLRKRKRSR CSGGPGPAGM   420
KGLPGSEVQL VESGGGLVQP GNSLRLSCAA SGFTFSKFGM SWVRQAPGKG LEWVSSISGS   480
GRDTLYAESV KGRFTISRDN AKTTLYLQMN SLRPEDTAVY YCTIGGSLSV SSQGTLVTVS   540
SHHHHHH                                                            547

SEQ ID NO: 83           moltype = AA  length = 166
FEATURE                 Location/Qualifiers
source                  1..166
                        mol_type = protein
                        organism = Homo sapiens
SEQUENCE: 83
MKYTSYILAF QLCIVLGSLG CYCQDPYVKE AENLKKYFNA GHSDVADNGT LFLGILKNWK   60
EESDRKIMQS QIVSFYFKLF KNFKDDQSIQ KSVETIKEDM NVKFFNSNKK KRDDFEKLTN   120
```

```
YSVTDLNVQR KAIHELIQVM AELSPAAKTG KRKRSQMLFR GRRASQ                        166

SEQ ID NO: 84               moltype = AA  length = 155
FEATURE                     Location/Qualifiers
source                      1..155
                            mol_type = protein
                            organism = Mus musculus
SEQUENCE: 84
MNATHCILAL QLFLMAVSGC YCHGTVIESL ESLNNYFNSS GIDVEEKSLF LDIWRNWQKD        60
GDMKILQSQI ISFYLRLFEV LKDNQAISNN ISVIESHLIT TFFSNSKAKK DAFMSIAKFE        120
VNNPQVQRQA FNELIRVVHQ LLPESSLRKR KRSRC                                   155

SEQ ID NO: 85               moltype = AA  length = 699
FEATURE                     Location/Qualifiers
source                      1..699
                            mol_type = protein
                            organism = synthetic construct
SEQUENCE: 85
MDMRVPAQLL GLLLLWLRGA RCEVQLVESG GGLVQPGNSL RLSCAASGFT FSKFGMSWVR        60
QAPGKGLEWV SSISGSGRDT LYAESVKGRF TISRDNAKTT LYLQMNSLRP EDTAVYYCTI        120
GGSLSVSSQG TLVTVSSSGG PGPAGMKGLP GSHGTVIESL ESLNNYFNSS GIDVEEKSLF        180
LDIWRNWQKD GDMKILQSQI ISFYLRLFEV LKDNQAISNN ISVIESHLIT TFFSNSKAKK        240
DAFMSIAKFE VNNPQVQRQA FNELIRVVHQ LLPESSLRKR KRSRCSGGPG PAGMKGLPGS        300
EVQLVESGGG LVQPGNSLRL SCAASGFTFS KFGMSWVRQA PGKGLEWVSS ISGSGRDTLY        360
AESVKGRFTI SRDNAKTTLY LQMNSLRPED TAVYYCTIGG SLSVSSQGTL VTVSSSGGPG        420
PAGMKGLPGS HGTVIESLES LNNYFNSSGI DVEEKSLFLD IWRNWQKDGD MKILQSQIIS        480
FYLRLFEVLK DNQAISNNIS VIESHLITTF FSNSKAKKDA FMSIAKFEVN NPQVQRQAFN        540
ELIRVVHQLL PESSLRKRKR SRCSGGPGPA GMKGLPGSEV QLVESGGGLV QPGNSLRLSC        600
AASGFTFSKF GMSWVRQAPG KGLEWVSSIS GSGRDTLYAE SVKGRFTISR DNAKTTLYLQ        660
MNSLRPEDTA VYYCTIGGSL SVSSQGTLVT VSSHHHHHH                               699

SEQ ID NO: 86               moltype = AA  length = 436
FEATURE                     Location/Qualifiers
source                      1..436
                            mol_type = protein
                            organism = synthetic construct
SEQUENCE: 86
EVQLVESGGG LVQPGNSLRL SCAASGFTFS KFGMSWVRQA PGKGLEWVSS ISGSGRDTLY        60
AESVKGRFTI SRDNAKTTLY LQMNSLRPED TAVYYCTIGG SLSVSSQGTL VTVSSSGGPG        120
PAGMKGLPGS CDLPQTHNLR NKRALTLLVQ MRRLSPLSCL KDRKDFGFPQ EKVDAQQIKK        180
AQAIPVLSEL TQQILNIFTS KDSSAAWNTT LLDSFCNDLH QQLNDLQGCL MQQVGVQEFP        240
LTQEDALLAV RKYFHRITVY LREKKHSPCA WEVVRAEVWR ALSSSANVLG RLREEKSGGP        300
GPAGMKGLPG SEVQLVESGG GLVQPGNSLR LSCAASGFTF SKFGMSWVRQ APGKGLEWVS        360
SISGSGRDTL YAESVKGRFT ISRDNAKTTL YLQMNSLRPE DTAVYYCTIG GSLSVSSQGT        420
LVTVSSHHHH HHEPEA                                                       436

SEQ ID NO: 87               moltype = AA  length = 428
FEATURE                     Location/Qualifiers
source                      1..428
                            mol_type = protein
                            organism = synthetic construct
SEQUENCE: 87
EVQLVESGGG LVQPGNSLRL SCAASGFTFS KFGMSWVRQA PGKGLEWVSS ISGSGRDTLY        60
AESVKGRFTI SRDNAKTTLY LQMNSLRPED TAVYYCTIGG SLSVSSQGTL VTVSSSGGPG        120
PAGMKGLPGS CDLPQTHNLR NKRALTLLVQ MRRLSPLSCL KDRKDFGFPQ EKVDAQQIKK        180
AQAIPVLSEL TQQILNIFTS KDSSAAWNTT LLDSFCNDLH QQLNDLQGCL MQQVGVQEFP        240
LTQEDALLAV RKYFHRITVY LREKKHSPCA WEVVRAEVWR ALSSSANVSG GPGPAGMKGL        300
PGSEVQLVES GGGLVQPGNS LRLSCAASGF TFSKFGMSWV RQAPGKGLEW VSSISGSGRD        360
TLYAESVKGR FTISRDNAKT TLYLQMNSLR PEDTAVYYCT IGGSLSVSSQ GTLVTVSSHH        420
HHHHEPEA                                                                428

SEQ ID NO: 88               moltype = AA  length = 489
FEATURE                     Location/Qualifiers
source                      1..489
                            mol_type = protein
                            note = IFNgR1 sequence
                            organism = unidentified
SEQUENCE: 88
MALLFLLPLV MQGVSRAEMG TADLGPSSVP TPTNVTIESY NMNPIVYWEY QIMPQVPVFT        60
VEVKNYGVKN SEWIDACINI SHHYCNISDH VGDPSNSLWV RVKARVGQKE SAYAKSEEFA        120
VCRDGKIGPP KLDIRKEEKQ IMIDIFHPSV FVNGDEQEVD YDPETTCYIR VYNVYVRMNG        180
SEIQYKILTQ KEDDCDEIQC QLAIPVSSLN SQYCVSAEGV LHVWGVTTEK SKEVCITIFN        240
SSIKGSLWIP VVAALLLFLV LSLVPICFYI KKINPLKEKS IILPKSLISV VRSATLETKP        300
ESKYVSLITS YQPFSLEKEV VCEEPLSPAT VPGMHTEDNP GKVEHTEELS SITEVVTTEE        360
NIPDVVPGSH LTPIERESSS PLSSNQSEPG SIALNSYHSR NCSESDHSRN GFDTDSSCLE        420
SHSSLSDSEF PPNNKGEIKT EGQELITVIK APTSFGYDKP HVLVDLLVDD SGKESLIGYR        480
PTEDSKEFS                                                               489

SEQ ID NO: 89               moltype = AA  length = 337
```

-continued

```
FEATURE              Location/Qualifiers
source               1..337
                     mol_type = protein
                     note = IFNgR2 sequence
                     organism = unidentified
SEQUENCE: 89
MRPTLLWSLL LLLGVFAAAA AAPPDPLSQL PAPQHPKIRL YNAEQVLSWE PVALSNSTRP  60
VVYQVQFKYT DSKWFTADIM SIGVNCTQIT ATECDFTAAS PSAGFPMDFN VTLRLRAELG  120
ALHSAWVTMP WFQHYRNVTV GPPENIEVTP GEGSLIIRFS SPPDIADTST AFFCYVVHYW  180
EKGGIQQVKG PFRSNSISLD NLKPSRVYCL QVQAQLLWNK SNIFRVGHLS NISCYETMAD  240
ASTELQQVIL ISVGTFSLLS VLAGACFFLV LKYRGLIKYW FHTPPSIPLQ IEEYLKDPTQ  300
PILEALDKDS SPKDDVWDSV SIISFPEKEQ EDVLQTL                           337

SEQ ID NO: 90        moltype = AA  length = 528
FEATURE              Location/Qualifiers
source               1..528
                     mol_type = protein
                     organism = synthetic construct
SEQUENCE: 90
QVQLQESGGG LVQAGGSLRL SCAASGRIFS IDIMSWYRQA PGKQRELVAR ITRGGTISYD  60
DSVKGRFTIS RDNAKNTVYL QMNSLKPEDT GVYYCNALYG TDYWGKGTQV TVSSGGGGSG  120
GGGSGGGGSE VQLVESGGGL VQPGNSLRLS CAASGFTFSK FGMSWVRQAP GKGLEWVSSI  180
SGSGRDTLYA ESVKGRFTIS RDNAKTTLYL QMNSLRPEDT AVYYCTIGGS LSVSSQGTLV  240
TVSSSGGPGP AGMKGLPGSH GTVIESLESL NNYFNSSGID VEEKSLFLDI WRNWQKDGDM  300
KILQSQIISF YLRLFEVLKD NQAISNNISV IESHLITTFF SNSKAKKDAF MSIAKFEVNN  360
PQVQRQAFNE LIRVVHQLLP ESSLRKRKRS RCSGGPGPAG MKGLPGSEVQ LVESGGGLVQ  420
PGNSLRLSCA ASGFTFSKFG MSWVRQAPGK GLEWVSSISG SGRDTLYAES VKGRFTISRD  480
NAKTTLYLQM NSLRPEDTAV YYCTIGGSLS VSSQGTLVTV SSHHHHHH                528

SEQ ID NO: 91        moltype = AA  length = 658
FEATURE              Location/Qualifiers
source               1..658
                     mol_type = protein
                     organism = synthetic construct
SEQUENCE: 91
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS HGTVIESLES LNNYFNSSGI DVEEKSLFLD IWRNWQKDGD MKILQSQIIS  180
FYLRLFEVLK DNQAISNNIS VIESHLITTF FSNSKAKKDA FMSIAKFEVN NPQVQRQAFN  240
ELIRVVHQLL PESSLRKRKR SRCSGGPGPA GMKGLPGSEV QLVESGGGLV QPGNSLRLSC  300
AASGFTFSKF GMSWVRQAPG KGLEWVSSIS GSGRDTLYAE SVKGRFTISR DNAKTTLYLQ  360
MNSLRPEDTA VYYCTIGGSL SVSSQGTLVT VSSSGGPGPA GMKGLPGSEV QLVESGGGLV  420
QPGNSLRLSC AASGFTFSKF GMSWVRQAPG KGLEWVSSIS GSGRDTLYAE SVKGRFTISR  480
DNAKTTLYLQ MNSLRPEDTA VYYCTIGGSL SVSSQGTLVT VSSGGGGSGG GGSGGGGSQV  540
QLQESGGGLV QAGGSLRLSC AASGRIFSID IMSWYRQAPG KQRELVARIT RGGTISYDDS  600
VKGRFTISRD NAKNTVYLQM NSLKPEDTGV YYCNALYGTD YWGKGTQVTV SSHHHHHH     658

SEQ ID NO: 92        moltype = AA  length = 1337
FEATURE              Location/Qualifiers
source               1..1337
                     mol_type = protein
                     organism = synthetic construct
SEQUENCE: 92
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALASGGPGP AGMKGLPGSH  600
GTVIESLESL NNYFNSSGID VEEKSLFLDI WRNWQKDGDM KILQSQIISF YLRLFEVLKD  660
NQAISNNISV IESHLITTFF SNSKAKKDAF MSIAKFEVNN PQVQRQAFNE LIRVVHQLLP  720
ESSLRKRKRS RCSGGPGPAG MKGLPGSEAH KSEIAHRYND LGEQHFKGLV LIAFSQYLQK  780
CSYDEHAKLV QEVTDFAKTC VADESAANCD KSLHTLFGDK LCAIPNLREN YGELADCCTK  840
QEPERNECFL QHKDDNPSLP FERPEAEAM CTSFKENPTT FMGHYLHEVA RRHPYFYAPE  900
LLYYAEQYNE ILTQCCAEAD KESCLTPKLD GVKEKALVSS VRQRMKCSSM QKFGERAFKA  960
WAVARLSQTF PNADFAEITK LATDLTKVNK ECCHGDLLEC ADDRAELAKY MCENQATISS  1020
KLQTCCDKPL LKKAHCLSEV EHDTMPADLP AIAADFVEDQ EVCKNYAEAK DVFLGTFLYE  1080
YSRRHPDYSV SLLLRLAKKY EATLEKCCAE ANPPACYGTV LAEFQPLVEE PKNLVKTNCD  1140
LYEKLGEYGF QNAILVRYTQ KAPQVSTPTL VEAARNLGRV GTKCCTLPED QRLPCVEDYL  1200
SAILNRVCLL HEKTPVSEHV TKCCSGSLVE RRPCFSALTV DETYVPKEFK AETFTFHSDI  1260
CTLPEKEKQI KKQTALAELV KHKPKATAEQ LKTVMDDFAQ FLDTCCKAAD KDTCFSTEGP  1320
NLVTRCKDAL AHHHHHH                                                 1337

SEQ ID NO: 93        moltype = AA  length = 1485
FEATURE              Location/Qualifiers
```

-continued

```
source                  1..1485
                        mol_type = protein
                        organism = synthetic construct SEQUENCE: 93
EAHKSEIAHR YNDLGEQHFK GLVLIAFSQY LQKCSYDEHA KLVQEVTDFA KTCVADESAA  60
NCDKSLHTLF GDKLCAIPNL RENYGELADC CTKQEPERNE CFLQHKDDNP SLPPFERPEA  120
EAMCTSFKEN PTTFMGHYLH EVARRHPYFY APELLYYAEQ YNEILTQCCA EADKESCLTP  180
KLDGVKEKAL VSSVRQRMKC SSMQKFGERA FKAWAVARLS QTFPNADFAE ITKLATDLTK  240
VNKECCHGDL LECADDRAEL AKYMCENQAT ISSKLQTCCD KPLLKKAHCL SEVEHDTMPA  300
DLPAIAADFV EDQEVCKNYA EAKDVFLGTF LYEYSRRHPD YSVSLLLRLA KKYEATLEKC  360
CAEANPPACY GTVLAEFQPL VEEPKNLVKT NCDLYEKLGE YGFQNAILVR YTQKAPQVST  420
PTLVEAARNL GRVGTKCCTL PEDQRLPCVE DYLSAILNRV CLLHEKTPVS EHVTKCCSGS  480
LVERRPCFSA LTVDETYVPK EFKAETFTFH SDICTLPEKE KQIKKQTALA ELVKHKPKAT  540
AEQLKTVMDD FAQFLDTCCK AADKDTCFST EGPNLVTRCK DALASGGPGP AGMKGLPGSH  600
GTVIESLESL NNYFNSSGID VEEKSLFLDI WRNWQKDGDM KILQSQIISF YLRLFEVLKD  660
NQAISNNISV IESHLITTFF SNSKAKKDAF MSIAKFEVNN PQVQRQAFNE LIRVVHQLLP  720
ESSLRKRKRS RCGGGGSGGG GSGGGGSHGT VIESLESLNN YFNSSGIDVE EKSLFLDIWR  780
NWQKDGDMKI LQSQIISFYL RLFEVLKDNQ AISNNISVIE SHLITTFFSN SKAKKDAFMS  840
IAKFEVNNPQ VQRQAFNELI RVVHQLLPES SLRKRKRSRC SGGPGPAGMK GLPGSEAHKS  900
EIAHRYNDLG EQHFKGLVLI AFSQYLQKCS YDEHAKLVQE VTDFAKTCVA DESAANCDKS  960
LHTLFGDKLC AIPNLRENYG ELADCCTKQE PERNECFLQH KDDNPSLPPF ERPEAEAMCT  1020
SFKENPTTFM GHYLHEVARR HPYFYAPELL YYAEQYNEIL TQCCAEADKE SCLTPKLDGV  1080
KEKALVSSVR QRMKCSSMQK FGERAFKAWA VARLSQTFPN ADFAEITKLA TDLTKVNKEC  1140
CHGDLLECAD DRAELAKYMC ENQATISSKL QTCCDKPLLK AHCLSEVEH DTMPADLPAI  1200
AADFVEDQEV CKNYAEAKDV FLGTFLYEYS RRHPDYSVSL LLRLAKKYEA TLEKCCAEAN  1260
PPACYGTVLA EFQPLVEEPK NLVKTNCDLY EKLGEYGFQN AILVRYTQKA PQVSTPTLVE  1320
AARNLGRVGT KCCTLPEDQR LPCVEDYLSA ILNRVCLLHE KTPVSEHVTK CCSGSLVERR  1380
PCFSALTVDE TYVPKEFKAE TFTFHSDICT LPEKEKQIKK QTALAELVKH KPKATAEQLK  1440
TVMDDFAQFL DTCCKAADKD TCFSTEGPNL VTRCKDALAH HHHHH              1485

SEQ ID NO: 94         moltype = AA  length = 698
FEATURE               Location/Qualifiers
source                1..698
                      mol_type = protein
                      organism = synthetic construct SEQUENCE: 94
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSSGGP GPAGMKGLPG SHGTVIESLE SLNNYFNSSG  300
IDVEEKSLFL DIWRNWQKDG DMKILQSQII SFYLRLFEVL KDNQAISNNI SVIESHLITT  360
FFSNSKAKKD AFMSIAKFEV NNPQVQRQAF NELIRVVHQL LPESSLRKRK RSRCGGGGSG  420
GGGSGGGGSH GTVIESLESL NNYFNSSGID VEEKSLFLDI WRNWQKDGDM KILQSQIISF  480
YLRLFEVLKD NQAISNNISV IESHLITTFF SNSKAKKDAF MSIAKFEVNN PQVQRQAFNE  540
LIRVVHQLLP ESSLRKRKRS RCSGGPGPAG MKGLPGSEVQ LVESGGGLVQ PGNSLRLSCA  600
ASGFTFSKFG MSWVRQAPGK GLEWVSSISG SGRDTLYAES VKGRFTISRD NAKTTLYLQM  660
NSLRPEDTAV YYCTIGGSLS VSSQGTLVTV SSHHHHHH                       698

SEQ ID NO: 95         moltype = AA  length = 699
FEATURE               Location/Qualifiers
source                1..699
                      mol_type = protein
                      organism = synthetic construct SEQUENCE: 95
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSHGTVIESL ESLNNYFNSS GIDVEEKSLF  180
LDIWRNWQKD GDMKILQSQI ISFYLRLFEV LKDNQAISNN ISVIESHLIT TFFSNSKAKK  240
DAFMSIAKFE VNNPQVQRQA FNELIRVVHQ LLPESSLRKR KRSRCSGGPG PAGMKGLPGS  300
EVQLVESGGG LVQPGNSLRL SCAASGFTFS KFGMSWVRQA PGKGLEWVSS ISGSGRDTLY  360
AESVKGRFTI SRDNAKTTLY LQMNSLRPED TAVYYCTIGG SLSVSSQGTL VTVSSSGGPG  420
PAGMKGLPGS HGTVIESLES LNNYFNSSGI DVEEKSLFLD IWRNWQKDGD MKILQSQIIS  480
FYLRLFEVLK DNQAISNNIS VIESHLITTF FSNSKAKKDA FMSIAKFEVN NPQVQRQAFN  540
ELIRVVHQLL PESSLRKRKR SRCSGGPGPA GMKGLPGSEV QLVESGGGLV QPGNSLRLSC  600
AASGFTFSKF GMSWVRQAPG KGLEWVSSIS GSGRDTLYAE SVKGRFTISR DNAKTTLYLQ  660
MNSLRPEDTA VYYCTIGGSL SVSSQGTLVT VSSHHHHHH                      699

SEQ ID NO: 96         moltype = AA  length = 554
FEATURE               Location/Qualifiers
source                1..554
                      mol_type = protein
                      organism = synthetic construct SEQUENCE: 96
MDMRVPAQLL GLLLLWLRGA RCQVQLQESG GGLAQAGGSL SLSCAASGFT VSNSVMAWYR  60
QTPGKQREFV AIINSVGSTN YADSVKGRFT ISRDNAKNTV YLQMNNLKPE DTAVYVCNRN  120
FDRIYWGQGT QVTVSSGGGG SGGGGSGGGG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSSGGP GPAGMKGLPG SHGTVIESLE SLNNYFNSSG  300
```

-continued

```
IDVEEKSLFL DIWRNWQKDG DMKILQSQII SFYLRLFEVL KDNQAISNNI SVIESHLITT   360
FFSNSKAKKD AFMSIAKFEV NNPQVQRQAF NELIRVVHQL LPESSLRKRK RSRCSGGPGP   420
AGMKGLPGSE VQLVESGGGL VQPGNSLRLS CAASGFTFSK FGMSWVRQAP GKGLEWVSSI   480
SGSGRDTLYA ESVKGRFTIS RDNAKTTLYL QMNSLRPEDT AVYYCTIGGS LSVSSQGTLV   540
TVSSHHHHHH EPEA                                                   554

SEQ ID NO: 97           moltype = AA   length = 554
FEATURE                 Location/Qualifiers
source                  1..554
                        mol_type = protein
                        organism = synthetic construct
SEQUENCE: 97
MDMRVPAQLL GLLLLWLRGA RCEVQLVESG GGLVQPGNSL RLSCAASGFT FSKFGMSWVR   60
QAPGKGLEWV SSISGSGRDT LYAESVKGRF TISRDNAKTT LYLQMNSLRP EDTAVYYCTI   120
GGSLSVSSQG TLVTVSSSGG PGPAGMKGLP GSHGTVIESL ESLNNYFNSS GIDVEEKSLF   180
LDIWRNWQKD GDMKILQSQI ISFYLRLFEV LKDNQAISNN ISVIESHLIT TFFSNSKAKK   240
DAFMSIAKFE VNNPQVQRQA FNELIRVVHQ LLPESSLRKR KRSRCSGGPG PAGMKGLPGS   300
EVQLVESGGG LVQPGNSLRL SCAASGFTFS KFGMSWVRQA PGKGLEWVSS ISGSGRDTLY   360
AESVKGRFTI SRDNAKTTLY LQMNSLRPED TAVYYCTIGG SLSVSSQGTL VTVSSGGGGS   420
GGGGSGGGGS QVQLQESGGG LAQAGGSLSL SCAASGFTVS NSVMAWYRQT PGKQREFVAI   480
INSVGSTNYA DSVKGRFTIS RDNAKNTVYL QMNNLKPEDT AVYVCNRNFD RIYWGQGTQV   540
TVSSHHHHHH EPEA                                                   554

SEQ ID NO: 98           moltype = AA   length = 702
FEATURE                 Location/Qualifiers
source                  1..702
                        mol_type = protein
                        organism = synthetic construct
SEQUENCE: 98
MDMRVPAQLL GLLLLWLRGA RCEVQLVESG GGLVQPGNSL RLSCAASGFT FSKFGMSWVR   60
QAPGKGLEWV SSISGSGRDT LYAESVKGRF TISRDNAKTT LYLQMNSLRP EDTAVYYCTI   120
GGSLSVSSQG TLVTVSSSGG PGPAGMKGLP GSHGTVIESL ESLNNYFNSS GIDVEEKSLF   180
LDIWRNWQKD GDMKILQSQI ISFYLRLFEV LKDNQAISNN ISVIESHLIT TFFSNSKAKK   240
DAFMSIAKFE VNNPQVQRQA FNELIRVVHQ LLPESSLRKR KRSRCSGGPG PAGMKGLPGS   300
HGTVIESLES LNNYFNSSGI DVEEKSLFLD IWRNWQKDGD MKILQSQIIS FYLRLFEVLK   360
DNQAISNNIS VIESHLITTF FSNSKAKKDA FMSIAKFEVN NPQVQRQAFN ELIRVVHQLL   420
PESSLRKRKR SRCSGGPGPA GMKGLPGSEV QLVESGGGLV QPGNSLRLSC AASGFTFSKF   480
GMSWVRQAPG KGLEWVSSIS GSGRDTLYAE SVKGRFTISR DNAKTTLYLQ MNSLRPEDTA   540
VYYCTIGGSL SVSSQGTLVT VSSGGGGSGG GGSGGGGSQV QLQESGGGLV QAGGSLRLSC   600
AASGRIFSID IMSWYRQAPG KQRELVARIT RGGTISYDDS VKGRFTISRD NAKNTVYLQM   660
NSLKPEDTGV YYCNALYGTD YWGKGTQVTV SSHHHHHHEP EA                    702

SEQ ID NO: 99           moltype = AA   length = 702
FEATURE                 Location/Qualifiers
source                  1..702
                        mol_type = protein
                        organism = synthetic construct
SEQUENCE: 99
MDRVPAQLL GLLLLWLRGA RCQVQLQESG GGLAQAGGSL SLSCAASGFT VSNSVMAWYR   60
QTPGKQREFV AIINSVGSTN YADSVKGRFT ISRDNAKNTV YLQMNNLKPE DTAVYVCNRN   120
FDRIYWGQGT QVTVSSGGGG SGGGGSGGGG SEVQLVESGG GLVQPGNSLR LSCAASGFTF   180
SKFGMSWVRQ APGKGLEWVS SISGSGRDTL YAESVKGRFT ISRDNAKTTL YLQMNSLRPE   240
DTAVYYCTIG GSLSVSSQGT LVTVSSSGGP GPAGMKGLPG SHGTVIESLE SLNNYFNSSG   300
IDVEEKSLFL DIWRNWQKDG DMKILQSQII SFYLRLFEVL KDNQAISNNI SVIESHLITT   360
FFSNSKAKKD AFMSIAKFEV NNPQVQRQAF NELIRVVHQL LPESSLRKRK RSRCSGGPGP   420
AGMKGLPGSH GTVIESLESL NNYFNSSGID VEEKSLFLDI WRNWQKDGDM KILQSQIISF   480
YLRLFEVLKD NQAISNNISV IESHLITTFF SNSKAKKDAF MSIAKFEVNN PQVQRQAFNE   540
LIRVVHQLLP ESSLRKRKRS RCSGGPGPAG MKGLPGSEVQ LVESGGGLVQ PGNSLRLSCA   600
ASGFTFSKFG MSWVRQAPGK GLEWVSSISG SGRDTLYAES VKGRFTISRD NAKTTLYLQM   660
NSLRPEDTAV YYCTIGGSLS VSSQGTLVTV SSHHHHHHEP EA                    702

SEQ ID NO: 100          moltype = AA   length = 702
FEATURE                 Location/Qualifiers
source                  1..702
                        mol_type = protein
                        organism = synthetic construct
SEQUENCE: 100
MDMRVPAQLL GLLLLWLRGA RCEVQLVESG GGLVQPGNSL RLSCAASGFT FSKFGMSWVR   60
QAPGKGLEWV SSISGSGRDT LYAESVKGRF TISRDNAKTT LYLQMNSLRP EDTAVYYCTI   120
GGSLSVSSQG TLVTVSSSGG PGPAGMKGLP GSHGTVIESL ESLNNYFNSS GIDVEEKSLF   180
LDIWRNWQKD GDMKILQSQI ISFYLRLFEV LKDNQAISNN ISVIESHLIT TFFSNSKAKK   240
DAFMSIAKFE VNNPQVQRQA FNELIRVVHQ LLPESSLRKR KRSRCSGGPG PAGMKGLPGS   300
HGTVIESLES LNNYFNSSGI DVEEKSLFLD IWRNWQKDGD MKILQSQIIS FYLRLFEVLK   360
DNQAISNNIS VIESHLITTF FSNSKAKKDA FMSIAKFEVN NPQVQRQAFN ELIRVVHQLL   420
PESSLRKRKR SRCSGGPGPA GMKGLPGSEV QLVESGGGLV QPGNSLRLSC AASGFTFSKF   480
GMSWVRQAPG KGLEWVSSIS GSGRDTLYAE SVKGRFTISR DNAKTTLYLQ MNSLRPEDTA   540
VYYCTIGGSL SVSSQGTLVT VSSGGGGSGG GGSGGGGSQV QLQESGGGLA QAGGSLSLSC   600
AASGFTVSNS VMAWYRQTPG KQREFVAIIN SVGSTNYADS VKGRFTISRD NAKNTVYLQM   660
NNLKPEDTAV YVCNRNFDRI YWGQGTQVTV SSHHHHHHEP EA                    702
```

-continued

```
SEQ ID NO: 101          moltype = AA   length = 832
FEATURE                 Location/Qualifiers
source                  1..832
                        mol_type = protein
                        organism = synthetic construct
SEQUENCE: 101
MDMRVPAQLL GLLLLWLRGA RCEVQLVESG GGLVQPGNSL RLSCAASGFT FSKFGMSWVR    60
QAPGKGLEWV SSISGSGRDT LYAESVKGRF TISRDNAKTT LYLQMNSLRP EDTAVYYCTI   120
GGSLSVSSQG TLVTVSSSGG PGPAGMKGLP GSHGTVIESL ESLNNYFNSS GIDVEEKSLF   180
LDIWRNWQKD GDMKILQSQI ISFYLRLFEV LKDNQAISNN ISVIESHLIT TFFSNSKAKK   240
DAFMSIAKFE VNNPQVQRQA FNELIRVVHQ LLPESSLRKR KRSRCSGGPG PAGMKGLPGS   300
HGTVIESLES LNNYFNSSGI DVEEKSLFLD IWRNWQKDGD MKILQSQIIS FYLRLFEVLK   360
DNQAISNNIS VIESHLITTF FSNSKAKKDA FMSIAKFEVN NPQVQRQAFN ELIRVVHQLL   420
PESSLRKRKR SRCSGGPGPA GMKGLPGSEV QLVESGGGLV QPGNSLRLSC AASGFTFSKF   480
GMSWVRQAPG KGLEWVSSIS GSGRDTLYAE SVKGRFTISR DNAKTTLYLQ MNSLRPEDTA   540
VYYCTIGGSL SVSSQGTLVT VSSGGGGSGG GGSGGGGSEV QLVESGGGLV QPGGSLRLSC   600
AASGFTFSSY AMSWVRQAPG KGLEWVSAIS GSGGSTYYAD SVKGRFTISR DNSKNTLYLQ   660
MNSLRAEDTA VYYCARGVGA FRPYRKHEWG QGTLVTVSRG GGGSGGGGSG GGGSSSELTQ   720
DPAVSVALGQ TVRITCQGDS LRSYYASWYQ QKPGQAPVLV IYGKNNRPSG IPDRFSGSSS   780
GNTASLTTTG AQAEDEADYY CNSSPFEHNL VVFGGGTKLT VLHHHHHHEP EA           832

SEQ ID NO: 102          moltype = AA   length = 276
FEATURE                 Location/Qualifiers
source                  1..276
                        mol_type = protein
                        organism = synthetic construct
SEQUENCE: 102
MDMRVPAQLL GLLLLWLRGA RCEVQLVESG GGLVQPGGSL RLSCAASGFT FSSYAMSWVR    60
QAPGKGLEWV SAISGSGGST YYADSVKGRF TISRDNSKNT LYLQMNSLRA EDTAVYYCAR   120
GVGAFRPYRK HEWGQGTLVT VSRGGGGSGG GGSGGGGSSS ELTQDPAVSV ALGQTVRITC   180
QGDSLRSYYA SWYQQKPGQA PVLVIYGKNN RPSGIPDRFS GSSSGNTASL TTTGAQAEDE   240
ADYYCNSSPF EHNLVVFGGG TKLTVLHHHH HHEPEA                             276

SEQ ID NO: 103          moltype = AA   length = 573
FEATURE                 Location/Qualifiers
source                  1..573
                        mol_type = protein
                        organism = synthetic construct
SEQUENCE: 103
MDMRVPAQLL GLLLLWLRGA RCEVQLVESG GGLVQPGNSL RLSCAASGFT FSKFGMSWVR    60
QAPGKGLEWV SSISGSGRDT LYAESVKGRF TISRDNAKTT LYLQMNSLRP EDTAVYYCTI   120
GGSLSVSSQG TLVTVSSSGG PGPAGMKGLP GSHGTVIESL ESLNNYFNSS GIDVEEKSLF   180
LDIWRNWQKD GDMKILQSQI ISFYLRLFEV LKDNQAISNN ISVIESHLIT TFFSNSKAKK   240
DAFMSIAKFE VNNPQVQRQA FNELIRVVHQ LLPESSLRKR KRSRCSGGPG PAGMKGLPGS   300
EVQLVESGGG LVQPGNSLRL SCAASGFTFS KFGMSWVRQA PGKGLEWVSS ISGSGRDTLY   360
AESVKGRFTI SRDNAKTTLY LQMNSLRPED TAVYYCTIGG SLSVSSQGTL VTVSSSGGPG   420
PAGMKGLPGS HGTVIESLES LNNYFNSSGI DVEEKSLFLD IWRNWQKDGD MKILQSQIIS   480
FYLRLFEVLK DNQAISNNIS VIESHLITTF FSNSKAKKDA FMSIAKFEVN NPQVQRQAFN   540
ELIRVVHQLL PESSLRKRKR SRCHHHHHHE PEA                                573

SEQ ID NO: 104          moltype = AA   length = 573
FEATURE                 Location/Qualifiers
source                  1..573
                        mol_type = protein
                        organism = synthetic construct
SEQUENCE: 104
MDMRVPAQLL GLLLLWLRGA RCHGTVIESL ESLNNYFNSS GIDVEEKSLF LDIWRNWQKD    60
GDMKILQSQI ISFYLRLFEV LKDNQAISNN ISVIESHLIT TFFSNSKAKK DAFMSIAKFE   120
VNNPQVQRQA FNELIRVVHQ LLPESSLRKR KRSRCSGGPG PAGMKGLPGS EVQLVESGGG   180
LVQPGNSLRL SCAASGFTFS KFGMSWVRQA PGKGLEWVSS ISGSGRDTLY AESVKGRFTI   240
SRDNAKTTLY LQMNSLRPED TAVYYCTIGG SLSVSSQGTL VTVSSSGGPG PAGMKGLPGS   300
HGTVIESLES LNNYFNSSGI DVEEKSLFLD IWRNWQKDGD MKILQSQIIS FYLRLFEVLK   360
DNQAISNNIS VIESHLITTF FSNSKAKKDA FMSIAKFEVN NPQVQRQAFN ELIRVVHQLL   420
PESSLRKRKR SRCSGGPGPA GMKGLPGSEV QLVESGGGLV QPGNSLRLSC AASGFTFSKF   480
GMSWVRQAPG KGLEWVSSIS GSGRDTLYAE SVKGRFTISR DNAKTTLYLQ MNSLRPEDTA   540
VYYCTIGGSL SVSSQGTLVT VSSHHHHHHE PEA                                573

SEQ ID NO: 105          moltype = AA   length = 1511
FEATURE                 Location/Qualifiers
source                  1..1511
                        mol_type = protein
                        organism = synthetic construct
SEQUENCE: 105
MDMRVPAQLL GLLLLWLRGA RCHGTVIESL ESLNNYFNSS GIDVEEKSLF LDIWRNWQKD    60
GDMKILQSQI ISFYLRLFEV LKDNQAISNN ISVIESHLIT TFFSNSKAKK DAFMSIAKFE   120
VNNPQVQRQA FNELIRVVHQ LLPESSLRKR KRSRCSGGPG PAGMKGLPGS EAHKSEIAHR   180
YNDLGEQHFK GLVLIAFSQY LQKCSYDEHA KLVQEVTDFA KTCVADESAA NCDKSLHTLF   240
GDKLCAIPNL RENYGELADC CTKQEPERNE CFLQHKDDNP SLPPFERPEA EAMCTSFKEN   300
```

```
PTTFMGHYLH EVARRHPYFY APELLYYAEQ YNEILTQCCA EADKESCLTP KLDGVKEKAL 360
VSSVRQRMKC SSMQKFGERA FKAWAVARLS QTFPNADFAE ITKLATDLTK VNKECCHGDL 420
LECADDRAEL AKYMCENQAT ISSKLQTCCD KPLLKKAHCL SEVEHDTMPA DLPAIAADFV 480
EDQEVCKNYA EAKDVFLGTF LYEYSRRHPD YSVSLLLRLA KKYEATLEKC CAEANPPACY 540
GTVLAEFQPL VEEPKNLVKT NCDLYEKLGE YGFQNAILVR YTQKAPQVST PTLVEAARNL 600
GRVGTKCCTL PEDQRLPCVE DYLSAILNRV CLLHEKTPVS EHVTKCCSGS LVERRPCFSA 660
LTVDETYVPK EFKAETFTFH SDICTLPEKE KQIKKQTALA ELVKHKPKAT AEQLKTVMDD 720
FAQFLDTCCK AADKDTCFST EGPNLVTRCK DALASGGPGP AGMKGLPGSH GTVIESLESL 780
NNYFNSSGID VEEKSLFLDI WRNWQKDGDM KILQSQIISF YLRLFEVLKD NQAISNNISV 840
IESHLITTFF SNSKAKKDAF MSIAKFEVNN PQVQRQAFNE LIRVVHQLLP ESSLRKRKRS 900
RCSGGPGPAG MKGLPGSEAH KSEIAHRYND LGEQHFKGLV LIAFSQYLQK CSYDEHAKLV 960
QEVTDFAKTC VADESAANCD KSLHTLFGDK LCAIPNLREN YGELADCCTK QEPERNECFL 1020
QHKDDNPSLP PFERPEAEAM CTSFKENPTT FMGHYLHEVA RRHPYFYAPE LLYYAEQYNE 1080
ILTQCCAEAD KESCLTPKLD GVKEKALVSS VRQRMKCSSM QKFGERAFKA WAVARLSQTF 1140
PNADFAEITK LATDLTKVNK ECCHGDLLEC ADDRAELAKY MCENQATISS KLQTCCDKPL 1200
LKKAHCLSEV EHDTMPADLP AIAADFVEDQ EVCKNYAEAK DVFLGTFLYE YSRRHPDYSV 1260
SLLLRLAKKY EATLEKCCAE ANPPACYGTV LAEFQPLVEE PKNLVKTNCD LYEKLGEYGF 1320
QNAILVRYTQ KAPQVSTPTL VEAARNLGRV GTKCCTLPED QRLPCVEDYL SAILNRVCLL 1380
HEKTPVSEHV TKCCSGSLVE RRPCFSALTV DETYVPKEFK AETFTFHSDI CTLPEKEKQI 1440
KKQTALAELV KHKPKATAEQ LKTVMDDFAQ FLDTCCKAAD KDTCFSTEGP NLVTRCKDAL 1500
AHHHHHHEPE A                                                    1511
```

```
SEQ ID NO: 106          moltype = AA  length = 1511
FEATURE                 Location/Qualifiers
source                  1..1511
                        mol_type = protein
                        organism = synthetic construct
SEQUENCE: 106
MDMRVPAQLL GLLLLWLRGA RCEAHKSEIA HRYNDLGEQH FKGLVLIAFS QYLQKCSYDE 60
HAKLVQEVTD FAKTCVADES AANCDKSLHT LFGDKLCAIP NLRENYGELA DCCTKQEPER 120
NECFLQHKDD NPSLPPFERP EAEAMCTSFK ENPTTFMGHY LHEVARRHPY FYAPELLYYA 180
EQYNEILTQC CAEADKESCL TPKLDGVKEK ALVSSVRQRM KCSSMQKFGE RAFKAWAVAR 240
LSQTFPNADF AEITKLATDL TKVNKECCHG DLLECADDRA ELAKYMCENQ ATISSKLQTC 300
CDKPLLKKAH CLSEVEHDTM PADLPAIAAD FVEDQEVCKN YAEAKDVFLG TFLYEYSRRH 360
PDYSVSLLLR LAKKYEATLE KCCAEANPPA CYGTVLAEFQ PLVEEPKNLV KTNCDLYEKL 420
GEYGFQNAIL VRYTQKAPQV STPTLVEAAR NLGRVGTKCC TLPEDQRLPC VEDYLSAILN 480
RVCLLHEKTP VSEHVTKCCS GSLVERRPCF SALTVDETYV PKEFKAETFT FHSDICTLPE 540
KEKQIKKQTA LAELVKHKPK ATAEQLKTVM DDFAQFLDTC CKAADKDTCF STEGPNLVTR 600
CKDALASGGP GPAGMKGLPG SHGTVIESLE SLNNYFNSSG IDVEEKSLFL DIWRNWQKDG 660
DMKILQSQII SFYLRLFEVL KDNQAISNNI SVIESHLITT FFSNSKAKKD APMSIAKFEV 720
NNPQVQRQAF NELIRVVHQL LPESSLRKRK RSRCSGGPGP AGMKGLPGSE AHKSEIAHRY 780
NDLGEQHFKG LVLIAFSQYL QKCSYDEHAK LVQEVTDFAK TCVADESAAN CDKSLHTLFG 840
DKLCAIPNLR ENYGELADCC TKQEPERNEC FLQHKDDNPS LPPFERPEAE AMCTSFKENP 900
TTFMGHYLHE VARRHPYFYA PELLYYAEQY NEILTQCCAE ADKESCLTPK LDGVKEKALV 960
SSVRQRMKCS SMQKFGERAF KAWAVARLSQ TFPNADFAEI TKLATDLTKV NKECCHGDLL 1020
ECADDRAELA KYMCENQATI SSKLQTCCDK PLLKKAHCLS EVEHDTMPAD LPAIAADFVE 1080
DQEVCKNYAE AKDVFLGTFL YEYSRRHPDY SVSLLLRLAK KYEATLEKCC AEANPPACYG 1140
TVLAEFQPLV EEPKNLVKTN CDLYEKLGEY GFQNAILVRY TQKAPQVSTP TLVEAARNLG 1200
RVGTKCCTLP EDQRLPCVED YLSAILNRVC LLHEKTPVSE HVTKCCSGSL VERRPCFSAL 1260
TVDETYVPKE FKAETFTFHS DICTLPEKEK QIKKQTALAE LVKHKPKATA EQLKTVMDDF 1320
AQFLDTCCKA ADKDTCFSTE GPNLVTRCKD ALASGGPGPA GMKGLPGSHG TVIESLESLN 1380
NYFNSSGIDV EEKSLFLDIW RNWQKDGDMK ILQSQIISFY LRLFEVLKDN QAISNNISVI 1440
ESHLITTFFS NSKAKKDAFM SIAKFEVNNP QVQRQAFNEL IRVVHQLLPE SSLRKRKRSR 1500
CHHHHHHEPE A                                                    1511
```

```
SEQ ID NO: 107          moltype = AA  length = 2110
FEATURE                 Location/Qualifiers
source                  1..2110
                        mol_type = protein
                        organism = synthetic construct
SEQUENCE: 107
MDMRVPAQLL GLLLLWLRGA RCEAHKSEIA HRYNDLGEQH FKGLVLIAFS QYLQKCSYDE 60
HAKLVQEVTD FAKTCVADES AANCDKSLHT LFGDKLCAIP NLRENYGELA DCCTKQEPER 120
NECFLQHKDD NPSLPPFERP EAEAMCTSFK ENPTTFMGHY LHEVARRHPY FYAPELLYYA 180
EQYNEILTQC CAEADKESCL TPKLDGVKEK ALVSSVRQRM KCSSMQKFGE RAFKAWAVAR 240
LSQTFPNADF AEITKLATDL TKVNKECCHG DLLECADDRA ELAKYMCENQ ATISSKLQTC 300
CDKPLLKKAH CLSEVEHDTM PADLPAIAAD FVEDQEVCKN YAEAKDVFLG TFLYEYSRRH 360
PDYSVSLLLR LAKKYEATLE KCCAEANPPA CYGTVLAEFQ PLVEEPKNLV KTNCDLYEKL 420
GEYGFQNAIL VRYTQKAPQV STPTLVEAAR NLGRVGTKCC TLPEDQRLPC VEDYLSAILN 480
RVCLLHEKTP VSEHVTKCCS GSLVERRPCF SALTVDETYV PKEFKAETFT FHSDICTLPE 540
KEKQIKKQTA LAELVKHKPK ATAEQLKTVM DDFAQFLDTC CKAADKDTCF STEGPNLVTR 600
CKDALASGGP GPAGMKGLPG SHGTVIESLE SLNNYFNSSG IDVEEKSLFL DIWRNWQKDG 660
DMKILQSQII SFYLRLFEVL KDNQAISNNI SVIESHLITT FFSNSKAKKD APMSIAKFEV 720
NNPQVQRQAF NELIRVVHQL LPESSLRKRK RSRCSGGPGP AGMKGLPGSE AHKSEIAHRY 780
NDLGEQHFKG LVLIAFSQYL QKCSYDEHAK LVQEVTDFAK TCVADESAAN CDKSLHTLFG 840
DKLCAIPNLR ENYGELADCC TKQEPERNEC FLQHKDDNPS LPPFERPEAE AMCTSFKENP 900
TTFMGHYLHE VARRHPYFYA PELLYYAEQY NEILTQCCAE ADKESCLTPK LDGVKEKALV 960
SSVRQRMKCS SMQKFGERAF KAWAVARLSQ TFPNADFAEI TKLATDLTKV NKECCHGDLL 1020
ECADDRAELA KYMCENQATI SSKLQTCCDK PLLKKAHCLS EVEHDTMPAD LPAIAADFVE 1080
```

-continued

```
DQEVCKNYAE AKDVFLGTFL YEYSRRHPDY SVSLLLRLAK KYEATLEKCC AEANPPACYG  1140
TVLAEFQPLV EEPKNLVKTN CDLYEKLGEY GFQNAILVRY TQKAPQVSTP TLVEAARNLG  1200
RVGTKCCTLP EDQRLPCVED YLSAILNRVC LLHEKTPVSE HVTKCCSGSL VERRPCFSAL  1260
TVDETYVPKE FKAETFTFHS DICTLPEKEK QIKKQTALAE LVKHKPKATA EQLKTVMDDF  1320
AQFLDTCCKA ADKDTCFSTE GPNLVTRCKD ALASGGPGPA GMKGLPGSHG TVIESLESLN  1380
NYFNSSGIDV EEKSLFLDIW RNWQKDGDMK ILQSQIISFY LRLFEVLKDN QAISNNISVI  1440
ESHLITTFFS NSKAKKDAFM SIAKFEVNNP QVQRQAFNEL IRVVHQLLPE SSLRKRKRSR  1500
CSGGPGPAGM KGLPGSEAHK SEIAHRYNDL GEQHFKGLVL IAFSQYLQKC SYDEHAKLVQ  1560
EVTDFAKTCV ADESAANCDK SLHTLFGDKL CAIPNLRENY GELADCCTKQ EPERNECFLQ  1620
HKDDNPSLPP FERPEAEAMC TSFKENPTTF MGHYLHEVAR RHPYFYAPEL LYYAEQYNEI  1680
LTQCCAEADK ESCLTPKLDG VKEKALVSSR RQRMKCSSMQ KFGERAFKAW AVARLSQTFP  1740
NADFAEITKL ATDLTKVNKE CCHGDLLECA DDRAELAKYM CENQATISSK LQTCCDKPLL  1800
KKAHCLSEVE HDTMPADLPA IAADFVEDQE VCKNYAEAKD VFLGTFLYEY SRRHPDYSVS  1860
LLLRLAKKYE ATLEKCCAEA NPPACYGTVL AEFQPLVEEP KNLVKTNCDL YEKLGEYGFQ  1920
NAILVRYTQK APQVSTPTLV EAARNLGRVG TKCCTLPEDQ RLPCVEDYLS AILNRVCLLH  1980
EKTPVSEHVT KCCSGSLVER RPCFSALTVD ETYVPKEFKA ETFTFHSDIC TLPEKEKQIK  2040
KQTALAELVK HKPKATAEQL KTVMDDFAQF LDTCCKAADK DTCFSTEGPN LVTRCKDALA  2100
HHHHHHEPEA                                                         2110

SEQ ID NO: 108        moltype = AA  length = 2120
FEATURE               Location/Qualifiers
source                1..2120
                      mol_type = protein
                      organism = synthetic construct
SEQUENCE: 108
MDMRVPAQLL GLLLLWLRGA RCEAHKSEIA HRYNDLGEQH FKGLVLIAFS QYLQKCSYDE  60
HAKLVQEVTD FAKTCVADES AANCDKSLHT LFGDKLCAIP NLRENYGELA DCCTKQEPER  120
NECFLQHKDD NPSLPPFERP EAEAMCTSFK ENPTTFMGHY LHEVARRHPY FYAPELLYYA  180
EQYNEILTQC CAEADKESCL TPKLDGVKEK ALVSSVRQRM KCSSMQKFGE RAFKAWAVAR  240
LSQTFPNADF AEITKLATDL TKVNKECCHG DLLECADDRA ELAKYMCENQ ATISSKLQTC  300
CDKPLLKKAH CLSEVEHDTM PADLPAIAAD FVEDQEVCKN YAEAKDVFLG TFLYEYSRRH  360
PDYSVSLLLR LAKKYEATLE KCCAEANPPA CYGTVLAEFQ PLVEEPKNLV KTNCDLYEKL  420
GEYGFQNAIL VRYTQKAPQV STPTLVEAAR NLGRVGTKCC TLPEDQRLPC VEDYLSAILN  480
RVCLLHEKTP VSEHVTKCCS GSLVERRPCF SALTVDETYV PKEFKAETFT FHSDICTLPE  540
KEKQIKKQTA LAELVKHKPK ATAEQLKTVM DDFAQFLDTC CKAADKDTCF STEGPNLVTR  600
CKDALASGGP GPAGMKGLPG SHGTVIESLE SLNNYFNSSG IDVEEKSLFL DIWRNWQKDG  660
DMKILQSQII SFYLRLFEVL KDNQAISNNI SVIESHLITT FFSNSKAKKD AFMSIAKFEV  720
NNPQVQRQAF NELIRVVHQL LPESSLRKRK RSRCSGGPGP AGMKGLPGSG GGGSEAHKSE  780
IAHRYNDLGE QHFKGLVLIA FSQYLQKCSY DEHAKLVQEV TDFAKTCVAD ESAANCDKSL  840
HTLFGDKLCA IPNLRENYGE LADCCTKQEP ERNECFLQHK DDNPSLPPFE RPEAEAMCTS  900
FKENPTTFMG HYLHEVARRH PYFYAPELLY YAEQYNEILT QCCAEADKES CLTPKLDGVK  960
EKALVSSVRQ RMKCSSMQKF GERAFKAWAV ARLSQTFPNA DFAEITKLAT DLTKVNKECC  1020
HGDLLECADD RAELAKYMCE NQATISSKLQ TCCDKPLLKK AHCLSEVEHD TMPADLPAIA  1080
ADFVEDQEVC KNYAEAKDVF LGTFLYEYSR RHPDYSVSLL LRLAKKYEAT LEKCCAEANP  1140
PACYGTVLAE FQPLVEEPKN LVKTNCDLYE KLGEYGFQNA ILVRYTQKAP QVSTPTLVEA  1200
ARNLGRVGTK CCTLPEDQRL PCVEDYLSAI LNRVCLLHEK TPVSEHVTKC CSGSLVERRP  1260
CFSALTVDET YVPKEFKAET FTFHSDICTL PEKEKQIKKQ TALAELVKHK PKATAEQLKT  1320
VMDDFAQFLD TCCKAADKDT CFSTEGPNLV TRCKDALAGG GGSSGGPGPA GMKGLPGSHG  1380
TVIESLESLN NYFNSSGIDV EEKSLFLDIW RNWQKDGDMK ILQSQIISFY LRLFEVLKDN  1440
QAISNNISVI ESHLITTFFS NSKAKKDAFM SIAKFEVNNP QVQRQAFNEL IRVVHQLLPE  1500
SSLRKRKRSR CSGGPGPAGM KGLPGSEAHK SEIAHRYNDL GEQHFKGLVL IAFSQYLQKC  1560
SYDEHAKLVQ EVTDFAKTCV ADESAANCDK SLHTLFGDKL CAIPNLRENY GELADCCTKQ  1620
EPERNECFLQ HKDDNPSLPP FERPEAEAMC TSFKENPTTF MGHYLHEVAR RHPYFYAPEL  1680
LYYAEQYNEI LTQCCAEADK ESCLTPKLDG VKEKALVSSV RQRMKCSSMQ KFGERAFKAW  1740
AVARLSQTFP NADFAEITKL ATDLTKVNKE CCHGDLLECA DDRAELAKYM CENQATISSK  1800
LQTCCDKPLL KKAHCLSEVE HDTMPADLPA IAADFVEDQE VCKNYAEAKD VFLGTFLYEY  1860
SRRHPDYSVS LLLRLAKKYE ATLEKCCAEA NPPACYGTVL AEFQPLVEEP KNLVKTNCDL  1920
YEKLGEYGFQ NAILVRYTQK APQVSTPTLV EAARNLGRVG TKCCTLPEDQ RLPCVEDYLS  1980
AILNRVCLLH EKTPVSEHVT KCCSGSLVER RPCFSALTVD ETYVPKEFKA ETFTFHSDIC  2040
TLPEKEKQIK KQTALAELVK HKPKATAEQL KTVMDDFAQF LDTCCKAADK DTCFSTEGPN  2100
LVTRCKDALA HHHHHHEPEA                                               2120

SEQ ID NO: 109        moltype = AA  length = 2130
FEATURE               Location/Qualifiers
source                1..2130
                      mol_type = protein
                      organism = synthetic construct
SEQUENCE: 109
MDMRVPAQLL GLLLLWLRGA RCEAHKSEIA HRYNDLGEQH FKGLVLIAFS QYLQKCSYDE  60
HAKLVQEVTD FAKTCVADES AANCDKSLHT LFGDKLCAIP NLRENYGELA DCCTKQEPER  120
NECFLQHKDD NPSLPPFERP EAEAMCTSFK ENPTTFMGHY LHEVARRHPY FYAPELLYYA  180
EQYNEILTQC CAEADKESCL TPKLDGVKEK ALVSSVRQRM KCSSMQKFGE RAFKAWAVAR  240
LSQTFPNADF AEITKLATDL TKVNKECCHG DLLECADDRA ELAKYMCENQ ATISSKLQTC  300
CDKPLLKKAH CLSEVEHDTM PADLPAIAAD FVEDQEVCKN YAEAKDVFLG TFLYEYSRRH  360
PDYSVSLLLR LAKKYEATLE KCCAEANPPA CYGTVLAEFQ PLVEEPKNLV KTNCDLYEKL  420
GEYGFQNAIL VRYTQKAPQV STPTLVEAAR NLGRVGTKCC TLPEDQRLPC VEDYLSAILN  480
RVCLLHEKTP VSEHVTKCCS GSLVERRPCF SALTVDETYV PKEFKAETFT FHSDICTLPE  540
KEKQIKKQTA LAELVKHKPK ATAEQLKTVM DDFAQFLDTC CKAADKDTCF STEGPNLVTR  600
CKDALASGGP GPAGMKGLPG SHGTVIESLE SLNNYFNSSG IDVEEKSLFL DIWRNWQKDG  660
```

-continued

```
DMKILQSQII SFYLRLFEVL KDNQAISNNI SVIESHLITT FFSNSKAKKD AFMSIAKFEV  720
NNPQVQRQAF NELIRVVHQL LPESSLRKRK RSRCSGGPGP AGMKGLPGSG GGGSGGGGSE  780
AHKSEIAHRY NDLGEQHFKG LVLIAFSQYL QKCSYDEHAK LVQEVTDFAK TCVADESAAN  840
CDKSLHTLFG DKLCAIPNLR ENYGELADCC TKQEPERNEC FLQHKDDNPS LPPFERPEAE  900
AMCTSFKENP TTFMGHYLHE VARRHPYFYA PELLYYAEQY NEILTQCCAE ADKESCLTPK  960
LDGVKEKALV SSVRQRMKCS SMQKFGERAF KAWAVARLSQ TFPNADFAEI TKLATDLTKV  1020
NKECCHGDLL ECADDRAELA KYMCENQATI SSKLQTCCDK PLLKKAHCLS EVEHDTMPAD  1080
LPAIAADFVE DQEVCKNYAE AKDVFLGTFL YEYSRRHPDY SVSLLLRLAK KYEATLEKCC  1140
AEANPPACYG TVLAEFQPLV EEPKNLVKTN CDLYEKLGEY GFQNAILVRY TQKAPQVSTP  1200
TLVEAARNLG RVGTKCCTLP EDQRLPCVED YLSAILNRVC LLHEKTPVSE HVTKCCSGSL  1260
VERRPCFSAL TVDETYVPKE FKAETFTFHS DICTLPEKEK QIKKQTALAE LVKHKPKATA  1320
EQLKTVMDDF AQFLDTCCKA ADKDTCFSTE GPNLVTRCKD ALAGGGGSGG GGSSGGPGPA  1380
GMKGLPGSHG TVIESLESLN NYFNSSGIDV EEKSLFLDIW RNWQKDGDMK ILQSQIISFY  1440
LRLFEVLKDN QAISNNISVI ESHLITTFFS NSKAKKDAFM SIAKFEVNNP QVQRQAFNEL  1500
IRVVHQLLPE SSLRKRKRSR CSGGPGPAGM KGLPGSEAHK SEIAHRYNDL GEQHFKGLVL  1560
IAFSQYLQKC SYDEHAKLVQ EVTDFAKTCV ADESAANCDK SLHTLFGDKL CAIPNLRENY  1620
GELADCCTKQ EPERNECFLQ HKDDNPSLPP FERPEAEAMC TSFKENPTTF MGHYLHEVAR  1680
RHPYFYAPEL LYYAEQYNEI LTQCCAEADK ESCLTPKLDG VKEKALVSSV RQRMKCSSMQ  1740
KFGERAFKAW AVARLSQTFP NADFAEITKL ATDLTKVNKE CCHGDLLECA DDRAELAKYM  1800
CENQATISSK LQTCCDKPLL KKAHCLSEVE HDTMPADLPA IAADFVEDQE VCKNYAEAKD  1860
VFLGTFLYEY SRRHPDYSVS LLLRLAKKYE ATLEKCCAEA NPPACYGTVL AEFQPLVEEP  1920
KNLVKTNCDL YEKLGEYGFQ NAILVRYTQK APQVSTPTLV EAARNLGRVG TKCCTLPEDQ  1980
RLPCVEDYLS AILNRVCLLH EKTPVSEHVT KCCSGSLVER RPCFSALTVD ETYVPKEFKA  2040
ETFTFHSDIC TLPEKEKQIK KQTALAELVK HKPKATAEQL KTVMDDFAQF LDTCCKAADK  2100
DTCFSTEGPN LVTRCKDALA HHHHHHEPEA                                  2130

SEQ ID NO: 110        moltype = AA  length = 703
FEATURE               Location/Qualifiers
source                1..703
                      mol_type = protein
                      organism = synthetic construct
SEQUENCE: 110
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSGGG GSGGGGSGGG GSHGTVIESL ESLNNYFNSS GIDVEEKSLF  180
LDIWRNWQKD GDMKILQSQI ISFYLRLFEV LKDNQAISNN ISVIESHLIT TFFSNSKAKK  240
DAFMSIAKFE VNNPQVQRQA FNELIRVVHQ LLPESSLRKR KRSRCGGGGS GGGGSGGGGS  300
EVQLVESGGG LVQPGNSLRL SCAASGFTFS KFGMSWVRQA PGKGLEWVSS ISGSGRDTLY  360
AESVKGRFTI SRDNAKTTLY LQMNSLRPED TAVYYCTIGG SLSVSSQGTL VTVSSGGGGS  420
GGGGSGGGGS HGTVIESLES LNNYFNSSGI DVEEKSLFLD IWRNWQKDGD MKILQSQIIS  480
FYLRLFEVLK DNQAISNNIS VIESHLITTF FSNSKAKKDA FMSIAKFEVN PQVQRQAFN  540
ELIRVVHQLL PESSLRKRKR SRCGGGGSGG GGSGGGGSEV QLVESGGGLV QPGNSLRLSC  600
AASGFTFSKF GMSWVRQAPG KGLEWVSSIS GSGRDTLYAE SVKGRFTISR DNAKTTLYLQ  660
MNSLRPEDTA VYYCTIGGSL SVSSQGTLVT VSSHHHHHHE PEA                   703

SEQ ID NO: 111        moltype = AA  length = 832
FEATURE               Location/Qualifiers
source                1..832
                      mol_type = protein
                      organism = synthetic construct
SEQUENCE: 111
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSHGTVIESL ESLNNYFNSS GIDVEEKSLF  180
LDIWRNWQKD GDMKILQSQI ISFYLRLFEV LKDNQAISNN ISVIESHLIT TFFSNSKAKK  240
DAFMSIAKFE VNNPQVQRQA FNELIRVVHQ LLPESSLRKR KRSRCSGGPG PAGMKGLPGS  300
EVQLVESGGG LVQPGNSLRL SCAASGFTFS KFGMSWVRQA PGKGLEWVSS ISGSGRDTLY  360
AESVKGRFTI SRDNAKTTLY LQMNSLRPED TAVYYCTIGG SLSVSSQGTL VTVSSSGGPG  420
PAGMKGLPGS HGTVIESLES LNNYFNSSGI DVEEKSLFLD IWRNWQKDGD MKILQSQIIS  480
FYLRLFEVLK DNQAISNNIS VIESHLITTF FSNSKAKKDA FMSIAKFEVN PQVQRQAFN  540
ELIRVVHQLL PESSLRKRKR SRCSGGPGPA GMKGLPGSEV QLVESGGGLV QPGNSLRLSC  600
AASGFTFSKF GMSWVRQAPG KGLEWVSSIS GSGRDTLYAE SVKGRFTISR DNAKTTLYLQ  660
MNSLRPEDTA VYYCTIGGSL SVSSQGTLVT VSSGGGGSGG GGSGGGGSQV QLQESGGGLA  720
QAGGSLSLSC AASGFTVSNS VMAWYRQTPG KQREFVAIIN SVGSTNYADS VKGRFTISRD  780
NAKNTVYLQM NNLKPEDTAV YVCNRNFDRI YWGQGTQVTV SSHHHHHHEP EA          832

SEQ ID NO: 112        moltype = AA  length = 832
FEATURE               Location/Qualifiers
source                1..832
                      mol_type = protein
                      organism = synthetic construct
SEQUENCE: 112
MDMRVPAQLL GLLLLWLRGA RCQVQLQESG GGLAQAGGSL SLSCAASGFT VSNSVMAWYR  60
QTPGKQREFV AIINSVGSTN YADSVKGRFT ISRDNAKNTV YLQMNNLKPE DTAVYVCNRN  120
FDRIYWGQGT QVTVSSGGGG SGGGGSGGGG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSSGGP GPAGMKGLPG SHGTVIESLE SLNNYFNSSG  300
IDVEEKSLFL DIWRNWQKDG DMKILQSQII SFYLRLFEVL KDNQAISNNI SVIESHLITT  360
FFSNSKAKKD AFMSIAKFEV NNPQVQRQAF NELIRVVHQL LPESSLRKRK RSRCSGGPGP  420
```

```
AGMKGLPGSE  VQLVESGGGL  VQPGNSLRLS  CAASGFTFSK  FGMSWVRQAP  GKGLEWVSSI  480
SGSGRDTLYA  ESVKGRFTIS  RDNAKTTLYL  QMNSLRPEDT  AVYYCTIGGS  LSVSSQGTLV  540
TVSSSGGPGP  AGMKGLPGSH  GTVIESLESL  NNYFNSSGID  VEEKSLFLDI  WRNWQKDGDM  600
KILQSQIISF  YLRLFEVLKD  NQAISNNISV  IESHLITTFF  SNSKAKKDAF  MSIAKFEVNN  660
PQVQRQAFNE  LIRVVHQLLP  ESSLRKRKRS  RCSGGPGAGM  KGLPGSEVQ   LVESGGGLVQ  720
PGNSLRLSCA  ASGFTFSKFG  MSWVRQAPGK  GLEWVSSISG  SGRDTLYAES  VKGRFTISRD  780
NAKTTLYLQM  NSLRPEDTAV  YYCTIGGSLS  VSSQGTLVTV  SSHHHHHHEP  EA          832

SEQ ID NO: 113        moltype = AA  length = 549
FEATURE               Location/Qualifiers
source                1..549
                      mol_type = protein
                      organism = synthetic construct
SEQUENCE: 113
MDMRVPAQLL  GLLLLWLRGA  RCRVIPVSGP  ARCLSQSRNL  LKTTDDMVKT  AREKLKHYSC  60
TAEDIDHEDI  TRDQTSTLKT  CLPLELHKNE  SCLATRETSS  TTRGSCLPPQ  KTSLMMTLCL  120
GSIYEDLKMY  QTEFQAINAA  LQNHNHQQII  LDKGMLVAID  ELMQSLNHNG  ETLRQKPPVG  180
EADPYRVKMK  LCILLHAFST  RVVTINRVMG  YLSSASGGPG  PAGMKGLPGS  MWELEKDVYV  240
VEVDWTPDAP  GETVNLTCDT  PEEDDITWTS  DQRHGVIGSG  KTLTITVKEF  LDAGQYTCHK  300
GGETLSHSHL  LLHKKENGIW  STEILKNFKN  KTFLKCEAPN  YSGRFTCSWL  VQRNMDLKFN  360
IKSSSSSPDS  RAVTCGMASL  SAEKVTLDQR  DYEKYSVSCQ  EDVTCPTAEE  TLPIELALEA  420
RQQNKYENYS  TSFFIRDIIK  PDPPKNLQMK  PLKNSQVEVS  WEYPDSWSTP  HSYFSLKFFV  480
RIQRKKEKMK  ETEEGCNQKG  AFLVEKTSTE  VQCKGGNVCV  QAQDRYYNSS  CSKWACVPCR  540
VRSHHHHHH                                                              549

SEQ ID NO: 114        moltype = AA  length = 579
FEATURE               Location/Qualifiers
source                1..579
                      mol_type = protein
                      organism = synthetic construct
SEQUENCE: 114
MDMRVPAQLL  GLLLLWLRGA  RCRVIPVSGP  ARCLSQSRNL  LKTTDDMVKT  AREKLKHYSC  60
TAEDIDHEDI  TRDQTSTLKT  CLPLELHKNE  SCLATRETSS  TTRGSCLPPQ  KTSLMMTLCL  120
GSIYEDLKMY  QTEFQAINAA  LQNHNHQQII  LDKGMLVAID  ELMQSLNHNG  ETLRQKPPVG  180
EADPYRVKMK  LCILLHAFST  RVVTINRVMG  YLSSAGGGGS  GGGGSGGGGS  SGGPGPAGMK  240
GLPGSGGGGS  GGGGSGGGGS  MWELEKDVYV  VEVDWTPDAP  GETVNLTCDT  PEEDDITWTS  300
DQRHGVIGSG  KTLTITVKEF  LDAGQYTCHK  GGETLSHSHL  LLHKKENGIW  STEILKNFKN  360
KTFLKCEAPN  YSGRFTCSWL  VQRNMDLKFN  IKSSSSSPDS  RAVTCGMASL  SAEKVTLDQR  420
DYEKYSVSCQ  EDVTCPTAEE  TLPIELALEA  RQQNKYENYS  TSFFIRDIIK  PDPPKNLQMK  480
PLKNSQVEVS  WEYPDSWSTP  HSYFSLKFFV  RIQRKKEKMK  ETEEGCNQKG  AFLVEKTSTE  540
VQCKGGNVCV  QAQDRYYNSS  CSKWACVPCR  VRSHHHHHH                          579

SEQ ID NO: 115        moltype = AA  length = 809
FEATURE               Location/Qualifiers
source                1..809
                      mol_type = protein
                      organism = synthetic construct
SEQUENCE: 115
MDMRVPAQLL  GLLLLWLRGA  RCEVQLVESG  GGLVQPGNSL  RLSCAASGFT  FSKFGMSWVR  60
QAPGKGLEWV  SSISGSGRDT  LYAESVKGRF  TISRDNAKTT  LYLQMNSLRP  EDTAVYYCTI  120
GGSLSVSSQG  TLVTVSSSGG  PGPAGMKGLP  GSMWELEKDV  YVVEVDWTPD  APGETVNLTC  180
DTPEEDDITW  TSDQRHGVIG  SGKTLTITVK  EFLDAGQYTC  HKGGETLSHS  HLLLHKKENG  240
IWSTEILKNF  KNKTFLKCEA  PNYSGRFTCS  WLVQRNMDLK  FNIKSSSSSP  DSRAVTCGMA  300
SLSAEKVTLD  QRDYEKYSVS  CQEDVTCPTA  EETLPIELAL  EARQQNKYEN  YSTSFFIRDI  360
IKPDPPKNLQ  MKPLKNSQVE  VSWEYPDSWS  TPHSYFSLKF  FVRIQRKKEK  MKETEEGCNQ  420
KGAFLVEKTS  TEVQCKGGNV  CVQAQDRYYN  SSCSKWACVP  CRVRSGGGGS  GGGGSGGGGS  480
RVIPVSGPAR  CLSQSRNLLK  TTDDMVKTAR  EKLKHYSCTA  EDIDHEDITR  DQTSTLKTCL  540
PLELHKNESC  LATRETSSTT  RGSCLPPQKT  SLMMTLCLGS  IYEDLKMYQT  EFQAINAALQ  600
NHNHQQIILD  KGMLVAIDEL  MQSLNHNGET  LRQKPPVGEA  DPYRVKMKLC  ILLHAFSTRV  660
VTINRVMGYL  SSASGGPGPA  GMKGLPGSEV  QLVESGGGLV  QPGNSLRLSC  AASGFTFSKF  720
GMSWVRQAPG  KGLEWVSSIS  GSGRDTLYAE  SVKGRFTISR  DNAKTTLYLQ  MNSLRPEDTA  780
VYYCTIGGSL  SVSSQGTLVT  VSSHHHHHH                                      809

SEQ ID NO: 116        moltype = AA  length = 938
FEATURE               Location/Qualifiers
source                1..938
                      mol_type = protein
                      organism = synthetic construct
SEQUENCE: 116
MDMRVPAQLL  GLLLLWLRGA  RCQVQLQESG  GGLVQAGGSL  RLSCAASGRI  FSIDIMSWYR  60
QAPGKQRELV  ARITRGGTIS  YDDSVKGRFT  ISRDNAKNTV  YLQMNSLKPE  DTGVYYCNAL  120
YGTDYWGKGT  QVTVSSGGGG  SGGGGSGGGG  SEVQLVESGG  GLVQPGNSLR  LSCAASGFTF  180
SKFGMSWVRQ  APGKGLEWVS  SISGSGRDTL  YAESVKGRFT  ISRDNAKTTL  YLQMNSLRPE  240
DTAVYYCTIG  GSLSVSSQGT  LVTVSSSGGG  PGAGMKGLPG  SMWELEKDVY  VVEVDWTPDA  300
PGETVNLTCD  TPEEDDITWT  SDQRHGVIGS  GKTLTITVKE  FLDAGQYTCH  KGGETLSHSH  360
LLLHKKENGI  WSTEILKNFK  NKTFLKCEAP  NYSGRFTCSW  LVQRNMDLKF  NIKSSSSSPD  420
SRAVTCGMAS  LSAEKVTLDQ  RDYEKYSVSC  QEDVTCPTAE  ETLPIELALE  ARQQNKYENY  480
STSFFIRDII  KPDPPKNLQM  KPLKNSQVEV  SWEYPDSWST  PHSYFSLKFF  VRIQRKKEKM  540
KETEEGCNQK  GAFLVEKTST  EVQCKGGNVC  VQAQDRYYNS  SCSKWACVPC  RVRSGGGGS   600
```

-continued

```
GGGSGGGGSR VIPVSGPARC LSQSRNLLKT TDDMVKTARE KLKHYSCTAE DIDHEDITRD  660
QTSTLKTCLP LELHKNESCL ATRETSSTTR GSCLPPQKTS LMMTLCLGSI YEDLKMYQTE  720
FQAINAALQN HNHQQIILDK GMLVAIDELM QSLNHNGETL RQKPPVGEAD PYRVKMKLCI  780
LLHAFSTRVV TINRVMGYLS SASGGPGPAG MKGLPGSEVQ LVESGGGLVQ PGNSLRLSCA  840
ASGFTFSKFG MSWVRQAPGK GLEWVSSISG SGRDTLYAES VKGRFTISRD NAKTTLYLQM  900
NSLRPEDTAV YYCTIGGSLS VSSQGTLVTV SSHHHHHH                          938

SEQ ID NO: 117          moltype = AA  length = 938
FEATURE                 Location/Qualifiers
source                  1..938
                        mol_type = protein
                        organism = synthetic construct
SEQUENCE: 117
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSSGGP GPAGMKGLPG SMWELEKDVY VVEVDWTPDA  300
PGETVNLTCD TPEEDITWT SDQRHGVIGS GKTLTITVKE FLDAGQYTCH KGGETLSHSH  360
LLLHKKENGI WSTEILKNFK NKTFLKCEAP NYSGRFTCSW LVQRNMDLKF NIKSSSSSPD  420
SRAVTCGMAS LSAEKVTLDQ RDYEKYSVSC QEDVTCPTAE ETLPIELALE ARQQNKYENY  480
STSFFIRDII KPDPPKNLQM KPLKNSQVEV SWEYPDSWST PHSYFSLKFF VRIQRKKEKM  540
KETEEGCNQK GAFLVEKTST EVQCKGGNVC VQAQDRYYNS SCSKWACVPC RVRSGGGGSG  600
GGGSGGGGSR VIPVSGPARC LSQSRNLLKT TDDMVKTARE KLKHYSCTAE DIDHEDITRD  660
QTSTLKTCLP LELHKNESCL ATRETSSTTR GSCLPPQKTS LMMTLCLGSI YEDLKMYQTE  720
FQAINAALQN HNHQQIILDK GMLVAIDELM QSLNHNGETL RQKPPVGEAD PYRVKMKLCI  780
LLHAFSTRVV TINRVMGYLS SASGGPGPAG MKGLPGSEVQ LVESGGGLVQ PGNSLRLSCA  840
ASGFTFSKFG MSWVRQAPGK GLEWVSSISG SGRDTLYAES VKGRFTISRD NAKTTLYLQM  900
NSLRPEDTAV YYCTIGGSLS VSSQGTLVTV SSHHHHHH                          938

SEQ ID NO: 118          moltype = AA  length = 938
FEATURE                 Location/Qualifiers
source                  1..938
                        mol_type = protein
                        organism = synthetic construct
SEQUENCE: 118
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSMWELEKDV YVVEVDWTPD APGETVNLTC  180
DTPEEDDITW TSDQRHGVIG SGKTLTITVK EFLDAGQYTC HKGGETLSHS HLLLHKKENG  240
IWSTEILKNF KNKTFLKCEA PNYSGRFTCS WLVQRNMDLK FNIKSSSSSP DSRAVTCGMA  300
SLSAEKVTLD QRDYEKYSVS CQEDVTCPTA EETLPIELAL EARQQNKYEN YSTSFFIRDI  360
IKPDPPKNLQ MKPLKNSQVE VSWEYPDSWS TPHSYFSLKF FVRIQRKKEK MKETEEGCNQ  420
KGAFLVEKTS TEVQCKGGNV CVQAQDRYYN SSCSKWACVP CRVRSGGGGS GGGGSGGGGS  480
RVIPVSGPAR CLSQSRNLLK TTDDMVKTAR EKLKHYSCTA EDIDHEDITR DQTSTLKTCL  540
PLELHKNESC LATRETSSTT RGSCLPPQKT SLMMTLCLGS IYEDLKMYQT EFQAINAALQ  600
NHNHQQIILD KGMLVAIDEL MQSLNHNGET LRQKPPVGEA DPYRVKMKLC ILLHAFSTRV  660
VTINRVMGYL SSASGGPGPA GMKGLPGSEV QLVESGGGLV QPGNSLRLSC AASGFTFSKF  720
GMSWVRQAPG KGLEWVSSIS GSGRDTLYAE SVKGRFTISR DNAKTTLYLQ MNSLRPEDTA  780
VYYCTIGGSL SVSSQGTLVT VSSGGGGSGG GGSGGGGSQV QLQESGGGLV QAGGSLRLSC  840
AASGRIFSID IMSWYRQAPG KQRELVARIT RGGTISYDDS VKGRFTISRD NAKNTVYLQM  900
NSLKPEDTGV YYCNALYGTD YWGKGTQVTV SSHHHHHH                          938

SEQ ID NO: 119          moltype = AA  length = 962
FEATURE                 Location/Qualifiers
source                  1..962
                        mol_type = protein
                        organism = synthetic construct
SEQUENCE: 119
MDMRVPAQLL GLLLLWLRGA RCIWELKKDV YVVELDWYPD APGEMVVLTC DTPEEDGITW  60
TLDQSSEVLG SGKTLTIQVK EFGDAGQYTC HKGGEVLSHS LLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCSGG GGSGGGGSGG GGSRVIPVSG PARCLSQSRN  360
LLKTTDDMVK TAREKLKHYS CTAEDIDHED ITRDQTSTLK TCLPLELHKN ESCLATRETS  420
STTRGSCLPP QKTSLMMTLC LGSIYEDLKM YQTEFQAINA ALQNHNHQQI ILDKGMLVAI  480
DELMQSLNHN GETLRQKPPV GEADPYRVKM KLCILLHAFS TRVVTINRVM GYLSSAGGGG  540
SGGGGSGGGG SGGGGSGGGG SGGGGSGGGG SQSVLTQPPS VSGAPGQRVT  600
ISCSGSRSNI GSNTVKWYQQ LPGTAPKLLI YYNDQRPSGV PDRFSGSKSG TSASLAITGL  660
QAEDEADYYC QSYDRYTHPA LLFGTGTKVT VLGGGGSGGG GSGGGGSQVQ LVESGGGVVQ  720
PGRSLRLSCA ASGFTFSSYG MHWVRQAPGK GLEWVAFIRY DGSNKYYADS VKGRFTISRD  780
NSKNTLYLQM NSLRAEDTAV YYCKTHGSHD NWGQGTMVTV SSGGGGSGGG GSGGGGGSEVQ  840
LVESGGGLVQ PGNSLRLSCA ASGFTFSKFG MSWVRQAPGK GLEWVSSISG SGRDTLYAES  900
VKGRFTISRD NAKTTLYLQM NSLRPEDTAV YYCTIGGSLS VSSQGTLVTV SSHHHHHHEP  960
EA                                                                962

SEQ ID NO: 120          moltype = AA  length = 832
FEATURE                 Location/Qualifiers
```

```
source                  1..832
                        mol_type = protein
                        organism = synthetic construct
SEQUENCE: 120
MDMRVPAQLL GLLLLWLRGA RCIWELKKDV YVVELDWYPD APGEMVVLTC DTPEEDGITW   60
TLDQSSEVLG SGKTLTIQVK EFGDAGQYTC HKGGEVLSHS LLLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCSGG GGSGGGGSGG GGSRVIPVSG PARCLSQSRN  360
LLKTTDDMVK TAREKLKHYS CTAEDIDHED ITRDQTSTLK TCLPLELHKN ESCLATRETS  420
STTRGSCLPP QKTSLMMTLC LGSIYEDLKM YQTEFQAINA ALQNHNHQQI ILDKGMLVAI  480
DELMQSLNHN GETLRQKPPV GEADPYRVKM KLCILLHAFS TRVVTINRVM GYLSSASGGP  540
GPAGMKGLPG SGGGGSGGGG SGGGGSGGGG SGGGGSGGGG SQSVLTQPPS VSGAPGQRVT  600
ISCSGSRSNI GSNTVKWYQQ LPGTAPKLLI YYNDQRPSGV PDRFSGSKSG TSASLAITGL  660
QAEDEADYYC QSYDRYTHPA LLFGTGTKVT VLGGGGSGGG GSGGGGSQVQ LVESGGGVVQ  720
PGRSLRLSCA ASGFTFSSYG MHWVRQAPGK GLEWVAFIRY DGSNKYYADS VKGRFTISRD  780
NSKNTLYLQM NSLRAEDTAV YYCKTHGSHD NWGQGTMVTV SSHHHHHHEP EA         832

SEQ ID NO: 121         moltype = AA  length = 1091
FEATURE                Location/Qualifiers
source                 1..1091
                       mol_type = protein
                       organism = synthetic construct
SEQUENCE: 121
MDMRVPAQLL GLLLLWLRGA RCIWELKKDV YVVELDWYPD APGEMVVLTC DTPEEDGITW   60
TLDQSSEVLG SGKTLTIQVK EFGDAGQYTC HKGGEVLSHS LLLLLHKKEDG IWSTDILKDQ  120
KEPKNKTFLR CEAKNYSGRF TCWWLTTIST DLTFSVKSSR GSSDPQGVTC GAATLSAERV  180
RGDNKEYEYS VECQEDSACP AAEESLPIEV MVDAVHKLKY ENYTSSFFIR DIIKPDPPKN  240
LQLKPLKNSR QVEVSWEYPD TWSTPHSYFS LTFCVQVQGK SKREKKDRVF TDKTSATVIC  300
RKNASISVRA QDRYYSSSWS EWASVPCSGG GGSGGGGSGG GGSRVIPVSG PARCLSQSRN  360
LLKTTDDMVK TAREKLKHYS CTAEDIDHED ITRDQTSTLK TCLPLELHKN ESCLATRETS  420
STTRGSCLPP QKTSLMMTLC LGSIYEDLKM YQTEFQAINA ALQNHNHQQI ILDKGMLVAI  480
DELMQSLNHN GETLRQKPPV GEADPYRVKM KLCILLHAFS TRVVTINRVM GYLSSASGGP  540
GPAGMKGLPG SGGGGSGGGG SGGGGSGGGG SGGGGSGGGG SQSVLTQPPS VSGAPGQRVT  600
ISCSGSRSNI GSNTVKWYQQ LPGTAPKLLI YYNDQRPSGV PDRFSGSKSG TSASLAITGL  660
QAEDEADYYC QSYDRYTHPA LLFGTGTKVT VLGGGGSGGG GSGGGGSQVQ LVESGGGVVQ  720
PGRSLRLSCA ASGFTFSSYG MHWVRQAPGK GLEWVAFIRY DGSNKYYADS VKGRFTISRD  780
NSKNTLYLQM NSLRAEDTAV YYCKTHGSHD NWGQGTMVTV SSGGGGSGGG GSGGGGSEVQ  840
LVESGGGLVQ PGNSLRLSCA ASGFTFSKFG MSWVRQAPGK GLEWVSSISG SGRDTLYAES  900
VKGRFTISRD NAKTTLYLQM NSLRPEDTAV YYCTIGGSLS VSSQGTLVTV SSGGGGSGGG  960
GSGGGGSQVQ LQESGGGLAQ AGGSLSLSCA ASGFTVSNSV MAWYRQTPGK QREFVAIINS 1020
VGSTNYADSV KGRFTISRDN AKNTVYLQMN NLKPEDTAVY VCNRNFDRIY WGQGTQVTVS 1080
SHHHHHHEPE A                                                       1091

SEQ ID NO: 122         moltype = AA  length = 1091
FEATURE                Location/Qualifiers
source                 1..1091
                       mol_type = protein
                       organism = synthetic construct
SEQUENCE: 122
MDMRVPAQLL GLLLLWLRGA RCQVQLQESG GGLAQAGGSL SLSCAASGFT VSNSVMAWYR   60
QTPGKQREFV AIINSVGSTN YADSVKGRFT ISRDNAKNTV YLQMNNLKPE DTAVYVCNRN  120
FDRIYWGQGT QVTVSSGGGG SGGGGSGGGG SIWELKKDVY VVELDWYPDA PGEMVVLTCD  180
TPEEDGITWT LDQSSEVLGS GKTLTIQVKE FGDAGQYTCH KGGEVLSHSL LLLLHKKEDGI  240
WSTDILKDQK EPKNKTFLRC EAKNYSGRFT CWWLTTISTD LTFSVKSSRG SSDPQGVTCG  300
AATLSAERVR GDNKEYEYSV ECQEDSACPA AEESLPIEVM VDAVHKLKYE NYTSSFFIRD  360
IIKPDPPKNL QLKPLKNSRQ VEVSWEYPDT WSTPHSYFSL TFCVQVQGKS KREKKDRVFT  420
DKTSATVICR KNASISVRAQ DRYYSSSWSE WASVPCSGGG GSGGGGSGGG GSRVIPVSGP  480
ARCLSQSRNL LKTTDDMVKT AREKLKHYSC TAEDIDHEDI TRDQTSTLKT CLPLELHKNE  540
SCLATRETSS TTRGSCLPPQ KTSLMMTLCL GSIYEDLKMY QTEFQAINAA LQNHNHQQII  600
LDKGMLVAID ELMQSLNHNG ETLRQKPPVG EADPYRVKMK LCILLHAFST RVVTINRVMG  660
YLSSASGGPG PAGMKGLPGS GGGGSGGGGS GGGGSGGGGS QSVLTQPPSV SGAPGQRVTI  720
SCSGSRSNIG SNTVKWYQQL PGTAPKLLIY YNDQRPSGVP DRFSGSKSGT SASLAITGLQ  780
AEDEADYYCQ SYDRYTHPAL LFGTGTKVTV LGGGGSGGGG SGGGGSQVQL VESGGGVVQP  840
GRSLRLSCAA SGFTFSSYGM HWVRQAPGKG LEWVAFIRYD GSNKYYADSV KGRFTISRDN  900
SKNTLYLQMN SLRAEDTAVY YCKTHGSHDN WGQGTMVTVS SGGGGSGGGG SGGGGSEVQL  960
VESGGGLVQP GNSLRLSCAA SGFTFSKFGM SWVRQAPGKG LEWVSSISGS GRDTLYAESV 1020
KGRFTISRDN AKTTLYLQMN SLRPEDTAVY YCTIGGSLSV SSQGTLVTVS SHHHHHHEPE 1080
A                                                                  1091

SEQ ID NO: 123         moltype = AA  length = 1091
FEATURE                Location/Qualifiers
source                 1..1091
                       mol_type = protein
                       organism = synthetic construct
SEQUENCE: 123
MDMRVPAQLL GLLLLWLRGA RCQVQLQESG GGLAQAGGSL SLSCAASGFT VSNSVMAWYR   60
QTPGKQREFV AIINSVGSTN YADSVKGRFT ISRDNAKNTV YLQMNNLKPE DTAVYVCNRN  120
```

-continued

```
FDRIYWGQGT QVTVSSSGGP GPAGMKGLPG SIWELKKDVY VVELDWYPDA PGEMVVLTCD    180
TPEEDGITWT LDQSSEVLGS GKTLTIQVKE FGDAGQYTCH KGGEVLSHSL LLLHKKEDGI    240
WSTDILKDQK EPKNKTFLRC EAKNYSGRFT CWWLTTISTD LTFSVKSSRG SSDPQGVTCG    300
AATLSAERVR GDNKEYEYSV ECQEDSACPA AEESLPIEVM VDAVHKLKYE NYTSSFFIRD    360
IIKPDPPKNL QLKPLKNSRQ VEVSWEYPDT WSTPHSYFSL TFCVQVQGKS KREKKDRVFT    420
DKTSATVICR KNASISVRAQ DRYYSSSWSE WASVPCSGGG GSGGGGSGGG GSRVIPVSGP    480
ARCLSQSRNL LKTTDDMVKT AREKLKHYSC TAEDIDHEDI TRDQTSTLKT CLPLELHKNE    540
SCLATRETSS TTRGSCLPPQ KTSLMMTLCL GSIYEDLKMY QTEFQAINAA LQNHNHQQII    600
LDKGMLVAID ELMQSLNHNG ETLRQKPPVG EADPYRVKMK LCILLHAFST RVVTINRVMG    660
YLSSASGGPG PAGMKGLPGS GGGGSGGGGS GGGGSGGGGS GGGGSGGGGS QSVLTQPPSV    720
SGAPGQRVTI SCSGSRSNIG SNTVKWYQQL PGTAPKLLIY YNDQRPSGVP DRFSGSKSGT    780
SASLAITGLQ AEDEADYYCQ SYDRYTHPAL LFGTGTKVTV LGGGGSGGGG SGGGGSQVQL    840
VESGGGVVQP GRSLRLSCAA SGFTFSSYGM HWVRQAPGKG LEWVAFIRYD GSNKYYADSV    900
KGRFTISRDN SKNTLYLQMN SLRAEDTAVY YCKTHGSHDN WGQGTMVTVS SGGGGSGGGG    960
SGGGGSEVQL VESGGGLVQP GNSLRLSCAA SGFTFSKFGM SWVRQAPGKG LEWVSSISGS   1020
GRDTLYAESV KGRFTISRDN AKTTLYLQMN SLRPEDTAVY YCTIGGSLSV SSQGTLVTVS   1080
SHHHHHHEPE A                                                        1091
```

```
SEQ ID NO: 124          moltype = AA  length = 674
FEATURE                 Location/Qualifiers
source                  1..674
                        mol_type = protein
                        organism = synthetic construct
SEQUENCE: 124
MDMRVPAQLL GLLLLWLRGA RCAPTSSSTK KTQLQLEHLL LDLQMILNGI NNYKNPKLTR    60
MLTFKFYMPK KATELKHLQC LEEELKPLEE VLNLAQSKNF HLRPRDLISN INVIVLELKG   120
SETTFMCEYA DETATIVEFL NRWITFCQSI ISTLTSGGPG PAGMKGLPGS EVQLVESGGG   180
LVQPGGSLRL SCAASGFTFS SYTLAWVRQA PGKGLEWVAA IDSSSYTYSP DTVRGRFTIS   240
RDNAKNSLYL QMNSLRAEDT AVYYCARDSN WDALDYWGQG TTVTVSSGGG GSGGGGSGGG   300
GSDIQMTQSP SSLSASVGDR VTITCKASQN VGTNVGWYQQ KPGKAPKALI YSASFRYSGV   360
PSRFSGSGSG TDFTLTISSL QPEDFATYYC QQYYTYPYTF GGGTKVEIKG GGGSGGGGSG   420
GGGSEVQLVE SGGGLVQPGN SLRLSCAASG FTFSKFGMSW VRQAPGKGLE WVSSISGSGR   480
DTLYAESVKG RFTISRDNAK TTLYLQMNSL RPEDTAVYYC TIGGSLSVSS QGTLVTVSSG   540
GGGSGGGGSG GGGSQVQLQE SGGGLVQAGG SLRLSCAASG RIFSIDIMSW YRQAPGKQRE   600
LVARITRGGT ISYDDSVKGR FTISRDNAKN TVYLQMNSLK PEDTGVYYCN ALYGTDYWGK   660
GTQVTVSSHH HHHH                                                     674
```

```
SEQ ID NO: 125          moltype = AA  length = 674
FEATURE                 Location/Qualifiers
source                  1..674
                        mol_type = protein
                        organism = synthetic construct
SEQUENCE: 125
MDMRVPAQLL GLLLLWLRGA RCQVQLQESG GGLVQAGGSL RLSCAASGRI FSIDIMSWYR    60
QAPGKQRELV ARITRGGTIS YDDSVKGRFT ISRDNAKNTV YLQMNSLKPE DTGVYYCNAL   120
YGTDYWGKGT QVTVSSSGGP GPAGMKGLPG SEVQLVESGG GLVQPGNSLR LSCAASGFTF   180
SKFGMSWVRQ APGKGLEWVS SISGSGRDTL YAESVKGRFT ISRDNAKTTL YLQMNSLRPE   240
DTAVYYCTIG GSLSVSSQGT LVTVSSSGGP GPAGMKGLPG SEVQLVESGG GLVQPGGSLR   300
LSCAASGFTF SSYTLAWVRQ APGKGLEWVA AIDSSSYTYS PDTVRGRFTI SRDNAKNSLY   360
LQMNSLRAED TAVYYCARDS NWDALDYWGQ GTTVTVSSGG GGSGGGGSGG GGSDIQMTQS   420
PSSLSASVGD RVTITCKASQ NVGTNVGWYQ QKPGKAPKAL IYSASFRYSG VPSRFSGSGS   480
GTDFTLTISS LQPEDFATYY CQQYYTYPYT FGGGTKVEIK SGGPGPAGMK GLPGSAPTSS   540
STKKTQLQLE HLLLDLQMIL NGINNYKNPK LTRMLTFKFY MPKKATELKH LQCLEEELKP   600
LEEVLNLAQS KNFHLRPRDL ISNINVIVLE LKGSETTFMC EYADETATIV EFLNRWITFC   660
QSIISTLTHH HHHH                                                     674
```

```
SEQ ID NO: 126          moltype = AA  length = 425
FEATURE                 Location/Qualifiers
source                  1..425
                        mol_type = protein
                        organism = synthetic construct
SEQUENCE: 126
MDMRVPAQLL GLLLLWLRGA RCELCDDDPP EIPHATFKAM AYKEGTMLNC ECKRGFRRIK    60
SGSLYMLCTG NSSHSSWDNQ CQCTSSATRN TTKQVTPQPE EQKERKTTEM QSPMQPVDQA   120
SLPGHCREPP PWENEATERI YHFVVGQMVY YQCVQGYRAL HRGPAESVCK MTHGKTRWTQ   180
PQLICTGEME TSQFPGEEKP QASPEGRPES ETSCLVTTTD FQIQTEMAAT METSIFTTEY   240
QGGGGSGGGG SGGGGSGGGG SGGGGSGGGG SSGGPGPAGM KGLPGSAPTS SSTKKTQLQL   300
EHLLLDLQMI LNGINNYKNP KLTRMLTFKF YMPKKATELK HLQCLEEELK PLEEVLNLAQ   360
SKNFHLRPRD LISNINVIVL ELKGSETTFM CEYADETATI VEFLNRWITF CQSIISTLTH   420
HHHHH                                                               425
```

```
SEQ ID NO: 127          moltype = AA  length = 425
FEATURE                 Location/Qualifiers
source                  1..425
                        mol_type = protein
                        organism = synthetic construct
SEQUENCE: 127
MDMRVPAQLL GLLLLWLRGA RCAPTSSSTK KTQLQLEHLL LDLQMILNGI NNYKNPKLTR    60
MLTFKFYMPK KATELKHLQC LEEELKPLEE VLNLAQSKNF HLRPRDLISN INVIVLELKG   120
```

```
SETTFMCEYA DETATIVEFL NRWITFCQSI ISTLTSGGPG PAGMKGLPGS GGGGSGGGGS  180
GGGGSGGGGS GGGGSGGGGS ELCDDDPPEI PHATFKAMAY KEGTMLNCEC KRGFRRIKSG  240
SLYMLCTGNS SHSSWDNQCQ CTSSATRNTT KQVTPQPEEQ KERKTTEMQS PMQPVDQASL  300
PGHCREPPPW ENEATERIYH FVVGQMVYYQ CVQGYRALHR GPAESVCKMT HGKTRWTQPQ  360
LICTGEMETS QFPGEEKPQA SPEGRPESET SCLVTTTDFQ IQTEMAATME TSIFTTEYQH  420
HHHHH                                                               425

SEQ ID NO: 128          moltype = AA  length = 555
FEATURE                 Location/Qualifiers
source                  1..555
                        mol_type = protein
                        organism = synthetic construct
SEQUENCE: 128
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSGGG GSGGGGSGGG GSELCDDDPP EIPHATFKAM AYKEGTMLNC  180
ECKRGFRRIK SGSLYMLCTG NSSHSSWDNQ CQCTSSATRN TTKQVTPQPE EQKERKTTEM  240
QSPMQPVDQA SLPGHCREPP PWENEATERI YHFVVGQMVY YQCVQGYRAL HRGPAESVCK  300
MTHGKTRWTQ PQLICTGEME TSQFPGEEKP QASPEGRPES ETSCLVTTTD FQIQTEMAAT  360
METSIFTTEY QGGGGSGGGG SGGGGSGGGG SGGGPGPAGM KGLPGSAPTS  420
SSTKKTQLQL EHLLLDLQMI LNGINNYKNP KLTRMLTFKF YMPKKATELK HLQCLEEELK  480
PLEEVLNLAQ SKNFHLRPRD LISNINIVVL ELKGSETTFM CEYADETATI VEFLNRWITF  540
CQSIISTLTH HHHHH                                                    555

SEQ ID NO: 129          moltype = AA  length = 555
FEATURE                 Location/Qualifiers
source                  1..555
                        mol_type = protein
                        organism = synthetic construct
SEQUENCE: 129
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INIVLELKG  120
SETTFMCEYA DETATIVEFL NRWITFCQSI ISTLTSGGPG PAGMKGLPGS GGGGSGGGGS  180
GGGGSGGGGS GGGGSGGGGS ELCDDDPPEI PHATFKAMAY KEGTMLNCEC KRGFRRIKSG  240
SLYMLCTGNS SHSSWDNQCQ CTSSATRNTT KQVTPQPEEQ KERKTTEMQS PMQPVDQASL  300
PGHCREPPPW ENEATERIYH FVVGQMVYYQ CVQGYRALHR GPAESVCKMT HGKTRWTQPQ  360
LICTGEMETS QFPGEEKPQA SPEGRPESET SCLVTTTDFQ IQTEMAATME TSIFTTEYQG  420
GGGSGGGGSG GGGSEVQLVE SGGGLVQPGN SLRLSCAASG FTFSKFGMSW VRQAPGKGLE  480
WVSSISGSGR DTLYAESVKG RFTISRDNAK TTLYLQMNSL RPEDTAVYYC TIGGSLSVSS  540
QGTLVTVSSH HHHHH                                                    555

SEQ ID NO: 130          moltype = AA  length = 555
FEATURE                 Location/Qualifiers
source                  1..555
                        mol_type = protein
                        organism = synthetic construct
SEQUENCE: 130
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INIVLELKG  120
SETTFMCEYA DETATIVEFL NRWITFCQSI ISTLTSGGPG PAGMKGLPGS GGGGSGGGGS  180
GGGGSGGGGS GGGGSGGGGS ELCDDDPPEI PHATFKAMAY KEGTMLNCEC KRGFRRIKSG  240
SLYMLCTGNS SHSSWDNQCQ CTSSATRNTT KQVTPQPEEQ KERKTTEMQS PMQPVDQASL  300
PGHCREPPPW ENEATERIYH FVVGQMVYYQ CVQGYRALHR GPAESVCKMT HGKTRWTQPQ  360
LICTGEMETS QFPGEEKPQA SPEGRPESET SCLVTTTDFQ IQTEMAATME TSIFTTEYQS  420
GGPGPAGMKG LPGSEVQLVE SGGGLVQPGN SLRLSCAASG FTFSKFGMSW VRQAPGKGLE  480
WVSSISGSGR DTLYAESVKG RFTISRDNAK TTLYLQMNSL RPEDTAVYYC TIGGSLSVSS  540
QGTLVTVSSH HHHHH                                                    555

SEQ ID NO: 131          moltype = AA  length = 575
FEATURE                 Location/Qualifiers
source                  1..575
                        mol_type = protein
                        organism = synthetic construct
SEQUENCE: 131
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSEVQLVESG GGLVQPGGSL RLSCAASGFT  180
FSSYTLAWVR QAPGKGLEWV AAIDSSSYTY SPDTVRGRFT ISRDNAKNSL YLQMNSLRAE  240
DTAVYYCARD SNWDALDYWG QGTTVTVSSG GGGSGGGGSG GGGSDIQMTQ SPSSLSASVG  300
DRVTITCKAS QNVGTNVGWY QQKPGKAPKA LIYSASFRYS GVPSRFSGSG SGTDFTLTIS  360
SLQPEDFATY YCQQYYTYPY TFGGGTKVEI KGGGGSGGGG SGGGGSGGGG SGGGGSGGGG  420
SSGGPGPAGM KGLPGSAPTS SSTKKTQLQL EHLLLDLQMI LNGINNYKNP KLTRMLTFKF  480
YMPKKATELK HLQCLEEELK PLEEVLNLAQ SKNFHLRPRD LISNINIVVL ELKGSETTFM  540
CEYADETATI VEFLNRWITF CQSIISTLTH HHHHH                              575

SEQ ID NO: 132          moltype = AA  length = 704
FEATURE                 Location/Qualifiers
source                  1..704
                        mol_type = protein
```

-continued

```
                          organism = synthetic construct
SEQUENCE: 132
MDMRVPAQLL GLLLLWLRGA RCAPTSSSTK KTQLQLEHLL LDLQMILNGI NNYKNPKLTR   60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS GGGGSGGGGS  180
GGGGSGGGGS GGGGSGGGGS EVQLVESGGG LVQPGGSLRL SCAASGFTFS SYTLAWVRQA  240
PGKGLEWVAA IDSSSYTYSP DTVRGRFTIS RDNAKNSLYL QMNSLRAEDT AVYYCARDSN  300
WDALDYWGQG TTVTVSSSGG PGPAGMKGLP GSDIQMTQSP SSLSASVGDR VTITCKASQN  360
VGTNVGWYQQ KPGKAPKALI YSASFRYSGV PSRFSGSGSG TDFTLTISSL QPEDFATYYC  420
QQYYTYPYTF GGGTKVEIKG GGGSGGGGS GGGSEVQLVE SGGGLVQPGN SLRLSCAASG  480
FTFSKFGMSW VRQAPGKGLE WVSSISGSGR DTLYAESVKG RFTISRDNAK TTLYLQMNSL  540
RPEDTAVYYC TIGGSLSVSS QGTLVTVSSG GGGSGGGGSG GGGSQVQLQE SGGGLVQAGG  600
SLRLSCAASG RIFSIDIMSW YRQAPGKQRE LVARITRGGT ISYDDSVKGR FTISRDNAKN  660
TVYLQMNSLK PEDTGVYYCN ALYGTDYWGK GTQVTVSSHH HHHH                  704

SEQ ID NO: 133         moltype = AA  length = 689
FEATURE                Location/Qualifiers
source                 1..689
                       mol_type = protein
                       organism = synthetic construct
SEQUENCE: 133
MDMRVPAQLL GLLLLWLRGA RCQVQLQESG GGLVQAGGSL RLSCAASGRI FSIDIMSWYR   60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSGGGGSG  420
GGGSGGGGSG GGGSGGGGSG GGGSEVQLVE SGGGLVQPGG SLRLSCAASG FTFSSYTLAW  480
VRQAPGKGLE WVAAIDSSSY TYSPDTVRGR FTISRDNAKN SLYLQMNSLR AEDTAVYYCA  540
RDSNWDALDY WGQGTTVTVS SGGGGSGGGG SGGGGSDIQM TQSPSSLSAS VGDRVTITCK  600
ASQNVGTNVG WYQQKPGKAP KALIYSASFR YSGVPSRFSG SGSGTDFTLT ISSLQPEDFA  660
TYYCQQYYTY PYTFGGGTKV EIKHHHHHH                                  689

SEQ ID NO: 134         moltype = AA  length = 545
FEATURE                Location/Qualifiers
source                 1..545
                       mol_type = protein
                       organism = synthetic construct
SEQUENCE: 134
MDMRVPAQLL GLLLLWLRGA RCAPTSSSTK KTQLQLEHLL LDLQMILNGI NNYKNPKLTR   60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS EVQLVESGGG  180
LVQPGGSLRL SCAASGFTFS SYTLAWVRQA PGKGLEWVAA IDSSSYTYSP DTVRGRFTIS  240
RDNAKNSLYL QMNSLRAEDT AVYYCARDSN WDALDYWGQG TTVTVSSSGG GSGGGGSGGG  300
GSDIQMTQSP SSLSASVGDR VTITCKASQN VGTNVGWYQQ KPGKAPKALI YSASFRYSGV  360
PSRFSGSGSG TDFTLTISSL QPEDFATYYC QQYYTYPYTF GGGTKVEIKG GGGSGGGGS  420
GGGSEVQLVE SGGGLVQPGN SLRLSCAASG FTFSKFGMSW VRQAPGKGLE WVSSISGSGR  480
DTLYAESVKG RFTISRDNAK TTLYLQMNSL RPEDTAVYYC TIGGSLSVSS QGTLVTVSSH  540
HHHH                                                            545

SEQ ID NO: 135         moltype = AA  length = 575
FEATURE                Location/Qualifiers
source                 1..575
                       mol_type = protein
                       organism = synthetic construct
SEQUENCE: 135
MDMRVPAQLL GLLLLWLRGA RCAPTSSSTK KTQLQLEHLL LDLQMILNGI NNYKNPKLTR   60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPG PAGMKGLPGS GGGGSGGGGS  180
GGGGSGGGGS GGGGSGGGGS EVQLVESGGG LVQPGGSLRL SCAASGFTFS SYTLAWVRQA  240
PGKGLEWVAA IDSSSYTYSP DTVRGRFTIS RDNAKNSLYL QMNSLRAEDT AVYYCARDSN  300
WDALDYWGQG TTVTVSSGGG GSGGGGSGGG GSDIQMTQSP SSLSASVGDR VTITCKASQN  360
VGTNVGWYQQ KPGKAPKALI YSASFRYSGV PSRFSGSGSG TDFTLTISSL QPEDFATYYC  420
QQYYTYPYTF GGGTKVEIKG GGGSGGGGS GGGSEVQLVE SGGGLVQPGN SLRLSCAASG  480
FTFSKFGMSW VRQAPGKGLE WVSSISGSGR DTLYAESVKG RFTISRDNAK TTLYLQMNSL  540
RPEDTAVYYC TIGGSLSVSS QGTLVTVSSH HHHH                            575

SEQ ID NO: 136         moltype = AA  length = 421
FEATURE                Location/Qualifiers
source                 1..421
                       mol_type = protein
                       organism = synthetic construct
SEQUENCE: 136
MDMRVPAQLL GLLLLWLRGA RCEVQLVESG GGLVQPGNSL RLSCAASGFT FSKFGMSWVR   60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSAPTSSSTK KTQLQLEHLL LDLQMILNGI  180
NNYKNPKLTR MLTFKFYMPK KATELKHLQC LEEELKPLEE VLNLAQSKNF HLRPRDLISN  240
INVIVLELKG SETTFMCEYA DETATIVEFL NRWITFCQSI ISTLTSGGPG PAGMKGLPGS  300
```

```
EVQLVESGGG LVQPGNSLRL SCAASGFTFS KFGMSWVRQA PGKGLEWVSS ISGSGRDTLY  360
AESVKGRFTI SRDNAKTTLY LQMNSLRPED TAVYYCTIGG SLSVSSQGTL VTVSSHHHHH  420
H                                                                 421

SEQ ID NO: 137           moltype = AA  length = 806
FEATURE                  Location/Qualifiers
source                   1..806
                         mol_type = protein
                         organism = synthetic construct
SEQUENCE: 137
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGSGS GSGSGSGSGS GSEVQLVESG GGLVQPGNSL RLSCAASGFT  180
FSKFGMSWVR QAPGKGLEWV SSISGSGRDT LYAESVKGRF TISRDNAKTT LYLQMNSLRP  240
EDTAVYYCTI GGSLSVSSQG TLVTVSSGSG SGSGSGSGSG SGSQVQLQES GGGLVQAGGS  300
LRLSCAASGR IFSIDIMSWY RQAPGKQREL VARITRGGTI SYDDSVKGRF TISRDNAKNT  360
VYLQMNSLKP EDTGVYYCNA LYGTDYWGKG TQVTVSSGSG SGSGSGSGSG SGSEVQLVES  420
GGGLVQPGGS LRLSCAASGF TFSSYTLAWV RQAPGKGLEW VAAIDSSSYT YSPDTVRGRF  480
TISRDNAKNS LYLQMNSLRA EDTAVYYCAR DSNWDALDYW GQGTTVTVSS GGGGSGGGGS  540
GGGGSDIQMT QSPSSLSASV GDRVTITCKA SQNVGTNVGW YQQKPGKAPK ALIYSASFRY  600
SGVPSRFSGS GSGTDFTLTI SSLQPEDFAT YYCQQYYTYP YTFGGGTKVE IKSGGPGPAG  660
MKGLPGSAPT SSSTKKTQLQ LEHLLLDLQM ILNGINNYKN PKLTRMLTFK FYMPKKATEL  720
KHLQCLEEEL KPLEEVLNLA QSKNFHLRPR DLISNINVIV LELKGSETTF MCEYADETAT  780
IVEFLNRWIT FCQSIISTLT HHHHHH                                       806

SEQ ID NO: 138           moltype = AA  length = 676
FEATURE                  Location/Qualifiers
source                   1..676
                         mol_type = protein
                         organism = synthetic construct
SEQUENCE: 138
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGSGS GSGSGSGSGS GSEVQLVESG GGLVQPGNSL RLSCAASGFT  180
FSKFGMSWVR QAPGKGLEWV SSISGSGRDT LYAESVKGRF TISRDNAKTT LYLQMNSLRP  240
EDTAVYYCTI GGSLSVSSQG TLVTVSSGSG SGSGSGSGSG SGSEVQLVES GGGLVQPGGS  300
LRLSCAASGF TFSSYTLAWV RQAPGKGLEW VAAIDSSSYT YSPDTVRGRF TISRDNAKNS  360
LYLQMNSLRA EDTAVYYCAR DSNWDALDYW GQGTTVTVSS GGGGSGGGGS GGGGSDIQMT  420
QSPSSLSASV GDRVTITCKA SQNVGTNVGW YQQKPGKAPK ALIYSASFRY SGVPSRFSGS  480
GSGTDFTLTI SSLQPEDFAT YYCQQYYTYP YTFGGGTKVE IKSGGPGPAG MKGLPGSAPT  540
SSSTKKTQLQ LEHLLLDLQM ILNGINNYKN PKLTRMLTFK FYMPKKATEL KHLQCLEEEL  600
KPLEEVLNLA QSKNFHLRPR DLISNINVIV LELKGSETTF MCEYADETAT IVEFLNRWIT  660
FCQSIISTLT HHHHHH                                                  676

SEQ ID NO: 139           moltype = AA  length = 421
FEATURE                  Location/Qualifiers
source                   1..421
                         mol_type = protein
                         organism = synthetic construct
SEQUENCE: 139
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGSGS GSGSGSGSGS GSEVQLVESG GGLVQPGNSL RLSCAASGFT  180
FSKFGMSWVR QAPGKGLEWV SSISGSGRDT LYAESVKGRF TISRDNAKTT LYLQMNSLRP  240
EDTAVYYCTI GGSLSVSSQG TLVTVSSSGG PGPAGMKGLP GSAPTSSSTK KTQLQLEHLL  300
LDLQMILNGI NNYKNPKLTR MLTFKFYMPK KATELKHLQC LEEELKPLEE VLNLAQSKNF  360
HLRPRDLISN INIVLELKG SETTFMCEYA DETATIVEFL NRWITFCQSI ISTLTHHHHH  420
H                                                                 421

SEQ ID NO: 140           moltype = AA  length = 420
FEATURE                  Location/Qualifiers
source                   1..420
                         mol_type = protein
                         organism = synthetic construct
SEQUENCE: 140
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSSGGP GPAGMKGLPG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSHHHHHH  420

SEQ ID NO: 141           moltype = AA  length = 550
FEATURE                  Location/Qualifiers
source                   1..550
                         mol_type = protein
                         organism = synthetic construct
SEQUENCE: 141
```

```
MDMRVPAQLL GLLLLWLRGA RCQVQLQESG GGLVQAGGSL RLSCAASGRI FSIDIMSWYR    60
QAPGKQRELV ARITRGGTIS YDDSVKGRFT ISRDNAKNTV YLQMNSLKPE DTGVYYCNAL   120
YGTDYWGKGT QVTVSSGGGG SGGGGSGGGG SEVQLVESGG GLVQPGNSLR LSCAASGFTF   180
SKFGMSWVRQ APGKGLEWVS SISGSGRDTL YAESVKGRFT ISRDNAKTTL YLQMNSLRPE   240
DTAVYYCTIG GSLSVSSQGT LVTVSSSGGP GPAGMKGLPG SAPTSSSTKK TQLQLEHLLL   300
DLQMILNGIN NYKNPKLTRM LTFKFYMPKK ATELKHLQCL EEELKPLEEV LNLAQSKNFH   360
LRPRDLISNI NVIVLELKGS ETTFMCEYAD ETATIVEFLN RWITFCQSII STLTSGGPGP   420
AGMKGLPGSE VQLVESGGGL VQPGNSLRLS CAASGFTFSK FGMSWVRQAP GKGLEWVSSI   480
SGSGRDTLYA ESVKGRFTIS RDNAKTTLYL QMNSLRPEDT AVYYCTIGGS LSVSSQGTLV   540
TVSSHHHHHH                                                        550

SEQ ID NO: 142          moltype = AA   length = 420
FEATURE                 Location/Qualifiers
source                  1..420
                        mol_type = protein
                        organism = synthetic construct
SEQUENCE: 142
MDMRVPAQLL GLLLLWLRGA RCQVQLQESG GGLVQAGGSL RLSCAASGRI FSIDIMSWYR    60
QAPGKQRELV ARITRGGTIS YDDSVKGRFT ISRDNAKNTV YLQMNSLKPE DTGVYYCNAL   120
YGTDYWGKGT QVTVSSGGGG SGGGGSGGGG SAPTSSSTKK TQLQLEHLLL DLQMILNGIN   180
NYKNPKLTRM LTFKFYMPKK ATELKHLQCL EEELKPLEEV LNLAQSKNFH LRPRDLISNI   240
NVIVLELKGS ETTFMCEYAD ETATIVEFLN RWITFCQSII STLTSGGPGP AGMKGLPGSE   300
VQLVESGGGL VQPGNSLRLS CAASGFTFSK FGMSWVRQAP GKGLEWVSSI SGSGRDTLYA   360
ESVKGRFTIS RDNAKTTLYL QMNSLRPEDT AVYYCTIGGS LSVSSQGTLV TVSSHHHHHH   420

SEQ ID NO: 143          moltype = AA   length = 290
FEATURE                 Location/Qualifiers
source                  1..290
                        mol_type = protein
                        organism = synthetic construct
SEQUENCE: 143
MDMRVPAQLL GLLLLWLRGA RCQVQLQESG GGLVQAGGSL RLSCAASGRI FSIDIMSWYR    60
QAPGKQRELV ARITRGGTIS YDDSVKGRFT ISRDNAKNTV YLQMNSLKPE DTGVYYCNAL   120
YGTDYWGKGT QVTVSSGGGG SGGGGSGGGG SAPTSSSTKK TQLQLEHLLL DLQMILNGIN   180
NYKNPKLTRM LTFKFYMPKK ATELKHLQCL EEELKPLEEV LNLAQSKNFH LRPRDLISNI   240
NVIVLELKGS ETTFMCEYAD ETATIVEFLN RWITFCQSII STLTHHHHHH               290

SEQ ID NO: 144          moltype = AA   length = 291
FEATURE                 Location/Qualifiers
source                  1..291
                        mol_type = protein
                        organism = synthetic construct
SEQUENCE: 144
MDMRVPAQLL GLLLLWLRGA RCAPTSSSTK KTQLQLEHLL LDLQMILNGI NNYKNPKLTR    60
MLTFKFYMPK KATELKHLQC LEEELKPLEE VLNLAQSKNF HLRPRDLISN INIVLELKG    120
SETTFMCEYA DETATIVEFL NRWITFCQSI ISTLTSGGPG PAGMKGLPGS EVQLVESGGG   180
LVQPGNSLRL SCAASGFTFS KFGMSWVRQA PGKGLEWVSS ISGSGRDTLY AESVKGRFTI   240
SRDNAKTTLY LQMNSLRPED TAVYYCTIGG SLSVSSQGTL VTVSSHHHHH H            291

SEQ ID NO: 145          moltype = AA   length = 689
FEATURE                 Location/Qualifiers
source                  1..689
                        mol_type = protein
                        organism = synthetic construct
SEQUENCE: 145
MDMRVPAQLL GLLLLWLRGA RCQVQLQESG GGLVQAGGSL RLSCAASGRI FSIDIMSWYR    60
QAPGKQRELV ARITRGGTIS YDDSVKGRFT ISRDNAKNTV YLQMNSLKPE DTGVYYCNAL   120
YGTDYWGKGT QVTVSSGGGP GPAGMKGLPG SAPTSSSTKK TQLQLEHLLL DLQMILNGIN   180
NYKNPKLTRM LTFKFYMPKK ATELKHLQCL EEELKPLEEV LNLAQSKNFH LRPRDLISNI   240
NVIVLELKGS ETTFMCEYAD ETATIVEFLN RWITFCQSII STLTSGGPGP AGMKGLPGSE   300
VQLVESGGGL VQPGNSLRLS CAASGFTFSK FGMSWVRQAP GKGLEWVSSI SGSGRDTLYA   360
ESVKGRFTIS RDNAKTTLYL QMNSLRPEDT AVYYCTIGGS LSVSSQGTLV TVSSGGGGSG   420
GGGSGGGGSG GGGSGGGGSG GGGSEVQLVE SGGGLVQPGS SLRLSCAASG FTFSSYTLAW   480
VRQAPGKGLE WVAAIDSSSY TYSPDTVRGR FTISRDNAKN SLYLQMNSLR AEDTAVYYCA   540
RDSNWDALDY WGQGTTVTVS SGGGGSGGGG SGGGGSDIQM TQSPSSLSAS VGDRVTITCK   600
ASQNVGTNVG WYQQKPGKAP KALIYSASFR YSGVPSRFSG SGSGTDFTLT ISSLQPEDFA   660
TYYCQQYYTY PYTFGGGTKV EIKHHHHHH                                     689

SEQ ID NO: 146          moltype = AA   length = 704
FEATURE                 Location/Qualifiers
source                  1..704
                        mol_type = protein
                        organism = synthetic construct
SEQUENCE: 146
MDMRVPAQLL GLLLLWLRGA RCAPTSSSTK KTQLQLEHLL LDLQMILNGI NNYKNPKLTR    60
MLTFKFYMPK KATELKHLQC LEEELKPLEE VLNLAQSKNF HLRPRDLISN INIVLELKG    120
SETTFMCEYA DETATIVEFL NRWITFCQSI ISTLTSGGPG PAGMKGLPGS GGGGSGGGGS   180
GGGGSGGGGS GGGGSGGGGS EVQLVESGGG LVQPGGSLRL SCAASGFTFS SYTLAWVRQA   240
PGKGLEWVAA IDSSSYTYSP DTVRGRFTIS RDNAKNSLYL QMNSLRAEDT AVYYCARDSN   300
```

-continued

```
WDALDYWGQG TTVTVSSGGG GSGGGGSGGG GSDIQMTQSP SSLSASVGDR VTITCKASQN  360
VGTNVGWYQQ KPGKAPKALI YSASFRYSGV PSRFSGSGSG TDFTLTISSL QPEDFATYYC  420
QQYYTYPYTF GGGTKVEIKG GGGSGGGGS GGGSEVQLVE SGGGLVQPGN SLRLSCAASG  480
FTFSKFGMSW VRQAPGKGLE WVSSISGSGR DTLYAESVKG RFTISRDNAK TTLYLQMNSL  540
RPEDTAVYYC TIGGSLSVSS QGTLVTVSSG GGGSGGGGS GGGSQVQLQE SGGGLAQAGG  600
SLSLSCAASG FTVSNSVMAW YRQTPGKQRE FVAIINSVGS TNYADSVKGR FTISRDNAKN  660
TVYLQMNNLK PEDTAVYVCN RNFDRIYWGQ GTQVTVSSHH HHHH             704

SEQ ID NO: 147        moltype = AA  length = 674
FEATURE               Location/Qualifiers
source                1..674
                      mol_type = protein
                      organism = synthetic construct
SEQUENCE: 147
MDMRVPAQLL GLLLLWLRGA RCQVQLQESG GGLAQAGGSL SLSCAASGFT VSNSVMAWYR  60
QTPGKQREFV AIINSVGSTN YADSVKGRFT ISRDNAKNTV YLQMNNLKPE DTAVYVCNRN  120
FDRIYWGQGT QVTVSSAPTS SSTKKTQLQL EHLLLDLQMI LNGINNYKNP KLTRMLTFKF  180
YMPKKATELK HLQCLEEELK PLEEVLNLAQ SKNFHLRPRD LISNINVIVL ELKGSETTFM  240
CEYADETATI VEFLNRWITF CQSIISTLTS GGPGPAGMKG LPGSEVQLVE SGGGLVQPGN  300
SLRLSCAASG FTFSKFGMSW VRQAPGKGLE WVSSISGSGR DTLYAESVKG RFTISRDNAK  360
TTLYLQMNSL RPEDTAVYYC TIGGSLSVSS QGTLVTVSSG GGGSGGGGS GGGSGGGGSG  420
GGGSGGGGSG VQLVESGGGL VQPGGSLRLS CAASGFTFSS YTLAWVRQAP GKGLEWVAAI  480
DSSSYTYSPD TVRGRFTISR DNAKNSLYLQ MNSLRAEDTA VYYCARDSNW DALDYWGQGT  540
TVTVSSGGGG SGGGGSGGGG SDIQMTQSPS SLSASVGDRV TITCKASQNV GTNVGWYQQK  600
PGKAPKALIY SASFRYSGVP SRFSGSGSGT DFTLTISSLQ PEDFATYYCQ QYYTYPYTFG  660
GGTKVEIKHH HHHH                                                 674

SEQ ID NO: 148        moltype = AA  length = 704
FEATURE               Location/Qualifiers
source                1..704
                      mol_type = protein
                      organism = synthetic construct
SEQUENCE: 148
MDMRVPAQLL GLLLLWLRGA RCEVQLVESG GGLVQPGGSL RLSCAASGFT FSSYTLAWVR  60
QAPGKGLEWV AAIDSSSYTY SPDTVRGRFT ISRDNAKNSL YLQMNSLRAE DTAVYYCARD  120
SNWDALDYWG QGTTVTVSSG GGGSGGGGS GGGSDIQMTQ SPSSLSASVG DRVTITCKAS  180
QNVGTNVGWY QQKPGKAPKA LIYSASFRYS GVPSRFSGSG SGTDFTLTIS SLQPEDFATY  240
YCQQYYTYPY TFGGGTKVEI KGGGGSGGGG SGGGGSGGGG SGGGGSGGGG SSGGPGPAGM  300
KGLPGSAPTS SSTKKTQLQL EHLLLDLQMI LNGINNYKNP KLTRMLTFKF YMPKKATELK  360
HLQCLEEELK PLEEVLNLAQ SKNFHLRPRD LISNINVIVL ELKGSETTFM CEYADETATI  420
VEFLNRWITF CQSIISTLTS GGPGPAGMKG LPGSEVQLVE SGGGLVQPGN SLRLSCAASG  480
FTFSKFGMSW VRQAPGKGLE WVSSISGSGR DTLYAESVKG RFTISRDNAK TTLYLQMNSL  540
RPEDTAVYYC TIGGSLSVSS QGTLVTVSSG GGGSGGGGS GGGSQVQLQE SGGGLAQAGG  600
SLSLSCAASG FTVSNSVMAW YRQTPGKQRE FVAIINSVGS TNYADSVKGR FTISRDNAKN  660
TVYLQMNNLK PEDTAVYVCN RNFDRIYWGQ GTQVTVSSHH HHHH             704

SEQ ID NO: 149        moltype = AA  length = 704
FEATURE               Location/Qualifiers
source                1..704
                      mol_type = protein
                      organism = synthetic construct
SEQUENCE: 149
MDMRVPAQLL GLLLLWLRGA RCQVQLQESG GGLAQAGGSL SLSCAASGFT VSNSVMAWYR  60
QTPGKQREFV AIINSVGSTN YADSVKGRFT ISRDNAKNTV YLQMNNLKPE DTAVYVCNRN  120
FDRIYWGQGT QVTVSSGGGG SGGGGSGGGG SEVQLVESGG GLVQPGNSLR LSCAASGFTF  180
SKFGMSWVRQ APGKGLEWVS SISGSGRDTL YAESVKGRFT ISRDNAKTTL YLQMNSLRPE  240
DTAVYYCTIG GSLSVSSQGT LVTVSSSGGP GPAGMKGLPG SEVQLVESGG GLVQPGGSLR  300
LSCAASGFTF SSYTLAWVRQ APGKGLEWVA AIDSSSYTYS PDTVRGRFTI SRDNAKNSLY  360
LQMNSLRAED TAVYYCARDS NWDALDYWGQ GTTVTVSSGG GGSGGGGSG GGSDIQMTQS  420
PSSLSASVGD RVTITCKASQ NVGTNVGWYQ QKPGKAPKAL IYSASFRYSG VPSRFSGSGS  480
GTDFTLTISS LQPEDFATYY CQQYYTYPYT FGGGTKVEIK GGGGSGGGGS GGGGSGGGGS  540
GGGGSGGGGS SGGPGPAGMK GLPGSAPTSS STKKTQLQLE HLLLDLQMIL NGINNYKNPK  600
LTRMLTFKFY MPKKATELKH LQCLEEELKP LEEVLNLAQS KNFHLRPRDL ISNINVIVLE  660
LKGSETTFMC EYADETATIV EFLNRWITFC QSIISTLTHH HHHH             704

SEQ ID NO: 150        moltype = AA  length = 689
FEATURE               Location/Qualifiers
source                1..689
                      mol_type = protein
                      organism = synthetic construct
SEQUENCE: 150
MDMRVPAQLL GLLLLWLRGA RCEVQLVESG GGLVQPGGSL RLSCAASGFT FSSYTLAWVR  60
QAPGKGLEWV AAIDSSSYTY SPDTVRGRFT ISRDNAKNSL YLQMNSLRAE DTAVYYCARD  120
SNWDALDYWG QGTTVTVSSG GGGSGGGGS GGGSDIQMTQ SPSSLSASVG DRVTITCKAS  180
QNVGTNVGWY QQKPGKAPKA LIYSASFRYS GVPSRFSGSG SGTDFTLTIS SLQPEDFATY  240
YCQQYYTYPY TFGGGTKVEI KGGGGSGGGG SGGGGSGGGG SGGGGSGGGG SEVQLVESGG  300
GLVQPGNSLR LSCAASGFTF SKFGMSWVRQ APGKGLEWVS SISGSGRDTL YAESVKGRFT  360
ISRDNAKTTL YLQMNSLRPE DTAVYYCTIG GSLSVSSQGT LVTVSSSGGP GPAGMKGLPG  420
SAPTSSSTKK TQLQLEHLLL DLQMILNGIN NYKNPKLTRM LTFKFYMPKK ATELKHLQCL  480
```

```
EEELKPLEEV LNLAQSKNFH LRPRDLISNI NVIVLELKGS ETTFMCEYAD ETATIVEFLN  540
RWITFCQSII STLTGGGGSG GGGSGGGGSQ VQLQESGGGL AQAGGSLSLS CAASGFTVSN  600
SVMAWYRQTP GKQREFVAII NSVGSTNYAD SVKGRFTISR DNAKNTVYLQ MNNLKPEDTA  660
VYVCNRNFDR IYWGQGTQVT VSSHHHHHH                                    689
```

SEQ ID NO: 151           moltype = AA  length = 700
FEATURE                  Location/Qualifiers
source                   1..700
                         mol_type = protein
                         organism = synthetic construct
SEQUENCE: 151
```
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSR  300
GETGPAAPGS EVQLVESGGG LVQPGNSLRL SCAASGFTFS KFGMSWVRQA PGKGLEWVSS  360
ISGSGRDTLY AESVKGRFTI SRDNAKTTLY LQMNSLRPED TAVYYCTIGG SLSVSSQGTL  420
VTVSSGGGGS GGGGSGGGGS GGGGSGGGGS GGGGSEVQLV ESGGGLVQPG GSLRLSCAAS  480
GFTFSSYTLA WVRQAPGKGL EWVAAIDSSS YTYSPDTVRG RFTISRDNAK NSLYLQMNSL  540
RAEDTAVYYC ARDSNWDALD YWGQGTTVTV SSGGGGSGGG GSGGGGSDIQ MTQSPSSLSA  600
SVGDRVTITC KASQNVGTNV GWYQQKPGKA PKALIYSASF RYSGVPSRFS GSGSGTDFTL  660
TISSLQPEDF ATYYCQQYYT YPYTFGGGTK VEIKHHHHHH                        700
```

SEQ ID NO: 152           moltype = AA  length = 276
FEATURE                  Location/Qualifiers
source                   1..276
                         mol_type = protein
                         organism = synthetic construct
SEQUENCE: 152
```
MDMRVPAQLL GLLLLWLRGA RCEVQLVESG GGLVQPGGSL RLSCAASGFT FSSYAMSWVR  60
QAPGKGLEWV SAISGSGGST YYADSVKGRF TISRDNSKNT LYLQMNSLRA EDTAVYCAR   120
GVGAFRPYRK HEWGQGTLVT VSRGGGGSGG GGSGGGGSSS ELTQDPAVSV ALGQTVRITC  180
QGDSLRSYYA SWYQQKPGQA PVLVIYGKNN RPSGIPDRFS GSSSGNTASL TTTGAQAEDE  240
ADYYCNSSPF EHNLVVFGGG TKLTVLHHHH HHEPEA                            276
```

SEQ ID NO: 153           moltype = AA  length = 279
FEATURE                  Location/Qualifiers
source                   1..279
                         mol_type = protein
                         organism = synthetic construct
SEQUENCE: 153
```
MDMRVPAQLL GLLLLWLRGA RCQVQLQQSG AELVRPGTSV KVSCKASGYA FTNYLIEWVK  60
QRPGQGLEWI GVINPGSGGT NYNEKFKGKA TLTADKSSST AYMQLSSLTS DDSAVYFCAR  120
WRGDGYYAYF DVWGAGTTVT VSSGGGGSGG GGSGGGGSDI VLTQSPASLA VSLGQRATIS  180
CKASQSVDYD GDSYMNWYQQ KPGQPPKLLI YAASNLESGI PARFSGSGSG TDFTLNIHPV  240
EEEDAATYYC QQSNEDPYTF GGGTKLEIKH HHHHHEPEA                         279
```

SEQ ID NO: 154           moltype = AA  length = 279
FEATURE                  Location/Qualifiers
source                   1..279
                         mol_type = protein
                         organism = synthetic construct
SEQUENCE: 154
```
MDMRVPAQLL GLLLLWLRGA RCQVQLQQSG AELVRPGTSV KVSCKASGYA FTNYLIEWVK  60
QRPGQGLEWI GVINPGSGGT NYNEKFKGKA TLTADKSSST AYMQLSSLTS DDSAVYFCAR  120
WRGDGYYAYF DVWGAGTTVT VSSSGGPGPA GMKGLPGSDI VLTQSPASLA VSLGQRATIS  180
CKASQSVDYD GDSYMNWYQQ KPGQPPKLLI YAASNLESGI PARFSGSGSG TDFTLNIHPV  240
EEEDAATYYC QQSNEDPYTF GGGTKLEIKH HHHHHEPEA                         279
```

SEQ ID NO: 155           moltype = AA  length = 279
FEATURE                  Location/Qualifiers
source                   1..279
                         mol_type = protein
                         organism = synthetic construct
SEQUENCE: 155
```
MDMRVPAQLL GLLLLWLRGA RCDIVLTQSP ASLAVSLGQR ATISCKASQS VDYDGDSYMN  60
WYQQKPGQPP KLLIYAASNL ESGIPARFSG SGSGTDFTLN IHPVEEEDAA TYYCQQSNED  120
PYTFGGGTKL EIKGGGGSGG GGSGGGGSQV QLQQSGAELV RPGTSVKVSC KASGYAFTNY  180
LIEWVKQRPG QGLEWIGVIN PGSGGTNYNE KFKGKATLTA DKSSSTAYMQ LSSLTSDDSA  240
VYFCARWRGD GYYAYFDVWG AGTTVTVSSH HHHHHEPEA                         279
```

SEQ ID NO: 156           moltype = AA  length = 279
FEATURE                  Location/Qualifiers
source                   1..279
                         mol_type = protein
                         organism = synthetic construct
SEQUENCE: 156
```
MDMRVPAQLL GLLLLWLRGA RCDIVLTQSP ASLAVSLGQR ATISCKASQS VDYDGDSYMN  60
```

-continued

```
WYQQKPGQPP KLLIYAASNL ESGIPARFSG SGSGTDFTLN IHPVEEEDAA TYYCQQSNED 120
PYTFGGGTKL EIKSGGPGPA GMKGLPGSQV QLQQSGAELV RPGTSVKVSC KASGYAFTNY 180
LIEWVKQRPG QGLEWIGVIN PGSGGTNYNE KFKGKATLTA DKSSSTAYMQ LSSLTSDDSA 240
VYFCARWRGD GYYAYFDVWG AGTTVTVSSH HHHHHEPEA              279

SEQ ID NO: 157          moltype = AA  length = 295
FEATURE                 Location/Qualifiers
source                  1..295
                        mol_type = protein
                        organism = synthetic construct
SEQUENCE: 157
MDMRVPAQLL GLLLLWLRGA RCAPTSSSTK KTQLQLEHLL LDLQMILNGI NNYKNPKLTR 60
MLTFKFYMPK KATELKHLQC LEEELKPLEE VLNLAQSKNF HLRPRDLISN INVIVLELKG 120
SETTFMCEYA DETATIVEFL NRWITFCQSI ISTLTGGGGS GGGGSGGGGS EVQLVESGGG 180
LVQPGNSLRL SCAASGFTFS KFGMSWVRQA PGKGLEWVSS ISGSGRDTLY AESVKGRFTI 240
SRDNAKTTLY LQMNSLRPED TAVYYCTIGG SLSVSSQGTL VTVSSHHHHH HEPEA     295

SEQ ID NO: 158          moltype = AA  length = 765
FEATURE                 Location/Qualifiers
source                  1..765
                        mol_type = protein
                        organism = synthetic construct
SEQUENCE: 158
MDMRVPAQLL GLLLLWLRGA RCAPTSSSTK KTQLQLEHLL LDLQMILNGI NNYKNPKLTR 60
MLTFKFYMPK KATELKHLQC LEEELKPLEE VLNLAQSKNF HLRPRDLISN INVIVLELKG 120
SETTFMCEYA DETATIVEFL NRWITFCQSI ISTLTGGGGS GGGGSGGGGS DAHKSEVAHR 180
FKDLGEENFK ALVLIAFAQY LQQCPFEDHV KLVNEVTEFA KTCVADESAE NCDKSLHTLF 240
GDKLCTVATL RETYGEMADC CAKQEPERNE CFLQHKDDNP NLPRLVRPEV DVMCTAFHDN 300
EETFLKKYLY EIARRHPYFY APELLFFAKR YKAAFTECCQ AADKAACLLP KLDELRDEGK 360
ASSAKQRLKC ASLQKFGERA FKAWAVARLS QRFPKAEFAE VSKLVTDLTK VHTECCHGDL 420
LECADDRADL AKYICENQDS ISSKLKECCE KPLLEKSHCI AEVENDEMPA DLPSLAADFV 480
ESKDVCKNYA EAKDVFLGMF LYEYARRHPD YSVVLLLRLA KTYETTLEKC CAAADPHECY 540
AKVFDEFKPL VEEPQNLIKQ NCELFEQLGE YKFQNALLVR YTKKVPQVST PTLVEVSRNL 600
GKVGSKCCKH PEAKRMPCAE DYLSVVLNQL CVLHEKTPVS DRVTKCCTES LVNRRPCFSA 660
LEVDETYVPK EFNAETFTFH ADICTLSEKE RQIKKQTALV ELVKHKPKAT KEQLKAVMDD 720
FAAFVEKCCK ADDKETCFAE EGKKLVAASQ AALGLHHHHH HEPEA              765

SEQ ID NO: 159          moltype = AA  length = 765
FEATURE                 Location/Qualifiers
source                  1..765
                        mol_type = protein
                        organism = synthetic construct
SEQUENCE: 159
MDMRVPAQLL GLLLLWLRGA RCAPTSSSTK KTQLQLEHLL LDLQMILNGI NNYKNPKLTR 60
MLTFKFYMPK KATELKHLQC LEEELKPLEE VLNLAQSKNF HLRPRDLISN INVIVLELKG 120
SETTFMCEYA DETATIVEFL NRWITFCQSI ISTLTGGGGS GGGGSGGGGS DAHKSEVAHR 180
FKDLGEENFK ALVLIAFAQY LQQCPFEDHV KLVNEVTEFA KTCVADESAE NCDKSLHTLF 240
GDKLCTVATL RETYGEMADC CAKQEPERNE CFLQHKDDNP NLPRLVRPEV DVMCTAFHDN 300
EETFLKKYLY EIARRHPYFY APELLFFAKR YKAAFTECCQ AADKAACLLP KLDELRDEGK 360
ASSAKQRLKC ASLQKFGERA FKAWAVARLS QRFPKAEFAE VSKLVTDLTK VHTECCHGDL 420
LECADDRADL AKYICENQDS ISSKLKECCE KPLLEKSHCI AEVENDEMPA DLPSLAADFV 480
ESKDVCKNYA EAKDVFLGMF LYEYARRHPD YSVVLLLRLA KTYETTLEKC CAAADPHECY 540
AKVFDEFKPL VEEPQNLIKQ NCELFEQLGE YKFQNALLVR YTKKVPQVST PTLVEVSRNL 600
GKVGSKCCKH PEAKRMPCAE DYLSVVLNQL CVLHEKTPVS DRVTKCCTES LVNRRPCFSA 660
LEVDETYVPK EFNAETFTFH ADICTLSEKE RQIKKQTALV ELVKHKPKAT KEQLKAVMDD 720
FAAFVEKCCK ADDKETCFAE EGKKLVAASQ AALGLHHHHH HEPEA              765

SEQ ID NO: 160          moltype = AA  length = 765
FEATURE                 Location/Qualifiers
source                  1..765
                        mol_type = protein
                        organism = synthetic construct
SEQUENCE: 160
MDMRVPAQLL GLLLLWLRGA RCAPTSSSTK KTQLQLEHLL LDLQMILNGI NNYKNPKLTR 60
MLTFKFYMPK KATELKHLQC LEEELKPLEE VLNLAQSKNF HLRPRDLISN INVIVLELKG 120
SETTFMCEYA DETATIVEFL NRWITFCQSI ISTLTSGGPG PAGMKGLPGS DAHKSEVAHR 180
FKDLGEENFK ALVLIAFAQY LQQCPFEDHV KLVNEVTEFA KTCVADESAE NCDKSLHTLF 240
GDKLCTVATL RETYGEMADC CAKQEPERNE CFLQHKDDNP NLPRLVRPEV DVMCTAFHDN 300
EETFLKKYLY EIARRHPYFY APELLFFAKR YKAAFTECCQ AADKAACLLP KLDELRDEGK 360
ASSAKQRLKC ASLQKFGERA FKAWAVARLS QRFPKAEFAE VSKLVTDLTK VHTECCHGDL 420
LECADDRADL AKYICENQDS ISSKLKECCE KPLLEKSHCI AEVENDEMPA DLPSLAADFV 480
ESKDVCKNYA EAKDVFLGMF LYEYARRHPD YSVVLLLRLA KTYETTLEKC CAAADPHECY 540
AKVFDEFKPL VEEPQNLIKQ NCELFEQLGE YKFQNALLVR YTKKVPQVST PTLVEVSRNL 600
GKVGSKCCKH PEAKRMPCAE DYLSVVLNQL CVLHEKTPVS DRVTKCCTES LVNRRPCFSA 660
LEVDETYVPK EFNAETFTFH ADICTLSEKE RQIKKQTALV ELVKHKPKAT KEQLKAVMDD 720
FAAFVEKCCK ADDKETCFAE EGKKLVAASQ AALGLHHHHH HEPEA              765

SEQ ID NO: 161          moltype = AA  length = 708
FEATURE                 Location/Qualifiers
```

-continued

```
source                      1..708
                            mol_type = protein
                            organism = synthetic construct
SEQUENCE: 161
MDMRVPAQLL GLLLLWLRGA RCAPTSSSTK KTQLQLEHLL LDLQMILNGI NNYKNPKLTR   60
MLTFKFYMPK KATELKHLQC LEEELKPLEE VLNLAQSKNF HLRPRDLISN INIVLELKG   120
SETTFMCEYA DETATIVEFL NRWITFCQSI ISTLTSGGPG PAGMKGLPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSGGGGS GGGGSGGGGS  300
GGGGSGGGGS GGGGSSGGPG PAGMKGLPGS EVQLVESGGG LVQPGGSLRL SCAASGFTFS  360
SYTLAWVRQA PGKGLEWVAA IDSSSYTYSP DTVRGRFTIS RDNAKNSLYL QMNSLRAEDT  420
AVYYCARDSN WDALDYWGQG TTVTVSSGGG GSGGGGSGGG GSDIQMTQSP SSLSASVGDR  480
VTITCKASQN VGTNVGWYQQ KPGKAPKALI YSASFRYSGV PSRFSGSGSG TDFTLTISSL  540
QPEDFATYYC QQYYTYPYTF GGGTKVEIKG GGGSGGGGSG GGGSQVQLQE SGGGLAQAGG  600
SLSLSCAASG FTVSNSVMAW YRQTPGKQRE FVAIINSVGS TNYADSVKGR FTISRDNAKN  660
TVYLQMNNLK PEDTAVYVCN RNFDRIYWGQ GTQVTVSSHH HHHHEPEA              708

SEQ ID NO: 162              moltype = AA   length = 708
FEATURE                     Location/Qualifiers
source                      1..708
                            mol_type = protein
                            organism = synthetic construct
SEQUENCE: 162
MDMRVPAQLL GLLLLWLRGA RCQVQLQESG GGLAQAGGSL SLSCAASGFT VSNSVMAWYR   60
QTPGKQREFV AIINSVGSTN YADSVKGRFT ISRDNAKNTV YLQMNNLKPE DTAVYVCNRN  120
FDRIYWGQGT QVTVSSGGGG SGGGGSGGGG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSGGGGSG  420
GGGSGGGGSG GGGSGGGGSG GGGSSGGPGP AGMKGLPGSE VQLVESGGGL VQPGGSLRLS  480
CAASGFTFSS YTLAWVRQAP GKGLEWVAAI DSSSYTYSPD TVRGRFTISR DNAKNSLYLQ  540
MNSLRAEDTA VYYCARDSNW DALDYWGQGT TVTVSSGGGG SGGGGSGGGG SDIQMTQSPS  600
SLSASVGDRV TITCKASQNV GTNVGWYQQK PGKAPKALIY SASFRYSGVP SRFSGSGSGT  660
DFTLTISSLQ PEDFATYYCQ QYYTYPYTFG GGTKVEIKHH HHHHEPEA              708

SEQ ID NO: 163              moltype = AA   length = 708
FEATURE                     Location/Qualifiers
source                      1..708
                            mol_type = protein
                            organism = synthetic construct
SEQUENCE: 163
MDMRVPAQLL GLLLLWLRGA RCQVQLQESG GGLAQAGGSL SLSCAASGFT VSNSVMAWYR   60
QTPGKQREFV AIINSVGSTN YADSVKGRFT ISRDNAKNTV YLQMNNLKPE DTAVYVCNRN  120
FDRIYWGQGT QVTVSSGGGP GPAGMKGLPG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSGGGGSG  420
GGGSGGGGSG GGGSGGGGSG GGGSSGGPGP AGMKGLPGSE VQLVESGGGL VQPGGSLRLS  480
CAASGFTFSS YTLAWVRQAP GKGLEWVAAI DSSSYTYSPD TVRGRFTISR DNAKNSLYLQ  540
MNSLRAEDTA VYYCARDSNW DALDYWGQGT TVTVSSGGGG SGGGGSGGGG SDIQMTQSPS  600
SLSASVGDRV TITCKASQNV GTNVGWYQQK PGKAPKALIY SASFRYSGVP SRFSGSGSGT  660
DFTLTISSLQ PEDFATYYCQ QYYTYPYTFG GGTKVEIKHH HHHHEPEA              708

SEQ ID NO: 164              moltype = AA   length = 161
FEATURE                     Location/Qualifiers
source                      1..161
                            mol_type = protein
                            organism = synthetic construct
SEQUENCE: 164
MDMRVPAQLL GLLLLWLRGA RCAPTSSSTK KTQLQLEHLL LDLQMILNGI NNYKNPKLTR   60
MLTFKFYMPK KATELKHLQC LEEELKPLEE VLNLAQSKNF HLRPRDLISN INIVLELKG   120
SETTFMCEYA DETATIVEFL NRWITFCQSI ISTLTHHHHH H                     161

SEQ ID NO: 165              moltype = AA   length = 708
FEATURE                     Location/Qualifiers
source                      1..708
                            mol_type = protein
                            organism = synthetic construct
SEQUENCE: 165
MDMRVPAQLL GLLLLWLRGA RCAPTSSSTK KTQLQLEHLL LDLQMILNGI NNYKNPKLTR   60
MLTFKFYMPK KATELKHLQC LEEELKPLEE VLNLAQSKNF HLRPRDLISN INIVLELKG   120
SETTFMCEYA DETATIVEFL NRWITFCQSI ISTLTSGGPG PAGMKGLPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSGGGGS GGGGSGGGGS  300
GGGGSGGGGS GGGGSSGGPG PAGMKGLPGS EVQLVESGGG LVQPGGSLRL SCAASGFTFS  360
SYTLAWVRQA PGKGLEWVAA IDSSSYTYSP DTVRGRFTIS RDNAKNSLYL QMNSLRAEDT  420
AVYYCARDSN WDALDYWGQG TTVTVSSGGG GSGGGGSGGG GSDIQMTQSP SSLSASVGDR  480
```

-continued

```
VTITCKASQN VGTNVGWYQQ KPGKAPKALI YSASFRYSGV PSRFSGSGSG TDFTLTISSL  540
QPEDFATYYC QQYYTYPYTF GGGTKVEIKG GGGSGGGSG  GGGSQVQLQE SGGGLVQAGG  600
SLRLSCAASG RIFSIDIMSW YRQAPGKQRE LVARITRGGT ISYDDSVKGR FTISRDNAKN  660
TVYLQMNSLK PEDTGVYYCN ALYGTDYWGK GTQVTVSSHH HHHHEPEA               708

SEQ ID NO: 166          moltype = AA  length = 708
FEATURE                 Location/Qualifiers
source                  1..708
                        mol_type = protein
                        organism = synthetic construct
SEQUENCE: 166
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGGGG SGGGGSGGGG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSGGGGSG  420
GGGSGGGGSG GGGSGGGGSG GGGSSGGPGP AGMKGLPGSE VQLVESGGGL VQPGGSLRLS  480
CAASGFTFSS YTLAWVRQAP GKGLEWVAAI DSSSYTYSPD TVRGRFTISR DNAKNSLYLQ  540
MNSLRAEDTA VYYCARDSNW DALDYWGQGT TVTVSSGGGG SGGGGSGGGG SDIQMTQSPS  600
SLSASVGDRV TITCKASQNV GTNVGWYQQK PGKAPKALIY SASFRYSGVP SRFSGSGSGT  660
DFTLTISSLQ PEDFATYYCQ QYYTYPYTFG GGTKVEIKHH HHHHEPEA               708

SEQ ID NO: 167          moltype = AA  length = 708
FEATURE                 Location/Qualifiers
source                  1..708
                        mol_type = protein
                        organism = synthetic construct
SEQUENCE: 167
MDMRVPAQLL GLLLLWLRGA RCQVQLQESG GGLVQAGGSL RLSCAASGRI FSIDIMSWYR  60
QAPGKQRELV ARITRGGTIS YDDSVKGRFT ISRDNAKNTV YLQMNSLKPE DTGVYYCNAL  120
YGTDYWGKGT QVTVSSGGGP GPAGMKGLPG SAPTSSSTKK TQLQLEHLLL DLQMILNGIN  180
NYKNPKLTRM LTFKFYMPKK ATELKHLQCL EEELKPLEEV LNLAQSKNFH LRPRDLISNI  240
NVIVLELKGS ETTFMCEYAD ETATIVEFLN RWITFCQSII STLTSGGPGP AGMKGLPGSE  300
VQLVESGGGL VQPGNSLRLS CAASGFTFSK FGMSWVRQAP GKGLEWVSSI SGSGRDTLYA  360
ESVKGRFTIS RDNAKTTLYL QMNSLRPEDT AVYYCTIGGS LSVSSQGTLV TVSSGGGGSG  420
GGGSGGGGSG GGGSGGPGP  AGMKGLPGSE VQLVESGGGL VQPGGSLRLS             480
CAASGFTFSS YTLAWVRQAP GKGLEWVAAI DSSSYTYSPD TVRGRFTISR DNAKNSLYLQ  540
MNSLRAEDTA VYYCARDSNW DALDYWGQGT TVTVSSGGGG SGGGGSGGGG SDIQMTQSPS  600
SLSASVGDRV TITCKASQNV GTNVGWYQQK PGKAPKALIY SASFRYSGVP SRFSGSGSGT  660
DFTLTISSLQ PEDFATYYCQ QYYTYPYTFG GGTKVEIKHH HHHHEPEA               708

SEQ ID NO: 168          moltype = AA  length = 450
FEATURE                 Location/Qualifiers
source                  1..450
                        mol_type = protein
                        organism = synthetic construct
SEQUENCE: 168
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSCDLPQTHN LRNKRALTLL VQMRRLSPLS  180
CLKDRKDFGF PQEKVDAQQI KKAQAIPVLS ELTQQILNIF TSKDSSAAWN TTLLDSFCND  240
LHQQLNDLQG CLMQQVGVQE FPLTQEDALL AVRKYFHRIT VYLREKKHSP CAWEVVRAEV  300
WRALSSSANV SGGPGPAGMK GLPGSEVQLV ESGGGLVQPG NSLRLSCAAS GFTFSKFGMS  360
WVRQAPGKGL EWVSSISGSG RDTLYAESVK GRFTISRDNA KTTLYLQMNS LRPEDTAVYY  420
CTIGGSLSVS SQGTLVTVSS HHHHHHEPEA                                  450

SEQ ID NO: 169          moltype = AA  length = 198
FEATURE                 Location/Qualifiers
source                  1..198
                        mol_type = protein
                        organism = synthetic construct
SEQUENCE: 169
MDMRVPAQLL GLLLLWLRGA RCCDLPQTHN LRNKRALTLL VQMRRLSPLS CLKDRKDFGF  60
PQEKVDAQQI KKAQAIPVLS ELTQQILNIF TSKDSSAAWN TTLLDSFCND LHQQLNDLQG  120
CLMQQVGVQE FPLTQEDALL AVRKYFHRIT VYLREKKHSP CAWEVVRAEV WRALSSSANV  180
LGRLREEKHH HHHHEPEA                                               198

SEQ ID NO: 170          moltype = AA  length = 328
FEATURE                 Location/Qualifiers
source                  1..328
                        mol_type = protein
                        organism = synthetic construct
SEQUENCE: 170
MDMRVPAQLL GLLLLWLRGA RCEVQLVESG GGLVQPGNSL RLSCAASGFT FSKFGMSWVR  60
QAPGKGLEWV SSISGSGRDT LYAESVKGRF TISRDNAKTT LYLQMNSLRP EDTAVYYCTI  120
GGSLSVSSQG TLVTVSSSGG PGPAGMKGLP GSCDLPQTHN LRNKRALTLL VQMRRLSPLS  180
CLKDRKDFGF PQEKVDAQQI KKAQAIPVLS ELTQQILNIF TSKDSSAAWN TTLLDSFCND  240
```

```
LHQQLNDLQG CLMQQVGVQE FPLTQEDALL AVRKYFHRIT VYLREKKHSP CAWEVVRAEV    300
WRALSSSANV LGRLREEKHH HHHHEPEA                                       328

SEQ ID NO: 171          moltype = AA  length = 328
FEATURE                 Location/Qualifiers
source                  1..328
                        mol_type = protein
                        organism = synthetic construct
SEQUENCE: 171
MDMRVPAQLL GLLLLWLRGA RCCDLPQTHN LRNKRALTLL VQMRRLSPLS CLKDRKDFGF    60
PQEKVDAQQI KKAQAIPVLS ELTQQILNIF TSKDSSAAWN TTLLDSFCND LHQQLNDLQG    120
CLMQQVGVQE FPLTQEDALL AVRKYFHRIT VYLREKKHSP CAWEVVRAEV WRALSSSANV    180
LGRLREEKSG GPGPAGMKGL PGSEVQLVES GGGLVQPGNS LRLSCAASGF TFSKFGMSWV    240
RQAPGKGLEW VSSISGSGRD TLYAESVKGR FTISRDNAKT TLYLQMNSLR PEDTAVYYCT    300
IGGSLSVSSQ GTLVTVSSHH HHHHEPEA                                       328

SEQ ID NO: 172          moltype = AA  length = 1396
FEATURE                 Location/Qualifiers
source                  1..1396
                        mol_type = protein
                        organism = synthetic construct
SEQUENCE: 172
MDMRVPAQLL GLLLLWLRGA RCEAHKSEIA HRYNDLGEQH FKGLVLIAFS QYLQKCSYDE    60
HAKLVQEVTD FAKTCVADES AANCDKSLHT LFGDKLCAIP NLRENYGELA DCCTKQEPER    120
NECFLQHKDD NPSLPPFERP EAEAMCTSFK ENPTTFMGHY LHEVARRHPY FYAPELLYYA    180
EQYNEILTQC CAEADKESCL TPKLDGVKEK ALVSSVRQRM KCSSMQKFGE RAFKAWAVAR    240
LSQTFPNADF AEITKLATDL TKVNKECCHG DLLECADDRA ELAKYMCENQ ATISSKLQTC    300
CDKPLLKKAH CLSEVEHDTM PADLPAIAAD FVEDQEVCKN YAEAKDVFLG TFLYEYSRRH    360
PDYSVSLLLR LAKKYEATLE KCCAEANPPA CYGTVLAEFQ PLVEEPKNLV KTNCDLYEKL    420
GEYGFQNAIL VRYTQKAPQV STPTLVEAAR NLGRVGTKCC TLPEDQRLPC VEDYLSAILN    480
RVCLLHEKTP VSEHVTKCCS GSLVERRPCF SALTVDETYV PKEFKAETFT FHSDICTLPE    540
KEKQIKKQTA LAELVKHKPK ATAEQLKTVM DDFAQFLDTC CKAADKDTCF STEGPNLVTR    600
CKDALASGGP GPAGMKGLPG SCDLPQTHNL RNKRALTLLV QMRRLSPLSC LKDRKDFGFP    660
QEKVDAQQIK KAQAIPVLSE LTQQILNIFT SKDSSAAWNT TLLDSFCNDL HQQLNDLQGC    720
LMQQVGVQEF PLTQEDALLA VRKYFHRITV YLREKKHSPC AWEVVRAEVW RALSSSANVL    780
GRLREEKSGG PGPAGMKGLP GSEAHKSEIA HRYNDLGEQH FKGLVLIAFS QYLQKCSYDE    840
HAKLVQEVTD FAKTCVADES AANCDKSLHT LFGDKLCAIP NLRENYGELA DCCTKQEPER    900
NECFLQHKDD NPSLPPFERP EAEAMCTSFK ENPTTFMGHY LHEVARRHPY FYAPELLYYA    960
EQYNEILTQC CAEADKESCL TPKLDGVKEK ALVSSVRQRM KCSSMQKFGE RAFKAWAVAR    1020
LSQTFPNADF AEITKLATDL TKVNKECCHG DLLECADDRA ELAKYMCENQ ATISSKLQTC    1080
CDKPLLKKAH CLSEVEHDTM PADLPAIAAD FVEDQEVCKN YAEAKDVFLG TFLYEYSRRH    1140
PDYSVSLLLR LAKKYEATLE KCCAEANPPA CYGTVLAEFQ PLVEEPKNLV KTNCDLYEKL    1200
GEYGFQNAIL VRYTQKAPQV STPTLVEAAR NLGRVGTKCC TLPEDQRLPC VEDYLSAILN    1260
RVCLLHEKTP VSEHVTKCCS GSLVERRPCF SALTVDETYV PKEFKAETFT FHSDICTLPE    1320
KEKQIKKQTA LAELVKHKPK ATAEQLKTVM DDFAQFLDTC CKAADKDTCF STEGPNLVTR    1380
CKDALAHHHH HHEPEA                                                    1396

SEQ ID NO: 173          moltype = AA  length = 797
FEATURE                 Location/Qualifiers
source                  1..797
                        mol_type = protein
                        organism = synthetic construct
SEQUENCE: 173
MDMRVPAQLL GLLLLWLRGA RCEAHKSEIA HRYNDLGEQH FKGLVLIAFS QYLQKCSYDE    60
HAKLVQEVTD FAKTCVADES AANCDKSLHT LFGDKLCAIP NLRENYGELA DCCTKQEPER    120
NECFLQHKDD NPSLPPFERP EAEAMCTSFK ENPTTFMGHY LHEVARRHPY FYAPELLYYA    180
EQYNEILTQC CAEADKESCL TPKLDGVKEK ALVSSVRQRM KCSSMQKFGE RAFKAWAVAR    240
LSQTFPNADF AEITKLATDL TKVNKECCHG DLLECADDRA ELAKYMCENQ ATISSKLQTC    300
CDKPLLKKAH CLSEVEHDTM PADLPAIAAD FVEDQEVCKN YAEAKDVFLG TFLYEYSRRH    360
PDYSVSLLLR LAKKYEATLE KCCAEANPPA CYGTVLAEFQ PLVEEPKNLV KTNCDLYEKL    420
GEYGFQNAIL VRYTQKAPQV STPTLVEAAR NLGRVGTKCC TLPEDQRLPC VEDYLSAILN    480
RVCLLHEKTP VSEHVTKCCS GSLVERRPCF SALTVDETYV PKEFKAETFT FHSDICTLPE    540
KEKQIKKQTA LAELVKHKPK ATAEQLKTVM DDFAQFLDTC CKAADKDTCF STEGPNLVTR    600
CKDALASGGP GPAGMKGLPG SCDLPQTHNL RNKRALTLLV QMRRLSPLSC LKDRKDFGFP    660
QEKVDAQQIK KAQAIPVLSE LTQQILNIFT SKDSSAAWNT TLLDSFCNDL HQQLNDLQGC    720
LMQQVGVQEF PLTQEDALLA VRKYFHRITV YLREKKHSPC AWEVVRAEVW RALSSSANVL    780
GRLREEKHHH HHEPEA                                                    797

SEQ ID NO: 174          moltype = AA  length = 797
FEATURE                 Location/Qualifiers
source                  1..797
                        mol_type = protein
                        organism = synthetic construct
SEQUENCE: 174
MDMRVPAQLL GLLLLWLRGA RCCDLPQTHN LRNKRALTLL VQMRRLSPLS CLKDRKDFGF    60
PQEKVDAQQI KKAQAIPVLS ELTQQILNIF TSKDSSAAWN TTLLDSFCND LHQQLNDLQG    120
CLMQQVGVQE FPLTQEDALL AVRKYFHRIT VYLREKKHSP CAWEVVRAEV WRALSSSANV    180
LGRLREEKSG GPGPAGMKGL PGSEAHKSEI AHRYNDLGEQ HFKGLVLIAF SQYLQKCSYD    240
EHAKLVQEVT DFAKTCVADE SAANCDKSLH TLFGDKLCAI PNLRENYGEL ADCCTKQEPE    300
```

-continued

```
RNECFLQHKD DNPSLPPFER PEAEAMCTSF KENPTTFMGH YLHEVARRHP YFYAPELLYY   360
AEQYNEILTQ CCAEADKESC LTPKLDGVKE KALVSSVRQR MKCSSMQKFG ERAFKAWAVA   420
RLSQTFPNAD FAEITKLATD LTKVNKECCH GDLLECADDR AELAKYMCEN QATISSKLQT   480
CCDKPLLKKA HCLSEVEHDT MPADLPAIAA DFVEDQEVCK NYAEAKDVFL GTFLYEYSRR   540
HPDYSVSLLL RLAKKYEATL EKCCAEANPP ACYGTVLAEF QPLVEEPKNL VKTNCDLYEK   600
LGEYGFQNAI LVRYTQKAPQ VSTPTLVEAA RNLGRVGTKC CTLPEDQRLP CVEDYLSAIL   660
NRVCLLHEKT PVSEHVTKCC SGSLVERRPC FSALTVDETY VPKEFKAETF TFHSDICTLP   720
EKEKQIKKQT ALAELVKHKP KATAEQLKTV MDDFAQFLDT CCKAADKDTC FSTEGPNLVT   780
RCKDALAHHH HHHEPEA                                                  797
```

SEQ ID NO: 175         moltype = AA   length = 587
FEATURE                Location/Qualifiers
source                 1..587
                       mol_type = protein
                       organism = synthetic construct
SEQUENCE: 175

```
MDMRVPAQLL GLLLLWLRGA RCQVQLQESG GGLAQAGGSL SLSCAASGFT VSNSVMAWYR   60
QTPGKQREFV AIINSVGSTN YADSVKGRFT ISRDNAKNTV YLQMNNLKPE DTAVYVCNRN   120
FDRIYWGQGT QVTVSSGGGG SGGGGSGGGG SEVQLVESGG GLVQPGNSLR LSCAASGFTF   180
SKFGMSWVRQ APGKGLEWVS SISGSGRDTL YAESVKGRFT ISRDNAKTTL YLQMNSLRPE   240
DTAVYYCTIG GSLSVSSQGT LVTVSSSGGP GPAGMKGLPG SCDLPQTHNL RNKRALTLLV   300
QMRRLSPLSC LKDRKDFGFP QEKVDAQQIK KAQAIPVLSE LTQQILNIFT SKDSSAAWNT   360
TLLDSFCNDL HQQLNDLQGC LMQQVGVQEF PLTQEDALLA VRKYFHRITV YLREKKHSPC   420
AWEVVRAEVW RALSSSANVL GRLREEKSGG PGPAGMKGLP GSEVQLVESG GGLVQPGNSL   480
RLSCAASGFT FSKFGMSWVR QAPGKGLEWV SSISGSGRDT LYAESVKGRF TISRDNAKTT   540
LYLQMNSLRP EDTAVYYCTI GGSLSVSSQG TLVTVSSHHH HHHEPEA                 587
```

SEQ ID NO: 176         moltype = AA   length = 587
FEATURE                Location/Qualifiers
source                 1..587
                       mol_type = protein
                       organism = synthetic construct
SEQUENCE: 176

```
MDMRVPAQLL GLLLLWLRGA RCEVQLVESG GGLVQPGNSL RLSCAASGFT FSKFGMSWVR   60
QAPGKGLEWV SSISGSGRDT LYAESVKGRF TISRDNAKTT LYLQMNSLRP EDTAVYYCTI   120
GGSLSVSSQG TLVTVSSSGG PGPAGMKGLP GSCDLPQTHN LRNKRALTLL VQMRRLSPLS   180
CLKDRKDFGF PQEKVDAQQI KKAQAIPVLS ELTQQILNIF TSKDSSAAWN TTLLDSFCND   240
LHQQLNDLQG CLMQQVGVQE FPLTQEDALL AVRKYFHRIT VYLREKKHSP CAWEVVRAEV   300
WRALSSSANV LGRLREEKSG GPGPAGMKGL PGSEVQLVES GGGLVQPGNS LRLSCAASGF   360
TFSKFGMSWV RQAPGKGLEW VSSISGSGRD TLYAESVKGR FTISRDNAKT TLYLQMNSLR   420
PEDTAVYYCT IGGSLSVSSQ GTLVTVSSGG GGSGGGGSGG GGSQVQLQES GGGLAQAGGS   480
LSLSCAASGF TVSNSVMAWY RQTPGKQREF VAIINSVGST NYADSVKGRF TISRDNAKNT   540
VYLQMNNLKP EDTAVYVCNR NFDRIYWGQG TQVTVSSHHH HHHEPEA                 587
```

SEQ ID NO: 177         moltype = AA   length = 458
FEATURE                Location/Qualifiers
source                 1..458
                       mol_type = protein
                       organism = synthetic construct
SEQUENCE: 177

```
MDMRVPAQLL GLLLLWLRGA RCEVQLVESG GGLVQPGNSL RLSCAASGFT FSKFGMSWVR   60
QAPGKGLEWV SSISGSGRDT LYAESVKGRF TISRDNAKTT LYLQMNSLRP EDTAVYYCTI   120
GGSLSVSSQG TLVTVSSGGG GSGGGGSGGG GSCDLPQTHN LRNKRALTLL VQMRRLSPLS   180
CLKDRKDFGF PQEKVDAQQI KKAQAIPVLS ELTQQILNIF TSKDSSAAWN TTLLDSFCND   240
LHQQLNDLQG CLMQQVGVQE FPLTQEDALL AVRKYFHRIT VYLREKKHSP CAWEVVRAEV   300
WRALSSSANV LGRLREEKGG GGSGGGGSGG GGSEVQLVES GGGLVQPGNS LRLSCAASGF   360
TFSKFGMSWV RQAPGKGLEW VSSISGSGRD TLYAESVKGR FTISRDNAKT TLYLQMNSLR   420
PEDTAVYYCT IGGSLSVSSQ GTLVTVSSHH HHHHEPEA                           458
```

SEQ ID NO: 178         moltype = AA   length = 579
FEATURE                Location/Qualifiers
source                 1..579
                       mol_type = protein
                       organism = synthetic construct
SEQUENCE: 178

```
MDMRVPAQLL GLLLLWLRGA RCAPTSSSTK KTQLQLEHLL LDLQMILNGI NNYKNPKLTR   60
MLTFKFYMPK KATELKHLQC LEEELKPLEE VLNLAQSKNF HLRPRDLISN INVIVLELKG   120
SETTFMCEYA DETATIVEFL NRWITFCQSI ISTLTSGGPG PAGLYAQPGS EVQLVESGGG   180
LVQPGNSLRL SCAASGFTFS KFGMSWVRQA PGKGLEWVSS ISGSGRDTLY AESVKGRFTI   240
SRDNAKTTLY LQMNSLRPED TAVYYCTIGG SLSVSSQGTL VTVSSGGGGS GGGGSGGGGS   300
GGGGSGGGGS GGGGSSGGPG PAGLYAQPGS EVQLVESGGG LVQPGGSLRL SCAASGFTFS   360
SYTLAWVRQA PGKGLEWVAA IDSSSYTYSP DTVRGRFTIS RDNAKNSLYL QMNSLRAEDT   420
AVYYCARDSN WDALDYWGQG TTVTVSSGGG GSGGGGSGGG GSDIQMTQSP SSLSASVGDR   480
VTITCKASQN VGTNVGWYQQ KPGKAPKALI YSASFRYSGV PSRFSGSGSG TDFTLTISSL   540
QPEDFATYYC QQYYTYPYTF GGGTKVEIKH HHHHHEPEA                          579
```

SEQ ID NO: 179         moltype = AA   length = 579
FEATURE                Location/Qualifiers
source                 1..579

```
                              mol_type = protein
                              organism = synthetic construct
SEQUENCE: 179
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPP GGPAGIGPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSGGGGS GGGGSGGGGS  300
GGGGSGGGGS GGGGSSGGPP GGPAGIGPGS EVQLVESGGG LVQPGGSLRL SCAASGFTFS  360
SYTLAWVRQA PGKGLEWVAA IDSSSYTYSP DTVRGRFTIS RDNAKNSLYL QMNSLRAEDT  420
AVYYCARDSN WDALDYWGQG TTVTVSSGGG GSGGGGSGGG GSDIQMTQSP SSLSASVGDR  480
VTITCKASQN VGTNVGWYQQ KPGKAPKALI YSASFRYSGV PSRFSGSGSG TDFTLTISSL  540
QPEDFATYYC QQYYTYPYTF GGGTKVEIKH HHHHHEPEA                        579

SEQ ID NO: 180          moltype = AA  length = 579
FEATURE                 Location/Qualifiers
source                  1..579
                        mol_type = protein
                        organism = synthetic construct
SEQUENCE: 180
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPA LFKSSFPPGS EVQLVESGGG  180
LVQPGNSLRL SCAASGFTFS KFGMSWVRQA PGKGLEWVSS ISGSGRDTLY AESVKGRFTI  240
SRDNAKTTLY LQMNSLRPED TAVYYCTIGG SLSVSSQGTL VTVSSGGGGS GGGGSGGGGS  300
GGGGSGGGGS GGGGSSGGPA LFKSSFPPGS EVQLVESGGG LVQPGGSLRL SCAASGFTFS  360
SYTLAWVRQA PGKGLEWVAA IDSSSYTYSP DTVRGRFTIS RDNAKNSLYL QMNSLRAEDT  420
AVYYCARDSN WDALDYWGQG TTVTVSSGGG GSGGGGSGGG GSDIQMTQSP SSLSASVGDR  480
VTITCKASQN VGTNVGWYQQ KPGKAPKALI YSASFRYSGV PSRFSGSGSG TDFTLTISSL  540
QPEDFATYYC QQYYTYPYTF GGGTKVEIKH HHHHHEPEA                        579

SEQ ID NO: 181          moltype = AA  length = 581
FEATURE                 Location/Qualifiers
source                  1..581
                        mol_type = protein
                        organism = synthetic construct
SEQUENCE: 181
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPP LAQKLKSSPG SEVQLVESGG  180
GLVQPGNSLR LSCAASGFTF SKFGMSWVRQ APGKGLEWVS SISGSGRDTL YAESVKGRFT  240
ISRDNAKTTL YLQMNSLRPE DTAVYYCTIG GSLSVSSQGT LVTVSSGGGG SGGGGSGGGG  300
SGGGGSGGGG SGGGGSSGGP PLAQKLKSSP GSEVQLVESG GGLVQPGGSL RLSCAASGFT  360
FSSYTLAWVR QAPGKGLEWV AAIDSSSYTY SPDTVRGRFT ISRDNAKNSL YLQMNSLRAE  420
DTAVYYCARD SNWDALDYWG QGTTVTVSSG GGGSGGGGSG GGGSDIQMTQ SPSSLSASVG  480
DRVTITCKAS QNVGTNVGWY QQKPGKAPKA LIYSASFRYS GVPSRFSGSG SGTDFTLTIS  540
SLQPEDFATY YCQQYYTYPY TFGGGTKVEI KHHHHHHEPE A                     581

SEQ ID NO: 182          moltype = AA  length = 613
FEATURE                 Location/Qualifiers
source                  1..613
                        mol_type = protein
                        organism = synthetic construct
SEQUENCE: 182
MDMRVPAQLL GLLLLWLRGA RCAPTSSSTK KTQLQLEHLL LDLQMILNGI NNYKNPKLTR  60
MLTFKFYMPK KATELKHLQC LEEELKPLEE VLNLAQSKNF HLRPRDLISN INVIVLELKG  120
SETTFMCEYA DETATIVEFL NRWITFCQSI ISTLTSGGPP GGPAGIGALF KSSFPPLAQK  180
LKSSPGSEVQ LVESGGGLVQ PGNSLRLSCA ASGFTFSKFG MSWVRQAPGK GLEWVSSISG  240
SGRDTLYAES VKGRFTISRD NAKTTLYLQM NSLRPEDTAV YYCTIGGSLS VSSQGTLVTV  300
SSGGGGSGGG GSGGGGSGGG GSGGGGSGGG GSSGGPPGGP AGIGALFKSS FPPLAQKLKS  360
SPGSEVQLVE SGGGLVQPGG SLRLSCAASG FTFSSYTLAW VRQAPGKGLE WVAAIDSSSY  420
TYSPDTVRGR FTISRDNAKN SLYLQMNSLR AEDTAVYYCA RDSNWDALDY WGQGTTVTVS  480
SGGGGSGGGG SGGGGSDIQM TQSPSSLSAS VGDRVTITCK ASQNVGTNVG WYQQKPGKAP  540
KALIYSASFR YSGVPSRFSG SGSGTDFTLT ISSLQPEDFA TYYCQQYYTY PYTFGGGTKV  600
EIKHHHHHHE PEA                                                    613

SEQ ID NO: 183          moltype =    length =
SEQUENCE: 183
000

SEQ ID NO: 184          moltype =    length =
SEQUENCE: 184
000

SEQ ID NO: 185          moltype =    length =
SEQUENCE: 185
000

SEQ ID NO: 186          moltype =    length =
```

-continued

```
SEQUENCE: 186
000

SEQ ID NO: 187          moltype =   length =
SEQUENCE: 187
000

SEQ ID NO: 188          moltype =   length =
SEQUENCE: 188
000

SEQ ID NO: 189          moltype =   length =
SEQUENCE: 189
000

SEQ ID NO: 190          moltype =   length =
SEQUENCE: 190
000

SEQ ID NO: 191          moltype = AA   length = 267
FEATURE                 Location/Qualifiers
source                  1..267
                        mol_type = protein
                        organism = synthetic construct
SEQUENCE: 191
MDMRVPAQLL GLLLLWLRGA RCEVQLVESG GGLVQPGGSL RLSCAASGFT FSSYTLAWVR   60
QAPGKGLEWV AAIDSSSYTY SPDTVRGRFT ISRDNAKNSL YLQMNSLRAE DTAVYYCARD  120
SNWDALDYWG QGTTVTVSSG GGGSGGGGSG GGGSDIQMTQ SPSSLSASVG DRVTITCKAS  180
QNVGTNVGWY QQKPGKAPKA LIYSASFRYS GVPSRFSGSG SGTDFTLTIS SLQPEDFATY  240
YCQQYYTYPY TFGGGTKVEI KHHHHHH                                      267

SEQ ID NO: 192          moltype = AA   length = 269
FEATURE                 Location/Qualifiers
source                  1..269
                        mol_type = protein
                        organism = synthetic construct
SEQUENCE: 192
MDMRVPAQLL GLLLLWLRGA RCQSVLTQPP SVSGAPGQRV TISCSGSRSN IGSNTVKWYQ   60
QLPGTAPKLL IYYNDQRPSG VPDRFSGSKS GTSASLAITG LQAEDEADYY CQSYDRYTHP  120
ALLFGTGTKV TVLGGGGSGG GGSGGGGSQV QLVESGGGVV QPGRSLRLSC AASGFTFSSY  180
GMHWVRQAPG KGLEWVAFIR YDGSNKYYAD SVKGRFTISR DNSKNTLYLQ MNSLRAEDTA  240
VYYCKTHGSH DNWGQGTMVT VSSHHHHHH                                    269

SEQ ID NO: 193          moltype = AA   length = 171
FEATURE                 Location/Qualifiers
source                  1..171
                        mol_type = protein
                        organism = synthetic construct
SEQUENCE: 193
CDLPQTHSLG SRRTLMLLAQ MRRISLFSCL KDRHDFGFPQ EEFGNQFQKA ETIPVLHEMI   60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKEHHHHH H           171

SEQ ID NO: 194          moltype = AA   length = 520
FEATURE                 Location/Qualifiers
source                  1..520
                        mol_type = protein
                        organism = synthetic construct
SEQUENCE: 194
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRVIPVSGPA RCLSQSRNLL KTTDDMVKTA REKLKHYSCT  360
AEDIDHEDIT RDQTSTLKTC LPLELHKNES CLATRETSST TRGSCLPPQK TSLMMTLCLG  420
SIYEDLKMYQ TEFQAINAAL QNHNHQQIIL DKGMLVAIDE LMQSLNHNGE TLRQKPPVGE  480
ADPYRVKMKL CILLHAFSTR VVTINRVMGY LSSAHHHHHH                        520

SEQ ID NO: 195          moltype = AA   length = 141
FEATURE                 Location/Qualifiers
source                  1..141
                        mol_type = protein
                        organism = synthetic construct
SEQUENCE: 195
QVQLQESGGG LVQAGGSLRL SCAASGRTFS SVYDMGWFRQ APGKDREFVA RITESARNTR   60
YADSVRGRFT ISRDNAKNTV YLQMNNLELE DAAVYYCAAD PQTVVVGTPD YWGQGTQVTV  120
SSAAAYPYDV PDYGSHHHHH H                                            141
```

```
SEQ ID NO: 196          moltype = AA  length = 247
FEATURE                 Location/Qualifiers
source                  1..247
                        mol_type = protein
                        organism = synthetic construct
SEQUENCE: 196
QSVLTQPPSV SGAPGQRVTI SCTGSSSNIG SNTVKWYQQL PGTAPKLLIY GNDQRPSGVP  60
DRFSGSKSGT SASLAITGLQ AEDEADYYCQ SYDRYTHPAY VFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 197          moltype = AA  length = 247
FEATURE                 Location/Qualifiers
source                  1..247
                        mol_type = protein
                        organism = synthetic construct
SEQUENCE: 197
QSVLTQPPSV SGAPGQRVTI SCTGSSSNIG SNTVKWYQQL PGTAPKLLIY YNDQRPSGVP  60
DRFSGSKSGT SASLAITGLQ AEDEADYYCQ SYDRYTHPAY VFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 198          moltype = AA  length = 247
FEATURE                 Location/Qualifiers
source                  1..247
                        mol_type = protein
                        organism = synthetic construct
SEQUENCE: 198
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYAM HWVRQAPGKG LEWVAVISYD  180
GSNKYYADSV KGRFTISRDN SKNTLYLQMN SLRAEDTAVY YCARHGSHDN WGQGTMVTVS  240
SHHHHHH                                                            247

SEQ ID NO: 199          moltype = AA  length = 247
FEATURE                 Location/Qualifiers
source                  1..247
                        mol_type = protein
                        organism = synthetic construct
SEQUENCE: 199
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYE  180
GSNKYYADSV KGRFTISRDN SKNTLYLQMN SLRAEDTAVY YCKTHGSHDN WGQGTMVTVS  240
SHHHHHH                                                            247

SEQ ID NO: 200          moltype = AA  length = 247
FEATURE                 Location/Qualifiers
source                  1..247
                        mol_type = protein
                        organism = synthetic construct
SEQUENCE: 200
QSVLTQPPSV SGAPGQRVTI SCSGSRSNIG SNTVKWYQQL PGTAPKLLIY YNDQRPSGVP  60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYAESV KGRFTISRDN SKNTLYLQMN SLRAEDTAVY YCKTHGSHDN WGQGTMVTVS  240
SHHHHHH                                                            247

SEQ ID NO: 201          moltype = AA  length = 247
FEATURE                 Location/Qualifiers
source                  1..247
                        mol_type = protein
                        organism = synthetic construct
SEQUENCE: 201
QSVLTQPPSV SGAPGQRVTI SCSGSRSNIG SQTVKWYQQL PGTAPKLLIY YNDQRPSGVP  60
DRFSGSKSGT SASLAITGLQ AEDEADYYCQ SYERYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 202          moltype = AA  length = 247
FEATURE                 Location/Qualifiers
source                  1..247
                        mol_type = protein
                        organism = synthetic construct
SEQUENCE: 202
QSVLTQPPSV SGAPGQRVTI SCSGSRSNIG SQTVKWYQQL PGTAPKLLIY YNDQRPSGVP  60
```

-continued

```
DRFSGSKSGT SASLAITGLQ AEDEADYYCQ SYSRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 203               moltype = AA   length = 247
FEATURE                      Location/Qualifiers
source                       1..247
                             mol_type = protein
                             organism = synthetic construct
SEQUENCE: 203
QSVLTQPPSV SGAPGQRVTI SCSGSESNIG SNTVKWYQQL PGTAPKLLIY YNDQRPSGVP   60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 204               moltype = AA   length = 247
FEATURE                      Location/Qualifiers
source                       1..247
                             mol_type = protein
                             organism = synthetic construct
SEQUENCE: 204
QSVLTQPPSV SGAPGQRVTI SCSGSSSNIG SNTVKWYQQL PGTAPKLLIY YNDQRPSGVP   60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 205               moltype = AA   length = 247
FEATURE                      Location/Qualifiers
source                       1..247
                             mol_type = protein
                             organism = synthetic construct
SEQUENCE: 205
QSVLTQPPSV SGAPGQRVTI SCSGSRSNIG DNTVKWYQQL PGTAPKLLIY YNDQRPSGVP   60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 206               moltype = AA   length = 247
FEATURE                      Location/Qualifiers
source                       1..247
                             mol_type = protein
                             organism = synthetic construct
SEQUENCE: 206
QSVLTQPPSV SGAPGQRVTI SCSGSRSNIG ENTVKWYQQL PGTAPKLLIY YNDQRPSGVP   60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 207               moltype = AA   length = 247
FEATURE                      Location/Qualifiers
source                       1..247
                             mol_type = protein
                             organism = synthetic construct
SEQUENCE: 207
QSVLTQPPSV SGAPGQRVTI SCSGSRSNIG SDTVKWYQQL PGTAPKLLIY YNDQRPSGVP   60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 208               moltype = AA   length = 247
FEATURE                      Location/Qualifiers
source                       1..247
                             mol_type = protein
                             organism = synthetic construct
SEQUENCE: 208
QSVLTQPPSV SGAPGQRVTI SCSGSRSNIG SETVKWYQQL PGTAPKLLIY YNDQRPSGVP   60
DRFSGSKSGT SASLAITGLQ AEDEADYYCQ SYDRYTHPAL LFGTGTKVTV LGGGGSGGGG   120
SGGGGSQVQL VESGGGVVQP GRSLRLSCAA SGFTFSSYGM HWVRQAPGKG LEWVAFIRYD   180
GSNKYYADSV KGRFTISRDN SKNTLYLQMN SLRAEDTAVY YCKTHGSHDN WGQGTMVTVS   240
SHHHHHH                                                            247

SEQ ID NO: 209               moltype = AA   length = 247
FEATURE                      Location/Qualifiers
```

```
source                    1..247
                          mol_type = protein
                          organism = synthetic construct
SEQUENCE: 209
QSVLTQPPSV SGAPGQRVTI SCSGSRSNIG SNDVKWYQQL PGTAPKLLIY YNDQRPSGVP   60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 210            moltype = AA  length = 247
FEATURE                   Location/Qualifiers
source                    1..247
                          mol_type = protein
                          organism = synthetic construct
SEQUENCE: 210
QSVLTQPPSV SGAPGQRVTI SCSGSRSNIG SNTVDWYQQL PGTAPKLLIY YNDQRPSGVP   60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 211            moltype = AA  length = 247
FEATURE                   Location/Qualifiers
source                    1..247
                          mol_type = protein
                          organism = synthetic construct
SEQUENCE: 211
QSVLTQPPSV SGAPGQRVTI SCSGSRSNIG SNTVEWYQQL PGTAPKLLIY YNDQRPSGVP   60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 212            moltype = AA  length = 247
FEATURE                   Location/Qualifiers
source                    1..247
                          mol_type = protein
                          organism = synthetic construct
SEQUENCE: 212
QSVLTQPPSV SGAPGQRVTI SCSGSRSNIG SNTVKWYQQL PGTAPKLLIY YNDQDPSGVP   60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 213            moltype = AA  length = 247
FEATURE                   Location/Qualifiers
source                    1..247
                          mol_type = protein
                          organism = synthetic construct
SEQUENCE: 213
QSVLTQPPSV SGAPGQRVTI SCSGSRSNIG SNTVKWYQQL PGTAPKLLIY YNDQEPSGVP   60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 214            moltype = AA  length = 247
FEATURE                   Location/Qualifiers
source                    1..247
                          mol_type = protein
                          organism = synthetic construct
SEQUENCE: 214
QSVLTQPPSV SGAPGQRVTI SCSGSRSNIG SNTVKWYQQL PGTAPKLLIY YNDQRPDGVP   60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 215            moltype = AA  length = 247
FEATURE                   Location/Qualifiers
source                    1..247
                          mol_type = protein
                          organism = synthetic construct
SEQUENCE: 215
QSVLTQPPSV SGAPGQRVTI SCSGSRSNIG SNTVKWYQQL PGTAPKLLIY YNDQRPSGVP   60
DRFSGSKSGT SASLAITGLQ AEDEADYYCQ SYDEYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
```

```
GSNKYYADSV KGRFTISRDN SKNTLYLQMN SLRAEDTAVY YCKTHGSHDN WGQGTMVTVS  240
SHHHHHH                                                            247

SEQ ID NO: 216          moltype = AA  length = 247
FEATURE                 Location/Qualifiers
source                  1..247
                        mol_type = protein
                        organism = synthetic construct
SEQUENCE: 216
QSVLTQPPSV SGAPGQRVTI SCSGSRSNIG SNTVKWYQQL PGTAPKLLIY YNDQRPSGVP   60
DRFSGSKSGT SASLAITGLQ AEDEADYYCQ SYDRYTDPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 217          moltype = AA  length = 247
FEATURE                 Location/Qualifiers
source                  1..247
                        mol_type = protein
                        organism = synthetic construct
SEQUENCE: 217
QSVLTQPPSV SGAPGQRVTI SCSGSESNIG SNTVKWYQQL PGTAPKLLIY YNDQEPSGVP   60
DRFSGSKSGT SASLAITGLQ AEDEADYYCQ SYDEYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 218          moltype = AA  length = 247
FEATURE                 Location/Qualifiers
source                  1..247
                        mol_type = protein
                        organism = synthetic construct
SEQUENCE: 218
QSVLTQPPSV SGAPGQRVTI SCSGSESNIG SNDVKWYQQL PGTAPKLLIY YNDQRPSGVP   60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 219          moltype = AA  length = 247
FEATURE                 Location/Qualifiers
source                  1..247
                        mol_type = protein
                        organism = synthetic construct
SEQUENCE: 219
QSVLTQPPSV SGAPGQRVTI SCSGSRSNIG SNTVKWYQQL PGTAPKLLIY YNDQRPSGVP   60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFESYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 220          moltype = AA  length = 247
FEATURE                 Location/Qualifiers
source                  1..247
                        mol_type = protein
                        organism = synthetic construct
SEQUENCE: 220
QSVLTQPPSV SGAPGQRVTI SCSGSRSNIG SNTVKWYQQL PGTAPKLLIY YNDQRPSGVP   60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSEYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 221          moltype = AA  length = 247
FEATURE                 Location/Qualifiers
source                  1..247
                        mol_type = protein
                        organism = synthetic construct
SEQUENCE: 221
QSVLTQPPSV SGAPGQRVTI SCSGSRSNIG SNTVKWYQQL PGTAPKLLIY YNDQRPSGVP   60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSDYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 222          moltype = AA  length = 247
FEATURE                 Location/Qualifiers
source                  1..247
                        mol_type = protein
```

-continued

```
                              organism = synthetic construct
SEQUENCE: 222
QSVLTQPPSV SGAPGQRVTI SCSGSRSNIG SNTVKWYQQL PGTAPKLLIY YNDQRPSGVP     60
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIEYD    180
GSNKYYADSV KGRFTISRDN SKNTLYLQMN SLRAEDTAVY YCKTHGSHDN WGQGTMVTVS    240
SHHHHHH                                                             247

SEQ ID NO: 223            moltype = AA  length = 247
FEATURE                   Location/Qualifiers
source                    1..247
                          mol_type = protein
                          organism = synthetic construct
SEQUENCE: 223
QSVLTQPPSV SGAPGQRVTI SCSGSRSNIG SNTVKWYQQL PGTAPKLLIY YNDQRPSGVP     60
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIDYD    180
GSNKYYADSV KGRFTISRDN SKNTLYLQMN SLRAEDTAVY YCKTHGSHDN WGQGTMVTVS    240
SHHHHHH                                                             247

SEQ ID NO: 224            moltype = AA  length = 247
FEATURE                   Location/Qualifiers
source                    1..247
                          mol_type = protein
                          organism = synthetic construct
SEQUENCE: 224
QSVLTQPPSV SGAPGQRVTI SCSGSRSNIG SNTVKWYQQL PGTAPKLLIY YNDQRPSGVP     60
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIRYD    180
GSNDYYADSV KGRFTISRDN SKNTLYLQMN SLRAEDTAVY YCKTHGSHDN WGQGTMVTVS    240
SHHHHHH                                                             247

SEQ ID NO: 225            moltype = AA  length = 247
FEATURE                   Location/Qualifiers
source                    1..247
                          mol_type = protein
                          organism = synthetic construct
SEQUENCE: 225
QSVLTQPPSV SGAPGQRVTI SCSGSRSNIG SNTVKWYQQL PGTAPKLLIY YNDQRPSGVP     60
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIRYD    180
GSNEYYADSV KGRFTISRDN SKNTLYLQMN SLRAEDTAVY YCKTHGSHDN WGQGTMVTVS    240
SHHHHHH                                                             247

SEQ ID NO: 226            moltype = AA  length = 247
FEATURE                   Location/Qualifiers
source                    1..247
                          mol_type = protein
                          organism = synthetic construct
SEQUENCE: 226
QSVLTQPPSV SGAPGQRVTI SCSGSRSNIG SNTVKWYQQL PGTAPKLLIY YNDQRPSGVP     60
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIRYD    180
GSNKYYADSV EGRFTISRDN SKNTLYLQMN SLRAEDTAVY YCKTHGSHDN WGQGTMVTVS    240
SHHHHHH                                                             247

SEQ ID NO: 227            moltype = AA  length = 247
FEATURE                   Location/Qualifiers
source                    1..247
                          mol_type = protein
                          organism = synthetic construct
SEQUENCE: 227
QSVLTQPPSV SGAPGQRVTI SCSGSRSNIG SNTVKWYQQL PGTAPKLLIY YNDQRPSGVP     60
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIRYD    180
GSNKYYADSV KGRFTISRDN SKNTLYLQMN SLRAEDTAVY YCKTHGSEDN WGQGTMVTVS    240
SHHHHHH                                                             247

SEQ ID NO: 228            moltype = AA  length = 247
FEATURE                   Location/Qualifiers
source                    1..247
                          mol_type = protein
                          organism = synthetic construct
SEQUENCE: 228
QSVLTQPPSV SGAPGQRVTI SCSGSRSNIG SNTVKWYQQL PGTAPKLLIY YNDQRPSGVP     60
DRFSGSKSGT SASLAITGLQ AEDEADYYCQ SYDRYTHPAL LFGTGTKVTV LGGGGSGGGG    120
SGGGGSQVQL VESGGGVVQP GRSLRLSCAA SGFTFSSYGM HWVRQAPGKG LEWVAFIEYD    180
GSNKYYADSV EGRFTISRDN SKNTLYLQMN SLRAEDTAVY YCKTHGSHDN WGQGTMVTVS    240
SHHHHHH                                                             247
```

-continued

```
SEQ ID NO: 229          moltype = AA  length = 247
FEATURE                 Location/Qualifiers
source                  1..247
                        mol_type = protein
                        organism = synthetic construct
SEQUENCE: 229
QSVLTQPPSV SGAPGQRVTI SCSGSRSNIG SNTVKWYQQL PGTAPKLLIY YNDQRPSGVP   60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIEYD  180
GSNKYYADSV EGRFTISRDN SKNTLYLQMN SLRAEDTAVY YCKTHGSEDN WGQGTMVTVS  240
SHHHHHH                                                            247

SEQ ID NO: 230          moltype = AA  length = 247
FEATURE                 Location/Qualifiers
source                  1..247
                        mol_type = protein
                        organism = synthetic construct
SEQUENCE: 230
QSVLTQPPSV SGAPGQRVTI SCSGSRSNIG SNTVKWYQQL PGTAPKLLIY YNDQRPSGVP   60
DRFSGSKSGT SASLAITGLQ AEDEADYYCQ SYDRYTHPAL LFGTGTKVTV LGGGGSGGGG  120
SGGGGSQVQL VESGGGVVQP GRSLRLSCAA SGFTFSSYGM HWVRQAPGKG LEWVAFIRYD  180
GSNKYYADSV KGRFTISRDN SKNTLYLQMN SLRAEDTAVY YCKTHGSHDN WGQGTMVTVS  240
SHHHHHH                                                            247

SEQ ID NO: 231          moltype = AA  length = 306
FEATURE                 Location/Qualifiers
source                  1..306
                        mol_type = protein
                        organism = synthetic construct
SEQUENCE: 231
IWELKKDVYV VELDWYPDAP GEMVVLTCDT PEEDGITWTL DQSSEVLGSG KTLTIQVKEF   60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCS                                                             306

SEQ ID NO: 232          moltype = AA  length = 137
FEATURE                 Location/Qualifiers
source                  1..137
                        mol_type = protein
                        organism = synthetic construct
SEQUENCE: 232
QVQLQESGGG LVQTGGSLRL SCTTSGTIFS GYTMGWYRQA PGEQRELVAV ISGGGDTNYA   60
DSVKGRFTIS RDNTKDTMYL QMNSLKPEDT AVYYCSREV TPPWKLYWGQ GTQVTVSSAA   120
AYPYDVPDYG SHHHHHH                                                 137

SEQ ID NO: 233          moltype = AA  length = 137
FEATURE                 Location/Qualifiers
source                  1..137
                        mol_type = protein
                        organism = synthetic construct
SEQUENCE: 233
QVQLQESGGG LVQEGGSLRL SCAASERIFS TDVMGWYRQA AEKQRELVAV VSARGTTNYL   60
DAVKGRFTIS RDNARNTLTL QMNDLKPEDT ASYYCVRET TSPWRIYWGQ GTQVTVSSAA   120
AYPYDVPDYG SHHHHHH                                                 137

SEQ ID NO: 234          moltype = AA  length = 138
FEATURE                 Location/Qualifiers
source                  1..138
                        mol_type = protein
                        organism = synthetic construct
SEQUENCE: 234
QVQLQESGGG LVQAGGSLRL SCAASGSIFS ANAMGWYRQA PGKQRELVAV ISSGGSTNYA   60
DSVKGRFTIS RDNAKNTVYL QMNSLKPEDT AVYYCMYSGS YYYTPNDYWG QGTQVTVSSA  120
AAYPYDVPDY GSHHHHHH                                                138

SEQ ID NO: 235          moltype = AA  length = 245
FEATURE                 Location/Qualifiers
source                  1..245
                        mol_type = protein
                        organism = synthetic construct
SEQUENCE: 235
EVQLVESGGG LVQPGGSLRL SCAASGFTFS SYTLAWVRQA PGKGLEWVAA IDSSSYTYSP   60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKASQN VGTNVGWYQQ KPGKAPKALI  180
YSASFRYSGV PSRFSGSGSG TDFTLTISSL QPEDFATYYC QQYYTYPYTF GGGTKVEIKH  240
HHHHH                                                              245
```

SEQ ID NO: 236          moltype = AA  length = 138
FEATURE                 Location/Qualifiers
source                  1..138
                        mol_type = protein
                        organism = synthetic construct
SEQUENCE: 236
EVQLLESGGG LVQPGGSLRL SCAASGSIFS ANAMGWYRQA PGKQRELVAV ISSGGSTNYA 60
DSVKGRFTIS RDNSKNTVYL QMNSLRAEDT AVYYCMYSGS YYYTPNDYWG QGTLVTVSSA 120
AAYPYDVPDY GSHHHHHH                                               138

SEQ ID NO: 237          moltype = AA  length = 138
FEATURE                 Location/Qualifiers
source                  1..138
                        mol_type = protein
                        organism = synthetic construct
SEQUENCE: 237
EVQLLESGGG LVQPGGSLRL SCAASGSIFS ANAMGWYRQA PGKGLELVAV ISSGGSTNYA 60
DSVKGRFTIS RDNSKNTVYL QMNSLRAEDT AVYYCMYSGS YYYTPNDYWG QGTLVTVSSA 120
AAYPYDVPDY GSHHHHHH                                               138

SEQ ID NO: 238          moltype = AA  length = 138
FEATURE                 Location/Qualifiers
source                  1..138
                        mol_type = protein
                        organism = synthetic construct
SEQUENCE: 238
EVQLLESGGG LVQPGGSLRL SCAASGSIFS ANAMGWVRQA PGKGLEWVSV ISSGGSTNYA 60
DSVKGRFTIS RDNSKNTLYL QMNSLRAEDT AVYYCMYSGS YYYTPNDYWG QGTLVTVSSA 120
AAYPYDVPDY GSHHHHHH                                               138

SEQ ID NO: 239          moltype = AA  length = 138
FEATURE                 Location/Qualifiers
source                  1..138
                        mol_type = protein
                        organism = synthetic construct
SEQUENCE: 239
QVQLLESGGG LVQPGGSLRL SCAASGSIFS ANAMGWYRQA PGKQRELVAV ISSGGSTNYA 60
DSVKGRFTIS RDNSKNTVYL QMNSLRAEDT AVYYCMYSGS YYYTPNDYWG QGTLVTVSSA 120
AAYPYDVPDY GSHHHHHH                                               138

SEQ ID NO: 240          moltype = AA  length = 138
FEATURE                 Location/Qualifiers
source                  1..138
                        mol_type = protein
                        organism = synthetic construct
SEQUENCE: 240
EVQLLESGGG LVQPGGSLRL SCAASGSIFS ANAMGWYRQA PGKGRELVAV ISSGGSTNYA 60
DSVKGRFTIS RDNSKNTVYL QMNSLRAEDT AVYYCMYSGS YYYTPNDYWG QGTLVTVSSA 120
AAYPYDVPDY GSHHHHHH                                               138

SEQ ID NO: 241          moltype = AA  length = 138
FEATURE                 Location/Qualifiers
source                  1..138
                        mol_type = protein
                        organism = synthetic construct
SEQUENCE: 241
QVQLLESGGG LVQAGGSLRL SCAASGSIFS ANAMGWYRQA PGKQRELVAV ISSGGSTNYA 60
DSVKGRFTIS RDNSKNTVYL QMNSLRAEDT AVYYCMYSGS YYYTPNDYWG QGTLVTVSSA 120
AAYPYDVPDY GSHHHHHH                                               138

SEQ ID NO: 242          moltype = AA  length = 137
FEATURE                 Location/Qualifiers
source                  1..137
                        mol_type = protein
                        organism = synthetic construct
SEQUENCE: 242
EVQLLESGGG LVQPGGSLRL SCAASERIFS TDVMGWYRQA PGKQRELVAV VSARGTTNYL 60
DAVKGRFTIS RDNSKNTLYL QMNSLRAEDT AVYYCYVRET TSPWRIYWGQ GTLVTVSSAA 120
AYPYDVPDYG SHHHHHH                                                137

SEQ ID NO: 243          moltype = AA  length = 137
FEATURE                 Location/Qualifiers
source                  1..137
                        mol_type = protein
                        organism = synthetic construct
SEQUENCE: 243
EVQLLESGGG LVQPGGSLRL SCAASERIFS TDVMGWYRQA PGKGLELVAV VSARGTTNYL 60
DAVKGRFTIS RDNSKNTLYL QMNSLRAEDT AVYYCYVRET TSPWRIYWGQ GTLVTVSSAA 120

-continued

```
AYPYDVPDYG SHHHHHH                                                          137

SEQ ID NO: 244          moltype = AA   length = 137
FEATURE                 Location/Qualifiers
source                  1..137
                        mol_type = protein
                        organism = synthetic construct
SEQUENCE: 244
EVQLLESGGG LVQPGGSLRL SCAASERIFS TDVMGWVRQA PGKGLEWVSV VSARGTTNYL   60
DAVKGRFTIS RDNSKNTLYL QMNSLRAEDT AVYYCYVRET TSPWRIYWGQ GTLVTVSSAA   120
AYPYDVPDYG SHHHHHH                                                          137

SEQ ID NO: 245          moltype = AA   length = 137
FEATURE                 Location/Qualifiers
source                  1..137
                        mol_type = protein
                        organism = synthetic construct
SEQUENCE: 245
QVQLLESGGG LVQPGGSLRL SCAASERIFS TDVMGWYRQA PGKQRELVAV VSARGTTNYL   60
DAVKGRFTIS RDNSKNTLYL QMNSLRAEDT AVYYCYVRET TSPWRIYWGQ GTLVTVSSAA   120
AYPYDVPDYG SHHHHHH                                                          137

SEQ ID NO: 246          moltype = AA   length = 137
FEATURE                 Location/Qualifiers
source                  1..137
                        mol_type = protein
                        organism = synthetic construct
SEQUENCE: 246
EVQLLESGGG LVQPGGSLRL SCAASERIFS TDVMGWYRQA PGKGRELVAV VSARGTTNYL   60
DSVKGRFTIS RDNSKNTLYL QMNSLRAEDT AVYYCYVRET TSPWRIYWGQ GTLVTVSSAA   120
AYPYDVPDYG SHHHHHH                                                          137

SEQ ID NO: 247          moltype = AA   length = 137
FEATURE                 Location/Qualifiers
source                  1..137
                        mol_type = protein
                        organism = synthetic construct
SEQUENCE: 247
QVQLLESGGG LVQEGGSLRL SCAASERIFS TDVMGWYRQA AGKQRELVAV VSARGTTNYL   60
DAVKGRFTIS RDNSKNTLYL QMNSLRAEDT ASYYCYVRET TSPWRIYWGQ GTLVTVSSAA   120
AYPYDVPDYG SHHHHHH                                                          137

SEQ ID NO: 248          moltype = AA   length = 137
FEATURE                 Location/Qualifiers
source                  1..137
                        mol_type = protein
                        organism = synthetic construct
SEQUENCE: 248
EVQLLESGGG LVQPGGSLRL SCAASERIFS TDVMGWYRQA PGKGLELVAV VSARGTTNYL   60
DSVKGRFTIS RDNSKNTLYL QMNSLRAEDT AVYYCYVRET TSPWRIYWGQ GTLVTVSSAA   120
AYPYDVPDYG SHHHHHH                                                          137

SEQ ID NO: 249          moltype = AA   length = 137
FEATURE                 Location/Qualifiers
source                  1..137
                        mol_type = protein
                        organism = synthetic construct
SEQUENCE: 249
EVQLLESGGG LVQPGGSLRL SCATSGTIFS GYTMGWYRQA PGKQRELVAV ISGGGDTNYA   60
DSVKGRFTIS RDNSKDTMYL QMNSLRAEDT AVYYCSREV TPPWKLYWGQ GTLVTVSSAA    120
AYPYDVPDYG SHHHHHH                                                          137

SEQ ID NO: 250          moltype = AA   length = 137
FEATURE                 Location/Qualifiers
source                  1..137
                        mol_type = protein
                        organism = synthetic construct
SEQUENCE: 250
EVQLLESGGG LVQPGGSLRL SCATSGTIFS GYTMGWYRQA PGKGLELVAV ISGGGDTNYA   60
DSVKGRFTIS RDNSKDTMYL QMNSLRAEDT AVYYCSREV TPPWKLYWGQ GTLVTVSSAA    120
AYPYDVPDYG SHHHHHH                                                          137

SEQ ID NO: 251          moltype = AA   length = 137
FEATURE                 Location/Qualifiers
source                  1..137
                        mol_type = protein
                        organism = synthetic construct
SEQUENCE: 251
EVQLLESGGG LVQPGGSLRL SCAASGTIFS GYTMGWVRQA PGKGLEWVSV ISGGGDTNYA   60
```

```
DSVKGRFTIS RDNSKNTLYL QMNSLRAEDT AVYYCYSREV TPPWKLYWGQ GTLVTVSSAA    120
AYPYDVPDYG SHHHHHH                                                    137

SEQ ID NO: 252         moltype = AA   length = 137
FEATURE                Location/Qualifiers
source                 1..137
                       mol_type = protein
                       organism = synthetic construct
SEQUENCE: 252
QVQLLESGGG LVQPGGSLRL SCATSGTIFS GYTMGWYRQA PGKQRELVAV ISGGGDTNYA    60
DSVKGRFTIS RDNSKDTMYL QMNSLRAEDT AVYYCYSREV TPPWKLYWGQ GTLVTVSSAA    120
AYPYDVPDYG SHHHHHH                                                    137

SEQ ID NO: 253         moltype = AA   length = 137
FEATURE                Location/Qualifiers
source                 1..137
                       mol_type = protein
                       organism = synthetic construct
SEQUENCE: 253
EVQLLESGGG LVQPGGSLRL SCATSGTIFS GYTMGWYRQA PGKQRELVAV ISGGGDTNYA    60
DSVKGRFTIS RDNSKNTMYL QMNSLRAEDT AVYYCYSREV TPPWKLYWGQ GTLVTVSSAA    120
AYPYDVPDYG SHHHHHH                                                    137

SEQ ID NO: 254         moltype = AA   length = 137
FEATURE                Location/Qualifiers
source                 1..137
                       mol_type = protein
                       organism = synthetic construct
SEQUENCE: 254
EVQLLESGGG LVQPGGSLRL SCATSGTIFS GYTMGWYRQA PGKGRELVAV ISGGGDTNYA    60
DSVKGRFTIS RDNSKNTMYL QMNSLRAEDT AVYYCYSREV TPPWKLYWGQ GTLVTVSSAA    120
AYPYDVPDYG SHHHHHH                                                    137

SEQ ID NO: 255         moltype = AA   length = 137
FEATURE                Location/Qualifiers
source                 1..137
                       mol_type = protein
                       organism = synthetic construct
SEQUENCE: 255
QVQLLESGGG LVQTGGSLRL SCATSGTIFS GYTMGWYRQA PGKQRELVAV ISGGGDTNYA    60
DSVKGRFTIS RDNSKDTMYL QMNSLRAEDT AVYYCYSREV TPPWKLYWGQ GTLVTVSSAA    120
AYPYDVPDYG SHHHHHH                                                    137

SEQ ID NO: 256         moltype = AA   length = 137
FEATURE                Location/Qualifiers
source                 1..137
                       mol_type = protein
                       organism = synthetic construct
SEQUENCE: 256
EVQLLESGGG LVQPGGSLRL SCATSGTIFS GYTMGWYRQA PGKGLELVAV ISGGGDTNYA    60
DSVKGRFTIS RDNSKNTMYL QMNSLRAEDT AVYYCYSREV TPPWKLYWGQ GTLVTVSSAA    120
AYPYDVPDYG SHHHHHH                                                    137

SEQ ID NO: 257         moltype = AA   length = 245
FEATURE                Location/Qualifiers
source                 1..245
                       mol_type = protein
                       organism = synthetic construct
SEQUENCE: 257
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSGGG    120
GSGGGGSGGG GSDIQMTQSP SSLSASVGDR VTITCKAREK LWSAVAWYQQ KPGKAPKALI    180
YSASFRYSGV PSRFSGSGSG TDFTLTISSL QPEDFATYYC QQYYTYPYTF GGGTKVEIKH    240
HHHHH                                                                245

SEQ ID NO: 258         moltype = AA   length = 245
FEATURE                Location/Qualifiers
source                 1..245
                       mol_type = protein
                       organism = synthetic construct
SEQUENCE: 258
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSGGG    120
GSGGGGSGGG GSDIQMTQSP SSLSASVGDR VTITCKAREK LWSAVAWYQQ KPGKAPKSLI    180
YSASFRYSGV PSRFSGSGSG TDFTLTISSL QPEDFATYYC QQYYTYPYTF GGGTKVEIKH    240
HHHHH                                                                245

SEQ ID NO: 259         moltype = AA   length = 245
FEATURE                Location/Qualifiers
```

-continued

```
source                  1..245
                        mol_type = protein
                        organism = synthetic construct
SEQUENCE: 259
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSGGG   120
GSGGGGSGGG GSDIQMTQSP SSLSASVGDR VTITCKVTEK VWGNVAWYQQ KPGKAPISLI   180
YSPSLRKSGV PSRFSGSGSG TDFTLTISSL QPEDFATYYC QQYYTYPYTF GGGTKVEIKH   240
HHHHH                                                               245

SEQ ID NO: 260          moltype = AA  length = 245
FEATURE                 Location/Qualifiers
source                  1..245
                        mol_type = protein
                        organism = synthetic construct
SEQUENCE: 260
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSGGG   120
GSGGGGSGGG GSDIQMTQSP SSLSASVGDR VTITCKSSEK LWANVAWYQQ KPGKAPKALI   180
YSASFRYSGV PSRFSGSGSG TDFTLTISSL QPEDFATYYC QQYYTYPYTF GGGTKVEIKH   240
HHHHH                                                               245

SEQ ID NO: 261          moltype = AA  length = 245
FEATURE                 Location/Qualifiers
source                  1..245
                        mol_type = protein
                        organism = synthetic construct
SEQUENCE: 261
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSGGG   120
GSGGGGSGGG GSDIQMTQSP SSLSASVGDR VTITCKSSEK LWANVAWYQQ KPGKAPKSLI   180
YSASFRYSGV PSRFSGSGSG TDFTLTISSL QPEDFATYYC QQYYTYPYTF GGGTKVEIKH   240
HHHHH                                                               245

SEQ ID NO: 262          moltype = AA  length = 214
FEATURE                 Location/Qualifiers
source                  1..214
                        mol_type = protein
                        organism = synthetic construct
SEQUENCE: 262
DIQMTQSPSS LSASVGDRVT ITCKASQNVG TNVGWYQQKP GKAPKALIYS ASFRYSGVPS    60
RFSGSGSGTD FTLTISSLQP EDFATYYCQQ YYTYPYTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 263          moltype = AA  length = 214
FEATURE                 Location/Qualifiers
source                  1..214
                        mol_type = protein
                        organism = synthetic construct
SEQUENCE: 263
DIQMTQSPSS LSASVGDRVT ITCKAREKLW SAVAWYQQKP GKAPKSLIYS ASFRYSGVPS    60
RFSGSGSGTD FTLTISSLQP EDFATYYCQQ YYTYPYTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 264          moltype = AA  length = 214
FEATURE                 Location/Qualifiers
source                  1..214
                        mol_type = protein
                        organism = synthetic construct
SEQUENCE: 264
DIQMTQSPSS LSASVGDRVT ITCKVTEKVW GNVAWYQQKP GKAPISLIYS PSLRKSGVPS    60
RFSGSGSGTD FTLTISSLQP EDFATYYCQQ YYTYPYTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 265          moltype = AA  length = 363
FEATURE                 Location/Qualifiers
source                  1..363
                        mol_type = protein
                        organism = synthetic construct
SEQUENCE: 265
DIQMTQSPSS LSASVGDRVT ITCKAREKLW SAVAWYQQKP GKAPKSLIYS ASFRYSGVPS    60
RFSGSGSGTD FTLTISSLQP EDFATYYCQQ YYTYPYTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGECGGGGSG GGGSGGGGSG GGGSGGGGSG   240
GGGSEVQLLE SGGGLVQPGG SLRLSCAASG SIFSANAMGW YRQAPGKQRE LVAVISSGGS   300
TNYADSVKGR FTISRDNSKN TVYLQMNSLR AEDTAVYYCM YSGSYYYTPN DYWGQGTLVT   360
```

-continued

```
VSS                                                                    363

SEQ ID NO: 266            moltype = AA  length = 363
FEATURE                   Location/Qualifiers
source                    1..363
                          mol_type = protein
                          organism = synthetic construct
SEQUENCE: 266
DIQMTQSPSS LSASVGDRVT ITCKAREKLW SAVAWYQQKP GKAPKSLIYS ASFRYSGVPS    60
RFSGSGSGTD FTLTISSLQP EDFATYYCQQ YYTYPYTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECGGGGSG GGGSGGGGSG GGGSGGGGSG    240
GGGSEVQLLE SGGGLVQPGG SLRLSCAASG SIFSANAMGW YRQAPGKGLE LVAVISSGGS    300
TNYADSVKGR FTISRDNSKN TVYLQMNSLR AEDTAVYYCM YSGSYYYTPN DYWGQGTLVT    360
VSS                                                                    363

SEQ ID NO: 267            moltype = AA  length = 363
FEATURE                   Location/Qualifiers
source                    1..363
                          mol_type = protein
                          organism = synthetic construct
SEQUENCE: 267
DIQMTQSPSS LSASVGDRVT ITCKVTEKVW GNVAWYQQKP GKAPISLIYS PSLRKSGVPS    60
RFSGSGSGTD FTLTISSLQP EDFATYYCQQ YYTYPYTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECGGGGSG GGGSGGGGSG GGGSGGGGSG    240
GGGSEVQLLE SGGGLVQPGG SLRLSCAASG SIFSANAMGW YRQAPGKQRE LVAVISSGGS    300
TNYADSVKGR FTISRDNSKN TVYLQMNSLR AEDTAVYYCM YSGSYYYTPN DYWGQGTLVT    360
VSS                                                                    363

SEQ ID NO: 268            moltype = AA  length = 363
FEATURE                   Location/Qualifiers
source                    1..363
                          mol_type = protein
                          organism = synthetic construct
SEQUENCE: 268
DIQMTQSPSS LSASVGDRVT ITCKVTEKVW GNVAWYQQKP GKAPISLIYS PSLRKSGVPS    60
RFSGSGSGTD FTLTISSLQP EDFATYYCQQ YYTYPYTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGECGGGGSG GGGSGGGGSG GGGSGGGGSG    240
GGGSEVQLLE SGGGLVQPGG SLRLSCAASG SIFSANAMGW YRQAPGKGLE LVAVISSGGS    300
TNYADSVKGR FTISRDNSKN TVYLQMNSLR AEDTAVYYCM YSGSYYYTPN DYWGQGTLVT    360
VSS                                                                    363

SEQ ID NO: 269            moltype = AA  length = 214
FEATURE                   Location/Qualifiers
source                    1..214
                          mol_type = protein
                          organism = synthetic construct
SEQUENCE: 269
DIQMTQSPSS LSASVGDRVT ITCKSSEKLW ANVAWYQQKP GKAPKSLIYS ASFRYSGVPS    60
RFSGSGSGTD FTLTISSLQP EDFATYYCQQ YYTYPYTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                 214

SEQ ID NO: 270            moltype = AA  length = 214
FEATURE                   Location/Qualifiers
source                    1..214
                          mol_type = protein
                          organism = synthetic construct
SEQUENCE: 270
DIQMTQSPSS LSASVGDRVT ITCKSSEKLW ANVAWYQQKP GKAPKLLIYS ASFRYSGVPS    60
RFSGSGSGTD FTLTISSLQP EDFATYYCQQ YYTYPYTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                 214

SEQ ID NO: 271            moltype = AA  length = 214
FEATURE                   Location/Qualifiers
source                    1..214
                          mol_type = protein
                          organism = synthetic construct
SEQUENCE: 271
DIQMTQSPSS LSASVGDRVT ITCKAREKLW SAVAWYQQKP GKAPKLLIYS ASFRYSGVPS    60
RFSGSGSGTD FTLTISSLQP EDFATYYCQQ YYTYPYTFGG GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                 214

SEQ ID NO: 272            moltype = AA  length = 547
FEATURE                   Location/Qualifiers
```

-continued

```
source                  1..547
                        mol_type = protein
                        organism = synthetic construct
SEQUENCE: 272
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGPGPA               300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKSSEKLW ANVAWYQQKP   480
GKAPKALIYS ASFRYSGVPS RFSGSGSGTD FTLTISSLQP EDFATYYCQQ YYTYPYTFGG   540
GTKVEIK                                                            547

SEQ ID NO: 273         moltype = AA  length = 547
FEATURE                 Location/Qualifiers
source                  1..547
                        mol_type = protein
                        organism = synthetic construct
SEQUENCE: 273
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGPGPA               300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKSSEKLW ANVAWYQQKP   480
GKAPKSLIYS ASFRYSGVPS RFSGSGSGTD FTLTISSLQP EDFATYYCQQ YYTYPYTFGG   540
GTKVEIK                                                            547

SEQ ID NO: 274         moltype = AA  length = 547
FEATURE                 Location/Qualifiers
source                  1..547
                        mol_type = protein
                        organism = synthetic construct
SEQUENCE: 274
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGPGPA               300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKSSEKLW ANVAWYQQKP   480
GKAPKLLIYS ASFRYSGVPS RFSGSGSGTD FTLTISSLQP EDFATYYCQQ YYTYPYTFGG   540
GTKVEIK                                                            547

SEQ ID NO: 275         moltype = AA  length = 547
FEATURE                 Location/Qualifiers
source                  1..547
                        mol_type = protein
                        organism = synthetic construct
SEQUENCE: 275
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGPGPA               300
GLYAQPGSEV QLVESGGGLV QPGGSLRLSC AASGFTFSSY TLAWVRQAPG KCLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKSSEKLW ANVAWYQQKP   480
GKAPKSLIYS ASFRYSGVPS RFSGSGSGTD FTLTISSLQP EDFATYYCQQ YYTYPYTFGC   540
GTKVEIK                                                            547

SEQ ID NO: 276         moltype = AA  length = 547
FEATURE                 Location/Qualifiers
source                  1..547
                        mol_type = protein
                        organism = synthetic construct
SEQUENCE: 276
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA  300
GLYAQPGSEV QLVESGGGLV QPGGSLRLSC AASGFTFSSY TLAWVRQAPG KCLEWVAAID   360
SSSYTYSPDT VRGRFTISRD NAKNSLYLQM NSLRAEDTAV YYCARDSNWD ALDYWGQGTT   420
```

-continued

```
VTVSSGGGGS GGGGSGGGGS DIQMTQSPSS LSASVGDRVT ITCKSSEKLW ANVAWYQQKP    480
GKAPKLLIYS ASFRYSGVPS RFSGSGSGTD FTLTISSLQP EDFATYYCQQ YYTYPYTFGC    540
GTKVEIK                                                              547

SEQ ID NO: 277              moltype = AA   length = 547
FEATURE                     Location/Qualifiers
source                      1..547
                            mol_type = protein
                            organism = synthetic construct
SEQUENCE: 277
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGCGTT    420
VTVSSGGGGS GGGGSGGGGS DIQMTQSPSS LSASVGDRVT ITCKSSEKLW ANVAWYQQKP    480
GKCPKALIYS ASFRYSGVPS RFSGSGSGTD FTLTISSLQP EDFATYYCQQ YYTYPYTFGG    540
GTKVEIK                                                              547

SEQ ID NO: 278              moltype = AA   length = 547
FEATURE                     Location/Qualifiers
source                      1..547
                            mol_type = protein
                            organism = synthetic construct
SEQUENCE: 278
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGQGTT    420
VTVSSSGGPG PAGLYAQPGS DIQMTQSPSS LSASVGDRVT ITCKAREKLW SAVAWYQQKP    480
GKAPKLLIYS ASFRYSGVPS RFSGSGSGTD FTLTISSLQP EDFATYYCQQ YYTYPYTFGG    540
GTKVEIK                                                              547

SEQ ID NO: 279              moltype = AA   length = 547
FEATURE                     Location/Qualifiers
source                      1..547
                            mol_type = protein
                            organism = synthetic construct
SEQUENCE: 279
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGCGTT    420
VTVSSGGGGS GGGGSGGGGS DIQMTQSPSS LSASVGDRVT ITCKAREKLW SAVAWYQQKP    480
GKAPKLLIYS ASFRYSGVPS RFSGSGSGTD FTLTISSLQP EDFATYYCQQ YYTYPYTFGG    540
GTKVEIK                                                              547

SEQ ID NO: 280              moltype = AA   length = 547
FEATURE                     Location/Qualifiers
source                      1..547
                            mol_type = protein
                            organism = synthetic construct
SEQUENCE: 280
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KCLEWVAAID    360
SSSYTYSPDT VRGRFTISRD NAKNSLYLQM NSLRAEDTAV YYCARDSNWD ALDYWGCGTT    420
VTVSSGGGGS GGGGSGGGGS DIQMTQSPSS LSASVGDRVT ITCKAREKLW SAVAWYQQKP    480
GKAPKLLIYS ASFRYSGVPS RFSGSGSGTD FTLTISSLQP EDFATYYCQQ YYTYPYTFGC    540
GTKVEIK                                                              547

SEQ ID NO: 281              moltype = AA   length = 547
FEATURE                     Location/Qualifiers
source                      1..547
                            mol_type = protein
                            organism = synthetic construct
SEQUENCE: 281
APTSSSTKKT QLQLEHLLLD LQMILNGINN YKNPKLTRML TFKFYMPKKA TELKHLQCLE    60
```

-continued

```
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKAREKLW SAVAWYQQKP  480
GKAPKSLIYS ASFRYSGVPS RFSGSGSGTD FTLTISSLQP EDFATYYCQQ YYTYPYTFGG  540
GTKVEIK                                                           547

SEQ ID NO: 282          moltype = AA  length = 547
FEATURE                 Location/Qualifiers
source                  1..547
                        mol_type = protein
                        organism = synthetic construct
SEQUENCE: 282
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKVTEKVW GNVAWYQQKP  480
GKAPISLIYS PSLRKSGVPS RFSGSGSGTD FTLTISSLQP EDFATYYCQQ YYTYPYTFGG  540
GTKVEIK                                                           547

SEQ ID NO: 283          moltype = AA  length = 547
FEATURE                 Location/Qualifiers
source                  1..547
                        mol_type = protein
                        organism = synthetic construct
SEQUENCE: 283
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKAREKLW SAVAWYQQKP  480
GKAPKSLIYS ASFRYSGVPS RFSGSGSGTD FTLTISSLQP EDFATYYCQQ YYTYPYTFGC  540
GTKVEIK                                                           547

SEQ ID NO: 284          moltype = AA  length = 547
FEATURE                 Location/Qualifiers
source                  1..547
                        mol_type = protein
                        organism = synthetic construct
SEQUENCE: 284
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGCGTT  420
VTVSSGGGGS GGGGSGGGGS DIQMTQSPSS LSASVGDRVT ITCKAREKLW SAVAWYQQKP  480
GKCPKALIYS ASFRYSGVPS RFSGSGSGTD FTLTISSLQP EDFATYYCQQ YYTYPYTFGG  540
GTKVEIK                                                           547

SEQ ID NO: 285          moltype = AA  length = 547
FEATURE                 Location/Qualifiers
source                  1..547
                        mol_type = protein
                        organism = synthetic construct
SEQUENCE: 285
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KCLEWVAAID  360
SSSYTYSPDT VRGRFTISRD NAKNSLYLQM NSLRAEDTAV YYCARDSNWD ALDYWGQGTT  420
VTVSSGGGGS GGGGSGGGGS DIQMTQSPSS LSASVGDRVT ITCKVTEKVW GNVAWYQQKP  480
GKAPISLIYS PSLRKSGVPS RFSGSGSGTD FTLTISSLQP EDFATYYCQQ YYTYPYTFGC  540
GTKVEIK                                                           547

SEQ ID NO: 286          moltype = AA  length = 528
```

```
FEATURE              Location/Qualifiers
source               1..528
                     mol_type = protein
                     organism = synthetic construct
SEQUENCE: 286
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPALF KSSFPPGSEV QLVESGGGLV QPGNSLRLSC AASGFTFSKF  180
GMSWVRQAPG KGLEWVSSIS GSGRDTLYAE SVKGRFTISR DNAKTTLYLQ MNSLRPEDTA  240
VYYCTIGGSL SVSSQGTLVT VSSGGGGSGG GGSGGGGSGG GGSGGGGSGG GGSSGGPALF  300
KSSFPPGSEV QLVESGGGLV QPGGSLRLSC AASGFTFSSY TLAWVRQAPG KGLEWVAAID  360
SSSYTYSPDT VRGRFTISRD NAKNSLYLQM NSLRAEDTAV YYCARDSNWD ALDYWGQGTT  420
VTVSSASTKG PSVFPLAPSS KSTSGGTAAL GCLVKDYFPE PVTVSWNSGA LTSGVHTFPA  480
VLQSSGLYSL SSVVTVPSSS LGTQTYICNV NHKPSNTKVD KRVEPKSC               528

SEQ ID NO: 287       moltype = AA  length = 642
FEATURE              Location/Qualifiers
source               1..642
                     mol_type = protein
                     organism = synthetic construct
SEQUENCE: 287
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPALFKSSF  240
PPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINIVILEL KGSETTFMCE YADETATIVE  360
FLNRWITFCQ SIISTLTGGG GSGGGGSGGG GSGGGGSGGG GSGGGGSSGG PALFKSSFPP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG QGTTVTVSSA  540
STKGPSVFPL APSSKSTSGG TAALGCLVKD YFPEPVTVSW NSGALTSGVH TFPAVLQSSG  600
LYSLSSVVTV PSSSLGTQTY ICNVNHKPSN TKVDKRVEPK SC                    642

SEQ ID NO: 288       moltype = AA  length = 661
FEATURE              Location/Qualifiers
source               1..661
                     mol_type = protein
                     organism = synthetic construct
SEQUENCE: 288
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPALFKSSF  240
PPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINIVILEL KGSETTFMCE YADETATIVE  360
FLNRWITFCQ SIISTLTGGG GSGGGGSGGG GSGGGGSGGG GSGGGGSSGG PALFKSSFPP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKAR EKLWSAVAWY QQKPGKAPKS  600
LIYSASFRYS GVPSRFSGSG SGTDFTLTIS SLQPEDFATY YCQQYYTYPY TFGGGTKVEI  660
K                                                                 661

SEQ ID NO: 289       moltype = AA  length = 661
FEATURE              Location/Qualifiers
source               1..661
                     mol_type = protein
                     organism = synthetic construct
SEQUENCE: 289
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPALFKSSF  240
PPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINIVILEL KGSETTFMCE YADETATIVE  360
FLNRWITFCQ SIISTLTGGG GSGGGGSGGG GSGGGGSGGG GSGGGGSSGG PALFKSSFPP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKVT EKVWGNVAWY QQKPGKAPIS  600
LIYSPSLRKS GVPSRFSGSG SGTDFTLTIS SLQPEDFATY YCQQYYTYPY TFGGGTKVEI  660
K                                                                 661

SEQ ID NO: 290       moltype = AA  length = 661
FEATURE              Location/Qualifiers
source               1..661
                     mol_type = protein
                     organism = synthetic construct
SEQUENCE: 290
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
```

```
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKS GGPALFKSSF    240
PPGSAPTSSS TKKTQLQLEH LLLDLQMILN GINNYKNPKL TRMLTFKFYM PKKATELKHL    300
QCLEEELKPL EEVLNLAQSK NFHLRPRDLI SNINVIVLEL KGSETTFMCE YADETATIVE    360
FLNRWITFCQ SIISTLTGGG GSGGGGSGGG GSGGGGSGGG GSGGGGSSGG PALFKSSFPP    420
GSEVQLVESG GGLVQPGGSL RLSCAASGFT FSSYTLAWVR QAPGKCLEWV AAIDSSSYTY    480
SPDTVRGRFT ISRDNAKNSL YLQMNSLRAE DTAVYYCARD SNWDALDYWG QGTTVTVSSG    540
GGGSGGGGSG GGGSDIQMTQ SPSSLSASVG DRVTITCKAR EKLWSAVAWY QQKPGKAPKS    600
LIYSASFRYS GVPSRFSGSG SGTDFTLTIS SLQPEDFATY YCQQYYTYPY TFGCGTKVEI    660
K                                                                    661

SEQ ID NO: 291         moltype = AA  length = 661
FEATURE                Location/Qualifiers
source                 1..661
                       mol_type = protein
                       organism = synthetic construct
SEQUENCE: 291
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKS GGPALFKSSF    240
PPGSAPTSSS TKKTQLQLEH LLLDLQMILN GINNYKNPKL TRMLTFKFYM PKKATELKHL    300
QCLEEELKPL EEVLNLAQSK NFHLRPRDLI SNINVIVLEL KGSETTFMCE YADETATIVE    360
FLNRWITFCQ SIISTLTGGG GSGGGGSGGG GSGGGGSGGG GSGGGGSSGG PALFKSSFPP    420
GSEVQLVESG GGLVQPGGSL RLSCAASGFT FSSYTLAWVR QAPGKGLEWV AAIDSSSYTY    480
SPDTVRGRFT ISRDNAKNSL YLQMNSLRAE DTAVYYCARD SNWDALDYWG CGTTVTVSSG    540
GGGSGGGGSG GGGSDIQMTQ SPSSLSASVG DRVTITCKAR EKLWSAVAWY QQKPGKCPKA    600
LIYSASFRYS GVPSRFSGSG SGTDFTLTIS SLQPEDFATY YCQQYYTYPY TFGGGTKVEI    660
K                                                                    661

SEQ ID NO: 292         moltype = AA  length = 661
FEATURE                Location/Qualifiers
source                 1..661
                       mol_type = protein
                       organism = synthetic construct
SEQUENCE: 292
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKS GGPALFKSSF    240
PPGSAPTSSS TKKTQLQLEH LLLDLQMILN GINNYKNPKL TRMLTFKFYM PKKATELKHL    300
QCLEEELKPL EEVLNLAQSK NFHLRPRDLI SNINVIVLEL KGSETTFMCE YADETATIVE    360
FLNRWITFCQ SIISTLTGGG GSGGGGSGGG GSGGGGSGGG GSGGGGSSGG PALFKSSFPP    420
GSEVQLVESG GGLVQPGGSL RLSCAASGFT FSSYTLAWVR QAPGKCLEWV AAIDSSSYTY    480
SPDTVRGRFT ISRDNAKNSL YLQMNSLRAE DTAVYYCARD SNWDALDYWG QGTTVTVSSG    540
GGGSGGGGSG GGGSDIQMTQ SPSSLSASVG DRVTITCKVT EKVWGNVAWY QQKPGKAPIS    600
LIYSPSLRKS GVPSRFSGSG SGTDFTLTIS SLQPEDFATY YCQQYYTYPY TFGCGTKVEI    660
K                                                                    661

SEQ ID NO: 293         moltype = AA  length = 661
FEATURE                Location/Qualifiers
source                 1..661
                       mol_type = protein
                       organism = synthetic construct
SEQUENCE: 293
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKS GGPALFKSSF    240
PPGSAPTSSS TKKTQLQLEH LLLDLQMILN GINNYKNPKL TRMLTFKFYM PKKATELKHL    300
QCLEEELKPL EEVLNLAQSK NFHLRPRDLI SNINVIVLEL KGSETTFMCE YADETATIVE    360
FLNRWITFCQ SIISTLTGGG GSGGGGSGGG GSGGGGSGGG GSGGGGSSGG PALFKSSFPP    420
GSEVQLVESG GGLVQPGGSL RLSCAASGFT FSSYTLAWVR QAPGKGLEWV AAIDSSSYTY    480
SPDTVRGRFT ISRDNAKNSL YLQMNSLRAE DTAVYYCARD SNWDALDYWG CGTTVTVSSG    540
GGGSGGGGSG GGGSDIQMTQ SPSSLSASVG DRVTITCKVT EKVWGNVAWY QQKPGKCPIS    600
LIYSPSLRKS GVPSRFSGSG SGTDFTLTIS SLQPEDFATY YCQQYYTYPY TFGGGTKVEI    660
K                                                                    661

SEQ ID NO: 294         moltype = AA  length = 659
FEATURE                Location/Qualifiers
source                 1..659
                       mol_type = protein
                       organism = synthetic construct
SEQUENCE: 294
VPRDCGCKPC ICTVPEVSSV FIFPPKPKDV LTITLTPKVT CVVVDISKDD PEVQFSWFVD    60
DVEVHTAQTQ PREEQFNSTF RSVSELPIMH QDWLNGKEFK CRVNSAAFPA PIEKTISKTK    120
GRPKAPQVYT IPPPKEQMAK DKVSLTCMIT DFFPEDITVE WQWNGQPAEN YKNTQPIMDT    180
DGSYFVYSKL NVQKSNWEAG NTFTCSVLHE GLHNHHTEKS LSHSPGKSGG PALFKSSFPP    240
GSAPTSSSTK KTQLQLEHLL LDLQMILNGI NNYKNPKLTR MLTFKFYMPK KATELKHLQC    300
```

-continued

```
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPA LFKSSFPPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKAREK LWSAVAWYQQ KPGKAPKSLI  600
YSASFRYSGV PSRFSGSGSG TDFTLTISSL QPEDFATYYQ QQYYTYPYTF GGGTKVEIK   659
```

```
SEQ ID NO: 295          moltype = AA  length = 659
FEATURE                 Location/Qualifiers
source                  1..659
                        mol_type = protein
                        organism = synthetic construct
SEQUENCE: 295
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PALFKSSFPP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPA LFKSSFPPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKVTEK VWGNVAWYQQ KPGKAPISLI  600
YSPSLRKSGV PSRFSGSGSG TDFTLTISSL QPEDFATYYC QQYYTYPYTF GGGTKVEIK   659
```

```
SEQ ID NO: 296          moltype = AA  length = 659
FEATURE                 Location/Qualifiers
source                  1..659
                        mol_type = protein
                        organism = synthetic construct
SEQUENCE: 296
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PALFKSSFPP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPA LFKSSFPPGS  420
EVQLVESGGG LVQPGGSLRL SCAASGFTFS SYTLAWVRQA PGKCLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKAREK LWSAVAWYQQ KPGKAPKSLI  600
YSASFRYSGV PSRFSGSGSG TDFTLTISSL QPEDFATYYC QQYYTYPYTF GCGTKVEIK   659
```

```
SEQ ID NO: 297          moltype = AA  length = 659
FEATURE                 Location/Qualifiers
source                  1..659
                        mol_type = protein
                        organism = synthetic construct
SEQUENCE: 297
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PALFKSSFPP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPA LFKSSFPPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGCG TTVTVSSGGG  540
GSGGGGSGGG GSDIQMTQSP SSLSASVGDR VTITCKAREK LWSAVAWYQQ KPGKCPKALI  600
YSASFRYSGV PSRFSGSGSG TDFTLTISSL QPEDFATYYC QQYYTYPYTF GGGTKVEIK   659
```

```
SEQ ID NO: 298          moltype = AA  length = 659
FEATURE                 Location/Qualifiers
source                  1..659
                        mol_type = protein
                        organism = synthetic construct
SEQUENCE: 298
VPRDCGCKPC ICTVPEVSSV FIFPPKPKDV LTITLTPKVT CVVVDISKDD PEVQFSWFVD  60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PALFKSSFPP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPA LFKSSFPPGS  420
EVQLVESGGG LVQPGGSLRL SCAASGFTFS SYTLAWVRQA PGKCLEWVAA IDSSSYTYSP  480
DTVRGRFTIS RDNAKNSLYL QMNSLRAEDT AVYYCARDSN WDALDYWGQG TTVTVSSGGG  540
GSGGGGSGGG GSDIQMTQSP SSLSASVGDR VTITCKVTEK VWGNVAWYQQ KPGKAPISLI  600
YSPSLRKSGV PSRFSGSGSG TDFTLTISSL QPEDFATYYC QQYYTYPYTF GCGTKVEIK   659
```

-continued

```
SEQ ID NO: 299            moltype = AA   length = 659
FEATURE                   Location/Qualifiers
source                    1..659
                          mol_type = protein
                          organism = synthetic construct
SEQUENCE: 299
VPRDCGCKPC ICTVPEVSSV FIFPPKPKDV LTITLTPKVT CVVVDISKDD PEVQFSWFVD   60
DVEVHTAQTQ PREEQFNSTF RSVSELPIMH QDWLNGKEFK CRVNSAAFPA PIEKTISKTK  120
GRPKAPQVYT IPPPKEQMAK DKVSLTCMIT DFFPEDITVE WQWNGQPAEN YKNTQPIMDT  180
DGSYFVYSKL NVQKSNWEAG NTFTCSVLHE GLHNHHTEKS LSHSPGKSGG PALFKSSFPP  240
GSAPTSSSTK KTQLQLEHLL LDLQMILNGI NNYKNPKLTR MLTFKFYMPK KATELKHLQC  300
LEEELKPLEE VLNLAQSKNF HLRPRDLISN INVIVLELKG SETTFMCEYA DETATIVEFL  360
NRWITFCQSI ISTLTGGGGS GGGGSGGGGS GGGGSGGGGS GGGGSSGGPA LFKSSFPPGS  420
EVQLVESGGG LVQPGGSLRL SCAASGFTFS SYTLAWVRQA PGKGLEWVAA IDSSSYTYSP  480
DTVRGRFTIS RDNAKNSLYL QMNSLRAEDT AVYYCARDSN WDALDYWGCG TTVTVSSGGG  540
GSGGGGSGGG GSDIQMTQSP SSLSASVGDR VTITCKVTEK VWGNVAWYQQ KPGKCPISLI  600
YSPSLRKSGV PSRFSGSGSG TDFTLTISSL QPEDFATYYC QQYYTYPYTF GGGTKVEIK   659

SEQ ID NO: 300            moltype = AA   length = 662
FEATURE                   Location/Qualifiers
source                    1..662
                          mol_type = protein
                          organism = synthetic construct
SEQUENCE: 300
MDMRVPAQLL GLLLLWLRGA RCVPRDCGCK PCICTVPEVS SVFIFPPKPK DVLTITLTPK   60
VTCVVVDISK DDPEVQFSWF VDDVEVHTAQ TQPREEQFNS TFRSVSELPI MHQDWLNGKE  120
FKCRVNSAAF PAPIEKTISK TKGRPKAPQV YTIPPPKEQM AKDKVSLTCM ITDFFPEDIT  180
VEWQWNGQPA ENYKNTQPIM DTDGSYFVYS KLNVQKSNWE AGNTFTCSVL HEGLHNHHTE  240
KSLSHSPGKS GGPALFKSSF PPGSAPTSSS TKKTQLQLEH LLLDLQMILN GINNYKNPKL  300
TRMLTFKFYM PKKATELKHL QCLEEELKPL EEVLNLAQSK NFHLRPRDLI SNINVIVLEL  360
KGSETTFMCE YADETATIVE FLNRWITFCQ SIISTLTGGG GSGGGGSGGG GSGGGGSGGG  420
GSGGGGSSGG PALFKSSFPP GSEVQLVESG GGLVQPGGSL RLSCAASGFT FSSYTLAWVR  480
QAPGKGLEWV AAIDSSSYTY SPDTVRGRFT ISRDNAKNSL YLQMNSLRAE DTAVYYCARD  540
SNWDALDYWG QGTTVTVSSA STKGPSVFPL APSSKSTSGG TAALGCLVKD YFPEPVTVSW  600
NSGALTSGVH TFPAVLQSSG LYSLSSVVTV PSSSLGTQTY ICNVNHKPSN TKVDKRVEPK  660
SC                                                                662

SEQ ID NO: 301            moltype = AA   length = 214
FEATURE                   Location/Qualifiers
source                    1..214
                          mol_type = protein
                          organism = synthetic construct
SEQUENCE: 301
DIQMTQSPSS LSASVGDRVT ITCKVTEKVW GNVAWYQQKP GKAPISLIYS PSLRKSGVPS   60
RFSGSGSGTD FTLTISSLQP EDFATYYCQQ YYTYPYTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 302            moltype = AA   length = 661
FEATURE                   Location/Qualifiers
source                    1..661
                          mol_type = protein
                          organism = synthetic construct
SEQUENCE: 302
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKCLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKAS QNVGTNVGWY QQKPGKAPKA  600
LIYSASFRYS GVPSRFSGSG SGTDFTLTIS SLQPEDFATY YCQQYYTYPY TFGCGTKVEI  660
K                                                                 661

SEQ ID NO: 303            moltype = AA   length = 661
FEATURE                   Location/Qualifiers
source                    1..661
                          mol_type = protein
                          organism = synthetic construct
SEQUENCE: 303
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
```

-continued

```
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG CGTTVTVSSG  540
GGGSGGGGSG GGGSDIQMTQ SPSSLSASVG DRVTITCKAS QNVGTNVGWY QQKPGKCPKA  600
LIYSASFRYS GVPSRFSGSG SGTDFTLTIS SLQPEDFATY YCQQYYTYPY TFGGGTKVEI  660
K                                                                 661

SEQ ID NO: 304          moltype = AA  length = 661
FEATURE                 Location/Qualifiers
source                  1..661
                        mol_type = protein
                        organism = synthetic construct
SEQUENCE: 304
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKCLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKAR EKLWSAVAWY QQKPGKAPKA  600
LIYSASFRYS GVPSRFSGSG SGTDFTLTIS SLQPEDFATY YCQQYYTYPY TFGCGTKVEI  660
K                                                                 661

SEQ ID NO: 305          moltype = AA  length = 661
FEATURE                 Location/Qualifiers
source                  1..661
                        mol_type = protein
                        organism = synthetic construct
SEQUENCE: 305
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG CGTTVTVSSG  540
GGGSGGGGSG GGGSDIQMTQ SPSSLSASVG DRVTITCKAR EKLWSAVAWY QQKPGKCPKA  600
LIYSASFRYS GVPSRFSGSG SGTDFTLTIS SLQPEDFATY YCQQYYTYPY TFGGGTKVEI  660
K                                                                 661

SEQ ID NO: 306          moltype = AA  length = 661
FEATURE                 Location/Qualifiers
source                  1..661
                        mol_type = protein
                        organism = synthetic construct
SEQUENCE: 306
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKCLEWV AAIDSSSYTY  480
SPDTVRGRFT ISRDNAKNSL YLQMNSLRAE DTAVYYCARD SNWDALDYWG QGTTVTVSSG  540
GGGSGGGGSG GGGSDIQMTQ SPSSLSASVG DRVTITCKVT EKVWGNVAWY QQKPGKAPIS  600
LIYSPSLRKS GVPSRFSGSG SGTDFTLTIS SLQPEDFATY YCQQYYTYPY TFGCGTKVEI  660
K                                                                 661

SEQ ID NO: 307          moltype = AA  length = 661
FEATURE                 Location/Qualifiers
source                  1..661
                        mol_type = protein
                        organism = synthetic construct
SEQUENCE: 307
ESKYGPPCPP CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGKS GGPGPAGLYA  240
QPGSAPTSSS TKKTQLQLEH LLLDLQMILN GINNYKNPKL TRMLTFKFYM PKKATELKHL  300
QCLEEELKPL EEVLNLAQSK NFHLRPRDLI SNINVIVLEL KGSETTFMCE YADETATIVE  360
FLNRWITFCQ SIISTLTGGG GSGGGGSGGG GSGGGGSGGG GSGGGGSSGG PGPAGLYAQP  420
GSEVQLVESG GGLVQPGGSL RLSCAASGFT FSSYTLAWVR QAPGKGLEWV AAIDSSSYTY  480
SPDTVRGRFT ISRDNAKNSL YLQMNSLRAE DTAVYYCARD SNWDALDYWG CGTTVTVSSG  540
```

-continued

```
GGGSGGGGSG GGGSDIQMTQ SPSSLSASVG DRVTITCKVT EKVWGNVAWY QQKPGKCPIS    600
LIYSPSLRKS GVPSRFSGSG SGTDFTLTIS SLQPEDFATY YCQQYYTYPY TFGGGTKVEI    660
K                                                                    661

SEQ ID NO: 308          moltype = AA   length = 541
FEATURE                 Location/Qualifiers
source                  1..541
                        mol_type = protein
                        organism = synthetic construct
SEQUENCE: 308
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKS GGPGPAGLYA    240
QPGSAPTSSS TKKTQLQLEH LLLDLQMILN GINNYKNPKL TRMLTFKFYM PKKATELKHL    300
QCLEEELKPL EEVLNLAQSK NFHLRPRDLI SNINVIVLEL KGSETTFMCE YADETATIVE    360
FLNRWITFCQ SIISTLTGGG GSGGGGSGGG GSGGGGSGGG GSGGGGSSGG PGPAGLYAQP    420
GSEVQLLESG GGLVQPGGSL RLSCAASGSI FSANAMGWYR QAPGKQRELV AVISSGGSTN    480
YADSVKGRFT ISRDNSKNTV YLQMNSLRAE DTAVYYCMYS GSYYYTPNDY WGQGTLVTVS    540
S                                                                    541

SEQ ID NO: 309          moltype = AA   length = 547
FEATURE                 Location/Qualifiers
source                  1..547
                        mol_type = protein
                        organism = synthetic construct
SEQUENCE: 309
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KCLEWVAAID    360
SSSYTYSPDT VRGRFTISRD NAKNSLYLQM NSLRAEDTAV YYCARDSNWD ALDYWGQGTT    420
VTVSSGGGGS GGGGSGGGGS DIQMTQSPSS LSASVGDRVT ITCKAREKLW SAVAWYQQKP    480
GKAPKSLIYS ASFRYSGVPS RFSGSGSGTD FTLTISSLQP EDFATYYCQQ YYTYPYTFGC    540
GTKVEIK                                                              547

SEQ ID NO: 310          moltype = AA   length = 661
FEATURE                 Location/Qualifiers
source                  1..661
                        mol_type = protein
                        organism = synthetic construct
SEQUENCE: 310
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKS GGPGPAGLYA    240
QPGSAPTSSS TKKTQLQLEH LLLDLQMILN GINNYKNPKL TRMLTFKFYM PKKATELKHL    300
QCLEEELKPL EEVLNLAQSK NFHLRPRDLI SNINVIVLEL KGSETTFMCE YADETATIVE    360
FLNRWITFCQ SIISTLTGGG GSGGGGSGGG GSGGGGSGGG GSGGGGSSGG PGPAGLYAQP    420
GSEVQLVESG GGLVQPGGSL RLSCAASGFT FSSYTLAWVR QAPGKCLEWV AAIDSSSYTY    480
SPDTVRGRFT ISRDNAKNSL YLQMNSLRAE DTAVYYCARD SNWDALDYWG QGTTVTVSSG    540
GGGSGGGGSG GGGSDIQMTQ SPSSLSASVG DRVTITCKAR EKLWSAVAWY QQKPGKAPKS    600
LIYSASFRYS GVPSRFSGSG SGTDFTLTIS SLQPEDFATY YCQQYYTYPY TFGCGTKVEI    660
K                                                                    661

SEQ ID NO: 311          moltype = AA   length = 811
FEATURE                 Location/Qualifiers
source                  1..811
                        mol_type = protein
                        organism = synthetic construct
SEQUENCE: 311
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSGG GGSGGGGSGG GGSGGGGSGG GGSGGGGSEL    180
CDDDPPEIPH ATFKAMAYKE GTMLNCECKR GFRRIKSGSL YMLCTGNSSH SSWDNQCQCT    240
SSATRNTTKQ VTPQPEEQKE RKTTEMQSPM QPVDQASLPG HCREPPPWEN EATERIYHFV    300
VGQMVYYQCV QGYRALHRGP AESVCKMTHG KTRWTQPLQI CTGEMETSQF PGEEKPQASP    360
EGRPESETSS LVTTTDFQIQ TEMAATMETS IFTTEYQSGG PGPAGLYAQP GSEVQLVESG    420
GGLVQPGNSL RLSCAASGFT FSKFGMSWVR QAPGKGLEWV SSISGSGRDT LYAESVKGRF    480
TISRDNAKTT LYLQMNSLRP EDTAVYYCTI GGSLSVSSQG TLVTVSSGGG GSGGGGSGGG    540
GSGGGGSGGG GSGGGGSSGG PGPAGLYAQP GSEVQLVESG GGLVQPGGSL RLSCAASGFT    600
FSSYTLAWVR QAPGKCLEWV AAIDSSSYTY SPDTVRGRFT ISRDNAKNSL YLQMNSLRAE    660
DTAVYYCARD SNWDALDYWG QGTTVTVSSG GGGSGGGGSG GGGSDIQMTQ SPSSLSASVG    720
DRVTITCKAR EKLWSAVAWY QQKPGKAPKS LIYSASFRYS GVPSRFSGSG SGTDFTLTIS    780
SLQPEDFATY YCQQYYTYPY TFGCGTKVEI K                                   811

SEQ ID NO: 312          moltype = AA   length = 811
```

-continued

```
FEATURE              Location/Qualifiers
source               1..811
                     mol_type = protein
                     organism = synthetic construct
SEQUENCE: 312
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEL  180
CDDDPPEIPH ATFKAMAYKE GTMLNCECKR GFRRIKSGSL YMLCTGNSSH SSWDNQCQCT  240
SSATRNTTKQ VTPQPEEQKE RKTTEMQSPM QPVDQASLPG HCREPPPWEN EATERIYHFV  300
VGQMVYYQCV QGYRALHRGP AESVCKMTHG KTRWTQPQLI CTGEMETSQF PGEEKPQASP  360
EGRPESETSS LVTTTDFQIQ TEMAATMETS IFTTEYQSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLVESG GGLVQPGGSL RLSCAASGFT  600
FSSYTLAWVR QAPGKGLEWV AAIDSSSYTY SPDTVRGRFT ISRDNAKNSL YLQMNSLRAE  660
DTAVYYCARD SNWDALDYWG CGTTVTVSSG GGGSGGGGSG GGGSDIQMTQ SPSSLSASVG  720
DRVTITCKAR EKLWSAVAWY QQKPGKCPKA LIYSASFRYS GVPSRFSGSG SGTDFTLTIS  780
SLQPEDFATY YCQQYYTYPY TFGGGTKVEI K                                811

SEQ ID NO: 313          moltype = AA  length = 811
FEATURE              Location/Qualifiers
source               1..811
                     mol_type = protein
                     organism = synthetic construct
SEQUENCE: 313
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEL  180
CDDDPPEIPH ATFKAMAYKE GTMLNCECKR GFRRIKSGSL YMLCTGNSSH SSWDNQCQCT  240
SSATRNTTKQ VTPQPEEQKE RKTTEMQSPM QPVDQASLPG HCREPPPWEN EATERIYHFV  300
VGQMVYYQCV QGYRALHRGP AESVCKMTHG KTRWTQPQLI CTGEMETSQF PGEEKPQASP  360
EGRPESETSS LVTTTDFQIQ TEMAATMETS IFTTEYQSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLVESG GGLVQPGGSL RLSCAASGFT  600
FSSYTLAWVR QAPGKCLEWV AAIDSSSYTY SPDTVRGRFT ISRDNAKNSL YLQMNSLRAE  660
DTAVYYCARD SNWDALDYWG QGTTVTVSSG GGGSGGGGSG GGGSDIQMTQ SPSSLSASVG  720
DRVTITCKVT EKVWGNVAWY QQKPGKAPIS LIYSPSLRKS GVPSRFSGSG SGTDFTLTIS  780
SLQPEDFATY YCQQYYTYPY TFGCGTKVEI K                                811

SEQ ID NO: 314          moltype = AA  length = 811
FEATURE              Location/Qualifiers
source               1..811
                     mol_type = protein
                     organism = synthetic construct
SEQUENCE: 314
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEL  180
CDDDPPEIPH ATFKAMAYKE GTMLNCECKR GFRRIKSGSL YMLCTGNSSH SSWDNQCQCT  240
SSATRNTTKQ VTPQPEEQKE RKTTEMQSPM QPVDQASLPG HCREPPPWEN EATERIYHFV  300
VGQMVYYQCV QGYRALHRGP AESVCKMTHG KTRWTQPQLI CTGEMETSQF PGEEKPQASP  360
EGRPESETSS LVTTTDFQIQ TEMAATMETS IFTTEYQSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLVESG GGLVQPGGSL RLSCAASGFT  600
FSSYTLAWVR QAPGKGLEWV AAIDSSSYTY SPDTVRGRFT ISRDNAKNSL YLQMNSLRAE  660
DTAVYYCARD SNWDALDYWG CGTTVTVSSG GGGSGGGGSG GGGSDIQMTQ SPSSLSASVG  720
DRVTITCKVT EKVWGNVAWY QQKPGKCPIS LIYSPSLRKS GVPSRFSGSG SGTDFTLTIS  780
SLQPEDFATY YCQQYYTYPY TFGGGTKVEI K                                811

SEQ ID NO: 315          moltype = AA  length = 691
FEATURE              Location/Qualifiers
source               1..691
                     mol_type = protein
                     organism = synthetic construct
SEQUENCE: 315
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEL  180
CDDDPPEIPH ATFKAMAYKE GTMLNCECKR GFRRIKSGSL YMLCTGNSSH SSWDNQCQCT  240
SSATRNTTKQ VTPQPEEQKE RKTTEMQSPM QPVDQASLPG HCREPPPWEN EATERIYHFV  300
VGQMVYYQCV QGYRALHRGP AESVCKMTHG KTRWTQPQLI CTGEMETSQF PGEEKPQASP  360
EGRPESETSS LVTTTDFQIQ TEMAATMETS IFTTEYQSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLLESG GGLVQPGGSL RLSCAASGSI  600
FSANAMGWYR QAPGKQRELV AVISSGGSTN YADSVKGRFT ISRDNSKNTV YLQMNSLRAE  660
```

-continued

```
DTAVYYCMYS GSYYYTPNDY WGQGTLVTVS S                               691

SEQ ID NO: 316          moltype = AA  length = 691
FEATURE                 Location/Qualifiers
source                  1..691
                        mol_type = protein
                        organism = synthetic construct
SEQUENCE: 316
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEL  180
CDDDPPEIPH ATFKAMAYKE GTMLNCECKR GFRRIKSGSL YMLCTGNSSH SSWDNQCQCT  240
SSATRNTTKQ VTPQPEEQKE RKTTEMQSPM QPVDQASLPG HCREPPPWEN EATERIYHFV  300
VGQMVYYQCV QGYRALHRGP AESVCKMTHG KTRWTQPQLI CTGEMETSQF PGEEKPQASP  360
EGRPESETSS LVTTTDFQIQ TEMAATMETS IFTTEYQSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLLESG GGLVQPGGSL RLSCAASGSI  600
FSANAMGWYR QAPGKGLELV AVISSGGSTN YADSVKGRFT ISRDNSKNTV YLQMNSLRAE  660
DTAVYYCMYS GSYYYTPNDY WGQGTLVTVS S                               691

SEQ ID NO: 317          moltype = AA  length = 792
FEATURE                 Location/Qualifiers
source                  1..792
                        mol_type = protein
                        organism = synthetic construct
SEQUENCE: 317
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLTSGGPGPA GLYAQPGSGG GGSGGGGSGG GGSGGGGSGG GGSGGGGSEL  180
CDDDPPEIPH ATFKAMAYKE GTMLNCECKR GFRRIKSGSL YMLCTGNSSH SSWDNQCQCT  240
SSATRNTTKQ VTPQPEEQKE RKTTEMQSPM QPVDQASLPG HCREPPPWEN EATERIYHFV  300
VGQMVYYQCV QGYRALHRGP AESVCKMTHG KTRWTQPQLI CTGEMETSQF PGEEKPQASP  360
EGRPESETSS LVTTTDFQIQ TEMAATMETS IFTTEYQSGG PGPAGLYAQP GSEVQLVESG  420
GGLVQPGNSL RLSCAASGFT FSKFGMSWVR QAPGKGLEWV SSISGSGRDT LYAESVKGRF  480
TISRDNAKTT LYLQMNSLRP EDTAVYYCTI GGSLSVSSQG TLVTVSSGGG GSGGGGSGGG  540
GSGGGGSGGG GSGGGGSSGG PGPAGLYAQP GSEVQLVESG GGLVQPGGSL RLSCAASGFT  600
FSSYTLAWVR QAPGKGLEWV AAIDSSSYTY SPDTVRGRFT ISRDNAKNSL YLQMNSLRAE  660
DTAVYYCARD SNWDALDYWG QGTTVTVSSA STKGPSVFPL APSSKSTSGG TAALGCLVKD  720
YFPEPVTVSW NSGALTSGVH TFPAVLQSSG LYSLSSVVTV PSSSLGTQTY ICNVNHKPSN  780
TKVDKRVEPK SC                                                    792

SEQ ID NO: 318          moltype = AA  length = 676
FEATURE                 Location/Qualifiers
source                  1..676
                        mol_type = protein
                        organism = synthetic construct
SEQUENCE: 318
EVQLVESGGG LVQPGGSLRL SCAASGFTFS SYTLAWVRQA PGKCLEWVAA IDSSSYTYSP  60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKAREK LWSAVAWYQQ KPGKAPKSLI  180
YSASFRYSGV PSRFSGSGSG TDFTLTISSL QPEDFATYYC QQYYTYPYTF GCGTKVEIKS  240
GGPGPAGLYA QPGSGGGGSG GGGSGGGGSG GGGSGGGGSG GGGSEVQLVE SGGGLVQPGN  300
SLRLSCAASG FTFSKFGMSW VRQAPGKGLE WVSSISGSGR DTLYAESVKG RFTISRDNAK  360
TTLYLQMNSL RPEDTAVYYC TIGGSLSVSS QGTLVTVSSG PGPAGLYA QPGSTFKFYM  420
PKKATELKHL QCLEEELKPL EEVLNLAQSK NFHLRPRDLI SNINVIVLEL KGSETTFMCE  480
YADETATIVE FLNRWITFCQ SIISTLTGGS SSTKKTQLQL EHLLLDLQMI LNGINNYKNP  540
KLTRMLSGGP GPAGLYAQPG SEVQLVESGG GLVQPGNSLR LSCAASGFTF SKFGMSWVRQ  600
APGKGLEWVS SISGSGRDTL YAESVKGRFT ISRDNAKTTL YLQMNSLRPE DTAVYYCTIG  660
GSLSVSSQGT LVTVSS                                               676

SEQ ID NO: 319          moltype = AA  length = 676
FEATURE                 Location/Qualifiers
source                  1..676
                        mol_type = protein
                        organism = synthetic construct
SEQUENCE: 319
EVQLVESGGG LVQPGGSLRL SCAASGFTFS SYTLAWVRQA PGKGLEWVAA IDSSSYTYSP  60
DTVRGRFTIS RDNAKNSLYL QMNSLRAEDT AVYYCARDSN WDALDYWGCG TTVTVSSGGG  120
GSGGGGSGGG GSDIQMTQSP SSLSASVGDR VTITCKAREK LWSAVAWYQQ KPGKCPKALI  180
YSASFRYSGV PSRFSGSGSG TDFTLTISSL QPEDFATYYC QQYYTYPYTF GGGTKVEIKS  240
GGPGPAGLYA QPGSGGGGSG GGGSGGGGSG GGGSGGGGSG GGGSEVQLVE SGGGLVQPGN  300
SLRLSCAASG FTFSKFGMSW VRQAPGKGLE WVSSISGSGR DTLYAESVKG RFTISRDNAK  360
TTLYLQMNSL RPEDTAVYYC TIGGSLSVSS QGTLVTVSSS GGPGPAGLYA QPGSTFKFYM  420
PKKATELKHL QCLEEELKPL EEVLNLAQSK NFHLRPRDLI SNINVIVLEL KGSETTFMCE  480
YADETATIVE FLNRWITFCQ SIISTLTGGS SSTKKTQLQL EHLLLDLQMI LNGINNYKNP  540
KLTRMLSGGP GPAGLYAQPG SEVQLVESGG GLVQPGNSLR LSCAASGFTF SKFGMSWVRQ  600
APGKGLEWVS SISGSGRDTL YAESVKGRFT ISRDNAKTTL YLQMNSLRPE DTAVYYCTIG  660
GSLSVSSQGT LVTVSS                                               676
```

-continued

```
SEQ ID NO: 320          moltype = AA  length = 676
FEATURE                 Location/Qualifiers
source                  1..676
                        mol_type = protein
                        organism = synthetic construct
SEQUENCE: 320
EVQLVESGGG LVQPGGSLRL SCAASGFTFS SYTLAWVRQA PGKCLEWVAA IDSSSYTYSP   60
DTVRGRFTIS RDNAKNSLYL QMNSLRAEDT AVYYCARDSN WDALDYWGQG TTVTVSSGGG  120
GSGGGGSGGG GSDIQMTQSP SSLSASVGDR VTITCKVTEK VWGNVAWYQQ KPGKAPISLI  180
YSPSLRKSGV PSRFSGSGSG TDFTLTISSL QPEDFATYYC QQYYTYPYTF GCGTKVEIKS  240
GGPGPAGLYA QPGSGGGGSG GGGSGGGGSG GGGSGGGGSG GGGSEVQLVE SGGGLVQPGN  300
SLRLSCAASG FTFSKFGMSW VRQAPGKGLE WVSSISGSGR DTLYAESVKG RFTISRDNAK  360
TTLYLQMNSL RPEDTAVYYC TIGGSLSVSS QGTLVTVSSS GGPGPAGLYA QPGSTFKFYM  420
PKKATELKHL QCLEEELKPL EEVLNLAQSK NFHLRPRDLI SNINIVLEL KGSETTFMCE   480
YADETATIVE FLNRWITFCQ SIISTLTGGS SSTKKTQLQL EHLLLDLQMI LNGINNYKNP  540
KLTRMLSGGP GPAGLYAQPG SEVQLVESGG GLVQPGNSLR LSCAASGFTF SKFGMSWVRQ  600
APGKGLEWVS SISGSGRDTL YAESVKGRFT ISRDNAKTTL YLQMNSLRPE DTAVYYCTIG  660
GSLSVSSQGT LVTVSS                                                 676

SEQ ID NO: 321          moltype = AA  length = 676
FEATURE                 Location/Qualifiers
source                  1..676
                        mol_type = protein
                        organism = synthetic construct
SEQUENCE: 321
EVQLVESGGG LVQPGGSLRL SCAASGFTFS SYTLAWVRQA PGKGLEWVAA IDSSSYTYSP   60
DTVRGRFTIS RDNAKNSLYL QMNSLRAEDT AVYYCARDSN WDALDYWGCG TTVTVSSGGG  120
GSGGGGSGGG GSDIQMTQSP SSLSASVGDR VTITCKVTEK VWGNVAWYQQ KPGKCPISLI  180
YSPSLRKSGV PSRFSGSGSG TDFTLTISSL QPEDFATYYC QQYYTYPYTF GGGTKVEIKS  240
GGPGPAGLYA QPGSGGGGSG GGGSGGGGSG GGGSGGGGSG GGGSEVQLVE SGGGLVQPGN  300
SLRLSCAASG FTFSKFGMSW VRQAPGKGLE WVSSISGSGR DTLYAESVKG RFTISRDNAK  360
TTLYLQMNSL RPEDTAVYYC TIGGSLSVSS QGTLVTVSSS GGPGPAGLYA QPGSTFKFYM  420
PKKATELKHL QCLEEELKPL EEVLNLAQSK NFHLRPRDLI SNINIVLEL KGSETTFMCE   480
YADETATIVE FLNRWITFCQ SIISTLTGGS SSTKKTQLQL EHLLLDLQMI LNGINNYKNP  540
KLTRMLSGGP GPAGLYAQPG SEVQLVESGG GLVQPGNSLR LSCAASGFTF SKFGMSWVRQ  600
APGKGLEWVS SISGSGRDTL YAESVKGRFT ISRDNAKTTL YLQMNSLRPE DTAVYYCTIG  660
GSLSVSSQGT LVTVSS                                                 676

SEQ ID NO: 322          moltype = AA  length = 556
FEATURE                 Location/Qualifiers
source                  1..556
                        mol_type = protein
                        organism = synthetic construct
SEQUENCE: 322
EVQLLESGGG LVQPGGSLRL SCAASGSIFS ANAMGWYRQA PGKQRELVAV ISSGGSTNYA   60
DSVKGRFTIS RDNSKNTVYL QMNSLRAEDT AVYYCMYSGS YYYTPNDYWG QGTLVTVSSS  120
GGPGPAGLYA QPGSGGGGSG GGGSGGGGSG GGGSGGGGSG GGGSEVQLVE SGGGLVQPGN  180
SLRLSCAASG FTFSKFGMSW VRQAPGKGLE WVSSISGSGR DTLYAESVKG RFTISRDNAK  240
TTLYLQMNSL RPEDTAVYYC TIGGSLSVSS QGTLVTVSSS GGPGPAGLYA QPGSTFKFYM  300
PKKATELKHL QCLEEELKPL EEVLNLAQSK NFHLRPRDLI SNINIVLEL KGSETTFMCE   360
YADETATIVE FLNRWITFCQ SIISTLTGGS SSTKKTQLQL EHLLLDLQMI LNGINNYKNP  420
KLTRMLSGGP GPAGLYAQPG SEVQLVESGG GLVQPGNSLR LSCAASGFTF SKFGMSWVRQ  480
APGKGLEWVS SISGSGRDTL YAESVKGRFT ISRDNAKTTL YLQMNSLRPE DTAVYYCTIG  540
GSLSVSSQGT LVTVSS                                                 556

SEQ ID NO: 323          moltype = AA  length = 556
FEATURE                 Location/Qualifiers
source                  1..556
                        mol_type = protein
                        organism = synthetic construct
SEQUENCE: 323
EVQLLESGGG LVQPGGSLRL SCAASGSIFS ANAMGWYRQA PGKGLELVAV ISSGGSTNYA   60
DSVKGRFTIS RDNSKNTVYL QMNSLRAEDT AVYYCMYSGS YYYTPNDYWG QGTLVTVSSS  120
GGPGPAGLYA QPGSGGGGSG GGGSGGGGSG GGGSGGGGSG GGGSEVQLVE SGGGLVQPGN  180
SLRLSCAASG FTFSKFGMSW VRQAPGKGLE WVSSISGSGR DTLYAESVKG RFTISRDNAK  240
TTLYLQMNSL RPEDTAVYYC TIGGSLSVSS QGTLVTVSSS GGPGPAGLYA QPGSTFKFYM  300
PKKATELKHL QCLEEELKPL EEVLNLAQSK NFHLRPRDLI SNINIVLEL KGSETTFMCE   360
YADETATIVE FLNRWITFCQ SIISTLTGGS SSTKKTQLQL EHLLLDLQMI LNGINNYKNP  420
KLTRMLSGGP GPAGLYAQPG SEVQLVESGG GLVQPGNSLR LSCAASGFTF SKFGMSWVRQ  480
APGKGLEWVS SISGSGRDTL YAESVKGRFT ISRDNAKTTL YLQMNSLRPE DTAVYYCTIG  540
GSLSVSSQGT LVTVSS                                                 556

SEQ ID NO: 324          moltype = AA  length = 657
FEATURE                 Location/Qualifiers
source                  1..657
                        mol_type = protein
                        organism = synthetic construct
SEQUENCE: 324
```

-continued

```
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKRVEPKSC SGGPGPAGLY AQPGSGGGGS   240
GGGGSGGGGS GGGGSGGGGS GGGGSEVQLV ESGGGLVQPG NSLRLSCAAS GFTFSKFGMS   300
WVRQAPGKGL EWVSSISGSG RDTLYAESVK GRFTISRDNA KTTLYLQMNS LRPEDTAVYY   360
CTIGGSLSVS SQGTLVTVSS SGGPGPAGLY AQPGSTFKFY MPKKATELKH LQCLEEELKP   420
LEEVLNLAQS KNFHLRPRDL ISNINVIVLE LKGSETTFMC EYADETATIV EFLNRWITFC   480
QSIISTLTGG SSSTKKTQLQ LEHLLLDLQM ILNGINNYKN PKLTRMLSGG PGPAGLYAQP   540
GSEVQLVESG GGLVQPGNSL RLSCAASGFT FSKFGMSWVR QAPGKGLEWV SSISGSGRDT   600
LYAESVKGRF TISRDNAKTT LYLQMNSLRP EDTAVYYCTI GGSLSVSSQG TLVTVSS      657

SEQ ID NO: 325           moltype = AA   length = 640
FEATURE                  Location/Qualifiers
source                   1..640
                         mol_type = protein
                         organism = synthetic construct
SEQUENCE: 325
VPRDCGCKPC ICTVPEVSSV FIFPPKPKDV LTITLTPKVT CVVVDISKDD PEVQFSWFVD    60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGLYAQP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPG PAGLYAQPGS   420
EVQLVESGGG LVQPGGSLRL SCAASGFTFS SYTLAWVRQA PGKGLEWVAA IDSSSYTYSP   480
DTVRGRFTIS RDNAKNSLYL QMNSLRAEDT AVYYCARDSN WDALDYWGQG TTVTVSSAST   540
KGPSVFPLAP SSKSTSGGTA ALGCLVKDYF PEPVTVSWNS GALTSGVHTF PAVLQSSGLY   600
SLSSVVTVPS SSLGTQTYIC NVNHKPSNTK VDKRVEPKSC                        640

SEQ ID NO: 326           moltype = AA   length = 659
FEATURE                  Location/Qualifiers
source                   1..659
                         mol_type = protein
                         organism = synthetic construct
SEQUENCE: 326
VPRDCGCKPC ICTVPEVSSV FIFPPKPKDV LTITLTPKVT CVVVDISKDD PEVQFSWFVD    60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGLYAQP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPG PAGLYAQPGS   420
EVQLVESGGG LVQPGGSLRL SCAASGFTFS SYTLAWVRQA PGKCLEWVAA IDSSSYTYSP   480
DTVRGRFTIS RDNAKNSLYL QMNSLRAEDT AVYYCARDSN WDALDYWGQG TTVTVSSGGG   540
GSGGGGSGGG GSDIQMTQSP SSLSASVGDR VTITCKAREK LWSAVAWYQQ KPGKAPKALI   600
YSASFRYSGV PSRFSGSGSG TDFTLTISSL QPEDFATYYC QQYYTYPYTF GCGTKVEIK    659

SEQ ID NO: 327           moltype = AA   length = 659
FEATURE                  Location/Qualifiers
source                   1..659
                         mol_type = protein
                         organism = synthetic construct
SEQUENCE: 327
VPRDCGCKPC ICTVPEVSSV FIFPPKPKDV LTITLTPKVT CVVVDISKDD PEVQFSWFVD    60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGLYAQP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPG PAGLYAQPGS   420
EVQLVESGGG LVQPGGSLRL SCAASGFTFS SYTLAWVRQA PGKCLEWVAA IDSSSYTYSP   480
DTVRGRFTIS RDNAKNSLYL QMNSLRAEDT AVYYCARDSN WDALDYWGQG TTVTVSSGGG   540
GSGGGGSGGG GSDIQMTQSP SSLSASVGDR VTITCKAREK LWSAVAWYQQ KPGKAPKSLI   600
YSASFRYSGV PSRFSGSGSG TDFTLTISSL QPEDFATYYC QQYYTYPYTF GCGTKVEIK    659

SEQ ID NO: 328           moltype = AA   length = 659
FEATURE                  Location/Qualifiers
source                   1..659
                         mol_type = protein
                         organism = synthetic construct
SEQUENCE: 328
VPRDCGCKPC ICTVPEVSSV FIFPPKPKDV LTITLTPKVT CVVVDISKDD PEVQFSWFVD    60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGLYAQP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPG PAGLYAQPGS   420
```

-continued

```
EVQLVESGGG LVQPGGSLRL SCAASGFTFS SYTLAWVRQA PGKGLEWVAA IDSSSYTYSP   480
DTVRGRFTIS RDNAKNSLYL QMNSLRAEDT AVYYCARDSN WDALDYWGCG TTVTVSSGGG   540
GSGGGGSGGG GSDIQMTQSP SSLSASVGDR VTITCKAREK LWSAVAWYQQ KPGKCPKALI   600
YSASFRYSGV PSRFSGSGSG TDFTLTISSL QPEDFATYYC QQYYTYPYTF GGGTKVEIK    659

SEQ ID NO: 329          moltype = AA   length = 659
FEATURE                 Location/Qualifiers
source                  1..659
                        mol_type = protein
                        organism = synthetic construct
SEQUENCE: 329
VPRDCGCKPC ICTVPEVSSV FIFPPKPKDV LTITLTPKVT CVVVDISKDD PEVQFSWFVD   60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGLYAQP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPG PAGLYAQPGS   420
EVQLVESGGG LVQPGGSLRL SCAASGFTFS SYTLAWVRQA PGKCLEWVAA IDSSSYTYSP   480
DTVRGRFTIS RDNAKNSLYL QMNSLRAEDT AVYYCARDSN WDALDYWQCG TTVTVSSGGG   540
GSGGGGSGGG GSDIQMTQSP SSLSASVGDR VTITCKVTEK VWGNVAWYQQ KPGKAPISLI   600
YSPSLRKSGV PSRFSGSGSG TDFTLTISSL QPEDFATYYC QQYYTYPYTF GCGTKVEIK    659

SEQ ID NO: 330          moltype = AA   length = 659
FEATURE                 Location/Qualifiers
source                  1..659
                        mol_type = protein
                        organism = synthetic construct
SEQUENCE: 330
VPRDCGCKPC ICTVPEVSSV FIFPPKPKDV LTITLTPKVT CVVVDISKDD PEVQFSWFVD   60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGLYAQP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPG PAGLYAQPGS   420
EVQLVESGGG LVQPGGSLRL SCAASGFTFS SYTLAWVRQA PGKGLEWVAA IDSSSYTYSP   480
DTVRGRFTIS RDNAKNSLYL QMNSLRAEDT AVYYCARDSN WDALDYWGCG TTVTVSSGGG   540
GSGGGGSGGG GSDIQMTQSP SSLSASVGDR VTITCKVTEK VWGNVAWYQQ KPGKCPISLI   600
YSPSLRKSGV PSRFSGSGSG TDFTLTISSL QPEDFATYYC QQYYTYPYTF GGGTKVEIK    659

SEQ ID NO: 331          moltype = AA   length = 539
FEATURE                 Location/Qualifiers
source                  1..539
                        mol_type = protein
                        organism = synthetic construct
SEQUENCE: 331
VPRDCGCKPC ICTVPEVSSV FIFPPKPKDV LTITLTPKVT CVVVDISKDD PEVQFSWFVD   60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGLYAQP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPG PAGLYAQPGS   420
EVQLLESGGG LVQPGGSLRL SCAASGSIFS ANAMGWYRQA PGKQRELVAV ISSGGSTNYA   480
DSVKGRFTIS RDNSKNTVYL QMNSLRAEDT AVYYCMYSGS YYYTPNDYWG QGTLVTVSS    539

SEQ ID NO: 332          moltype = AA   length = 463
FEATURE                 Location/Qualifiers
source                  1..463
                        mol_type = protein
                        organism = synthetic construct
SEQUENCE: 332
ELCDDDPPEI PHATFKAMAY KEGTMLNCEC KRGFRRIKSG SLYMLCTGNS SHSSWDNQCQ   60
CTSSATRNTT KQVTPQPEEQ KERKTTEMQS PMQPVDQASL PGHCREPPPW ENEATERIYH   120
FVVGQMVYYQ CVQGYRALHR GPAESVCKMT HGKTRWTQPQ LICTGEMETS QFPGEEKPQA   180
SPEGRPESET SSLVTTTDFQ IQTEMAATME TSIFTTEYQG GGGSGGGGSG GGGSGGGGSG   240
GGGSGGGGSD IQMTQSPSSL SASVGDRVTI TCKAREKLWS AVAWYQQKPG KAPKSLIYSA   300
SFRYSGVPSR FSGSGSGTDF TLTISSLQPE DFATYYCQQY YTYPYTFGGG TKVEIKRTVA   360
APSVFIFPPS DEQLKSGTAS VVCLLNNFYP REAKVQWKVD NALQSGNSQE SVTEQDSKDS   420
TYSLSSTLTL SKADYEKHKV YACEVTHQGL SSPVTKSFNR GEC                     463

SEQ ID NO: 333          moltype = AA   length = 463
FEATURE                 Location/Qualifiers
source                  1..463
                        mol_type = protein
                        organism = synthetic construct
SEQUENCE: 333
ELCDDDPPEI PHATFKAMAY KEGTMLNCEC KRGFRRIKSG SLYMLCTGNS SHSSWDNQCQ   60
```

```
CTSSATRNTT KQVTPQPEEQ KERKTTEMQS PMQPVDQASL PGHCREPPPW ENEATERIYH    120
FVVGQMVYYQ CVQGYRALHR GPAESVCKMT HGKTRWTQPQ LICTGEMETS QFPGEEKPQA    180
SPEGRPESET SSLVTTTDFQ IQTEMAATME TSIFTTEYQG GGGSGGGGSG GGGSGGGGSG    240
GGGSGGGGSD IQMTQSPSSL SASVGDRVTI TCKVTEKVWG NVAWYQQKPG KAPISLIYSP    300
SLRKSGVPSR FSGSGSGTDF TLTISSLQPE DFATYYCQQY YTYPYTFGGG TKVEIKRTVA    360
APSVFIFPPS DEQLKSGTAS VVCLLNNFYP REAKVQWKVD NALQSGNSQE SVTEQDSKDS    420
TYSLSSTLTL SKADYEKHKV YACEVTHQGL SSPVTKSFNR GEC                     463

SEQ ID NO: 334          moltype = AA  length = 811
FEATURE                 Location/Qualifiers
source                  1..811
                        mol_type = protein
                        organism = synthetic construct
SEQUENCE: 334
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSGG GGSGGGGSGG GGSGGGGSGG GGSGGGGSEV    180
QLVESGGGLV QPGGSLRLSC AASGFTFSSY TLAWVRQAPG KCLEWVAAID SSSYTYSPDT    240
VRGRFTISRD NAKNSLYLQM NSLRAEDTAV YYCARDSNWD ALDYWGQGTT VTVSSGGGGS    300
GGGGSGGGGS DIQMTQSPSS LSASVGDRVT ITCKAREKLW SAVAWYQQKP GKAPKSLIYS    360
ASFRYSGVPS RFSGSGSGTD FTLTISSLQP EDFATYYCQQ YYTYPYTFGG GTKVEIKGGG    420
GSGGGGSGGG GSGGGGSGGG GSGGGGSGGG GSELCDDDPP EIPHATFKAM             480
AYKEGTMLNC ECKRGFRRIK SGSLYMLCTG NSSHSSWDNQ CQCTSSATRN TTKQVTPQPE    540
EQKERKTTEM QSPMQPVDQA SLPGHCREPP PWENEATERI YHFVVGQMVY YQCVQGYRAL    600
HRGPAESVCK MTHGKTRWTQ PQLICTGEME TSQFPGEEKP QASPEGRPES ETSSLVTTTD    660
FQIQTEMAAT METSIFTTEY QSGGGPGPAGL YAQPGSEVQL VESGGGLVQP GNSLRLSCAA    720
SGFTFSKFGM SWVRQAPGKG LEWVSSISGS GRDTLYAESV KGRFTISRDN AKTTLYLQMN    780
SLRPEDTAVY YCTIGGSLSV SSQGTLVTVS S                                  811

SEQ ID NO: 335          moltype = AA  length = 811
FEATURE                 Location/Qualifiers
source                  1..811
                        mol_type = protein
                        organism = synthetic construct
SEQUENCE: 335
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSGG GGSGGGGSGG GGSGGGGSGG GGSGGGGSEV    180
QLVESGGGLV QPGGSLRLSC AASGFTFSSY TLAWVRQAPG KGLEWVAAID SSSYTYSPDT    240
VRGRFTISRD NAKNSLYLQM NSLRAEDTAV YYCARDSNWD ALDYWGQGTT VTVSSGGGGS    300
GGGGSGGGGS DIQMTQSPSS LSASVGDRVT ITCKAREKLW SAVAWYQQKP GKCPKALIYS    360
ASFRYSGVPS RFSGSGSGTD FTLTISSLQP EDFATYYCQQ YYTYPYTFGG GTKVEIKGGG    420
GSGGGGSGGG GSGGGGSGGG GSGGGGSGGG GSELCDDDPP EIPHATFKAM             480
AYKEGTMLNC ECKRGFRRIK SGSLYMLCTG NSSHSSWDNQ CQCTSSATRN TTKQVTPQPE    540
EQKERKTTEM QSPMQPVDQA SLPGHCREPP PWENEATERI YHFVVGQMVY YQCVQGYRAL    600
HRGPAESVCK MTHGKTRWTQ PQLICTGEME TSQFPGEEKP QASPEGRPES ETSSLVTTTD    660
FQIQTEMAAT METSIFTTEY QSGGGPGPAGL YAQPGSEVQL VESGGGLVQP GNSLRLSCAA    720
SGFTFSKFGM SWVRQAPGKG LEWVSSISGS GRDTLYAESV KGRFTISRDN AKTTLYLQMN    780
SLRPEDTAVY YCTIGGSLSV SSQGTLVTVS S                                  811

SEQ ID NO: 336          moltype = AA  length = 811
FEATURE                 Location/Qualifiers
source                  1..811
                        mol_type = protein
                        organism = synthetic construct
SEQUENCE: 336
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSGG GGSGGGGSGG GGSGGGGSGG GGSGGGGSEV    180
QLVESGGGLV QPGGSLRLSC AASGFTFSSY TLAWVRQAPG KCLEWVAAID SSSYTYSPDT    240
VRGRFTISRD NAKNSLYLQM NSLRAEDTAV YYCARDSNWD ALDYWGQGTT VTVSSGGGGS    300
GGGGSGGGGS DIQMTQSPSS LSASVGDRVT ITCKVTEKVW GNVAWYQQKP GKAPISLIYS    360
PSLRKSGVPS RFSGSGSGTD FTLTISSLQP EDFATYYCQQ YYTYPYTFGC GTKVEIKGGG    420
GSGGGGSGGG GSGGGGSGGG GSGGGGSGGG GSELCDDDPP EIPHATFKAM             480
AYKEGTMLNC ECKRGFRRIK SGSLYMLCTG NSSHSSWDNQ CQCTSSATRN TTKQVTPQPE    540
EQKERKTTEM QSPMQPVDQA SLPGHCREPP PWENEATERI YHFVVGQMVY YQCVQGYRAL    600
HRGPAESVCK MTHGKTRWTQ PQLICTGEME TSQFPGEEKP QASPEGRPES ETSSLVTTTD    660
FQIQTEMAAT METSIFTTEY QSGGGPGPAGL YAQPGSEVQL VESGGGLVQP GNSLRLSCAA    720
SGFTFSKFGM SWVRQAPGKG LEWVSSISGS GRDTLYAESV KGRFTISRDN AKTTLYLQMN    780
SLRPEDTAVY YCTIGGSLSV SSQGTLVTVS S                                  811

SEQ ID NO: 337          moltype = AA  length = 811
FEATURE                 Location/Qualifiers
source                  1..811
                        mol_type = protein
                        organism = synthetic construct
SEQUENCE: 337
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
```

```
WITFCQSIIS TLTSGGPGPA GLYAQPGSGG GGSGGGGSGG GGSGGGGSGG GGSGGGGSEV   180
QLVESGGGLV QPGGSLRLSC AASGFTFSSY TLAWVRQAPG KGLEWVAAID SSSYTYSPDT   240
VRGRFTISRD NAKNSLYLQM NSLRAEDTAV YYCARDSNWD ALDYWGCGTT VTVSSGGGGS   300
GGGGSGGGGS DIQMTQSPSS LSASVGDRVT ITCKVTEKVW GNVAWYQQKP GKCPISLIYS   360
PSLRKSGVPS RFSGSGSGTD FTLTISSLQP EDFATYYCQQ YYTYPYTFGG GTKVEIKGGG   420
GSGGGGSGGG GSGGGGSGGG GSGGGGSGGG GSELCDDDPP EIPHATFKAM   480
AYKEGTMLNC ECKRGFRRIK SGSLYMLCTG NSSHSSWDNQ CQCTSSATRN TTKQVTPQPE   540
EQKERKTTEM QSPMQPVDQA SLPGHCREPP PWENEATERI YHFVVGQMVY YQCVQGYRAL   600
HRGPAESVCK MTHGKTRWTQ PQLICTGEME TSQFPGEEKP QASPEGRPES ETSSLVTTTD   660
FQIQTEMAAT METSIFTTEY QSGGPGPAGL YAQPGSEVQL VESGGGLVQP GNSLRLSCAA   720
SGFTFSKFGM SWVRQAPGKG LEWVSSISGS GRDTLYAESV KGRFTISRDN AKTTLYLQMN   780
SLRPEDTAVY YCTIGGSLSV SSQGTLVTVS S   811
```

```
SEQ ID NO: 338          moltype = AA  length = 691
FEATURE                 Location/Qualifiers
source                  1..691
                        mol_type = protein
                        organism = synthetic construct
SEQUENCE: 338
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR   120
WITFCQSIIS TLTSGGPGPA GLYAQPGSGG GGSGGGGSGG GGSGGGGSEV   180
QLLESGGGLV QPGGSLRLSC AASGSIFSAN AMGWYRQAPG KQRELVAVIS SGGSTNYADS   240
VKGRFTISRD NSKNTVYLQM NSLRAEDTAV YYCMYSGSYY YTPNDYWGQG TLVTVSSGGG   300
GSGGGGSGGG GSGGGGSGGG GSGGGGSGGG GSELCDDDPP EIPHATFKAM   360
AYKEGTMLNC ECKRGFRRIK SGSLYMLCTG NSSHSSWDNQ CQCTSSATRN TTKQVTPQPE   420
EQKERKTTEM QSPMQPVDQA SLPGHCREPP PWENEATERI YHFVVGQMVY YQCVQGYRAL   480
HRGPAESVCK MTHGKTRWTQ PQLICTGEME TSQFPGEEKP QASPEGRPES ETSSLVTTTD   540
FQIQTEMAAT METSIFTTEY QSGGPGPAGL YAQPGSEVQL VESGGGLVQP GNSLRLSCAA   600
SGFTFSKFGM SWVRQAPGKG LEWVSSISGS GRDTLYAESV KGRFTISRDN AKTTLYLQMN   660
SLRPEDTAVY YCTIGGSLSV SSQGTLVTVS S   691
```

```
SEQ ID NO: 339          moltype = AA  length = 691
FEATURE                 Location/Qualifiers
source                  1..691
                        mol_type = protein
                        organism = synthetic construct
SEQUENCE: 339
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR   120
WITFCQSIIS TLTSGGPGPA GLYAQPGSGG GGSGGGGSGG GGSGGGGSGG GGSGGGGSEV   180
QLLESGGGLV QPGGSLRLSC AASGSIFSAN AMGWYRQAPG KGLELVAVIS SGGSTNYADS   240
VKGRFTISRD NSKNTVYLQM NSLRAEDTAV YYCMYSGSYY YTPNDYWGQG TLVTVSSGGG   300
GSGGGGSGGG GSGGGGSGGG GSGGGGSGGG GSELCDDDPP EIPHATFKAM   360
AYKEGTMLNC ECKRGFRRIK SGSLYMLCTG NSSHSSWDNQ CQCTSSATRN TTKQVTPQPE   420
EQKERKTTEM QSPMQPVDQA SLPGHCREPP PWENEATERI YHFVVGQMVY YQCVQGYRAL   480
HRGPAESVCK MTHGKTRWTQ PQLICTGEME TSQFPGEEKP QASPEGRPES ETSSLVTTTD   540
FQIQTEMAAT METSIFTTEY QSGGPGPAGL YAQPGSEVQL VESGGGLVQP GNSLRLSCAA   600
SGFTFSKFGM SWVRQAPGKG LEWVSSISGS GRDTLYAESV KGRFTISRDN AKTTLYLQMN   660
SLRPEDTAVY YCTIGGSLSV SSQGTLVTVS S   691
```

```
SEQ ID NO: 340          moltype = AA  length = 811
FEATURE                 Location/Qualifiers
source                  1..811
                        mol_type = protein
                        organism = synthetic construct
SEQUENCE: 340
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG   120
PAGLYAQPGS EVQLVESGGG LVQPGGSLRL SCAASGFTFS SYTLAWVRQA PGKCLEWVAA   180
IDSSSYTYSP DTVRGRFTIS RDNAKNSLYL QMNSLRAEDT AVYYCARDSN WDALDYWGQG   240
TTVTVSSGGG GSGGGGSGGG GSDIQMTQSP SSLSASVGDR VTITCKAREK LWSAVAWYQQ   300
KPGKAPKSLI YSASFRYSGV PSRFSGSGSG TDFTLTISSL QPEDFATYYC QQYYTYPYTF   360
GCGTKVEIKG GGGSGGGGSG GGGSGGGGSG GGGSGGGGSG GGGSELCDDD   420
PPEIPHATFK AMAYKEGTML NCECKRGFRR IKSGSLYMLC TGNSSHSSWD NQCQCTSSAT   480
RNTTKQVTPQ PEEQKERKTT EMQSPMQPVD QASLPGHCRE PPPWENEATE RIYHFVVGQM   540
VYYQCVQGYR ALHRGPAESV CKMTHGKTRW TQPQLICTGE METSQFPGEE KPQASPEGRP   600
ESETSSLVTT TDFQIQTEMA ATMETSIFTT EYQGGGGSGG GGSGGGGSGG GGSGGGGSGG   660
GGSSGGPGPA GLYAQPGSAP TSSSTKKTQL QLEHLLLDLQ MILNGINNYK NPKLTRMLTF   720
KFYMPKKATE LKHLQCLEEE LKPLEEVLNL AQSKNFHLRP RDLISNINVI VLELKGSETT   780
FMCEYADETA TIVEFLNRWI TFCQSIISTL T   811
```

```
SEQ ID NO: 341          moltype = AA  length = 811
FEATURE                 Location/Qualifiers
source                  1..811
                        mol_type = protein
                        organism = synthetic construct
SEQUENCE: 341
EVQLVESGGG LVQPGNSLRL SCAASGFTFS KFGMSWVRQA PGKGLEWVSS ISGSGRDTLY   60
```

```
AESVKGRFTI SRDNAKTTLY LQMNSLRPED TAVYYCTIGG SLSVSSQGTL VTVTSSSGGPG  120
PAGLYAQPGS EVQLVESGGG LVQPGGSLRL SCAASGFTFS SYTLAWVRQA PGKGLEWVAA  180
IDSSSYTYSP DTVRGRFTIS RDNAKNSLYL QMNSLRAEDT AVYYCARDSN WDALDYWGCG  240
TTVTVSSGGG GSGGGGSGGG GSDIQMTQSP SSLSASVGDR VTITCKAREK LWSAVAWYQQ  300
KPGKCPKALI YSASFRYSGV PSRFSGSGSG TDFTLTISSL QPEDFATYYC QQYYTYPYTF  360
GGGTKVEIKG GGGSGGGGSG GGGSGGGGSG GGGSGGGGSG GGGSGGGGSG GGGSELCDDD  420
PPEIPHATFK AMAYKEGTML NCECKRGFRR IKSGSLYMLC TGNSSHSSWD NQCQCTSSAT  480
RNTTKQVTPQ PEEQKERKTT EMQSPMQPVD QASLPGHCRE PPPWENEATE RIYHFVVGQM  540
VYYQCVQGYR ALHRGPAESV CKMTHGKTRW TQPQLICTGE METSQFPGEE KPQASPEGRP  600
ESETSSLVTT TDFQIQTEMA ATMETSIFTT EYQGGGGSGG GGGSGGGGSG GGSGGGGSGG  660
GGGSSGGPGA GLYAQPGSAP TSSSTKKTQL QLEHLLLDLQ MILNGINNYK NPKLTRMLTF  720
KFYMPKKATE LKHLQCLEEE LKPLEEVLNL AQSKNFHLRP RDLISNINVI VLELKGSETT  780
FMCEYADETA TIVEFLNRWI TFCQSIISTL T                                811

SEQ ID NO: 342            moltype = AA  length = 811
FEATURE                   Location/Qualifiers
source                    1..811
                          mol_type = protein
                          organism = synthetic construct
SEQUENCE: 342
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS EVQLVESGGG LVQPGGSLRL SCAASGFTFS SYTLAWVRQA PGKCLEWVAA  180
IDSSSYTYSP DTVRGRFTIS RDNAKNSLYL QMNSLRAEDT AVYYCARDSN WDALDYWGQG  240
TTVTVSSGGG GSGGGGSGGG GSDIQMTQSP SSLSASVGDR VTITCKVTEK VWGNVAWYQQ  300
KPGKAPISLI YSPSLRKSGV PSRFSGSGSG TDFTLTISSL QPEDFATYYC QQYYTYPYTF  360
GCGTKVEIKG GGGSGGGGSG GGGSGGGGSG GGGSGGGGSG GGGSGGGGSG GGGSELCDDD  420
PPEIPHATFK AMAYKEGTML NCECKRGFRR IKSGSLYMLC TGNSSHSSWD NQCQCTSSAT  480
RNTTKQVTPQ PEEQKERKTT EMQSPMQPVD QASLPGHCRE PPPWENEATE RIYHFVVGQM  540
VYYQCVQGYR ALHRGPAESV CKMTHGKTRW TQPQLICTGE METSQFPGEE KPQASPEGRP  600
ESETSSLVTT TDFQIQTEMA ATMETSIFTT EYQGGGGSGG GGGSGGGGSG GGSGGGGSGG  660
GGGSSGGPGA GLYAQPGSAP TSSSTKKTQL QLEHLLLDLQ MILNGINNYK NPKLTRMLTF  720
KFYMPKKATE LKHLQCLEEE LKPLEEVLNL AQSKNFHLRP RDLISNINVI VLELKGSETT  780
FMCEYADETA TIVEFLNRWI TFCQSIISTL T                                811

SEQ ID NO: 343            moltype = AA  length = 811
FEATURE                   Location/Qualifiers
source                    1..811
                          mol_type = protein
                          organism = synthetic construct
SEQUENCE: 343
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS EVQLVESGGG LVQPGGSLRL SCAASGFTFS SYTLAWVRQA PGKGLEWVAA  180
IDSSSYTYSP DTVRGRFTIS RDNAKNSLYL QMNSLRAEDT AVYYCARDSN WDALDYWGCG  240
TTVTVSSGGG GSGGGGSGGG GSDIQMTQSP SSLSASVGDR VTITCKVTEK VWGNVAWYQQ  300
KPGKCPISLI YSPSLRKSGV PSRFSGSGSG TDFTLTISSL QPEDFATYYC QQYYTYPYTF  360
GGGTKVEIKG GGGSGGGGSG GGGSGGGGSG GGGSGGGGSG GGGSGGGGSG GGGSELCDDD  420
PPEIPHATFK AMAYKEGTML NCECKRGFRR IKSGSLYMLC TGNSSHSSWD NQCQCTSSAT  480
RNTTKQVTPQ PEEQKERKTT EMQSPMQPVD QASLPGHCRE PPPWENEATE RIYHFVVGQM  540
VYYQCVQGYR ALHRGPAESV CKMTHGKTRW TQPQLICTGE METSQFPGEE KPQASPEGRP  600
ESETSSLVTT TDFQIQTEMA ATMETSIFTT EYQGGGGSGG GGGSGGGGSG GGSGGGGSGG  660
GGGSSGGPGA GLYAQPGSAP TSSSTKKTQL QLEHLLLDLQ MILNGINNYK NPKLTRMLTF  720
KFYMPKKATE LKHLQCLEEE LKPLEEVLNL AQSKNFHLRP RDLISNINVI VLELKGSETT  780
FMCEYADETA TIVEFLNRWI TFCQSIISTL T                                811

SEQ ID NO: 344            moltype = AA  length = 691
FEATURE                   Location/Qualifiers
source                    1..691
                          mol_type = protein
                          organism = synthetic construct
SEQUENCE: 344
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGLYAQPGS EVQLLESGGG LVQPGGSLRL SCAASGSIFS ANAMGWYRQA PGKQRELVAV  180
ISSGGSTNYA DSVKGRFTIS RDNSKNTVYL QMNSLRAEDT AVYYCMYSGS YYYTPNDYWG  240
QGTLVTVSSG GGGSGGGGSG GGGSGGGGSG GGGSGGGGSG GGGSGGGGSG GGGSELCDDD  300
PPEIPHATFK AMAYKEGTML NCECKRGFRR IKSGSLYMLC TGNSSHSSWD NQCQCTSSAT  360
RNTTKQVTPQ PEEQKERKTT EMQSPMQPVD QASLPGHCRE PPPWENEATE RIYHFVVGQM  420
VYYQCVQGYR ALHRGPAESV CKMTHGKTRW TQPQLICTGE METSQFPGEE KPQASPEGRP  480
ESETSSLVTT TDFQIQTEMA ATMETSIFTT EYQGGGGSGG GGGSGGGGSG GGSGGGGSGG  540
GGGSSGGPGA GLYAQPGSAP TSSSTKKTQL QLEHLLLDLQ MILNGINNYK NPKLTRMLTF  600
KFYMPKKATE LKHLQCLEEE LKPLEEVLNL AQSKNFHLRP RDLISNINVI VLELKGSETT  660
FMCEYADETA TIVEFLNRWI TFCQSIISTL T                                691

SEQ ID NO: 345            moltype = AA  length = 691
FEATURE                   Location/Qualifiers
source                    1..691
                          mol_type = protein
```

-continued

```
                            organism = synthetic construct
SEQUENCE: 345
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGLYAQPGS EVQLLESGGG LVQPGGSLRL SCAASGSIFS ANAMGWYRQA PGKGLELVAV   180
ISSGGSTNYA DSVKGRFTIS RDNSKNTVYL QMNSLRAEDT AVYYCMYSGS YYYTPNDYWG   240
QGTLVTVSSG GGGSGGGGSG GGGSGGGGSG GGGSGGGGSG GGGSELCDDD              300
PPEIPHATFK AMAYKEGTML NCECKRGFRR IKGSLYMLC TGNSSHSSWD NQCQCTSSAT    360
RNTTKQVTPQ PEEQKERKTT EMQSPMQPVD QASLPGHCRE PPPWENEATE RIYHFVVGQM   420
VYYQCVQGYR ALHRGPAESV CKMTHGKTRW TQPQLICTGE METSQFPGEE KPQASPEGRP   480
ESETSSLVTT TDFQIQTEMA ATMETSIFTT EYQGGGGSGG GGSGGGGSGG GGSGGGGSGG   540
GGSSGGPGPA GLYAQPGSAP TSSSTKKTQL QLEHLLLDLQ MILNGINNYK NPKLTRMLTF   600
KFYMPKKATE LKHLQCLEEE LKPLEEVLNL AQSKNFHLRP RDLISNINVI VLELKGSETT   660
FMCEYADETA TIVEFLNRWI TFCQSIISTL T                                  691

SEQ ID NO: 346       moltype = AA  length = 696
FEATURE              Location/Qualifiers
source               1..696
                     mol_type = protein
                     organism = synthetic construct
SEQUENCE: 346
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KCLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKAREKLW SAVAWYQQKP   480
GKAPKSLIYS ASFRYSGVPS RFSGSGSGTD FTLTISSLQP EDFATYYCQQ YYTYPYTFGC   540
GTKVEIKGGG GSGGGGSGGG GSGGGGSGGG GSGGGGSEVQ LLESGGGLVQ PGGSLRLSCA   600
ASGSIFSANA MGWYRQAPGK QRELVAVISS GGSTNYADSV KGRFTISRDN SKNTVYLQMN   660
SLRAEDTAVY YCMYSGSYYY TPNDYWGQGT LVTVSS                             696

SEQ ID NO: 347       moltype = AA  length = 696
FEATURE              Location/Qualifiers
source               1..696
                     mol_type = protein
                     organism = synthetic construct
SEQUENCE: 347
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKAREKLW SAVAWYQQKP   480
GKCPKALIYS ASFRYSGVPS RFSGSGSGTD FTLTISSLQP EDFATYYCQQ YYTYPYTFGG   540
GTKVEIKGGG GSGGGGSGGG GSGGGGSGGG GSGGGGSEVQ LLESGGGLVQ PGGSLRLSCA   600
ASGSIFSANA MGWYRQAPGK QRELVAVISS GGSTNYADSV KGRFTISRDN SKNTVYLQMN   660
SLRAEDTAVY YCMYSGSYYY TPNDYWGQGT LVTVSS                             696

SEQ ID NO: 348       moltype = AA  length = 696
FEATURE              Location/Qualifiers
source               1..696
                     mol_type = protein
                     organism = synthetic construct
SEQUENCE: 348
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KCLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKVTEKVW GNVAWYQQKP   480
GKAPISLIYS PSLRKSGVPS RFSGSGSGTD FTLTISSLQP EDFATYYCQQ YYTYPYTFGC   540
GTKVEIKGGG GSGGGGSGGG GSGGGGSGGG GSGGGGSEVQ LLESGGGLVQ PGGSLRLSCA   600
ASGSIFSANA MGWYRQAPGK QRELVAVISS GGSTNYADSV KGRFTISRDN SKNTVYLQMN   660
SLRAEDTAVY YCMYSGSYYY TPNDYWGQGT LVTVSS                             696

SEQ ID NO: 349       moltype = AA  length = 696
FEATURE              Location/Qualifiers
source               1..696
                     mol_type = protein
                     organism = synthetic construct
SEQUENCE: 349
APTSSSTKKT QLQLEHLLLD LQMILNGINN YKNPKLTRML TFKFYMPKKA TELKHLQCLE    60
```

-continued

```
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGCGTT    420
VTVSSGGGGS GGGGSGGGGS DIQMTQSPSS LSASVGDRVT ITCKVTEKVW GNVAWYQQKP    480
GKCPISLIYS PSLRKSGVPS RFSGSGSGTD FTLTISSLQP EDFATYYCQQ YYTYPYTFGG    540
GTKVEIKGGG GSGGGGSGGG GSGGGGSGGG GSGGGGSEVQ LLESGGGLVQ PGGSLRLSCA    600
ASGSIFSANA MGWYRQAPGK QRELVAVISS GGSTNYADSV KGRFTISRDN SKNTVYLQMN    660
SLRAEDTAVY YCMYSGSYYY TPNDYWGQGT LVTVSS                              696
```

```
SEQ ID NO: 350          moltype = AA  length = 696
FEATURE                 Location/Qualifiers
source                  1..696
                        mol_type = protein
                        organism = synthetic construct
SEQUENCE: 350
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KCLEWVAAID    360
SSSYTYSPDT VRGRFTISRD NAKNSLYLQM NSLRAEDTAV YYCARDSNWD ALDYWGQGTT    420
VTVSSGGGGS GGGGSGGGGS DIQMTQSPSS LSASVGDRVT ITCKAREKLW SAVAWYQQKP    480
GKAPKSLIYS ASFRYSGVPS RFSGSGSGTD FTLTISSLQP EDFATYYCQQ YYTYPYTFGC    540
GTKVEIKGGG GSGGGGSGGG GSGGGGSGGG GSGGGGSEVQ LLESGGGLVQ PGGSLRLSCA    600
ASGSIFSANA MGWYRQAPGK GLELVAVISS GGSTNYADSV KGRFTISRDN SKNTVYLQMN    660
SLRAEDTAVY YCMYSGSYYY TPNDYWGQGT LVTVSS                              696
```

```
SEQ ID NO: 351          moltype = AA  length = 696
FEATURE                 Location/Qualifiers
source                  1..696
                        mol_type = protein
                        organism = synthetic construct
SEQUENCE: 351
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGCGTT    420
VTVSSGGGGS GGGGSGGGGS DIQMTQSPSS LSASVGDRVT ITCKAREKLW SAVAWYQQKP    480
GKCPKALIYS ASFRYSGVPS RFSGSGSGTD FTLTISSLQP EDFATYYCQQ YYTYPYTFGG    540
GTKVEIKGGG GSGGGGSGGG GSGGGGSGGG GSGGGGSEVQ LLESGGGLVQ PGGSLRLSCA    600
ASGSIFSANA MGWYRQAPGK GLELVAVISS GGSTNYADSV KGRFTISRDN SKNTVYLQMN    660
SLRAEDTAVY YCMYSGSYYY TPNDYWGQGT LVTVSS                              696
```

```
SEQ ID NO: 352          moltype = AA  length = 696
FEATURE                 Location/Qualifiers
source                  1..696
                        mol_type = protein
                        organism = synthetic construct
SEQUENCE: 352
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KCLEWVAAID    360
SSSYTYSPDT VRGRFTISRD NAKNSLYLQM NSLRAEDTAV YYCARDSNWD ALDYWGQGTT    420
VTVSSGGGGS GGGGSGGGGS DIQMTQSPSS LSASVGDRVT ITCKVTEKVW GNVAWYQQKP    480
GKAPISLIYS PSLRKSGVPS RFSGSGSGTD FTLTISSLQP EDFATYYCQQ YYTYPYTFGC    540
GTKVEIKGGG GSGGGGSGGG GSGGGGSGGG GSGGGGSEVQ LLESGGGLVQ PGGSLRLSCA    600
ASGSIFSANA MGWYRQAPGK GLELVAVISS GGSTNYADSV KGRFTISRDN SKNTVYLQMN    660
SLRAEDTAVY YCMYSGSYYY TPNDYWGQGT LVTVSS                              696
```

```
SEQ ID NO: 353          moltype = AA  length = 696
FEATURE                 Location/Qualifiers
source                  1..696
                        mol_type = protein
                        organism = synthetic construct
SEQUENCE: 353
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
```

```
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGCGTT   420
VTVSSGGGGS GGGGSGGGGS DIQMTQSPSS LSASVGDRVT ITCKVTEKVW GNVAWYQQKP   480
GKCPISLIYS PSLRKSGVPS RFSGSGSGTD FTLTISSLQP EDFATYYCQQ YYTYPYTFGG   540
GTKVEIKGGG GSGGGGSGGG GSGGGGSGGG GSGGGGSEVQ LLESGGGLVQ PGGSLRLSCA   600
ASGSIFSANA MGWYRQAPGK GLELVAVISS GGSTNYADSV KGRFTISRDN SKNTVYLQMN   660
SLRAEDTAVY YCMYSGSYYY TPNDYWGQGT LVTVSS                            696

SEQ ID NO: 354          moltype = AA   length = 6
FEATURE                 Location/Qualifiers
source                  1..6
                        mol_type = protein
                        note = 6xHis tag
                        organism = synthetic construct
SEQUENCE: 354
HHHHHH                                                               6

SEQ ID NO: 355          moltype = AA   length = 547
FEATURE                 Location/Qualifiers
source                  1..547
                        mol_type = protein
                        organism = synthetic construct
SEQUENCE: 355
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KCLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKASQNVG TNVGWYQQKP   480
GKAPKALIYS ASFRYSGVPS RFSGSGSGTD FTLTISSLQP EDFATYYCQQ YYTYPYTFGC   540
GTKVEIK                                                             547

SEQ ID NO: 356          moltype = AA   length = 547
FEATURE                 Location/Qualifiers
source                  1..547
                        mol_type = protein
                        organism = synthetic construct
SEQUENCE: 356
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGCGTT   420
VTVSSGGGGS GGGGSGGGGS DIQMTQSPSS LSASVGDRVT ITCKASQNVG TNVGWYQQKP   480
GKCPKALIYS ASFRYSGVPS RFSGSGSGTD FTLTISSLQP EDFATYYCQQ YYTYPYTFGG   540
GTKVEIK                                                             547

SEQ ID NO: 357          moltype = AA   length = 547
FEATURE                 Location/Qualifiers
source                  1..547
                        mol_type = protein
                        organism = synthetic construct
SEQUENCE: 357
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KCLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKAREKLW SAVAWYQQKP   480
GKAPKALIYS ASFRYSGVPS RFSGSGSGTD FTLTISSLQP EDFATYYCQQ YYTYPYTFGC   540
GTKVEIK                                                             547

SEQ ID NO: 358          moltype = AA   length = 547
FEATURE                 Location/Qualifiers
source                  1..547
                        mol_type = protein
                        organism = synthetic construct
SEQUENCE: 358
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
```

-continued

```
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGCGTT   420
VTVSSGGGGS GGGGSGGGGS DIQMTQSPSS LSASVGDRVT ITCKAREKLW SAVAWYQQKP   480
GKCPKALIYS ASFRYSGVPS RFSGSGSGTD FTLTISSLQP EDFATYYCQQ YYTYPYTFGG   540
GTKVEIK                                                            547

SEQ ID NO: 359           moltype = AA  length = 547
FEATURE                  Location/Qualifiers
source                   1..547
                         mol_type = protein
                         organism = synthetic construct
SEQUENCE: 359
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KCLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKVTEKVW GNVAWYQQKP   480
GKCPISLIYS PSLRKSGVPS RFSGSGSGTD FTLTISSLQP EDFATYYCQQ YYTYPYTFGC   540
GTKVEIK                                                            547

SEQ ID NO: 360           moltype = AA  length = 547
FEATURE                  Location/Qualifiers
source                   1..547
                         mol_type = protein
                         organism = synthetic construct
SEQUENCE: 360
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGCGTT   420
VTVSSGGGGS GGGGSGGGGS DIQMTQSPSS LSASVGDRVT ITCKVTEKVW GNVAWYQQKP   480
GKCPISLIYS PSLRKSGVPS RFSGSGSGTD FTLTISSLQP EDFATYYCQQ YYTYPYTFGG   540
GTKVEIK                                                            547

SEQ ID NO: 361           moltype = AA  length = 427
FEATURE                  Location/Qualifiers
source                   1..427
                         mol_type = protein
                         organism = synthetic construct
SEQUENCE: 361
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLLESGGGLV QPGGSLRLSC AASGSIFSAN AMGWYRQAPG KQRELVAVIS   360
SGGSTNYADS VKGRFTISRD NSKNTVYLQM NSLRAEDTAV YYCMYSGSYY YTPNDYWGQG   420
TLVTVSS                                                            427

SEQ ID NO: 362           moltype = AA  length = 528
FEATURE                  Location/Qualifiers
source                   1..528
                         mol_type = protein
                         organism = synthetic construct
SEQUENCE: 362
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSASTKG PSVFPLAPSS KSTSGGTAAL GCLVKDYFPE PVTVSWNSGA LTSGVHTFPA   480
VLQSSGLYSL SSVVTVPSSS LGTQTYICNV NHKPSNTKVD KRVEPKSC               528

SEQ ID NO: 363           moltype = AA  length = 642
FEATURE                  Location/Qualifiers
source                   1..642
                         mol_type = protein
                         organism = synthetic construct
SEQUENCE: 363
ESKYGPPCPP CPAPEFLGGP SVFLFPPKPK DTLMISRTPE VTCVVVDVSQ EDPEVQFNWY   60
```

-continued

```
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPGPAGLYA   240
QPGSAPTSSS TKKTQLQLEH LLLDLQMILN GINNYKNPKL TRMLTFKFYM PKKATELKHL   300
QCLEEELKPL EEVLNLAQSK NFHLRPRDLI SNINIVILEL KGSETTFMCE YADETATIVE   360
FLNRWITFCQ SIISTLTGGG GSGGGGSGGG GSGGGGSGGG GSGGGGSSGG PGPAGLYAQP   420
GSEVQLVESG GGLVQPGGSL RLSCAASGFT FSSYTLAWVR QAPGKGLEWV AAIDSSSYTY   480
SPDTVRGRFT ISRDNAKNSL YLQMNSLRAE DTAVYYCARD SNWDALDYWG QGTTVTVSSA   540
STKGPSVFPL APSSKSTSGG TAALGCLVKD YFPEPVTVSW NSGALTSGVH TFPAVLQSSG   600
LYSLSSVVTV PSSSLGTQTY ICNVNHKPSN TKVDKRVEPK SC                     642
```

SEQ ID NO: 364                moltype = AA    length = 245
FEATURE                       Location/Qualifiers
source                        1..245
                              mol_type = protein
                              organism = synthetic construct
SEQUENCE: 364
```
EVQLVESGGG LVQPGGSLRL SCAASGFTFS SYTLAWVRQA PGKGLEWVAA IDSSSYTYSP   60
DTVRGRFTIS RDNAKNSLYL QMNSLRAEDT AVYYCARDSN WDALDYWGQG TTVTVSSSGG   120
PGPAGLYAQP GSDIQMTQSP SSLSASVGDR VTITCKVTEK VWGNVAWYQQ KPGKAPISLI   180
YSPSLRKSGV PSRFSGSGSG TDFTLTISSL QPEDFATYYC QQYYTYPYTF GGGTKVEIKH   240
HHHHH                                                             245
```

SEQ ID NO: 365                moltype = AA    length = 245
FEATURE                       Location/Qualifiers
source                        1..245
                              mol_type = protein
                              organism = synthetic construct
SEQUENCE: 365
```
EVQLVESGGG LVQPGGSLRL SCAASGFTFS SYTLAWVRQA PGKGLEWVAA IDSSSYTYSP   60
DTVRGRFTIS RDNAKNSLYL QMNSLRAEDT AVYYCARDSN WDALDYWGQG TTVTVSSSGG   120
PGPAGLYAQP GSDIQMTQSP SSLSASVGDR VTITCKAREK LWSAVAWYQQ KPGKAPKALI   180
YSASFRYSGV PSRFSGSGSG TDFTLTISSL QPEDFATYYC QQYYTYPYTF GGGTKVEIKH   240
HHHHH                                                             245
```

SEQ ID NO: 366                moltype = AA    length = 245
FEATURE                       Location/Qualifiers
source                        1..245
                              mol_type = protein
                              organism = synthetic construct
SEQUENCE: 366
```
EVQLVESGGG LVQPGGSLRL SCAASGFTFS SYTLAWVRQA PGKGLEWVAA IDSSSYTYSP   60
DTVRGRFTIS RDNAKNSLYL QMNSLRAEDT AVYYCARDSN WDALDYWGQG TTVTVSSSGG   120
PGPAGLYAQP GSDIQMTQSP SSLSASVGDR VTITCKAREK LWSAVAWYQQ KPGKAPKSLI   180
YSASFRYSGV PSRFSGSGSG TDFTLTISSL QPEDFATYYC QQYYTYPYTF GGGTKVEIKH   240
HHHHH                                                             245
```

SEQ ID NO: 367                moltype = AA    length = 609
FEATURE                       Location/Qualifiers
source                        1..609
                              mol_type = protein
                              organism = synthetic construct
SEQUENCE: 367
```
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG   120
PAGMKGLPGS RVIPVSGPAR CLSQSRNLLK TTDDMVKTAR EKLKHYSCTA EDIDHEDITR   180
DQTSTLKTCL PLELHKNESC LATRETSSTT RGSCLPPQKT SLMMTLCLGS IYEDLKMYQT   240
EFQAINAALQ NHNHQQIILD KGMLVAIDEL MQSLNHNGET LRQKPPVGEA DPYRVKMKLC   300
ILLHAFSTRV VTINRVMGYL SSASGGPGPA GMKGLPGSGG GSGGGGSGGG GSGGGGSGG   360
GGSGGGGSQS VLTQPPSVSG APGQRVTISC SGSRSNIGSN TVKWYQQLPG TAPKLLIYYN   420
DQRPSGVPDR FSGSKSGTSA SLAITGLQAE DEADYYCQSY DRYTHPALLF GTGTKVTVLG   480
GGGSGGGGSG GGGSQVQLVE SGGGVVQPGR SLRLSCAASG FTFSSYGMHW VRQAPGKGLE   540
WVAFIRYDGS NKYYADSVKG RFTISRDNSK NTLYLQMNSL RAEDTAVYYC KTHGSHDNWG   600
QGTMVTVSS                                                          609
```

SEQ ID NO: 368                moltype = AA    length = 930
FEATURE                       Location/Qualifiers
source                        1..930
                              mol_type = protein
                              organism = synthetic construct
SEQUENCE: 368
```
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG   120
PAGMKGLPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSASPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
```

-continued

```
REKLKHYSCT AEDIDHEDIT RDQTSTLKTC LPLELHKNES SLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGMKGLPGSG  660
GGGSGGGGSG GGGSGGGGSG GGGSGGGGSQ SVLTQPPSVS GAPGQRVTIS CSGSRSNIGS  720
NTVKWYQQLP GTAPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GQGTMVTVSS                                   930

SEQ ID NO: 369           moltype = AA  length = 935
FEATURE                  Location/Qualifiers
source                   1..935
                         mol_type = protein
                         organism = synthetic construct
SEQUENCE: 369
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS IWELKKDVYV VELDWYPDAP GEMVVLTCDT PEEDGITWTL DQSSEVLGSG  180
KTLTIQVKEF GDAGQYTCHK GGEVLSHSLL LLHHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SGGGGSRVIP VSGPARCLSQ SRNLLKTTDD  480
MVKTAREKLK HYSCTAEDID HEDITRDQTS TLKTCLPLEL HKNESCLATR ETSSTTRGSC  540
LPPQKTSLMM TLCLGSIYED LKMYQTEFQA INAALQNHNH QQIILDKGML VAIDELMQSL  600
NHNGETLRQK PPVGEADPYR VKMKLCILLH AFSTRVVTIN RVMGYLSSAS GGPGPAGMKG  660
LPGSGGGGSG GGGSGGGGSG GGGSGGGGSG GGGSQSVLTQ PPSVSGAPGQ RVTISCSGSR  720
SNIGSNTVKW YQQLPGTAPK LLIYYNDQRP SGVPDRFSGS KSGTSASLAI TGLQAEDEAD  780
YYCQSYDRYT HPALLFGTGT KVTVLGGGGS GGGGSGGGGS QVQLVESGGG VVQPGRSLRL  840
SCAASGFTFS SYGMHWVRQA PGKGLEWVAF IRYDGSNKYY ADSVKGRFTI SRDNSKNTLY  900
LQMNSLRAED TAVYYCKTHG SHDNWGQGTM VTVSS                            935

SEQ ID NO: 370           moltype = AA  length = 930
FEATURE                  Location/Qualifiers
source                   1..930
                         mol_type = protein
                         organism = synthetic construct
SEQUENCE: 370
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS IWELKKDVYV VELDWYPDAP GEMVVLTCDT PEEDGITWTL DQSSEVLGSG  180
KTLTIQVKEF GDAGQYTCHK GGEVLSHSLL LLHHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGMKGLPGSG  660
GGGSGGGGSG GGGSGGGGSG GGGSGGGGSQ SVLTQPPSVS GAPGQRVTIS CSGSRSNIGS  720
NTVKWYQQLP GTAPKLLIYY NDQRPSGVPD RFSGSKSGTS ASLAITGLQA EDEADYYCQS  780
YDRYTHPALL FGCGTKVTVL GGGGSGGGGS GGGGSQVQLV ESGGGVVQPG RSLRLSCAAS  840
GFTFSSYGMH WVRQAPGKCL EWVAFIRYDG SNKYYADSVK GRFTISRDNS KNTLYLQMNS  900
LRAEDTAVYY CKTHGSHDNW GQGTMVTVSS                                   930

SEQ ID NO: 371           moltype = AA  length = 930
FEATURE                  Location/Qualifiers
source                   1..930
                         mol_type = protein
                         organism = synthetic construct
SEQUENCE: 371
EVQLVESGGG LVQPGNSLRL SCAASGFTFS KFGMSWVRQA PGKGLEWVSS ISGSGRDTLY  60
AESVKGRFTI SRDNAKTTLY LQMNSLRPED TAVYYCTIGG SLSVSSQGTL VTVSSSGGPG  120
PAGMKGLPGS IWELKKDVYV VELDWYPDAP GEMVVLTCDT PEEDGITWTL DQSSEVLGSG  180
KTLTIQVKEF GDAGQYTCHK GGEVLSHSLL LLHHKKEDGIW STDILKDQKE PKNKTFLRCE  240
AKNYSGRFTC WWLTTISTDL TFSVKSSRGS SDPQGVTCGA ATLSAERVRG DNKEYEYSVE  300
CQEDSACPAA EESLPIEVMV DAVHKLKYEN YTSSFFIRDI IKPDPPKNLQ LKPLKNSRQV  360
EVSWEYPDTW STPHSYFSLT FCVQVQGKSK REKKDRVFTD KTSATVICRK NASISVRAQD  420
RYYSSSWSEW ASVPCSGGGG SGGGGSGGGG SRVIPVSGPA RCLSQSRNLL KTTDDMVKTA  480
REKLKHYSCT AEDIDHEDIT RDQTSTLKTC LPLELHKNES CLATRETSST TRGSCLPPQK  540
TSLMMTLCLG SIYEDLKMYQ TEFQAINAAL QNHNHQQIIL DKGMLVAIDE LMQSLNHNGE  600
TLRQKPPVGE ADPYRVKMKL CILLHAFSTR VVTINRVMGY LSSASGGPGP AGMKGLPGSG  660
GGGSGGGGSG GGGSGGGGSG GGGSGGGGSQ SVLTQPPSVS GAPGQRVTIS CSGSRSNIGS  720
NTVKWYQQLP GTCPKLLIYY NDQRPSGVPD RFSGSKSGTS ASLAITGLQA EDEADYYCQS  780
YDRYTHPALL FGTGTKVTVL GGGGSGGGGS GGGGSQVQLV ESGGGVVQPG RSLRLSCAAS  840
GFTFSSYGMH WVRQAPGKGL EWVAFIRYDG SNKYYADSVK GRFTISRDNS KNTLYLQMNS  900
LRAEDTAVYY CKTHGSHDNW GCGTMVTVSS                                   930

SEQ ID NO: 372           moltype = AA  length = 553
```

-continued

```
FEATURE                 Location/Qualifiers
source                  1..553
                        mol_type = protein
                        organism = synthetic construct
SEQUENCE: 372
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GMKGLPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKASQNVG TNVGWYQQKP   480
GKAPKALIYS ASFRYSGVPS RFSGSGSGTD FTLTISSLQP EDFATYYCQQ YYTYPYTFGG   540
GTKVEIKHHH HHH                                                      553

SEQ ID NO: 373          moltype = AA  length = 444
FEATURE                 Location/Qualifiers
source                  1..444
                        mol_type = protein
                        organism = synthetic construct
SEQUENCE: 373
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GMKGLPGQVQ LQESGGGLVQ TGGSLRLSCT TSGTIFSGYT MGWYRQAPGE QRELVAVISG   360
GGDTNYADSV KGRFTISRDN TKDTMYLQMN SLKPEDTAVY YCYSREVTPP WKLYWGQGTQ   420
VTVSSAAAYP YDVPDYGSHH HHHH                                          444

SEQ ID NO: 374          moltype = AA  length = 444
FEATURE                 Location/Qualifiers
source                  1..444
                        mol_type = protein
                        organism = synthetic construct
SEQUENCE: 374
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GMKGLPGQVQ LQESGGGLVQ EGGSLRLSCA ASERIFSTDV MGWYRQAAEK QRELVAVVSA   360
RGTTNYLDAV KGRFTISRDN ARNTLTLQMN DLKPEDTASY YCYVRETTSP WRIYWGQGTQ   420
VTVSSAAAYP YDVPDYGSHH HHHH                                          444

SEQ ID NO: 375          moltype = AA  length = 445
FEATURE                 Location/Qualifiers
source                  1..445
                        mol_type = protein
                        organism = synthetic construct
SEQUENCE: 375
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GMKGLPGQVQ LQESGGGLVQ AGGSLRLSCA ASGSIFSANA MGWYRQAPGK QRELVAVISS   360
GGSTNYADSV KGRFTISRDN AKNTVYLQMN SLKPEDTAVY YCMYSGSYYY TPNDYWGQGT   420
QVTVSSAAAY PYDVPDYGSH HHHH                                          445

SEQ ID NO: 376          moltype = AA  length = 557
FEATURE                 Location/Qualifiers
source                  1..557
                        mol_type = protein
                        organism = synthetic construct
SEQUENCE: 376
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GMKGLPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSSGGPG PAGMKGLPGS DIQMTQSPSS LSASVGDRVT ITCKASQNVG TNVGWYQQKP   480
GKAPKALIYS ASFRYSGVPS RFSGSGSGTD FTLTISSLQP EDFATYYCQQ YYTYPYTFGG   540
GTKVEIKHHH HHHEPEA                                                  557

SEQ ID NO: 377          moltype = AA  length = 557
```

```
FEATURE            Location/Qualifiers
source             1..557
                   mol_type = protein
                   organism = synthetic construct
SEQUENCE: 377
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GMKGLPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKASQNVG TNVGWYQQKP   480
GKAPKLLIYS ASFRYSGVPS RFSGSGSGTD FTLTISSLQP EDFATYYCQQ YYTYPYTFGG   540
GTKVEIKHHH HHHEPEA                                                557

SEQ ID NO: 378     moltype = AA  length = 557
FEATURE            Location/Qualifiers
source             1..557
                   mol_type = protein
                   organism = synthetic construct
SEQUENCE: 378
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GMKGLPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKASQNVG TNVGWYQQKP   480
GKAPKGLIYS ASFRYSGVPS RFSGSGSGTD FTLTISSLQP EDFATYYCQQ YYTYPYTFGG   540
GTKVEIKHHH HHHEPEA                                                557

SEQ ID NO: 379     moltype = AA  length = 557
FEATURE            Location/Qualifiers
source             1..557
                   mol_type = protein
                   organism = synthetic construct
SEQUENCE: 379
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFSQSIIS TLTSGGPGPA GMKGLPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GMKGLPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKASQNVG TNVGWYQQKP   480
GKAPKALIYS ASFRYSGVPS RFSGSGSGTD FTLTISSLQP EDFATYYCQQ YYTYPYTFGG   540
GTKVEIKHHH HHHEPEA                                                557

SEQ ID NO: 380     moltype = AA  length = 1027
FEATURE            Location/Qualifiers
source             1..1027
                   mol_type = protein
                   organism = synthetic construct
SEQUENCE: 380
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSDA HKSEVAHRFK DLGEENFKAL VLIAFAQYLQ   180
QCPFEDHVKL VNEVTEFAKT CVADESAENC DKSLHTLFGD KLCTVATLRE TYGEMADCCA   240
KQEPERNECF LQHKDDNPNL PRLVRPEVDV MCTAFHDNEE TFLKKYLYEI ARRHPYFYAP   300
ELLFFAKRYK AAFTECCQAA DKAACLLPKL DELRDEGKAS SAKQRLKCAS LQKFGERAFK   360
AWAVARLSQR FPKAEFAEVS KLVTDLTKVH TECCHGDLLE CADDRADLAK YICENQDSIS   420
SKLKECCEKP LLEKSHCIAE VENDEMPADL PSLAADFVES KDVCKNYAEA KDVFLGMFLY   480
EYARRHPDYS VVLLLRLAKT YETTLEKCCA AADPHECYAK VFDEFKPLVE EPQNLIKQNC   540
ELFEQLGEYK FQNALLVRYT KKVPQVSTPT LVEVSRNLGK VGSKCCKHPE AKRMPCAEDY   600
LSVVLNQLCV LHEKTPVSDR VTKCCTESLV NRRPCFSALE VDETYVPKEF NAETFTFHAD   660
ICTLSEKERQ IKKQTALVEL VKHKPKATKE QLKAVMDDFA AFVEKCCKAD DKETCFAEEG   720
KKLVAASQAA LGLGGGGSGG GGSGGGGSGG GGSGGGGSGG GGSSGGPGPA GMKGLPGSEV   780
QLVESGGGLV QPGGSLRLSC AASGFTFSSY TLAWVRQAPG KGLEWVAAID SSSYTYSPDT   840
VRGRFTISRD NAKNSLYLQM NSLRAEDTAV YYCARDSNWD ALDYWGQGTT VTVSSGGGGS   900
GGGGSGGGGS DIQMTQSPSS LSASVGDRVT ITCKASQNVG TNVGWYQQKP GKAPKALIYS  960
ASFRYSGVPS RFSGSGSGTD FTLTISSLQP EDFATYYCQQ YYTYPYTFGG GTKVEIKHHH  1020
HHHEPEA                                                          1027

SEQ ID NO: 381     moltype = AA  length = 1022
FEATURE            Location/Qualifiers
source             1..1022
                   mol_type = protein
```

-continued

```
                     organism = synthetic construct
SEQUENCE: 381
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR   120
WITFCQSIIS TLTSGGPGPA GMKGLPGSEA HKSEIAHRYN DLGEQHFKGL VLIAFSQYLQ   180
KCSYDEHAKL VQEVTDFAKT CVADESAANC DKSLHTLFGD KLCAIPNLRE NYGELADCCT   240
KQEPERNECF LQHKDDNPSL PPFERPEAEA MCTSFKENPT TFMGHYLHEV ARRHPYFYAP   300
ELLYYAEQYN EILTQCCAEA DKESCLTPKL DGVKEKALVS SVRQRMKCSS MQKFGERAFK   360
AWAVARLSQT FPNADFAEIT KLATDLTKVN KECCHGDLLE CADDRAELAK YMCENQATIS   420
SKLQTCCDKP LLKKAHCLSE VEHDTMPADL PAIAADFVED QEVCKNYAEA KDVFLGTFLY   480
EYSRRHPDYS VSLLLRLAKK YEATLEKCCA EANPPACYGT VLAEFQPLVE EPKNLVKTNC   540
DLYEKLGEYG FQNAILVRYT QKAPQVSTPT LVEAARNLGR VGTKCCTLPE DQRLPCVEDY   600
LSAILNRVCL LHEKTPVSEH VTKCCSGSLV ERRPCFSALT VDETYVPKEF KAETFTFHSD   660
ICTLPEKEKQ IKKQTALAEL VKHKPKATAE QLKTVMDDFA QFLDTCCKAA DKDTCFSTEG   720
PNLVTRCKDA LAGGGGSGGG GSGGGGSGGG GSGGGGSGGG GSSGGPGPAG MKGLPGSEVQ   780
LVESGGGLVQ PGGSLRLSCA ASGFTFSSYT LAWVRQAPGK GLEWVAAIDS SSYTYSPDTV   840
RGRFTISRDN AKNSLYLQMN SLRAEDTAVY YCARDSNWDA LDYWGQGTTV TVSSGGGGSG   900
GGGSGGGGSD IQMTQSPSSL SASVGDRVTI TCKASQNVGT NVGWYQQKPG KAPKALIYSA   960
SFRYSGVPSR FSGSGSGTDF TLTISSLQPE DFATYYCQQY YTYPYTFGGG TKVEIKHHHH   1020
HH                                                                  1022

SEQ ID NO: 382          moltype = AA  length = 1336
FEATURE                 Location/Qualifiers
source                  1..1336
                        mol_type = protein
                        organism = synthetic construct
SEQUENCE: 382
EAHKSEIAHR YNDLGEQHFK GLVLIAFSQY LQKCSYDEHA KLVQEVTDFA KTCVADESAA   60
NCDKSLHTLF GDKLCAIPNL RENYGELADC CTKQEPERNE CFLQHKDDNP SLPPFERPEA   120
EAMCTSFKEN PTTFMGHYLH EVARRHPYFY APELLYYAEQ YNEILTQCCA EADKESCLTP   180
KLDGVKEKAL VSSVRQRMKC SSMQKFGERA FKAWAVARLS QTFPNADFAE ITKLATDLTK   240
VNKECCHGDL LECADDRAEL AKYMCENQAT ISSKLQTCCD KPLLKKAHCL SEVEHDTMPA   300
DLPAIAADFV EDQEVCKNYA EAKDVFLGTF LYEYSRRHPD YSVSLLLRLA KKYEATLEKC   360
CAEANPPACY GTVLAEFQPL VEEPKNLVKT NCDLYEKLGE YGFQNAILVR YTQKAPQVST   420
PTLVEAARNL GRVGTKCCTL PEDQRLPCVE DYLSAILNRV CLLHEKTPVS EHVTKCCSGS   480
LVERRPCFSA LTVDETYVPK EFKAETFTFH SDICTLPEKE KQIKKQTALA ELVKHKPKAT   540
AEQLKTVMDD FAQFLDTCCK AADKDTCFST EGPNLVTRCK DALASGGPGP AGMKGLPGST   600
FKFYMPKKAT ELKHLQCLEE LKPLEEVLN LAQSKNFHLR PRDLISNINV IVLELKGSET   660
TFMCEYADET ATIVEFLNRW ITFCQSIIST LTGGSSTKK TQLQLEHLLL DLQMILNGIN   720
NYKNPKLTRM LSGGPGPAGM KGLPGSEAHK SEIAHRYNDL GEQHFKGLVL IAFSQYLQKC   780
SYDEHAKLVQ EVTDFAKTCV ADESAANCDK SLHTLFGDKL CAIPNLRENY GELADCCTKQ   840
EPERNECFLQ HKDDNPSLPP FERPEAEAMC TSFKENPTTF MGHYLHEVAR RHPYFYAPEL   900
LYYAEQYNEI LTQCCAEADK ESCLTPKLDG VKEKALVSSV RQRMKCSSMQ KFGERAFKAW   960
AVARLSQTFP NADFAEITKL ATDLTKVNKE CCHGDLLECA DDRAELAKYM CENQATISSK   1020
LQTCCDKPLL KKAHCLSEVE HDTMPADLPA IAADFVEDQE VCKNYAEAKD VFLGTFLYEY   1080
SRRHPDYSVS LLLRLAKKYE ATLEKCCAEA NPPACYGTVL AEFQPLVEEP KNLVKTNCDL   1140
YEKLGEYGFQ NAILVRYTQK APQVSTPTLV EAARNLGRVG TKCCTLPEDQ RLPCVEDYLS   1200
AILNRVCLLH EKTPVSEHVT KCCSGSLVER RPCFSALTVD ETYVPKEFKA ETFTFHSDIC   1260
TLPEKEQIK KQTALAELVK HKPKATAEQL KTVMDDFAQF LDTCCKAADK DTCFSTEGPN   1320
LVTRCKDALA HHHHHH                                                   1336

SEQ ID NO: 383          moltype = AA  length = 817
FEATURE                 Location/Qualifiers
source                  1..817
                        mol_type = protein
                        organism = synthetic construct
SEQUENCE: 383
APTSSSTKKT QLQLEHLLLD LQMILNGINN YKNPKLTRML TFKFYMPKKA TELKHLQCLE   60
EELKPLEEVL NLAQSKNFHL RPRDLISNIN VIVLELKGSE TTFMCEYADE TATIVEFLNR   120
WITFCQSIIS TLTSGGPGPA GMKGLPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GMKGLPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKASQNVG TNVGWYQQKP   480
GKAPKALIYS ASFRYSGVPS RFSGSGSGTD FTLTISSLQP EDFATYYCQQ YYTYPYTFGG   540
GTKVEIKSGG PGPAGMKGLP GSGGGGSGGG GSGGGGSGGG GSGGGGSGGG GSELCDDDPP   600
EIPHATFKAM AYKEGTMLNC ECKRGFRRIK SGSLYMLCTG NSSHSSWDNQ CQCTSSATRN   660
TTKQVTPQPE EQKERKTTEM QSPMQPVDQA SLPGHCREPP PWENEATERI YHFVVGQMVY   720
YQCVQGYRAL HRGPAESVCK MTHGKTRWTQ PQLICTGEME TSQFPGEEKP QASPEGRPES   780
ETSCLVTTTD FQIQTEMAAT METSIFTTEY QHHHHHH                            817

SEQ ID NO: 384          moltype = AA  length = 817
FEATURE                 Location/Qualifiers
source                  1..817
                        mol_type = protein
                        organism = synthetic construct
SEQUENCE: 384
ELCDDDPPEI PHATFKAMAY KEGTMLNCEC KRGFRRIKSG SLYMLCTGNS SHSSWDNQCQ   60
```

-continued

```
CTSSATRNTT KQVTPQPEEQ KERKTTEMQS PMQPVDQASL PGHCREPPPW ENEATERIYH    120
FVVGQMVYYQ CVQGYRALHR GPAESVCKMT HGKTRWTQPQ LICTGEMETS QFPGEEKPQA    180
SPEGRPESET SCLVTTTDFQ IQTEMAATME TSIFTTEYQG GGGSGGGGSG GGGSGGGGSG    240
GGGSGGGGSS GGPGPAGMKG LPGSAPTSSS TKKTQLQLEH LLLDLQMILN GINNYKNPKL    300
TRMLTFKFYM PKKATELKHL QCLEEELKPL EEVLNLAQSK NFHLRPRDLI SNINVIVLEL    360
KGSETTFMCE YADETATIVE FLNRWITFCQ SIISTLTSGG PGPAGMKGLP GSEVQLVESG    420
GGLVQPGNSL RLSCAASGFT FSKFGMSWVR QAPGKGLEWV SSISGSGRDT LYAESVKGRF    480
TISRDNAKTT LYLQMNSLRP EDTAVYYCTI GGSLSVSSQG TLVTVSSGGG GSGGGGSGGG    540
GSGGGGSGGG GSGGGGSSGG PGPAGMKGLP GSEVQLVESG GGLVQPGGSL RLSCAASGFT    600
FSSYTLAWVR QAPGKGLEWV AAIDSSSYTY SPDTVRGRFT ISRDNAKNSL YLQMNSLRAE    660
DTAVYYCARD SNWDALDYWG QGTTVTVSSG GGGSGGGGSG GGGSDIQMTQ SPSSLSASVG    720
DRVTITCKAS QNVGTNVGWY QQKPGKAPKA LIYSASFRYS GVPSRFSGSG SGTDFTLTIS    780
SLQPEDFATY YCQQYYTYPY TFGGGTKVEI KHHHHHH                            817
```

```
SEQ ID NO: 385          moltype = AA  length = 817
FEATURE                 Location/Qualifiers
source                  1..817
                        mol_type = protein
                        organism = synthetic construct
SEQUENCE: 385
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GMKGLPGSGG GGSGGGGSGG GGSGGGGSGG GGSGGGGSEL    180
CDDDPPEIPH ATFKAMAYKE GTMLNCECKR GFRRIKSGSL YMLCTGNSSH SSWDNQCQCT    240
SSATRNTTKQ VTPQPEEQKE RKTTEMQSPM QPVDQASLPG HCREPPPWEN EATERIYHFV    300
VGQMVYYQCV QGYRALHRGP AESVCKMTHG KTRWTQPLI CTGEMETSQF PGEEKPQASP    360
EGRPESETSC LVTTTDFQIQ TEMAATMETS IFTTEYQSGG PGPAGMKGLP GSEVQLVESG    420
GGLVQPGNSL RLSCAASGFT FSKFGMSWVR QAPGKGLEWV SSISGSGRDT LYAESVKGRF    480
TISRDNAKTT LYLQMNSLRP EDTAVYYCTI GGSLSVSSQG TLVTVSSGGG GSGGGGSGGG    540
GSGGGGSGGG GSGGGGSSGG PGPAGMKGLP GSEVQLVESG GGLVQPGGSL RLSCAASGFT    600
FSSYTLAWVR QAPGKGLEWV AAIDSSSYTY SPDTVRGRFT ISRDNAKNSL YLQMNSLRAE    660
DTAVYYCARD SNWDALDYWG QGTTVTVSSG GGGSGGGGSG GGGSDIQMTQ SPSSLSASVG    720
DRVTITCKAS QNVGTNVGWY QQKPGKAPKA LIYSASFRYS GVPSRFSGSG SGTDFTLTIS    780
SLQPEDFATY YCQQYYTYPY TFGGGTKVEI KHHHHHH                            817
```

```
SEQ ID NO: 386          moltype = AA  length = 682
FEATURE                 Location/Qualifiers
source                  1..682
                        mol_type = protein
                        organism = synthetic construct
SEQUENCE: 386
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGMKGLPGS TFKFYMPKKA TELKHLQCLE EELKPLEEVL NLAQSKNFHL RPRDLISNIN    180
VIVLELKGSE TTFMCEYADE TATIVEFLNR WITFCQSIIS TLTGGSSSTK KTQLQLEHLL    240
LDLQMILNGI NNYKNPKLTR MLSGGPGPAG MKGLPGSEVQ LVESGGGLVQ PGNSLRLSCA    300
ASGFTFSKFG MSWVRQAPGK GLEWVSSISG SGRDTLYAES VKGRFTISRD NAKTTLYLQM    360
NSLRPEDTAV YYCTIGGSLS VSSQGTLVTV SSGGGGSGGG GSGGGGSGGG GSGGGGSGGG    420
GSSGGPGPAG MKGLPGSEVQ LVESGGGLVQ PGGSLRLSCA ASGFTFSSYT LAWVRQAPGK    480
GLEWVAAIDS SSYTYSPDTV RGRFTISRDN AKNSLYLQMN SLRAEDTAVY YCARDSNWDA    540
LDYWGQGTTV TVSSGGGGSG GGGSGGGGSD IQMTQSPSSL SASVGDRVTI TCKASQNVGT    600
NVGWYQQKPG KAPKALIYSA SFRYSGVPSR FSGSGSGTDF TLTISSLQPE DFATYYCQQY    660
YTYPYTFGGG TKVEIKHHHH HH                                            682
```

```
SEQ ID NO: 387          moltype = AA  length = 682
FEATURE                 Location/Qualifiers
source                  1..682
                        mol_type = protein
                        organism = synthetic construct
SEQUENCE: 387
EVQLVESGGG LVQPGGSLRL SCAASGFTFS SYTLAWVRQA PGKGLEWVAA IDSSSYTYSP     60
DTVRGRFTIS RDNAKNSLYL QMNSLRAEDT AVYYCARDSN WDALDYWGQG TTVTVSSGGG    120
GSGGGGSGGG GSDIQMTQSP SSLSASVGDR VTITCKASQN VGTNVGWYQQ KPGKAPKALI    180
YSASFRYSGV PSRFSGSGSG TDFTLTISSL QPEDFATYYC QQYYTYPYTF GGGTKVEIKS    240
GGPGPAGMKG LPGSGGGGSG GGGSGGGGSG GGGSGGGGSG GGGSEVQLVE SGGGLVQPGN    300
SLRLSCAASG FTFSKFGMSW VRQAPGKGLE WVSSISGSGR DTLYAESVKG RFTISRDNAK    360
TTLYLQMNSL RPEDTAVYYC TIGGSLSVSS QGTLVTVSSS GGPGPAGMKG LPGSTFKFYM    420
PKKATELKHL QCLEEELKPL EEVLNLAQSK NFHLRPRDLI SNINVIVLEL KGSETTFMCE    480
YADETATIVE FLNRWITFCQ SIISTLTGGS STKKTQLQL EHLLLDLQMI LNGINNYKNP    540
KLTRMLSGGP GPAGMKGLPG SEVQLVESG GLVQPGNSLR LSCAASGFTF SKFGMSWVRQ    600
APGKGLEWVS SISGSGRDTL YAESVKGRFT ISRDNAKTTL YLQMNSLRPE DTAVYYCTIG    660
GSLSVSSQGT LVTVSSHHHH HH                                            682
```

```
SEQ ID NO: 388          moltype = AA  length = 553
FEATURE                 Location/Qualifiers
source                  1..553
                        mol_type = protein
                        organism = synthetic construct
SEQUENCE: 388
```

-continued

```
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSSGGPGPA             300
GMKGLPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKASQNVG TNVGWYQQKP   480
GKAPKSLIYS ASFRYSGVPS RFSGSGSGTD FTLTISSLQP EDFATYYCQQ YYTYPYTFGG   540
GTKVEIKHHH HHH                                                     553

SEQ ID NO: 389              moltype = AA  length = 553
FEATURE                     Location/Qualifiers
source                      1..553
                            mol_type = protein
                            organism = synthetic construct
SEQUENCE: 389
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSSGGPGPA             300
GMKGLPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSGGGGS GGGGSGGGGS DIQMTQSPSS LSASVGDRVT ITCKASQNVG TNVGWYQQKP   480
GQAPRLLIYS ASFRYSGVPS RFSGSGSGTD FTLTISSLQP EDFATYYCQQ YYTYPYTFGG   540
GTKVEIKHHH HHH                                                     553

SEQ ID NO: 390              moltype = AA  length = 667
FEATURE                     Location/Qualifiers
source                      1..667
                            mol_type = protein
                            organism = synthetic construct
SEQUENCE: 390
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSES KYGPPCPPCP APEFLGGPSV FLFPPKPKDT   180
LMISRTPEVT CVVVDVSQED PEVQFNWYVD GVEVHNAKTK PREEQFNSTY RVVSVLTVLH   240
QDWLNGKEYK CKVSNKGLPS SIEKTISKAK GQPREPQVYT LPPSQEEMTK NQVSLTCLVK   300
GFYPSDIAVE WESNGQPENN YKTTPPVLDS DGSFFLYSRL TVDKSRWQEG NVFSCSVMHE   360
ALHNHYTQKS LSLSLGKGGG GSGGGGSGGG GSGGGGSGGG GSGGGGSSGG PGPAGMKGLP   420
GSEVQLVESG GGLVQPGGSL RLSCAASGFT FSSYTLAWVR QAPGKGLEWV AAIDSSSYTY   480
SPDTVRGRFT ISRDNAKNSL YLQMNSLRAE DTAVYYCARD SNWDALDYWG QGTTVTVSSG   540
GGGSGGGGSG GGGSDIQMTQ SPSSLSASVG DRVTITCKAS QNVGTNVGWY QQKPGKAPKA   600
LIYSASFRYS GVPSRFSGSG SGTDFTLTIS SLQPEDFATY YCQQYYTYPY TFGGGTKVEI   660
KHHHHHH                                                           667

SEQ ID NO: 391              moltype = AA  length = 667
FEATURE                     Location/Qualifiers
source                      1..667
                            mol_type = protein
                            organism = synthetic construct
SEQUENCE: 391
ESKYGPPCPP CPAPEFLGGP SVFLFPPKPK DTLMISRTPE VTCVVVDVSQ EDPEVQFNWY    60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPGPAGMKG   240
LPGSAPTSSS TKKTQLQLEH LLLDLQMILN GINNYKNPKL TRMLTFKFYM PKKATELKHL   300
QCLEEELKPL EEVLNLAQSK NFHLRPRDLI SNINVIVLEL KGSETTFMCE YADETATIVE   360
FLNRWITFCQ SIISTLTGGG GSGGGGSGGG GSGGGGSGGG GSGGGGSSGG PGPAGMKGLP   420
GSEVQLVESG GGLVQPGGSL RLSCAASGFT FSSYTLAWVR QAPGKGLEWV AAIDSSSYTY   480
SPDTVRGRFT ISRDNAKNSL YLQMNSLRAE DTAVYYCARD SNWDALDYWG QGTTVTVSSG   540
GGGSGGGGSG GGGSDIQMTQ SPSSLSASVG DRVTITCKAS QNVGTNVGWY QQKPGKAPKA   600
LIYSASFRYS GVPSRFSGSG SGTDFTLTIS SLQPEDFATY YCQQYYTYPY TFGGGTKVEI   660
KHHHHHH                                                           667

SEQ ID NO: 392              moltype = AA  length = 667
FEATURE                     Location/Qualifiers
source                      1..667
                            mol_type = protein
                            organism = synthetic construct
SEQUENCE: 392
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPGPA GMKGLPGSGG GGSGGGGSGG GGSGGGGSGG GGSGGGGSEV   180
QLVESGGGLV QPGGSLRLSC AASGFTFSSY TLAWVRQAPG KGLEWVAAID SSSYTYSPDT   240
VRGRFTISRD NAKNSLYLQM NSLRAEDTAV YYCARDSNWD ALDYWGQGTT VTVSSGGGGS   300
GGGGSGGGGS DIQMTQSPSS LSASVGDRVT ITCKASQNVG TNVGWYQQKP GKAPKALIYS   360
ASFRYSGVPS RFSGSGSGTD FTLTISSLQP EDFATYYCQQ YYTYPYTFGG GTKVEIKSGG   420
```

-continued

```
PGPAGMKGLP GSESKYGPPC PPCPAPEFLG GPSVFLFPPK PKDTLMISRT PEVTCVVVDV   480
SQEDPEVQFN WYVDGVEVHN AKTKPREEQF NSTYRVVSVL TVLHQDWLNG KEYKCKVSNK   540
GLPSSIEKTI SKAKGQPREP QVYTLPPSQE EMTKNQVSLT CLVKGFYPSD IAVEWESNGQ   600
PENNYKTTPP VLDSDGSFFL YSRLTVDKSR WQEGNVFSCS VMHEALHNHY TQKSLSLSLG   660
KHHHHHH                                                            667

SEQ ID NO: 393          moltype = AA  length = 665
FEATURE                 Location/Qualifiers
source                  1..665
                        mol_type = protein
                        organism = synthetic construct
SEQUENCE: 393
VPRDCGCKPC ICTVPEVSSV FIFPPKPKDV LTITLTPKVT CVVVDISKDD PEVQFSWFVD   60
DVEVHTAQTQ PREEQFNSTF RSVSELPIMH QDWLNGKEFK CRVNSAAFPA PIEKTISKTK   120
GRPKAPQVYT IPPPKEQMAK DKVSLTCMIT DFFPEDITVE WQWNGQPAEN YKNTQPIMDT   180
DGSYFVYSKL NVQKSNWEAG NTFTCSVLHE GLHNHHTEKS LSHSPGKSGG PGPAGMKGLP   240
GSAPTSSSTK KTQLQLEHLL LDLQMILNGI NNYKNPKLTR MLTFKFYMPK KATELKHLQC   300
LEEELKPLEE VLNLAQSKNF HLRPRDLISN INVIVLELKG SETTFMCEYA DETATIVEFL   360
NRWITFCQSI ISTLTGGGGS GGGGSGGGGS GGGGSGGGGS GGGGSSGGPG PAGMKGLPGS   420
EVQLVESGGG LVQPGGSLRL SCAASGFTFS SYTLAWVRQA PGKGLEWVAA IDSSSYTYSP   480
DTVRGRFTIS RDNAKNSLYL QMNSLRAEDT AVYYCARDSN WDALDYWGQG TTVTVSSGGG   540
GSGGGGSGGG GSDIQMTQSP SSLSASVGDR VTITCKASQN VGTNVGWYQQ KPGKAPKALI   600
YSASFRYSGV PSRFSGSGSG TDFTLTISSL QPEDFATYYC QQYYTYPYTF GGGTKVEIKH   660
HHHHH                                                              665

SEQ ID NO: 394          moltype = AA  length = 547
FEATURE                 Location/Qualifiers
source                  1..547
                        mol_type = protein
                        organism = synthetic construct
SEQUENCE: 394
APTSSSTKKT QLQLEHLLLD LQMILNGINN YKNPKLTRML TFKFYMPKKA TELKHLQCLE   60
EELKPLEEVL NLAQSKNFHL RPRDLISNIN IVIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSSGGPG PAGLYAQPGS DIQMTQSPSS LSASVGDRVT ITCKAREKLW SAVAWYQQKP   480
GKAPKSLIYS ASFRYSGVPS RFSGSGSGTD FTLTISSLQP EDFATYYCQQ YYTYPYTFGG   540
GTKVEIK                                                            547

SEQ ID NO: 395          moltype = AA  length = 547
FEATURE                 Location/Qualifiers
source                  1..547
                        mol_type = protein
                        organism = synthetic construct
SEQUENCE: 395
APTSSSTKKT QLQLEHLLLD LQMILNGINN YKNPKLTRML TFKFYMPKKA TELKHLQCLE   60
EELKPLEEVL NLAQSKNFHL RPRDLISNIN IVIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSSGGGS GGGSGGGGS DIQMTQSPSS LSASVGDRVT ITCKAREKLW SAVAWYQQKP   480
GKAPKSLIYS ASFRYSGVPS RFSGSGSGTD FTLTISSLQP EDFATYYCQQ YYTYPYTFGG   540
GTKVEIK                                                            547

SEQ ID NO: 396          moltype = AA  length = 547
FEATURE                 Location/Qualifiers
source                  1..547
                        mol_type = protein
                        organism = synthetic construct
SEQUENCE: 396
APTSSSTKKT QLQLEHLLLD LQMILNGINN YKNPKLTRML TFKFYMPKKA TELKHLQCLE   60
EELKPLEEVL NLAQSKNFHL RPRDLISNIN IVIVLELKGSE TTFMCEYADE TATIVEFLNR   120
WITFCQSIIS TLTSGGPGPA GLYAQPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPGPA   300
GLYAQPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGQGTT   420
VTVSSSGGPG PAGLYAQPGS DIQMTQSPSS LSASVGDRVT ITCKVTEKVW GNVAWYQQKP   480
GKAPISLIYS PSLRKSGVPS RFSGSGSGTD FTLTISSLQP EDFATYYCQQ YYTYPYTFGG   540
GTKVEIK                                                            547

SEQ ID NO: 397          moltype = AA  length = 547
FEATURE                 Location/Qualifiers
source                  1..547
```

```
                         mol_type = protein
                         organism = synthetic construct
SEQUENCE: 397
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLVESGGGLV QPGGSLRLSC AASGFTFSSY TLAWVRQAPG KGLEWVAAID    360
SSSYTYSPDT VRGRFTISRD NAKNSLYLQM NSLRAEDTAV YYCARDSNWD ALDYWGQGTT    420
VTVSSGGGGS GGGGSGGGGS DIQMTQSPSS LSASVGDRVT ITCKVTEKVW GNVAWYQQKP    480
GKAPISLIYS PSLRKSGVPS RFSGSGSGTD FTLTISSLQP EDFATYYCQQ YYTYPYTFGG    540
GTKVEIK                                                             547

SEQ ID NO: 398          moltype = AA  length = 427
FEATURE                 Location/Qualifiers
source                  1..427
                        mol_type = protein
                        organism = synthetic construct
SEQUENCE: 398
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLLESGGGLV QPGGSLRLSC AASGSIFSAN AMGWYRQAPG KGLELVAVIS    360
SGGSTNYADS VKGRFTISRD NSKNTVYLQM NSLRAEDTAV YYCMYSGSYY YTPNDYWGQG    420
TLVTVSS                                                             427

SEQ ID NO: 399          moltype = AA  length = 426
FEATURE                 Location/Qualifiers
source                  1..426
                        mol_type = protein
                        organism = synthetic construct
SEQUENCE: 399
APTSSSTKKT QLQLEHLLLD LQMILNGINN YKNPKLTRML TFKFYMPKKA TELKHLQCLE     60
EELKPLEEVL NLAQSKNFHL RPRDLISNIN VIVLELKGSE TTFMCEYADE TATIVEFLNR    120
WITFCQSIIS TLTSGGPGPA GLYAQPGSEV QLVESGGGLV QPGNSLRLSC AASGFTFSKF    180
GMSWVRQAPG KGLEWVSSIS GSGRDTLYAE SVKGRFTISR DNAKTTLYLQ MNSLRPEDTA    240
VYYCTIGGSL SVSSQGTLVT VSSGGGGSGG GGSGGGGSGG GGSGGGGSGG GGSSGGPGPA    300
GLYAQPGSEV QLLESGGGLV QPGGSLRLSC AASERIFSTD VMGWYRQAPG KQRELVAVVS    360
ARGTTNYLDA VKGRFTISRD NSKNTLYLQM NSLRAEDTAV YYCYVRETTS PWRIYWGQGT    420
LVTVSS                                                              426

SEQ ID NO: 400          moltype = AA  length = 811
FEATURE                 Location/Qualifiers
source                  1..811
                        mol_type = protein
                        organism = synthetic construct
SEQUENCE: 400
ELCDDDPPEI PHATFKAMAY KEGTMLNCEC KRGFRRIKSG SLYMLCTGNS SHSSWDNQCQ     60
CTSSATRNTT KQVTPQPEEQ KERKTTEMQS PMQPVDQASL PGHCREPPPW ENEATERIYH    120
FVVGQMVYYQ CVQGYRALHR GPAESVCKMT HGKTRWTQPQ LICTGEMETS QFPGEEKPQA    180
SPEGRPESET SSLVTTTDFQ IQTEMAATME TSIFTTEYQG GGGSGGGGSG GGGSGGGGSG    240
GGGSGGGGSS GGPGPAGLYA QPGSAPTSSS TKKTQLQLEH LLLDLQMILN GINNYKNPKL    300
TRMLTFKFYM PKKATELKHL QCLEEELKPL EEVLNLAQSK NFHLRPRDLI SNINVIVLEL    360
KGSETTFMCE YADETATIVE FLNRWITFCQ SIISTLTSGG PGPAGLYAQP GSEVQLVESG    420
GGLVQPGNSL RLSCAASGFT FSKFGMSWVR QAPGKGLEWV SSISGSGRDT LYAESVKGRF    480
TISRDNAKTT LYLQMNSLRP EDTAVYYCTI GGSLSVSSGG TLVTVSSGGG GSGGGGSGGG    540
GSGGGGSGGG GSGGGGSSGG PGPAGLYAQP GSEVQLVESG GGLVQPGGSL RLSCAASGFT    600
FSSYTLAWVR QAPGKGLEWV AAIDSSSYTY SPDTVRGRFT ISRDNAKNSL YLQMNSLRAE    660
DTAVYYCARD SNWDALDYWG QGTTVTVSSS GGPGPAGLYA QPGSDIQMTQ SPSSLSASVG    720
DRVTITCKAR EKLWSAVAWY QQKPGKAPKS LIYSASFRYS GVPSRFSGSG SGTDFTLTIS    780
SLQPEDFATY YCQQYYTYPY TFGGGTKVEI K                                   811

SEQ ID NO: 401          moltype = AA  length = 811
FEATURE                 Location/Qualifiers
source                  1..811
                        mol_type = protein
                        organism = synthetic construct
SEQUENCE: 401
ELCDDDPPEI PHATFKAMAY KEGTMLNCEC KRGFRRIKSG SLYMLCTGNS SHSSWDNQCQ     60
CTSSATRNTT KQVTPQPEEQ KERKTTEMQS PMQPVDQASL PGHCREPPPW ENEATERIYH    120
FVVGQMVYYQ CVQGYRALHR GPAESVCKMT HGKTRWTQPQ LICTGEMETS QFPGEEKPQA    180
SPEGRPESET SSLVTTTDFQ IQTEMAATME TSIFTTEYQG GGGSGGGGSG GGGSGGGGSG    240
GGGSGGGGSS GGPGPAGLYA QPGSAPTSSS TKKTQLQLEH LLLDLQMILN GINNYKNPKL    300
TRMLTFKFYM PKKATELKHL QCLEEELKPL EEVLNLAQSK NFHLRPRDLI SNINVIVLEL    360
KGSETTFMCE YADETATIVE FLNRWITFCQ SIISTLTSGG PGPAGLYAQP GSEVQLVESG    420
GGLVQPGNSL RLSCAASGFT FSKFGMSWVR QAPGKGLEWV SSISGSGRDT LYAESVKGRF    480
```

```
TISRDNAKTT LYLQMNSLRP EDTAVYYCTI GGSLSVSSQG TLVTVSSGGG GSGGGGSGGG    540
GSGGGGSGGG GSGGGGSSGG PGPAGLYAQP GSEVQLVESG GGLVQPGGSL RLSCAASGFT    600
FSSYTLAWVR QAPGKGLEWV AAIDSSSYTY SPDTVRGRFT ISRDNAKNSL YLQMNSLRAE    660
DTAVYYCARD SNWDALDYWG QGTTVTVSSG GGGSGGGGSG GGGSDIQMTQ SPSSLSASVG    720
DRVTITCKAR EKLWSAVAWY QQKPGKAPKS LIYSASFRYS GVPSRFSGSG SGTDFTLTIS    780
SLQPEDFATY YCQQYYTYPY TFGGGTKVEI K                                   811

SEQ ID NO: 402        moltype = AA   length = 811
FEATURE               Location/Qualifiers
source                1..811
                      mol_type = protein
                      organism = synthetic construct
SEQUENCE: 402
ELCDDDPPEI PHATFKAMAY KEGTMLNCEC KRGFRRIKSG SLYMLCTGNS SHSSWDNQCQ     60
CTSSATRNTT KQVTPQPEEQ KERKTTEMQS PMQPVDQASL PGHCREPPPW ENEATERIYH    120
FVVGQMVYYQ CVQGYRALHR GPAESVCKMT HGKTRWTQPQ LICTGEMETS QFPGEEKPQA    180
SPEGRPESET SSLVTTTDFQ IQTEMAATME TSIFTTEYQG GGGSGGGGSG GGGSGGGGSG    240
GGGSGGGGSS GGPGPAGLYA QPGSAPTSSS TKKTQLQLEH LLLDLQMILN GINNYKNPKL    300
TRMLTFKFYM PKKATELKHL QCLEEELKPL EEVLNLAQSK NFHLRPRDLI SNINIVLEL     360
KGSETTFMCE YADETATIVE FLNRWITFCQ SIISTLTSGG PGPAGLYAQP GSEVQLVESG    420
GGLVQPGNSL RLSCAASGFT FSKFGMSWVR QAPGKGLEWV SSISGSGRDT LYAESVKGRF    480
TISRDNAKTT LYLQMNSLRP EDTAVYYCTI GGSLSVSSQG TLVTVSSGGG GSGGGGSGGG    540
GSGGGGSGGG GSGGGGSSGG PGPAGLYAQP GSEVQLVESG GGLVQPGGSL RLSCAASGFT    600
FSSYTLAWVR QAPGKGLEWV AAIDSSSYTY SPDTVRGRFT ISRDNAKNSL YLQMNSLRAE    660
DTAVYYCARD SNWDALDYWG QGTTVTVSSS GGPGPAGLYA QPGSDIQMTQ SPSSLSASVG    720
DRVTITCKVT EKVWGNVAWY QQKPGKAPIS LIYSPSLRKS GVPSRFSGSG SGTDFTLTIS    780
SLQPEDFATY YCQQYYTYPY TFGGGTKVEI K                                   811

SEQ ID NO: 403        moltype = AA   length = 811
FEATURE               Location/Qualifiers
source                1..811
                      mol_type = protein
                      organism = synthetic construct
SEQUENCE: 403
ELCDDDPPEI PHATFKAMAY KEGTMLNCEC KRGFRRIKSG SLYMLCTGNS SHSSWDNQCQ     60
CTSSATRNTT KQVTPQPEEQ KERKTTEMQS PMQPVDQASL PGHCREPPPW ENEATERIYH    120
FVVGQMVYYQ CVQGYRALHR GPAESVCKMT HGKTRWTQPQ LICTGEMETS QFPGEEKPQA    180
SPEGRPESET SSLVTTTDFQ IQTEMAATME TSIFTTEYQG GGGSGGGGSG GGGSGGGGSG    240
GGGSGGGGSS GGPGPAGLYA QPGSAPTSSS TKKTQLQLEH LLLDLQMILN GINNYKNPKL    300
TRMLTFKFYM PKKATELKHL QCLEEELKPL EEVLNLAQSK NFHLRPRDLI SNINIVLEL     360
KGSETTFMCE YADETATIVE FLNRWITFCQ SIISTLTSGG PGPAGLYAQP GSEVQLVESG    420
GGLVQPGNSL RLSCAASGFT FSKFGMSWVR QAPGKGLEWV SSISGSGRDT LYAESVKGRF    480
TISRDNAKTT LYLQMNSLRP EDTAVYYCTI GGSLSVSSQG TLVTVSSGGG GSGGGGSGGG    540
GSGGGGSGGG GSGGGGSSGG PGPAGLYAQP GSEVQLVESG GGLVQPGGSL RLSCAASGFT    600
FSSYTLAWVR QAPGKGLEWV AAIDSSSYTY SPDTVRGRFT ISRDNAKNSL YLQMNSLRAE    660
DTAVYYCARD SNWDALDYWG QGTTVTVSSG GGGSGGGGSG GGGSDIQMTQ SPSSLSASVG    720
DRVTITCKVT EKVWGNVAWY QQKPGKAPIS LIYSPSLRKS GVPSRFSGSG SGTDFTLTIS    780
SLQPEDFATY YCQQYYTYPY TFGGGTKVEI K                                   811

SEQ ID NO: 404        moltype = AA   length = 691
FEATURE               Location/Qualifiers
source                1..691
                      mol_type = protein
                      organism = synthetic construct
SEQUENCE: 404
ELCDDDPPEI PHATFKAMAY KEGTMLNCEC KRGFRRIKSG SLYMLCTGNS SHSSWDNQCQ     60
CTSSATRNTT KQVTPQPEEQ KERKTTEMQS PMQPVDQASL PGHCREPPPW ENEATERIYH    120
FVVGQMVYYQ CVQGYRALHR GPAESVCKMT HGKTRWTQPQ LICTGEMETS QFPGEEKPQA    180
SPEGRPESET SSLVTTTDFQ IQTEMAATME TSIFTTEYQG GGGSGGGGSG GGGSGGGGSG    240
GGGSGGGGSS GGPGPAGLYA QPGSAPTSSS TKKTQLQLEH LLLDLQMILN GINNYKNPKL    300
TRMLTFKFYM PKKATELKHL QCLEEELKPL EEVLNLAQSK NFHLRPRDLI SNINIVLEL     360
KGSETTFMCE YADETATIVE FLNRWITFCQ SIISTLTSGG PGPAGLYAQP GSEVQLVESG    420
GGLVQPGNSL RLSCAASGFT FSKFGMSWVR QAPGKGLEWV SSISGSGRDT LYAESVKGRF    480
TISRDNAKTT LYLQMNSLRP EDTAVYYCTI GGSLSVSSQG TLVTVSSGGG GSGGGGSGGG    540
GSGGGGSGGG GSGGGGSSGG PGPAGLYAQP GSEVQLLESG GGLVQPGGSL RLSCAASGSI    600
FSANAMGWYR QAPGKGLELV AVISSGGSTN YADSVKGRFT ISRDNSKNTV YLQMNSLRAE    660
DTAVYYCMYS GSYYYTPNDY WGQGTLVTVS S                                   691

SEQ ID NO: 405        moltype = AA   length = 690
FEATURE               Location/Qualifiers
source                1..690
                      mol_type = protein
                      organism = synthetic construct
SEQUENCE: 405
ELCDDDPPEI PHATFKAMAY KEGTMLNCEC KRGFRRIKSG SLYMLCTGNS SHSSWDNQCQ     60
CTSSATRNTT KQVTPQPEEQ KERKTTEMQS PMQPVDQASL PGHCREPPPW ENEATERIYH    120
FVVGQMVYYQ CVQGYRALHR GPAESVCKMT HGKTRWTQPQ LICTGEMETS QFPGEEKPQA    180
SPEGRPESET SSLVTTTDFQ IQTEMAATME TSIFTTEYQG GGGSGGGGSG GGGSGGGGSG    240
GGGSGGGGSS GGPGPAGLYA QPGSAPTSSS TKKTQLQLEH LLLDLQMILN GINNYKNPKL    300
```

-continued

```
TRMLTFKFYM PKKATELKHL QCLEEELKPL EEVLNLAQSK NFHLRPRDLI SNINIVIVLEL   360
KGSETTFMCE YADETATIVE FLNRWITFCQ SIISTLTSGG PGPAGLYAQP GSEVQLVESG     420
GGLVQPGNSL RLSCAASGFT FSKFGMSWVR QAPGKGLEWV SSISGSGRDT LYAESVKGRF     480
TISRDNAKTT LYLQMNSLRP EDTAVYYCTI GGSLSVSSQG TLVTVSSGGG GSGGGGSGGG     540
GSGGGGSGGG GSGGGGSSGG PGPAGLYAQP GSEVQLLESG GGLVQPGGSL RLSCAASERI     600
FSTDVMGWYR QAPGKQRELV AVVSARGTTN YLDAVKGRFT ISRDNSKNTL YLQMNSLRAE     660
DTAVYYCYVR ETTSPWRIYW GQGTLVTVSS                                      690

SEQ ID NO: 406          moltype = AA   length = 661
FEATURE                 Location/Qualifiers
source                  1..661
                        mol_type = protein
                        organism = synthetic construct
SEQUENCE: 406
ESKYGPPCPP CPAPEFLGGP SVFLFPPKPK DTLMISRTPE VTCVVVDVSQ EDPEVQFNWY     60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKS GGPGPAGLYA    240
QPGSAPTSSS TKKTQLQLEH LLLDLQMILN GINNYKNPKL TRMLTFKFYM PKKATELKHL    300
QCLEEELKPL EEVLNLAQSK NFHLRPRDLI SNINIVIVLEL KGSETTFMCE YADETATIVE    360
FLNRWITFCQ SIISTLTGGG GSGGGGSGGG GSGGGGSGGG GSGGGGSSGG PGPAGLYAQP    420
GSEVQLVESG GGLVQPGGSL RLSCAASGFT FSSYTLAWVR QAPGKGLEWV AAIDSSSYTY    480
SPDTVRGRFT ISRDNAKNSL YLQMNSLRAE DTAVYYCARD SNWDALDYWG QGTTVTVSSS    540
GGPGPAGLYA QPGSDIQMTQ SPSSLSASVG DRVTITCKAR EKLWSAVAWY QQKPGKAPKS    600
LIYSASFRYS GVPSRFSGSG SGTDFTLTIS SLQPEDFATY YCQQYYTYPY TFGGGTKVEI    660
K                                                                    661

SEQ ID NO: 407          moltype = AA   length = 661
FEATURE                 Location/Qualifiers
source                  1..661
                        mol_type = protein
                        organism = synthetic construct
SEQUENCE: 407
ESKYGPPCPP CPAPEFLGGP SVFLFPPKPK DTLMISRTPE VTCVVVDVSQ EDPEVQFNWY     60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKS GGPGPAGLYA    240
QPGSAPTSSS TKKTQLQLEH LLLDLQMILN GINNYKNPKL TRMLTFKFYM PKKATELKHL    300
QCLEEELKPL EEVLNLAQSK NFHLRPRDLI SNINIVIVLEL KGSETTFMCE YADETATIVE    360
FLNRWITFCQ SIISTLTGGG GSGGGGSGGG GSGGGGSGGG GSGGGGSSGG PGPAGLYAQP    420
GSEVQLVESG GGLVQPGGSL RLSCAASGFT FSSYTLAWVR QAPGKGLEWV AAIDSSSYTY    480
SPDTVRGRFT ISRDNAKNSL YLQMNSLRAE DTAVYYCARD SNWDALDYWG QGTTVTVSSG    540
GGGSGGGGSG GGGSDIQMTQ SPSSLSASVG DRVTITCKAR EKLWSAVAWY QQKPGKAPKS    600
LIYSASFRYS GVPSRFSGSG SGTDFTLTIS SLQPEDFATY YCQQYYTYPY TFGGGTKVEI    660
K                                                                    661

SEQ ID NO: 408          moltype = AA   length = 661
FEATURE                 Location/Qualifiers
source                  1..661
                        mol_type = protein
                        organism = synthetic construct
SEQUENCE: 408
ESKYGPPCPP CPAPEFLGGP SVFLFPPKPK DTLMISRTPE VTCVVVDVSQ EDPEVQFNWY     60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKS GGPGPAGLYA    240
QPGSAPTSSS TKKTQLQLEH LLLDLQMILN GINNYKNPKL TRMLTFKFYM PKKATELKHL    300
QCLEEELKPL EEVLNLAQSK NFHLRPRDLI SNINIVIVLEL KGSETTFMCE YADETATIVE    360
FLNRWITFCQ SIISTLTGGG GSGGGGSGGG GSGGGGSGGG GSGGGGSSGG PGPAGLYAQP    420
GSEVQLVESG GGLVQPGGSL RLSCAASGFT FSSYTLAWVR QAPGKGLEWV AAIDSSSYTY    480
SPDTVRGRFT ISRDNAKNSL YLQMNSLRAE DTAVYYCARD SNWDALDYWG QGTTVTVSSS    540
GGPGPAGLYA QPGSDIQMTQ SPSSLSASVG DRVTITCKVT EKVWGNVAWY QQKPGKAPIS    600
LIYSPSLRKS GVPSRFSGSG SGTDFTLTIS SLQPEDFATY YCQQYYTYPY TFGGGTKVEI    660
K                                                                    661

SEQ ID NO: 409          moltype = AA   length = 661
FEATURE                 Location/Qualifiers
source                  1..661
                        mol_type = protein
                        organism = synthetic construct
SEQUENCE: 409
ESKYGPPCPP CPAPEFLGGP SVFLFPPKPK DTLMISRTPE VTCVVVDVSQ EDPEVQFNWY     60
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKS GGPGPAGLYA    240
QPGSAPTSSS TKKTQLQLEH LLLDLQMILN GINNYKNPKL TRMLTFKFYM PKKATELKHL    300
QCLEEELKPL EEVLNLAQSK NFHLRPRDLI SNINIVIVLEL KGSETTFMCE YADETATIVE    360
FLNRWITFCQ SIISTLTGGG GSGGGGSGGG GSGGGGSGGG GSGGGGSSGG PGPAGLYAQP    420
GSEVQLVESG GGLVQPGGSL RLSCAASGFT FSSYTLAWVR QAPGKGLEWV AAIDSSSYTY    480
```

-continued

```
SPDTVRGRFT ISRDNAKNSL YLQMNSLRAE DTAVYYCARD SNWDALDYWG QGTTVTVSSG   540
GGGSGGGGSG GGGSDIQMTQ SPSSLSASVG DRVTITCKVT EKVWGNVAWY QQKPGKAPIS   600
LIYSPSLRKS GVPSRFSGSG SGTDFTLTIS SLQPEDFATY YCQQYYTYPY TFGGGTKVEI   660
K                                                                 661

SEQ ID NO: 410            moltype = AA   length = 541
FEATURE                   Location/Qualifiers
source                    1..541
                          mol_type = protein
                          organism = synthetic construct
SEQUENCE: 410
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPGPAGLYA   240
QPGSAPTSSS TKKTQLQLEH LLLDLQMILN GINNYKNPKL TRMLTFKFYM PKKATELKHL   300
QCLEEELKPL EEVLNLAQSK NFHLRPRDLI SNINVIVLEL KGSETTFMCE YADETATIVE   360
FLNRWITFCQ SIISTLTGGG GSGGGGSGGG GSGGGGSGGG GSGGGGSSGG PGPAGLYAQP   420
GSEVQLLESG GGLVQPGGSL RLSCAASGSI FSANAMGWYR QAPGKGLELV AVISSGGSTN   480
YADSVKGRFT ISRDNSKNTV YLQMNSLRAE DTAVYYCMYS GSYYYTPNDY WGQGTLVTVS   540
S                                                                 541

SEQ ID NO: 411            moltype = AA   length = 540
FEATURE                   Location/Qualifiers
source                    1..540
                          mol_type = protein
                          organism = synthetic construct
SEQUENCE: 411
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPGPAGLYA   240
QPGSAPTSSS TKKTQLQLEH LLLDLQMILN GINNYKNPKL TRMLTFKFYM PKKATELKHL   300
QCLEEELKPL EEVLNLAQSK NFHLRPRDLI SNINVIVLEL KGSETTFMCE YADETATIVE   360
FLNRWITFCQ SIISTLTGGG GSGGGGSGGG GSGGGGSGGG GSGGGGSSGG PGPAGLYAQP   420
GSEVQLLESG GGLVQPGGSL RLSCAASERI FSTDVMGWYR QAPGKQRELV AVVSARGTTN   480
YLDAVKGRFT ISRDNSKNTL YLQMNSLRAE DTAVYYCYVR ETTSPWRIYW GQGTLVTVSS   540

SEQ ID NO: 412            moltype = AA   length = 925
FEATURE                   Location/Qualifiers
source                    1..925
                          mol_type = protein
                          organism = synthetic construct
SEQUENCE: 412
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPGPAGLYA   240
QPGSELCDDD PPEIPHATFK AMAYKEGTML NCECKRGFRR IKSGSLYMLC TGNSSHSSWD   300
NQCQCTSSAT RNTTKQVTPQ PEEQKERKTT EMQSPMQPVD QASLPGHCRE PPPWENEATE   360
RIYHFVVGQM VYYQCVQGYR ALHRGPAESV CKMTHGKTRW TQPQLICTGE METSQFPGEE   420
KPQASPEGRP ESETSSLVTT TDFQIQTEMA ATMETSIFTT EYQGGGGSGG GGSGGGGSGG   480
GGSGGGGSGG GGSSGPGPA GLYAQPGSAP TSSSTKKTQL QLEHLLLDLQ MILNGINNYK   540
NPKLTRMLTF KFYMPKKATE LKHLQCLEEE LKPLEEVLNL AQSKNFHLRP RDLISNINVI   600
VLELKGSETT FMCEYADETA TIVEFLNRWI TFCQSIISTL TGGGGSGGGG SGGGGSGGGG   660
SGGGGSGGGG SSGGPGPAGL YAQPGSEVQL VESGGGLVQP GGSLRLSCAA SGFTFSSYTL   720
AWVRQAPGKG LEWVAAIDSS SYTYSPDTVR GRFTISRDNA KNSLYLQMNS LRAEDTAVYY   780
CARDSNWDAL DYWGQGTTVT VSSSGPGPA GLYAQPGSDI QMTQSPSSLS ASVGDRVTIT   840
CKAREKLWSA VAWYQQKPGK APKSLIYSAS FRYSGVPSRF SGSGSGTDFT LTISSLQPED   900
FATYYCQQYY TYPYTFGGGT KVEIK                                        925

SEQ ID NO: 413            moltype = AA   length = 925
FEATURE                   Location/Qualifiers
source                    1..925
                          mol_type = protein
                          organism = synthetic construct
SEQUENCE: 413
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPGPAGLYA   240
QPGSELCDDD PPEIPHATFK AMAYKEGTML NCECKRGFRR IKSGSLYMLC TGNSSHSSWD   300
NQCQCTSSAT RNTTKQVTPQ PEEQKERKTT EMQSPMQPVD QASLPGHCRE PPPWENEATE   360
RIYHFVVGQM VYYQCVQGYR ALHRGPAESV CKMTHGKTRW TQPQLICTGE METSQFPGEE   420
KPQASPEGRP ESETSSLVTT TDFQIQTEMA ATMETSIFTT EYQGGGGSGG GGSGGGGSGG   480
GGSGGGGSGG GGSSGPGPA GLYAQPGSAP TSSSTKKTQL QLEHLLLDLQ MILNGINNYK   540
NPKLTRMLTF KFYMPKKATE LKHLQCLEEE LKPLEEVLNL AQSKNFHLRP RDLISNINVI   600
VLELKGSETT FMCEYADETA TIVEFLNRWI TFCQSIISTL TGGGGSGGGG SGGGGSGGGG   660
SGGGGSGGGG SSGGPGPAGL YAQPGSEVQL VESGGGLVQP GGSLRLSCAA SGFTFSSYTL   720
```

-continued

```
AWVRQAPGKG LEWVAAIDSS SYTYSPDTVR GRFTISRDNA KNSLYLQMNS LRAEDTAVYY   780
CARDSNWDAL DYWGQGTTVT VSSGGGGSGG GGSGGGGSDI QMTQSPSSLS ASVGDRVTIT   840
CKAREKLWSA VAWYQQKPGK APKSLIYSAS FRYSGVPSRF SGSGSGTDFT LTISSLQPED   900
FATYYCQQYY TYPYTFGGGT KVEIK                                         925

SEQ ID NO: 414          moltype = AA  length = 925
FEATURE                 Location/Qualifiers
source                  1..925
                        mol_type = protein
                        organism = synthetic construct
SEQUENCE: 414
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPGPAGLYA   240
QPGSELCDDD PPEIPHATFK AMAYKEGTML NCECKRGFRR IKSGSLYMLC TGNSSHSSWD   300
NQCQCTSSAT RNTTKQVTPQ PEEQKERKTT EMQSPMQPVD QASLPGHCRE PPPWENEATE   360
RIYHFVVGQM VYYQCVQGYR ALHRGPAESV CKMTHGKTRW TQPQLICTGE METSQFPGEE   420
KPQASPEGRP ESETSSLVTT TDFQIQTEMA ATMETSIFTT EYQGGGGSGG GGSGGGGSGG   480
GGSGGGGSGG GGSSGGPGPA GLYAQPGSAP TSSSTKKTQL QLEHLLLDLQ MILNGINNYK   540
NPKLTRMLTF KFYMPKKATE LKHLQCLEEE LKPLEEVLNL AQSKNFHLRP RDLISNINVI   600
VLELKGSETT FMCEYADETA TIVEFLNRWI TFCQSIISTL TGGGGSGGGG SGGGGSGGGG   660
SGGGGSGGGG SSGGPGPAGL YAQPGSEVQL VESGGGLVQP GGSLRLSCAA SGFTFSSYTL   720
AWVRQAPGKG LEWVAAIDSS SYTYSPDTVR GRFTISRDNA KNSLYLQMNS LRAEDTAVYY   780
CARDSNWDAL DYWGQGTTVT VSSSGGPGPA GLYAQPGSDI QMTQSPSSLS ASVGDRVTIT   840
CKVTEKVWGN VAWYQQKPGK APISLIYSPS LRKSGVPSRF SGSGSGTDFT LTISSLQPED   900
FATYYCQQYY TYPYTFGGGT KVEIK                                         925

SEQ ID NO: 415          moltype = AA  length = 925
FEATURE                 Location/Qualifiers
source                  1..925
                        mol_type = protein
                        organism = synthetic construct
SEQUENCE: 415
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPGPAGLYA   240
QPGSELCDDD PPEIPHATFK AMAYKEGTML NCECKRGFRR IKSGSLYMLC TGNSSHSSWD   300
NQCQCTSSAT RNTTKQVTPQ PEEQKERKTT EMQSPMQPVD QASLPGHCRE PPPWENEATE   360
RIYHFVVGQM VYYQCVQGYR ALHRGPAESV CKMTHGKTRW TQPQLICTGE METSQFPGEE   420
KPQASPEGRP ESETSSLVTT TDFQIQTEMA ATMETSIFTT EYQGGGGSGG GGSGGGGSGG   480
GGSGGGGSGG GGSSGGPGPA GLYAQPGSAP TSSSTKKTQL QLEHLLLDLQ MILNGINNYK   540
NPKLTRMLTF KFYMPKKATE LKHLQCLEEE LKPLEEVLNL AQSKNFHLRP RDLISNINVI   600
VLELKGSETT FMCEYADETA TIVEFLNRWI TFCQSIISTL TGGGGSGGGG SGGGGSGGGG   660
SGGGGSGGGG SSGGPGPAGL YAQPGSEVQL VESGGGLVQP GGSLRLSCAA SGFTFSSYTL   720
AWVRQAPGKG LEWVAAIDSS SYTYSPDTVR GRFTISRDNA KNSLYLQMNS LRAEDTAVYY   780
CARDSNWDAL DYWGQGTTVT VSSGGGGSGG GGSGGGGSDI QMTQSPSSLS ASVGDRVTIT   840
CKVTEKVWGN VAWYQQKPGK APISLIYSPS LRKSGVPSRF SGSGSGTDFT LTISSLQPED   900
FATYYCQQYY TYPYTFGGGT KVEIK                                         925

SEQ ID NO: 416          moltype = AA  length = 805
FEATURE                 Location/Qualifiers
source                  1..805
                        mol_type = protein
                        organism = synthetic construct
SEQUENCE: 416
ESKYGPPCPP CPAPEFLGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK   120
AKGQPREPQV YTLPPSQEEM TKNQVSLTCL VKGFYPSDIA VEWESNGQPE NNYKTTPPVL   180
DSDGSFFLYS RLTVDKSRWQ EGNVFSCSVM HEALHNHYTQ KSLSLSLGKS GGPGPAGLYA   240
QPGSELCDDD PPEIPHATFK AMAYKEGTML NCECKRGFRR IKSGSLYMLC TGNSSHSSWD   300
NQCQCTSSAT RNTTKQVTPQ PEEQKERKTT EMQSPMQPVD QASLPGHCRE PPPWENEATE   360
RIYHFVVGQM VYYQCVQGYR ALHRGPAESV CKMTHGKTRW TQPQLICTGE METSQFPGEE   420
KPQASPEGRP ESETSSLVTT TDFQIQTEMA ATMETSIFTT EYQGGGGSGG GGSGGGGSGG   480
GGSGGGGSGG GGSSGGPGPA GLYAQPGSAP TSSSTKKTQL QLEHLLLDLQ MILNGINNYK   540
NPKLTRMLTF KFYMPKKATE LKHLQCLEEE LKPLEEVLNL AQSKNFHLRP RDLISNINVI   600
VLELKGSETT FMCEYADETA TIVEFLNRWI TFCQSIISTL TGGGGSGGGG SGGGGSGGGG   660
SGGGGSGGGG SSGGPGPAGL YAQPGSEVQL LESGGGLVQP GGSLRLSCAA SGSIFSANAM   720
GWYRQAPGKG LELVAVISSG GSTNYADSVK GRFTISRDNS KNTVYLQMNS LRAEDTAVYY   780
CMYSGSYYYT PNDYWGQGTL VTVSS                                         805

SEQ ID NO: 417          moltype = AA  length = 804
FEATURE                 Location/Qualifiers
source                  1..804
                        mol_type = protein
                        organism = synthetic construct
SEQUENCE: 417
ESKYGPPCPP CPAPEFLGGP SVFLFPPKPK DTLMISRTPE VTCVVVDVSQ EDPEVQFNWY   60
```

-continued

```
VDGVEVHNAK TKPREEQFNS TYRVVSVLTV LHQDWLNGKE YKCKVSNKGL PSSIEKTISK    120
AKGQPREPQV YTLPPSQEEM TKNQVSLTCL VKGFYPSDIA VEWESNGQPE NNYKTTPPVL    180
DSDGSFFLYS RLTVDKSRWQ EGNVFSCSVM HEALHNHYTQ KSLSLSLGKS GGPGPAGLYA    240
QPGSELCDDD PPEIPHATFK AMAYKEGTML NCECKRGFRR IKSGSLYMLC TGNSSHSSWD    300
NQCQCTSSAT RNTTKQVTPQ PEEQKERKTT EMQSPMQPVD QASLPGHCRE PPPWENEATE    360
RIYHFVVGQM VYYQCVQGYR ALHRGPAESV CKMTHGKTRW TQPQLICTGE METSQFPGEE    420
KPQASPEGRP ESETSSLVTT TDFQIQTEMA ATMETSIFTT EYQGGGGSGG GGSGGGGSGG    480
GGSGGGGSGG GGSSGGPGPA GLYAQPGSAP TSSSTKKTQL QLEHLLLDLQ MILNGINNYK    540
NPKLTRMLTF KFYMPKKATE LKHLQCLEEE LKPLEEVLNL AQSKNFHLRP RDLISNINVI    600
VLELKGSETT FMCEYADETA TIVEFLNRWI TFCQSIISTL TGGGGSGGGG SGGGGSGGGG    660
SGGGGSGGGG SSSGGPGPAGL YAQPGSEVQL LESGGGLVQP GGSLRLSCAA SERIFSTDVM    720
GWYRQAPGKQ RELVAVVSAR GTTNYLDAVK GRFTISRDNS KNTLYLQMNS LRAEDTAVYY    780
CYVRETTSPW RIYWGQGTLV TVSS                                           804
```

```
SEQ ID NO: 418              moltype = AA   length = 245
FEATURE                     Location/Qualifiers
source                      1..245
                            mol_type = protein
                            organism = synthetic construct
SEQUENCE: 418
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSGGG    120
GSGGGGSGGG GSDIQMTQSP SSLSASVGDR VTITCKASQN VGTNVGWYQQ KPGKAPKSLI    180
YSASFRYSGV PSRFSGSGSG TDFTLTISSL QPEDFATYYC QQYYTYPYTF GGGTKVEIKH    240
HHHHH                                                                245
```

```
SEQ ID NO: 419              moltype = AA   length = 245
FEATURE                     Location/Qualifiers
source                      1..245
                            mol_type = protein
                            organism = synthetic construct
SEQUENCE: 419
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSSGG    120
PGPAGLYAQP GSDIQMTQSP SSLSASVGDR VTITCKASQN VGTNVGWYQQ KPGKAPKALI    180
YSASFRYSGV PSRFSGSGSG TDFTLTISSL QPEDFATYYC QQYYTYPYTF GGGTKVEIKH    240
HHHHH                                                                245
```

```
SEQ ID NO: 420              moltype = AA   length = 245
FEATURE                     Location/Qualifiers
source                      1..245
                            mol_type = protein
                            organism = synthetic construct
SEQUENCE: 420
EVQLVESGGG LVQPGGSLRL SCAASGFTFS SYTLAWVRQA PGKGLEWVAA IDSSSYTYSP    60
DTVRGRFTIS RDNAKNSLYL QMNSLRAEDT AVYYCARDSN WDALDYWGQG TTVTVSSSGG    120
PGPAGLYAQP GSDIQMTQSP SSLSASVGDR VTITCKASQN VGTNVGWYQQ KPGKAPKSLI    180
YSASFRYSGV PSRFSGSGSG TDFTLTISSL QPEDFATYYC QQYYTYPYTF GGGTKVEIKH    240
HHHHH                                                                245
```

```
SEQ ID NO: 421              moltype = AA   length = 612
FEATURE                     Location/Qualifiers
source                      1..612
                            mol_type = protein
                            organism = synthetic construct
SEQUENCE: 421
LVEEPKNLVK TNCDLYEKLG EYGFQNAILV RYTQKAPQVS TPTLVEAARN LGRVGTKCCT    60
LPEDQRLPCV EDYLSAILNR VCLLHEKTPV SEHVTKCCSG SLVERRPCFS ALTVDETYVP    120
KEFKAETFTF HSDICTLPEK EKQIKKQTAL AELVKHKPKA TAEQLKTVMD DPAQFLDTCC    180
KAADKDTCFS TEGPNLVTRC KDALASGGPG PAGMKGLPGS CDLPQTHNLR NKRALTLLVQ    240
MRRLSPLSCL KDRKDFGFPQ EKVDAQQIKK AQAIPVLSEL TQQILNIFTS KDSSAAWNTT    300
LLDSFCNDLH QQLNDLQGCL MQQVGVQEFP LTQEDALLAV RKYFHRITVY LREKKHSPCA    360
WEVVRAEVWR ALSSSANVLG RLREEKSGGP GPAGMKGLPG SLVEEPKNLV KTNCDLYEKL    420
GEYGFQNAIL VRYTQKAPQV STPTLVEAAR NLGRVGTKCC TLPEDQRLPC VEDYLSAILN    480
RVCLLHEKTP VSEHVTKCCS GSLVERRPCF SALTVDETYV PKEFKAETFT FHSDICTLPE    540
KEKQIKKQTA LAELVKHKPK ATAEQLKTVM DDFAQFLDTC CKAADKDTCF STEGPNLVTR    600
CKDALAHHHH HH                                                        612
```

```
SEQ ID NO: 422              moltype = AA   length = 1030
FEATURE                     Location/Qualifiers
source                      1..1030
                            mol_type = protein
                            organism = synthetic construct
SEQUENCE: 422
EAHKSEIAHR YNDLGEQHFK GLVLIAFSQY LQKCSYDEHA KLVQEVTDFA KTCVADESAA    60
NCDKSLHTLF GDKLCAIPNL RENYGELADC CTKQEPERNE CFLQHKDDNP SLPPFERPEA    120
EAMCTSFKEN PTTFMGHYLH EVARRHPYFY APELLYYAEQ YNEILTQCCA EADKESCLTP    180
KLDGVKEKAL VSSVRQGGGG SGGGGSGGSL VEEPKNLVKT NCDLYEKLGE YGFQNAILVR    240
YTQKAPQVST PTLVEAARNL GRVGTKCCTL PEDQRLPCVE DYLSAILNRV CLLHEKTPVS    300
```

```
EHVTKCCSGS LVERRPCFSA LTVDETYVPK EFKAETFTFH SDICTLPEKE KQIKKQTALA    360
ELVKHKPKAT AEQLKTVMDD FAQFLDTCCK AADKDTCFST EGPNLVTRCK DALASGGPGP    420
AGMKGLPGSC DLPQTHNLRN KRALTLLVQM RRLSPLSCLK DRKDFGFPQE KVDAQQIKKA    480
QAIPVLSELT QQILNIFTSK DSSAAWNTTL LDSFCNDLHQ QLNDLQGCLM QQVGVQEFPL    540
TQEDALLAVR KYFHRITVYL REKKHSPCAW EVVRAEVWRA LSSSANVLGR LREEKSGGPG    600
PAGMKGLPGS EAHKSEIAHR YNDLGEQHFK GLVLIAFSQY LQKCSYDEHA KLVQEVTDFA    660
KTCVADESAA NCDKSLHTLF GDKLCAIPNL RENYGELADC CTKQEPERNE CFLQHKDDNP    720
SLPPFERPEA EAMCTSFKEN PTTFMGHYLH EVARRHPYFY APELLYYAEQ YNEILTQCCA    780
EADKESCLTP KLDGVKEKAL VSSVRQGGGG SGGGGSGGSL VEEPKNLVKT NCDLYEKLGE    840
YGFQNAILVR YTQKAPQVST PTLVEAARNL GRVGTKCCTL PEDQRLPCVE DYLSAILNRV    900
CLLHEKTPVS EHVTKCCSGS LVERRPCFSA LTVDETYVPK EFKAETFTFH SDICTLPEKE    960
KQIKKQTALA ELVKHKPKAT AEQLKTVMDD FAQFLDTCCK AADKDTCFST EGPNLVTRCK   1020
DALAHHHHHH                                                          1030

SEQ ID NO: 423               moltype = AA   length = 466
FEATURE                      Location/Qualifiers
source                       1..466
                             mol_type = protein
                             organism = synthetic construct
SEQUENCE: 423
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSGGGGS    120
GGGSGGPGPA GMKGLPGSGG GGSGGGSCDL PQTHNLRNKR ALTLLVQMRR LSPLSCLKDR    180
KDFGFPQEKV DAQQIKKAQA IPVLSELTQQ ILNIFTSKDS SAAWNTTLLD SFCNDLHQQL    240
NDLQGCLMQQ VGVQEFPLTQ EDALLAVRKY FHRITVYLRE KKHSPCAWEV VRAEVWRALS    300
SSANVLGRLR EEKGGGGSGG GSGGGPGPAGM KGLPGSGGGS EVQLV ESGGGLVQ    360
NSLRLSCAAS GFTFSKFGMS WVRQAPGKGL EWVSSISGSG RDTLYAESVK GRFTISRDNA    420
KTTLYLQMNS LRPEDTAVYY CTIGGSLSVS SQGTLVTVSS HHHHHH                   466

SEQ ID NO: 424               moltype = AA   length = 426
FEATURE                      Location/Qualifiers
source                       1..426
                             mol_type = protein
                             organism = synthetic construct
SEQUENCE: 424
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPG    120
PAGLYAQPGS CDLPQTHNLR NKRALTLLVQ MRRLSPLSCL KDRKDFGFPQ EKVDAQQIKK    180
AQAIPVLSEL TQQILNIFTS KDSSAAWNTT LLDSFCNDLH QQLNDLQGCL MQQVGVQEFP    240
LTQEDALLAV RKYFHRITVY LREKKHSPCA WEVVRAEVWR ALSSSANVLG RLREEKSGGP    300
GPAGLYAQPG SEVQLVESGG GLVQPGNSLR LSCAASGFTF SKFGMSWVRQ APGKGLEWVS    360
SISGSGRDTL YAESVKGRFT ISRDNAKTTL YLQMNSLRPE DTAVYYCTIG GSLSVSSQGT    420
LVTVSS                                                               426

SEQ ID NO: 425               moltype = AA   length = 426
FEATURE                      Location/Qualifiers
source                       1..426
                             mol_type = protein
                             organism = synthetic construct
SEQUENCE: 425
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPA    120
LFKSSFPPGS CDLPQTHNLR NKRALTLLVQ MRRLSPLSCL KDRKDFGFPQ EKVDAQQIKK    180
AQAIPVLSEL TQQILNIFTS KDSSAAWNTT LLDSFCNDLH QQLNDLQGCL MQQVGVQEFP    240
LTQEDALLAV RKYFHRITVY LREKKHSPCA WEVVRAEVWR ALSSSANVLG RLREEKSGGP    300
ALFKSSFPPG SEVQLVESGG GLVQPGNSLR LSCAASGFTF SKFGMSWVRQ APGKGLEWVS    360
SISGSGRDTL YAESVKGRFT ISRDNAKTTL YLQMNSLRPE DTAVYYCTIG GSLSVSSQGT    420
LVTVSS                                                               426

SEQ ID NO: 426               moltype = AA   length = 428
FEATURE                      Location/Qualifiers
source                       1..428
                             mol_type = protein
                             organism = synthetic construct
SEQUENCE: 426
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSSGGPP    120
LAQKLKSSPG SCDLPQTHNL RNKRALTLLV QMRRLSPLSC LKDRKDFGFP QEKVDAQQIK    180
KAQAIPVLSE LTQQILNIFT SKDSSAAWNT TLLDSFCNDL HQQLNDLQGC LMQQVGVQEF    240
PLTQEDALLA VRKYFHRITV YLREKKHSPC AWEVVRAEVW RALSSSANVL GRLREEKSGG    300
PPLAQKLKSS PGSEVQLVES GGGLVQPGNS LRLSCAASGF TFSKFGMSWV RQAPGKGLEW    360
VSSISGSGRD TLYAESVKGR FTISRDNAKT TLYLQMNSLR PEDTAVYYCT IGGSLSVSSQ    420
GTLVTVSS                                                             428

SEQ ID NO: 427               moltype = AA   length = 425
FEATURE                      Location/Qualifiers
source                       1..425
                             mol_type = protein
                             organism = synthetic construct
```

```
SEQUENCE: 427
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG  120
PAGLYAQPGS CDLPQTHSLG SRRTLMLLAQ MRRISLFSCL KDRHDFGFPQ EEFGNQFQKA  180
ETIPVLHEMI QQIFNLFSTK DSSAAWDETL LDKFYTELYQ QLNDLEACVI QGVGVTETPL  240
MKEDSILAVR KYFQRITLYL KEKKYSPCAW EVVRAEIMRS FSLSTNLQES LRSKESGGPG  300
PAGLYAQPGS EVQLVESGGG LVQPGNSLRL SCAASGFTFS KFGMSWVRQA PGKGLEWVSS  360
ISGSGRDTLY AESVKGRFTI SRDNAKTTLY LQMNSLRPED TAVYYCTIGG SLSVSSQGTL  420
VTVSS                                                              425

SEQ ID NO: 428           moltype = AA   length = 425
FEATURE                  Location/Qualifiers
source                   1..425
                         mol_type = protein
                         organism = synthetic construct
SEQUENCE: 428
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPA  120
LFKSSFPPGS CDLPQTHSLG SRRTLMLLAQ MRRISLFSCL KDRHDFGFPQ EEFGNQFQKA  180
ETIPVLHEMI QQIFNLFSTK DSSAAWDETL LDKFYTELYQ QLNDLEACVI QGVGVTETPL  240
MKEDSILAVR KYFQRITLYL KEKKYSPCAW EVVRAEIMRS FSLSTNLQES LRSKESGGPA  300
LFKSSFPPGS EVQLVESGGG LVQPGNSLRL SCAASGFTFS KFGMSWVRQA PGKGLEWVSS  360
ISGSGRDTLY AESVKGRFTI SRDNAKTTLY LQMNSLRPED TAVYYCTIGG SLSVSSQGTL  420
VTVSS                                                              425

SEQ ID NO: 429           moltype = AA   length = 427
FEATURE                  Location/Qualifiers
source                   1..427
                         mol_type = protein
                         organism = synthetic construct
SEQUENCE: 429
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPP  120
LAQKLKSSPG SCDLPQTHSL GSRRTLMLLA QMRRISLFSC LKDRHDFGFP QEEFGNQFQK  180
AETIPVLHEM IQQIFNLFST KDSSAAWDET LLDKFYTELY QQLNDLEACV IQGVGVTETP  240
LMKEDSILAV RKYFQRITLY LKEKKYSPCA WEVVRAEIMR SFSLSTNLQE SLRSKESGGP  300
PLAQKLKSSP GSEVQLVESG GGLVQPGNSL RLSCAASGFT FSKFGMSWVR QAPGKGLEWV  360
SSISGSGRDT LYAESVKGRF TISRDNAKTT LYLQMNSLRP EDTAVYYCTI GGSLSVSSQG  420
TLVTVSS                                                            427

SEQ ID NO: 430           moltype = AA   length = 728
FEATURE                  Location/Qualifiers
source                   1..728
                         mol_type = protein
                         organism = synthetic construct
SEQUENCE: 430
EVQLVESGGG LVQPGNSLRL SCAASGFTFS KFGMSWVRQA PGKGLEWVSS ISGSGRDTLY   60
AESVKGRFTI SRDNAKTTLY LQMNSLRPED TAVYYCTIGG SLSVSSQGTL VTVSSSGGPG  120
PAGMKGLPGS HGTVIESLES LNNYFNSSGI DVEEKSLFLD IWRNWQKDGD MKILQSQIIS  180
FYLRLFEVLK DNQAISNNIS VIESHLITTF FSNSKAKKDA FMSIAKFEVN NPQVQRQAFN  240
ELIRVVHQLL PESSLRKRKR SRCSGGPGPA GMKGLPGSCD LPQTHNLRNK RALTLLVQMR  300
RLSPLSCLKD RKDFGFPQEK VDAQQIKKAQ AIPVLSELTQ QILNIFTSKD SSAAWNTTLL  360
DSFCNDLHQQ LNDLQGCLMQ QVGVQEFPLT QEDALLAVRK YFHRITVYLR EKKHSPCAWE  420
VVRAEVWRAL SSSANVLGRL REEKSGGPGP AGMKGLPGSH GTVIESLESL NNYFNSSGID  480
VEEKSLFLDI WRNWQKDGDM KILQSQIISF YLRLFEVLKD NQAISNNISV IESHLITTFF  540
SNSKAKKDAF MSIAKFEVNN PQVQRQAFNE LIRVVHQLLP ESSLRKRKRS RCSGGPGPAG  600
MKGLPGSEVQ LVESGGGLVQ PGNSLRLSCA ASGFTFSKFG MSWVRQAPGK GLEWVSSISG  660
SGRDTLYAES VKGRFTISRD NAKTTLYLQM NSLRPEDTAV YYCTIGGSLS VSSQGTLVTV  720
SSHHHHHH                                                           728

SEQ ID NO: 431           moltype = AA   length = 947
FEATURE                  Location/Qualifiers
source                   1..947
                         mol_type = protein
                         organism = synthetic construct
SEQUENCE: 431
LVEEPKNLVK TNCDLYEKLG EYGFQNAILV RYTQKAPQVS TPTLVEAARN LGRVGTKCCT   60
LPEDQRLPCV EDYLSAILNR VCLLHEKTPV SEHVTKCCSG SLVERRPCFS ALTVDETYVP  120
KEFKAETFTF HSDICTLPEK EKQIKKQTAL AELVKHKPKA TAEQLKTVMD DFAQFLDTCC  180
KAADKDTCFS TEGPNLVTRC KDALASGGPG PAGMKGLPGS HGTVIESLES LNNYFNSSGI  240
DVEEKSLFLD IWRNWQKDGD MKILQSQIIS FYLRLFEVLK DNQAISNNIS VIESHLITTF  300
FSNSKAKKDA FMSIAKFEVN NPQVQRQAFN ELIRVVHQLL PESSLRKRKR SRCSGGPGPA  360
GMKGLPGSLV EEPKNLVKTN CDLYEKLGEY GFQNAILVRY TQKAPQVSTP TLVEAARNLG  420
RVGTKCCTLP EDQRLPCVED YLSAILNRVC LLHEKTPVSE HVTKCCSGSL VERRPCFSAL  480
TVDETYVPKE FKAETFTFHS DICTLPEKEK QIKKQTALAE LVKHKPKATA EQLKTVMDDF  540
AQFLDTCCKA ADKDTCFSTE GPNLVTRCKD ALASGGPGPA GMKGLPGSHG TVIESLESLN  600
NYFNSSGIDV EEKSLFLDIW RNWQKDGDMK ILQSQIISFY LRLFEVLKDN QAISNNISVI  660
ESHLITTFFS NSKAKKDAFM SIAKFEVNNP QVQRQAFNEL IRVVHQLLPE SSLRKRKRSR  720
CSGGPGPAGM KGLPGSLVEE PKNLVKTNCD LYEKLGEYGF QNAILVRYTQ KAPQVSTPTL  780
```

```
VEAARNLGRV GTKCCTLPED QRLPCVEDYL SAILNRVCLL HEKTPVSEHV TKCCSGSLVE    840
RRPCFSALTV DETYVPKEFK AETFTFHSDI CTLPEKEKQI KKQTALAELV KHKPKATAEQ    900
LKTVMDDFAQ FLDTCCKAAD KDTCFSTEGP NLVTRCKDAL AHHHHHH                  947

SEQ ID NO: 432           moltype = AA  length = 1574
FEATURE                  Location/Qualifiers
source                   1..1574
                         mol_type = protein
                         organism = synthetic construct
SEQUENCE: 432
EAHKSEIAHR YNDLGEQHFK GLVLIAFSQY LQKCSYDEHA KLVQEVTDFA KTCVADESAA     60
NCDKSLHTLF GDKLCAIPNL RENYGELADC CTKQEPERNE CFLQHKDDNP SLPPFERPEA    120
EAMCTSFKEN PTTFMGHYLH EVARRHPYFY APELLYYAEQ YNEILTQCCA EADKESCLTP    180
KLDGVKEKAL VSSVRQGGGG SGGGGSGGSL VEEPKNLVKT NCDLYEKLGE YGFQNAILVR    240
YTQKAPQVST PTLVEAARNL GRVGTKCCTL PEDQRLPCVE DYLSAILNRV CLLHEKTPVS    300
EHVTKCCSGS LVERRPCFSA LTVDETYVPK EFKAETFTFH SDICTLPEKE KQIKKQTALA    360
ELVKHKPKAT AEQLKTVMDD FAQFLDTCCK AADKDTCFST EGPNLVTRCK DALASGGPGP    420
AGMKGLPGSH GTVIESLESL NNYFNSSGID VEEKSLFLDI WRNWQKDGDM KILQSQIISF    480
YLRLFEVLKD NQAISNNISV IESHLITTFF SNSKAKKDAF MSIAKFEVNN PQVQRQAFNE    540
LIRVVHQLLP ESSLRKRKRS RCSGGPGPAG MKGLPGSEAH KSEIAHRYND LGEQHFKGLV    600
LIAFSQYLQK CSYDEHAKLV QEVTDFAKTC VADESAANCD KSLHTLFGDK LCAIPNLREN    660
YGELADCCTK QEPERNECFL QHKDDNPSLP PFERPEAEAM CTSFKENPTT FMGHYLHEVA    720
RRHPYFYAPE LLYYAEQYNE ILTQCCAEAD KESCLTPKLD GVKEKALVSS VRQGGGGSGG    780
GGSGGSLVEE PKNLVKTNCD LYEKLGEYGF QNAILVRYTQ KAPQVSTPTL VEAARNLGRV    840
GTKCCTLPED QRLPCVEDYL SAILNRVCLL HEKTPVSEHV TKCCSGSLVE RRPCFSALTV    900
DETYVPKEFK AETFTFHSDI CTLPEKEKQI KKQTALAELV KHKPKATAEQ LKTVMDDFAQ    960
FLDTCCKAAD KDTCFSTEGP NLVTRCKDAL ASGGPGPAGM KGLPGSHGTV IESLESLNNY   1020
FNSSGIDVEE KSLFLDIWRN WQKDGDMKIL QSQIISFYLR LFEVLKDNQA ISNNISVIES   1080
HLITTFFSNS KAKKDAFMSI AKFEVNNPQV QRQAFNELIR VVHQLLPESS LRKRKRSRCS   1140
GGPGPAGMKG LPGSEAHKSE IAHRYNDLGE QHFKGLVLIA FSQYLQKCSY DEHAKLVQEV   1200
TDFAKTCVAD ESAANCDKSL HTLFGDKLCA IPNLRENYGE LADCCTKQEP ERNECFLQHK   1260
DDNPSLPPFE RPEAEAMCTS FKENPTTFMG HYLHEVARRH PYFYAPELLY YAEQYNEILT   1320
QCCAEADKES CLTPKLDGVK EKALVSSVRQ GGGGSGGGGS GGSLVEEPKN LVKTNCDLYE   1380
KLGEYGFQNA ILVRYTQKAP QVSTPTLVEA ARNLGRVGTK CCTLPEDQRL PCVEDYLSAI   1440
LNRVCLLHEK TPVSEHVTKC CSGSLVERRP CFSALTVDET YVPKEFKAET FTFHSDICTL   1500
PEKEKQIKKQ TALAELVKHK PKATAEQLKT VMDDFAQFLD TCCKAADKDT CFSTEGPNLV   1560
TRCKDALAHH HHHH                                                     1574

SEQ ID NO: 433           moltype = AA  length = 745
FEATURE                  Location/Qualifiers
source                   1..745
                         mol_type = protein
                         organism = synthetic construct
SEQUENCE: 433
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSGGGGS    120
GGGGSGGGGS GMKGLPGSGG GGSGGGGSHGT VIESLESLNN YFNSSGIDVE EKSLFLDIWR    180
NWQKDGDMKI LQSQIISFYL RLFEVLKDNQ AISNNISVIE SHLITTFFSN SKAKKDAFMS    240
IAKFEVNNPQ VQRQAFNELI RVVHQLLPES SLRKRKRSRC GGGGSGGGSG GPGPAGMKGL    300
PGSGGGGSGG GSEVQLVESG GGLVQPGNSL RLSCAASGFT FSKFGMSWVR QAPGKGLEWV    360
SSISGSGRDT LYAESVKGRF TISRDNAKTT LYLQMNSLRP EDTAVYYCTI GGSLSVSSQG    420
TLVTVSSGGG GSGGGGSGGPG PAGMKGLPGS GGGGSGGGGSH GTVIESLESL NNYFNSSGID    480
VEEKSLFLDI WRNWQKDGDM KILQSQIISF YLRLFEVLKD NQAISNNISV IESHLITTFF    540
SNSKAKKDAF MSIAKFEVNN PQVQRQAFNE LIRVVHQLLP ESSLRKRKRS RCGGGGSGGG    600
SGGPGPAGMK GLPGSGGGGS GGGSEVQLVE SGGGLVQPGN SLRLSCAASG FTFSKFGMSW    660
VRQAPGKGLE WVSSISGSGR DTLYAESVKG RFTISRDNAK TTLYLQMNSL RPEDTAVYYC    720
TIGGSLSVSS QGTLVTVSSH HHHH                                           745

SEQ ID NO: 434           moltype = AA  length = 936
FEATURE                  Location/Qualifiers
source                   1..936
                         mol_type = protein
                         organism = synthetic construct
SEQUENCE: 434
EVQLVESGGG LVQPGNSLRL SCAASGFTFS KFGMSWVRQA PGKGLEWVSS ISGSGRDTLY     60
AESVKGRFTI SRDNAKTTLY LQMNSLRPED TAVYYCTIGG SLSVSSQGTL VTVSSGGGGS    120
GGGGSGGGGS IWELKKDVYV VELDWYPDAP GEMVVLTCDT PEEDGITWTL DQSSEVLGSG    180
KTLTIQVKEF GDAGQYTCHK GGEVLSHSLL LLHKKEDGIW STDILKDQKE PKNKTFLRCE    240
AKNYSGRFTC WWLTTISTDL TFSVKSSRGS SDPQGVTCGA ATLSAERVRG DNKEYEYSVE    300
CQEDSACPAA EESLPIEVMV DAVHKLKYEN YTSSFFIRDI IKPDPPKNLQ LKPLKNSRQV    360
EVSWEYPDTW STPHSYFSLT FCVQVQGKSK REKKDRVFTD KTSATVICRK NASISVRAQD    420
RYYSSSWSEW ASVPCSGGGG SGGGGSGGGG SRVIPVSGPA RCLSQSRNLL KTTDDMVKTA    480
REKLKHYSCT AEDIDHEDIT RDQTSTLKTC LPLELHKNES CLATRETSST TRGSCLPPQK    540
TSLMMTLCLG SIYEDLKMYQ TEFQAINAAL QNHNHQQIIL DKGMLVAIDE LMQSLNHNGE    600
TLRQKPPVGE ADPYRVKMKL CILLHAFSTR VVTINRVMGY LSSAGGGGSG GGSGGGGGSG    660
GGGSGGGGSG GGGSGGGGSG GGSGGGGSQ SVLTQPPSVS GAPGQRVTIS CSGSRSNIGS    720
NTVKWYQQLP GTAPKLLIYY NDQRPSGVPD RFSGSKSGTS ASLAITGLQA EDEADYYCQS    780
YDRYTHPALL FGTGTKVTVL GGGGSGGGGS GGGGSQVQLV ESGGGVVQPG RSLRLSCAAS    840
GFTFSSYGMH WVRQAPGKGL EWVAFIRYDG SNKYYADSVK GRFTISRDNS KNTLYLQMNS    900
```

```
LRAEDTAVYY CKTHGSHDNW GQGTMVTVSS HHHHHH                               936

SEQ ID NO: 435          moltype = AA   length = 1405
FEATURE                 Location/Qualifiers
source                  1..1405
                        mol_type = protein
                        organism = synthetic construct
SEQUENCE: 435
EAHKSEIAHR YNDLGEQHFK GLVLIAFSQY LQKCSYDEHA KLVQEVTDFA KTCVADESAA     60
NCDKSLHTLF GDKLCAIPNL RENYGELADC CTKQEPERNE CFLQHKDDNP SLPPFERPEA    120
EAMCTSFKEN PTTFMGHYLH EVARRHPYFY APELLYYAEQ YNEILTQCCA EADKESCLTP    180
KLDGVKEKAL VSSVRQRMKC SSMQKFGERA FKAWAVARLS QTFPNADFAE ITKLATDLTK    240
VNKECCHGDL LECADDRAEL AKYMCENQAT ISSKLQTCCD KPLLKKAHCL SEVEHDTMPA    300
DLPAIAADFV EDQEVCKNYA EAKDVFLGTF LYEYSRRHPD YSVSLLLRLA KKYEATLEKC    360
CAEANPPACY GTVLAEFQPL VEEPKNLVKT NCDLYEKLGE YGFQNAILVR YTQKAPQVST    420
PTLVEAARNL GRVGTKCCTL PEDQRLPCVE DYLSAILNRV CLLHEKTPVS EHVTKCCSGS    480
LVERRPCFSA LTVDETYVPK EFKAETFTFH SDICTLPEKE KQIKKQTALA ELVKHKPKAT    540
AEQLKTVMDD FAQFLDTCCK AADKDTCFST EGPNLVTRCK DALASGGPGP AGMKGLPGSI    600
WELKKDVYVV ELDWYPDAPG EMVVLTCDTP EEDGITWTLD QSSEVLGSGK TLTIQVKEFG    660
DAGQYTCHKG GEVLSHSLLL LHKKEDGIWS TDILKDQKEP KNKTFLRCEA KNYSGRFTCW    720
WLTTISTDLT FSVKSSRGSS DPQGVTCGAA TLSAERVRGD NKEYEYSVEC QEDSACPAAE    780
ESLPIEVMVD AVHKLKYENY TSSFFIRDII KPDPPKNLQL KPLKNSRQVE VSWEYPDTWS    840
TPHSYFSLTF CVQVQGKSKR EKKDRVFTDK TSATVICRKN ASISVRAQDR YYSSSWSEWA    900
SVPCSGGGGS GGGGSGGGGS RVIPVSGPAR CLSQSRNLLK TTDDMVKTAR EKLKHYSCTA    960
EDIDHEDITR DQTSTLKTCL PLELHKNESC LATRETSSTT RGSCLPPQKT SLMMTLCLGS   1020
IYEDLKMYQT EFQAINAALQ NHNHQQIILD KGMLVAIDEL MQSLNHNGET LRQKPPVGEA   1080
DPYRVKMKLC ILLHAFSTRV VTINRVMGYL SSASGGPGPA GMKGLPGSGG GGSGGGGSGG   1140
GGSGGGGSGG GGSGGGGSQS VLTQPPSVSG APGQRVTISC SGSRSNIGSN TVKWYQQLPG   1200
TAPKLLIYYN DQRPSGVPDR FSGSKSGTSA SLAITGLQAE DEADYYCQSY DRYTHPALLF   1260
GTGTKVTVLG GGGSGGGGSG GGGSQVQLVE SGGGVVQPGR SLRLSCAASG FTFSSYGMHW   1320
VRQAPGKGLE WVAFIRYDGS NKYYADSVKG RFTISRDNSK NTLYLQMNSL RAEDTAVYYC   1380
KTHGSHDNWG QGTMVTVSSH HHHH                                         1405

SEQ ID NO: 436          moltype = AA   length = 1405
FEATURE                 Location/Qualifiers
source                  1..1405
                        mol_type = protein
                        organism = synthetic construct
SEQUENCE: 436
IWELKKDVYV VELDWYPDAP GEMVVLTCDT PEEDGITWTL DQSSEVLGSG KTLTIQVKEF     60
GDAGQYTCHK GGEVLSHSLL LLHKKEDGIW STDILKDQKE PKNKTFLRCE AKNYSGRFTC    120
WWLTTISTDL TFSVKSSRGS SDPQGVTCGA ATLSAERVRG DNKEYEYSVE CQEDSACPAA    180
EESLPIEVMV DAVHKLKYEN YTSSFFIRDI IKPDPPKNLQ LKPLKNSRQV EVSWEYPDTW    240
STPHSYFSLT FCVQVQGKSK REKKDRVFTD KTSATVICRK NASISVRAQD RYYSSSWSEW    300
ASVPCSGGGG SGGGGSGGGG SRVIPVSGPA RCLSQSRNLL KTTDDMVKTA REKLKHYSCT    360
AEDIDHEDIT RDQTSTLKTC LPLELHKNES CLATRETSST TRGSCLPPQK TSLMMTLCLG    420
SIYEDLKMYQ TEFQAINAAL QNHNHQQIIL DKGMLVAIDE LMQSLNHNGE TLRQKPPVGE    480
ADPYRVKMKL CILLHAFSTR VVTINRVMGY LSSASGGPGP AGMKGLPGSG GGGSGGGGSG    540
GGGSGGGGSG GGGSGGGGSQ SVLTQPPSVS GAPGQRVTIS CSGSRSNIGS NTVKWYQQLP    600
GTAPKLLIYY NDQRPSGVPD RFSGSKSGTS ASLAITGLQA EDEADYYCQS YDRYTHPALL    660
FGTGTKVTVL GGGGSGGGGS GGGGSQVQLV ESGGGVVQPG RSLRLSCAAS GFTFSSYGMH    720
WVRQAPGKGL EWVAFIRYDG SNKYYADSVK GRFTISRDNS KNTLYLQMNS LRAEDTAVYY    780
CKTHGSHDNW GQGTMVTVSS SGGPGPAGMK GLPGSEAHKS EIAHRYNDLG EQHFKGLVLI    840
AFSQYLQKCS YDEHAKLVQE VTDFAKTCVA DESAANCDKS LHTLFGDKLC AIPNLRENYG    900
ELADCCTKQE PERNECFLQH KDDNPSLPPF ERPEAEAMCT SFKENPTTFM GHYLHEVARR    960
HPYFYAPELL YYAEQYNEIL TQCCAEADKE SCLTPKLDGV KEKALVSSVR QRMKCSSMQK   1020
FGERAFKAWA VARLSQTFPN ADFAEITKLA TDLTKVNKEC CHGDLLECAD DRAELAKYMC   1080
ENQATISSKL QTCCDKPLLK AHCLSEVEH DTMPADLPAI AADFVEDQEV CKNYAEAKDV    1140
FLGTFLYEYS RRHPDYSVSL LLRLAKKYEA TLEKCCAEAN PPACYGTVLA EFQPLVEDYLSA 1200
NLVKTNCDLY EKLGEYGFQN AILVRYTQKA PQVSTPTLVE AARNLGRVGT KCCTLPEDQR   1260
LPCVEDYLSA ILNRVCLLHE KTPVSEHVTK CCSGSLVERR PCFSALTVDE TYVPKEFKAE   1320
TFTFHSDICT LPEKEKQIKK QTALAELVKH KPKATAEQLK TVMDDFAQFL DTCCKAADKD   1380
TCFSTEGPNL VTRCKDALAH HHHH                                         1405

SEQ ID NO: 437          moltype = AA   length = 1048
FEATURE                 Location/Qualifiers
source                  1..1048
                        mol_type = protein
                        organism = synthetic construct
SEQUENCE: 437
VPRDCGCKPC ICTVPEVSSV FIFPPKPKDV LTITLTPKVT CVVVDISKDD PEVQFSWFVD     60
DVEVHTAQTQ PREEQFNSTF RSVSELPIMH QDWLNGKEFK CRVNSAAFPA PIEKTISKTK    120
GRPKAPQVYT IPPPKEQMAK DKVSLTCMIT DFFPEDITVE WQWNGQPAEN YKNTQPIMDT    180
DGSYFVYSKL NVQKSNWEAG NTFTCSVLHE GLHNHHTEKS LSHSPGKSGG PGPAGMKGLP    240
GSIWELKKDV YVVELDWYPD APGEMVVLTC DTPEEDGITW TLDQSSEVLG SGKTLTIQVK    300
EFGDAGQYTC HKGGEVLSHS LLLLHKKEDG IWSTDILKDQ KEPKNKTFLR CEAKNYSGRF    360
TCWWLTTIST DLTFSVKSSR GSSDPQGVTC GAATLSAERV RGDNKEYEYS VECQEDSACP    420
AAEESLPIEV MVDAVHKLKY ENYTSSFFIR DIIKPDPPKN LQLKPLKNSR QVEVSWEYPD    480
TWSTPHSYFS LTFCVQVQGK SKREKKDRVF TDKTSATVIC RKNASISVRA QDRYYSSSWS    540
```

```
EWASVPCSGG GGSGGGGSGG GGSRVIPVSG PARCLSQSRN LLKTTDDMVK TAREKLKHYS    600
CTAEDIDHED ITRDQTSTLK TCLPLELHKN ESCLATRETS STTRGSCLPP QKTSLMMTLC    660
LGSIYEDLKM YQTEFQAINA ALQNHNHQQI ILDKGMLVAI DELMQSLNHN GETLRQKPPV    720
GEADPYRVKM KLCILLHAFS TRVVTINRVM GYLSSASGGP GPAGMKGLPG SGGGGSGGGG    780
SGGGGSGGGG SGGGGSGGGG SQSVLTQPPS VSGAPGQRVT ISCSGSRSNI GSNTVKWYQS    840
LPGTAPKLLI YYNDQRPSGV PDRFSGSKSG TSASLAITGL QAEDEADYYC QSYDRYTHPA    900
LLFGTGTKVT VLGGGGSGGG GSGGGGSQVQ LVESGGGVVQ PGRSLRLSCA ASGFTFSSYG    960
MHWVRQAPGK GLEWVAFIRY DGSNKYYADS VKGRFTISRD NSKNTLYLQM NSLRAEDTAV   1020
YYCKTHGSHD NWGQGTMVTV SSHHHHHH                                      1048

SEQ ID NO: 438          moltype = AA  length = 1048
FEATURE                 Location/Qualifiers
source                  1..1048
                        mol_type = protein
                        organism = synthetic construct
SEQUENCE: 438
IWELKKDVYV VELDWYPDAP GEMVVLTCDT PEEDGITWTL DQSSEVLGSG KTLTIQVKEF    60
GDAGQYTCHK GGEVLSHSLL LLHKKEDGIW STDILKDQKE PKNKTFLRCE AKNYSGRFTC   120
WWLTTISTDL TFSVKSSRGS SDPQGVTCGA ATLSAERVRG DNKEYEYSVE CQEDSACPAA   180
EESLPIEVMV DAVHKLKYEN YTSSFFIRDI IKPDPPKNLQ LKPLKNSRQV EVSWEYPDTW   240
STPHSYFSLT FCVQVQGKSK REKKDRVFTD KTSATVICRK NASISVRAQD RYYSSSWSEW   300
ASVPCSGGGG SGGGGSGGGG SRVIPVSGPA RCLSQSRNLL KTTDDMVKTA REKLKHYSCT   360
AEDIDHEDIT RDQTSTLKTC LPLELHKNES CLATRETSST TRGSCLPPQK TSLMMTLCLG   420
SIYEDLKMYQ TEFQAINAAL QNHNHQQIIL DKGMLVAIDE LMQSLNHNGE TLRQKPPVGE   480
ADPYRVKMKL CILLHAFSTR VVTINRVMGY LSSASGGPGP AGMKGLPGSG GGGSGGGGSG   540
GGGSGGGGSG GGGSGGGGSQ SVLTQPPSVS GAPGQRVTIS CSGSRSNIGS NTVKWYQQLP   600
GTAPKLLIYY NDQRPSGVPD RFSGSKSGTS ASLAITGLQA EDEADYYCQS YDRYTHPALL   660
FGTGTKVTVL GGGGSGGGGS GGGGSQVQLV ESGGGVVQPG RSLRLSCAAS GFTFSSYGMH   720
WVRQAPGKGL EWVAFIRYDG SNKYYADSVK GRFTISRDNS KNTLYLQMNS LRAEDTAVYY   780
CKTHGSHDNW GQGTMVTVSS SGGPGPAGMK GLPGSVPRDC GCKPCICTVP EVSSVFIFPP   840
KPKDVLTITL TPKVTCVVVD ISKDDPEVQF SWFVDDVEVH TAQTQPREEQ FNSTFRSVSE   900
LPIMHQDWLN GKEFKCRVNS AAFPAPIEKT ISKTKGRPKA PQVYTIPPPK EQMAKDKVSL   960
TCMITDFFPE DITVEWQWNG QPAENYKNTQ PIMDTDGSYF VYSKLNVQKS NWEAGNTFTC  1020
SVLHEGLHNH HTEKSLSHSP GKHHHHHH                                     1048

SEQ ID NO: 439          moltype = AA  length = 936
FEATURE                 Location/Qualifiers
source                  1..936
                        mol_type = protein
                        organism = synthetic construct
SEQUENCE: 439
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGMKGLPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPGP AGMKGLPGSG   660
GGGSGGGGSG GGGSGGGGSG GGGSGGGGSQ SVLTQPPSVS GAPGQRVTIS CSGSRSNIGS   720
NTVKWYQQLP GTAPKLLIYY NDQRPSGVPD RFSGSKSGTS ASLAITGLQA EDEADYYCQS   780
YDRYTHPALL FGTGTKVTVL SGGPGPAGMK GLPGSQVQLV ESGGGVVQPG RSLRLSCAAS   840
GFTFSSYGMH WVRQAPGKGL EWVAFIRYDG SNKYYADSVK GRFTISRDNS KNTLYLQMNS   900
LRAEDTAVYY CKTHGSHDNW GQGTMVTVSS HHHHHH                             936

SEQ ID NO: 440          moltype = AA  length = 817
FEATURE                 Location/Qualifiers
source                  1..817
                        mol_type = protein
                        organism = synthetic construct
SEQUENCE: 440
EVQLVESGGG LVQPGNSLRL SCAASGFTFS KFGMSWVRQA PGKGLEWVSS ISGSGRDTLY    60
AESVKGRFTI SRDNAKTTLY LQMNSLRPED TAVYYCTIGG SLSVSSQGTL VTVSSSGGPG   120
PAGMKGLPGS IWELKKDVYV VELDWYPDAP GEMVVLTCDT PEEDGITWTL DQSSEVLGSG   180
KTLTIQVKEF GDAGQYTCHK GGEVLSHSLL LLHKKEDGIW STDILKDQKE PKNKTFLRCE   240
AKNYSGRFTC WWLTTISTDL TFSVKSSRGS SDPQGVTCGA ATLSAERVRG DNKEYEYSVE   300
CQEDSACPAA EESLPIEVMV DAVHKLKYEN YTSSFFIRDI IKPDPPKNLQ LKPLKNSRQV   360
EVSWEYPDTW STPHSYFSLT FCVQVQGKSK REKKDRVFTD KTSATVICRK NASISVRAQD   420
RYYSSSWSEW ASVPCSGGGG SGGGGSGGGG SRVIPVSGPA RCLSQSRNLL KTTDDMVKTA   480
REKLKHYSCT AEDIDHEDIT RDQTSTLKTC LPLELHKNES CLATRETSST TRGSCLPPQK   540
TSLMMTLCLG SIYEDLKMYQ TEFQAINAAL QNHNHQQIIL DKGMLVAIDE LMQSLNHNGE   600
TLRQKPPVGE ADPYRVKMKL CILLHAFSTR VVTINRVMGY LSSASGGPGP AGMKGLPGSG   660
GGGSGGGGSG GGGSGGGGSG GGGSGGGGSQ VQLQESGGGL VQAGGSLRLS CAASGRTFSS   720
VYDMGWFRQA PGKDREFVAR ITESARNTRY ADSVRGRFTI SRDNAKNTVY LQMNNLELED   780
AAVYYCAADP QTVVVGTPDY WGQGTQVTVS SHHHHHH                            817
```

-continued

```
SEQ ID NO: 441           moltype = AA   length = 547
FEATURE                  Location/Qualifiers
source                   1..547
                         mol_type = protein
                         organism = synthetic construct
SEQUENCE: 441
APTSSSTKKT QLQLEHLLLD LQMILNGINN YKNPKLTRML TFKFYMPKKA TELKHLQCLE    60
EELKPLEEVL NLAQSKNFHL RPRDLISNIN VIVLELKGSE TTFMCEYADE TATIVEFLNR   120
WITFCQSIIS TLTSGGPALF KSSFPPGSEV QLVESGGGLV QPGNSLRLSC AASGFTFSKF   180
GMSWVRQAPG KGLEWVSSIS GSGRDTLYAE SVKGRFTISR DNAKTTLYLQ MNSLRPEDTA   240
VYYCTIGGSL SVSSQGTLVT VSSGGGGSGG GGSGGGGSGG GGSGGGGSGG GGSSGGPALF   300
KSSFPPGSEV QLVESGGGLV QPGGSLRLSC AASGFTFSSY TLAWVRQAPG KGLEWVAAID   360
SSSYTYSPDT VRGRFTISRD NAKNSLYLQM NSLRAEDTAV YYCARDSNWD ALDYWGCGTT   420
VTVSSGGGGS GGGGSGGGGS DIQMTQSPSS LSASVGDRVT ITCKVTEKVW GNVAWYQQKP   480
GKCPISLIYS PSLRKSGVPS RFSGSGSGTD FTLTISSLQP EDFATYYCQQ YYTYPYTFGG   540
GTKVEIK                                                            547

SEQ ID NO: 442           moltype = AA   length = 5
FEATURE                  Location/Qualifiers
VARIANT                  3
                         note = Any amino acid
source                   1..5
                         mol_type = protein
                         note = Sortase A cleavage site
                         organism = unidentified
SEQUENCE: 442
LPXTG                                                                 5

SEQ ID NO: 443           moltype = AA   length = 25
FEATURE                  Location/Qualifiers
source                   1..25
                         mol_type = protein
                         organism = synthetic construct
VARIANT                  6..25
                         note = GGGGS repeats may be deleted
SEQUENCE: 443
GGGGSGGGGS GGGGSGGGGS GGGGS                                          25

SEQ ID NO: 444           moltype = AA   length = 20
FEATURE                  Location/Qualifiers
source                   1..20
                         mol_type = protein
                         organism = synthetic construct
VARIANT                  5..20
                         note = GGGS repeats may be deleted
SEQUENCE: 444
GGGSGGGSGG GSGGGSGGGS                                                20

SEQ ID NO: 445           moltype = AA   length = 7
FEATURE                  Location/Qualifiers
source                   1..7
                         mol_type = protein
                         note = protease-cleavable sequence
                         organism = unidentified
SEQUENCE: 445
GPLGVRG                                                               7

SEQ ID NO: 446           moltype = AA   length = 8
FEATURE                  Location/Qualifiers
source                   1..8
                         mol_type = protein
                         note = protease-cleavable sequence
                         organism = unidentified
SEQUENCE: 446
IPVSLRSG                                                              8

SEQ ID NO: 447           moltype = AA   length = 8
FEATURE                  Location/Qualifiers
source                   1..8
                         mol_type = protein
                         note = protease-cleavable sequence
                         organism = unidentified
SEQUENCE: 447
VPLSLYSG                                                              8

SEQ ID NO: 448           moltype = AA   length = 10
FEATURE                  Location/Qualifiers
source                   1..10
                         mol_type = protein
```

-continued

```
                        note = protease-cleavable sequence
                        organism = unidentified
SEQUENCE: 448
SGESPAYYTA                                                              10

SEQ ID NO: 449         moltype = AA  length = 5
FEATURE                Location/Qualifiers
source                 1..5
                       mol_type = protein
                       organism = synthetic construct
SEQUENCE: 449
GGGGS                                                                   5

SEQ ID NO: 450         moltype = AA  length = 6
FEATURE                Location/Qualifiers
source                 1..6
                       mol_type = protein
                       organism = synthetic construct
SEQUENCE: 450
GSGSGS                                                                  6

SEQ ID NO: 451         moltype = AA  length = 13
FEATURE                Location/Qualifiers
source                 1..13
                       mol_type = protein
                       organism = synthetic construct
SEQUENCE: 451
GSGGGSGGGS GGT                                                          13

SEQ ID NO: 452         moltype = AA  length = 15
FEATURE                Location/Qualifiers
source                 1..15
                       mol_type = protein
                       organism = synthetic construct
SEQUENCE: 452
GGGGSGGGGS GGGGS                                                        15

SEQ ID NO: 453         moltype = AA  length = 20
FEATURE                Location/Qualifiers
source                 1..20
                       mol_type = protein
                       organism = synthetic construct
SEQUENCE: 453
GGGGSGGGGS GGGGSGGGGS                                                   20
```